United States Patent
Bamdad et al.

(10) Patent No.: US 12,202,799 B2
(45) Date of Patent: Jan. 21, 2025

(54) AGENTS FOR DIFFERENTIATING STEM CELLS AND TREATING CANCER

(71) Applicant: MINERVA BIOTECHNOLOGIES CORPORATION, Waltham, MA (US)

(72) Inventors: Cynthia Bamdad, Waltham, MA (US); Scott Moe, Waltham, MA (US)

(73) Assignee: MINERVA BIOTECHNOLOGIES CORPORATION, Waltham, MA (US)

( * ) Notice: Subject to any disclaimer, the term of this patent is extended or adjusted under 35 U.S.C. 154(b) by 0 days.

(21) Appl. No.: 17/512,978

(22) Filed: Oct. 28, 2021

(65) Prior Publication Data

US 2022/0242823 A1  Aug. 4, 2022

Related U.S. Application Data

(63) Continuation of application No. 16/498,640, filed as application No. PCT/US2018/025107 on Mar. 29, 2018, now abandoned.

(60) Provisional application No. 62/607,880, filed on Dec. 19, 2017, provisional application No. 62/478,382, filed on Mar. 29, 2017.

(51) Int. Cl.
| | |
|---|---|
| *C07D 211/16* | (2006.01) |
| *A61P 35/00* | (2006.01) |
| *C07D 213/74* | (2006.01) |
| *C07D 295/185* | (2006.01) |
| *C07D 401/04* | (2006.01) |
| *C07D 401/06* | (2006.01) |
| *C07D 471/04* | (2006.01) |

(52) U.S. Cl.
CPC ............ *C07D 211/16* (2013.01); *A61P 35/00* (2018.01); *C07D 213/74* (2013.01); *C07D 295/185* (2013.01); *C07D 401/04* (2013.01); *C07D 401/06* (2013.01); *C07D 471/04* (2013.01)

(58) Field of Classification Search
CPC ..... A61P 35/00; C07D 211/16; C07D 213/74; C07D 295/185; C07D 401/04; C07D 401/06; C07D 471/04
See application file for complete search history.

(56) References Cited

U.S. PATENT DOCUMENTS

| | | | |
|---|---|---|---|
| 5,665,719 A | 9/1997 | Bock et al. | |
| 6,960,588 B1 | 11/2005 | Martin | |
| 11,931,347 B2 * | 3/2024 | Bamdad | A61K 31/444 |
| 2009/0012077 A1 * | 1/2009 | Dossetter | C07D 491/04 |
| | | | 544/126 |
| 2009/0047675 A1 | 2/2009 | Roberts et al. | |
| 2015/0274671 A1 | 10/2015 | Pinto et al. | |
| 2018/0263964 A1 * | 9/2018 | Bamdad | G01N 33/5073 |
| 2021/0087143 A1 | 3/2021 | Bamdad et al. | |
| 2021/0299109 A1 * | 9/2021 | Bamdad | A61K 31/437 |

FOREIGN PATENT DOCUMENTS

| | | |
|---|---|---|
| JP | H0687810 A | 3/1994 |
| JP | 2008521910 A | 6/2008 |
| WO | WO-0014097 A2 | 3/2000 |
| WO | WO-0146168 A1 | 6/2001 |
| WO | WO-2009042815 A1 | 4/2009 |
| WO | WO-2010032856 A1 | 3/2010 |
| WO | WO-2011159960 A2 | 12/2011 |
| WO | WO-2014014050 A1 | 1/2014 |
| WO | WO-2015023694 A2 | 2/2015 |
| WO | WO-2015107724 A1 | 7/2015 |
| WO | WO-2015157322 A2 | 10/2015 |
| WO | WO-2017053886 A2 | 3/2017 |
| WO | WO-2018183654 A1 | 10/2018 |
| WO | WO-2019126357 A1 | 6/2019 |

OTHER PUBLICATIONS

Audia et al. Pictet-Spengler-like Synthesis of Tetrahydro-P-carbolines under Hydrolytic Conditions. Direct Use of Azalactones as Phenylacetaldehyde Equivalents, J. Org. Chem. 61(22):7937-7939 (1996).
Belkina et al. BET protein function is required for inflammation: Brd2 genetic disruption and BET inhibitor JQ1 impair mouse macrophage inflammatory responses. J Immunol. 190(7):3670-8 (2013).
Cahn et al. IUPAC 1974 Recommendations for Section E, Fundamental Stereochemistry, Pure Appl. Chem. 45:13-30 (1976).
Carter et al. A Primitive Growth Factor, NME7AB , Is Sufficient to Induce Stable Naïve State Human Pluripotency; Reprogramming in This Novel Growth Factor Confers Superior Differentiation. Stem Cells 34(4):847-59 (2016).
Chemical Abstracts STN Registry Database, record for RN 1212062-80-0, Entered into STN on Mar. 21, 2010. (2010).
Chemical Abstracts STN Registry Database, record for RN 1212206-18-2, Entered into STN on Mar. 21, 2010. (2010).
Chemical Abstracts STN Registry Database, record for RN 1212244-17-1, Entered into STN on Mar. 21, 2010. (2010).
Chemical Abstracts STN Registry Database, record for RN 1212257-84-5, Entered into STN on Mar. 21, 2010. (2010).
Chemical Abstracts STN Registry Database, record for RN 1212425-09-6, Entered into STN on Mar. 21, 2010. (2010).
Chemical Abstracts STN Registry Database, record for RN 1214627-71-0, Entered into STN on Mar. 25, 2010. (2010).
Filippakopoulos et al. Selective inhibition of BET bromodomains. Nature 468:1067-1073 (2010).

(Continued)

*Primary Examiner* — Daniel R Carcanague
(74) *Attorney, Agent, or Firm* — WILSON SONSINI GOODRICH & ROSATI

(57) ABSTRACT

The present application discloses a method for identifying an agent for the treatment or prevention of cancer or metastatic cancer comprising the steps of contacting stem cell with a potential agent, and identifying an agent that induces differentiation, or inhibits stem cell pluripotency or growth of the stem cell, wherein such agent is determined to be an anti-cancer agent.

18 Claims, 144 Drawing Sheets

Specification includes a Sequence Listing.

(56) References Cited

OTHER PUBLICATIONS

Gafni et al. Derivation of novel human ground state naive pluripotent stem cells. Nature 504:282-286 (2013).

Hanna et al. Human embryonic stem cells with biological and epigenetic characteristics similar to those of mouse ESCs. PNAS USA 107(20):9222-9227 (2010).

Herbst et al. α-Acetaminocinnamic acid. Organic Syntheses 19:1 (1939).

Hikita et al. MUC1 Mediates the Growth of Human Pluripotent Stem Cells. PLoS One 3(10):1-13 (2008).

Horm et al. MUC1 drives c-Met-dependent migration and scattering. Mol Cancer Res. 10(12):1544-54 (2012).

Mani et al. The Epithelial-Mesenchymal Transition Generates Cells with Properties of Stem Cells. Cell 133:704-715 (2008).

Meng et al. BET Inhibitor JQ1 Blocks Inflammation and Bone Destruction. J Dent Res. 93(7):657-662 (2014).

MENG et sl. Dexamethasone disrupts cytoskeleton organization and migration of T47D Human breast cancer cells by modulating the AKT/mTOR/RhoA pathway. Asian Pac J Cancer Prev 15(23):10245-50 (2014).

Nencini et al. Structure-activity relationship and properties optimization of a series of Quinazoline-2,4-diones as inhibitors of the canonical Wnt pathway. European Journal of Medicinal Chemistry 95:526-45 (2015).

Nichols et al. Naive and primed pluripotent states. Cell Stem Cell 4(6):487 (2009).

PCT/US2018/025107 International Search Report and Written Opinion dated Aug. 1, 2018.

Sachdeva. Drug targeting systems for cancer chemotherapy. Expert Opin Investig Drugs 7(11):1849-64 (Nov. 1998).

Silva et al., Promotion of reprogramming to ground state pluripotency by signal inhibition. PLoS Biol. 6(10):e253 (2008).

Smagghe et al. MUCI ligand, NM23-H1, is a novel growth factor that maintains human stem cells in a more naive state. PLoS One 8(3):E58601 (2013).

Tang et al. Assessment of Brd4 inhibition in idiopathic pulmonary fibrosis lung fibroblasts and in vivo models of lung fibrosis. Am J Pathol183(2):470-9 (2013).

Theunissen et al., Systematic identification of culture conditions for induction and maintenance of naive human pluripotency. Cell Stem Cell. 15(4):524-526 (2014).

U.S. Appl. No. 16/498,640 Office Action dated Apr. 29, 2021.

Ware et al. Derivation of naive human embryonic stem cells. PNAS USA 111:4484-4489 (2014).

Xu et al. MicroRNA-145 Regulates OCT4, SOX2, and KLF4 and Represses Pluripotency in Human Embryonic Stem Cells. Cell. 137(4):647-658 (2009).

Zheng et al. Synthesis and biological evaluation of novel tetrahydro-β-carboline derivatives as antitumor growth and metastasis agents through inhibiting the transforming growth factor-β signaling pathway. J Med Chem. 57(3):600-12 (2014).

* cited by examiner

Summary of results in stem cell drug screen: drug candidates added to naïve stem cells versus primed stem cells photographed at 96h; small molecules dosed once at 6µM; "-" indicates no inhibition of pluripotency or proliferation at 6uM, "+" indicates inhibition of pluripotency or proliferation; ND = no data

| Compound | Primed Stem Cells not in MEFs | Primed Stem Cells on MEFs growth factor depleted experiment | Naïve Stem Cells NME7-AB MNC depletion/toxicity effects | Naïve Stem Cells Cell growth blocking |
|---|---|---|---|---|
| E6 Fab 40 ug/mL | - | - | + | ++ |
| MUC1* ect peptide 10 uM | - | - | + | ++ |
| PBS control | - | ND | - | ND |
| DMSO 0.2% control | - | ND | - | ND |
| Anti-NME7 Ab #56 | ND | - | ND | - |
| Anti-NME7 Ab #61 | ND | - | ND | ++ |
| MN0642 | + | + | ++ | ++ |
| MN1130 | - | + | +++ | ++++ |
| MN0572 | - | - | - | + |
| MN0947 | - | - | - | - |
| MN0129 | - | - | - | - |
| MN0676 | - | - | - | - |
| MN0402 | - | - | - | - |
| MN0992 | - | - | - | - |

Figure 2

Primed State Stem Cells: Human ES cells grown in bFGF over MEFs 96h; bFGF added to media during test period, 10X magnification All compounds present at 6 µM in 0.2% DMSO

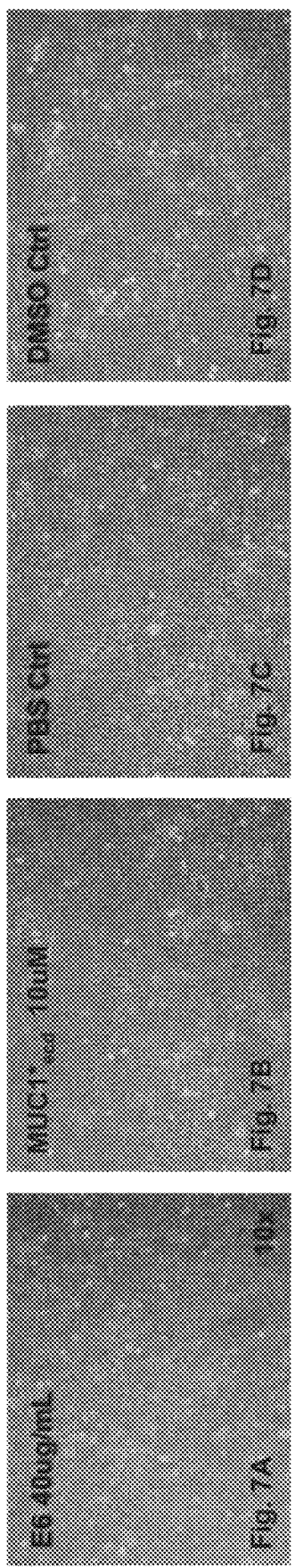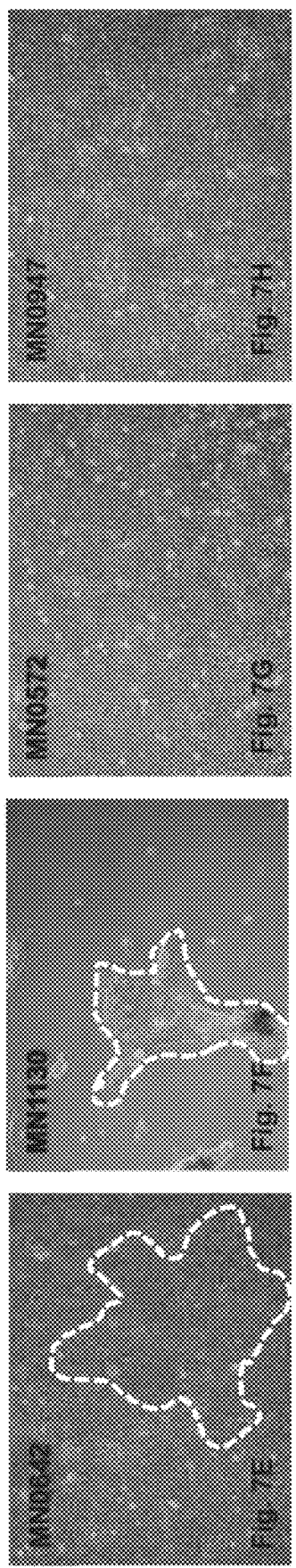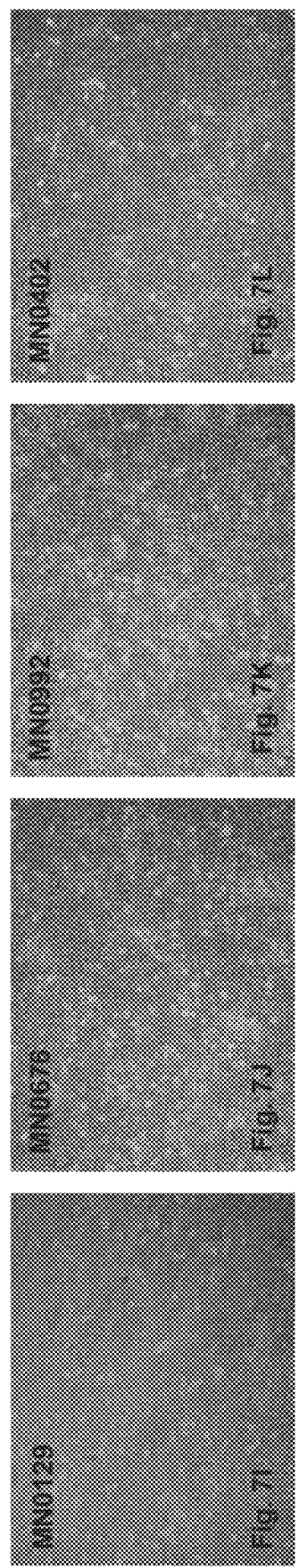
Figure 7A-7L

Primed State Stem Cells: Human iPS cells grown in bFGF over MEFs 96h
No bFGF added to media during test period, 4X magnification Fig. 11B +BRD4 siRNA Fig. 11E (+)JQ1 500nM Fig. 11C +JMJD6 siRNA Fig. 11F (+)JQ1 1µM Fig. 11A +NTC siRNA Fig. 11D (−)JQ1 1µM

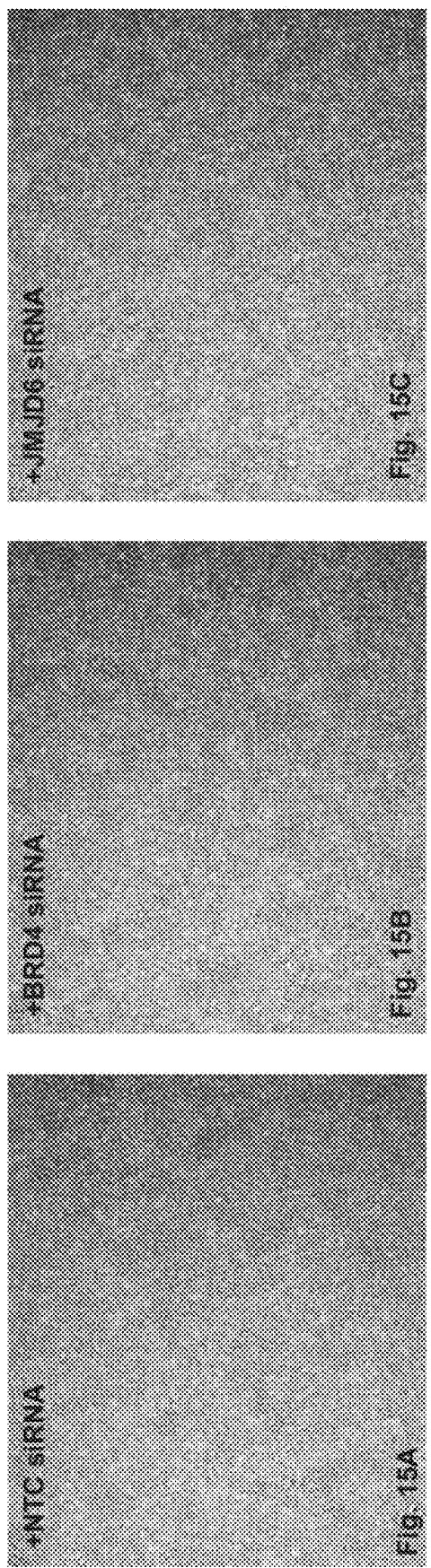
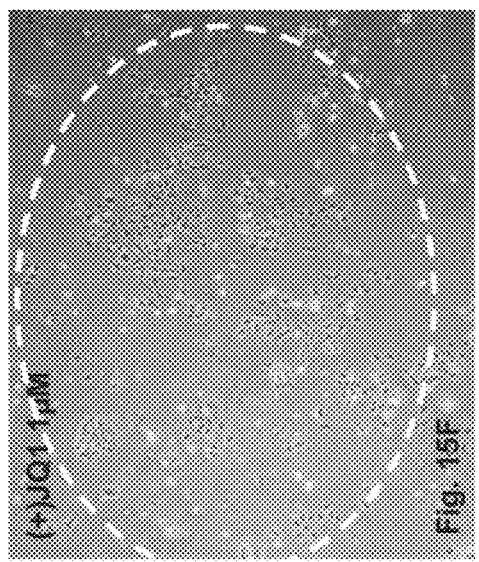
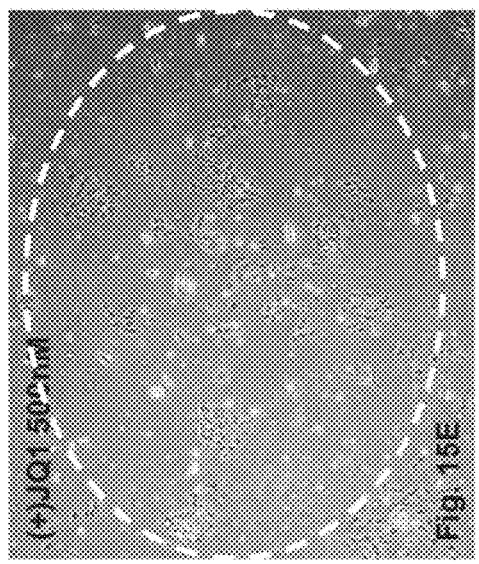
Figure 15A-15F

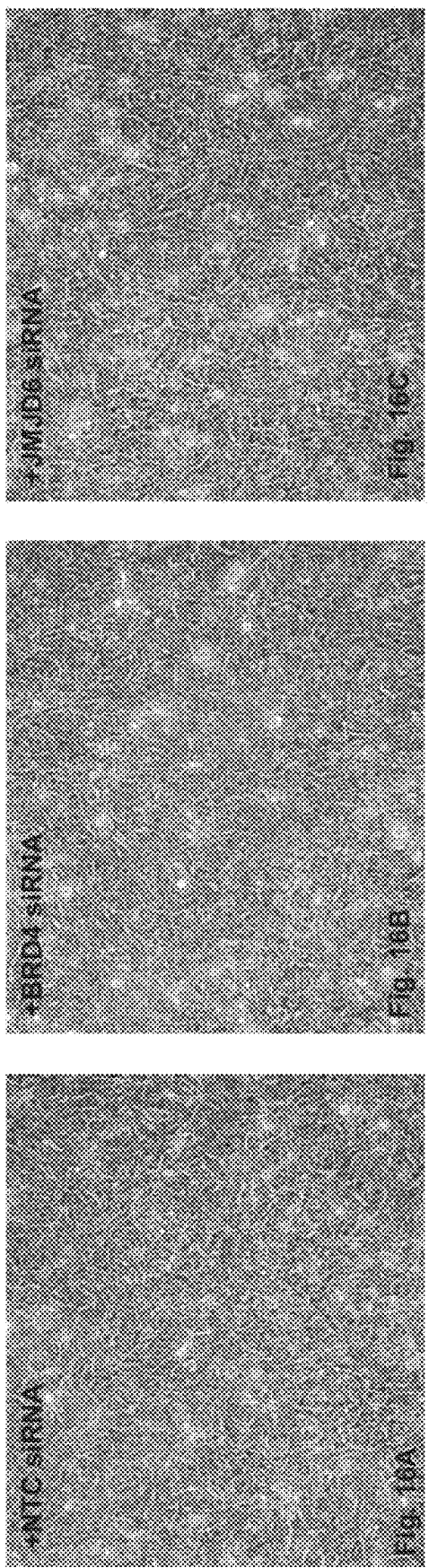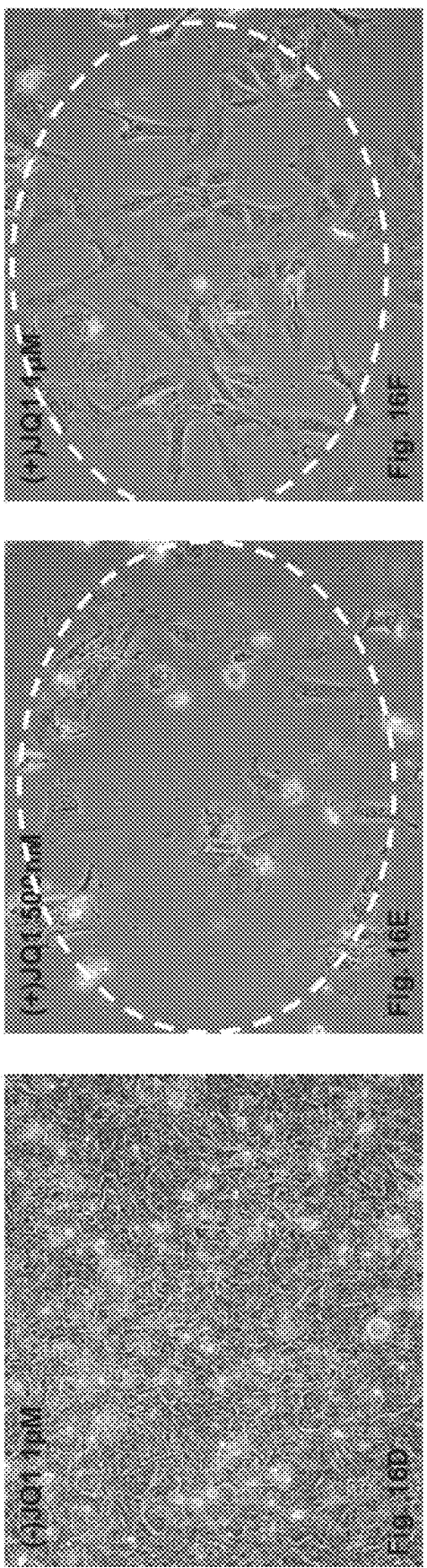
Figure 16A-16F

Figure 17
Reference Compounds:
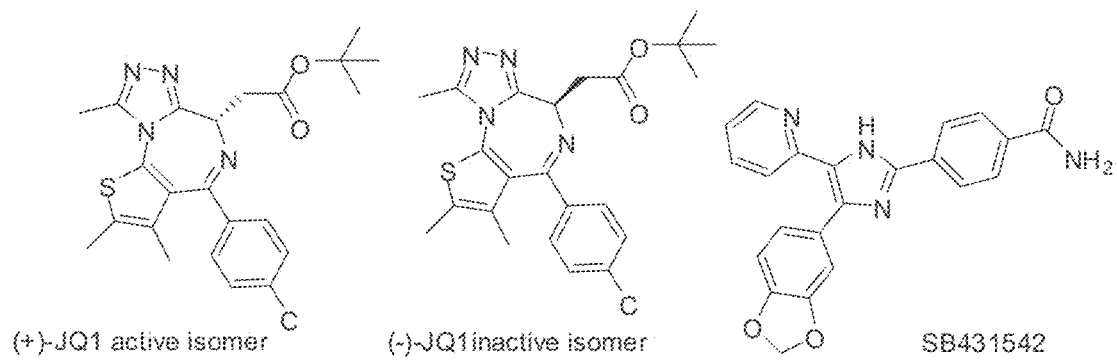
(+)-JQ1 active isomer    (-)-JQ1 inactive isomer    SB431542
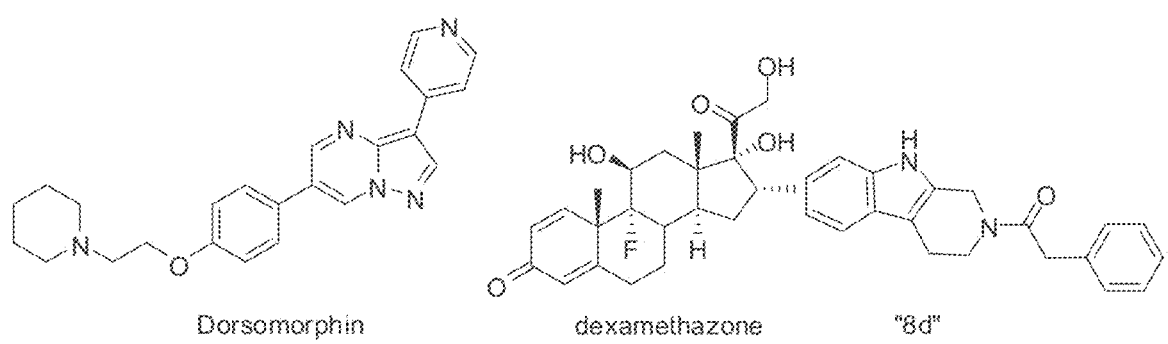
Dorsomorphin    dexamethazone    "8d"
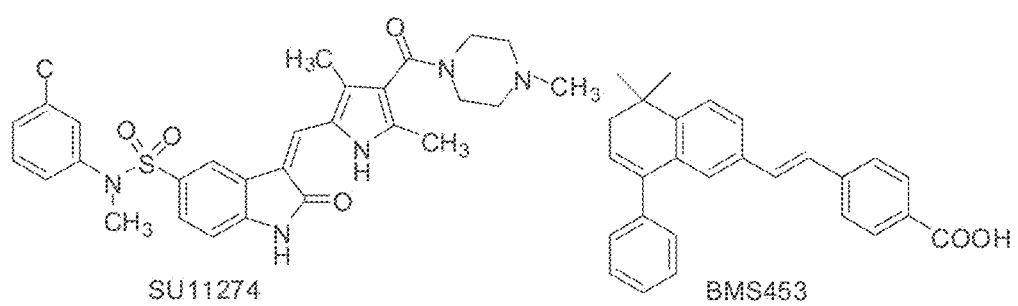
SU11274    BMS453

Fig. 18A

| Minerva Compound Number | | Inhibition of Cancer Cell Migration @ 6uM | Cancer Cell Migration IC50 (uM) | Proliferation IC50 | Inhibit Cancer Cell Proliferation @ 6uM | Naive State Stem Cells Score @ 6uM | Primed State Stem Cells Score @ 6uM | Fibroblast Progenitor Cells Score @ 6 uM |
|---|---|---|---|---|---|---|---|---|
| | SU11274 | 69% | 2.62 | | 1 | 1 | 0 | 2 |
| MN1173 | (+)-JQ1 | 0% | | | 4 | 4 | 2 | 2 |
| MN1174 | (-)-JQ1 | 10% | | | 0 | 1 | 1 | 0 |
| MN1175 | SB431542 | 3% | | | 0 | 2 | 1 | - |
| MN1176 | SU5402 | 0% | | | 1 | 4 | 2 | - |
| MN1177 | dorsomorphin | 31% | | | 1 | 1 | 0 | - |
| MN1204 | "8d" | 50% | 14.86 | | - | 0 | 0 | - |
| MN1205 | dexamethazone | 34% | | | - | 1 | 1 | - |
| MN1215 | BMS453 | 7% | | | - | 0 | 0 | - |
| MN0642 | | 11% | | | 3 | 3 | 0 | - |
| MN1130 | | 10% | 13.42 | | 1 | 4 | 1 | 0 |
| MN1292 | | 50% | 5.84 | 8.75 | 3 | 4 | 0 | 0 |
| MN1293 | | 59% | 0.88 | 15.7 | 1 | 3 | 0 | 0 |
| MN1294 | | 31% | - | | 1 | 3 | 2 | 0 |
| MN1305 | | 51% | 5.98 | | 1 | 0 | 1 | 0 |
| MN1306 | | 69% | 3.09 | | 2 | 0 | 0 | 0 |
| MN1307 | | 72% | 2.54 | | 3 | 0 | 0 | 0 |
| MN1308 | | 17% | 9.7 | | 1 | 0 | 0 | 0 |
| MN1309 | | 6% | - | | 1 | 0 | 0 | 0 |
| MN1310 | | 24% | 7.5 | | 3 | 0 | 0 | 0 |
| MN1311 | | 24% | 6.2 | | 4 | 0 | 0 | 0 |
| MN1312 | | 8% | - | | 0 | 0 | 0 | 0 |
| MN1317 | | 43% | 17.7 | | 2 | 2 | 0 | 1 |
| MN1318 | | 52% | 2.8 | | 0 | 3 | 1 | 1 |
| MN1319 | | 66% | 2.8 | | 1 | 3 | 1 | 1 |
| MN1320 | | 49% | 6 | | 2 | 0 | 0 | 0 |
| MN1321 | | 69% | 0.663 | 1.59 | 2 | 4 | 2 | 0 |
| MN1322 | | 51% | 27 | | 1 | 3 | 1 | 0 |
| MN1329 | | 6% | 12 | | 0 | 0 | 2 | 0 |
| MN1330 | | 55% | 0.74 | | 2 | 4 | 1 | 0 |
| MN1331 | | 59% | 1.2 | | 1 | 4 | 3 | 0 |
| MN1332 | | 73% | 0.256 | | 1 | 4 | 0 | 0 |
| MN1333 | | 76% | 0.99 | | 1 | 4 | 1 | 0 |

Fig. 18B

| Minerva Compound Number | | Inhibition of Cancer Cell Migration @ 6uM | Cancer Cell Migration IC50 (uM) | Prolifer-ation IC50 | Inhibit Cancer Cell Prolifer-ation @ 6uM | Naive State Stem Cells Score @ 6uM | Primed State Stem Cells Score @ 6uM | Fibroblast Progenitor Cells Score @ 6 uM |
|---|---|---|---|---|---|---|---|---|
| MN1334 | | 69% | 0.4 | | 2 | 3 | 0 | 0 |
| MN1335 | | 72% | 0.246 | | 1 | 4 | 2 | 0 |
| MN1336 | | 69% | 1.089 | | 1 | 4 | 3 | 1 |
| MN1337 | | 72% | 0.529 | | 1 | 4 | 2 | 0 |
| MN1338 | | 71% | 1.031 | | 1 | 4 | 3 | 0 |
| MN1339 | | 66% | 0.22 | | 1 | 4 | 0 | 0 |
| MN1340 | | 66% | 0.15 | | 2 | 4 | 0 | 0 |
| MN1341 | | 68% | 0.113 | 2.77 | 2 | 3 | 3 | 0 |
| MN1351 | | 7% | 12 | | 0 | 0 | 0 | 0 |
| MN1352 | | 65% | 0.13 | 3.44 | 4 | 4 | 0 | 0 |
| MN1353 | | 60% | 0.341 | | 4 | 2 | 1 | 0 |
| MN1354 | | 66% | 1.16 | | 2 | 4 | 0 | 1 |
| MN1355 | | 66% | 0.033 | 4.29 | 4 | 4 | 0 | 0 |
| MN1356 | | 58% | 0.85 | | 3 | 4 | 2 | 0 |
| MN1357 | | 62% | 0.243 | | 3 | 4 | 3 | 0 |
| MN1358 | | 64% | 0.399 | | 2 | 4 | 0 | 0 |
| MN1359 | | 61% | 1.24 | | 2 | 4 | 0 | 0 |
| MN1360 | | 55% | 1.038 | | 3 | 3 | 1 | 0 |
| MN1362 | | 69% | 0.014 | | 2 | 3 | 0 | 0 |
| MN1363 | | 66% | 1.28 | | 2-3 | 2 | 0 | 0 |
| MN1369 | | 70% | 0.853 | | 2-3 | 3 | 0 | 0 |
| MN1370 | | 0% | 12 | | 0 | 0 | 0 | 0 |
| MN1371 | | 0% | 12 | | 0 | 2 | 0 | 0 |
| MN1372 | | 0% | 12 | | 0 | 1 | 0 | 0 |
| MN1377 | | 80% | 0.501 | 2.73 | 3 | 3 | 1 | 0 |
| MN1378 | | 82% | 0.126 | 2.5 | 4 | 1 | 0 | 0 |
| MN1379 | | 80% | 0.176 | 3.86 | 4 | 3 | 2 | 1 |
| MN1380 | | 82% | 0.32 | 3.74 | 4 | 3 | 0 | 0 |
| MN1381 | | 75% | 0.142 | 3.06 | 4 | 1 | 0 | 0 |
| MN1382 | | 89% | 0.154 | 3.6 | 4 | 2 | 0 | 0 |
| MN1383 | | 68% | 1.27 | 3.61 | 4 | 3 | 0 | 0 |
| MN1384 | | 86% | 0.211 | 2.99 | 4 | 4 | 0 | 0 |
| MN1385 | | 70% | 0.214 | 2.76 | 4 | 3 | 0 | 0 |

Fig. 18C

| Minerva Compound Number | | Inhibition of Cancer Cell Migration @ 6uM | Cancer Cell Migration IC50 (uM) | Proliferation IC50 | Inhibit Cancer Cell Proliferation @ 6uM | Naive State Stem Cells Score @ 6uM | Primed State Stem Cells Score @ 6uM | Fibroblast Progenitor Cells Score @ 6 uM |
|---|---|---|---|---|---|---|---|---|
| MN1386 | | 86% | 0.287 | 3.79 | 4 | 3 | 0 | 0 |
| MN1387 | | 83% | 1.083 | 8.63 | 3 | 2 | 0 | 0 |
| MN1388 | | 81% | 1.004 | 12 | 2 | 2 | 0 | 0 |
| MN1389 | | 92% | 0.096 | 6.75 | 3 | 2 | 0 | 0 |
| MN1390 | | 74% | 1.432 | 7.44 | 3 | 3 | 0 | 0 |
| MN1391 | | 88% | 0.159 | 12 | 2 | 1 | 0 | 0 |
| MN1392 | | 88% | 0.057 | 5.59 | 2 | 1 | 0 | 0 |
| MN1393 | | 82% | 1.885 | 12 | 2 | 2 | 0 | 0 |
| MN1394 | | 85% | 0.057 | 6.86 | 2 | 4 | 0 | 0 |
| MN1395 | | 86% | 0.679 | 7.13 | 2 | 0 | 0 | 0 |
| MN1396 | | 43% | - | 14.4 | 1 | 4 | 0 | 0 |
| MN1397 | | 45% | 10.4 | 11.2 | 1 | 4 | 4 | 0 |
| MN1398 | | 42% | 10.3 | 13.1 | 1 | 4 | 4 | 0 |
| MN1399 | | 50% | - | 7.3 | 2 | 1 | 0 | 0 |
| MN1400 | | 43% | - | 12 | 1 | 0 | 0 | 0 |
| MN1401 | | 75% | 0.556 | 12 | 0 | 0 | 0 | 0 |
| MN1402 | | 71% | 1.601 | 6.81 | 3 | 2 | 0 | 0 |
| MN1403 | | 82% | 0.027 | 3.34 | 3 | 4 | 0 | 0 |
| MN1409 | | 77% | 0.014 | 5.17 | 3 | 3 | 0 | 0 |
| MN1410 | | 78% | 0.261 | 2.37 | 3 | 2 | 0 | 0 |
| MN1411 | | 75% | 0.799 | 12 | 1 | 0 | 0 | 0 |
| MN1412 | | 81% | 1 | 4.73 | 2 | 2 | 2 | 0 |
| MN1413 | | 83% | 0.01 | 8 | 2 | 4 | 0 | 0 |
| MN1414 | | 81% | 0.018 | 12.2 | 2 | 4 | 0 | 0 |
| MN1415 | | 75% | 5.2 | 21.3 | 1 | 0 | 0 | 0 |
| MN1419 | | 82% | 0.164 | | 0 | 2 | 0 | 0 |
| MN1420 | | 84% | 0.029 | | 3 | 4 | 0 | 0 |
| MN1422 | | 84% | 0.100 | | 2 | 4 | 0 | 0 |
| MN1423 | | 84% | 0.012 | | 2 | 4 | 0 | 0 |
| MN1424 | | 79% | 0.046 | | 1 | 4 | 0 | 0 |
| MN1425 | | 80% | 1.28 | | N/A | 4 | 0 | 0 |
| MN1426 | | 80% | 0.889 | | N/A | 4 | 0 | 0 |
| MN1427 | | 80% | 0.076 | 0.272 | 2 | 3 | 0 | 0 |

Fig. 18D

| Minerva Compound Number | | Inhibition of Cancer Cell Migration @ 6uM | Cancer Cell Migration IC50 (uM) | Prolifer-ation IC50 | Inhibit Cancer Cell Prolifer-ation @ 6uM | Naïve State Stem Cells Score @ 6uM | Primed State Stem Cells Score @ 6uM | Fibroblast Progenitor Cells Score @ 6 uM |
|---|---|---|---|---|---|---|---|---|
| MN1428 | | 79% | 0.007 | 18 | 0 | 4 | 0 | 0 |
| MN1429 | | 81% | 0.873 | 24 | 2 | 0 | 0 | 0 |
| MN1430 | | 77% | 0.244 | 2.7 | 2 | 0 | 0 | 0 |
| MN1431 | | 79% | 0.098 | 2.8 | 2 | 3 | 0 | 0 |
| MN1432 | | 81% | 0.485 | 2.7 | 2 | 3 | 0 | 0 |
| MN1433 | | 82% | 1.037 | 0.5 | 2 | 4 | 0 | 0 |
| MN1434 | | 84% | 0.014 | 24 | 2 | 4 | 0 | 0 |
| MN1435 | | 45% | -- | | N/A | 1 | 0 | 0 |
| MN1436 | | 81% | 2.55 | | N/A | 3 | 0 | 0 |
| MN1437 | | 78% | 0.113 | | N/A | 1 | 0 | 0 |
| MN1438 | | 76% | 0.091 | | N/A | 4 | 0 | 0 |
| MN1439 | | 40% | 23.47 | | N/A | 0 | 0 | 0 |
| MN1440 | | 55% | 6.78 | | N/A | 4 | 0 | 0 |
| MN1441 | | 90% | 0.028 | | N/A | 1 | 0 | 0 |
| MN1442 | | 80% | 0.018 | | N/A | 1 | 0 | 0 |
| MN1443 | | 80% | 0.167 | | N/A | 4 | 0 | 0 |
| MN1444 | | 77% | 0.185 | | N/A | 1 | 0 | 0 |
| MN1445 | | 74% | 0.348 | | N/A | 1 | 0 | 0 |
| MN1447 | | 77% | 0.015 | | N/A | 3 | 0 | 0 |
| MN1448 | | 78% | 0.027 | | N/A | 1 | 0 | 0 |
| MN1449 | | 76% | 0.030 | | N/A | 1 | 0 | 0 |
| MN1450 | | 80% | 0.125 | | N/A | 0 | 0 | 0 |
| MN1451 | | 85% | 0.013 | | N/A | 2 | 0 | 0 |
| MN1452 | | 89% | 0.037 | | N/A | 3 | 0 | 0 |
| MN1453 | | 91% | 0.018 | | N/A | 2 | 0 | 0 |
| MN1454 | | 91% | 0.043 | | N/A | 1 | 0 | 0 |
| MN1455 | | 77% | 0.003 | | N/A | 3 | 2 | 0 |
| MN1456 | | 90% | 0.105 | | N/A | 2 | 0 | 0 |
| MN1457 | | 86% | 0.409 | | N/A | 0 | 0 | 0 |
| MN1458 | | 65% | 5.1 | | N/A | 0 | 0 | 0 |
| MN1459 | | 55% | 2.2 | | N/A | 0 | 0 | 0 |
| MN1460 | | 65% | 2.01 | | N/A | 0 | 0 | 0 |
| MN1461 | | 81% | 136 | | N/A | 3 | 2 | 0 |

Fig. 18E

| Minerva Compound Number | | Inhibition of Cancer Cell Migration @ 6uM | Cancer Cell Migration IC50 (uM) | Proliferation IC50 | Inhibit Cancer Cell Proliferation @ 6uM | Naive State Stem Cells Score @ 6uM | Primed State Stem Cells Score @ 6uM | Fibroblast Progenitor Cells Score @ 6 uM |
|---|---|---|---|---|---|---|---|---|
| MN1462 | | 85% | 0.505 | | N/A | 3 | 2 | 0 |
| MN1463 | | 88% | 0.073 | | N/A | 1 | 1 | 0 |
| MN1464 | | 88% | 0.671 | | N/A | 4 | 2 | 0 |
| MN1465 | | 89% | 0.846 | | N/A | 1 | 1 | 0 |
| MN1466 | | 91% | 4.472 | | N/A | 1 | 0 | 0 |
| MN1467 | | 80% | - | | N/A | 0 | 0 | 0 |
| MN1468 | | 69% | 0.734 | | N/A | 1 | 0 | 0 |
| MN1469 | | 80% | 1 | | N/A | 0 | 0 | 0 |
| MN1470 | | 69% | 0.019 | | N/A | 3 | 0 | 0 |
| MN1471 | | 73% | 0.007 | | N/A | 4 | 0 | 0 |
| MN1291 | | - | - | | 1 | 1 | 3 | 0 |

Naive Stem Cell

MN1292 6uMMN1293 6uMMN1294 6uM

Primed Stem Cell

MN1292 6uM             MN1293 6uM             MN1294 6uM

Naïve Stem Cell

MN1351 6uM  MN1291 6uM  MN1292 6uM

Primed Stem Cell

| MN1351 6uM | MN1291 6uM | MN1292 6uM |
|---|---|---|
|  |  |  |
|  |  |  |

Fibroblasts

| MN1351 6uM | MN1291 6uM | MN1292 6uM |
|---|---|---|
|  |  |  |
|  |  |  |

Stem Cell Controls:

Naïve Stem Cell

MN1355 6uM | MN1352 6uM | MN1353 6uM

Primed Stem Cell

MN1355 6uM          MN1352 6uM          MN1353 6uM

Fibroblasts

MN1355 6uM    MN1352 6uM    MN1353 6uM

Naïve Stem Cell

MN1358 6uM    MN1359 6uM    MN1360 6uM

Primed Stem Cell

MN1358 6uM        MN1359 6uM        MN1360 6uM

Fibroblasts

MN1358 6uM  MN1359 6uM  MN1360 6uM

Stem Cell Controls:

Fibroblasts
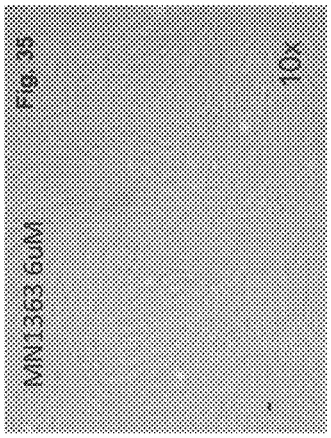
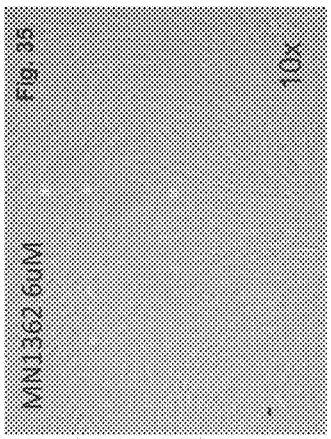
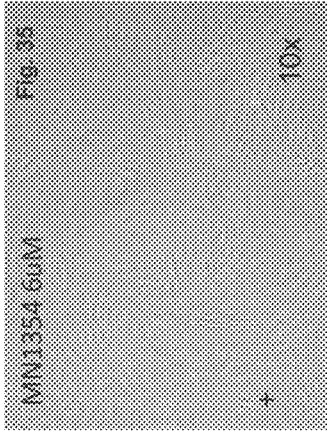
Figure 35M-35

Primed Stem Cell

MN1377 6uM

MN1378 6uM

MN1379 6uM

Naïve Stem Cell

Naïve Stem Cell

Figure NC11 Cancer Migration T47D @120hr

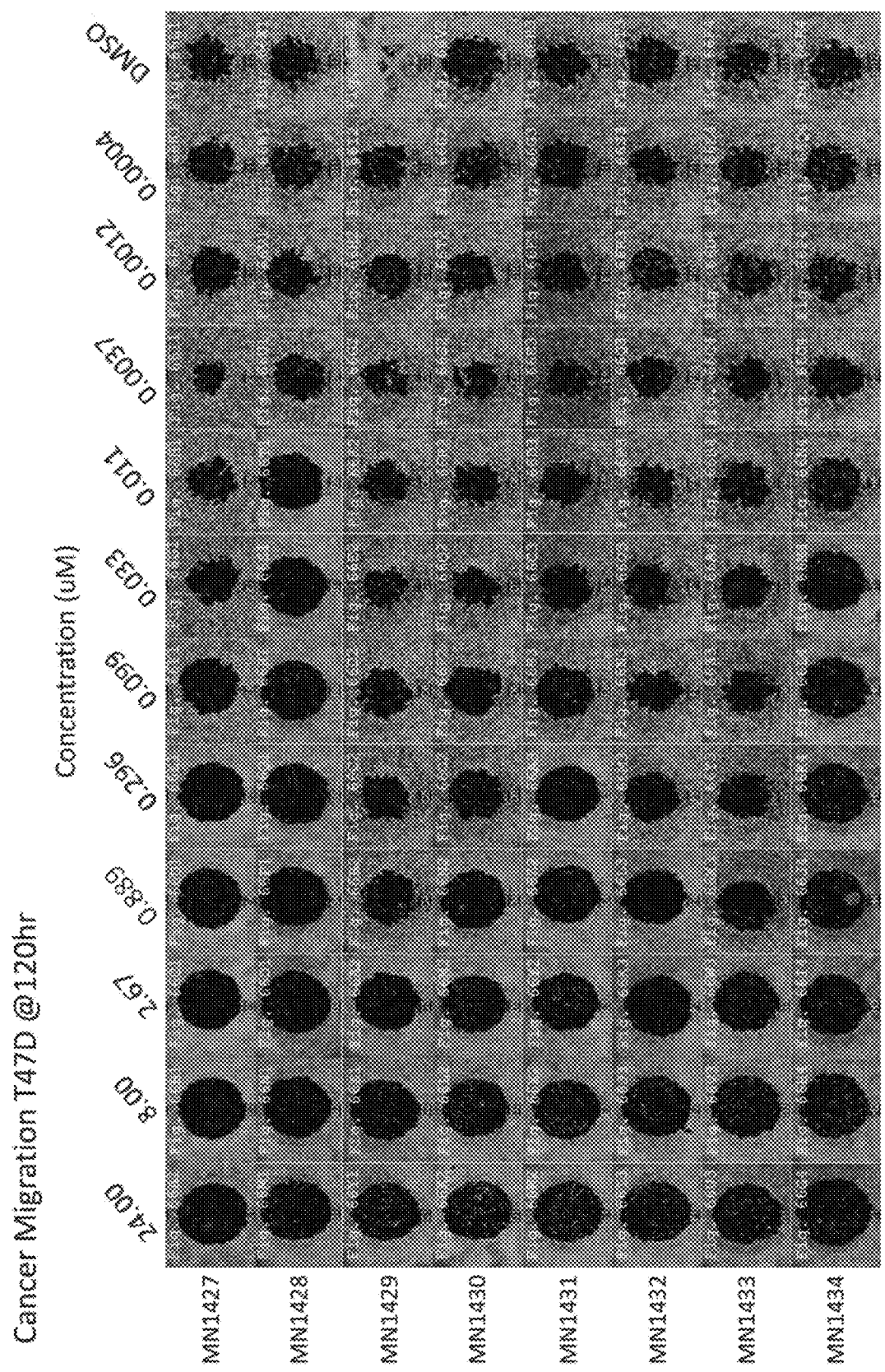
Figure 66A1-66R4

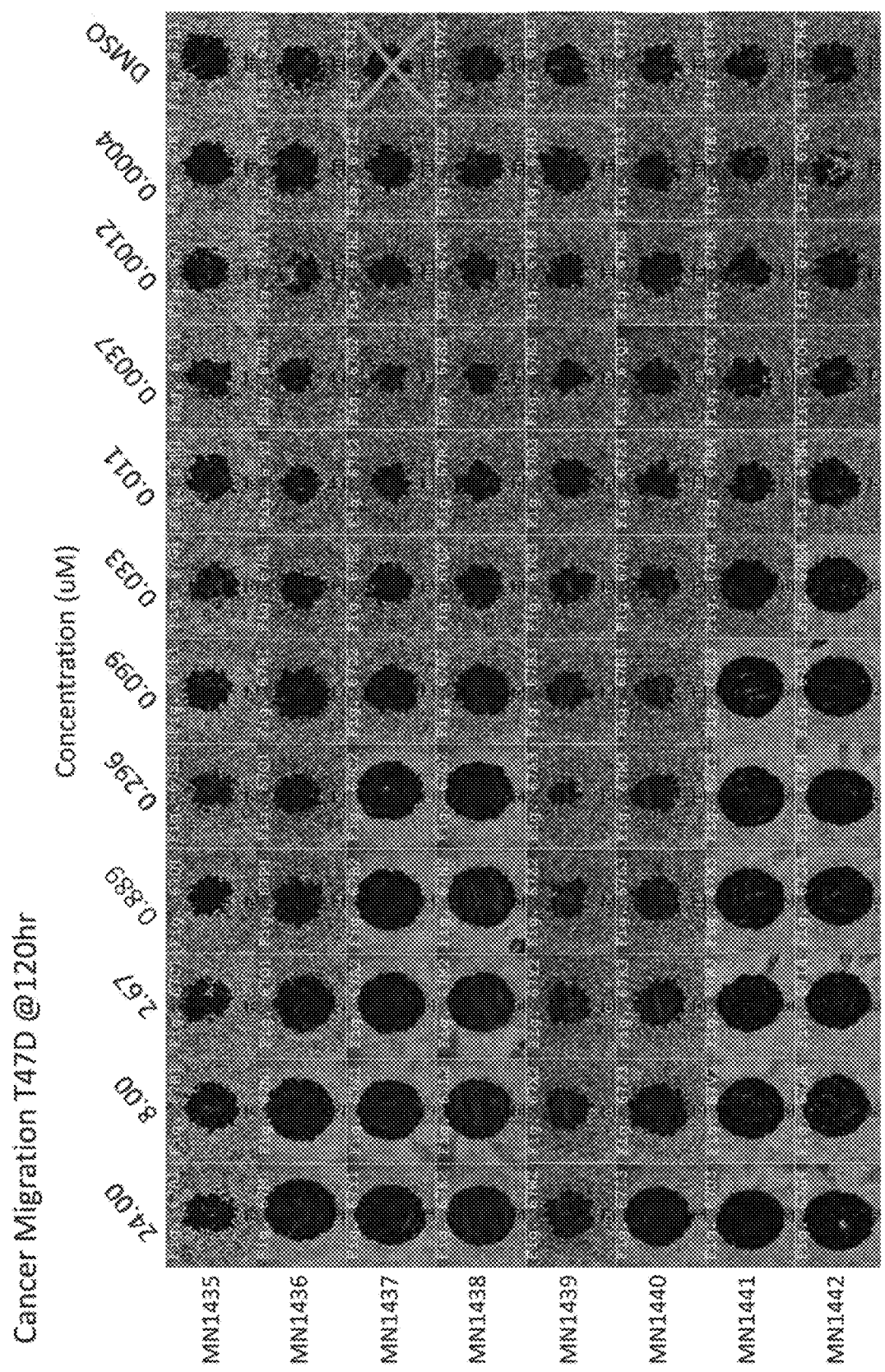
Figure 67A1-67R4

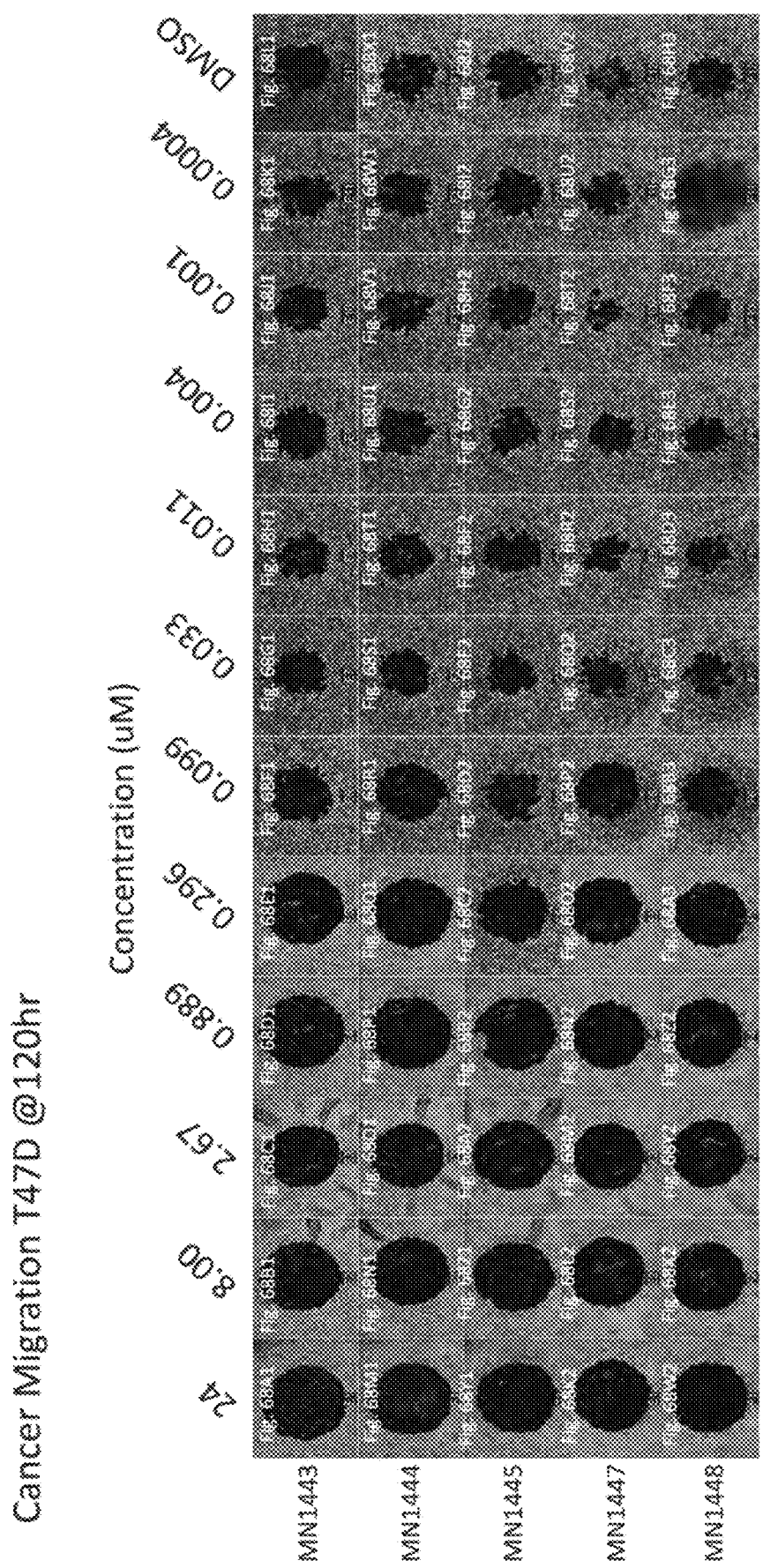
Figure 68A1-68H3

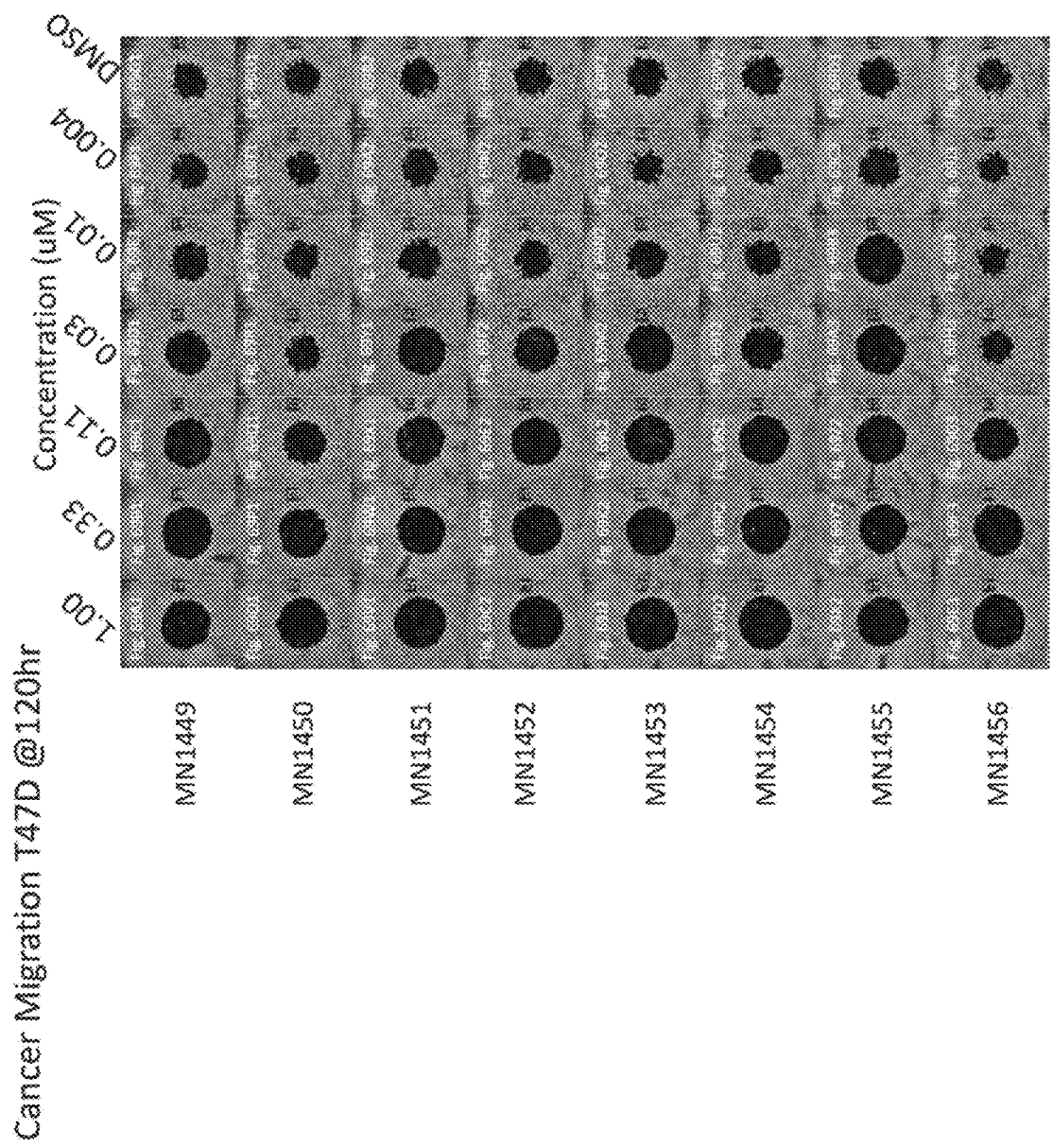
Figure 69A1-69K3

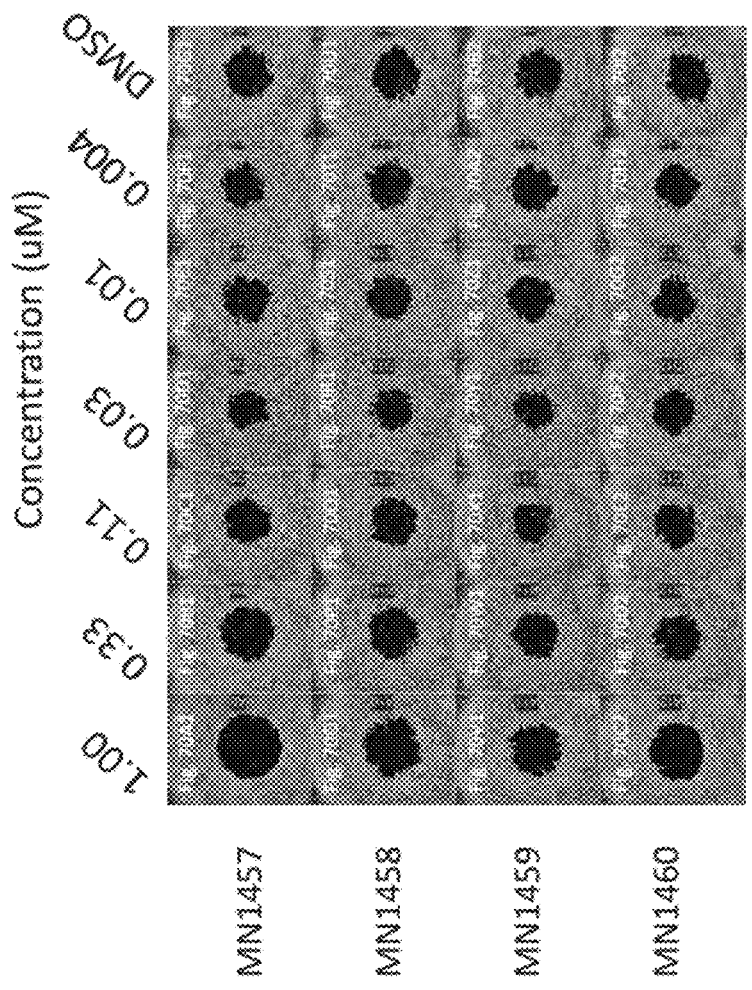
Figure 70A1-70I2

SEQUENCE LISTING

```
<160> NUMBER OF SEQ ID NOS: 12

<210> SEQ ID NO 1
<211> LENGTH: 1255
<212> TYPE: PRT
<213> ORGANISM: Artificial Sequence
<220> FEATURE:
<223> OTHER INFORMATION: full-length MUC1 Receptor (Mucin 1 precursor,
      Genbank Accession number: P15941)

<400> SEQUENCE: 1

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240
```

```
Ala Pro Asp Thr Arg Pro Ala Pro Gly Ser Thr Ala Pro Pro Ala His
                245                 250                 255
Gly Val Thr Ser Ala Pro Asp Thr Arg Pro Ala Pro Gly Ser Thr Ala
                260                 265                 270
Pro Pro Ala His Gly Val Thr Ser Ala Pro Asp Thr Arg Pro Ala Pro
                275                 280                 285
Gly Ser Thr Ala Pro Pro Ala His Gly Val Thr Ser Ala Pro Asp Thr
                290                 295                 300
Arg Pro Ala Pro Gly Ser Thr Ala Pro Pro Ala His Gly Val Thr Ser
305                 310                 315                 320
Ala Pro Asp Thr Arg Pro Ala Pro Gly Ser Thr Ala Pro Pro Ala His
                325                 330                 335
Gly Val Thr Ser Ala Pro Asp Thr Arg Pro Ala Pro Gly Ser Thr Ala
                340                 345                 350
Pro Pro Ala His Gly Val Thr Ser Ala Pro Asp Thr Arg Pro Ala Pro
                355                 360                 365
Gly Ser Thr Ala Pro Pro Ala His Gly Val Thr Ser Ala Pro Asp Thr
                370                 375                 380
Arg Pro Ala Pro Gly Ser Thr Ala Pro Pro Ala His Gly Val Thr Ser
385                 390                 395                 400
Ala Pro Asp Thr Arg Pro Ala Pro Gly Ser Thr Ala Pro Pro Ala His
                405                 410                 415
Gly Val Thr Ser Ala Pro Asp Thr Arg Pro Ala Pro Gly Ser Thr Ala
                420                 425                 430
Pro Pro Ala His Gly Val Thr Ser Ala Pro Asp Thr Arg Pro Ala Pro
                435                 440                 445
Gly Ser Thr Ala Pro Pro Ala His Gly Val Thr Ser Ala Pro Asp Thr
                450                 455                 460
Arg Pro Ala Pro Gly Ser Thr Ala Pro Pro Ala His Gly Val Thr Ser
465                 470                 475                 480
Ala Pro Asp Thr Arg Pro Ala Pro Gly Ser Thr Ala Pro Pro Ala His
                485                 490                 495
Gly Val Thr Ser Ala Pro Asp Thr Arg Pro Ala Pro Gly Ser Thr Ala
                500                 505                 510
Pro Pro Ala His Gly Val Thr Ser Ala Pro Asp Thr Arg Pro Ala Pro
                515                 520                 525
Gly Ser Thr Ala Pro Pro Ala His Gly Val Thr Ser Ala Pro Asp Thr
                530                 535                 540
Arg Pro Ala Pro Gly Ser Thr Ala Pro Pro Ala His Gly Val Thr Ser
545                 550                 555                 560
Ala Pro Asp Thr Arg Pro Ala Pro Gly Ser Thr Ala Pro Pro Ala His
                565                 570                 575
Gly Val Thr Ser Ala Pro Asp Thr Arg Pro Ala Pro Gly Ser Thr Ala
                580                 585                 590
Pro Pro Ala His Gly Val Thr Ser Ala Pro Asp Thr Arg Pro Ala Pro
                595                 600                 605
Gly Ser Thr Ala Pro Pro Ala His Gly Val Thr Ser Ala Pro Asp Thr
                610                 615                 620
Arg Pro Ala Pro Gly Ser Thr Ala Pro Pro Ala His Gly Val Thr Ser
625                 630                 635                 640
Ala Pro Asp Thr Arg Pro Ala Pro Gly Ser Thr Ala Pro Pro Ala His
                645                 650                 655
Gly Val Thr Ser Ala Pro Asp Thr Arg Pro Ala Pro Gly Ser Thr Ala
```

```
                    660             665             670
Pro Pro Ala His Gly Val Thr Ser Ala Pro Asp Thr Arg Pro Ala Pro
                675             680             685

Gly Ser Thr Ala Pro Ala His Gly Val Thr Ser Ala Pro Asp Thr
            690             695             700

Arg Pro Ala Pro Gly Ser Thr Ala Pro Pro Ala His Gly Val Thr Ser
705             710             715             720

Ala Pro Asp Thr Arg Pro Ala Pro Gly Ser Thr Ala Pro Pro Ala His
                725             730             735

Gly Val Thr Ser Ala Pro Asp Thr Arg Pro Ala Pro Gly Ser Thr Ala
            740             745             750

Pro Pro Ala His Gly Val Thr Ser Ala Pro Asp Thr Arg Pro Ala Pro
            755             760             765

Gly Ser Thr Ala Pro Pro Ala His Gly Val Thr Ser Ala Pro Asp Thr
            770             775             780

Arg Pro Ala Pro Gly Ser Thr Ala Pro Pro Ala His Gly Val Thr Ser
785             790             795             800

Ala Pro Asp Thr Arg Pro Ala Pro Gly Ser Thr Ala Pro Pro Ala His
                805             810             815

Gly Val Thr Ser Ala Pro Asp Thr Arg Pro Ala Pro Gly Ser Thr Ala
            820             825             830

Pro Pro Ala His Gly Val Thr Ser Ala Pro Asp Thr Arg Pro Ala Pro
            835             840             845

Gly Ser Thr Ala Pro Pro Ala His Gly Val Thr Ser Ala Pro Asp Thr
            850             855             860

Arg Pro Ala Pro Gly Ser Thr Ala Pro Pro Ala His Gly Val Thr Ser
865             870             875             880

Ala Pro Asp Thr Arg Pro Ala Pro Gly Ser Thr Ala Pro Pro Ala His
                885             890             895

Gly Val Thr Ser Ala Pro Asp Thr Arg Pro Ala Pro Gly Ser Thr Ala
            900             905             910

Pro Pro Ala His Gly Val Thr Ser Ala Pro Asp Thr Arg Pro Ala Pro
            915             920             925

Gly Ser Thr Ala Pro Pro Ala His Gly Val Thr Ser Ala Pro Asp Asn
            930             935             940

Arg Pro Ala Leu Gly Ser Thr Ala Pro Pro Val His Asn Val Thr Ser
945             950             955             960

Ala Ser Gly Ser Ala Ser Gly Ser Ala Ser Thr Leu Val His Asn Gly
                965             970             975

Thr Ser Ala Arg Ala Thr Thr Thr Pro Ala Ser Lys Ser Thr Pro Phe
            980             985             990

Ser Ile Pro Ser His His Ser Asp Thr Pro Thr Thr Leu Ala Ser His
            995            1000            1005

Ser Thr Lys Thr Asp Ala Ser Ser Thr His His Ser Ser Val Pro
            1010            1015            1020

Pro Leu Thr Ser Ser Asn His Ser Thr Ser Pro Gln Leu Ser Thr
            1025            1030            1035

Gly Val Ser Phe Phe Phe Leu Ser Phe His Ile Ser Asn Leu Gln
            1040            1045            1050

Phe Asn Ser Ser Leu Glu Asp Pro Ser Thr Asp Tyr Tyr Gln Glu
            1055            1060            1065

Leu Gln Arg Asp Ile Ser Glu Met Phe Leu Gln Ile Tyr Lys Gln
            1070            1075            1080
```

```
Gly Gly Phe Leu Gly Leu Ser Asn Ile Lys Phe Arg Pro Gly Ser
    1085            1090                1095

Val Val Val Gln Leu Thr Leu Ala Phe Arg Glu Gly Thr Ile Asn
    1100            1105                1110

Val His Asp Val Glu Thr Gln Phe Asn Gln Tyr Lys Thr Glu Ala
    1115            1120                1125

Ala Ser Arg Tyr Asn Leu Thr Ile Ser Asp Val Ser Val Ser Asp
    1130            1135                1140

Val Pro Phe Pro Phe Ser Ala Gln Ser Gly Ala Gly Val Pro Gly
    1145            1150                1155

Trp Gly Ile Ala Leu Leu Val Leu Val Cys Val Leu Val Ala Leu
    1160            1165                1170

Ala Ile Val Tyr Leu Ile Ala Leu Ala Val Cys Gln Cys Arg Arg
    1175            1180                1185

Lys Asn Tyr Gly Gln Leu Asp Ile Phe Pro Ala Arg Asp Thr Tyr
    1190            1195                1200

His Pro Met Ser Glu Tyr Pro Thr Tyr His Thr His Gly Arg Tyr
    1205            1210                1215

Val Pro Pro Ser Ser Thr Asp Arg Ser Pro Tyr Glu Lys Val Ser
    1220            1225                1230

Ala Gly Asn Gly Gly Ser Ser Leu Ser Tyr Thr Asn Pro Ala Val
    1235            1240                1245

Ala Ala Ala Ser Ala Asn Leu
    1250            1255

<210> SEQ ID NO 2
<211> LENGTH: 146
<212> TYPE: PRT
<213> ORGANISM: Artificial Sequence
<220> FEATURE:
<223> OTHER INFORMATION: a truncated MUC1 receptor isoform having
      nat-PSMGFR at its N-terminus and including the transmembrane and
      cytoplasmic sequences of a full-length MUC1 receptor

<400> SEQUENCE: 2

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala Gly Val Pro
        35                  40                  45

Gly Trp Gly Ile Ala Leu Leu Val Leu Val Cys Val Leu Val Ala Leu
    50                  55                  60

Ala Ile Val Tyr Leu Ile Ala Leu Ala Val Cys Gln Cys Arg Arg Lys
65                  70                  75                  80

Asn Tyr Gly Gln Leu Asp Ile Phe Pro Ala Arg Asp Thr Tyr His Pro
                85                  90                  95

Met Ser Glu Tyr Pro Thr Tyr His Thr His Gly Arg Tyr Val Pro Pro
            100                 105                 110

Ser Ser Thr Asp Arg Ser Pro Tyr Glu Lys Val Ser Ala Gly Asn Gly
        115                 120                 125

Gly Ser Ser Leu Ser Tyr Thr Asn Pro Ala Val Ala Ala Ala Ser Ala
    130                 135                 140

Asn Leu
145
```

<210> SEQ ID NO 3
<211> LENGTH: 45
<212> TYPE: PRT
<213> ORGANISM: Artificial Sequence
<220> FEATURE:
<223> OTHER INFORMATION: the extracellular domain of Native Primary
      Sequence of the MUC1 Growth Factor Receptor (nat-PSMGFR - an
      example of "PSMGFR")

<400> SEQUENCE: 3

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala
        35                  40                  45

<210> SEQ ID NO 4
<211> LENGTH: 35
<212> TYPE: PRT
<213> ORGANISM: Artificial Sequence
<220> FEATURE:
<223> OTHER INFORMATION: N-10 peptide of PSMGFR in which ten amino acids
      at the N-terminus has been removed

<400> SEQUENCE: 4

Gln Phe Asn Gln Tyr Lys Thr Glu Ala Ala Ser Arg Tyr Asn Leu Thr
1               5                   10                  15

Ile Ser Asp Val Ser Val Ser Asp Val Pro Phe Pro Phe Ser Ala Gln
            20                  25                  30

Ser Gly Ala
        35

<210> SEQ ID NO 5
<211> LENGTH: 283
<212> TYPE: PRT
<213> ORGANISM: Artificial Sequence
<220> FEATURE:
<223> OTHER INFORMATION: NME7 amino acid sequence (NME7: GENBANK
      ACCESSION AB209049)

<400> SEQUENCE: 5

Asp Pro Glu Thr Met Asn His Ser Glu Arg Phe Val Phe Ile Ala Glu
1               5                   10                  15

Trp Tyr Asp Pro Asn Ala Ser Leu Leu Arg Arg Tyr Glu Leu Leu Phe
            20                  25                  30

Tyr Pro Gly Asp Gly Ser Val Glu Met His Asp Val Lys Asn His Arg
        35                  40                  45

Thr Phe Leu Lys Arg Thr Lys Tyr Asp Asn Leu His Leu Glu Asp Leu
    50                  55                  60

Phe Ile Gly Asn Lys Val Asn Val Phe Ser Arg Gln Leu Val Leu Ile
65                  70                  75                  80

Asp Tyr Gly Asp Gln Tyr Thr Ala Arg Gln Leu Gly Ser Arg Lys Glu
                85                  90                  95

Lys Thr Leu Ala Leu Ile Lys Pro Asp Ala Ile Ser Lys Ala Gly Glu
            100                 105                 110

Ile Ile Glu Ile Ile Asn Lys Ala Gly Phe Thr Ile Thr Lys Leu Lys
        115                 120                 125

Met Met Met Leu Ser Arg Lys Glu Ala Leu Asp Phe His Val Asp His
    130                 135                 140

```
Gln Ser Arg Pro Phe Phe Asn Glu Leu Ile Gln Phe Ile Thr Thr Gly
145                 150                 155                 160

Pro Ile Ile Ala Met Glu Ile Leu Arg Asp Asp Ala Ile Cys Glu Trp
                165                 170                 175

Lys Arg Leu Leu Gly Pro Ala Asn Ser Gly Val Ala Arg Thr Asp Ala
            180                 185                 190

Ser Glu Ser Ile Arg Ala Leu Phe Gly Thr Asp Gly Ile Arg Asn Ala
        195                 200                 205

Ala His Gly Pro Asp Ser Phe Ala Ser Ala Ala Arg Glu Met Glu Leu
    210                 215                 220

Phe Phe Pro Ser Ser Gly Gly Cys Gly Pro Ala Asn Thr Ala Lys Phe
225                 230                 235                 240

Thr Asn Cys Thr Cys Cys Ile Val Lys Pro His Ala Val Ser Glu Gly
                245                 250                 255

Met Leu Asn Thr Leu Tyr Ser Val His Phe Val Asn Arg Arg Ala Met
            260                 265                 270

Phe Ile Phe Leu Met Tyr Phe Met Tyr Arg Lys
        275                 280

<210> SEQ ID NO 6
<211> LENGTH: 286
<212> TYPE: PRT
<213> ORGANISM: Artificial Sequence
<220> FEATURE:
<223> OTHER INFORMATION: human NME7-AB

<400> SEQUENCE: 6

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe Pro Ser Ser Gly Gly Cys Gly Pro Ala Asn Thr Ala
    130                 135                 140

Lys Phe Thr Asn Cys Thr Cys Cys Ile Val Lys Pro His Ala Val Ser
145                 150                 155                 160

Glu Gly Leu Leu Gly Lys Ile Leu Met Ala Ile Arg Asp Ala Gly Phe
                165                 170                 175

Glu Ile Ser Ala Met Gln Met Phe Asn Met Asp Arg Val Asn Val Glu
            180                 185                 190

Glu Phe Tyr Glu Val Tyr Lys Gly Val Val Thr Glu Tyr His Asp Met
        195                 200                 205

Val Thr Glu Met Tyr Ser Gly Pro Cys Val Ala Met Glu Ile Gln Gln
    210                 215                 220
```

```
Asn Asn Ala Thr Lys Thr Phe Arg Glu Phe Cys Gly Pro Ala Asp Pro
225                 230                 235                 240

Glu Ile Ala Arg His Leu Arg Pro Gly Thr Leu Arg Ala Ile Phe Gly
            245                 250                 255

Lys Thr Lys Ile Gln Asn Ala Val His Cys Thr Asp Leu Pro Glu Asp
                260                 265                 270

Gly Leu Leu Glu Val Gln Tyr Phe Phe Lys Ile Leu Asp Asn
        275                 280                 285
```

<210> SEQ ID NO 7
<211> LENGTH: 252
<212> TYPE: PRT
<213> ORGANISM: Artificial Sequence
<220> FEATURE:
<223> OTHER INFORMATION: human NME7-X1

<400> SEQUENCE: 7

```
Met Met Met Leu Ser Arg Lys Glu Ala Leu Asp Phe His Val Asp His
1               5                   10                  15

Gln Ser Arg Pro Phe Phe Asn Glu Leu Ile Gln Phe Ile Thr Thr Gly
            20                  25                  30

Pro Ile Ile Ala Met Glu Ile Leu Arg Asp Asp Ala Ile Cys Glu Trp
        35                  40                  45

Lys Arg Leu Leu Gly Pro Ala Asn Ser Gly Val Ala Arg Thr Asp Ala
    50                  55                  60

Ser Glu Ser Ile Arg Ala Leu Phe Gly Thr Asp Gly Ile Arg Asn Ala
65                  70                  75                  80

Ala His Gly Pro Asp Ser Phe Ala Ser Ala Ala Arg Glu Met Glu Leu
                85                  90                  95

Phe Phe Pro Ser Ser Gly Gly Cys Gly Pro Ala Asn Thr Ala Lys Phe
            100                 105                 110

Thr Asn Cys Thr Cys Cys Ile Val Lys Pro His Ala Val Ser Glu Gly
        115                 120                 125

Leu Leu Gly Lys Ile Leu Met Ala Ile Arg Asp Ala Gly Phe Glu Ile
    130                 135                 140

Ser Ala Met Gln Met Phe Asn Met Asp Arg Val Asn Val Glu Glu Phe
145                 150                 155                 160

Tyr Glu Val Tyr Lys Gly Val Val Thr Glu Tyr His Asp Met Val Thr
                165                 170                 175

Glu Met Tyr Ser Gly Pro Cys Val Ala Met Glu Ile Gln Gln Asn Asn
            180                 185                 190

Ala Thr Lys Thr Phe Arg Glu Phe Cys Gly Pro Ala Asp Pro Glu Ile
        195                 200                 205

Ala Arg His Leu Arg Pro Gly Thr Leu Arg Ala Ile Phe Gly Lys Thr
    210                 215                 220

Lys Ile Gln Asn Ala Val His Cys Thr Asp Leu Pro Glu Asp Gly Leu
225                 230                 235                 240

Leu Glu Val Gln Tyr Phe Phe Lys Ile Leu Asp Asn
                245                 250
```

<210> SEQ ID NO 8
<211> LENGTH: 132
<212> TYPE: PRT
<213> ORGANISM: Artificial Sequence
<220> FEATURE:
<223> OTHER INFORMATION: Human NME7-A1

<400> SEQUENCE: 8

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65              70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe
    130

<210> SEQ ID NO 9
<211> LENGTH: 155
<212> TYPE: PRT
<213> ORGANISM: Artificial Sequence
<220> FEATURE:
<223> OTHER INFORMATION: Human NME7-B3

<400> SEQUENCE: 9

Met Pro Ser Ser Gly Gly Cys Gly Pro Ala Asn Thr Ala Lys Phe Thr
1               5                   10                  15

Asn Cys Thr Cys Cys Ile Val Lys Pro His Ala Val Ser Glu Gly Leu
            20                  25                  30

Leu Gly Lys Ile Leu Met Ala Ile Arg Asp Ala Gly Phe Glu Ile Ser
        35                  40                  45

Ala Met Gln Met Phe Asn Met Asp Arg Val Asn Val Glu Glu Phe Tyr
    50                  55                  60

Glu Val Tyr Lys Gly Val Val Thr Glu Tyr His Asp Met Val Thr Glu
65              70                  75                  80

Met Tyr Ser Gly Pro Cys Val Ala Met Glu Ile Gln Gln Asn Asn Ala
                85                  90                  95

Thr Lys Thr Phe Arg Glu Phe Cys Gly Pro Ala Asp Pro Glu Ile Ala
            100                 105                 110

Arg His Leu Arg Pro Gly Thr Leu Arg Ala Ile Phe Gly Lys Thr Lys
        115                 120                 125

Ile Gln Asn Ala Val His Cys Thr Asp Leu Pro Glu Asp Gly Leu Leu
    130                 135                 140

Glu Val Gln Tyr Phe Phe Lys Ile Leu Asp Asn
145                 150                 155

```
<210> SEQ ID NO 10
<211> LENGTH: 29
<212> TYPE: PRT
<213> ORGANISM: Artificial Sequence
<220> FEATURE:
<223> OTHER INFORMATION: B3, which is NME7B peptide 3 (B domain)

<400> SEQUENCE: 10

Ala Ile Phe Gly Lys Thr Lys Ile Gln Asn Ala Val His Cys Thr Asp
1               5                   10                  15

Leu Pro Glu Asp Gly Leu Leu Glu Val Gln Tyr Phe Phe
            20                  25

<210> SEQ ID NO 11
<211> LENGTH: 45
<212> TYPE: PRT
<213> ORGANISM: Artificial Sequence
<220> FEATURE:
<223> OTHER INFORMATION: the extracellular domain of "SPY" functional
      variant of the native Primary Sequence of the MUC1 Growth Factor
      Receptor having enhanced stability (var-PSMGFR - An example of
      "PSMGFR")

<400> SEQUENCE: 11

Gly Thr Ile Asn Val His Asp Val Glu Thr Gln Phe Asn Gln Tyr Lys
1               5                   10                  15

Thr Glu Ala Ala Ser Pro Tyr Asn Leu Thr Ile Ser Asp Val Ser Val
            20                  25                  30

Ser Asp Val Pro Phe Pro Phe Ser Ala Gln Ser Gly Ala
            35                  40                  45

<210> SEQ ID NO 12
<211> LENGTH: 91
<212> TYPE: PRT
<213> ORGANISM: Artificial Sequence
<220> FEATURE:
<223> OTHER INFORMATION: DM10 domain of NME7

<400> SEQUENCE: 12

Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
            35                  40                  45

Arg Thr Lys Tyr Asp Asn Leu His Leu Glu Asp Leu Phe Ile Gly Asn
        50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys
            85                  90
```

AGENTS FOR DIFFERENTIATING STEM CELLS AND TREATING CANCER

CROSS-REFERENCE TO RELATED APPLICATIONS

This application is a continuation of U.S. patent application Ser. No. 16/498,640, filed Sep. 27, 2019, now abandoned, which is a U.S. National Phase of PCT Application No. PCT/US2018/025107, filed Mar. 29, 2018, which claims the benefit of U.S. Provisional Application No. 62/478,382, filed Mar. 29, 2017; and U.S. Provisional Application No. 62/607,880, filed Dec. 19, 2017, each of which is incorporated herein by reference in its entirety.

REFERENCE TO SEQUENCE LISTING SUBMITTED ELECTRONICALLY

The content of the electronically submitted sequence listing named: 56699-736_301SL.txt; Size: 25,960 bytes; and Date of Creation: Sep. 24, 2019 filed with the application is incorporated herein by reference in its entirety.

BACKGROUND

Field of the Invention

This invention generally relates to methods and compositions for the treatment of cancers that are characterized by the function of the compounds to differentiate stem cells.

Description of the Related Art

It was recently discovered that human stem cells, cultured under standard conditions, are not in a truly pluripotent state. Rather they have undergone some differentiation and have made certain cell fate decisions as evidenced by the accumulation of various methylation marks. When comparing human cultured stem cells to cells of mouse embryos it was determined that the human cultured stem cells look and behave more like mouse stem cells from the epiblast portion of the embryo, which has begun to differentiate, rather than the truly pluripotent stem cells of the inner cell mass. Researchers dubbed the true pluripotent stem cells of the inner cell mass 'naïve' and the more differentiated cells 'primed'. Further studies showed that both mouse and human primed state stem cells self-replicate by culture in bFGF, whereas mouse naïve stem cells self-replicate by culture in LIF. The growth factor that makes human stem cells grow in the naïve state was not known. Primed state stem cells are prone to spontaneous differentiation and must be manually dissected to remove the differentiating parts whereas naïve stem cells naturally resist spontaneous differentiation. In addition, primed stem cells cannot be passed as single cells and have a very low cloning efficiency, whereas naïve stem cells can be passed as single cells and have a high cloning efficiency. Female naïve stem cells have two active X chromosomes whereas primed state stem cells have already inactivated one X chromosome by methylation. Additionally, it is now known that naïve state stem cells have far less methylation marks, which essentially are early differentiation decisions, also known as cell fate decisions, which limit the types of mature cells that the stem cells can become.

SUMMARY OF THE INVENTION

In one aspect of the invention, a drug screen is disclosed in which agents are screened for their ability to preferentially inhibit pluripotency of naïve stem cells more than primed stem cells. Agents that are screened may be antibodies or antibody like molecules, polyclonal, monoclonal, antibody fragment fusion proteins, antibody mimics, peptides or peptide mimics, small molecules or natural products.

In another aspect of the invention agents are disclosed that inhibit cancer growth, inhibit the growth of metastatic cancer cells, or inhibit the metastatic potential of cancer cells wherein the agents were identified by their ability to induce differentiation or inhibit pluripotency of naïve stem cells and their relative inability to induce differentiation or inhibit pluripotency of primed stem cells.

In yet another aspect of the invention, the agents that are disclosed are disclosed for use as an anti-cancer or anti-metastasis therapeutic for the treatment or prevention of cancers.

In another aspect of the invention, novel anti-cancer or anti-metastasis drug targets are identified by identifying genes that are upregulated in naïve stem cells but not in primed stem cells.

In yet another aspect of the invention, novel anti-cancer or anti-metastasis drug targets are identified by identifying microRNAs that are upregulated in naïve stem cells but not in primed stem cells.

In one aspect, the invention is directed to a method for identifying an agent for the treatment or prevention of cancer or metastatic cancer comprising the steps of (i) contacting stem cell with a potential agent, and (ii) identifying an agent that induces differentiation, or inhibits stem cell pluripotency or growth of the stem cell, wherein such agent is determined to be an anti-cancer agent. The stem cell may be naïve state stem cell. Or, in step (i), the stem cell may be naïve state or primed state stem cell, wherein the effect of the agent on naïve state stem cell is compared to the effect on primed state stem cell, wherein if the agent has a greater effect on the naïve state stem cell compared with primed state stem cell, then the agent is determined to be an anti-cancer agent. The agent may be a polyclonal antibody, monoclonal antibody, antibody like molecule, antibody fragment fusion protein, antibody mimic, peptide, peptide mimic, small molecule or natural product. The stem cell may be human. The stem cell may be maintained in a naïve state by culturing in a medium comprising $NME7_{AB}$ or NME7-X1. The cancer may be breast, ovarian, melanoma, prostate, colon, lung or pancreatic. The cancer may be MUC1 positive or MUC1* positive cancer. The cancer may be $NME7_{AB}$ or NME7-X1 positive cancer. The agent may not be generally cytotoxic. The agent may not be cytotoxic to fibroblasts or fibroblast progenitor cells.

In another aspect, the invention is directed to a method for preventing or treating cancer comprising administering to the subject the agent obtained by the method according to above. The cancer may be breast, ovarian, melanoma, prostate, colon, lung or pancreatic. The cancer may be a MUC1 positive or MUC1* positive cancer. The cancer may be an $NME7_{AB}$ or NME7-X1 positive cancer.

In another aspect, the invention is directed to a method for preventing metastasis of cancer comprising administering to the subject the agent obtained by the method according to above.

In another aspect, the invention is directed to a method of inhibiting cancer growth, migration or invasiveness comprising administering to the subject the agent obtained by the method according to above.

In another aspect, the invention is directed to a method of inhibiting the growth of metastatic cancer cells comprising administering to the subject the agent obtained by the method according to above.

In another aspect, the invention is directed to a method of identifying anti-cancer or anti-metastasis target for drug discovery comprising identifying a gene or gene product that is upregulated in naïve state stem cells compared to primed state stem cells.

In another aspect, the invention is directed to a method of identifying anti-cancer or anti-metastasis target for drug discovery comprising identifying a gene or gene product that is downregulated in naïve state stem cells compared to primed state stem cells.

In another aspect, the invention is directed to a method of identifying anti-cancer or anti-metastasis agent comprising (i) identifying gene or gene product that is downregulated in naïve state stem cells compared to primed state stem cells; (ii) contacting the naïve stem cells with an agent; and (iii) identifying an agent that increases expression or activity of the downregulated gene or gene product in naïve state stem cells. The down-regulated gene may be a gene that is upregulated when stem cells initiate differentiation. The down-regulated gene may be fibronectin, vimentin, or NF1.

In another aspect, the invention is directed to a method of identifying anti-cancer or anti-metastasis agent comprising (i) identifying gene or gene product that is upregulated in naïve state stem cells compared to primed state stem cells; (ii) contacting the naïve stem cells with an agent; and (iii) identifying an agent that inhibits expression or activity of the upregulated gene or gene product in naïve state stem cells. The upregulated gene may be E-cadherin, CXCR4, β-catenin, AXIN2, MUC1, NME7, or NME7-X1.

In another aspect, the invention is directed to a method of identifying anti-cancer or anti-metastasis agent comprising (i) identifying gene or gene product that is upregulated in naïve state stem cells compared to fibroblast cells; (ii) contacting the naïve stem cells with an agent; and (iii) identifying an agent that inhibits expression or activity of the upregulated gene or gene product in naïve state stem cells. The upregulated gene may be E-cadherin, CXCR4, β-catenin, AXIN2, MUC1, NME7, or NME7-X1.

In another aspect, the invention is directed to a method of identifying anti-cancer or anti-metastasis agent comprising (i) identifying gene or gene product that is downregulated in naïve state stem cells compared to fibroblast cells; (ii) contacting the naïve stem cells with an agent; and (iii) identifying an agent that increases expression or activity of the downregulated gene or gene product in naïve state stem cells. The down-regulated gene may be a gene that is upregulated when stem cells initiate differentiation. The down-regulated gene may be fibronectin, vimentin, NF1, or microRNA-145. The down-regulated gene may be a super-enhancer target gene, such as HES3, GNAS, VLDLR, EXT1, FBXL17, RHOC or GREB1L.

In another aspect, the invention is directed to a method of identifying anti-cancer or anti-metastasis agent comprising (i) identifying microRNA that is upregulated in naïve state stem cells compared to primed stem cells or fibroblast cells; (ii) contacting the naïve stem cells with an agent; and (iii) identifying an agent that inhibits expression or activity of the upregulated microRNA in naïve state stem cells.

In another aspect, the invention is directed to the compounds of Formulae 1 to 17.

In another aspect, the invention is directed to a method of treating cancer in a subject, comprising administering to the subject a compound of Formula 1 to 17 or as set forth in FIG. 18A-18E, or as drawn out in the present specification at or about pages 48-64. The cancer may be a MUC1 positive, or MUC1* positive, or a MUC1 negative cancer. The cancer may be an $NME7_{AB}$ or NME7-X1 positive cancer.

In another aspect, the invention is directed to a method for preventing or treating cancer or cancer metastasis comprising the steps of: (i) analyzing a cancerous sample from the patient and determining that it is MUC1* positive, $NME7_{AB}$ positive or NME7-X1 positive; and (ii) administering to the patient an effective amount of a compound of Formula 1 to 17. The analyzing step may be carried out by PCR. In one aspect, when the cancerous sample may express mRNA level of MUC1 gene, NME7 gene or NME7-X1 gene that is at least 0.5% of the mRNA expression level of EEF1A1 gene, it is determined to be MUC1* positive, $NME7_{AB}$ positive or NME7-X1 positive. The analyzing step may be carried out by immunohistochemistry. In one aspect, when the cancerous sample may be contacted with an antibody that binds to the PSMGFR peptide or the N-10 peptide and stains the tissue with a pathologist's standard score 1-4 ("+-++++"), it is determined to be MUC1* positive. When the cancerous sample may be contacted with an antibody that binds to the B3 peptide of NME7 and stains the tissue with a pathologist's standard score 1-4 ("+-++++"), it is determined to be $NME7_{AB}$ positive or NME7-X1 positive.

In another aspect, the invention is directed to a method of identifying an agent for the prevention or treatment of an inflammatory disease or condition, comprising the steps of (i) exposing stem cells to an agent, and (ii) identifying an agent that inhibits stem cell pluripotency or growth, or induces stem cell differentiation, wherein the agent or its analog is an agent for treating inflammatory disease or condition. The inflammatory disease or condition may be rheumatoid arthritis, inflammatory bowel syndrome, Crohn's disease, osteoarthritis, asthma, dermatitis, psoriasis, cystic fibrosis, post transplantation late and chronic solid organ rejection, multiple sclerosis, systemic lupus erythematosus, Sjogren syndrome, Hashimoto thyroiditis, polymyositis, scleroderma, Addison disease, vitiligo, pernicious anemia, glomerulonephritis, pulmonary fibrosis, autoimmune diabetes, diabetic retinopathy, rhinitis, ischemia-reperfusion injury, post-angioplasty restenosis, chronic obstructive pulmonary diseases (COPD), Graves' disease, gastrointestinal allergy, conjunctivitis, atherosclerosis, coronary artery disease, angina, cancer metastasis, small artery disease, or mitochondrial disease.

In another aspect, the invention is directed to a method of treating an inflammatory disease or condition comprising administering to a person in need thereof, an agent that when contacted with stem cells, inhibits stem pluripotency or growth or induces stem cell differentiation. The inflammatory disease or condition may be rheumatoid arthritis, inflammatory bowel syndrome, Crohn's disease, osteoarthritis, asthma, dermatitis, psoriasis, cystic fibrosis, post transplantation late and chronic solid organ rejection, multiple sclerosis, systemic lupus erythematosus, Sjogren syndrome, Hashimoto thyroiditis, polymyositis, scleroderma, Addison disease, vitiligo, pernicious anemia, glomerulonephritis, pulmonary fibrosis, autoimmune diabetes, diabetic retinopathy, rhinitis, ischemia-reperfusion injury, post-angioplasty restenosis, chronic obstructive pulmonary diseases (COPD), Graves' disease, gastrointestinal allergy, conjunctivitis, atherosclerosis, coronary artery disease, angina, cancer metastasis, small artery disease, or mitochondrial disease. The agent may be a compound of Formula 1 to 17 or as set forth in FIG. 18A-18E, or as drawn out in the present specification at or about pages 48-64.

These and other objects of the invention will be more fully understood from the following description of the invention, the referenced drawings attached hereto and the claims appended hereto.

DESCRIPTION OF THE DRAWINGS

The present invention will become more fully understood from the detailed description given herein below, and the accompanying drawings which are given by way of illustration only, and thus are not limitative of the present invention, and wherein;

FIG. 2 is a Table that summarizes the results of testing small molecules, an anti-MUC1* Fab "E6", a MUC1* extracellular domain peptide "FLR" and anti-NME7 antibodies #56 and #61.

FIG. 3A shows photograph of primed stem cells cultured in presence of an anti-MUC1* Fab, named E6, FIG. 3B shows photograph of primed stem cells cultured in presence of a MUC1* extracellular domain peptide, FLR, FIG. 3C shows photograph of control primed stem cells, FIG. 3D shows photograph of primed stem cells cultured in 0.2% DMSO as control for small molecules in 0.2% DMSO, FIG. 3E shows photograph of primed stem cells cultured in the presence of MN0642, FIG. 3F shows photograph of primed stem cells cultured in the presence of MN1130, FIG. 3G shows photograph of primed stem cells cultured in the presence of MN0572, FIG. 3H shows photograph of primed stem cells cultured in the presence of MN0947, FIG. 3I shows photograph of primed stem cells cultured in the presence of MN0129, FIG. 3J shows photograph of primed stem cells cultured in the presence of MN0676, FIG. 3K shows photograph of primed stem cells cultured in the presence of MN0992, and FIG. 3L shows photograph of primed stem cells cultured in the presence of MN0402.

FIG. 4A shows photograph of primed stem cells cultured in presence of an anti-MUC1* Fab, named E6, FIG. 4B shows photograph of primed stem cells cultured in presence of a MUC1*$_{ecd\ peptide}$ extracellular domain peptide, also known as FLR, FIG. 4C shows photograph of control primed stem cells, FIG. 4D shows photograph of primed stem cells cultured in 0.2% DMSO as control for small molecules in 0.2% DMSO, FIG. 4E shows photograph of primed stem cells cultured in the presence of MN0642, FIG. 4F shows photograph of primed stem cells cultured in the presence of MN1130, FIG. 4G shows photograph of primed stem cells cultured in the presence of MN0572, FIG. 4H shows photograph of primed stem cells cultured in the presence of MN0947, FIG. 4I shows photograph of primed stem cells cultured in the presence of MN0129, FIG. 4J shows photograph of primed stem cells cultured in the presence of MN0676, FIG. 4K shows photograph of primed stem cells cultured in the presence of MN0992, and FIG. 3L shows photograph of primed stem cells cultured in the presence of MN0402.

FIG. 5A shows photograph of primed stem cells cultured in presence of an anti-MUC1* Fab, named E6, FIG. 5B shows photograph of primed stem cells cultured in presence of a MUC1* extracellular domain peptide, FLR, FIG. 5C shows photograph of primed stem cells cultured in presence of an anti-NME7 polyclonal antibody #56, FIG. 5D shows photograph of primed stem cells cultured in presence of an anti-NME7 polyclonal antibody #61, FIG. 5E shows photograph of primed stem cells cultured in the presence of MN0642, FIG. 5F shows photograph of primed stem cells cultured in the presence of MN1130, FIG. 5G shows photograph of primed stem cells cultured in the presence of MN0572, FIG. 5H shows photograph of primed stem cells cultured in the presence of MN0947, FIG. 5I shows photograph of primed stem cells cultured in the presence of MN0129, FIG. 5J shows photograph of primed stem cells cultured in the presence of MN0676, FIG. 5K shows photograph of primed stem cells cultured in the presence of MN0992, and FIG. 5L shows photograph of primed stem cells cultured in the presence of MN0402.

FIG. 6A shows photograph of primed stem cells cultured in presence of an anti-MUC1* Fab, named E6, FIG. 6B shows photograph of primed stem cells cultured in presence of a MUC1* extracellular domain peptide, FLR, FIG. 6C shows photograph of primed stem cells cultured in presence of an anti-NME7 polyclonal antibody #56, FIG. 6D shows photograph of primed stem cells cultured in presence of an anti-NME7 polyclonal antibody #61, FIG. 6E shows photograph of primed stem cells cultured in the presence of MN0642, FIG. 6F shows photograph of primed stem cells cultured in the presence of MN1130, FIG. 6G shows photograph of primed stem cells cultured in the presence of MN0572, FIG. 6H shows photograph of primed stem cells cultured in the presence of MN0947, FIG. 6I shows photograph of primed stem cells cultured in the presence of MN0129, FIG. 6J shows photograph of primed stem cells cultured in the presence of MN0676, FIG. 6K shows photograph of primed stem cells cultured in the presence of MN0992, and FIG. 6L shows photograph of primed stem cells cultured in the presence of MN0402.

FIG. 7A-7L shows photographs at 10× magnification of human naïve state stem cells, grown in stem cell media with growth factor NME7$_{AB}$, over a MUC1* antibody, C3, surface and treated for 3 days with in the presence of a test agent. Dotted lines indicate areas where stem cell pluripotency or growth is inhibited or differentiation is induced. FIG. 7A shows photograph of naïve stem cells cultured in presence of an anti-MUC1* Fab, named E6, FIG. 7B shows photograph of naïve stem cells cultured in presence of a MUC1* extracellular domain peptide, FLR, FIG. 7C shows photograph of control naïve stem cells, FIG. 7D shows photograph of naïve stem cells cultured in 0.2% DMSO as control for small molecules in 0.2% DMSO, FIG. 7E shows photograph of naïve stem cells cultured in the presence of MN0642, FIG. 7F shows photograph of naïve stem cells cultured in the presence of MN1130, FIG. 7G shows photograph of naïve stem cells cultured in the presence of MN0572, FIG. 7H shows photograph of naïve stem cells cultured in the presence of MN0947, FIG. 7I shows photograph of naïve stem cells cultured in the presence of MN0129, FIG. 7J shows photograph of naïve stem cells cultured in the presence of MN0676, FIG. 7K shows photograph of naïve stem cells cultured in the presence of MN0992, and FIG. 7L shows photograph of naïve stem cells cultured in the presence of MN0402.

FIG. 8A shows photograph of naïve stem cells cultured in presence of an anti-MUC1* Fab, named E6, FIG. 8B shows photograph of naïve stem cells cultured in presence of a MUC1* extracellular domain peptide, FLR, FIG. 8C shows photograph of control naïve stem cells, FIG. 8D shows photograph of naïve stem cells cultured in 0.2% DMSO as control for small molecules in 0.2% DMSO, FIG. 8E shows photograph of naïve stem cells cultured in the presence of MN0642, FIG. 8F shows photograph of naïve stem cells cultured in the presence of MN1130, FIG. 8G shows photograph of naïve stem cells cultured in the presence of MN0572, FIG. 8H shows photograph of naïve stem cells cultured in the presence of MN0947, FIG. 8I shows photograph of naïve stem cells cultured in the presence of MN0129, FIG. 8J shows photograph of naïve stem cells cultured in the presence of MN0676, FIG. 8K shows photograph of naïve stem cells cultured in the presence of MN0992, and FIG. 8L shows photograph of naïve stem cells cultured in the presence of MN0402.

FIG. 9A shows photograph of naïve stem cells cultured in presence of an anti-MUC1* Fab, named E6, FIG. 9B shows photograph of naïve stem cells cultured in presence of a MUC1* extracellular domain peptide, FLR, FIG. 9C shows photograph of naïve stem cells cultured in presence of an anti-NME7 polyclonal antibody #56, FIG. 9D shows photograph of naïve stem cells cultured in presence of an anti-NME7 polyclonal antibody #61, FIG. 9E shows photograph of naïve stem cells cultured in the presence of MN0642, FIG. 9F shows photograph of naïve stem cells cultured in the presence of MN1130, FIG. 9G shows photograph of naïve stem cells cultured in the presence of MN0572, FIG. 9H shows photograph of naïve stem cells cultured in the presence of MN0947, FIG. 9I shows photograph of naïve stem cells cultured in the presence of MN0129, FIG. 9J shows photograph of naïve stem cells cultured in the presence of MN0676, FIG. 9K shows photograph of naïve stem cells cultured in the presence of MN0992, and FIG. 9L shows photograph of naïve stem cells cultured in the presence of MN0402.

FIG. 10A shows photograph of naïve stem cells cultured in presence of an anti-MUC1* Fab, named E6, FIG. 10B shows photograph of naïve stem cells cultured in presence of a MUC1* extracellular domain peptide, FLR, FIG. 10C shows photograph of naïve stem cells cultured in presence of an anti-NME7 polyclonal antibody #56, FIG. 10D shows photograph of naïve stem cells cultured in presence of an anti-NME7 polyclonal antibody #61, FIG. 10E shows photograph of naïve stem cells cultured in the presence of MN0642, FIG. 10F shows photograph of naïve stem cells cultured in the presence of MN1130, FIG. 10G shows photograph of naïve stem cells cultured in the presence of MN0572, FIG. 10H shows photograph of naïve stem cells cultured in the presence of MN0947, FIG. 10I shows photograph of naïve stem cells cultured in the presence of MN0129, FIG. 10J shows photograph of naïve stem cells cultured in the presence of MN0676, FIG. 10K shows photograph of naïve stem cells cultured in the presence of MN0992, and FIG. 10L shows photograph of näive stem cells cultured in the presence of MN0402.

FIG. 11A shows photograph of primed stem cells cultured in presence of a control scrambled sequence siRNA, FIG. 11B shows photograph of primed stem cells cultured in presence of a BRD4 specific siRNA, FIG. 11C shows photograph of primed stem cells cultured in presence of a JMJD6 specific siRNA, FIG. 11D shows photograph of primed stem cells cultured in presence of an inactive stereoisomer of purported BRD4 inhibitor JQ1 aka JQ1–, FIG. 11E shows photograph of primed stem cells cultured in presence of the active stereoisomer of purported BRD4 inhibitor JQ1 aka JQ1+ at 500 nM, and FIG. 11F shows photograph of primed stem cells cultured in presence of the active stereoisomer of purported BRD4 inhibitor JQ1+ at 1 uM.

FIG. 12A shows photograph of primed stem cells cultured in presence of a control scrambled sequence siRNA, FIG. 12B shows photograph of primed stem cells cultured in presence of a BRD4 specific siRNA, FIG. 12C shows photograph of primed stem cells cultured in presence of a JMJD6 specific siRNA, FIG. 12D shows photograph of primed stem cells cultured in presence of an inactive stereoisomer of purported BRD4 inhibitor JQ1 aka JQ1–, FIG. 12E shows photograph of primed stem cells cultured in presence of the active stereoisomer of purported BRD4 inhibitor JQ1 aka JQ1+ at 500 nM, and FIG. 12F shows photograph of primed stem cells cultured in presence of the active stereoisomer of purported BRD4 inhibitor JQ1+ at 1 uM.

FIG. 13A shows photograph of naïve stem cells cultured in presence of a control scrambled sequence siRNA, FIG. 13B shows photograph of naïve stem cells cultured in presence of a BRD4 specific siRNA, FIG. 13C shows photograph of naïve stem cells cultured in presence of a JMJD6 specific siRNA, FIG. 13D shows photograph of naïve stem cells cultured in presence of an inactive stereoisomer of purported BRD4 inhibitor JQ1 aka JQ1−, FIG. 13E shows photograph of naïve stem cells cultured in presence of the active stereoisomer of purported BRD4 inhibitor JQ1 aka JQ1+ at 500 nM, and FIG. 13F shows photograph of naïve stem cells cultured in presence of the active stereoisomer of purported BRD4 inhibitor JQ1+ at 1 uM.

FIG. 14A shows photograph of naïve stem cells cultured in presence of a control scrambled sequence siRNA, FIG. 14B shows photograph of naïve stem cells cultured in presence of a BRD4 specific siRNA, FIG. 14C shows photograph of naïve stem cells cultured in presence of a JMJD6 specific siRNA, FIG. 14D shows photograph of naïve stem cells cultured in presence of an inactive stereoisomer of purported BRD4 inhibitor JQ1 aka JQ1−, FIG. 14E shows photograph of naïve stem cells cultured in presence of the active stereoisomer of purported BRD4 inhibitor JQ1 aka JQ1+ at 500 nM, and FIG. 14F shows photograph of naïve stem cells cultured in presence of the active stereoisomer of purported BRD4 inhibitor JQ1+ at 1 uM.

FIG. 15A-15F shows photographs at 4× magnification of human naïve state stem cells, previously grown in NME1 dimers over a MUC1* antibody surface, C3, but cultured in the absence of $NME7_{AB}$ during the experiment, and treated for 3 days with a test agent. Dotted lines indicate areas where stem cell pluripotency or growth is inhibited or differentiation is induced. FIG. 15A shows photograph of naïve stem cells cultured in presence of a control scrambled sequence siRNA, FIG. 15B shows photograph of naïve stem cells cultured in presence of a BRD4 specific siRNA, FIG. 15C shows photograph of naïve stem cells cultured in presence of a JMJD6 specific siRNA, FIG. 15D shows photograph of naïve stem cells cultured in presence of an inactive stereoisomer of purported BRD4 inhibitor JQ1 aka JQ1−, FIG. 15E shows photograph of naïve stem cells cultured in presence of the active stereoisomer of purported BRD4 inhibitor JQ1 aka JQ1+ at 500 nM, and FIG. 15F shows photograph of naïve stem cells cultured in presence of the active stereoisomer of purported BRD4 inhibitor JQ1+ at 1 uM.

FIG. 16A-16F shows photographs at 20× magnification of human naïve state stem cells, previously grown in NME1 dimers over a MUC1* antibody surface, C3, but cultured in the absence of NME1 dimers during the experiment, and treated for 3 days with a test agent. Dotted lines indicate areas where stem cell pluripotency or growth is inhibited or differentiation is induced. FIG. 16A shows photograph of naïve stem cells cultured in presence of a control scrambled sequence siRNA, FIG. 16B shows photograph of naïve stem cells cultured in presence of a BRD4 specific siRNA, FIG. 16C shows photograph of naïve stem cells cultured in presence of a JMJD6 specific siRNA, FIG. 16D shows photograph of naïve stem cells cultured in presence of an inactive stereoisomer of purported BRD4 inhibitor JQ1 aka JQ1−, FIG. 16E shows photograph of naïve stem cells cultured in presence of the active stereoisomer of purported BRD4 inhibitor JQ1+ at 500 nM, and FIG. 16F shows photograph of naïve stem cells cultured in presence of the active stereoisomer of purported BRD4 inhibitor JQ1+ at 1 uM.

FIGS. 18A-18E shows summary of biological data for compounds of the invention and various other previously known chemical compounds.

FIG. 19A-19P shows photographs of human stem cells cultured for 3 days with either control media or a small molecule that had been previously reported to inhibit cancer cell migration, which is a characteristic of cancer metastasis. In FIG. 19A-19H, the cells were naïve state stem cells, previously grown in the growth factor $NME7_{AB}$ over a MUC1* antibody surface, C3, but cultured in the absence of $NME7_{AB}$ during the experiment. In FIG. 19I-19P, the cells were primed state stem cells, previously grown in the growth factor FGF over a layer of inactivated MEFs, but cultured in the absence of FGF during the experiment.

FIG. 21A cells were treated with control PBS. FIG. 21B-21D cells were treated with anti-MUC1* Fab E6. FIG. 21E-21I shows cells treated with control amount of DMSO at time zero. FIG. 21F-21G cells were treated with JQ1. FIG. 21H-21M shows cells treated with control amount of DMSO at 126 hours. FIG. 21J shows cells treated with novel molecule MN1194. FIG. 21K shows cells treated with novel molecule MN1186. FIG. 21L shows cells treated with novel molecule MN1137. FIG. 21N shows cells treated with novel molecule MN1193. FIG. 21O shows cells treated with novel molecule MN1203. FIG. 21P shows cells treated with novel molecule MN1184.

FIG. 22A-22U shows photographs of a migration, invasion assay performed on T47D breast cancer cells in the presence of novel compounds of the invention or the control, DMSO alone, at 120 hours. FIG. 22V is a graph showing the measured inhibition of cancer cell migration at time 0, 24 hours or 48 hours for a number of compounds. FIG. 22W is a graph showing the inhibitory effect of the small molecules as a function of concentration, where units are uM. FIG. 22X is a graph showing how IC50's of the small molecules of the invention were measured and calculated.

FIG. 26A-26B show primed state stem cells culture in same concentration of DMSO that the compounds were dissolved in. FIGS. 26E-26F show naïve state stem cells culture in same concentration of DMSO that the compounds were dissolved in. FIG. 26C-26D show the effect of Dorsomorphin on primed state stem cells. FIG. 26G-26H show the effect of Dorsomorphin on naïve state stem cells.

FIG. 28A, 28B, 28E, 28F show photographs of a female induced pluripotent stem cell line, iPS 9X, that is in the naïve state as evidenced by documentation that the second X chromosome has been re-activated. FIG. 28C, 28D, 28G, 28H are human embryonic stem cell line, HES-3, growing in bFGF which keeps stem cells in primed state. FIG. 28I-28L shows photographs of human fibroblasts, BJ line available from the ATCC.

FIGS. 31G-31L, 32G-32L, 33G-33L, 34G-34L, and 35G-35L show photographs of human primed state stem cells, previously grown in FGF over a layer of MEFs, but cultured in the absence of FGF during the experiment, and treated for 3 days with a small molecule drug candidate at a final concentration of 6 uM, unless otherwise indicated. In each panel, a score of −, or +, ++, +++, or ++++ is given, wherein "−" indicates that at the indicated concentartion the drug candidate did not have an obvious effect on the pluripotency or proliferation of the stem cells. A "+" indicates a mild effect and "++++" indicates a profound effect on pluripotency or proliferation. Primed state stem cells grow in defined colonies rather than a uniform layer like naïve stem cells. Inhibition of proliferation can be seen as a reduction in the colony size. Inhibition of pluripotency, which is also induction of differentiation, is seen as increase in cell size with a decrease in the size of the nucleus, elongation and flattening of cells or rounding up of cells and floating off the plate.

FIGS. 31M-31R, 32M-32R, 33M-33R, 34M-34R, and 35M-35R show photographs of human fibroblast cells treated for 3 days with a small molecule drug candidate at a final concentration of 6 uM, unless otherwise indicated. In each panel, a score of −, or +, ++, +++, or ++++ is given, wherein "−" indicates that at the indicated concentration the drug candidate did not have an obvious effect on the morphology or proliferation of the cells. A "+" indicates a mild effect and "++++" indicates a profound effect on morphology or proliferation of the cells.

FIGS. 46A-46C are 10× magnification photographs. FIGS. 46D-46F are 20× magnification photographs. FIGS. 46A and 46D are photographs of naïve state stem cells. FIGS. 46B and 46E are photographs of primed state stem cells. FIGS. 46C and 46F are photographs of human fibroblast cells.

Figures 47A, 47B, 47C, 47D, 47E, 47F:
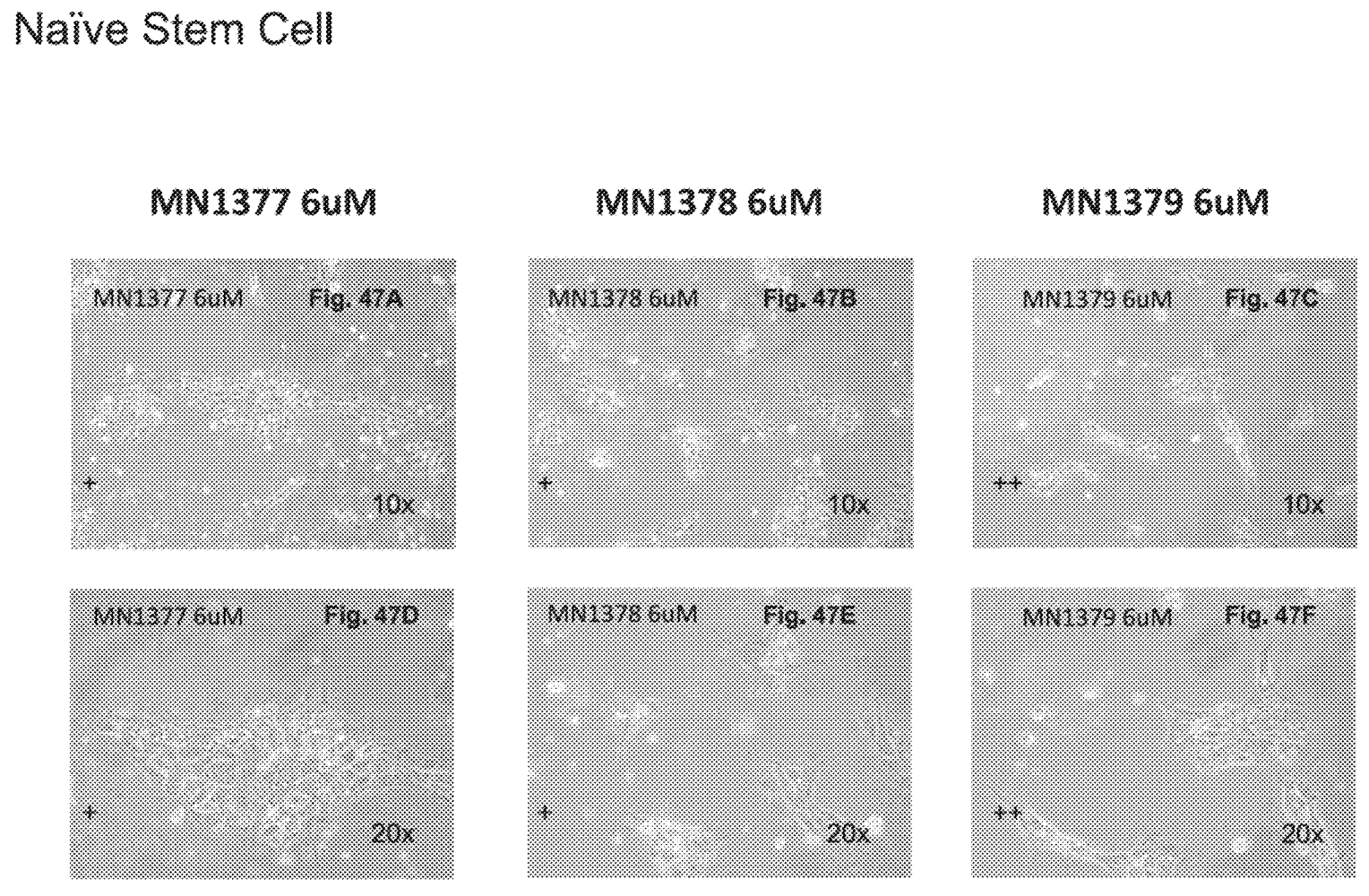
Figures 49G, 49H, 49I, 49J, 49K, 49L:
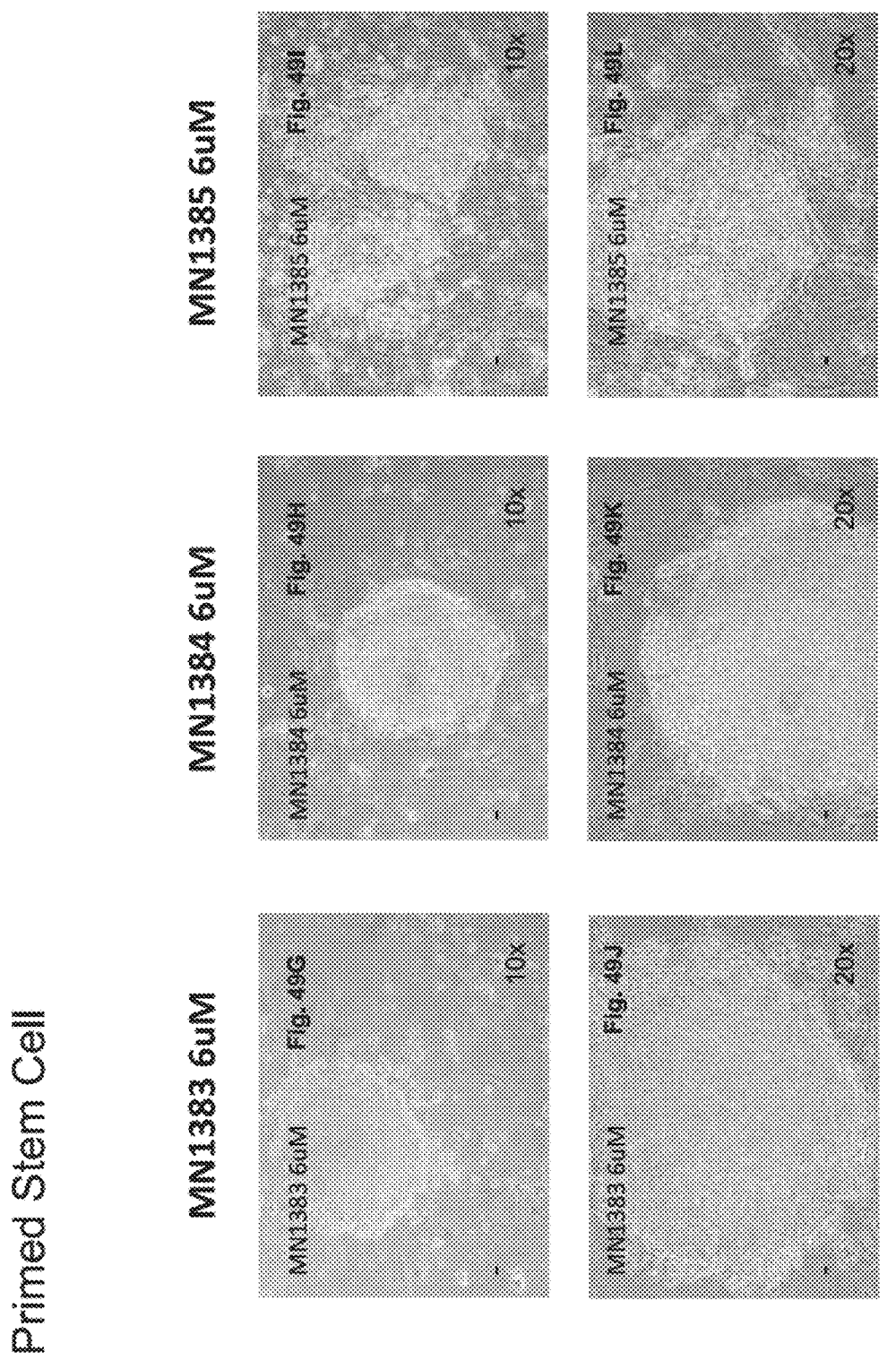

FIGS. 47A-47F, 48A-48F, and 49A-49F show photographs of human naïve state stem cells, previously grown in NME7$_{AB}$ over a MUC1* antibody surface, C3, but cultured in the absence of NME7$_{AB}$ during the experiment, and treated for a brief 24 hours with a small molecule drug candidate at a final concentration of 6 uM. In each panel, a score of −, or +, ++, +++, or ++++ is given, wherein "−" indicates that at the indicated concentration the drug candidate did not have an obvious effect on the pluripotency or proliferation of the stem cells. A "+" indicates a mild effect and "++++" indicates a profound effect on pluripotency or proliferation. Inhibition of proliferation can be seen as holes, or blank areas, in the layer of stem cells. Inhibition of pluripotency, which is also induction of differentiation, is seen as increase in cell size with a decrease in the size of the nucleus, elongation and flattening of cells or rounding up of cells and floating off the plate.

FIGS. 47G-47L, 48G-48L, and 49G-49L show photographs of human primed state stem cells, previously grown in FGF over a layer of MEFs, but cultured in the absence of FGF during the experiment, and treated for a brief 24 hours with a small molecule drug candidate at a final concentration of 6 uM. In each panel, a score of −, or +, ++, +++, or ++++ is given, wherein "−" indicates that at the indicated concentartion the drug candidate did not have an obvious effect on the pluripotency or proliferation of the stem cells. A "+" indicates a mild effect and "++++" indicates a profound effect on pluripotency or proliferation. Primed state stem cells grow in defined colonies rather than a uniform layer like naïve stem cells. Inhibition of proliferation can be seen as a reduction in the colony size. Inhibition of pluripotency, which is also induction of differentiation, is seen as increase in cell size with a decrease in the size of the nucleus, elongation and flattening of cells or rounding up of cells and floating off the plate.

FIGS. 50A-50C are 10× magnification photographs. FIGS. 50D-50F are 20× magnification photographs. FIGS. 50A and 50D are photographs of naïve state stem cells. FIGS. 50B and 50E are photographs of primed state stem cells. FIGS. 50C and 50F are photographs of human fibroblast cells.

FIGS. 55A-55C are 10× magnification photographs. FIGS. 55D-55F are 20× magnification photographs. FIGS. 55A and 55D are photographs of naïve state stem cells. FIGS. 55B and 55E are photographs of primed state stem cells. FIGS. 55C and 55F are photographs of human fibroblast cells.

FIG. 66 shows photographs of a cancer cell migration assay in which the effect of compounds of the invention are tested for their ability to inhibit the migration of T47D breast cancer cells, 120 hours after single addition of the compound at the indicated concentrations.

FIG. 67 shows photographs of a cancer cell migration assay in which the effect of compounds of the invention are tested for their ability to inhibit the migration of T47D breast cancer cells, 120 hours after single addition of the compound at the indicated concentrations.

FIG. 68 shows photographs of a cancer cell migration assay in which the effect of compounds of the invention are tested for their ability to inhibit the migration of T47D breast cancer cells, 120 hours after single addition of the compound at the indicated concentrations.

FIG. 69 shows photographs of a cancer cell migration assay in which the effect of compounds of the invention are tested for their ability to inhibit the migration of T47D breast cancer cells, 120 hours after single addition of the compound at the indicated concentrations.

FIG. 70 shows photographs of a cancer cell migration assay in which the effect of compounds of the invention are tested for their ability to inhibit the migration of T47D breast cancer cells, 120 hours after single addition of the compound at the indicated concentrations.

DETAILED DESCRIPTION OF THE INVENTION

Definitions

Figure 1:
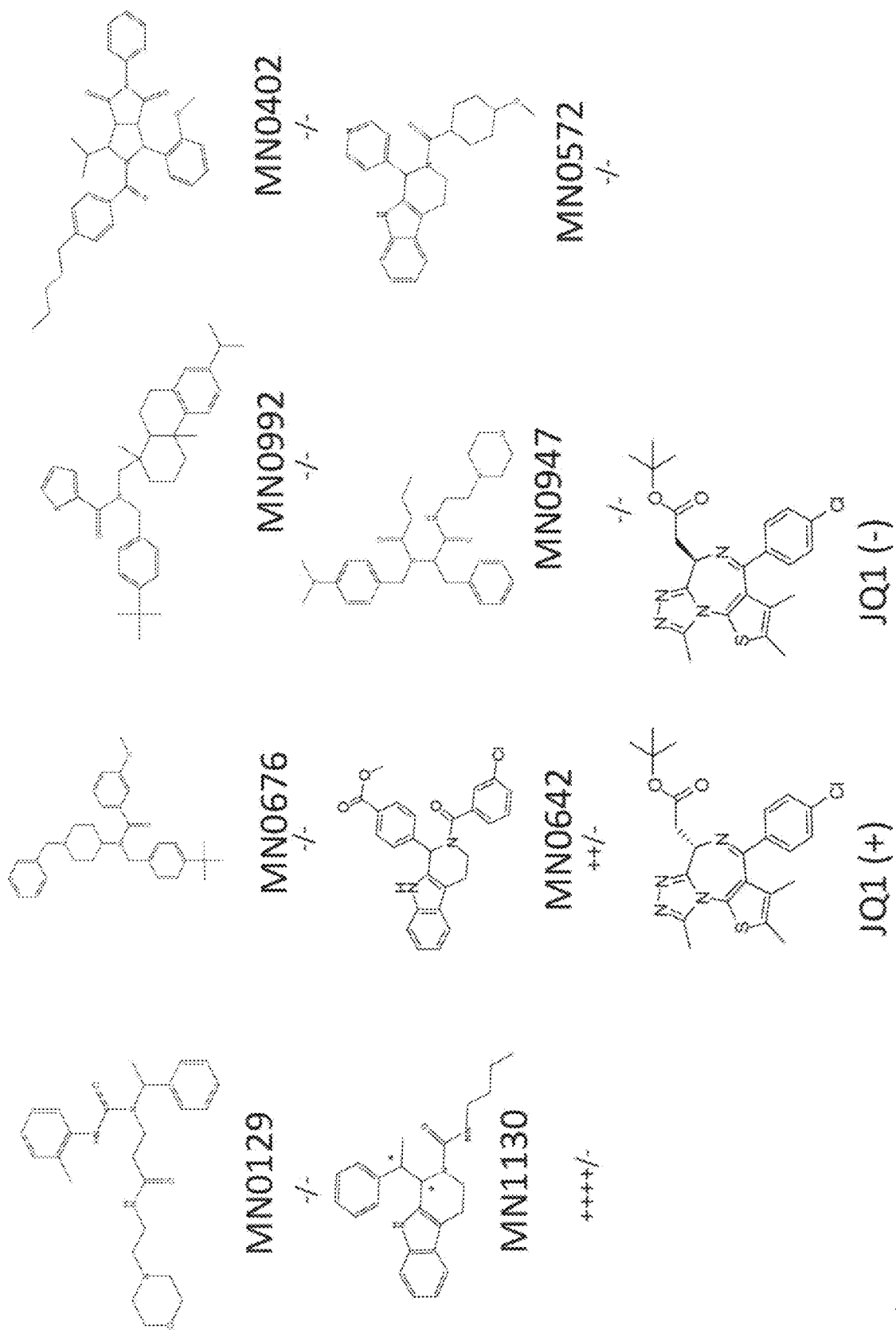
FIG. 1 shows the chemical structures of a set of small molecules that were tested for their ability to inhibit pluripotency, growth or induce differentiation of naïve state or primed state stem cells.
Figure 3A:
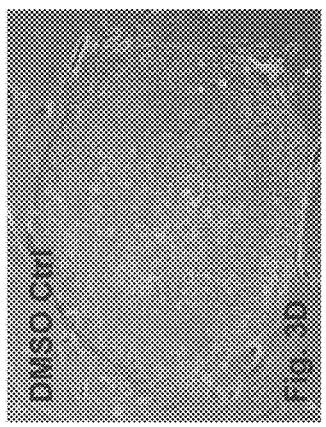
FIG. 3A-3L shows photographs at 10× magnification of human primed state stem cells, grown in stem cell media with growth factor FGF, over a layer of MEFs and treated for 3 days with in the presence of a test agent.
Figure 3B:
Figure 3C:
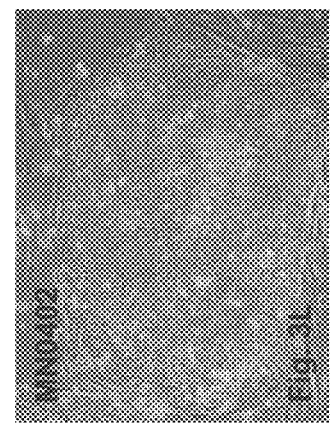
Figure 3D:
Figure 3E:
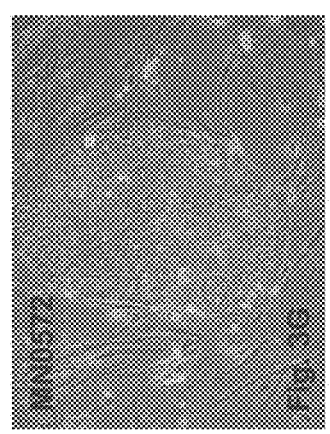
Figure 3F:
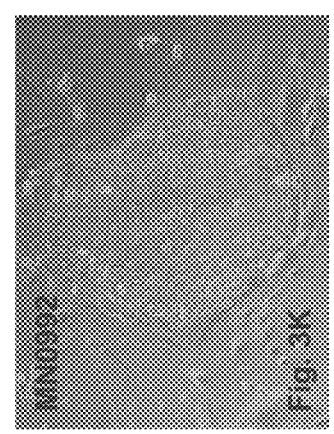
Figure 3G:
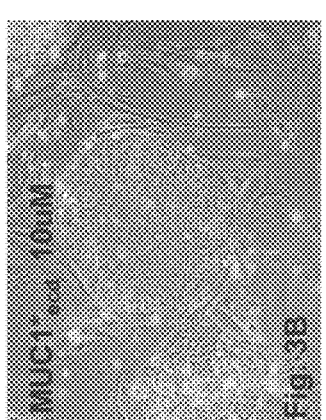
Figure 3H:
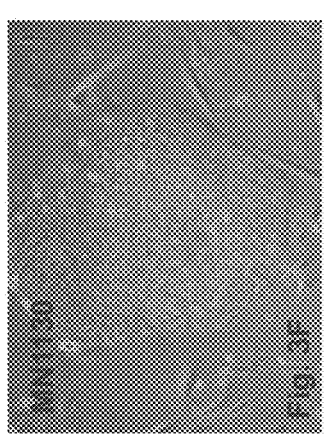
Figure 3I:
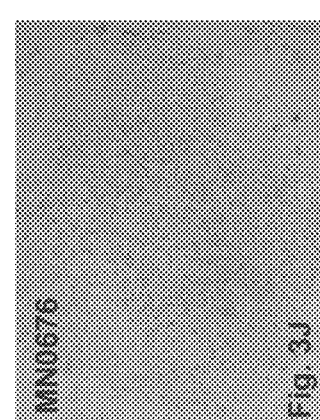
Figure 3J:
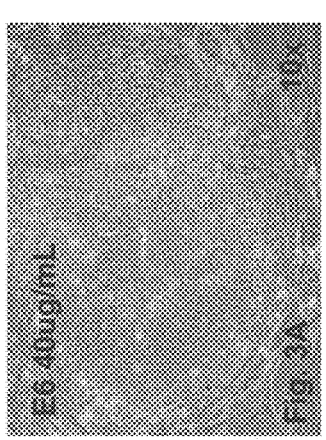
Figure 3K:
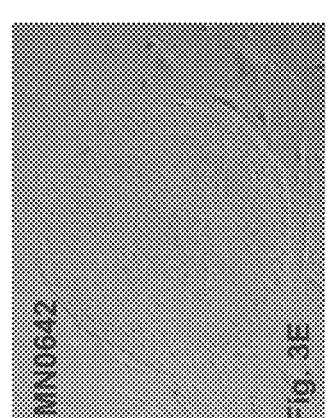
Figure 3L:
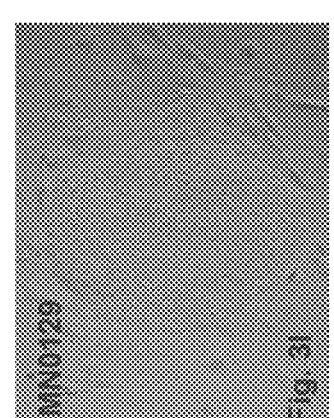
Figures 4A, 4B, 4C, 4D, 4E, 4F, 4G, 4H, 4I, 4J, 4K, 4L:
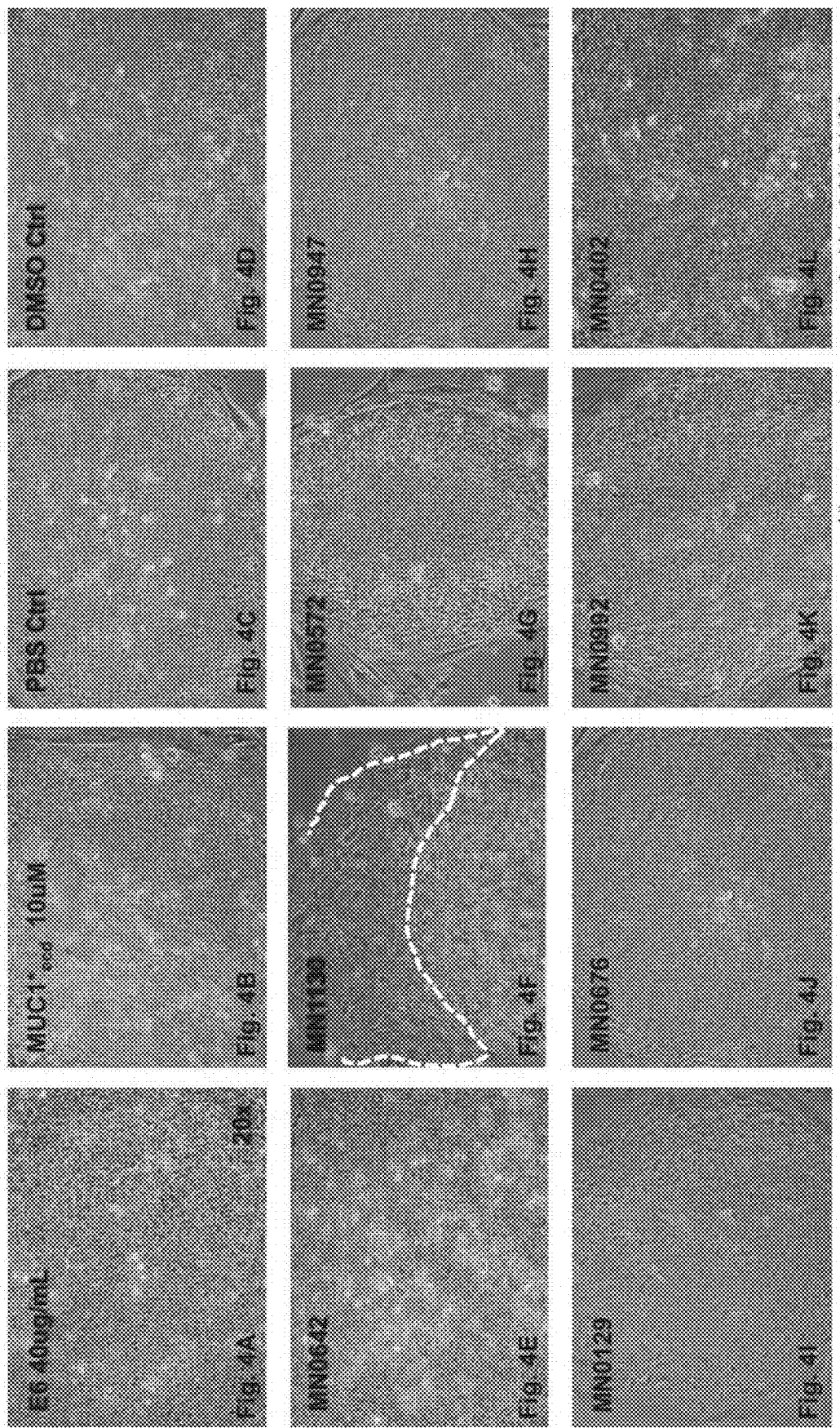
FIG. 4A-4L shows photographs at 20× magnification of human primed state stem cells, grown in stem cell media with growth factor FGF, over a layer of MEFs and treated for 3 days with in the presence of a test agent. Dotted lines indicate areas where stem cell pluripotency or growth is inhibited or differentiation is induced.
Figures 5A, 5B, 5C, 5D, 5E, 5F, 5G, 5H, 5I, 5J, 5K, 5L:
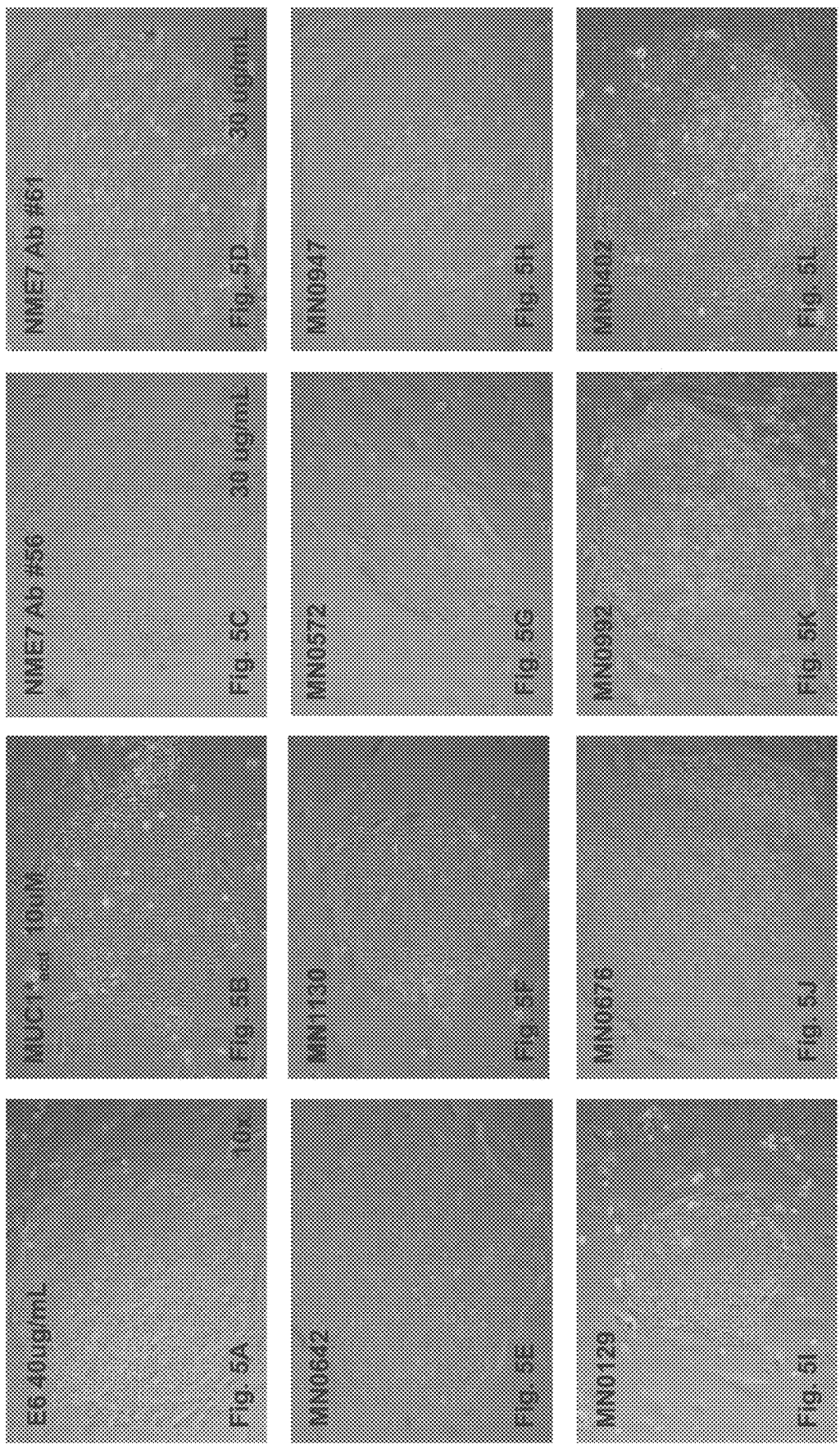
FIG. 5A-5L shows photographs at 10× magnification of human primed state stem cells, grown in stem cell media without growth factor FGF, over a layer of MEFs and treated for 3 days with in the presence of a test agent.
Figures 6A, 6B, 6C, 6D, 6E, 6F, 6G, 6H, 6I, 6J, 6K, 6L:
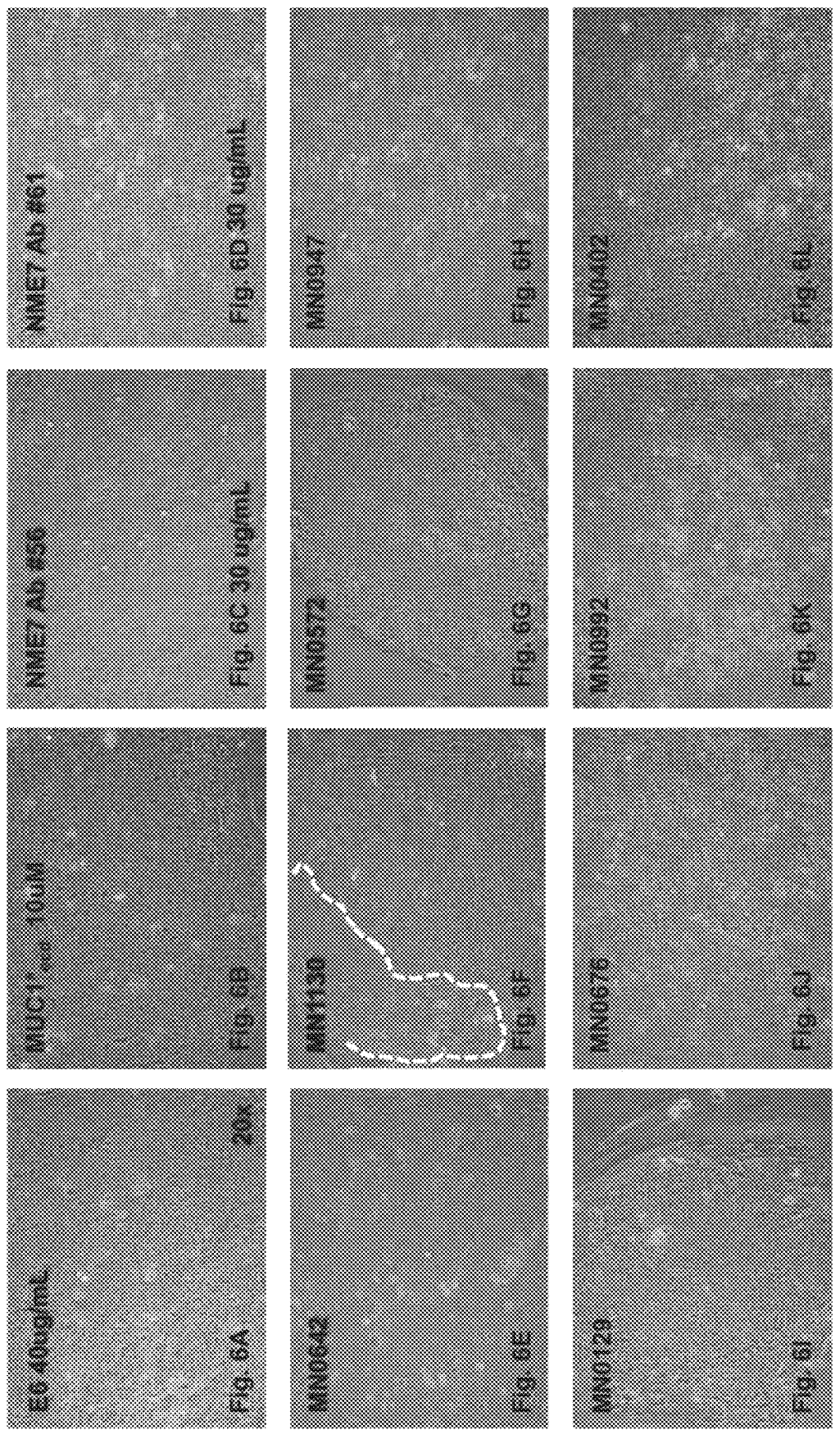
FIG. 6A-6L shows photographs at 20× magnification of human primed state stem cells, grown in stem cell media without growth factor FGF, over a layer of MEFs and treated for 3 days with in the presence of a test agent. Dotted lines indicate areas where stem cell pluripotency or growth is inhibited or differentiation is induced.
Figures 8A, 8B, 8C, 8D, 8E, 8F, 8G, 8H, 8I, 8J, 8K, 8L:
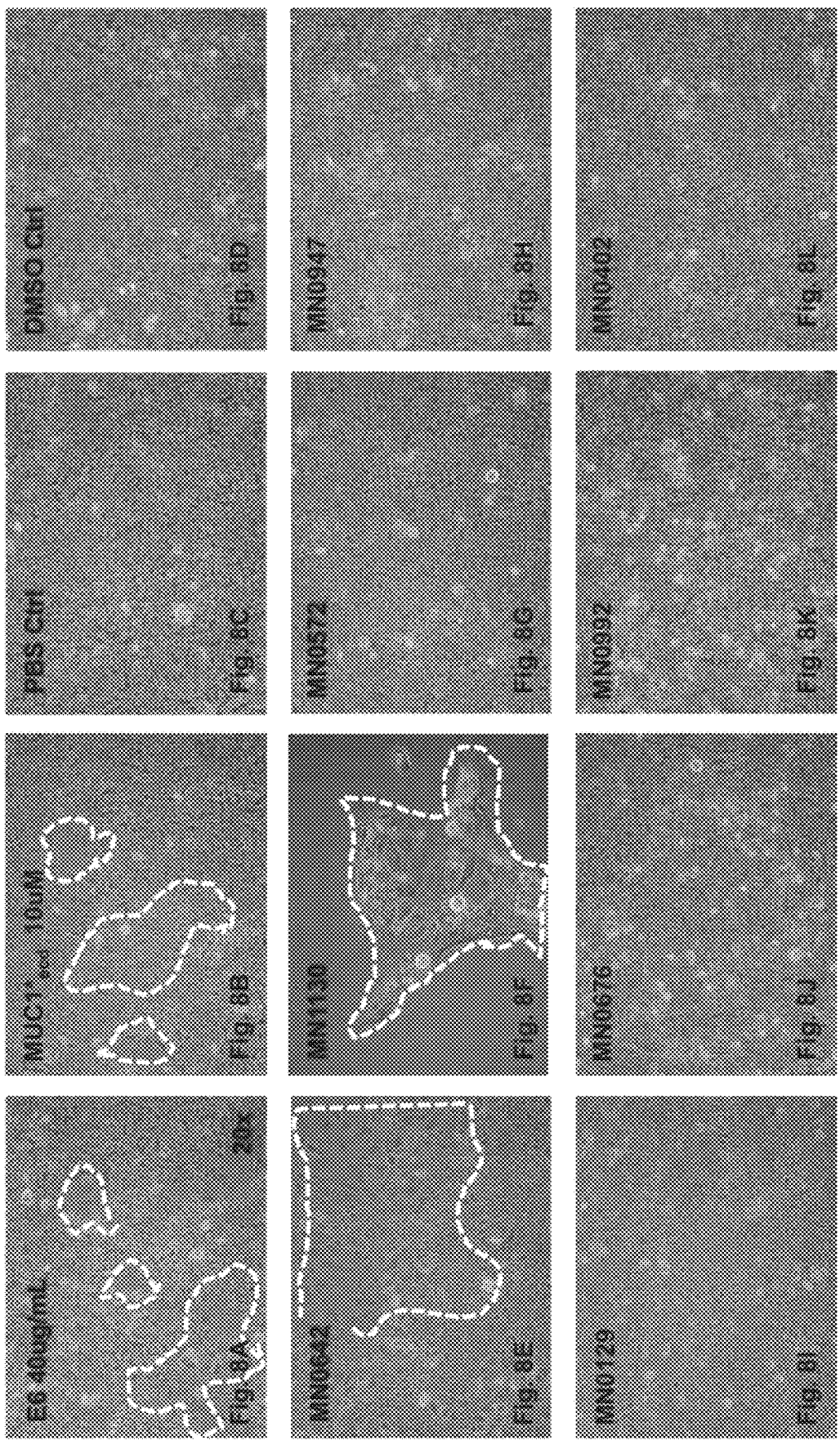
FIG. 8A-8L shows photographs at 20× magnification of human naïve state stem cells, grown in stem cell media with growth factor $NME7_{AB}$, over a MUC1* antibody, C3, surface and treated for 3 days with in the presence of a test agent. Dotted lines indicate areas where stem cell pluripotency or growth is inhibited or differentiation is induced.
Figures 9A, 9B, 9C, 9D, 9E, 9F, 9G, 9H, 9I, 9J, 9K, 9L:
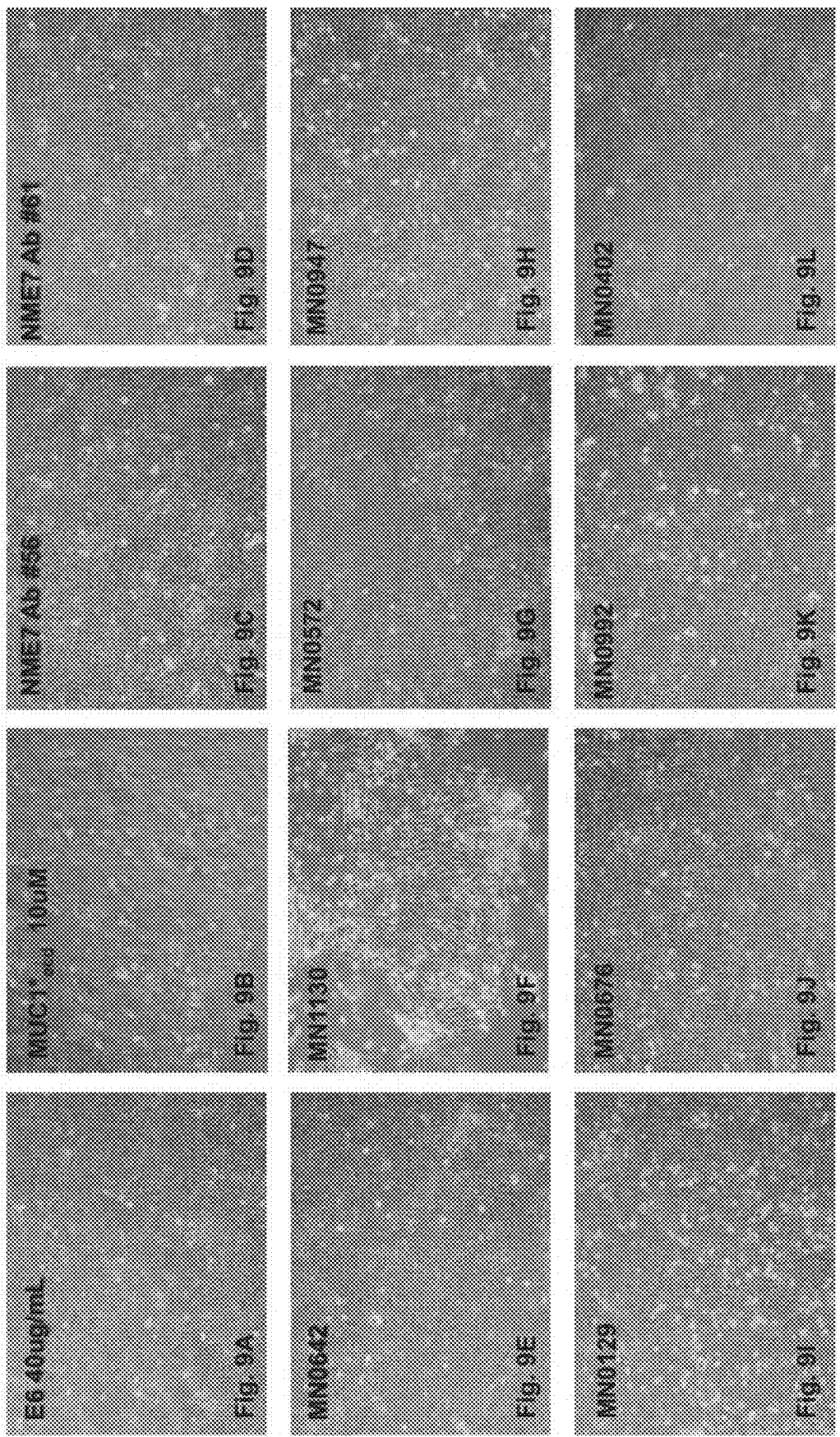
FIG. 9A-9L shows photographs at 10× magnification of human naïve state stem cells, grown in stem cell media without growth factor $NME7_{AB}$, over a MUC1* antibody, C3, surface and treated for 3 days with in the presence of a test agent. Dotted lines indicate areas where stem cell pluripotency or growth is inhibited or differentiation is induced.
Figures 10A, 10B, 10C, 10D, 10E, 10F, 10G, 10H, 10I, 10J, 10K, 10L:
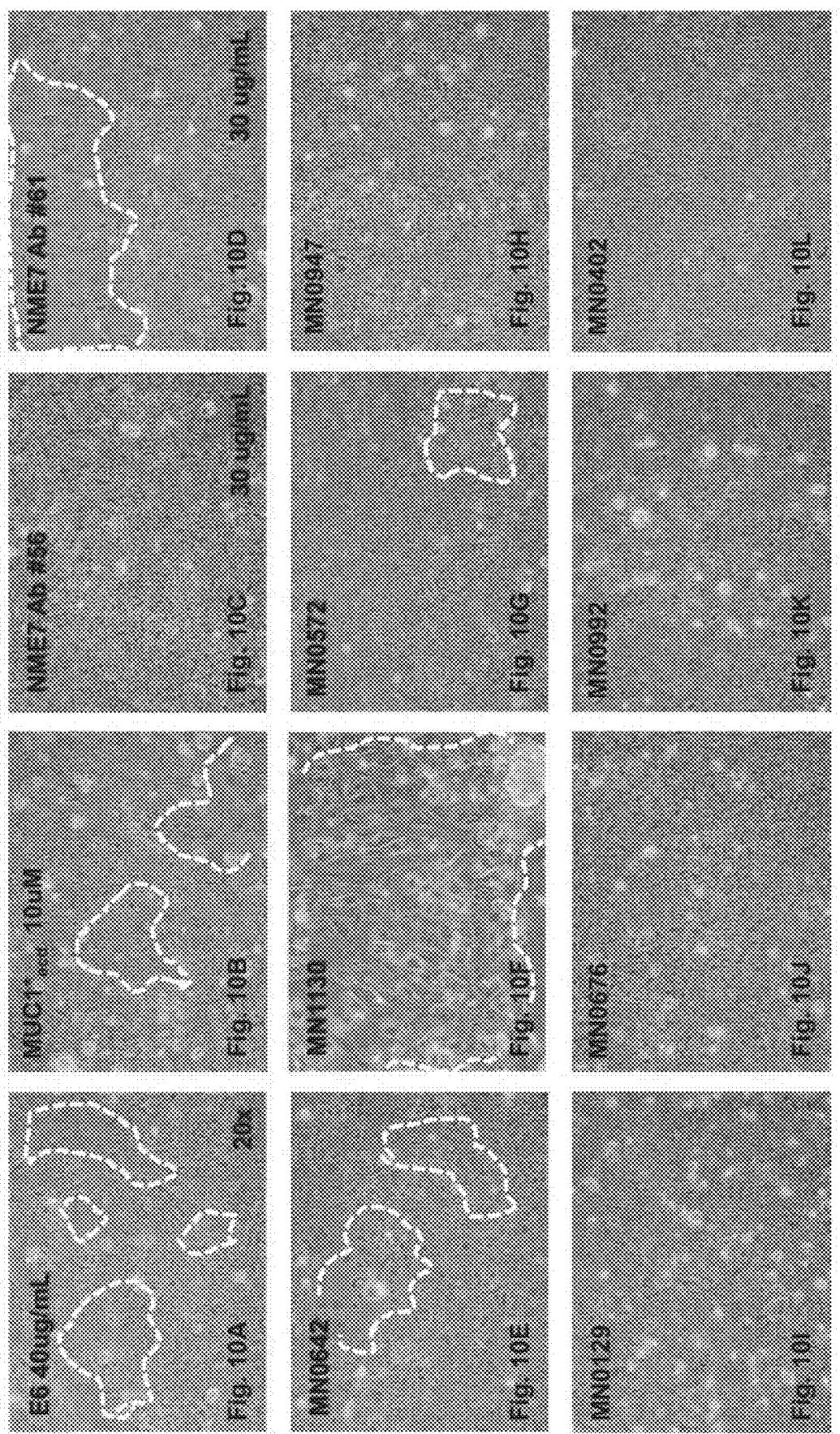
FIG. 10A-10L shows photographs at 20× magnification of human naïve state stem cells, grown in stem cell media without $NME7_{AB}$, over a MUC1* antibody, C3, surface and treated for 3 days with in the presence of a test agent. Dotted lines indicate areas where stem cell pluripotency or growth is inhibited or differentiation is induced.
Figure 11A:
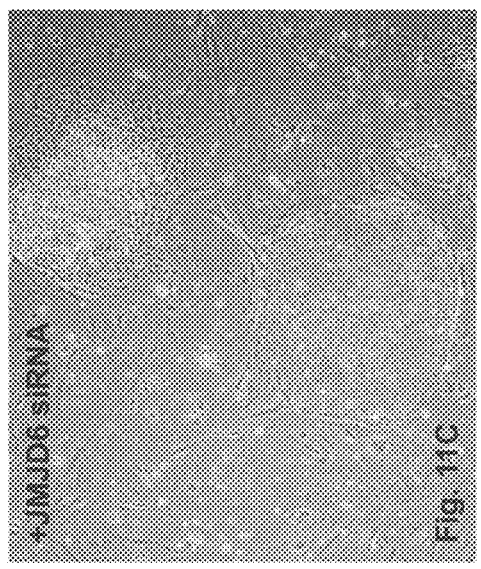
FIG. 11A-11F shows photographs at 4× magnification of human primed state stem cells, previously grown in bFGF over MEFs, but cultured in the absence of bFGF during the experiment, and treated for 3 days with a test agent. Dotted lines indicate areas where stem cell pluripotency or growth is inhibited or differentiation is induced.
Figure 11B:
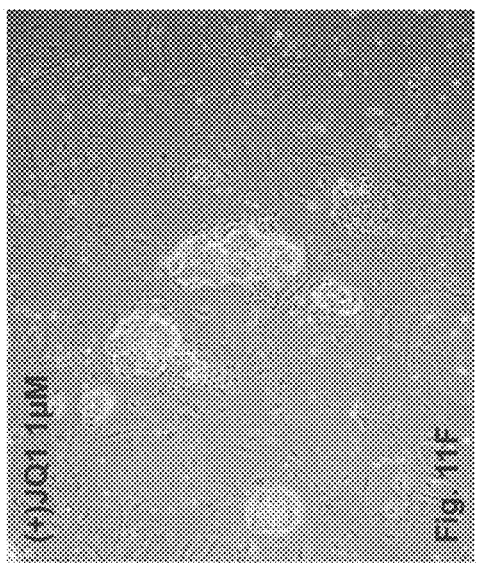
Figure 11C:
Figure 11D:
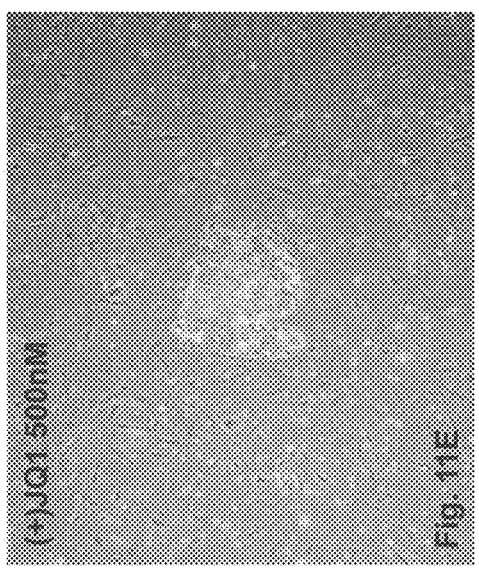
Figure 11E:
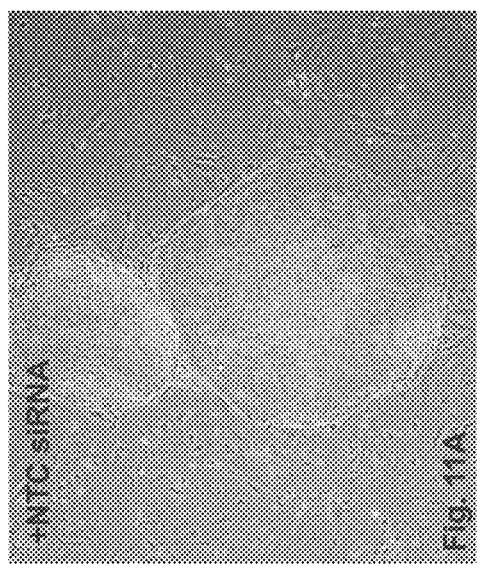
Figure 11F:
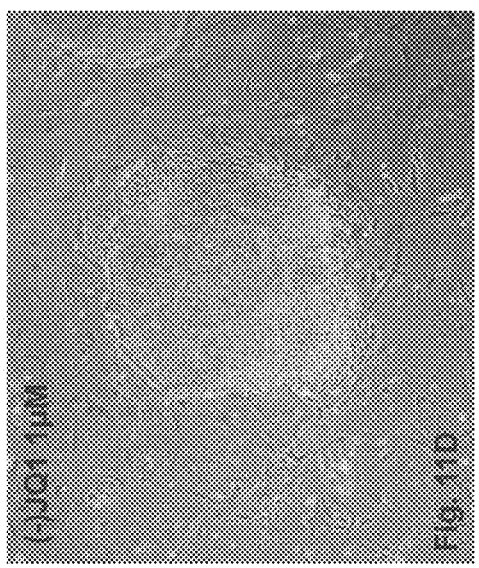

In the present application, "a" and "an" are used to refer to both single and a plurality of objects.

As used herein, "about" or "substantially" generally provides a leeway from being limited to an exact number. For example, as used in the context of the length of a polypeptide sequence, "about" or "substantially" indicates that the polypeptide is not to be limited to the recited number of amino acids. A few amino acids add to or subtracted from the N-terminus or C-terminus may be included so long as the functional activity such as its binding activity is present.

As used herein, administration "in combination with" one or more further therapeutic agents include simultaneous (concurrent) and consecutive administration in any order.

As used herein, "carriers" include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 µg/ml of carrier. In the case of compositions containing supplementary active ingredients, the dosages are determined by reference to the usual dose and manner of administration of the said ingredients.

The term "MUC1 Growth Factor Receptor" (MGFR) is a functional definition meaning that portion of the MUC1 receptor that interacts with an activating ligand, such as a growth factor or a modifying enzyme such as a cleavage enzyme, to promote cell proliferation. The MGFR region of MUC1 is that extracellular portion that is closest to the cell surface and is defined by most or all by the primary sequence of MGFR (PSMGFR). The MGFR is inclusive of both unmodified peptides and peptides that have undergone enzyme modifications, such as, for example, phosphorylation, glycosylation, etc. Results of the invention are consistent with a mechanism in which this portion is made accessible to the ligand upon MUC1 cleavage at a site associated with tumorigenesis that causes release of the some or all of the IBR from the cell. MGFR is also known as MUC1*.

The term "Primary Sequence of the MUC1 Growth Factor Receptor" (PSMGFR) or "FLR" is a peptide sequence that defines most or all of the MGFR in some cases, and functional variants and fragments of the peptide sequence, as defined below. The PSMGFR is defined as SEQ ID NO:3 listed below in Table 1, and all functional variants and fragments thereof having any integer value of amino acid substitutions up to 20 (i.e. 1, 2, 3, 4, 5, 6, 7, 8, 9, 10, 11, 12, 13, 14, 15, 16, 17, 18, 19, or 20) and/or any integer value of amino acid additions or deletions up to 20 at its N-terminus and/or C-terminus. A "functional variant or fragment" in the above context refers to such variant or fragment having the ability to specifically bind to, or otherwise specifically interact with, ligands that specifically bind to, or otherwise specifically interact with, the peptide of SEQ ID NO:3. One example of a PSMGFR that is a functional variant of the PSMGFR peptide of SEQ NO:3 (referred to as nat-PSMGFR—for "native") is SEQ ID NO:11 (referred to as var-PSMGFR), which differs from nat-PSMGFR by including an -SPY- sequence instead of the native -SRY- (see bold text in sequence listings). Var-PSMGFR may have enhanced conformational stability, when compared to the native form, which may be important for certain applications such as for antibody production. The PSMGFR is inclusive of both unmodified peptides and peptides that have undergone enzyme modifications, such as, for example, phosphorylation, glycosylation, etc.

As used herein, the term "PSMGFR" is an acronym for Primary Sequence of MUC1 Growth Factor Receptor as set forth as GTINVHDVETQFNQYKTEAAS-RYNLTISDVSVSDVPFPFSAQSGA (SEQ ID NO:3). In this regard, the "N-number" as in "N-10 PSMGFR", "N-15 PSMGFR", or "N-20 PSMGFR" refers to the number of amino acid residues that have been deleted at the N-terminal end of PSMGFR. Likewise "C-number" as in "C-10 PSMGFR", "C-15 PSMGFR", or "C-20 PSMGFR" refers to the number of amino acid residues that have been deleted at the C-terminal end of PSMGFR.

As used herein, the "extracellular domain of MUC1*" refers to the extracellular portion of a MUC1 protein that is devoid of the tandem repeat domain. In most cases, MUC1* is a cleavage product wherein the MUC1* portion consists of a short extracellular domain devoid of tandem repeats, a transmembrane domain and a cytoplasmic tail. The precise location of cleavage of MUC1 is not known perhaps because it appears that it can be cleaved by more than one enzyme. The extracellular domain of MUC1* will include most of the PSMGFR sequence but may have an additional 10-20 N-terminal amino acids.

As used herein, "NME family proteins" or "NME family member proteins", numbered 1-10, are proteins grouped together because they all have at least one NDPK (nucleotide diphosphate kinase) domain. In some cases, the NDPK domain is not functional in terms of being able to catalyze the conversion of ATP to ADP. NME proteins were formerly known as NM23 proteins, numbered H1 and H2. Recently, as many as ten (10) NME family members have been identified. Herein, the terms NM23 and NME are interchangeable. Herein, terms NME1, NME2, LAMES, NME6, NME7, NME8 and NME9 are used to refer to the native protein as well as NME variants. In some cases these variants are more soluble, express better in *E. coli* or are more soluble than the native sequence protein. For example, NME7 as used in the specification can mean the native protein or a variant, such as NME7-AB that has superior commercial applicability because variations allow high yield expression of the soluble, properly folded protein in *E. coli*. NME7-AB consists primarily of the NME7 A and B domains but is devoid of most of the DM10 domain (SEQ ID NO:12), which is at the N-terminus of the native protein. "NME1" as referred to herein is interchangeable with "NM23-H1". It is also intended that the invention not be limited by the exact sequence of the NME proteins. The mutant NME1-S120G, also called NM23-S120G, are used interchangeably throughout the application. The S120G mutants and the P96S mutant are preferred because of their preference for dimer formation, but may be referred to herein as NM23 dimers, NME1 dimers, or dimeric NME1, or dimeric NM23.

NME7 as referred to herein is intended to mean native NME7 having a molecular weight of about 42 kDa.

A "family of NME7" refers to full length NME7 as well as naturally occurring or artificially created cleaved form having a molecular weight about 30 kDa, 33 kDa, or a cleaved form having a molecular weight of about 25 kDa, a variant devoid or partially devoid of the DM10 leader sequence (SEQ ID NO:12), which is NME7 about amino acids 1-95 of NME7 represented by SEQ ID NO:5, such as NME7b, NME7-X1, NME7-AB or a recombinant NME7 protein, or variants thereof whose sequence may be altered to allow for efficient expression or that increase yield, solubility or other characteristics that make the NME7 more effective or commercially more viable. The "family of NME7" may also include "NME7-AB-like" protein, which is a protein in the range of 30 to 33 kDa that is expressed in cancer cells.

As used herein, an agent that "induces differentiation, or inhibits stem cell pluripotency or growth of the stem cell" refers to a protein, small molecule or nucleic acid that alone or in combination causes the stem cells either in the prime state or in the naïve state, to differentiate or inhibit stem cell pluripotency or growth of the stem cell. Examples of such agents include SMAD inhibitors and dorsomorphin.

As used herein, an agent that "inhibits expression or activity of an up regulated gene in the naïve state" with reference to primed stem cell refers to a protein, small molecule or nucleic acid that alone or in combination causes the inhibition of the normally upregulated gene in naïve stem cells. Examples of such agents include siRNA, antisense nucleic acids and small molecules.

As used herein, an agent that "increases expression or activity of down regulated gene in the naïve state" with reference to primed cell refers to a protein, small molecule or nucleic acid that alone or in combination causes the upregulation of the normally down regulated gene in naïve stem cells. Examples of such agents include genes coding for proteins that are indicative of differentiation such as vimentin, fibronectin and NF1 ans also microRNAs such as miR-145.

As used herein, an agent that "inhibits expression or activity of an up regulated gene in the naïve state" with reference to fibroblasts refers to a protein, small molecule or nucleic acid that alone or in combination causes the inhibition of the normally upregulated gene in naïve stem cells. Examples of such agents include anti-sense nucleic acids or siRNA specific for pluripotency genes OCT4, SOX2, KLF4 or c-Myc, and genes that encode vimentin, fibronectin, NF1 or the gene products themselves.

As used herein, an agent that "increases expression or activity of down regulated gene in the naïve state" with reference to fibroblasts refers to a protein, small molecule or nucleic acid that alone or in combination causes the upregulation of the normally down regulated gene in naïve stem cells. Examples of such agents include nucleic acids that encode the downregulated genes or the proteins themselves, and agents that induce differentiation such as SMAD inhibitors, dorsomorphin and the like.

As used herein, an "an agent that promotes pluripotency" or "reverts somatic cells to a stem-like or cancer-like state" refers to a protein, small molecule or nucleic acid that alone or in combination induces expression of or suppresses expression of certain genes such that the genetic signature shifts to one that more closely resembles stem cells or cancer cells. Examples include but are not limited to NME1 dimers, NME7, NME7-X1, NME7-AB, 2i, 5i, nucleic acids such as siRNA that suppress expression of MBD3, CHD4, BRD4, or JMJD6, microbial NME proteins that have high sequence homology to human NME1, NME2, NME5, NME6, NME7, NME8, or NME9, preferably with the regions that house NDPK domains.

As used herein, in reference to an agent being referred to as a "small molecule", it may be a synthetic chemical or chemically based molecule having a molecular weight between 50 Da and 2000 Da, more preferably between 150 Da and 1000 Da, still more preferably between 200 Da and 750 Da.

As used herein, in reference to an agent being referred to as a "natural product", it may be chemical molecule or a biological molecule, so long as the molecule exists in nature.

The term "cancer", as used herein, may include but is not limited to: biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; colon cancer, rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Preferred cancers are; breast, prostate, colon, lung, ovarian, colorectal, and brain cancer. Neoplasms in benign or malignant form are also considered within the purview of cancerous state.

The term "cancer treatment" as described herein, may include but is not limited to: chemotherapy, radiotherapy, adjuvant therapy, or any combination of the aforementioned methods. Aspects of treatment that may vary include, but are not limited to: dosages, timing of administration, or duration or therapy; and may or may not be combined with other treatments, which may also vary in dosage, timing, or duration. Another treatment for cancer is surgery, which can be utilized either alone or in combination with any of the aforementioned treatment methods. One of ordinary skill in the medical arts may determine an appropriate treatment.

As used herein, "inflammatory disease" or condition refers to disease or conditions characterized by an immune response that involves non-specific immune responses in particular areas. Such disease or condition may include without limitation, rheumatoid arthritis, inflammatory bowel syndrome, Crohn's disease, osteoarthritis, asthma, dermatitis, psoriasis, cystic fibrosis, post transplantation late and chronic solid organ rejection, multiple sclerosis, systemic lupus erythematosus, Sjogren syndrome, Hashimoto thyroiditis, polymyositis, scleroderma, Addison disease, vitiligo, pernicious anemia, glomerulonephritis, pulmonary fibrosis, autoimmune diabetes, diabetic retinopathy, rhinitis, ischemia-reperfusion injury, post-angioplasty restenosis, chronic obstructive pulmonary diseases (COPD), Graves' disease, gastrointestinal allergy, conjunctivitis, atherosclerosis, coronary artery disease, angina, cancer metastasis, small artery disease, or mitochondrial disease.

As used herein, "bodily sample" refers to any body tissue or body fluid sample obtained from a subject. Preferred are body fluids, for example lymph, saliva, blood, urine, milk and breast secretions, and the like. Blood is preferred in certain embodiments. Samples of tissue and/or cells for use in the various methods described herein can be obtained through standard methods including, but not limited to: tissue biopsy, including punch biopsy and cell scraping, needle biopsy, and collection of blood or other bodily fluids by aspiration or other methods.

A "subject", as used herein, refers to any mammal (preferably, a human), and preferably a mammal that has a disease that may be treated by administering the inventive composition to a site within the subject. Examples include a human, non-human primate, cow, horse, pig, sheep, goat, dog, or cat. Generally, the invention is directed toward use with humans.

As used herein, a "MUC1-positive cancer" or a "MUC1*-positive cancer" refers to a cancer that is characterized by the aberrant expression of MUC1, wherein aberrant may refer to the overexpression of the MUC1 gene or gene product, or the loss of the normal expression pattern of MUC1 or MUC1* which, in the healthy state, is restricted to the apical border of the cell or the luminal edge of a duct or an increase in the amount of MUC1 that is cleaved and shed from the cell surface.

Sequence Listing Free Text

As regards the use of nucleotide symbols other than a, g, c, t, they follow the convention set forth in WIPO Standard ST.25, Appendix 2, Table 1, wherein k represents t or g; n represents a, c, t or g; m represents a or c; r represents a or g; s represents c or g; w represents a or t and y represents c or t.

```
describes full-length MUC1 Receptor (Mucin 1 precursor, Genbank
Accession number: P15941)
                                                            (SEQ ID NO: 1)
    MTPGTQSPFF LLLLLTVLTV VTGSGHASST PGGEKETSAT QRSSVPSSTE

KNAVSMTSSV LSSHSPGSGS STTQGQDVTL APATEPASGS AATWGQDVTS

VPVTRPALGS TTPPAHDVTS APDNKPAPGS TAPPAHGVTS APDTRPAPGS

TAPPAHGVTS APDTRPAPGS TAPPAHGVTS APDTRPAPGS TAPPAHGVTS

APDTRPAPGS TAPPAHGVTS APDTRPAPGS TAPPAHGVTS APDTRPAPGS

TAPPAHGVTS APDTRPAPGS TAPPAHGVTS APDTRPAPGS TAPPAHGVTS

APDTRPAPGS TAPPAHGVTS APDTRPAPGS TAPPAHGVTS APDTRPAPGS

TAPPAHGVTS APDTRPAPGS TAPPAHGVTS APDTRPAPGS TAPPAHGVTS

APDTRPAPGS TAPPAHGVTS APDTRPAPGS TAPPAHGVTS APDTRPAPGS

TAPPAHGVTS APDTRPAPGS TAPPAHGVTS APDTRPAPGS TAPPAHGVTS

APDTRPAPGS TAPPAHGVTS APDTRPAPGS TAPPAHGVTS APDTRPAPGS

TAPPAHGVTS APDTRPAPGS TAPPAHGVTS APDTRPAPGS TAPPAHGVTS

APDTRPAPGS TAPPAHGVTS APDTRPAPGS TAPPAHGVTS APDTRPAPGS

TAPPAHGVTS APDTRPAPGS TAPPAHGVTS APDTRPAPGS TAPPAHGVTS

APDTRPAPGS TAPPAHGVTS APDTRPAPGS TAPPAHGVTS APDTRPAPGS

TAPPAHGVTS APDTRPAPGS TAPPAHGVTS APDTRPAPGS TAPPAHGVTS

APDTRPAPGS TAPPAHGVTS APDTRPAPGS TAPPAHGVTS APDNRPALGS

TAPPVHNVTS ASGSASGSAS TLVHNGTSAR ATTTPASKST PFSIPSHHSD

TPTTLASHST KTDASSTHHS SVPPLTSSNH STSPQLSTGV SFFFLSFHIS

NLQFNSSLED PSTDYYQELQ RDISEMFLQI YKQGGFLGLS NIKFRPGSVV

VQLTLAFREG TINVHDVETQ FNQYKTEAAS RYNLTISDVS VSDVPFPFSA

QSGAGVPGWG IALLVLVCVL VALAIVYLIA LAVCQCRRKN YGQLDIFPAR

DTYHPMSEYP TYHTHGRYVP PSSTDRSPYE KVSAGNGGSS LSYTNPAVAA

ASANL.

describes a truncated MUC1 receptor isoform having
nat-PSMGFR at its N-terminus and including the transmembrane
``` and cytoplasmic sequences of a full-length MUC1 receptor (SEQ ID NO: 2)
GTINVHDVETQFNQYKTEAASRYNLTISDVSVSDVPFPFSAQSGAGVPGWGI

ALLVLVCVLVALAIVYLIALAVCQCRRKNYGQLDIFPARDTYHPMSEYPTYHTHGRYVP

PSSTDRSPYEKVSAGNGGSSLSYTNPAVAAASANL.

describes the extracellular domain of Native Primary Sequence
of the MUC1 Growth Factor Receptor (nat-PSMGFR-an example of "PSMGFR")

(SEQ ID NO: 3)
GTINVHDVETQFNQYKTEAASRYNLTISDVSVSDVPFPFSAQSGA.

describes N-10 peptide of PSMGFR in which ten amino acids at the
N-terminus has been removed (SEQ ID NO: 4)
QFNQYKTEAASRYNLTISDVSVSDVPFPFSAQSGA.

describes NME7 amino acid sequence (NME7: GENBANK ACCESSION AB209049)

(SEQ ID NO: 5)
DPETMNHSERFVFIAEWYDPNASLLRRYELLFYPGDGSVEMHDVKNHRTFL

KRTKYDNLHLEDLFIGNKVNVFSRQLVLIDYGDQYTARQLGSRKEKTLALIKPDAISKA

GEIIEIINKAGFTITKLKMMMLSRKEALDFHVDHQSRPFFNELIQFITTGPIIAMEILRDDAI

CEWKRLLGPANSGVARTDASESIRALFGTDGIRNAAHGPDSFASAAREMELFFPSSGGC

GPANTAKFTNCTCCIVKPHAVSEGMLNTLYSVHFVNRRAMFIFLMYFMYRK.

describes human NME7-AB (SEQ ID NO: 6)
MEKTLALIKPDAISKAGEIIEIINKAGFTITKLKMMMLSRKEALDFHVDHQSRP

FFNELIQFITTGPIIAMEILRDDAICEWKRLLGPANSGVARTDASESIRALFGTDGIRNAAH

GPDSFASAAREMELFFPSSGGCGPANTAKFTNCTCCIVKPHAVSEGLLGKILMAIRDAGF

EISAMQMFNMDRVNVEEFYEVYKGVVTEYHDMVTEMYSGPCVAMEIQQNNATKTFRE

FCGPADPEIARHLRPGTLRAIFGKTKIQNAVHCTDLPEDGLLEVQYFFKILDN.

describes human NME7-X1

(SEQ ID NO: 7)
MMMLSRKEALDFHVDHQSRPFFNELIQFITTGPIIAMEILRDDAICEWKRLLGP

ANSGVARTDASESIRALFGTDGIRNAAHGPDSFASAAREMELFFPSSGGCGPANTAKFTN

CTCCIVKPHAVSEGLLGKILMAIRDAGFEISAMQMFNMDRVNVEEFYEVYKGVVTEYH

DMVTEMYSGPCVAMEIQQNNATKTFREFCGPADPEIARHLRPGTLRAIFGKTKIQNAVH

CTDLPEDGLLEVQYFFKILDN*.

describes Human NME7-A1

(SEQ ID NO: 8)
MEKTLALIKPDAISKAGEIIEIINKAGFTITKLKMMMLSRKEALDFHVDHQSRP

FFNELIQFITTGPIIAMEILRDDAICEWKRLLGPANSGVARTDASESIRALFGTDGIRNAAH

GPDSFASAAREMELFF-.

describes Human NME7-B3

(SEQ ID NO: 9)
MPSSGGCGPANTAKFTNCTCCIVKPHAVSEGLLGKILMAIRDAGFEISAMQM

FNMDRVNVEEFYEVYKGVVTEYHDMVTEMYSGPCVAMEIQQNNATKTFREFCGPADP

EIARHLRPGTLRAIFGKTKIQNAVHCTDLPEDGLLEVQYFFKILDN.

describes B3, which is NME7B peptide 3 (B domain)

(SEQ ID NO: 10)
AIFGKTKIQNAVHCTDLPEDGLLEVQYFF.

describes the extracellular domain of "SPY" functional variant of
the native Primary Sequence of the MUC1 Growth Factor Receptor having
enhanced stability (var-PSMGFR-An example of "PSMGFR")

(SEQ ID NO: 11)
GTINVHDVETQFNQYKTEAASPYNLTISDVSVSDVPFPFSAQSGA.

describes DM10 domain of NME7

-continued (SEQ ID NO: 12)

MNHSERFVFIAEWYDPNASLLRRYELLFYPGDGSVEMHDVKNHRTFLKRTK

YDNLHLEDLFIGNKVNVFSRQLVLIDYGDQYTARQLGSRK.

Cancer Cells and Stems Cells

Stem cells and cancer cells have a lot in common. Researchers are now discovering that many of the markers of undifferentiated stem cells are in fact also markers of cancer cells. Conversely, many of the molecular markers that were once considered markers of cancer are now being redefined as stem cell markers. For example, we have found that CXCR4 which was previously identified as a marker of metastatic cancer, is a marker of naïve stem cells. Cancer cells have also been characterized as undergoing epithelial to mesenchymal transition (EMT), where epithelial cells are terminally differentiated and mesenchymal cells are less differentiated and stem-like cell (Mani et al., 2008). Oncologists have long observed that as cancer stage progresses, the cells of the affected tissue look less and less mature or differentiated and look more like stem cells. Pathologists use the appearance of the degree of differentiation to classify cancer stage, with early cancers classified as moderately differentiated and aggressive or metastatic cancers being classified as poorly differentiated.

Further, we previously reported our discovery that the growth factor receptor MUC1* that mediates the growth of over 75% of all cancers is present on 100% of pluripotent human stem cells (Hikita et al., 2008; Smagghe et al., 2013). More recently, we discovered a growth factor, $NME7_{AB}$, that binds to and activates growth, survival and self-renewal functions of MUC1* (Carter et al., 2016). Human stem cells can be maintained in a pluripotent state by culturing in a minimal media containing $NME7_{AB}$ as the only growth factor. Stem cells cultured in $NME7_{AB}$ are maintained in the earliest state called naïve. $NME7_{AB}$ is in every cell of Day 3 human morula, where all the cells are in the earliest naïve state. By Day 5 of the human blastocyst, $NME7_{AB}$ is confined to the inner cell mass, where the cells are naïve by definition. $NME7_{AB}$ should be turned off after Day 5 of a human blastocyst except that it is found in testis. However, we found that NME7, in truncated forms corresponding to $NME7_{AB}$ and NME7-X1, are expressed in aggressive and metastatic cancers (WO2015/023694). We demonstrated that adding $NME7_{AB}$ to regular cancer cells made them transition to more metastatic cancer cells that formed tumors in animals from as few as 50 implanted cancer cells, whereas non-metastatic cancer cells require 4-6M implanted cells to form a tumor. Additionally, injecting the animals with $NME7_{AB}$ caused the engrafted cancer cells to metastasize. These data further establish a functional link, at the molecular level, between stem cells and cancer cells and more particularly between aggressive or metastatic cancers and naïve stem cells.

These results imply that the pathways that promote pluripotency in stem cells are the same pathways that promote cancer. Agents that inhibit stem pluripotency or growth, or induce stem cell differentiation are agents that, when administered to a patient, are effective anti-cancer agents for the prevention or treatment of cancers.

The inventors have shown that agents that convert or maintain stem cells in a naïve state are able to transition cancer cells to a more metastatic state. Thus, naïve stem cells are similar in many ways to aggressive or metastatic cancer cells. These results imply that the pathways that promote pluripotency in naïve stem cells are the same pathways that promote metastasis in cancer cells. The prediction is that agents that inhibit naïve stem pluripotency or growth, or induce stem cell differentiation are agents that, when administered to a patient, are effective anti-cancer agents for the prevention or treatment of metastatic cancers.

The vast differences between naïve stem cells and primed stem cells suggest that these two distinct types of stem cells grow pluripotently and resist differentiation by different pathways. Therefore, drug candidates that inhibit the pluripotency or proliferation of naïve stem cells, but not of primed state stem cells, or have a milder effect on primed state stem cells, are drug candidates that would be most effective in the treatment or prevention of aggressive or metastatic cancers.

In one aspect of the invention, stem cells are cultured in the presence of an agent that may be a drug candidate, it is observed that the agent inhibits stem cell pluripotency, or growth, or induces stem cell differentiation and said agent is administered to a patient for the prevention or treatment of cancers. In one aspect of the invention, the stem cells are human. In another aspect the stem cells are in the naïve state. In some cases the stem cells are maintained in the naïve state by culturing in NME1 dimers, NME7, $NME7_{AB}$, NME7-X1 or by other methods reported to maintain stem cells in a more naïve state (Silva et al., 2008; Hanna et al., 2010; Gafni et al., 2013; Theunissen et al., 2014; Ware et al., 2014). In yet another aspect, the agent is observed to inhibit pluripotency, or growth, or induce differentiation of naïve stem cells, but not primed state stem cells, or the agent has a lesser effect on primed state stem cells and the agent is administered to a patient at risk of developing or has been diagnosed with metastatic cancer. Because we have found that all pluripotent stem cells are MUC1* positive, and naïve stem cells express $NME7_{AB}$, agents identified as described above will be most effective for the treatment of MUC1* positive, or $NME7_{AB}$ positive, or NME7-X1 positive cancers.

Cancer Terms

The terms cancer "migration" and "invasion", as used herein are synonymous and are characteristic of metastatic cancer cells.

Migration assay as used herein refers to coating a surface with an extracellular matrix protein such as collagen, fibronectin or the like, plating cancer cells onto that surface, but either removing them from an area or restricting them from being plated onto an area, and then photographing the cells as they move into the restricted space or, in the presence of an effective inhibitory agent, are inhibited from moving into the restricted space. Migration assays in which cells are removed from an area are called scratch assays or wound assays and those that restrict cells from being plated in an area, herein is called a platypus assay.

Metastatic cancer as used herein includes cancers that have infiltrated or invaded neighboring tissues, or that have moved into lymph nodes, or have moved into organs other than the organ of original cancer. As used herein, the term metastatic cancer includes those cancers that are known to readily become metastatic. For example, melanoma that are of a certain depth of skin are statistically going to metastasize within a predictable period of time. Another example is pancreatic cancer, which is known to metastasize, especially to the liver, within a predictable period of time.

Pathologists have two major ways of assessing tumor aggressiveness or metastatic potential. One way is to assign a Grade or Stage. Grade 1 means the tumor cells look the most like normal cells, called well-differentiated. Well-differentiated cancer cells are slow growing. Grade 2 means the tumor are moderately differentiated and so are faster growing. Grade 3 means the tumor cells look very abnormal and look poorly differentiated, which are the fastest growing cancer cells.

Pathologists also use a TNM system of scoring tumors based on analysis of biopsied tissues and other diagnostic techniques. "T" stands for extension into adjacent tissues, "N" stands for involvement of lymph nodes and "M" stands for metastasis to distal organs. Specifically, the T score ranges from 0-4 where zero indicates no evidence of tumor and 4 relates to large tumor that has extended into adjacent tissues. The N score ranges from 0-3, where N0 means no evidence of lymph node involvement, N1 means cancer has spread to nearby lymph nodes or a small number of nodes. N2 and N3 indicates tumor has spread to greater number of lymph nodes and/or to more distant nodes. The M score is either 0 or 1, where M0 means no evidence of metastasis and M1 means cancer has spread to distant organs or organs other than the organ of origin.

Drug Screen

Here we describe therapeutics and methods for identifying therapeutics for the prevention or treatment of cancers, metastatic cancers or for the prevention of cancer recurrence. In one embodiment, these therapeutics are for the prevention or treatment of cancers that are MUC1-positive, MUC1*-positive, NME7-positive, $NME7_{AB}$ positive or NME7-X1-positive. We have determined that the signaling pathways that control the growth and pluripotency of naïve stem cells are different from those that control the growth and pluripotency of primed stem cells. Further, we discovered that the same pathways that mediate growth or pluripotency of naïve stem cells also mediate the growth and metastatic potential of cancer cells. We found that agents that inhibit stem cell pluripotency or growth, or induce stem cell differentiation are agents that inhibit cancer cell proliferation and when administered to a patient, are effective agents for the prevention or treatment of cancers. Agents that inhibit naïve stem cell pluripotency or growth, or induce naïve stem cell differentiation are agents that inhibit cancer cell migration, which is a characteristic of metastatic cancers, and when administered to a patient, would be effective anti-cancer agents for the prevention or treatment of aggressive or metastatic cancers. Agents that inhibit pluripotency or growth, or induce stem cell differentiation of naïve stem cells but not primed stem cells, or have a far lesser effect on primed stem cells are effective agents for the prevention or treatment of aggressive or metastatic cancers.

Thus, to identify therapeutic agents to treat patients at risk of developing or diagnosed with cancer: 1) grow stem cells in pluripotent state; 2) contact populations of pluripotent stem cells with drug candidates; 3) identify drug candidates that inhibit pluripotency or growth, or induce differentiation of pluripotent stem cells; and 4) conclude that drug candidates that inhibit pluripotency or growth, or induce differentiation of pluripotent stem cells are anti-cancer agents.

To identify therapeutic agents to treat patients at risk of developing or diagnosed with metastatic cancer: 1) grow stem cells in naïve state; 2) contact stem cells with drug candidates; 3) identify drug candidates that inhibit pluripotency or growth, or induce differentiation of naïve stem cells; and 4) conclude that drug candidates that inhibit pluripotency or growth, or induce differentiation of naïve stem cells are anti-cancer agents for the treatment or prevention of aggressive cancers or cancer metastasis.

Alternatively, to identify therapeutic agents to treat patients at risk of developing or diagnosed with metastatic cancer: 1) grow stem cells in naïve state and, optionally, in parallel grow stem cells in primed state; 2) contact both populations of stem cells with drug candidates; 3) identify drug candidates that inhibit pluripotency or growth, or induce differentiation of naïve stem cells, but, optionally, not primed stem cells or have a far lesser effect on primed stem cells; and 4) conclude that drug candidates that inhibit pluripotency or growth, or induce differentiation of naïve stem cells, but, optionally not primed stem cells, or have a far lesser effect on primed stem cells, are anti-cancer agents for the treatment or prevention of cancer metastasis.

Agents screened in these ways to assess their potential as anti-cancer or anti-metastasis agents may be of any form including but not limited to small molecules, natural products, antibodies, antibody fragments, libraries or antibodies or antibody fragments, peptides, peptide mimics, nucleic acids, anti-sense nucleic acids, DNA, RNA, coding or non-coding, inhibitory RNAs, bacteria and microbes. In one aspect of the invention, the stem cells are of human origin. In yet another aspect of the invention, the stem cells are of primate origin. In yet another aspect of the invention, the stem cells are of mammal origin. In yet another aspect of the invention, the stem cells are of rodent origin.

In another aspect of the invention, novel anti-cancer or anti-metastasis drug targets are identified by identifying genes that are upregulated in naïve stem cells but not in primed stem cells. In yet another aspect of the invention, novel anti-cancer or anti-metastasis drug targets are identified by identifying microRNAs that are upregulated in naïve stem cells but not in primed stem cells.

Drug Screen Results

WO2009/042815 discloses that in a direct binding assay a series of carboline molecules inhibited the interaction between the extracellular domain of MUC1* and NME proteins, especially NME1 dimers and $NME7_{AB}$. We also previously showed that the same series of carbolines that inhibited MUC1*-NME interaction also inhibited cancer cell growth. We tested a panel of ten small molecules, including three carbolines (FIG. 1), and biologicals for their ability to inhibit naïve stem cell pluripotency or growth compared to primed state stem cells. We previously demonstrated that the Fab of anti-MUC1* monoclonal antibody, E6, or a synthetic peptide corresponding to the extracellular domain of MUC1*, FLR also known as PSMGFR, inhibit both cancer and stem cell pluripotency and growth by inhibiting the MUC1*-$NME7_{AB}$ or MUC1*-NME1 interaction. We also tested novel anti-NME7 antibodies #56 and #61; we had previously shown that they inhibit $NME7_{AB}$'s ability to transform regular cancer cells into metastatic cancer cells, although #61 is much more potent than #56. We also previously showed that some carboline small molecules inhibit the growth of cancers by inhibiting the MUC1*-$NME7_{AB}$ or MUC1*-NME1 interaction.

JQ1 is a small molecule that reportedly inhibits BRD4 and has been shown to inhibit cancer cell migration and cancer cell proliferation, but has not been reported to have any effect on stem cells. The stem cell screening assay, was performed in both the presence and absence of the stem cell growth factors: $NME7_{AB}$ for growing naïve stem cells or FGF for growing primed stem cells. If the cognate growth factor was present, then the biological or small molecule would have to compete away the growth factor to get an effect. Therefore, we expected to see more of an effect when the growth factor, FGF for primed stem cells or NME7$_{AB}$ or NME1 dimers for naïve stem cells, was absent. The results are summarized in the table of FIG. 2. The effect of the compounds on stem cells was visually determined and compounds were ranked 0-4, with 4 being the greatest effect and 0 being no observable effect. The major effect that was observed was a change from pluripotent stem cell morphology, which is a cobblestone pattern of small round cells with a large nucleus to cytoplasm ratio, to that of differentiating stem cells, which are elongated, large and flattened cells with a smaller nucleus to cytoplasm ratio. Some compounds also severely inhibited growth of the stem cells. The compounds were added to a final concentration of 6 uM to either naïve state stem cells or primed state stem cells. In this particular case, the naïve state stem cells were maintained in a naïve state by culturing in a media containing NME7$_{AB}$ or NME1 dimers. However, other methods such as 2i and 5i (Silva et al., 2008, Nichols and Smith, 2009, Theunissen et al., 2014)] can be used to maintain stem cells in a more naïve state. In this case primed state stem cells were cultured in bFGF over a layer of MEFs, although it is known that any bFGF containing media will maintain stem cells in the primed state.

We have shown that JQI has an inhibitory effect on naïve stem cell growth but not primed stem cell growth. In addition, previous studies have shown JQ1 has anti-inflammatory effects (Belkina et al, 2013; Meng et al, 2014). Therefore, the compounds identified in this study should also have anti-inflammatory effects and be useful in the treatment of inflammation in obesity, asthma, chronic peptic ulcer, tuberculosis, rheumatoid arthritis, chronic periodontitis, ulcerative colitis and Crohn's disease, chronic sinusitis, Chronic active hepatitis etc.

Of the ten small molecules and four biologicals tested, none had any effect on primed stem cells except MN1130, which had a modest effect on primed stem cell colonies. However, when the same agents were tested on naïve stem cells, three of the four biologicals and two of the three carbolines profoundly inhibited stem cells pluripotency and growth and induced differentiation. Note that the agents induced changes in the morphology of the naïve stem cells that are consistent with the morphological changes that take place when stem cells initiate differentiation (indicated by dotted line). The cells flatten, take on a more spindle shape and the ratio of nucleus to cytoplasm decreases.

In addition to the small molecules pictured in FIG. 1, an anti-MUC1* Fab, the FLR peptide, aka PSMGFR peptide, and anti-NME7 antibodies #56 and #61 were tested. FIG. 2 is a summary of how those drug candidates performed in the naïve versus primed stem cell drug in which a confirmed drug hit is one in which the compound induced differentiation of the naïve stem cells but had no effect or a lesser effect on the FGF-grown primed stem cells. FIGS. 3-10 show photographs of stem cells that were treated with the small molecules, the Fab, the MUC1* extracellular domain peptide "FLR" or the small molecules. FIGS. 3-6 shows that none of the agents or compounds significantly induced differentiation of primed state stem cells. However, FIGS. 7-10 show that several agents induced differentiation of naïve state stem cells. Differentiating portions are indicated by dashed lines. Specifically, at these concentrations, the anti-MUC1* E6 Fab, the FLR peptide, anti-NME7 #61, MN572, MN0642 and MN1130 all induced differentiation of naïve state stem cells and are predicted to be potent inhibitors of cancer and inhibitors of metastatic cancers. They could be administered to patients for the prevention or treatment of cancers or metastatic cancers. The E6 Fab has been shown to inhibit the growth of all MUC1* positive cancer cells. In addition, the anti-MUC1* E6 Fab was shown to robustly inhibit MUC1* positive tumor growth in animals. Compound MN0642 similarly has been shown to inhibit the growth of cancer cells in vitro. The FLR (PSMGFR) peptide and anti-NME7 #61 have been shown to inhibit the transition of regular cancer cells to metastatic cancer cells.

Figures 12A, 12B, 12C, 12D, 12E, 12F:
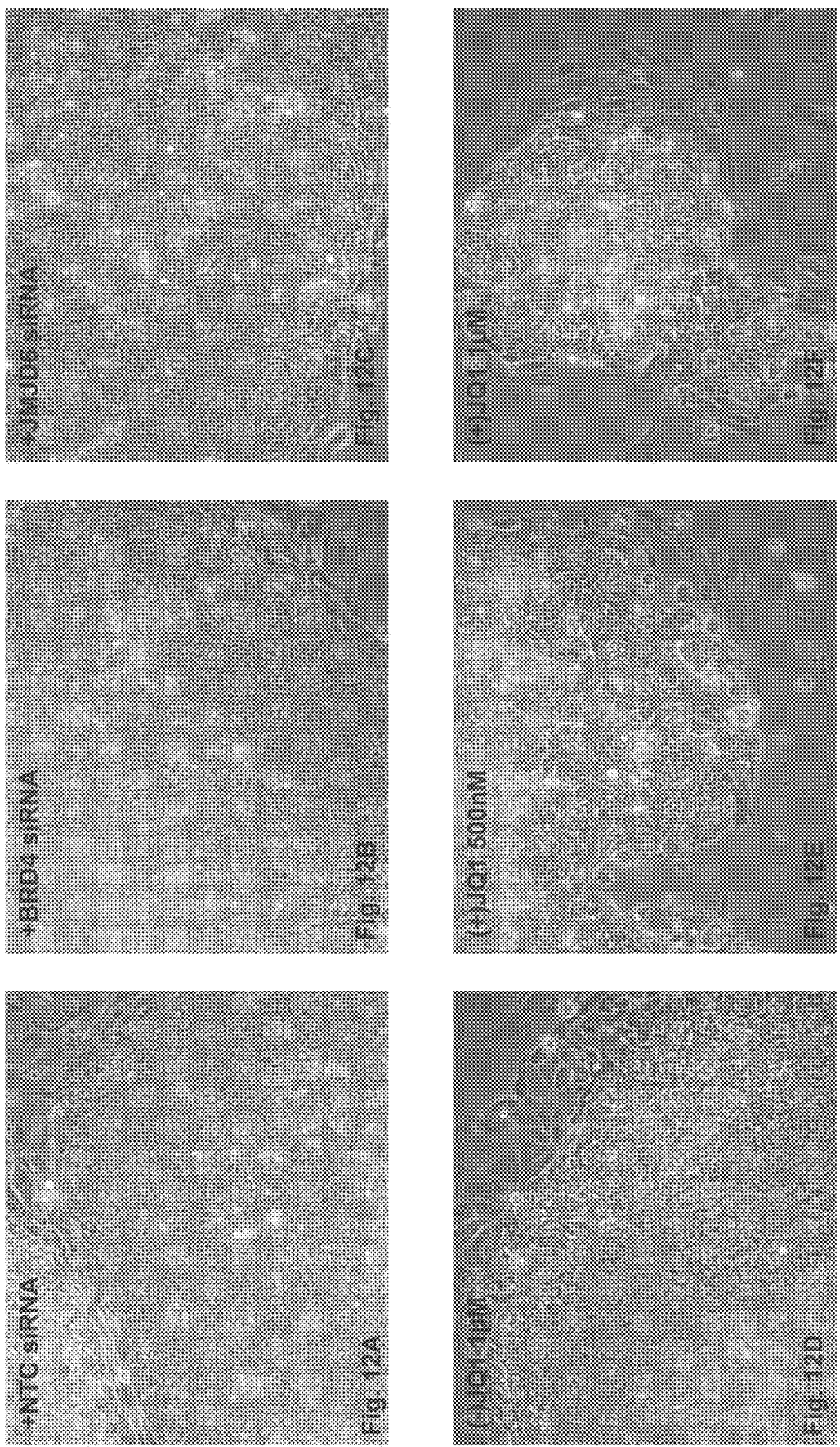
FIG. 12A-12F shows photographs at 20× magnification of human primed state stem cells, previously grown in bFGF over MEFs, but cultured in the absence of bFGF during the experiment, and treated for 3 days with a test agent. Dotted lines indicate areas where stem cell pluripotency or growth is inhibited or differentiation is induced.
Figures 13A, 13B, 13C, 13D, 13E, 13F:
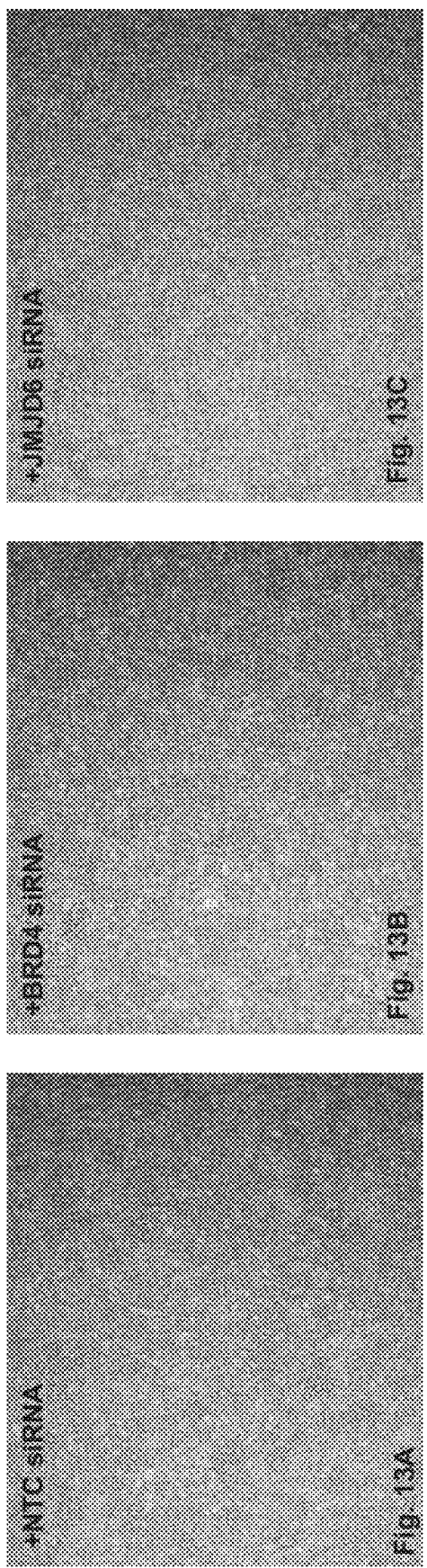
FIG. 13A-13F shows photographs at 4× magnification of human naïve state stem cells, previously grown in $NME7_{AB}$ over a MUC1* antibody surface, C3, but cultured in the absence of $NME7_{AB}$ during the experiment, and treated for 3 days with a test agent. Dotted lines indicate areas where stem cell pluripotency or growth is inhibited or differentiation is induced.
Figure 14A:

FIG. 14A-14F shows photographs at 20× magnification of human naïve state stem cells, previously grown in $NME7_{AB}$ over a MUC1* antibody surface, C3, but cultured in the absence of $NME7_{AB}$ during the experiment, and treated for 3 days with a test agent. Dotted lines indicate areas where stem cell pluripotency or growth is inhibited or differentiation is induced.
Figure 14B:
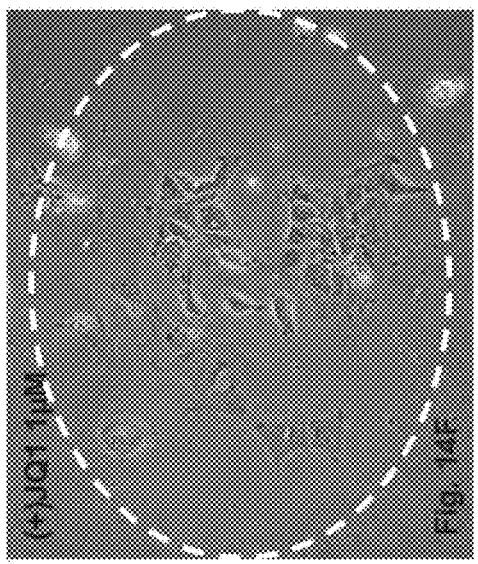
Figure 14C:
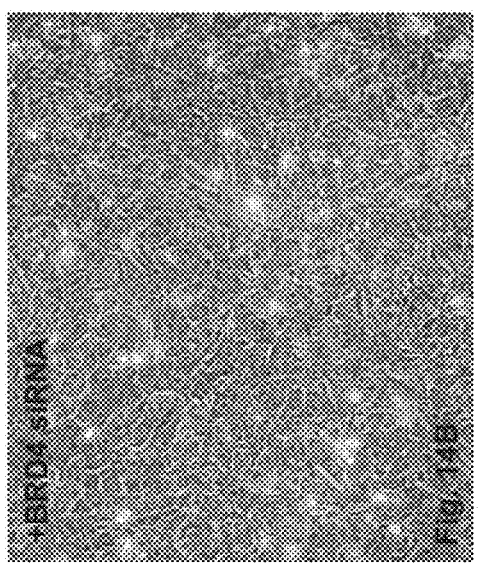
Figure 14D:
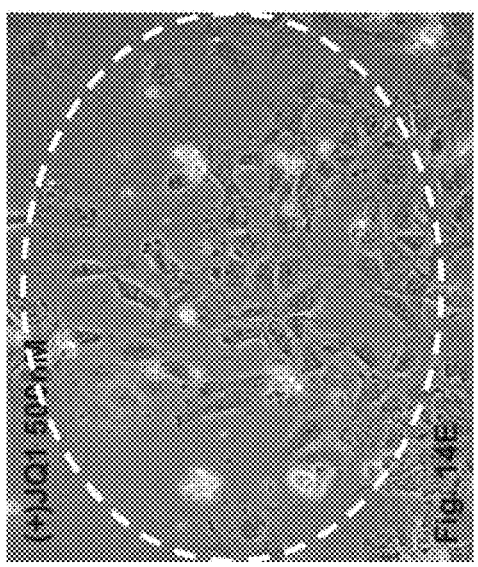
Figure 14E:
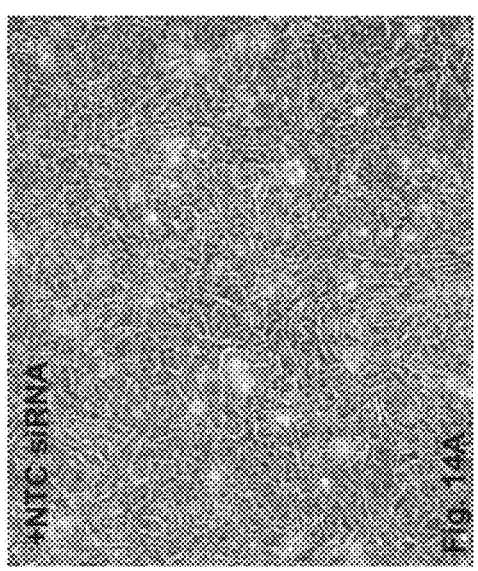
Figure 14F:
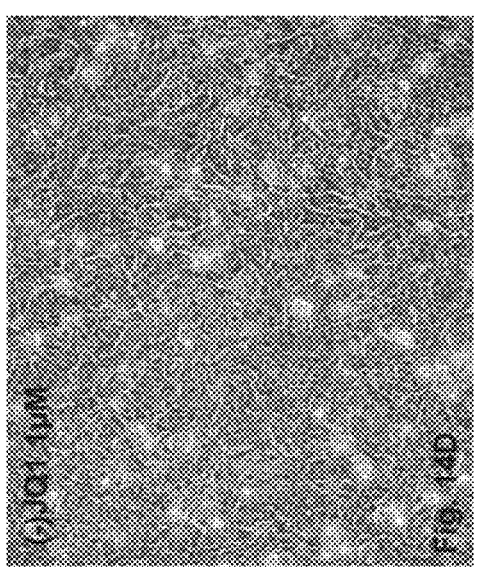

Several other small molecules that bear no resemblance to compounds of the invention but that were reported to inhibit cancer growth or migration were tested and found to inhibit pluripotency, or growth or induce differentiation of stem cells, particularly naïve stem cells. For example, a small molecule that bears no resemblance to carbolines, JQ1(+) (FIG. 1), reportedly inhibits inflammation (Belkina et al., 2013), cancer pluripotency (Fillippakopoulos et al., 2010) and cancer cell migration (Tang et al., 2013). JQ1(+) reportedly inhibits BRD4 and its inactive enantiomer, JQ1(-), has no effect (Fillippakopoulos et al., 2010). BRD4 has been reported to be a regulator of NME7, a regulator of oncogene c-Myc and a component of super-enhancers that overexpress a selected few genes in cancer cells and in stem cells. At this time, it is not entirely clear which of these purported functions of BRD4 are correct. Primed state stem cells were treated for 3 days with JQ1(+), inactive stereoisomer JQ1 (-), BRD4 specific siRNA, or JMJD6 specific siRNA. None of these agents appeared to induce differentiation of primed state stem cells, but JQ1(+) may have a modest effect on the size of primed stem cell colonies (FIG. 11), and also appeared to cause some abnormal morphology (FIG. 12). However, JQ1(+) dramatically induced differentiation of naïve state stem cells and inhibited their growth (FIGS. 14 E-F, 15 E-F and 16 E-F). Whether the naïve stem cells were cultured in NME7$_{AB}$ (FIG. 13-14) or NME1 dimers (FIG. 15-16), JQ1(+) inhibited naïve stem cell pluripotency and growth and induced differentiation. Since JQ1 (+) is a known inhibitor of inflammation, cancer cell migration and cancer cell proliferation, these results show that agents that are effective treatments for inflammation or the prevention or treatment of cancers, also inhibit naïve stem cell pluripotency or growth or induce stem cell differentiation. Therefore, the agents that inhibit naïve stem cell pluripotency or growth or induce stem cell differentiation are also effective treatments for inflammation or the prevention or treatment of cancers.

We then tested an expanded panel of agents, including agents known to inhibit cancer growth or migration (FIG. 17) (Horm et al., 2012; Meng & Yue, 2014; Zhen et al., 2014), which is characteristic of aggressive or metastatic cancers. We also synthesized a series of novel small molecules, tested them in the stem cell drug screening assay, and then tested them in a series of biological assays to test their ability to inhibit cancer cell migration, invasion or proliferation. The results of the stem cell screen and biological assays are summarized in the Table of FIGS. 18A-18E.

Figures 19A, 19B, 19C, 19D, 19E, 19F, 19G, 19H:
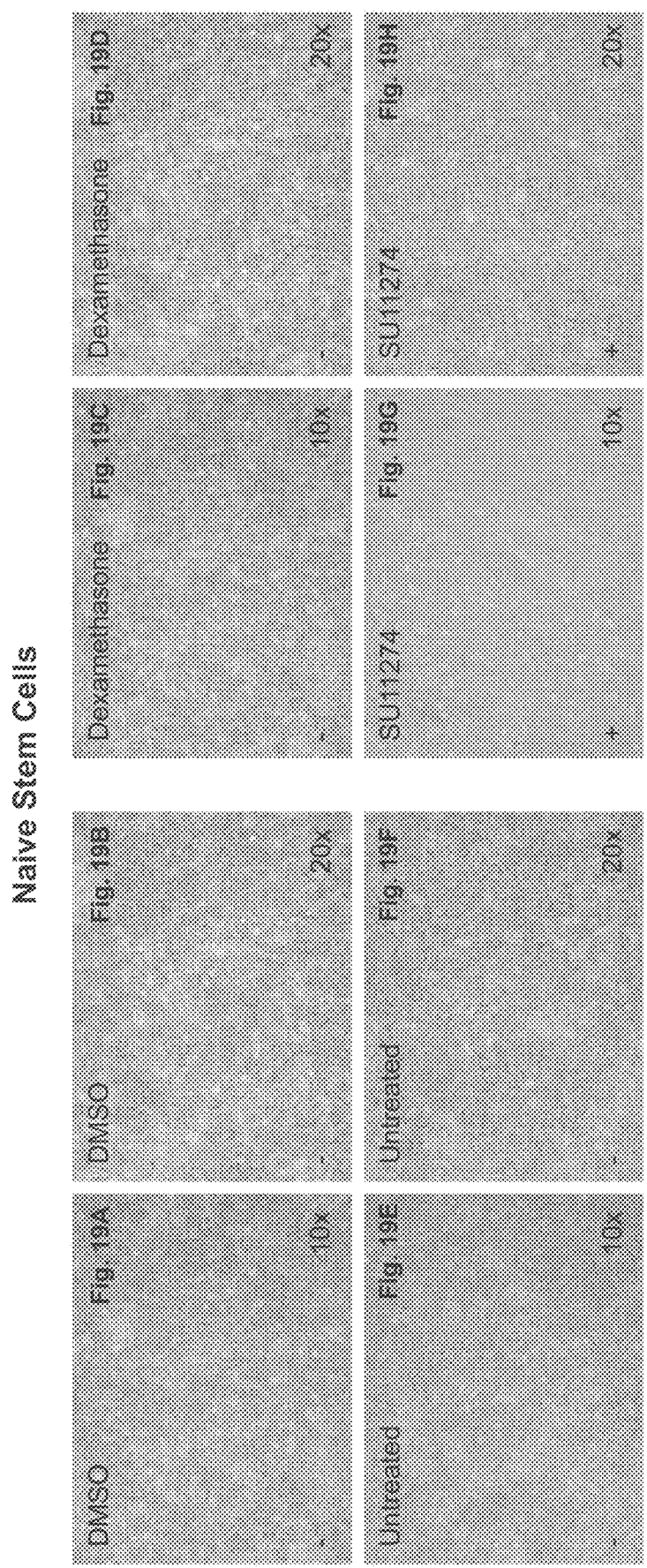
Figures 19I, 19J, 19K, 19L, 19M, 19N, 19O, 19P:
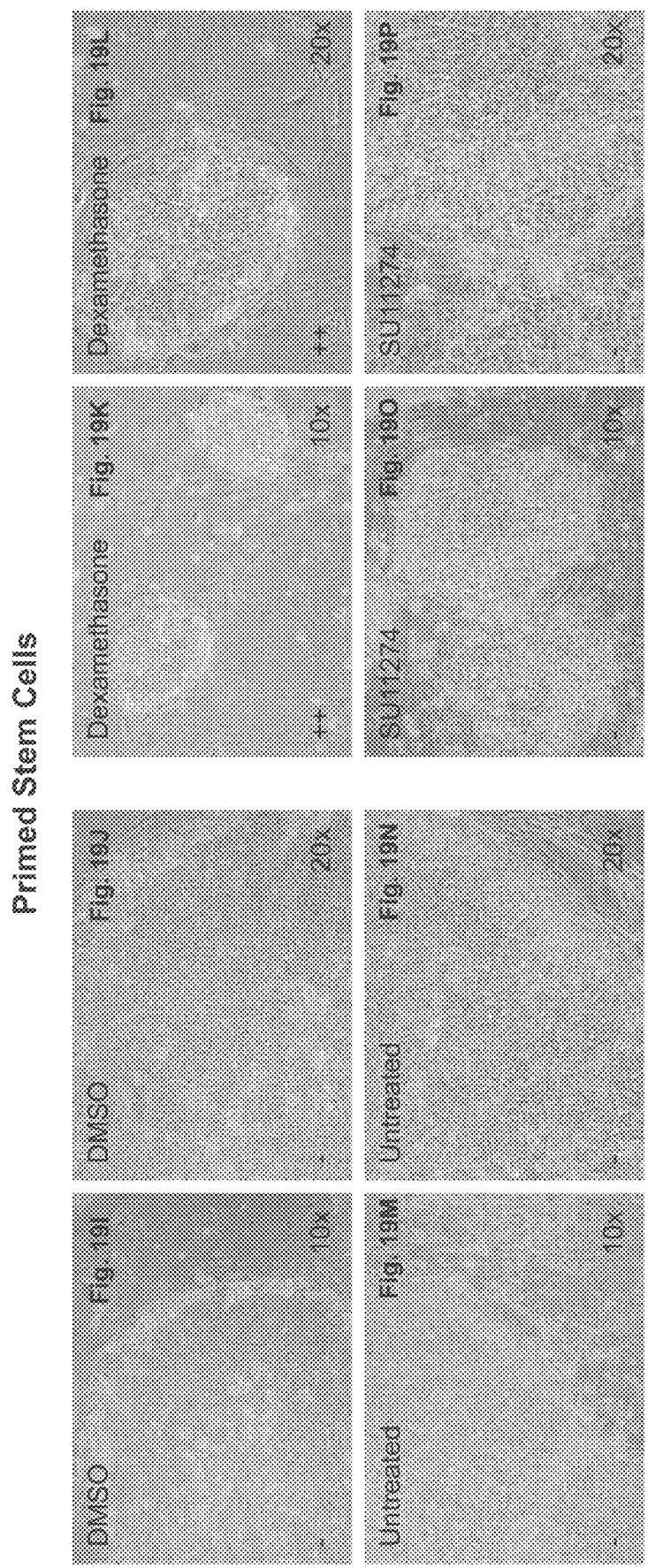

FIG. 19A-19P shows photographs of control stem cells or stem cells to which was added known anti-migration compounds Dexamethasone and SU11274.

Figure 20:
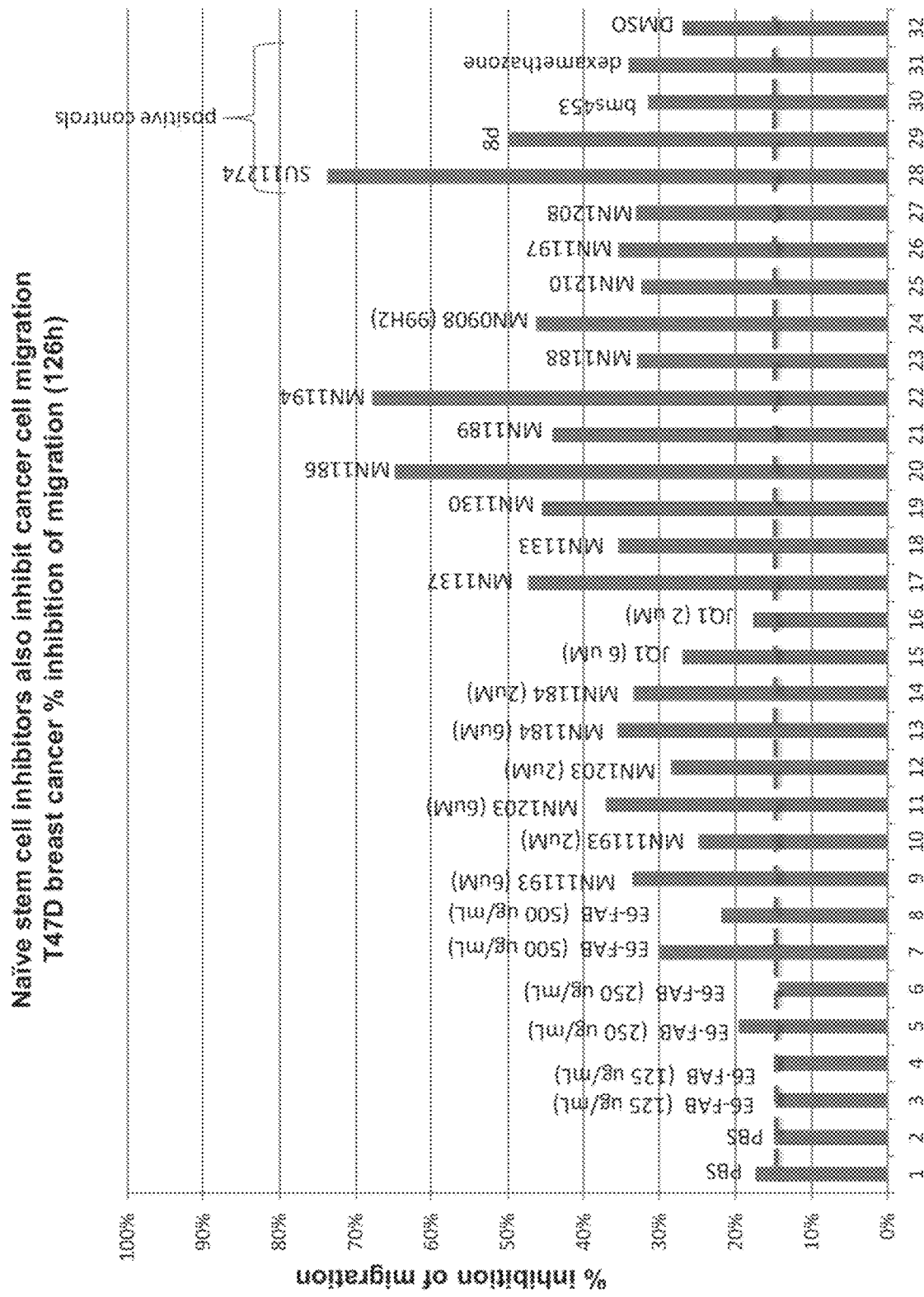
FIG. 20 is a bar graph showing the measured percent inhibition of cancer cell migration. The cancer cell line used was T47D breast cancer cell line. Multi-well plate was coated with collagen and cells were plated using Platypus system that restricts cells from entering center of wells until cells have attached. The percent area that remains free of cells at 126 hrs was measured using Image J and graphed. The agents that were tested were: an anti-MUC1* Fab "E6", which has been shown to inhibit proliferation of virtually all MUC1* positive cells tested, in vitro and in vivo; JQ1, a BRD4 inhibitor reported to inhibit cancer cell migration and proliferation in vitro and in vivo; small molecules reported by others to inhibit migration of a range of cancer cells; and novel small molecules of the invention.
Figures 21A, 21P:
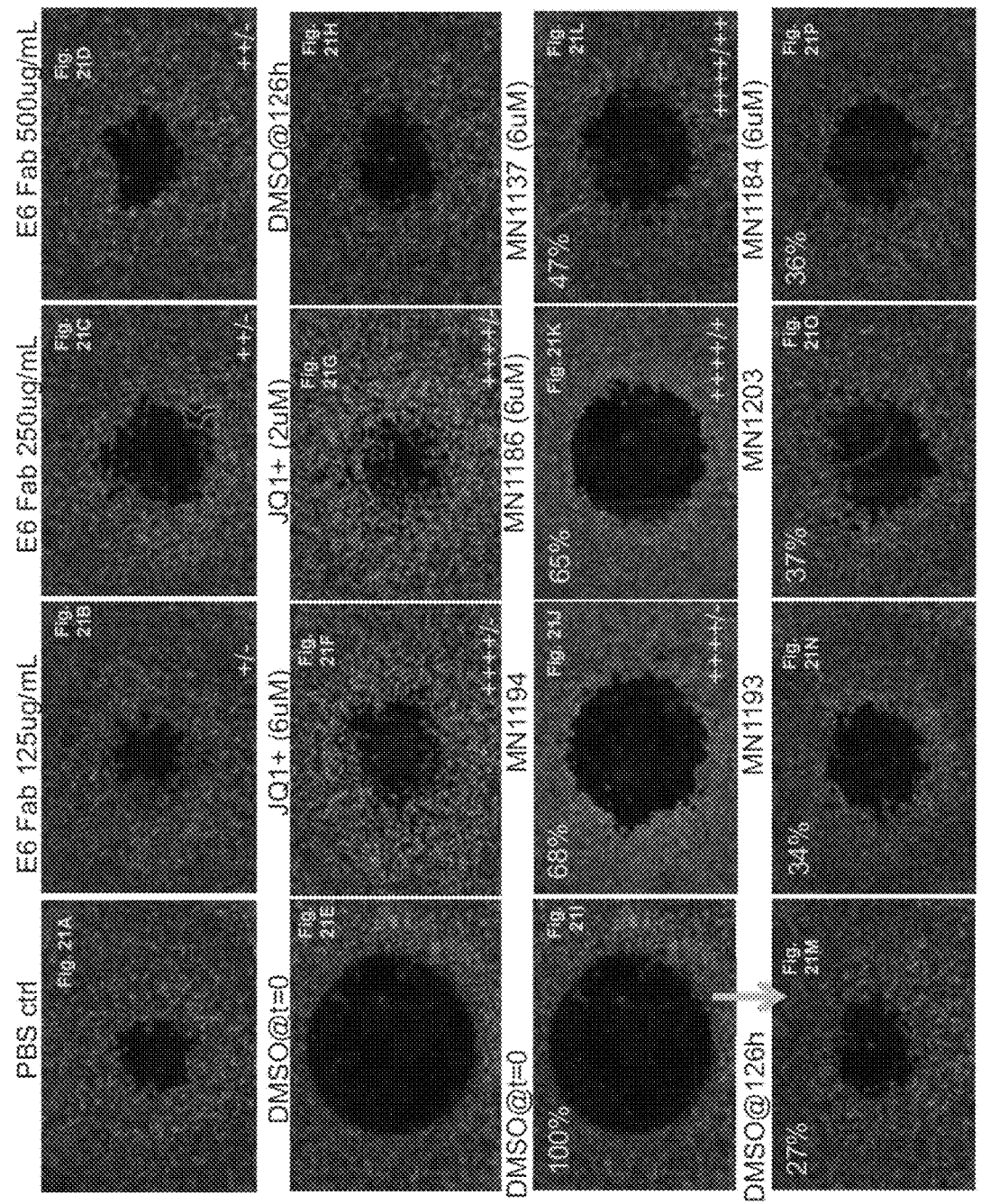
FIG. 21A-21P shows representative photographs of the cancer cell migration assay at 126 hours, wherein the cancer cells were treated with a panel of agents. Small molecules were dosed at 6 uM final concentration unless otherwise indicated. The "+" or "−" indicates the score each agents received in the naïve/primed stem cell assay. For example +++/− indicates the compound profoundly inhibited the pluripotency and proliferation of naïve stem cells but had no effect on primed stem cells.
Figure 22A:
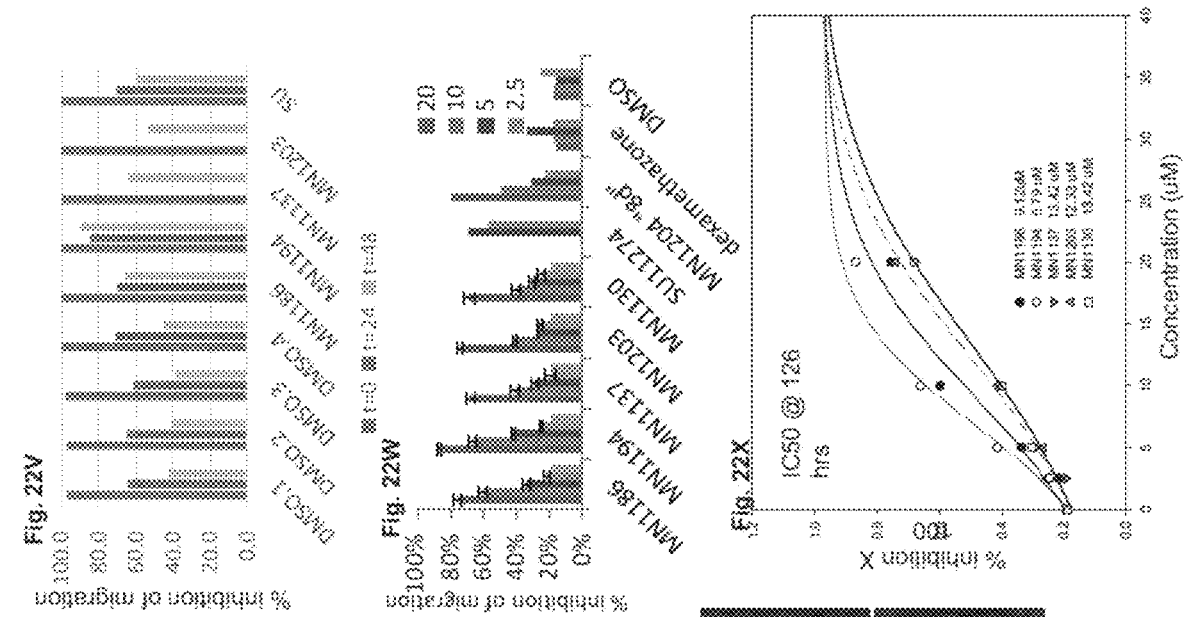
FIG. 22A-22X shows the results of cancer cell migration assays in which novel compounds of the invention that inhibited naïve stem cell pluripotency or proliferation were tested for their ability to inhibit cancer cell invasion or migration.
Figure 22X:
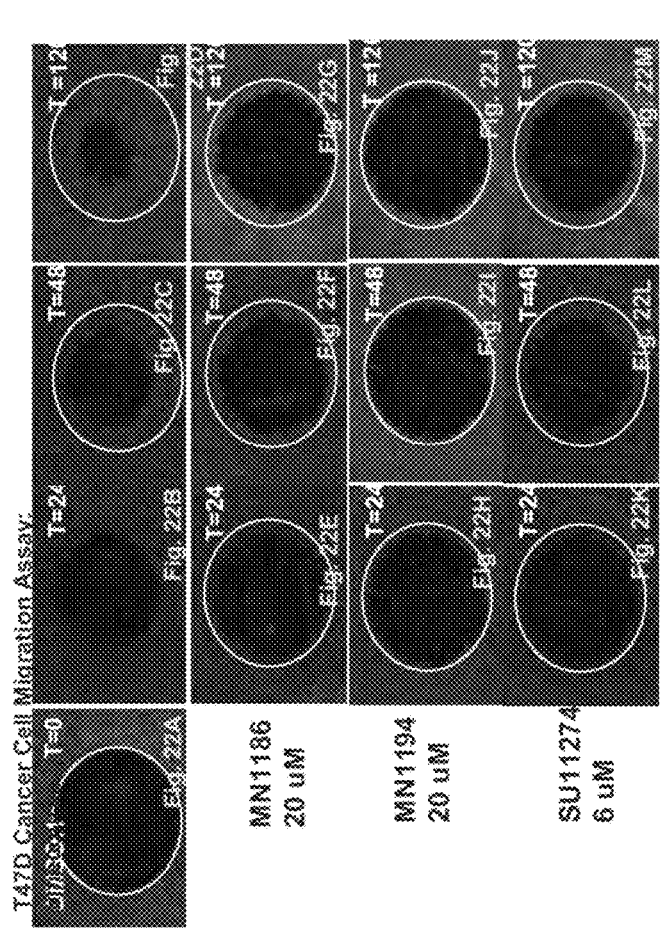
Figures 23A, 23B, 23C, 23D:
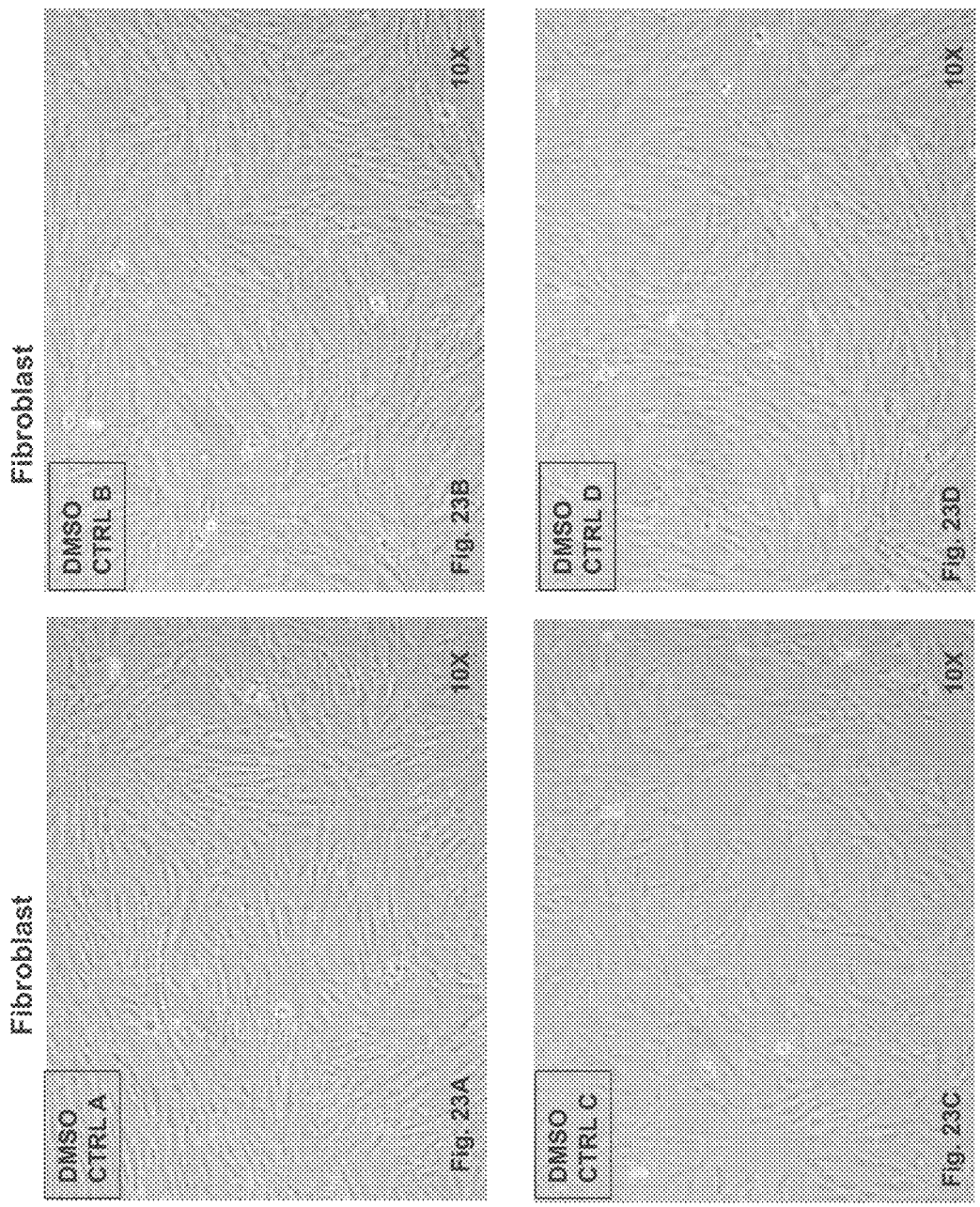
FIG. 23A-23D shows photographs of human fibroblasts in culture, treated only with 0.2% DMSO as a control.

Potent cancer cell migration is characteristic of cancer cell invasion of other tissues and of metastasis. Typical migration assays involve coating a cell culture plate with fibronectin, collagen or the like, plating cancer cells and making a scar across through the cells and measuring the time it takes for the cancer cells to invade the void space. An alternative approach that gives more reliable data is the Platypus System which is a special multi-well cell culture plate with a juxtaposed set of plugs that block off a circle in the center of each well. Cancer cells are plated while the plugs are in place, then they are removed after the cells attach to the plate surface. Drug candidates are added to each well and photographs are then taken as a function of time to track the inhibitory effect of the drug candidates on cancer cell migration or invasion. In our cancer cell migration assays, the number of cells that have migrated into the empty space is quantified using Image J software. A bar graph summarizing the results of such a cancer cell migration assay is shown in FIG. 20. The effects of known anti-migration compounds are compared to the anti-MUC1* Fab E6 and the first few small molecule leads. The results of the cancer cell migration assay are shown in FIG. 21. Photographs of the cancer cell migration assay and bar graphs summarizing their activities are shown in FIG. 22. The effect of two novel small molecules MN1186 and MN1194, compared to the known anti-migration molecule SU11274, is shown in FIG. 22A-22U. FIG. 22V is a graph showing the measured inhibition of cancer cell migration at time 0, 24 hours or 48 hours for a number of compounds. FIG. 22W is a graph showing the inhibitory effect of the small molecules as a function of its concentration. FIG. 22X is a graph showing how IC50's of the small molecules of the invention were measured and calculated.

All human pluripotent stem cells are MUC1* positive. Naïve state stem cells also express the primitive growth factor $NME7_{AB}$ which is an activating ligand of MUC1*. The breast cancer cell line T47D was derived from a metastatic breast cancer patient. T47D cells express the highest levels of MUC1* of any commercially available cell line. We discovered that T47D cells also express $NME7_{AB}$ and an alternative splice isoform NME7-X1, which are both growth factors that activate the MUC1* growth factor receptor.

Compound hits are first identified in the stem cell drug screening assay for their ability to inhibit stem cell pluripotency or proliferation. We then test the hits for their ability to inhibit cancer cell migration, invasion, which is a characteristic of metastatic cancers, and then finally we test the hits for their ability to inhibit cancer cell proliferation. The result is that compounds that inhibit stem cell pluripotency and/or proliferation also inhibited cancer cell migration, invasiveness and/or proliferation. These studies showed that compounds of the invention inhibit migration and/or invasion of a wide range of cancer cells. Compounds of the invention were shown to inhibit migration, invasion and/or proliferation of DU145 (MUC1*+/$NME7_{AB}$+++/NME7-X1+++) prostate cancer cells, and SK-OV-3 (MUC1*+) ovarian cancer cells, A549 (MUC1*$^{LO}$) lung cancer cells, PC-3 (MUC1*−/$NME7_{AB}$+++/NME7-X1+++) prostate cancer cells, CHL-1 (MUC1*+/NME7+) melanoma cells, OV-90 (MUC1*−) ovarian cancer cells, CAPAN-2 (MUC1*+) pancreatic cancer cells, ZR-75-1 (MUC1*+++) breast cancer cells, as well as others.

Figure 17:
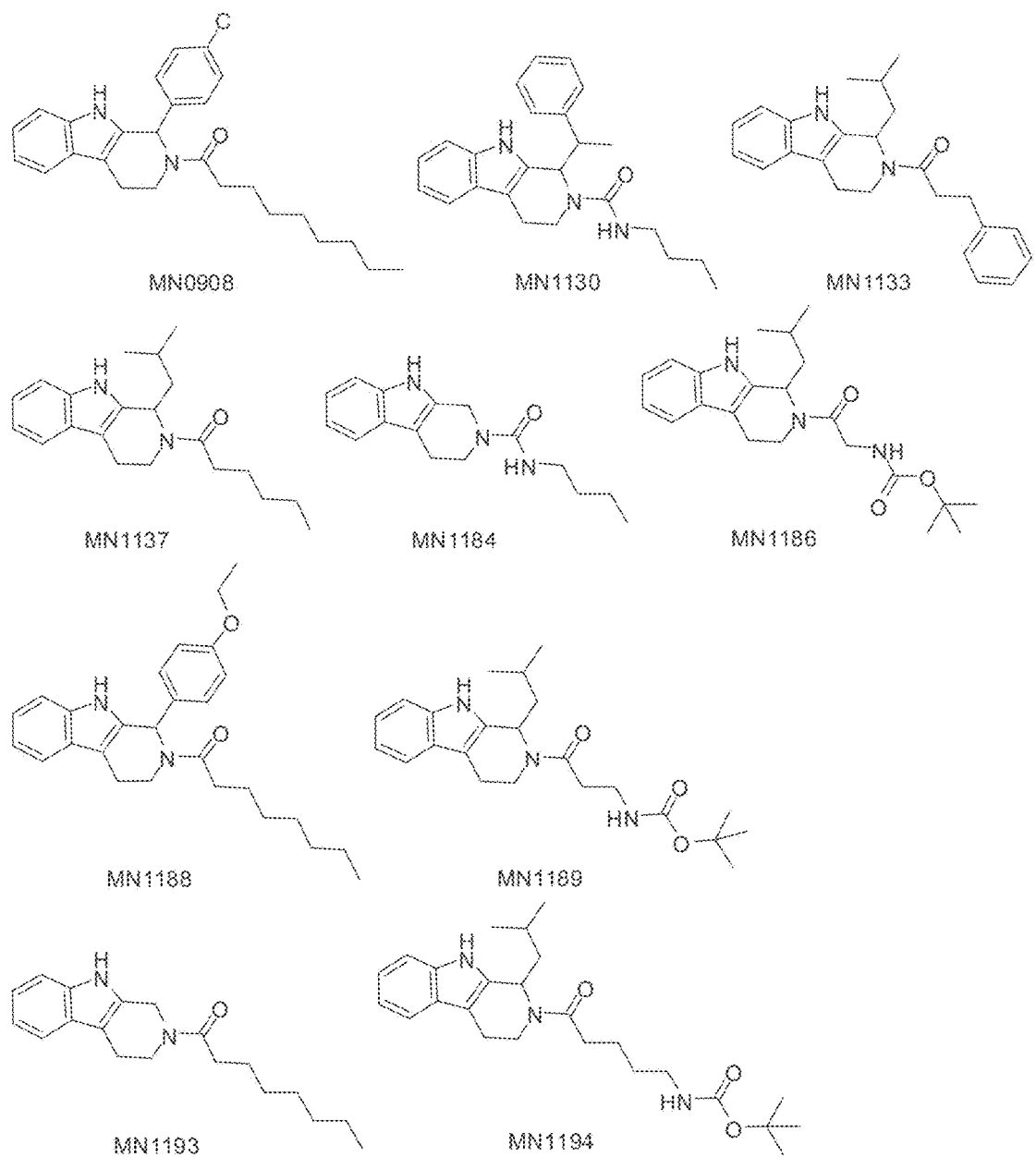
FIG. 17 shows chemical structures of some compounds previously reported to inhibit cancer cell migration as well as some that the inventors previously disclosed.
Figure 17:
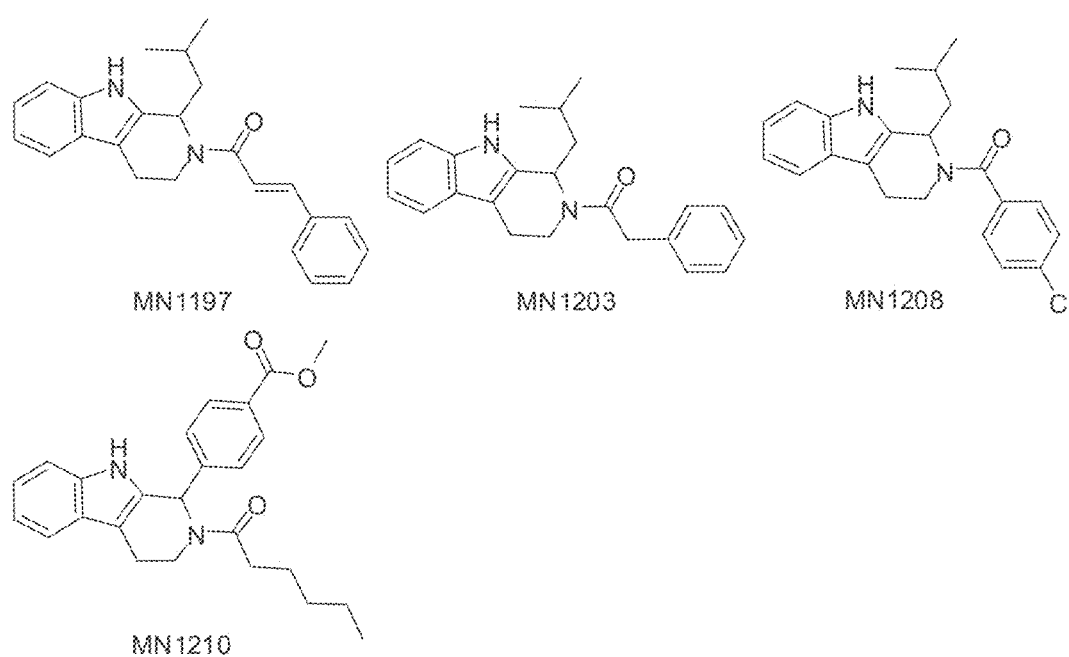

Small molecule inhibition of cancer cell migration or proliferation studies were also performed using previously reported inhibitors of cancer cell migration or invasion, such as the BRD4 inhibitor JQ1+ and its inactive enantiomer JQ1−, c-Met inhibitor SU11274, and others shown in FIG. 17. Some of these compounds inhibited cancer cell migration or invasion to some degree, however most also inhibited the growth of fibroblast cells, which are a surrogate for normal healthy cells, which implies they could have toxic side effects on patients.

The biological testing data for compounds of the invention are shown in FIG. 18A-18E.

Figures 24A, 24B, 24C, 24D, 24E, 24F:
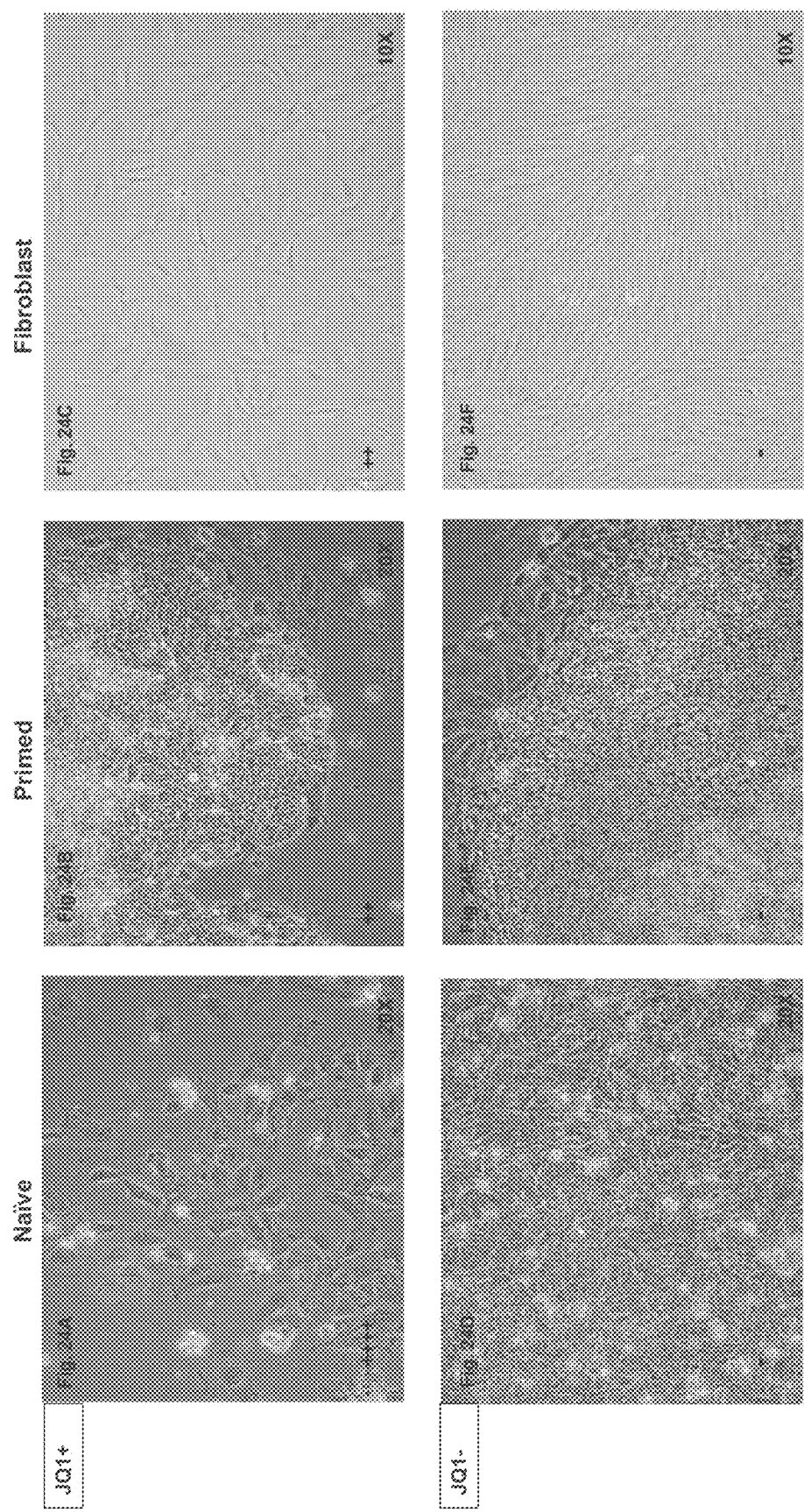
FIG. 24A-24F shows photographs of the effect of JQ1+ (FIG. 24A-24C) versus the effect of the inactive enantiomer JQ1- (FIG. 24D-24F) on human naïve state stem cells (FIG. 24A, 24D), human primed state stem cells (FIG. 24B, 24E), or human fibroblasts (FIG. 24C, 24F).
Figures 25A, 25B, 25C, 25D, 25E, 25F:
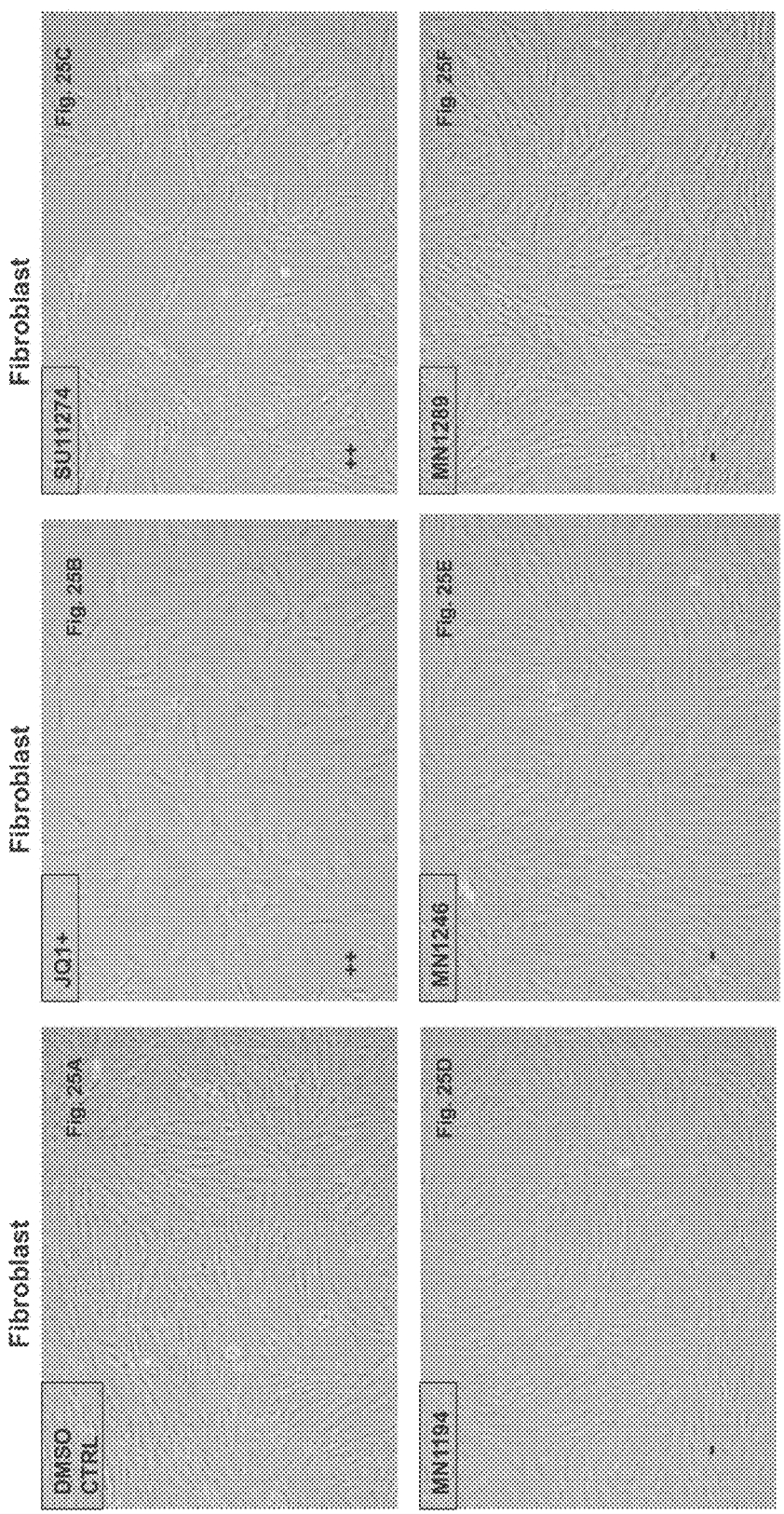
FIG. 25A-25F show photographs of the effect of JQ1 compared to previously known cancer cell migration inhibitors, versus compounds of the invention, on the growth of human fibroblast progenitor cells.
Figures 26A, 26B, 26C, 26D, 26E, 26F, 26G, 26H:
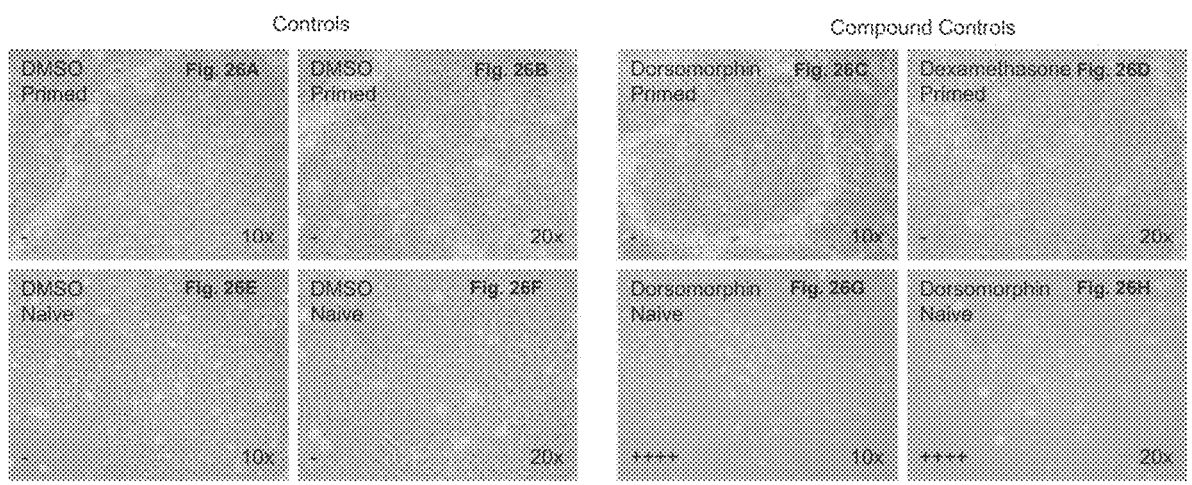
FIG. 26A-26H show photographs of stem cell control experiments and a previously known compound, Dorsomorphin.
Figure 27A:
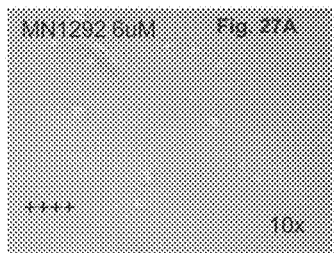
FIG. 27A-27F show photographs of human naïve state stem cells, previously grown in $NME7_{AB}$ over a MUC1* antibody surface, C3, but cultured in the absence of NME7A during the experiment, and treated for 3 days with a small molecule drug candidate at a final concentration of 6 uM, unless otherwise indicated. In each panel, a score of –, or +, ++, +++, or ++++ is given, wherein "–" indicates that at the indicated concentration the drug candidate did not have an obvious effect on the pluripotency or proliferation of the stem cells. A "+" indicates a mild effect and "++++" indicates a profound effect on pluripotency or proliferation. Inhibition of proliferation can be seen as holes, or blank areas, in the layer of stem cells. Inhibition of pluripotency, which is also induction of differentiation, is seen as increase in cell size with a decrease in the size of the nucleus, elongation and flattening of cells or rounding up of cells and floating off the plate.
Figure 27B:
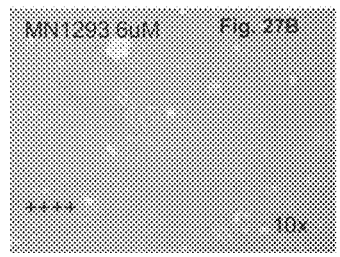
Figure 27C:
Figure 27D:
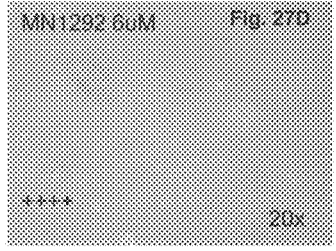
Figure 27E:
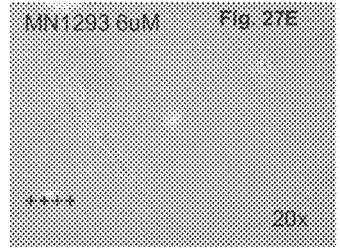
Figure 27F:
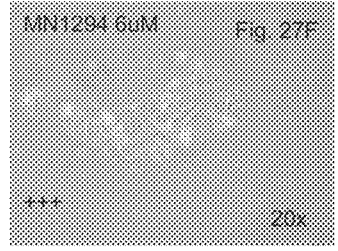
Figure 27G:
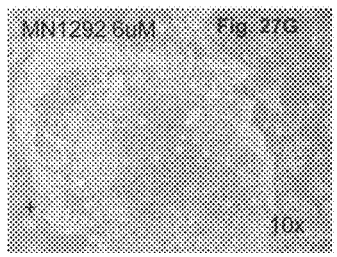
FIG. 27G-27L show photographs of human primed state stem cells, previously grown in FGF over a layer of MEFs, but cultured in the absence of FGF during the experiment, and treated for 3 days with a small molecule drug candidate at a final concentration of 6 uM, unless otherwise indicated. In each panel, a score of –, or +, ++, +++, or ++++ is given, wherein "–" indicates that at the indicated concentartion the drug candidate did not have an obvious effect on the pluripotency or proliferation of the stem cells. A "+" indicates a mild effect and "++++" indicates a profound effect on pluripotency or proliferation. Primed state stem cells grow in defined colonies rather than a uniform layer like naïve stem cells. Inhibition of proliferation can be seen as a reduction in the colony size. Inhibition of pluripotency, which is also induction of differentiation, is seen as increase in cell size with a decrease in the size of the nucleus, elongation and flattening of cells or rounding up of cells and floating off the plate.
Figure 27H:
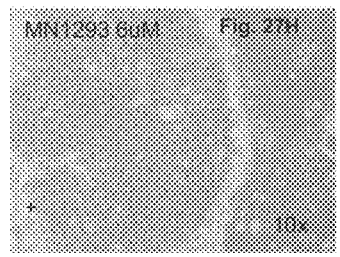
Figure 27I:
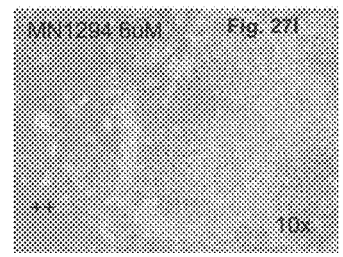
Figure 27J:
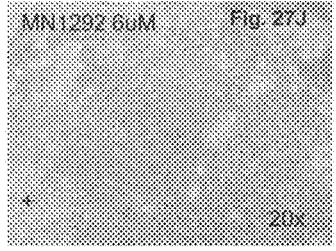
Figure 27K:
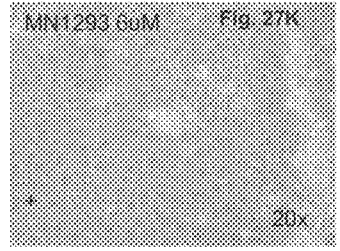
Figure 27L:
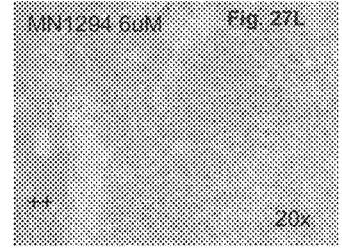
Figures 28A, 28B, 28C, 28D, 28E, 28F, 28G, 28H:
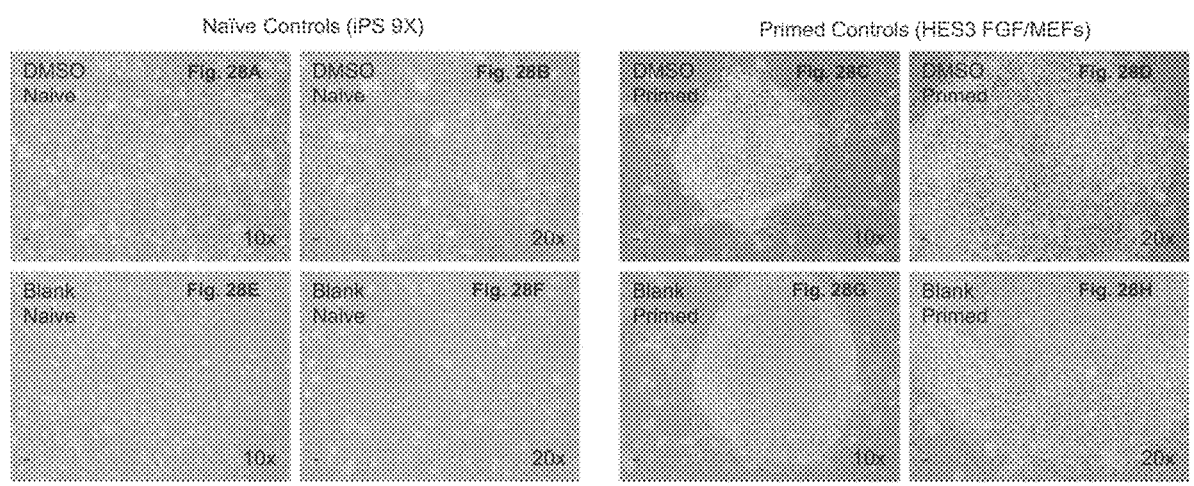
FIG. 28A-28L show photographs of control experiments carried out on different human stem cell lines.
Figures 28I, 28J, 28K, 28L:
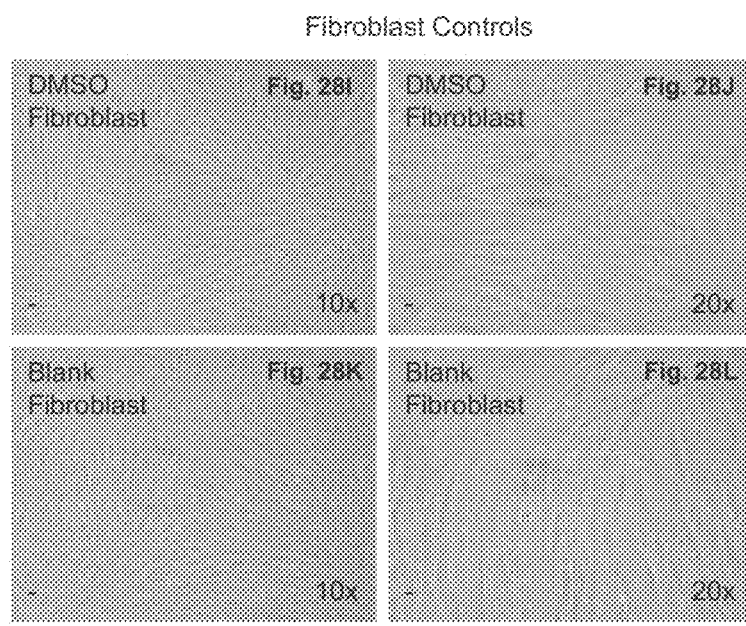
Figure 29A:
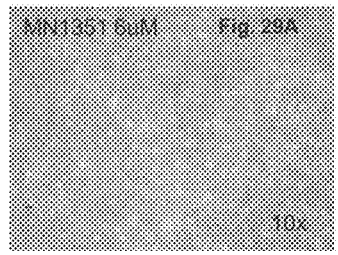
FIG. 29A-29F shows photographs of human naïve state stem cells, previously grown in $NME7_{AB}$ over a MUC1* antibody surface, C3, but cultured in the absence of $NME7_{AB}$ during the experiment, and treated for 3 days with a small molecule drug candidate at a final concentration of 6 uM, unless otherwise indicated. In each panel, a score of –, or +, ++, +++, or ++++ is given, wherein "–" indicates that at the indicated concentration the drug candidate did not have an obvious effect on the pluripotency or proliferation of the stem cells. A "+" indicates a mild effect and "++++" indicates a profound effect on pluripotency or proliferation. Inhibition of proliferation can be seen as holes, or blank areas, in the layer of stem cells. Inhibition of pluripotency, which is also induction of differentiation, is seen as increase in cell size with a decrease in the size of the nucleus, elongation and flattening of cells or rounding up of cells and floating off the plate.
Figure 29B:
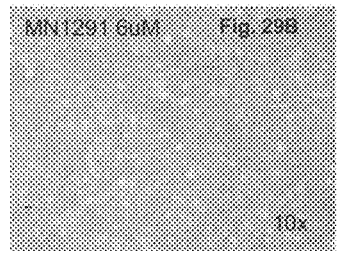
Figure 29C:
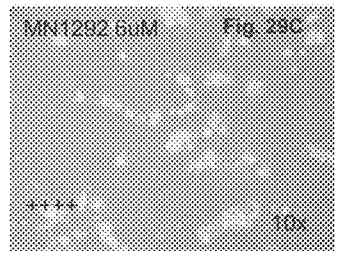
Figure 29D:
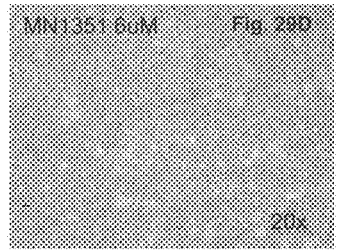
Figure 29E:
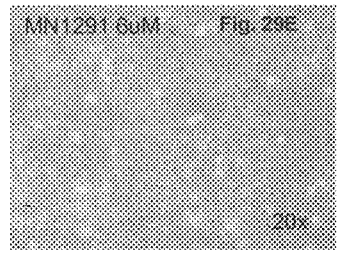
Figure 29F:
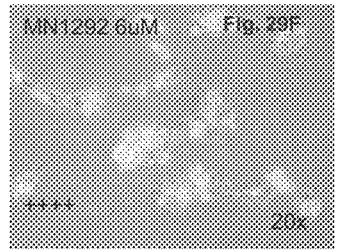
Figure 29G:
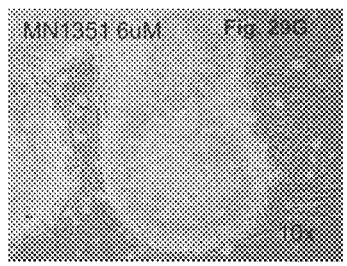
FIG. 29G-29L show photographs of human primed state stem cells, previously grown in FGF over a layer of MEFs, but cultured in the absence of FGF during the experiment, and treated for 3 days with a small molecule drug candidate at a final concentration of 6 uM, unless otherwise indicated. In each panel, a score of –, or +, ++, +++, or ++++ is given, wherein "–" indicates that at the indicated concentartion the drug candidate did not have an obvious effect on the pluripotency or proliferation of the stem cells. A "+" indicates a mild effect and "++++" indicates a profound effect on pluripotency or proliferation. Primed state stem cells grow in defined colonies rather than a uniform layer like naïve stem cells. Inhibition of proliferation can be seen as a reduction in the colony size. Inhibition of pluripotency, which is also induction of differentiation, is seen as increase in cell size with a decrease in the size of the nucleus, elongation and flattening of cells or rounding up of cells and floating off the plate.
Figure 29H:
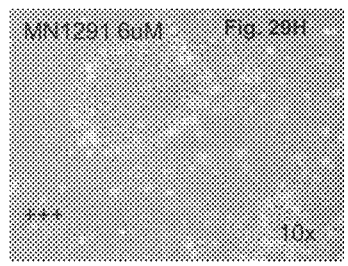
Figure 29I:
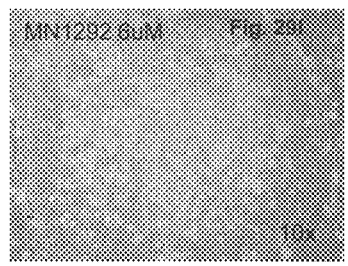
Figure 29J:
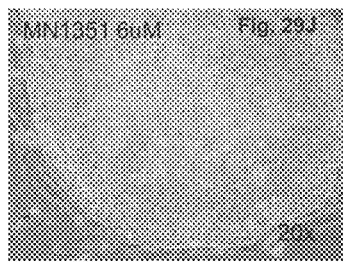
Figure 29K:
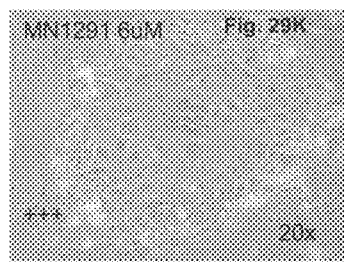
Figure 29L:
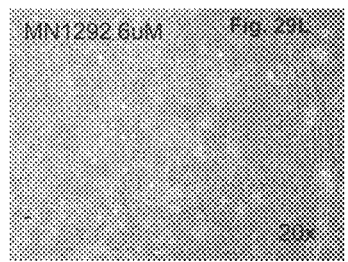
Figure 29M:
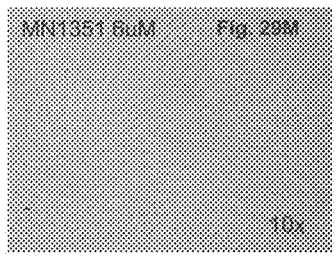
FIG. 29M-29R show photographs of human fibroblast cells treated for 3 days with a small molecule drug candidate at a final concentration of 6 uM, unless otherwise indicated. In each panel, a score of –, or +, ++, +++, or ++++ is given, wherein "–" indicates that at the indicated concentration the drug candidate did not have an obvious effect on the morphology or proliferation of the cells. A "+" indicates a mild effect and "++++" indicates a profound effect on morphology or proliferation of the cells.
Figure 29N:
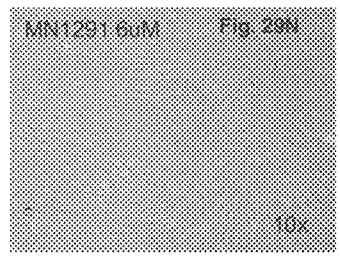
Figure 29O:
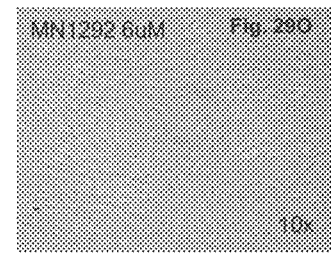
Figure 29P:
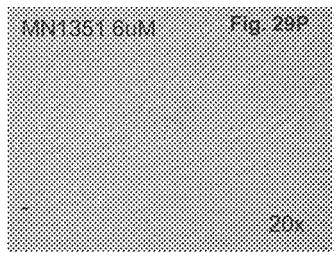
Figure 29Q:
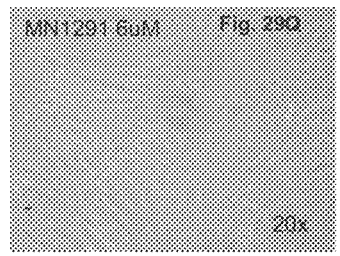
Figure 29R:
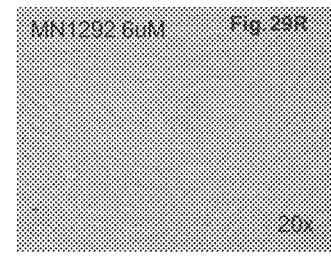
Figures 30A, 30B, 30C, 30D, 30E, 30F:
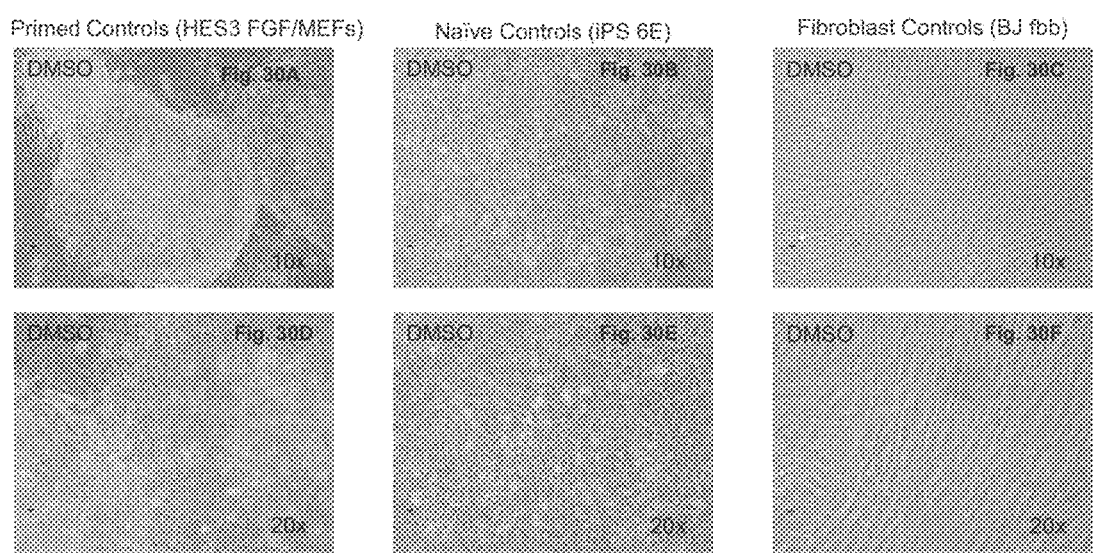
FIG. 30A-30F shows photographs of control experiments on stem cell lines that were used in the next series of drug screening experiments.
Figure 31A:
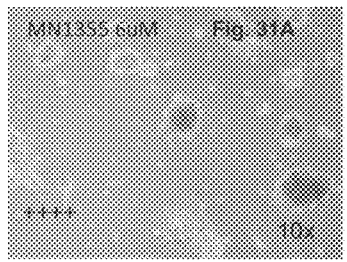
FIGS. 31A-31F, 32A-32F, 33A-33F, 34A-34F, and 35A-35F show photographs of human naïve state stem cells, previously grown in $NME7_{AB}$ over a MUC1* antibody surface, C3, but cultured in the absence of $NME7_{AB}$ during the experiment, and treated for 3 days with a small molecule drug candidate at a final concentration of 6 uM, unless otherwise indicated. In each panel, a score of –, or +, ++, +++, or ++++ is given, wherein "–" indicates that at the indicated concentration the drug candidate did not have an obvious effect on the pluripotency or proliferation of the stem cells. A "+" indicates a mild effect and "++++" indicates a profound effect on pluripotency or proliferation. Inhibition of proliferation can be seen as holes, or blank areas, in the layer of stem cells. Inhibition of pluripotency, which is also induction of differentiation, is seen as increase in cell size with a decrease in the size of the nucleus, elongation and flattening of cells or rounding up of cells and floating off the plate.
Figure 31B:
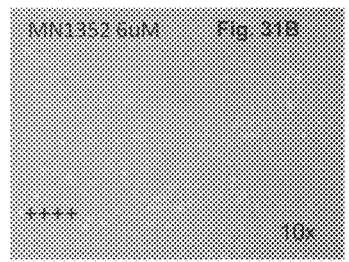
Figure 31C:
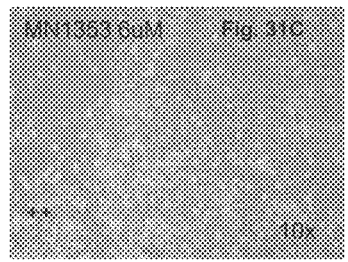
Figure 31D:
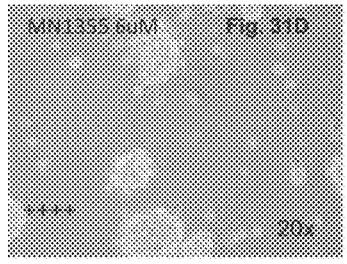
Figure 31E:
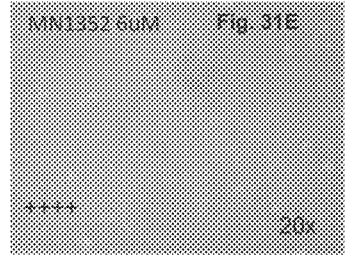
Figure 31F:
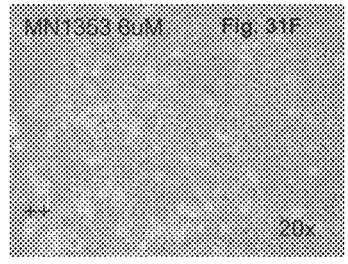
Figure 31G:
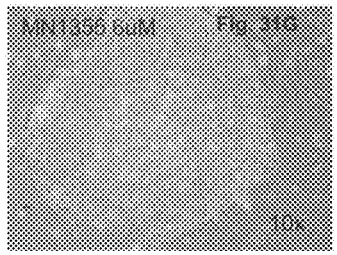
Figure 31H:
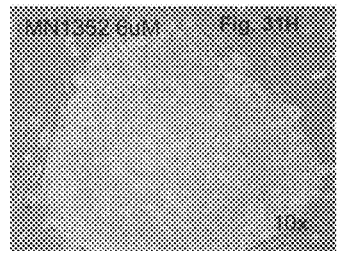
Figure 31I:
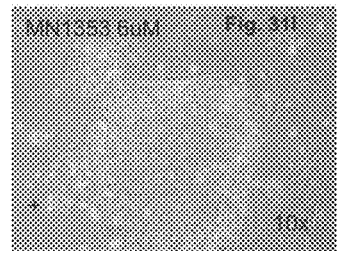
Figure 31J:
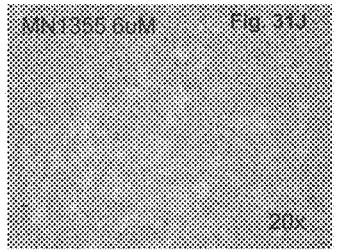
Figure 31K:
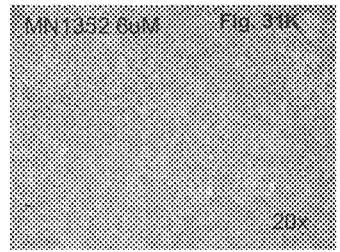
Figure 31L:
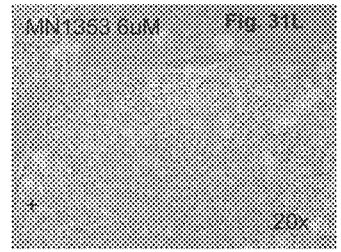
Figure 31M:
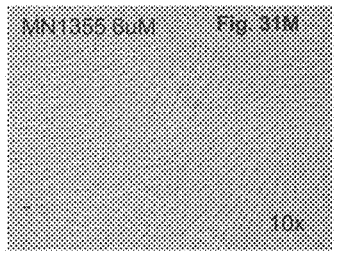
Figure 31N:
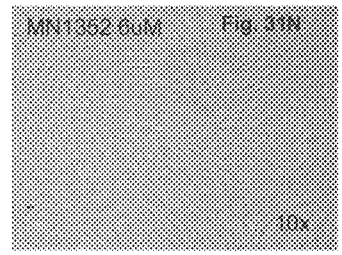
Figure 31O:
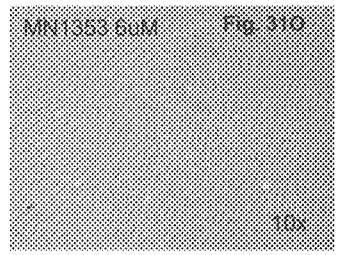
Figure 31P:
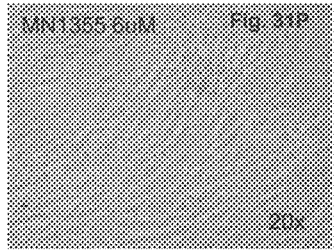
Figure 31Q:
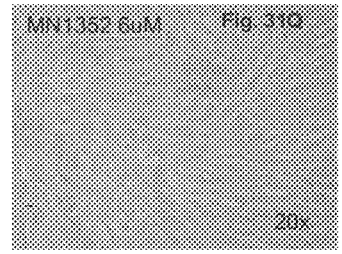
Figure 31R:
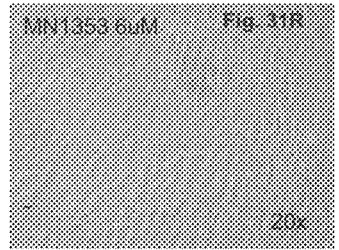
Figure 32A:
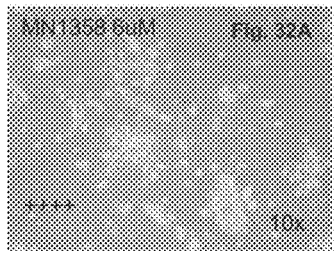
Figure 32B:
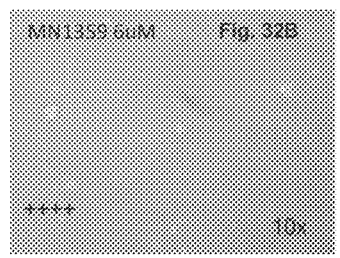
Figure 32C:
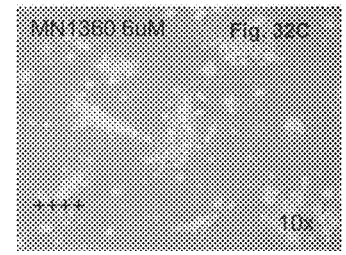
Figure 32D:
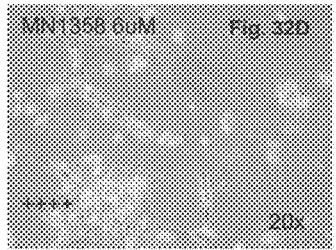
Figure 32E:
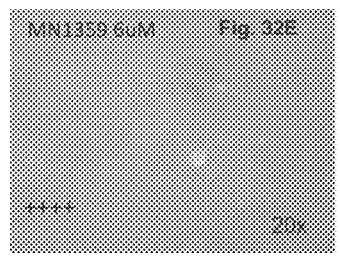
Figure 32F:
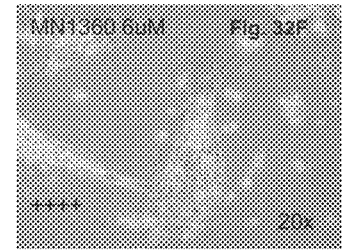
Figure 32G:
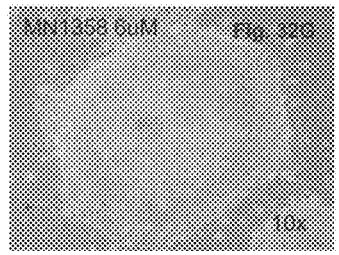
Figure 32H:
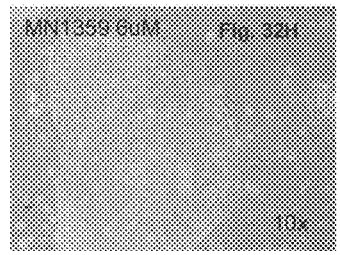
Figure 32I:
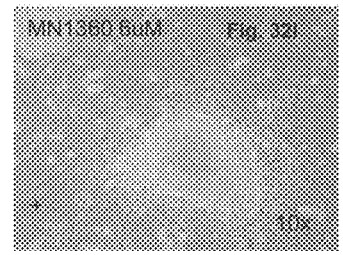
Figure 32J:
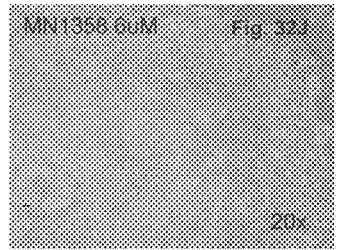
Figure 32K:
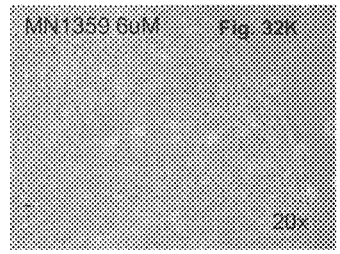
Figure 32L:
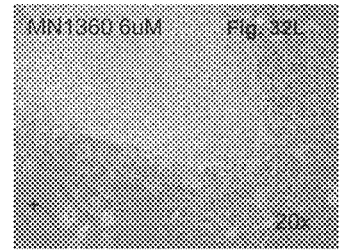
Figure 32M:
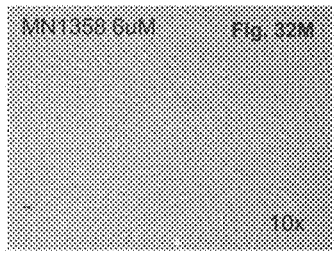
Figure 32N:
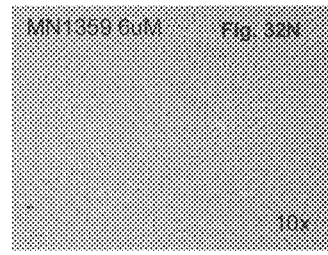
Figure 32O:
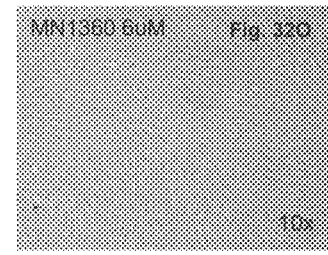
Figure 32P:
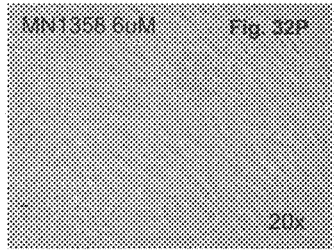
Figure 32Q:
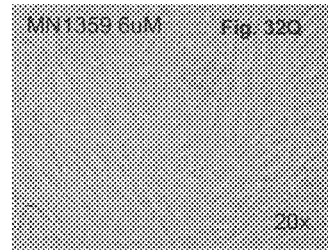
Figure 32R:
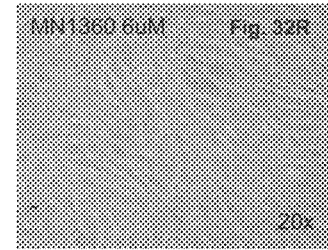
Figures 33A, 33B, 33C, 33D, 33E, 33F:
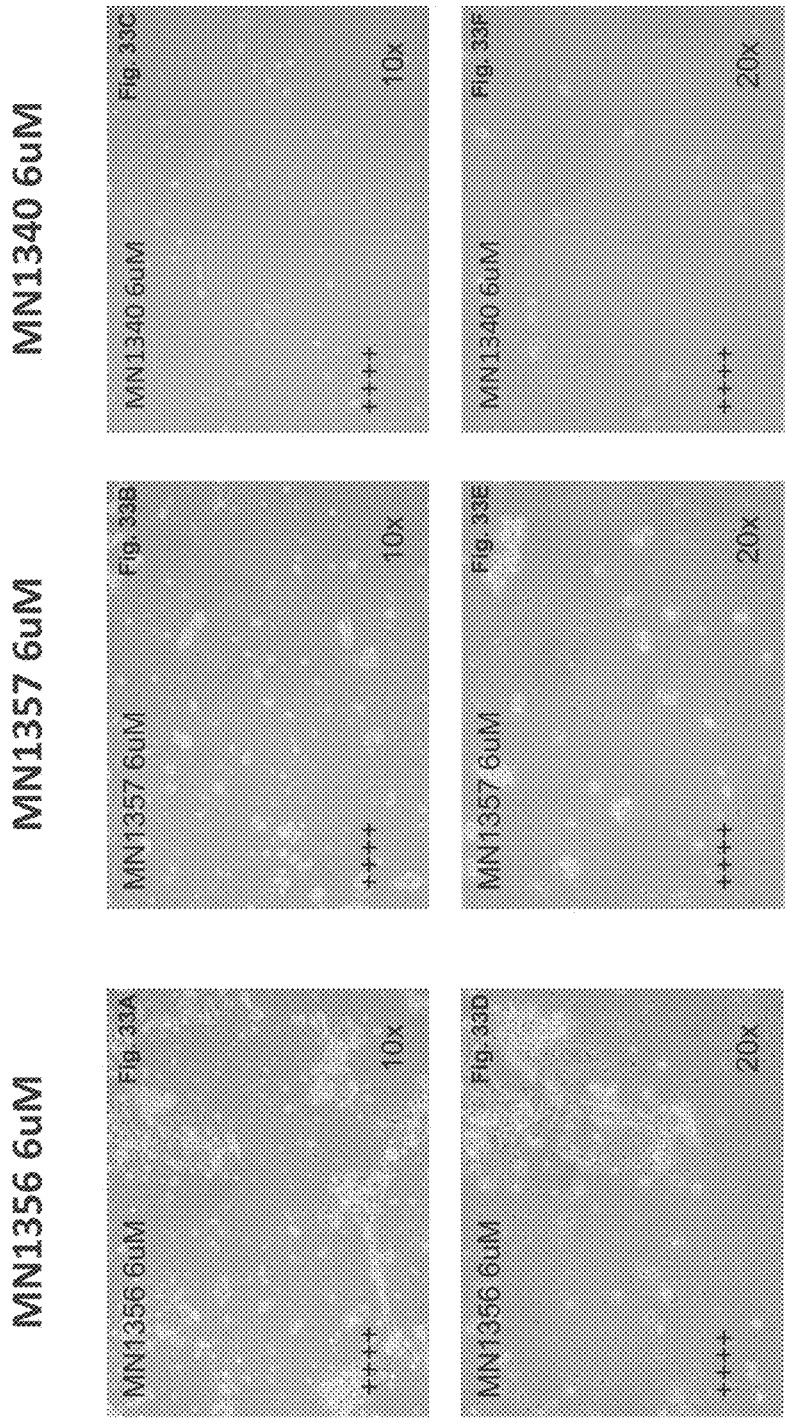
Figures 33G, 33H, 33I, 33J, 33K, 33L:
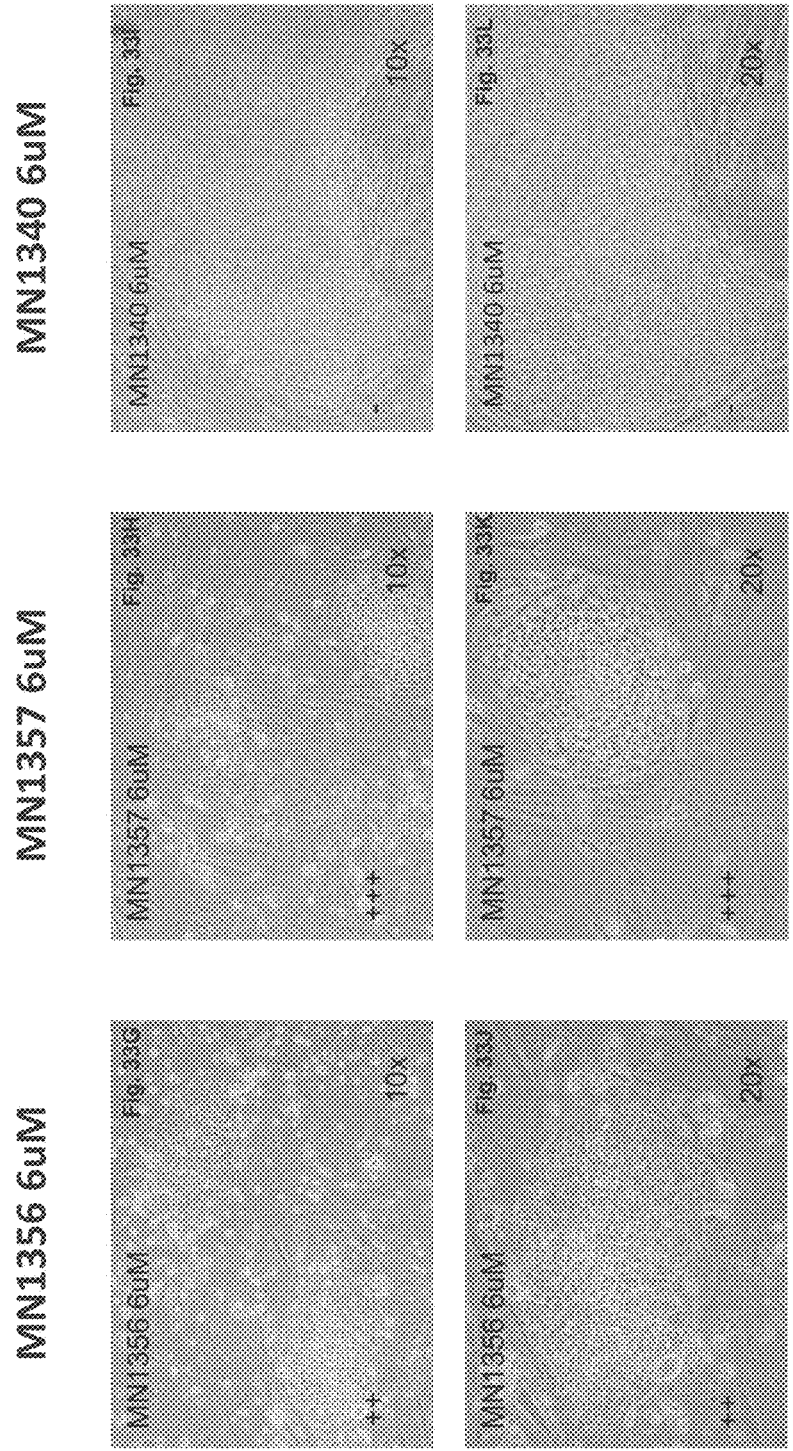
Figures 33M, 33N, 33O, 33P, 33Q, 33R:
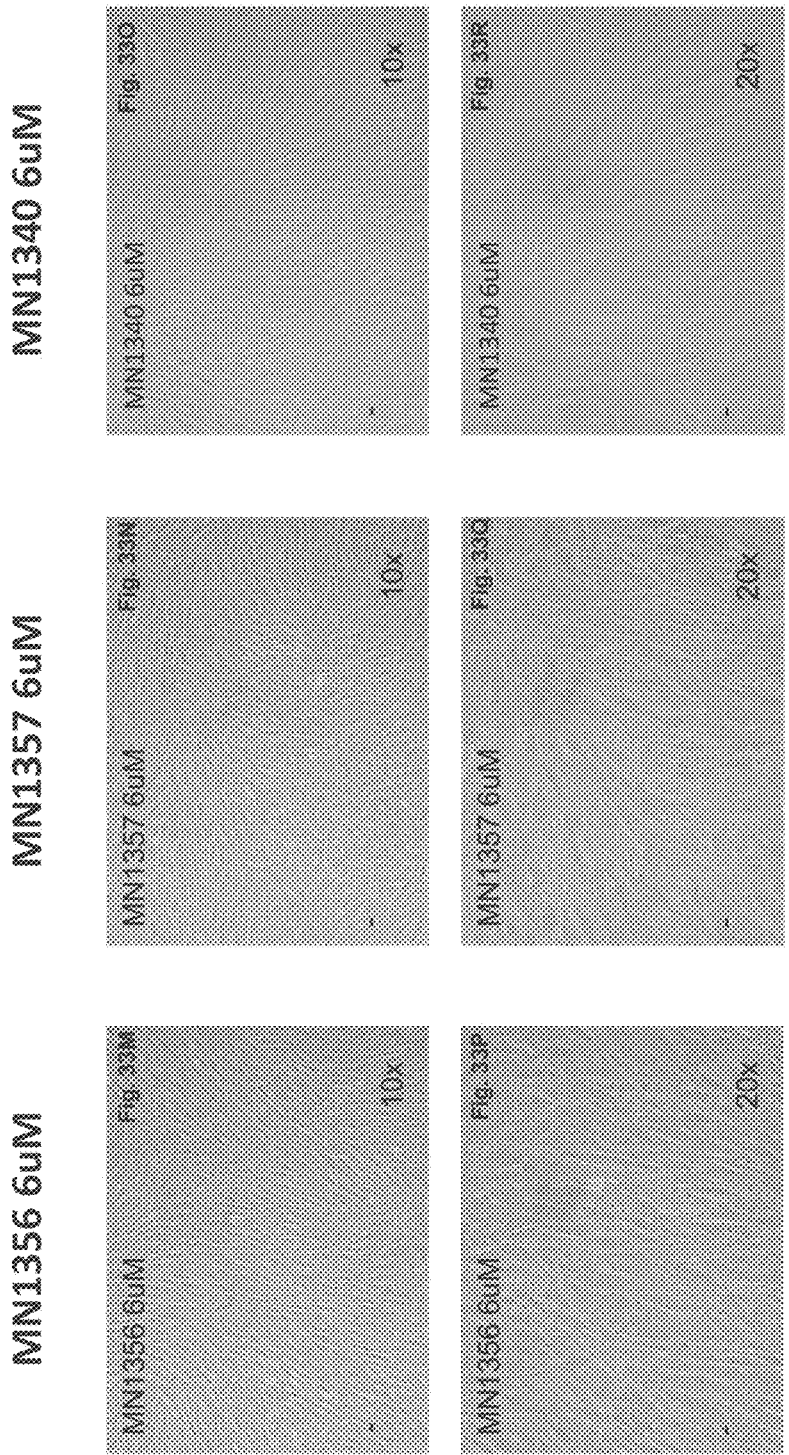
Figures 34A, 34B, 34C, 34D, 34E, 34F:
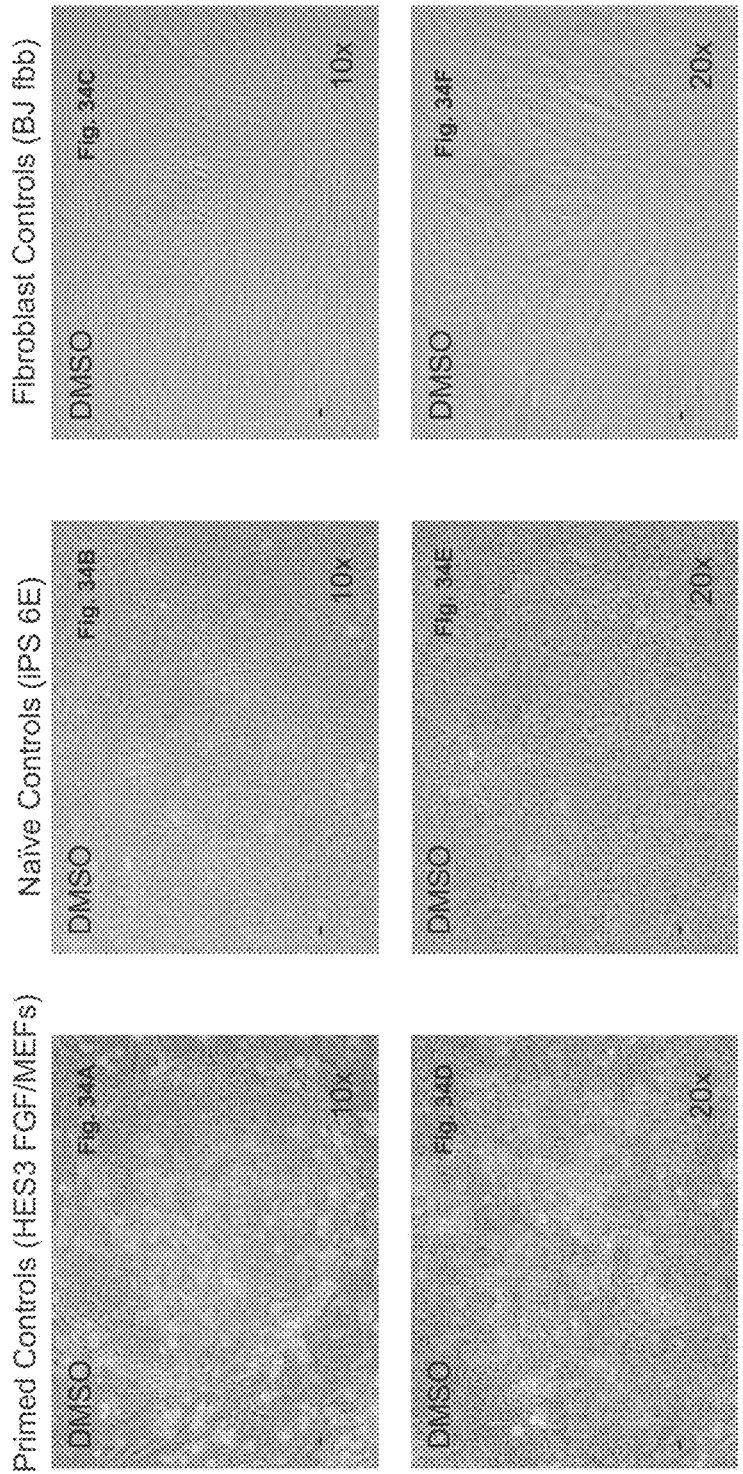
Figures 35A, 35B, 35C, 35D, 35E, 35F:
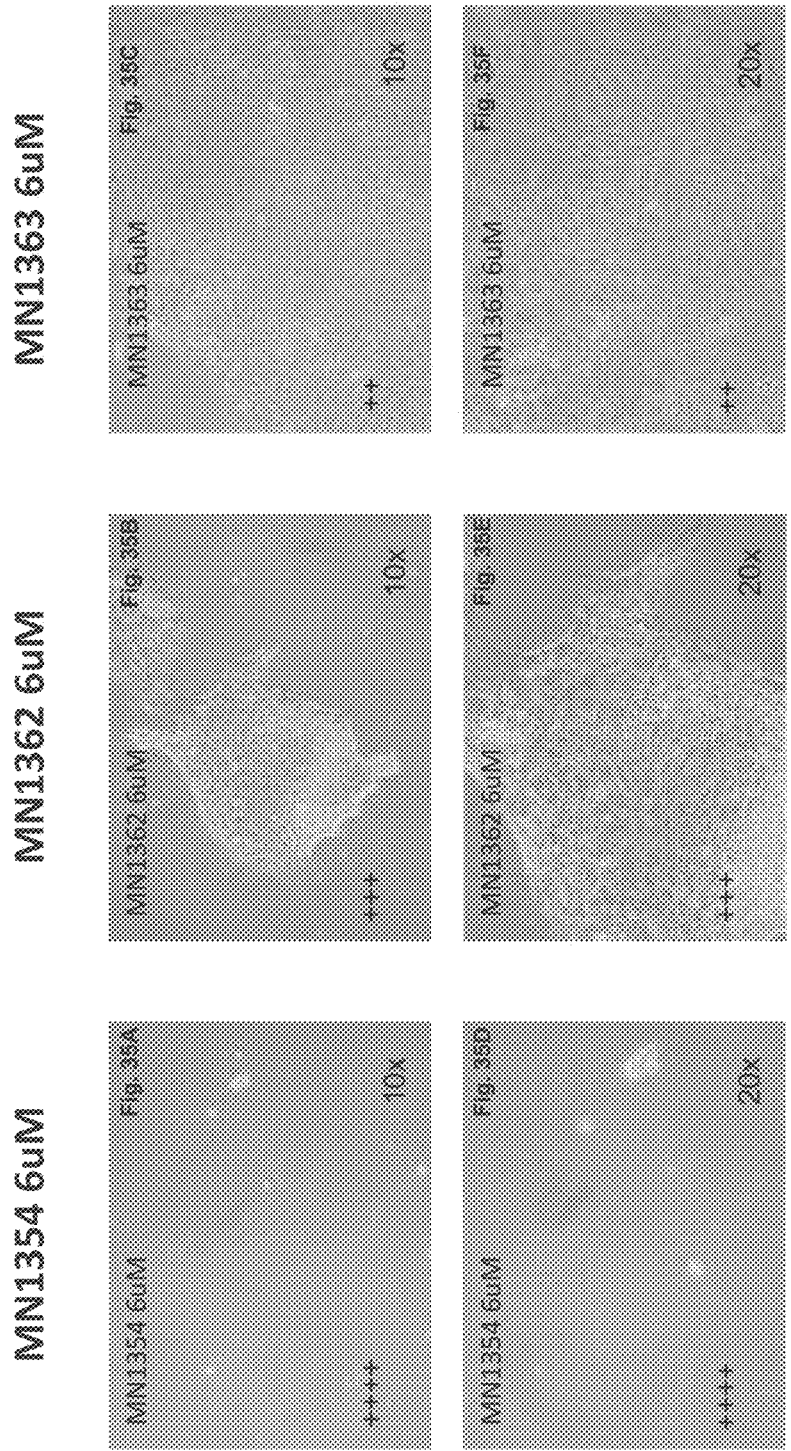
Figures 35G, 35H, 35I, 35J, 35K, 35L:
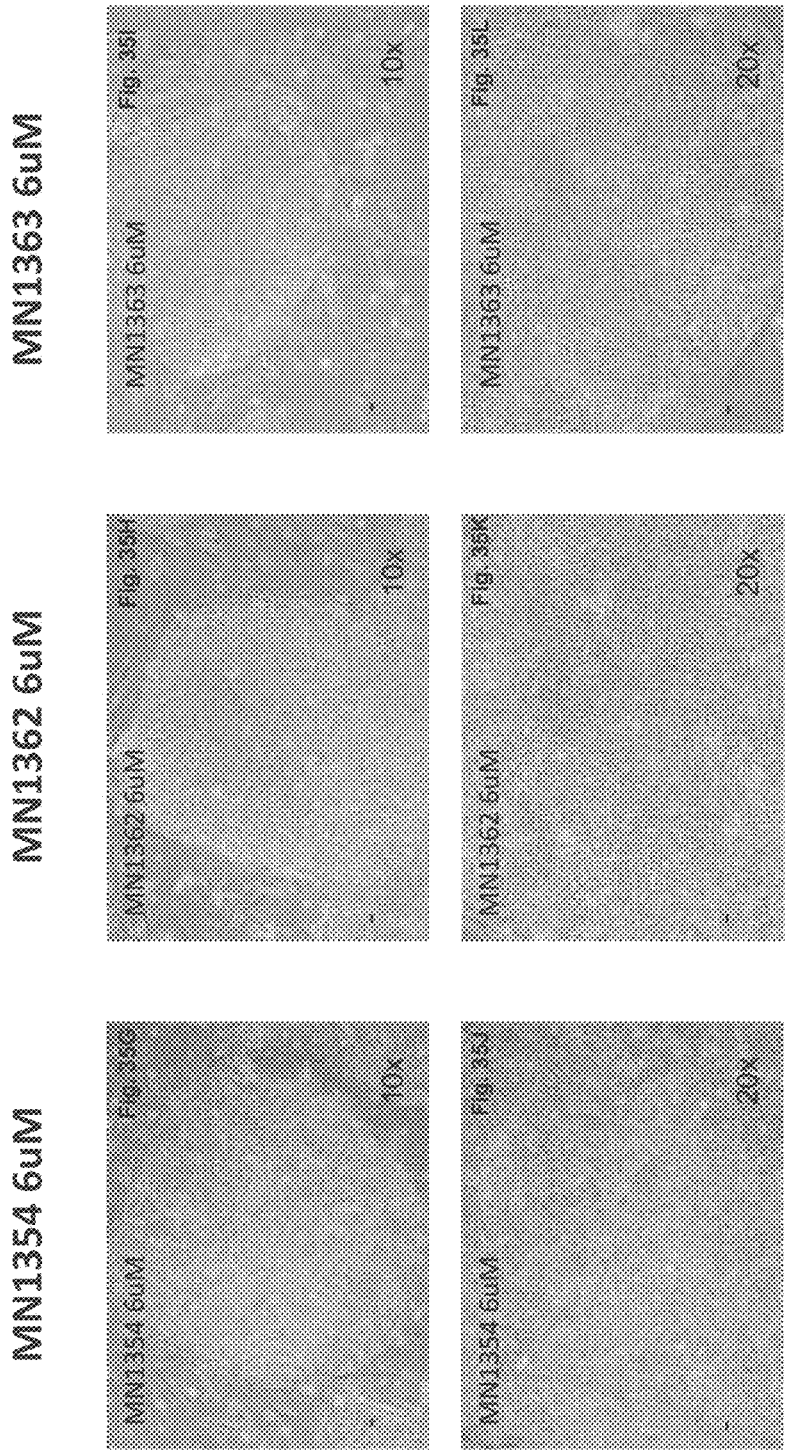
Figure 36:
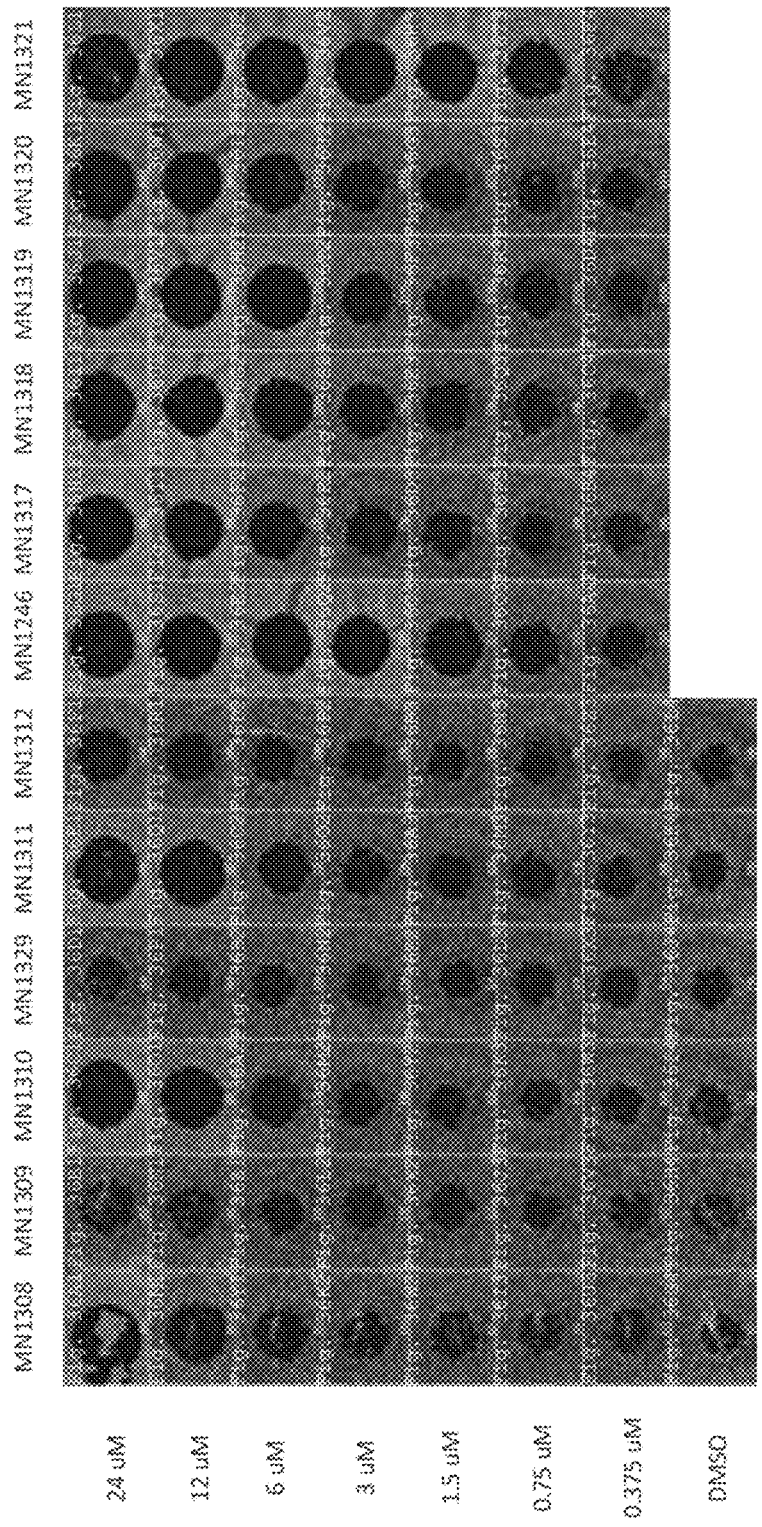
FIG. 36 shows photographs of a cancer cell migration, invasion assay performed on T47D breast cancer cells in the presence of compounds of the invention, over a range of concentrations, or the control, DMSO alone, at 120 hours.
Figure 37:
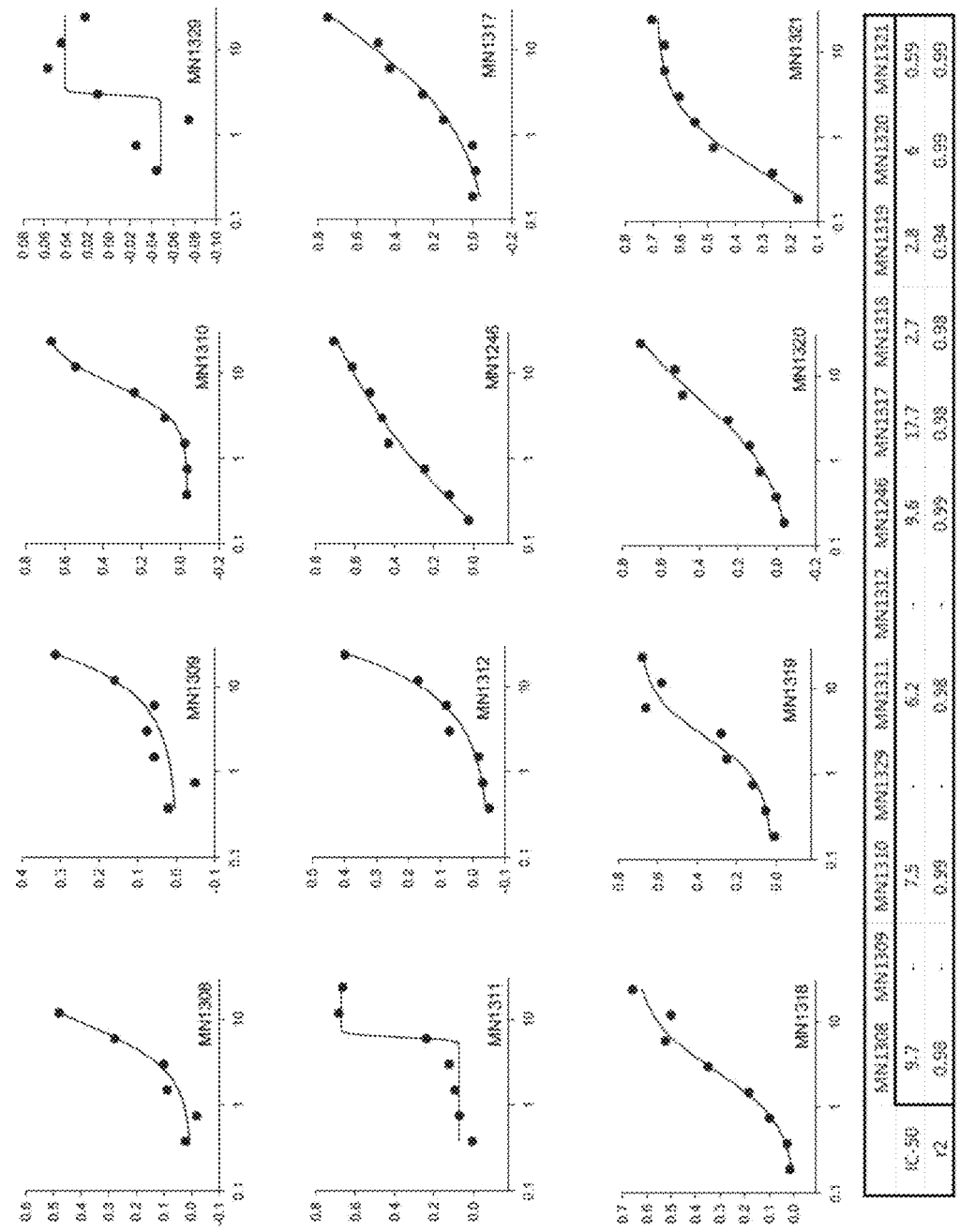
FIG. 37 shows measured IC50 curves for each of the compounds for the ability to inhibit cancer cell migration or invasion of T47D breast cancer cells in the presence of compounds of the invention, over a range of concentrations, or the control, DMSO alone, at 120 hours.
Figure 38:
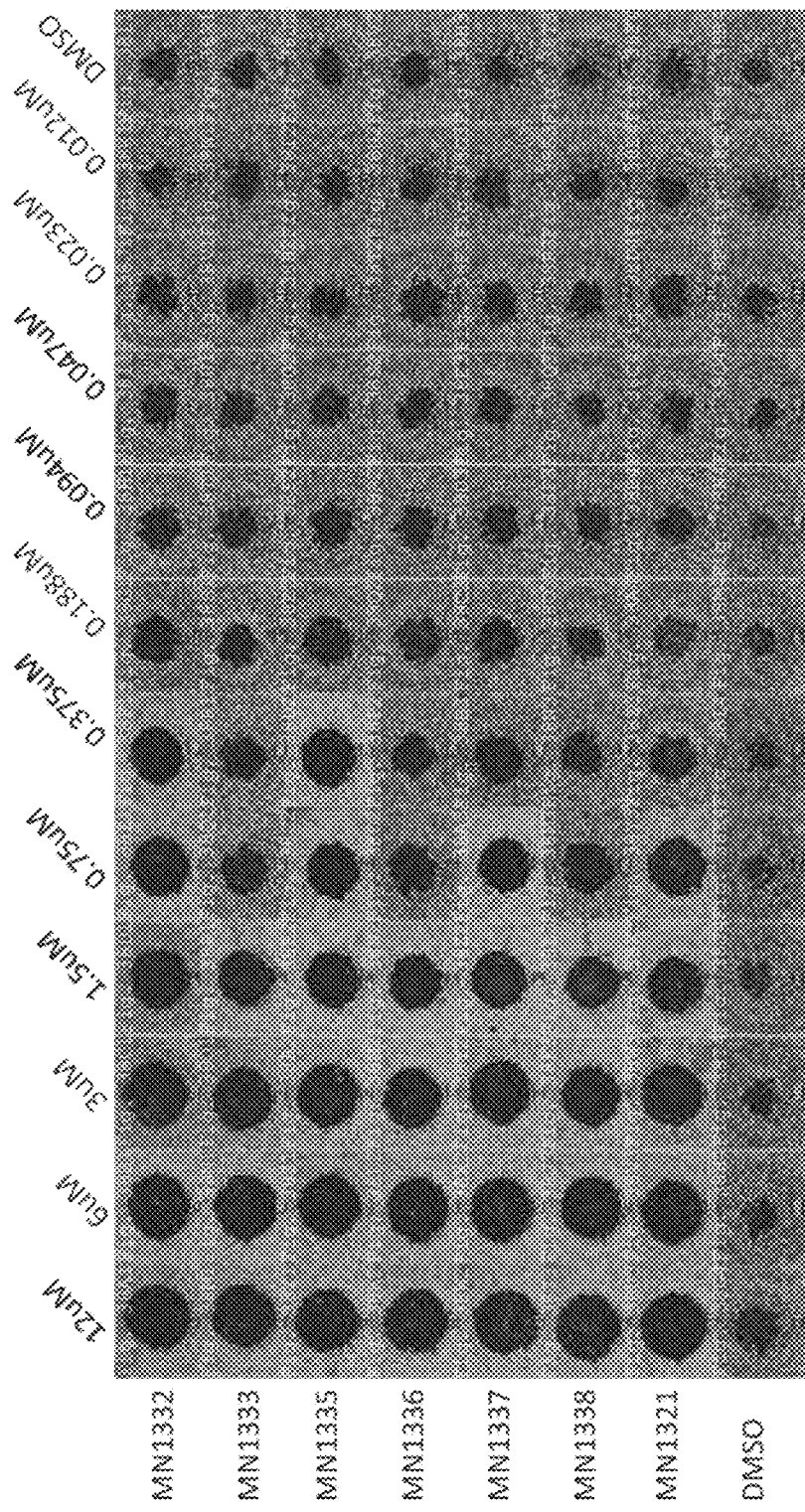
FIG. 38 shows photographs of a cancer cell migration, invasion assay performed on T47D breast cancer cells in the presence of compounds of the invention, over a range of concentrations, or the control, DMSO alone, at 120 hours.
Figure 39:
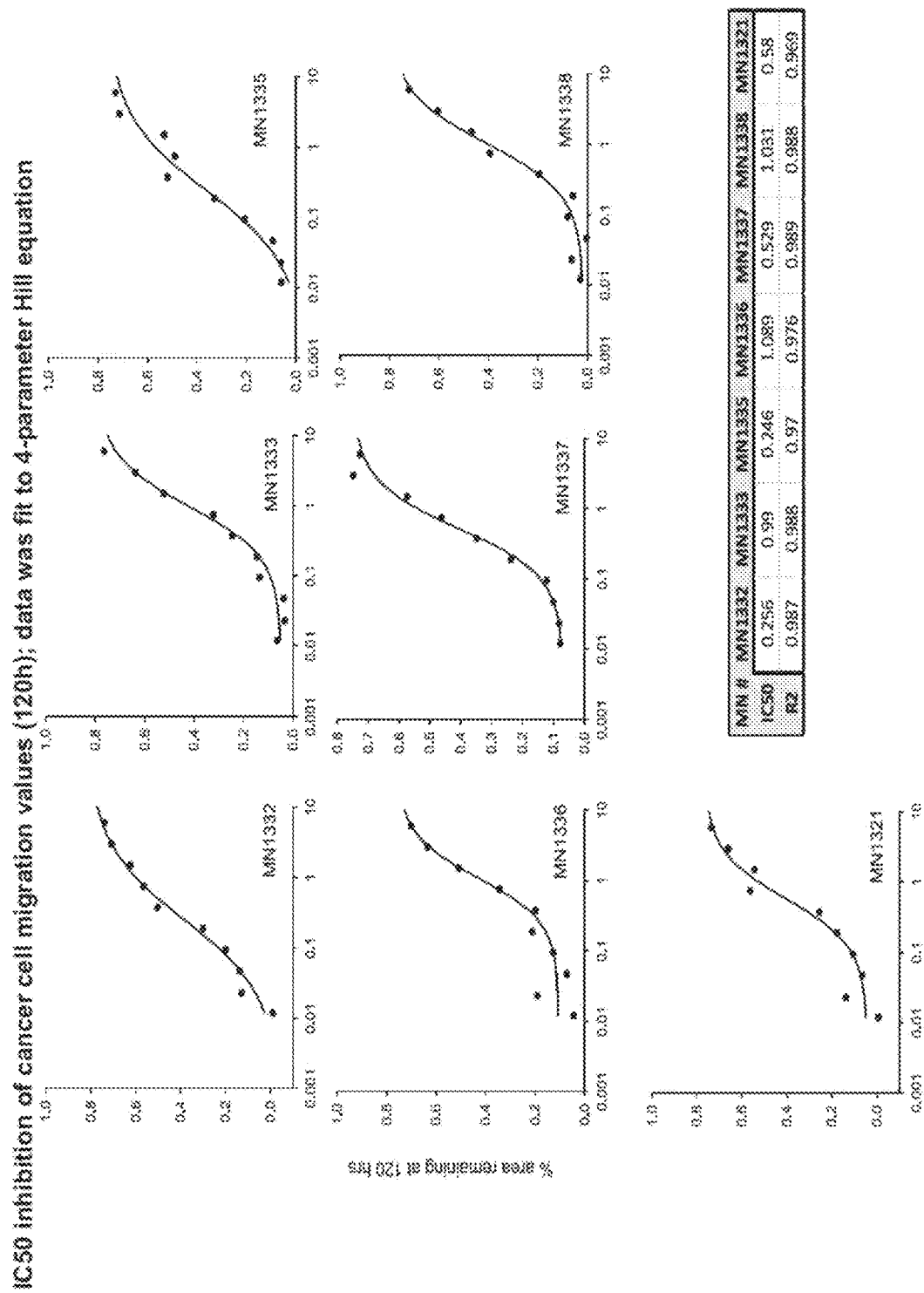
FIG. 39 shows measured IC50 curves for each of the compounds for the ability to inhibit cancer cell migration or invasion of T47D breast cancer cells in the presence of compounds of the invention, over a range of concentrations, or the control, DMSO alone, at 120 hours.
Figure 40:
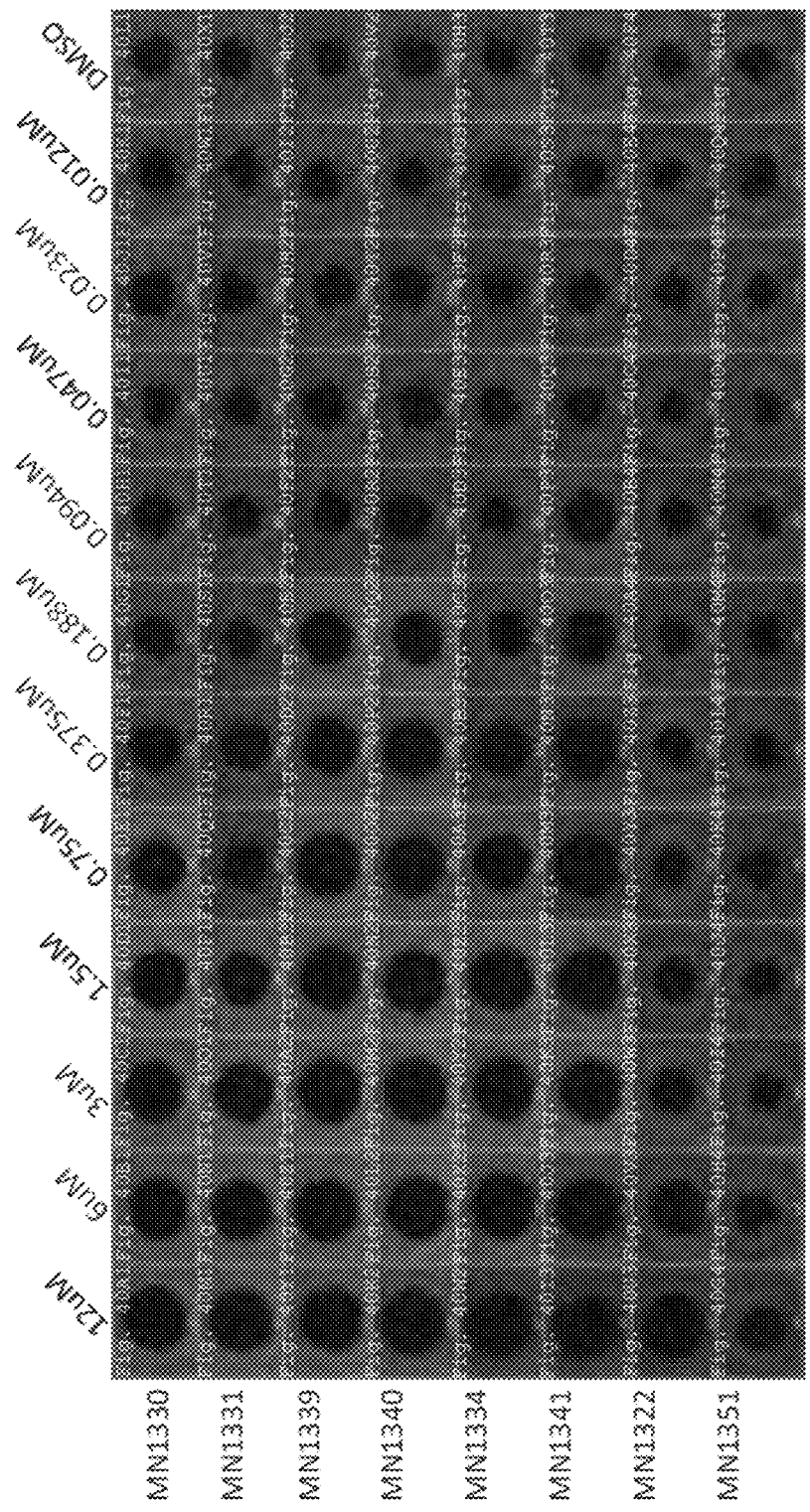
FIG. 40 shows photographs of a cancer cell migration, invasion assay performed on T47D breast cancer cells in the presence of compounds of the invention, over a range of concentrations, or the control, DMSO alone, at 120 hours.
Figure 41:
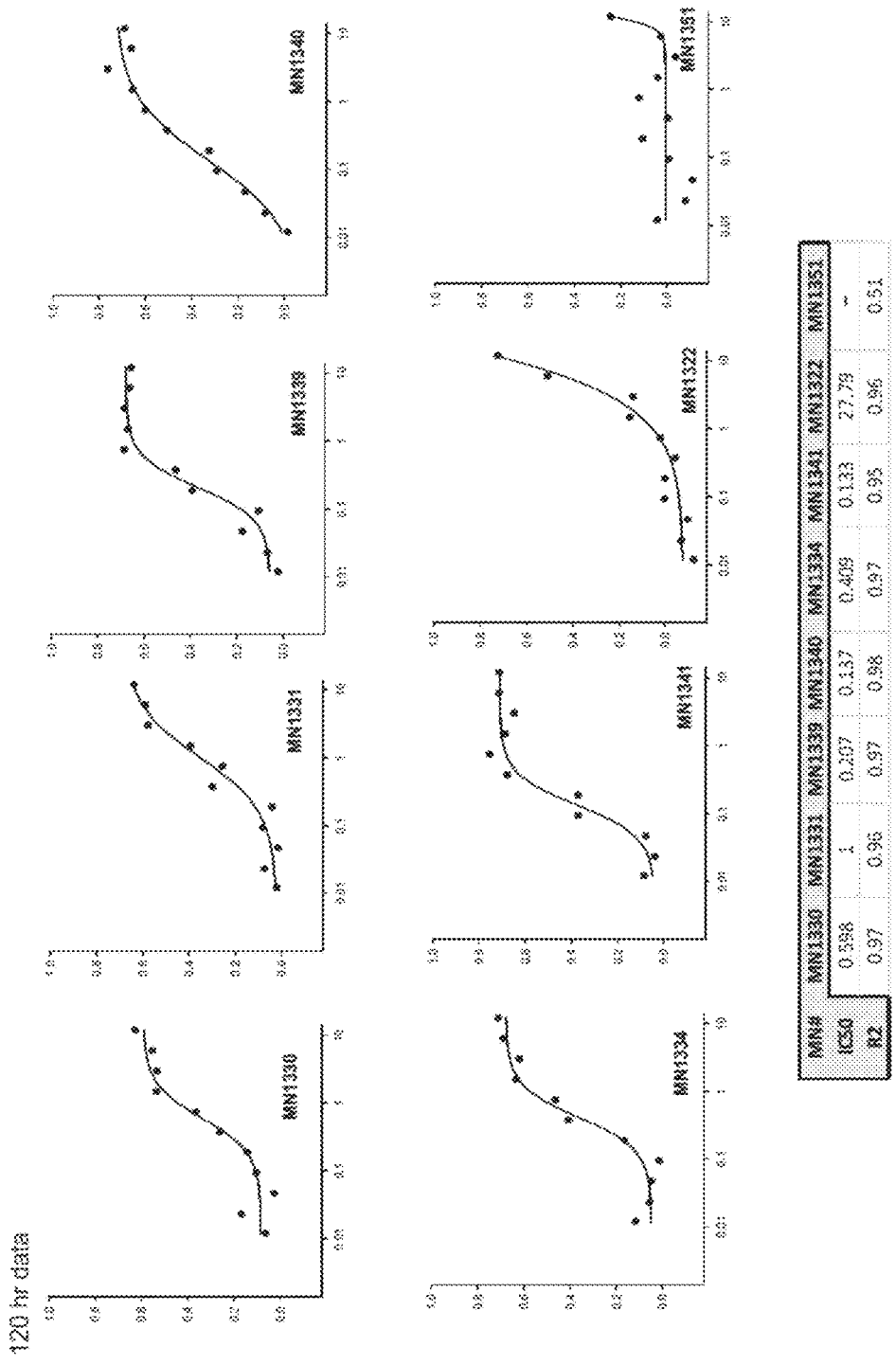
FIG. 41 shows measured IC50 curves for each of the compounds for the ability to inhibit cancer cell migration or invasion of T47D breast cancer cells in the presence of compounds of the invention, over a range of concentrations, or the control, DMSO alone, at 120 hours.
Figure 42:
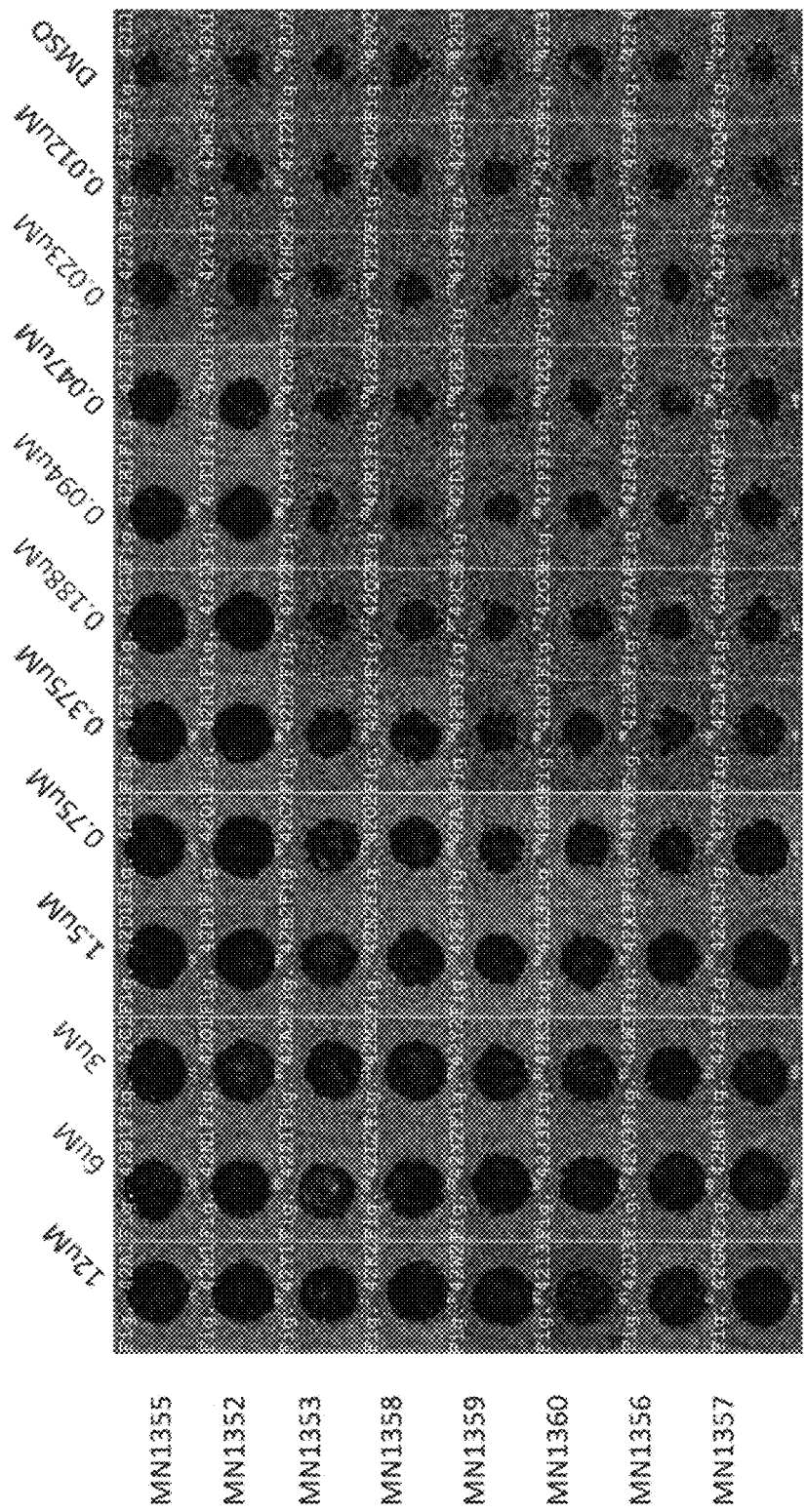
FIG. 42 shows photographs of a cancer cell migration, invasion assay performed on T47D breast cancer cells in the presence of compounds of the invention, over a range of concentrations, or the control, DMSO alone, at 122 hours.
Figure 43:
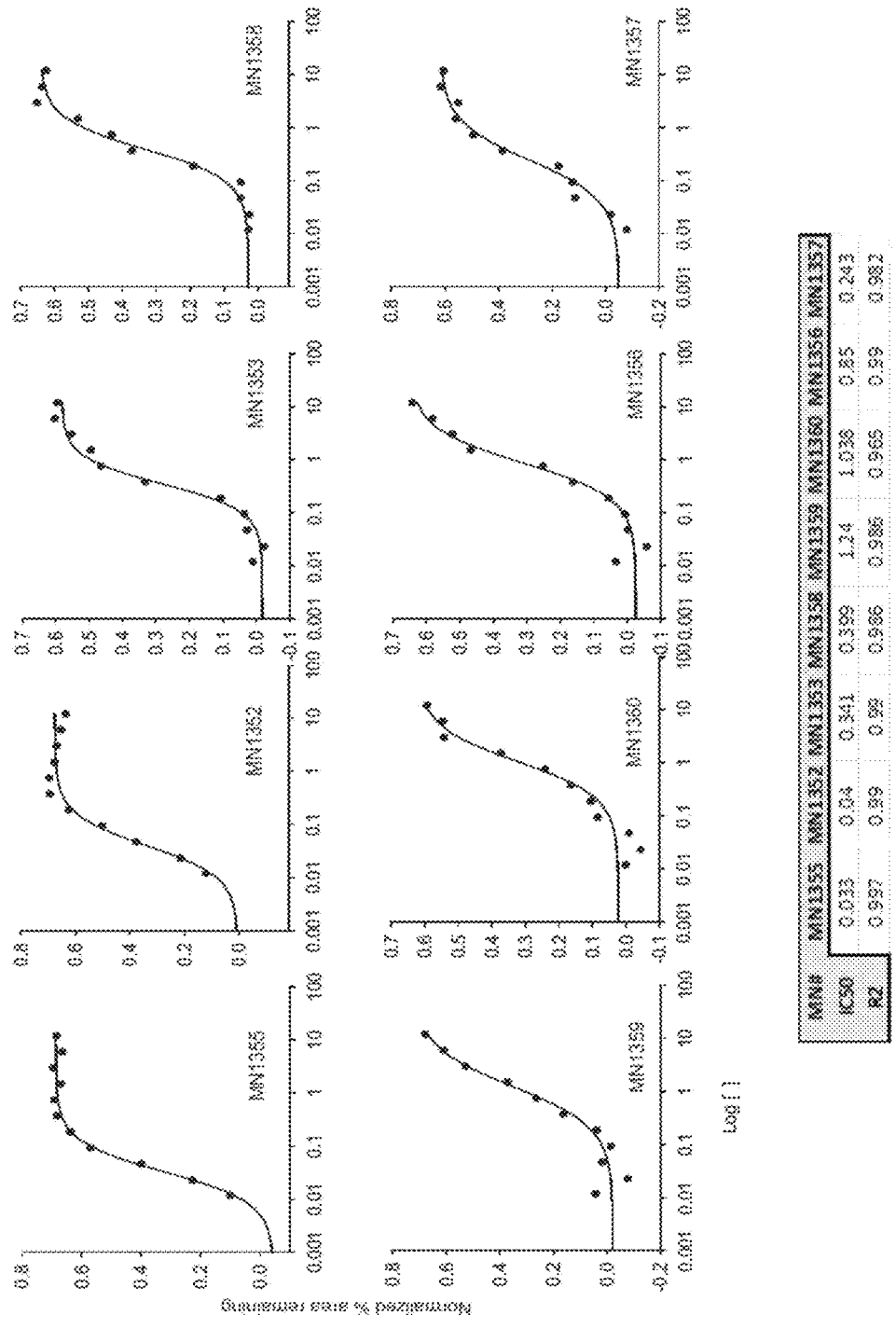
FIG. 43 shows measured IC50 curves for each of the compounds for the ability to inhibit cancer cell migration or invasion of T47D breast cancer cells in the presence of compounds of the invention, over a range of concentrations, or the control, DMSO alone, at 122 hours.
Figure 44:
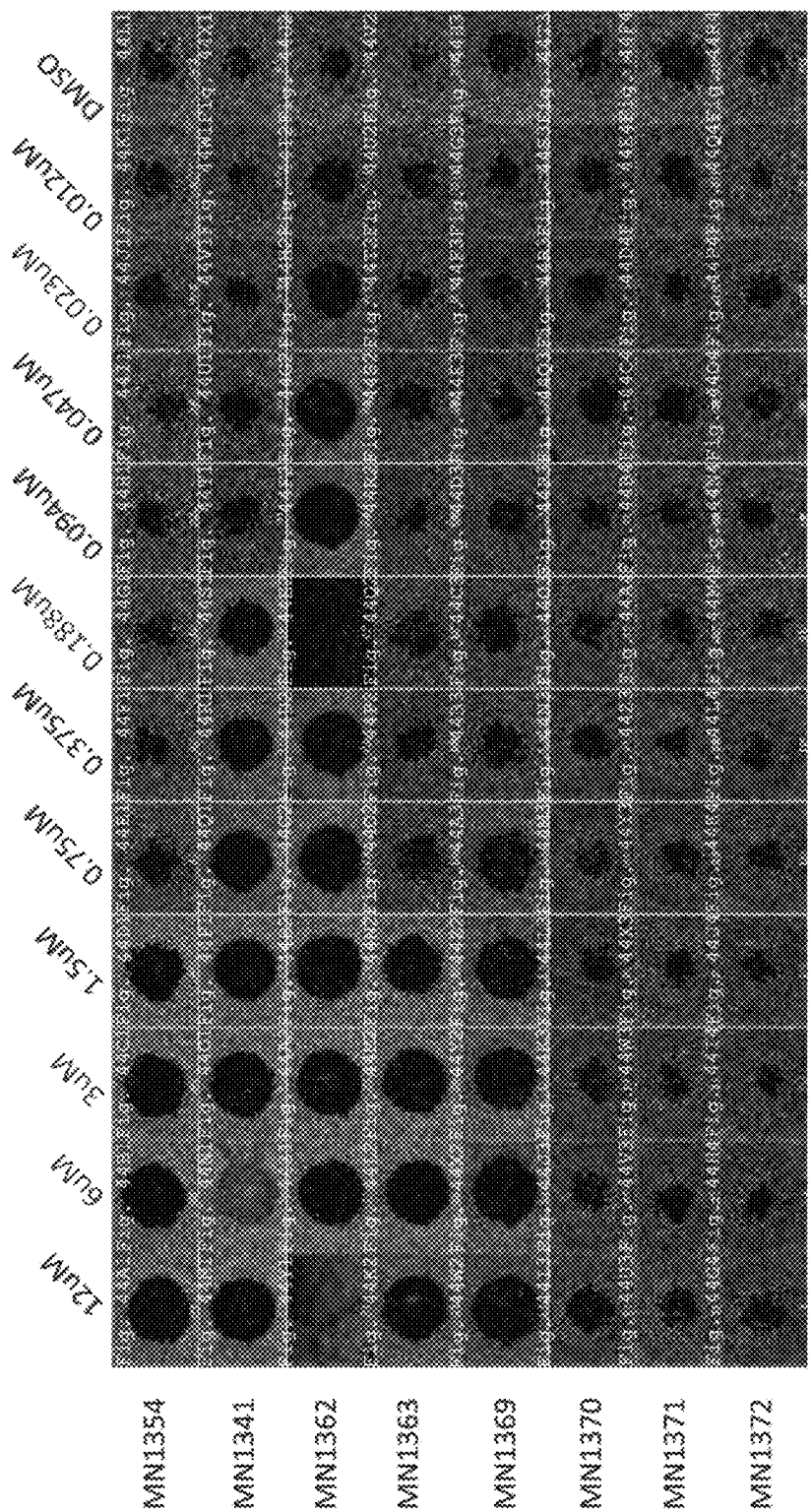
FIG. 44 shows photographs of a cancer cell migration, invasion assay performed on T47D breast cancer cells in the presence of compounds of the invention, over a range of concentrations, or the control, DMSO alone, at 124 hours.
Figure 45:
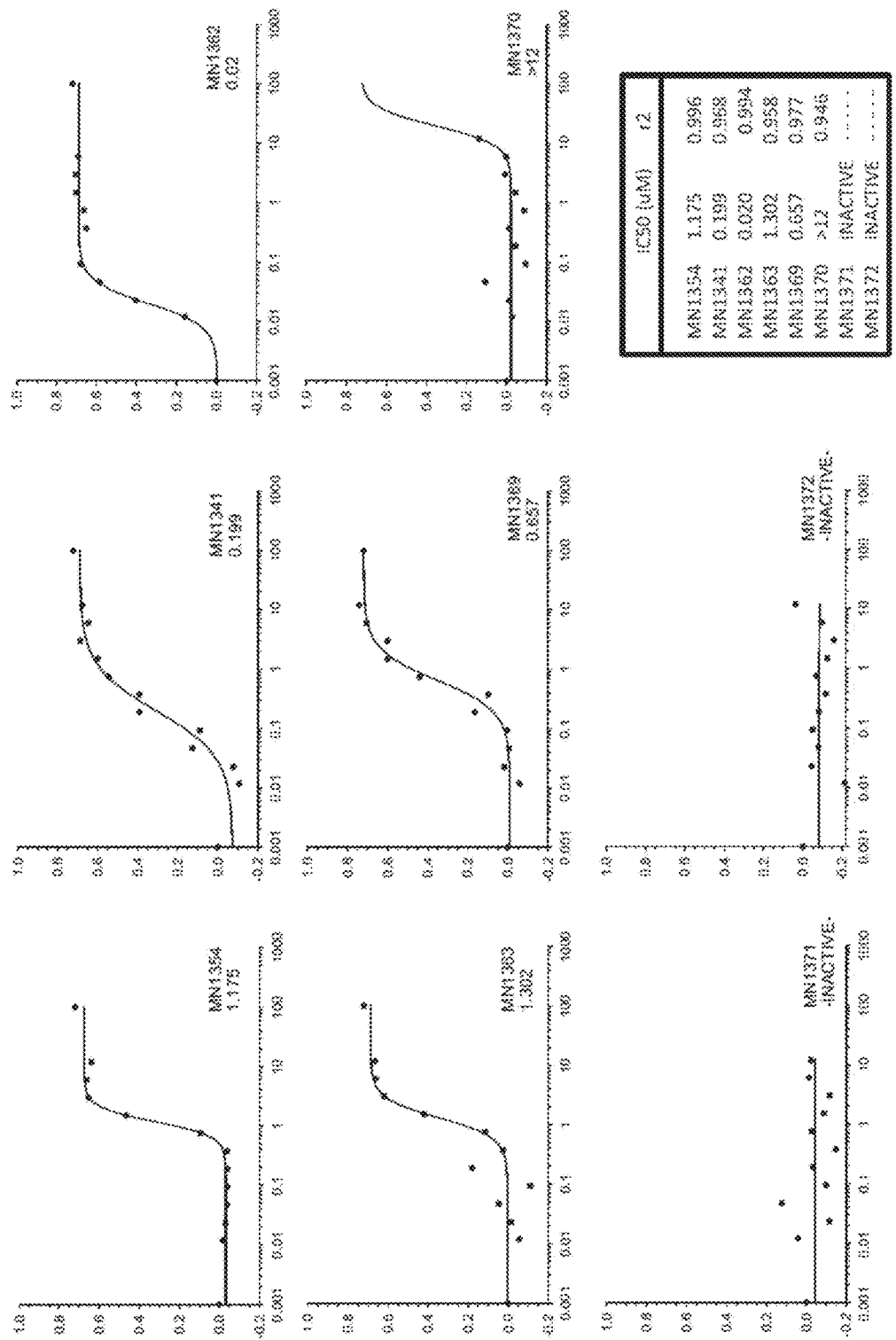
FIG. 45 shows measured IC50 curves for each of the compounds for the ability to inhibit cancer cell migration or invasion of T47D breast cancer cells in the presence of compounds of the invention, over a range of concentrations, or the control, DMSO alone, at 124 hours.
Figures 46A, 46B, 46C, 46D, 46E, 46F:
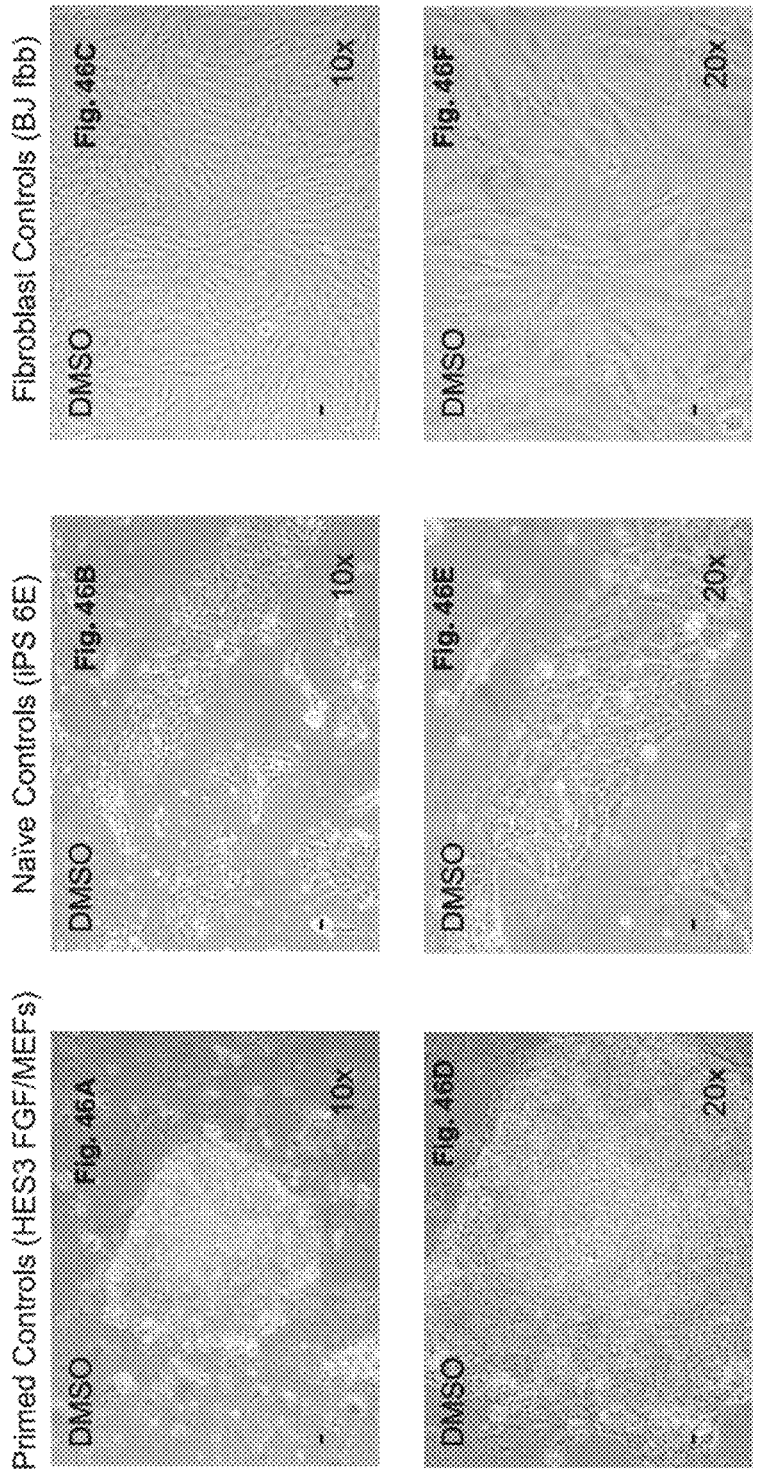
FIG. 46A-46F shows photographs of the control stem cells and fibroblast cells treated with the same concentration of DMSO as is in the test compounds.
Figure 47G:
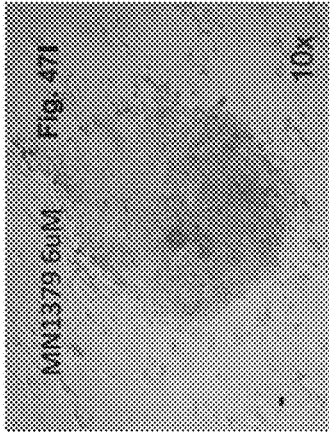
Figure 47H:
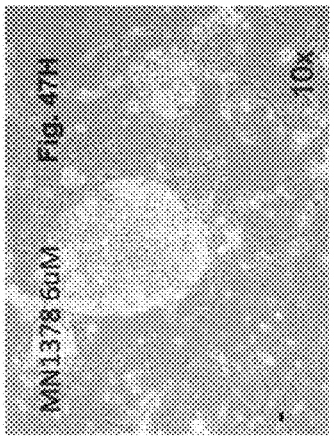
Figure 47I:
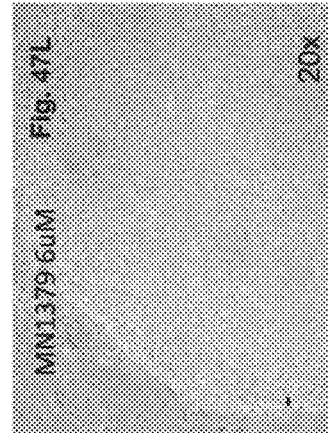
Figure 47J:
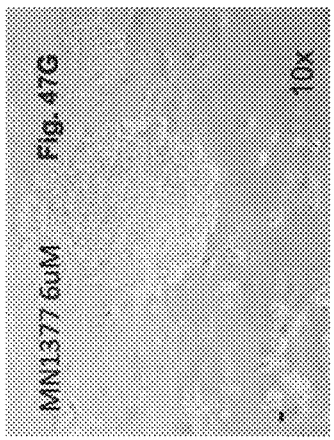
Figure 47K:
Figure 47L:
Figures 47M, 47N, 47O, 47P, 47Q, 47R:
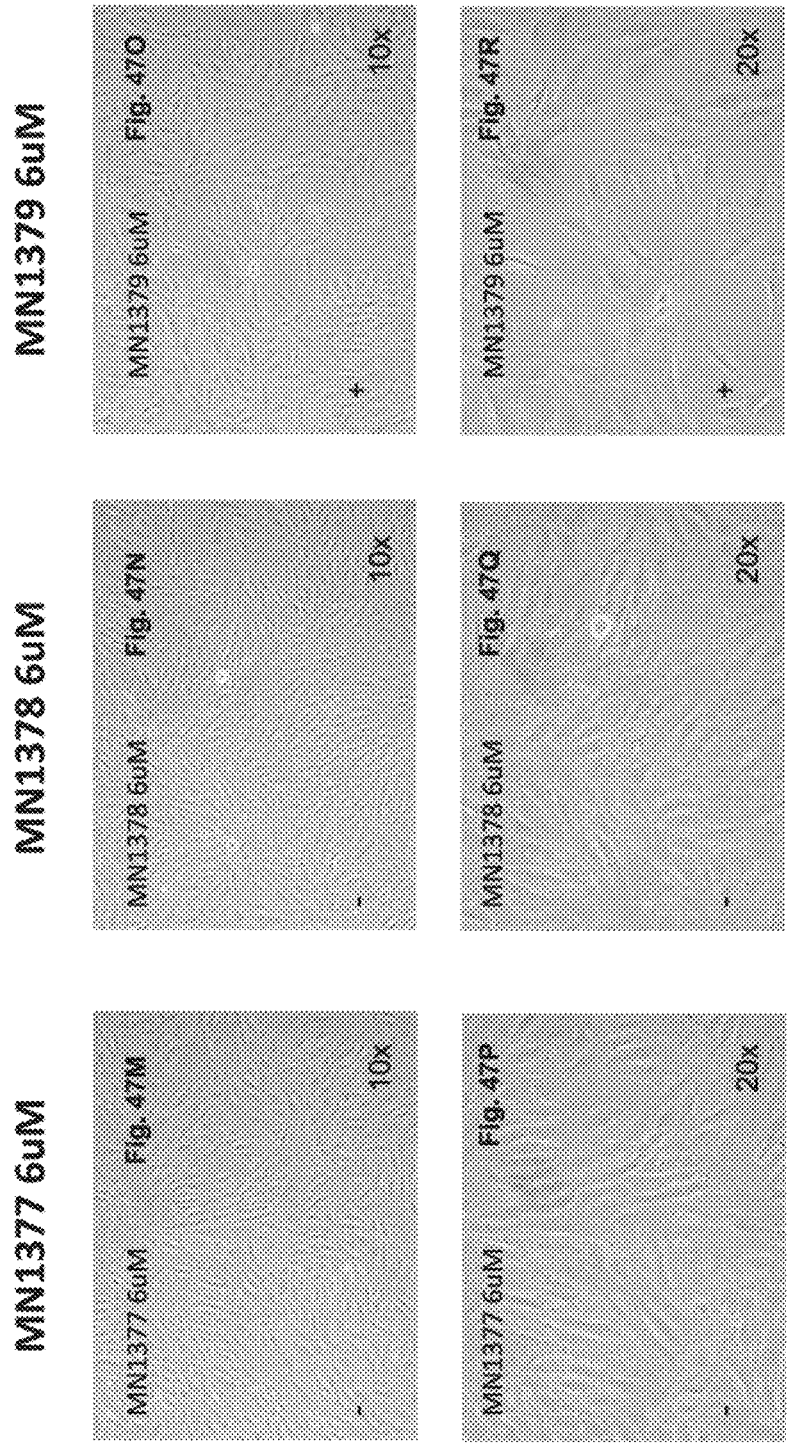
FIGS. 47M-47R, 48M-48R, and 49M-49R show photographs of human fibroblast cells treated for 3 days with a small molecule drug candidate at a final concentration of 6 uM. In each panel, a score of −, or +, ++, +++, or ++++ is given, wherein "−" indicates that at the indicated concentration the drug candidate did not have an obvious effect on the morphology or proliferation of the cells. A "+" indicates a mild effect and "++++" indicates a profound effect on morphology or proliferation of the cells.
Figure 48A:
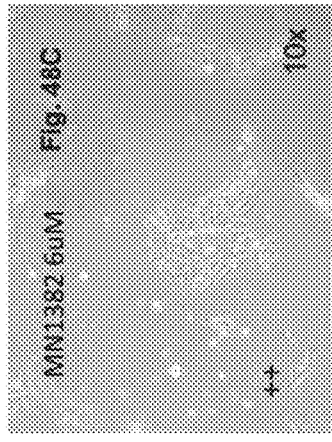
Figure 48B:
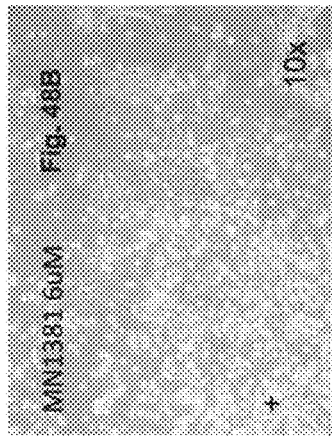
Figure 48C:
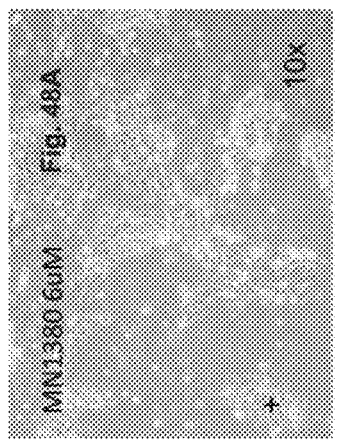
Figure 48D:
Figure 48E:
Figure 48F:
Figures 48G, 48H, 48I, 48J, 48K, 48L:
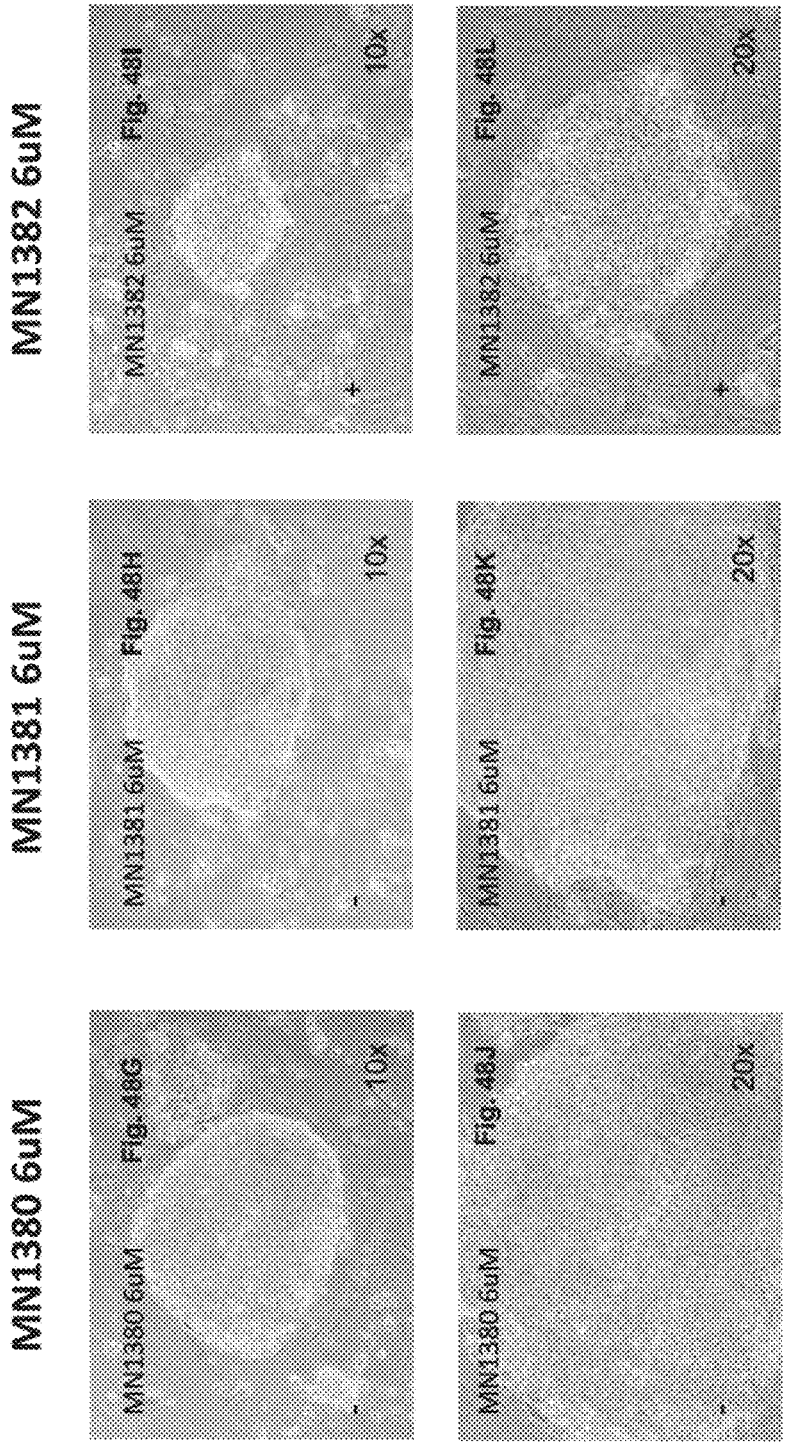
Figures 48M, 48N, 48O, 48P, 48Q, 48R:
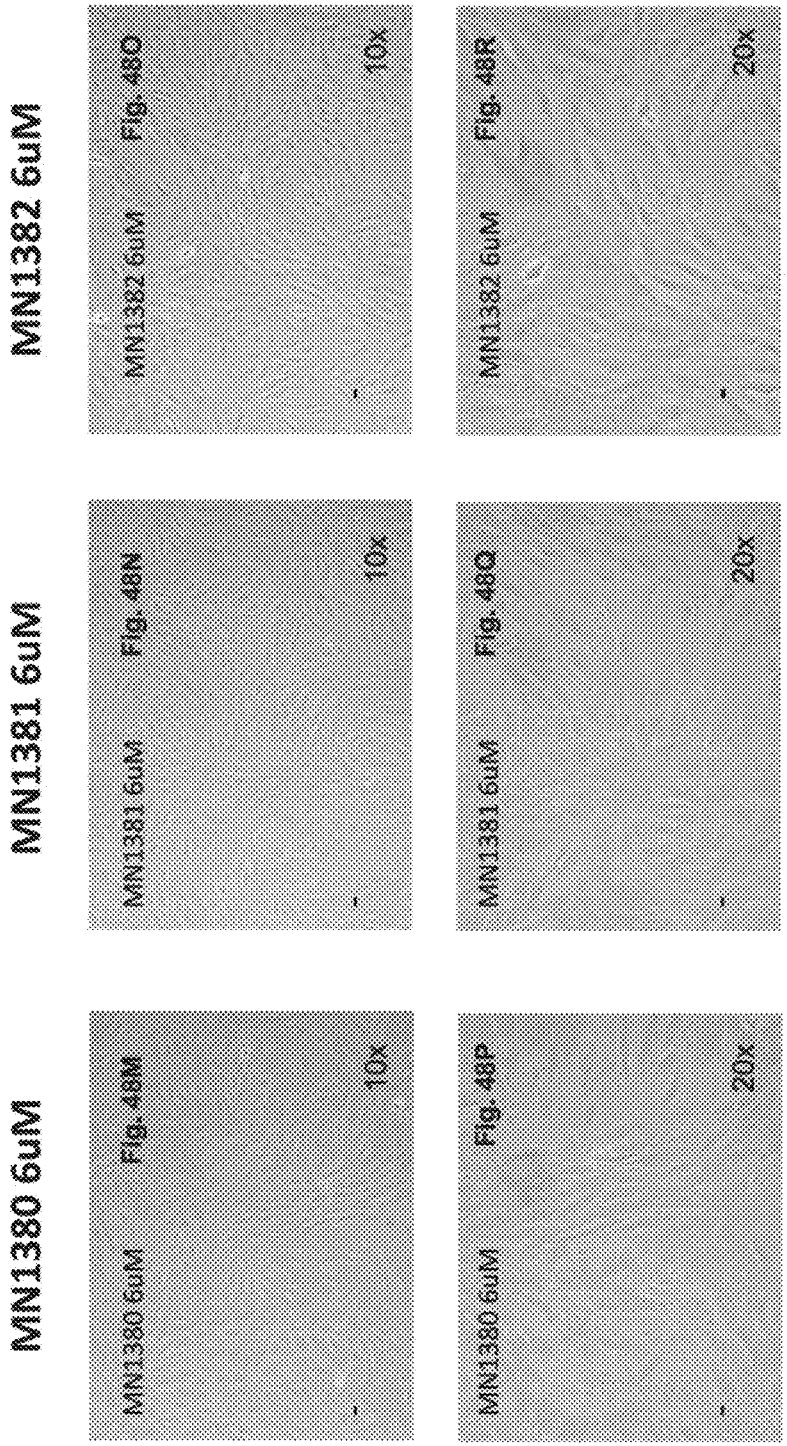
Figure 49A:
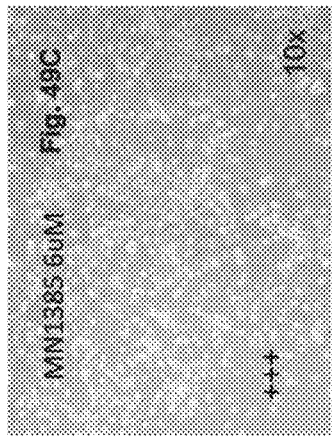
Figure 49B:
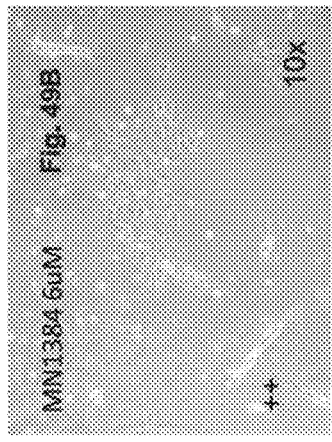
Figure 49C:
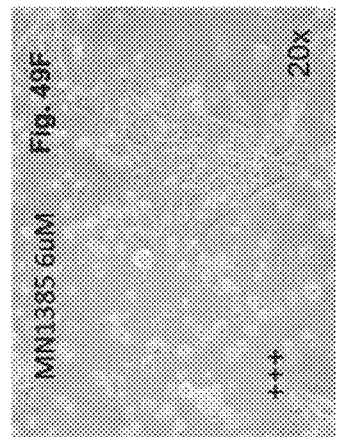
Figure 49D:
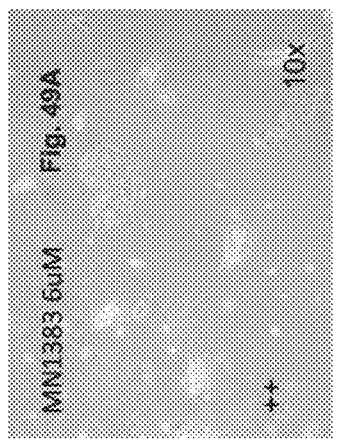
Figure 49E:
Figure 49F:
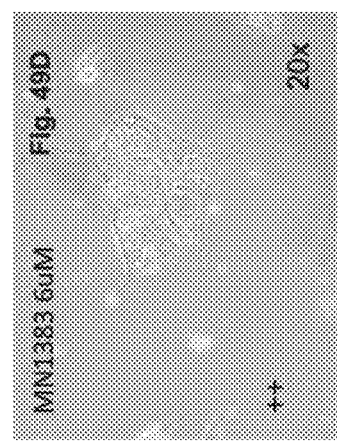
Figures 49M, 49N, 49O, 49P, 49Q, 49R:
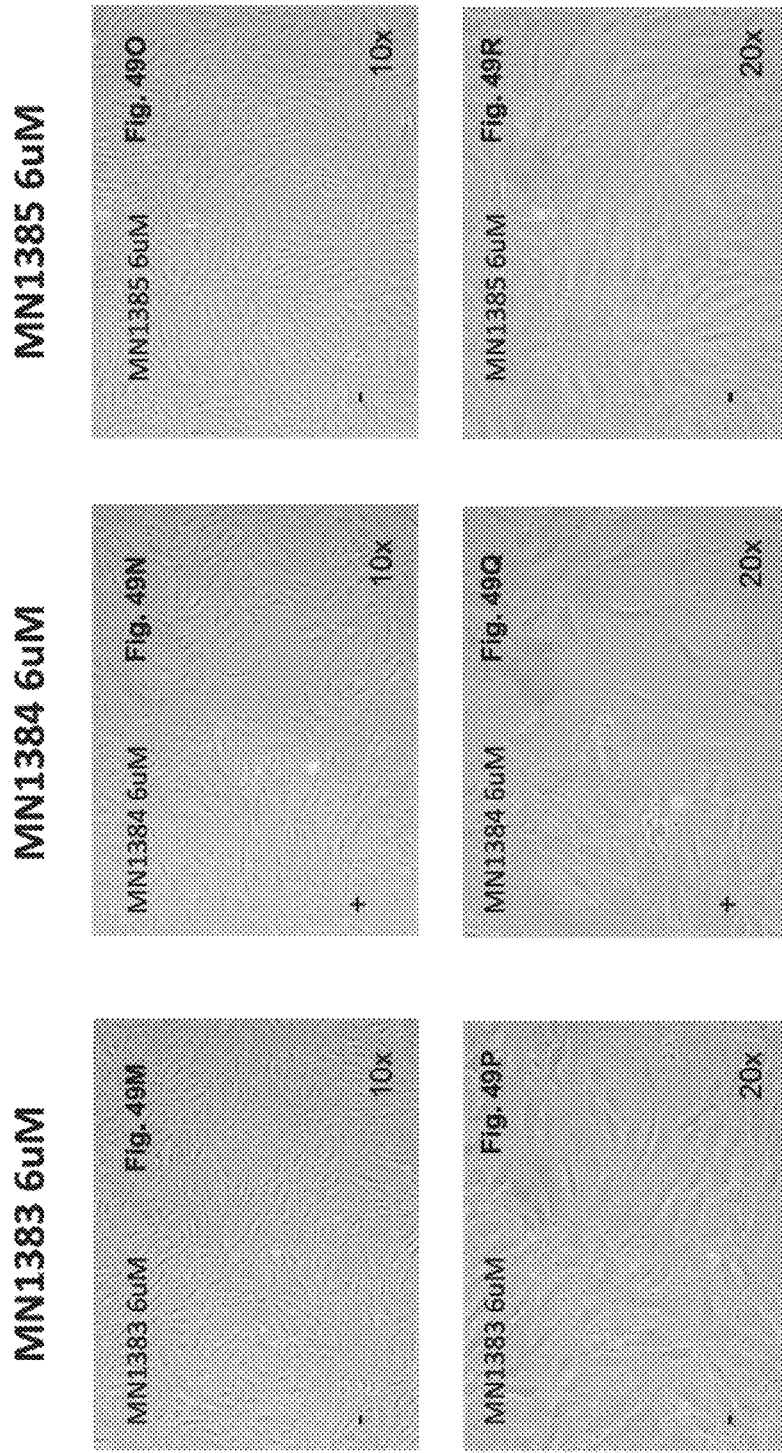
Figures 50A, 50B, 50C, 50D, 50E, 50F:
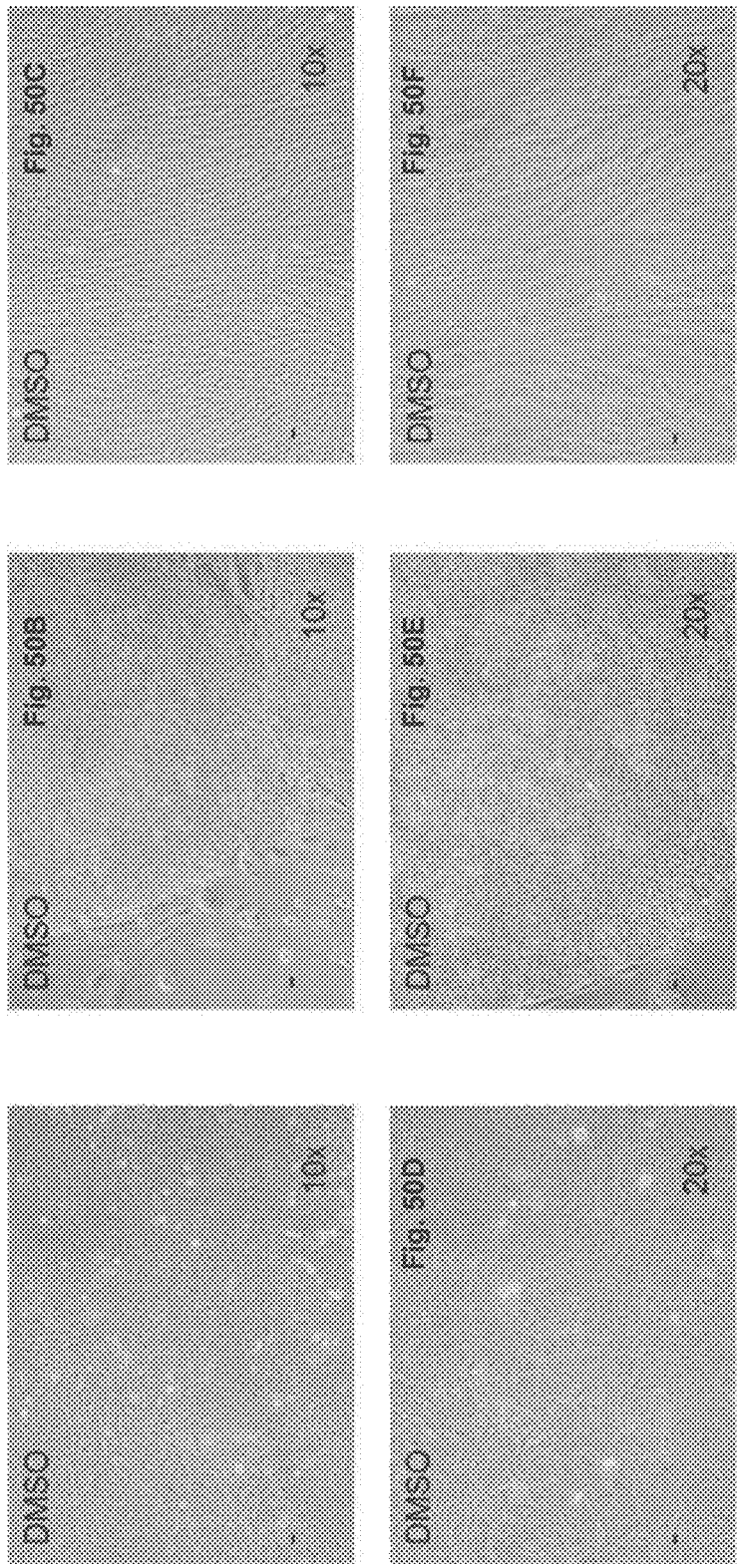
FIG. 50A-50F shows photographs of the control stem cells and fibroblast cells for the next set of experiments, where the cells were treated with the same concentration of DMSO as is in the test compounds.
Figures 51A, 51B, 51C, 51D, 51E, 51F:
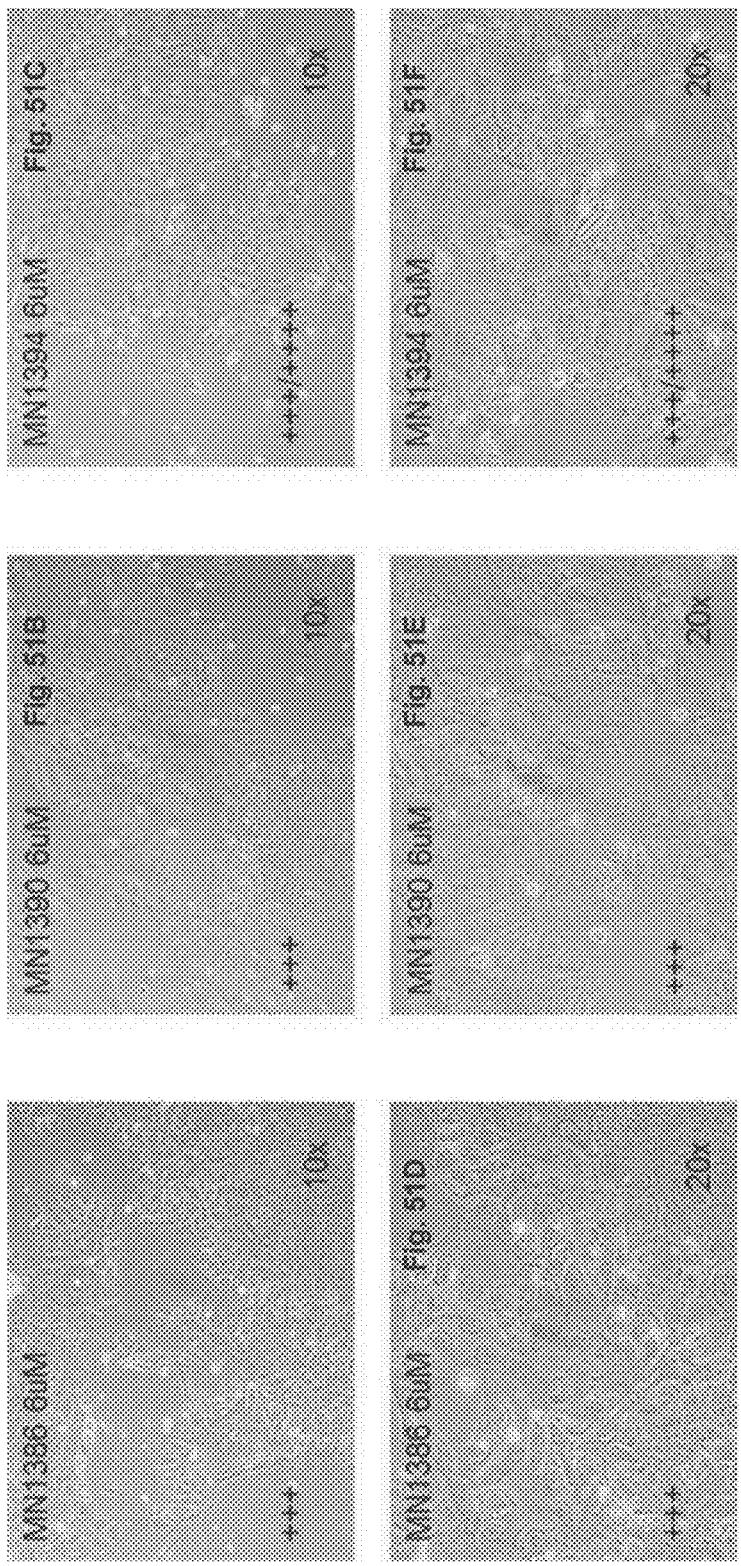
FIGS. 51A-51F, 52A-52F, 53A-53F, and 54A-54F_show photographs of human naïve state stem cells, previously grown in NME7$_{AB}$ over a MUC1* antibody surface, C3, but cultured in the absence of NME7$_{AB}$ during the experiment, and treated for a brief 24 hours with a small molecule drug candidate at a final concentration of 6 uM. In each panel, a score of −, or +, ++, +++, or ++++ is given, wherein "−" indicates that at the indicated concentration the drug candidate did not have an obvious effect on the pluripotency or proliferation of the stem cells. A "+" indicates a mild effect and "++++" indicates a profound effect on pluripotency or proliferation. Inhibition of proliferation can be seen as holes, or blank areas, in the layer of stem cells. Inhibition of pluripotency, which is also induction of differentiation, is seen as increase in cell size with a decrease in the size of the nucleus, elongation and flattening of cells or rounding up of cells and floating off the plate.
Figures 51G, 51H, 51I, 51J, 51K, 51L:
FIGS. 51G-51L, 52G-52L, 53G-53L, and 54G-54L show photographs of human primed state stem cells, previously grown in FGF over a layer of MEFs, but cultured in the absence of FGF during the experiment, and treated for a brief 24 hours with a small molecule drug candidate at a final concentration of 6 uM. In each panel, a score of −, or +, ++, +++, or ++++ is given, wherein "−" indicates that at the indicated concentartion the drug candidate did not have an obvious effect on the pluripotency or proliferation of the stem cells. A "+" indicates a mild effect and "++++" indicates a profound effect on pluripotency or proliferation. Primed state stem cells grow in defined colonies rather than a uniform layer like naïve stem cells. Inhibition of proliferation can be seen as a reduction in the colony size. Inhibition of pluripotency, which is also induction of differentiation, is seen as increase in cell size with a decrease in the size of the nucleus, elongation and flattening of cells or rounding up of cells and floating off the plate.
Figures 51M, 51N, 51O, 51P, 51Q, 51R:
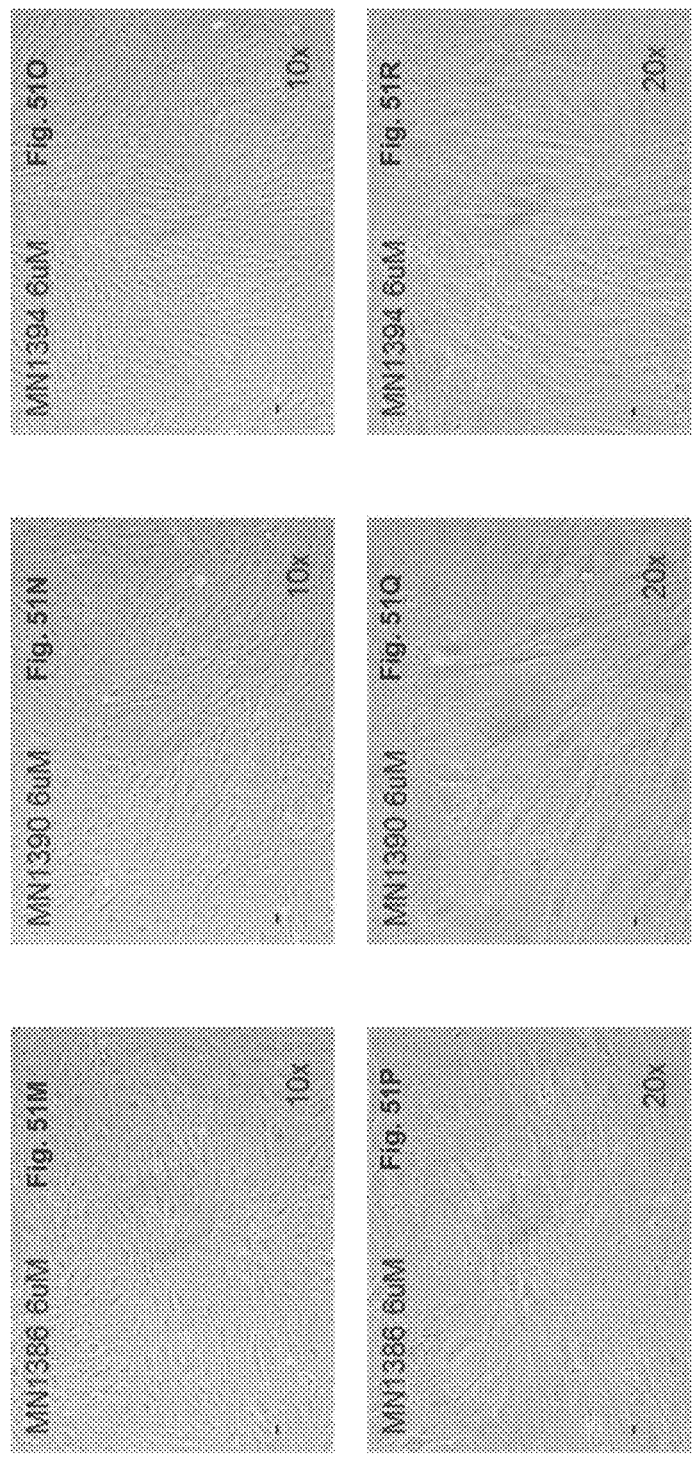
FIGS. 51M-51R, 52M-52R, 53M-53R, and 54M-54R show photographs of human fibroblast cells treated for 3 days with a small molecule drug candidate at a final concentration of 6 uM. In each panel, a score of −, or +, ++, +++, or ++++ is given, wherein "−" indicates that at the indicated concentration the drug candidate did not have an obvious effect on the morphology or proliferation of the cells. A "+" indicates a mild effect and "++++" indicates a profound effect on morphology or proliferation of the cells.
Figures 52A, 52B, 52C, 52D, 52E, 52F:
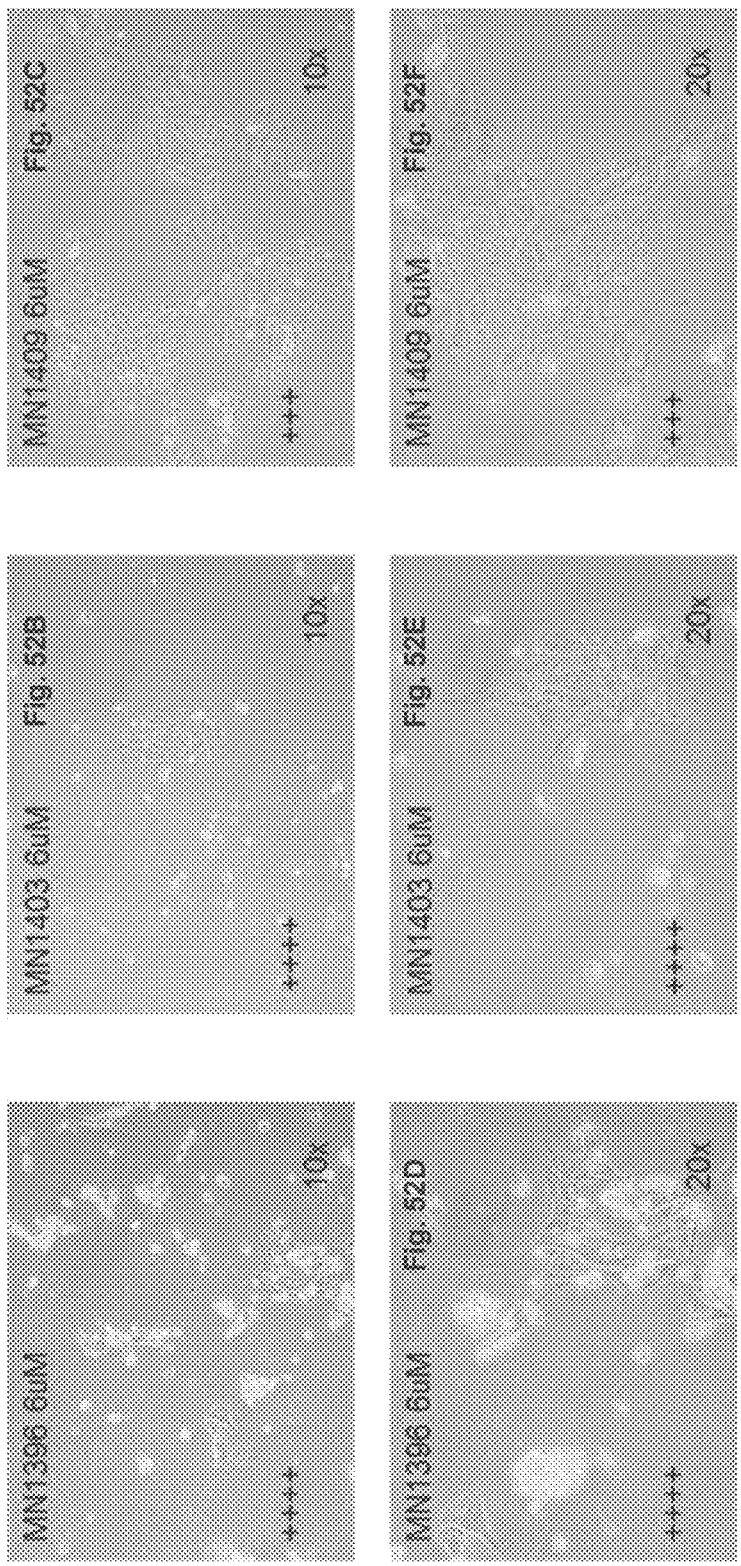
Figures 52G, 52H, 52I, 52J, 52K, 52L:
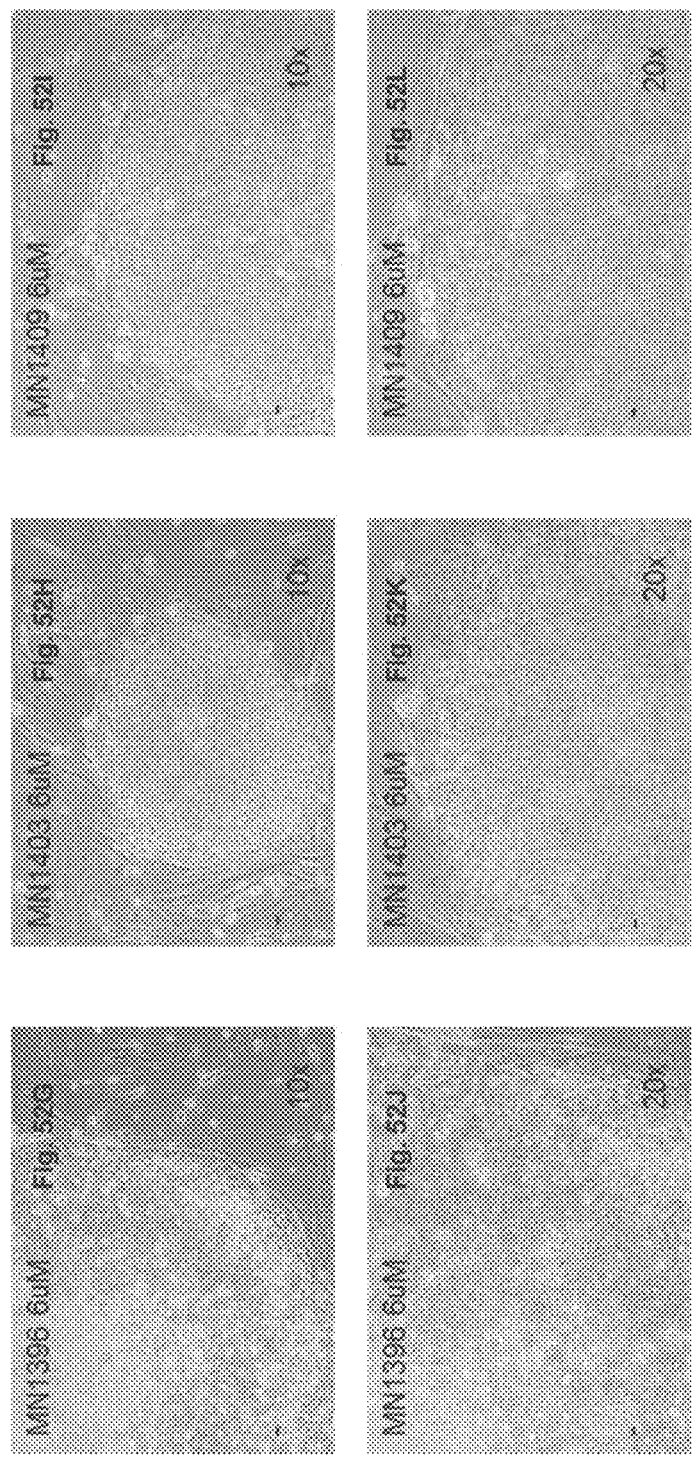
Figures 52M, 52N, 52O, 52P, 52Q, 52R:
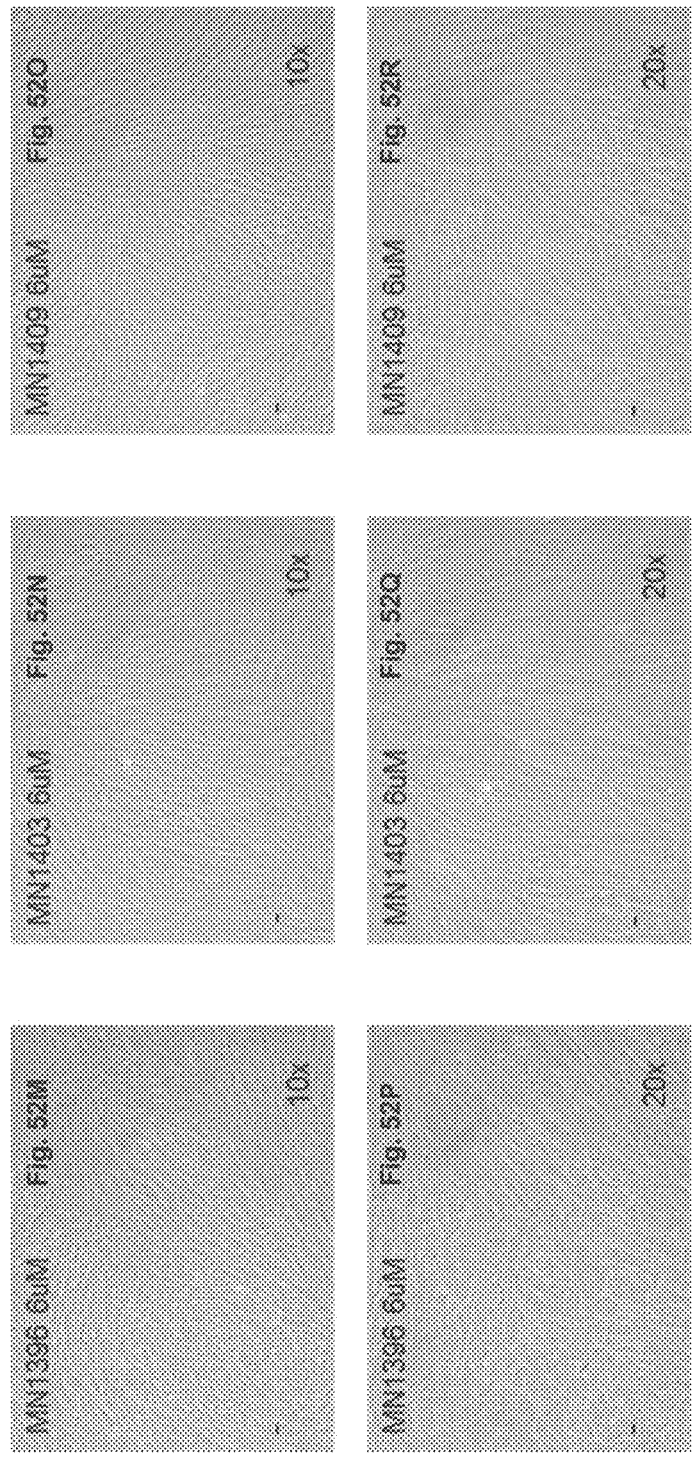
Figures 53A, 53B, 53C, 53D, 53E, 53F:
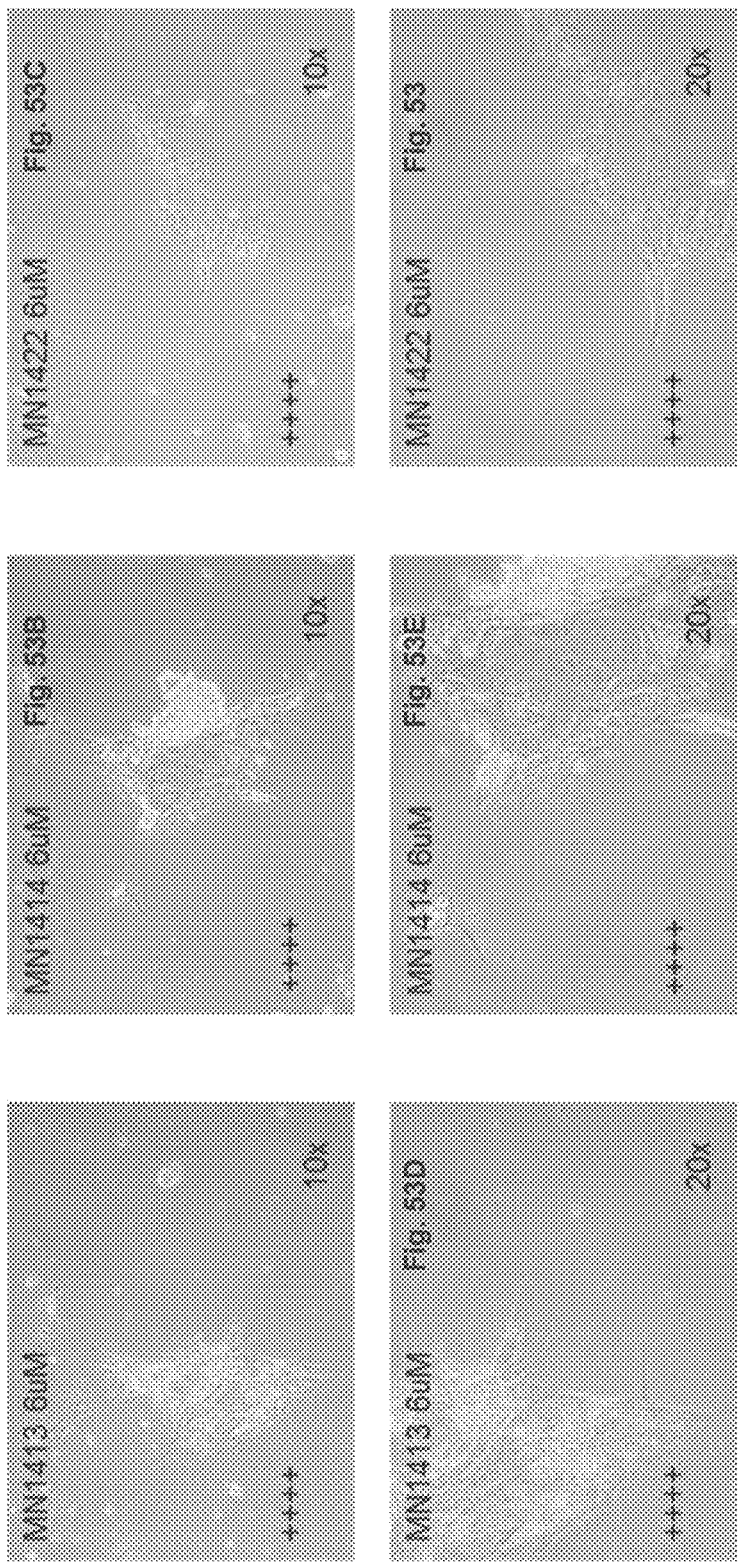
Figures 53G, 53H, 53I, 53J, 53K, 53L:
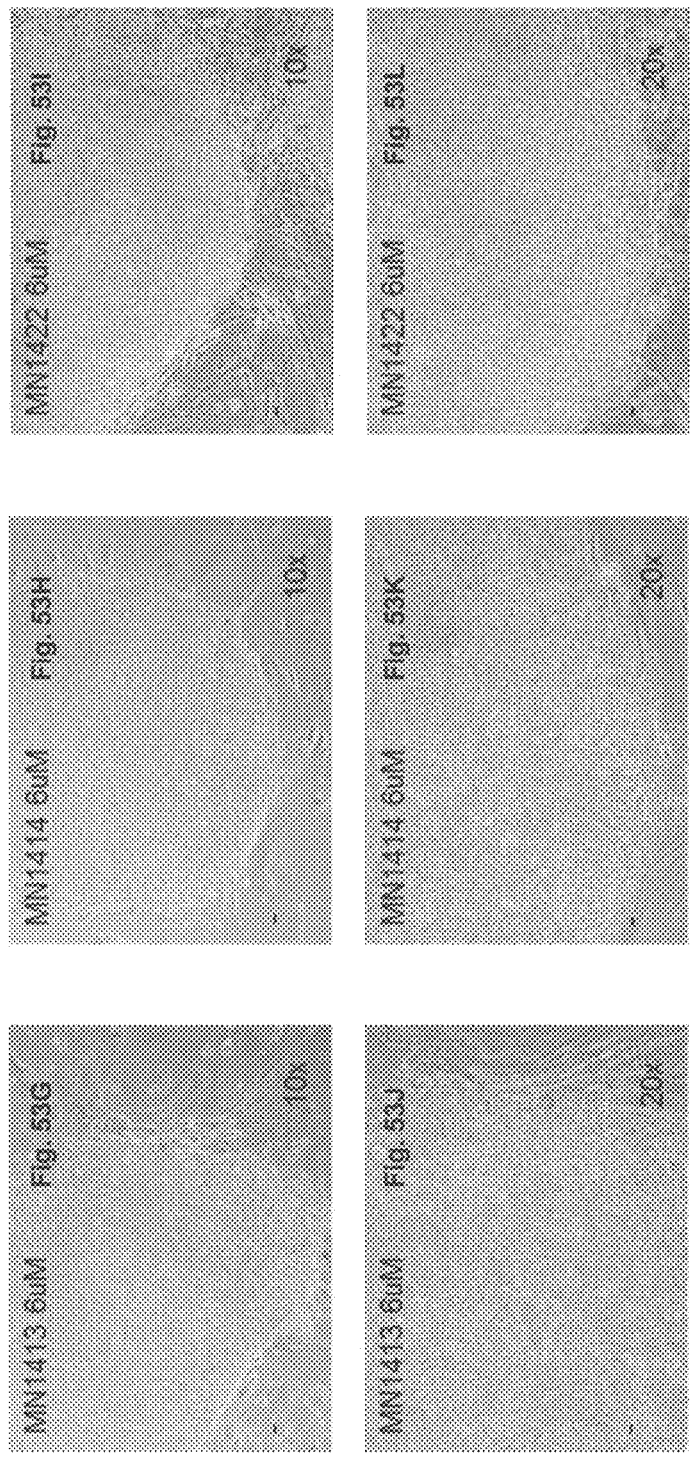
Figures 53M, 53N, 53O, 53P, 53Q, 53R:
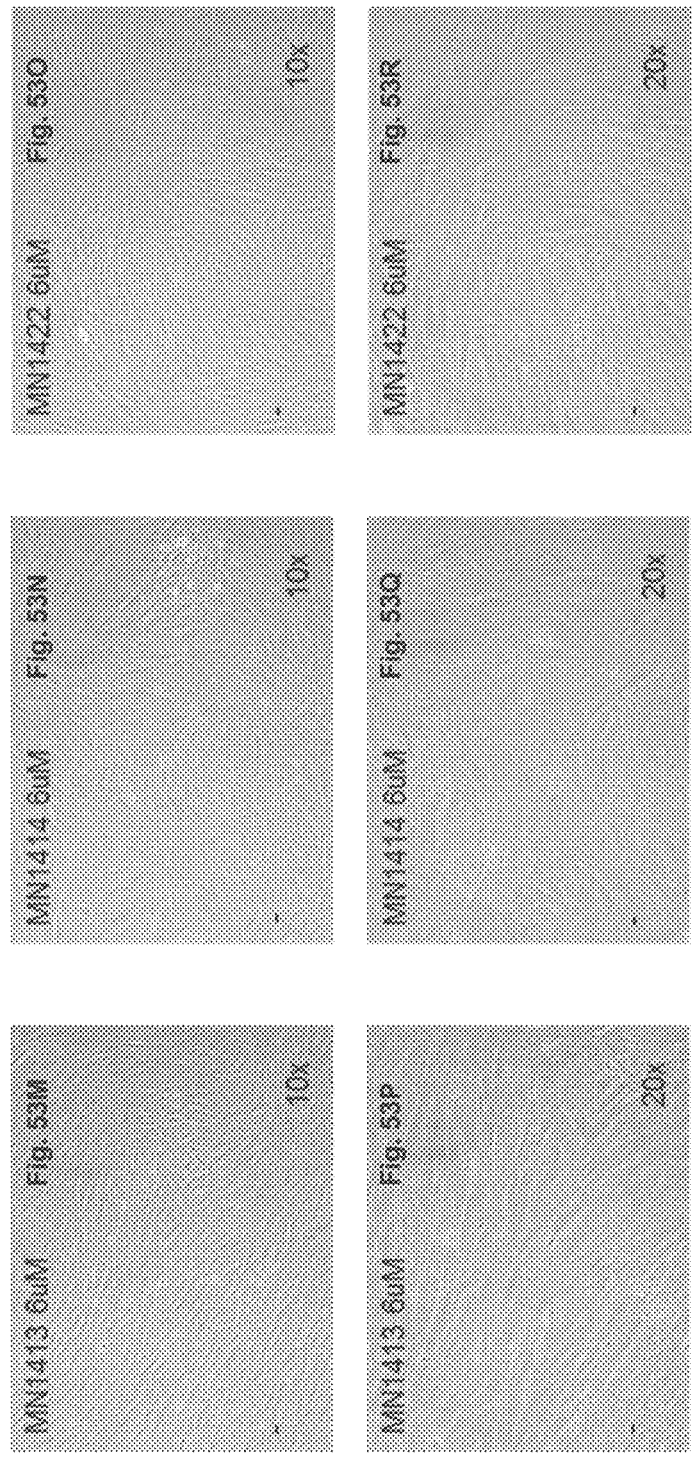
Figures 54A, 54B, 54C, 54D, 54E, 54F:
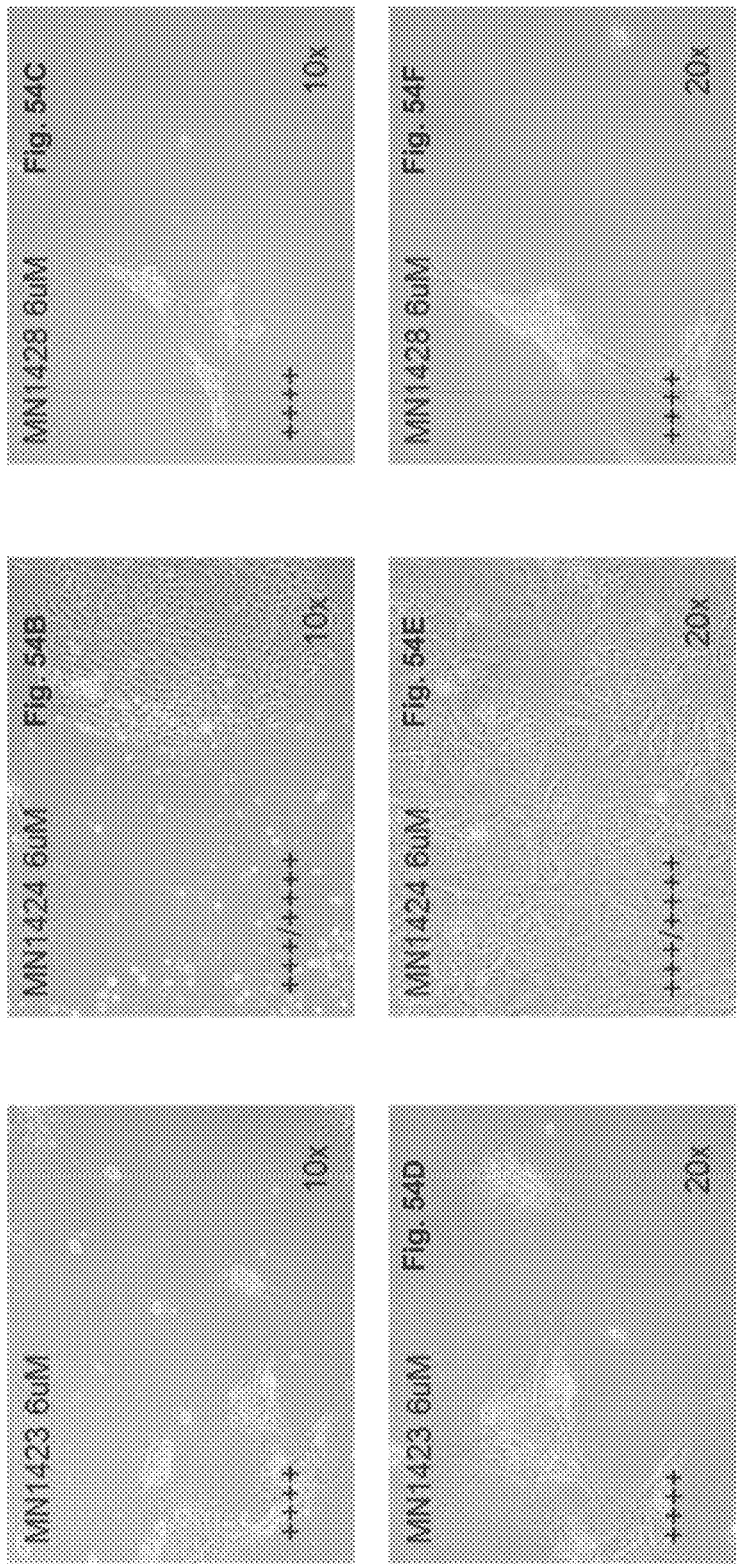
Figures 54G, 54H, 54I, 54J, 54K, 54L:
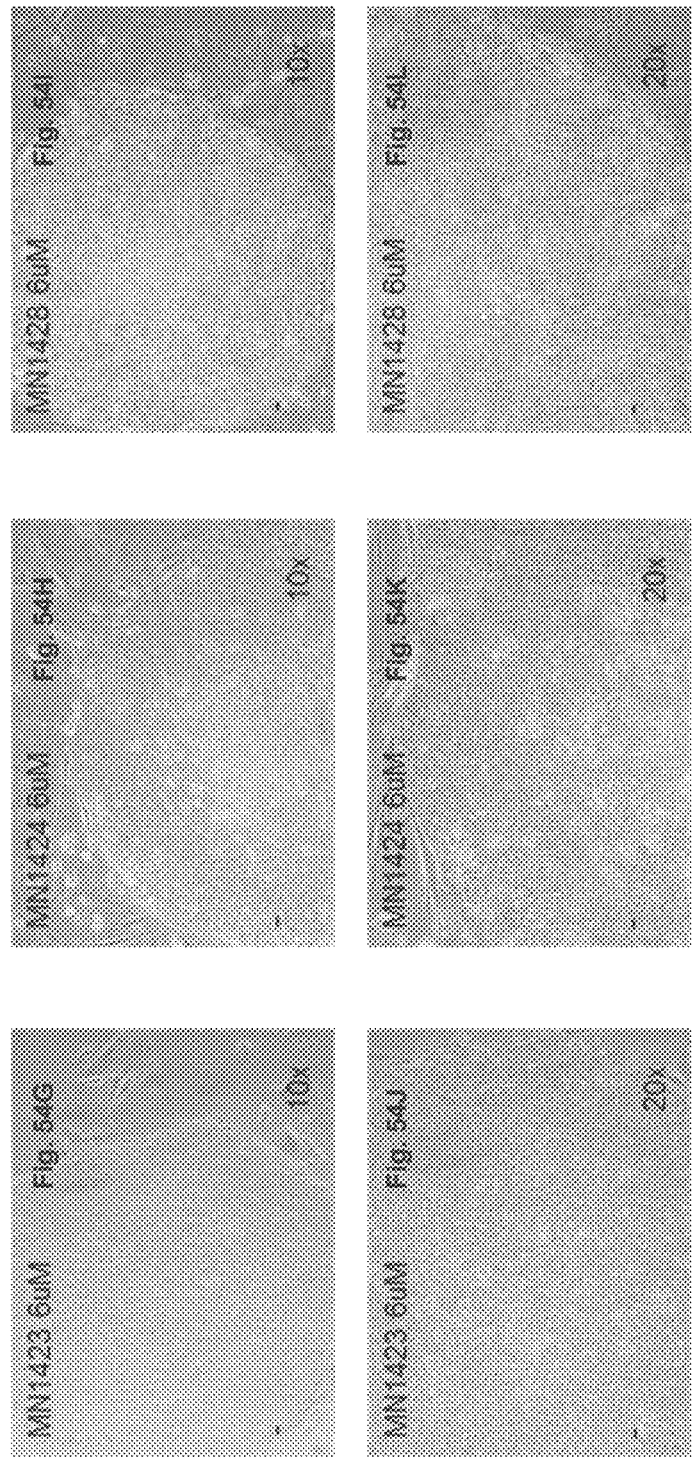
Figures 54M, 54N, 54O, 54P, 54Q, 54R:
Figures 55A, 55B, 55C, 55D, 55E, 55F:
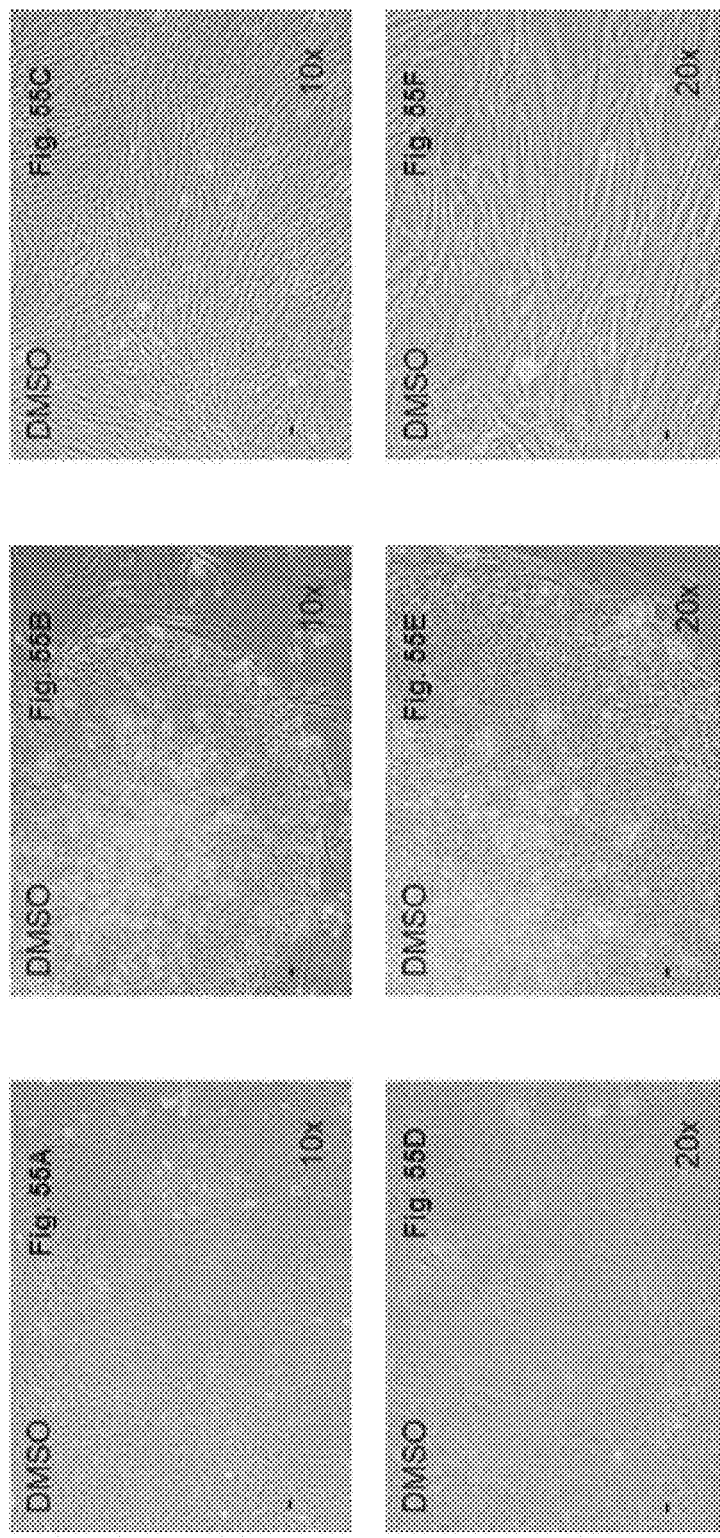
FIG. 55A-55F shows photographs of the control stem cells and fibroblast cells for the next set of experiments, where the cells were treated with the same concentration of DMSO as is in the test compounds.
Figures 56A, 56B, 56C, 56D, 56E, 56F:
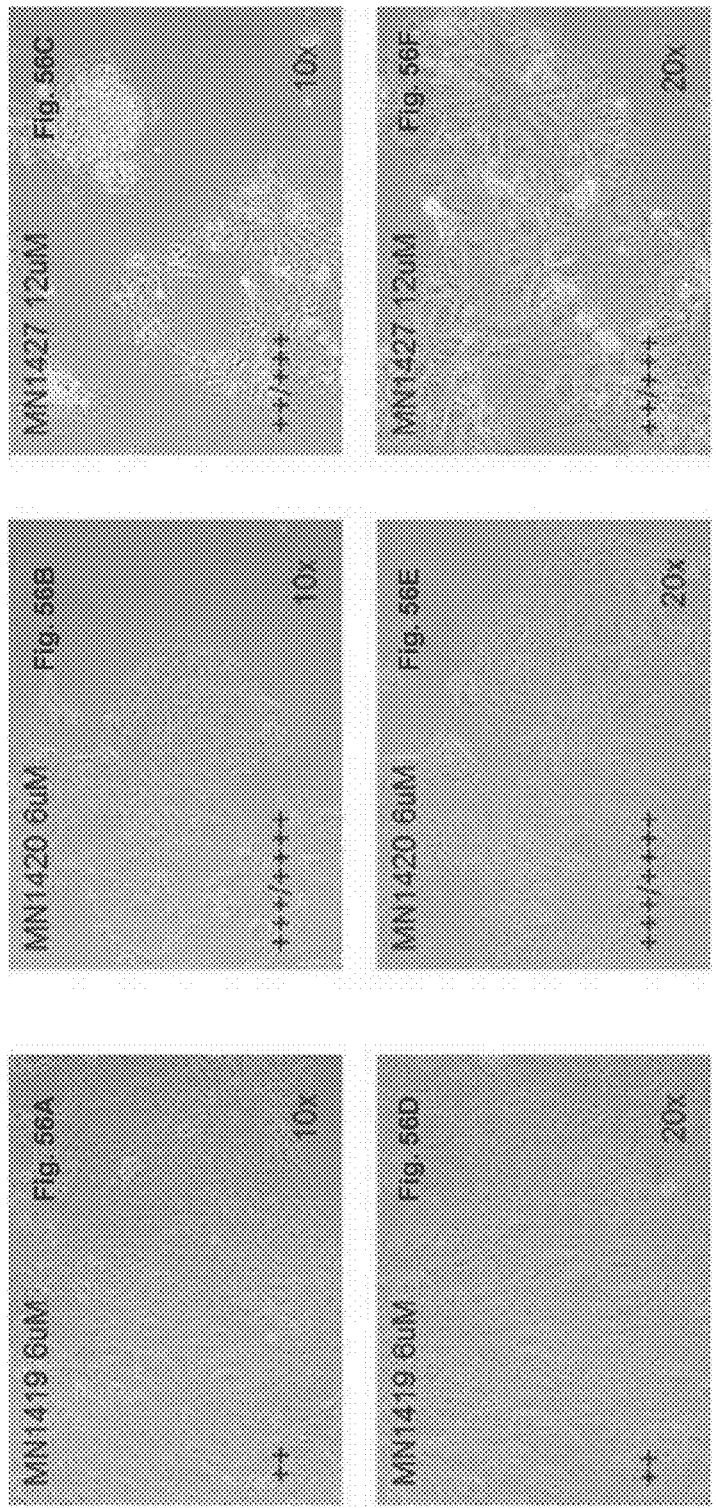
FIGS. 56A-56F, 57A-57F, 58A-58F, 59A-59F, 60A-60F, 61A-61F, 62A-62F, 63A-63F, and 64A-64D show photographs of human naïve state stem cells, previously grown in NME7$_{AB}$ over a MUC1* antibody surface, C3, but cultured in the absence of NME7$_{AB}$ during the experiment, and treated for a brief 24 hours with a small molecule drug candidate at a final concentration of 6 uM. In each panel, a score of −, or +, ++, +++, or ++++ is given, wherein "−" indicates that at the indicated concentration the drug candidate did not have an obvious effect on the pluripotency or proliferation of the stem cells. A "+" indicates a mild effect and "++++" indicates a profound effect on pluripotency or proliferation. Inhibition of proliferation can be seen as holes, or blank areas, in the layer of stem cells. Inhibition of pluripotency, which is also induction of differentiation, is seen as increase in cell size with a decrease in the size of the nucleus, elongation and flattening of cells or rounding up of cells and floating off the plate.
Figures 56G, 56H, 56I, 56J, 56K, 56L:
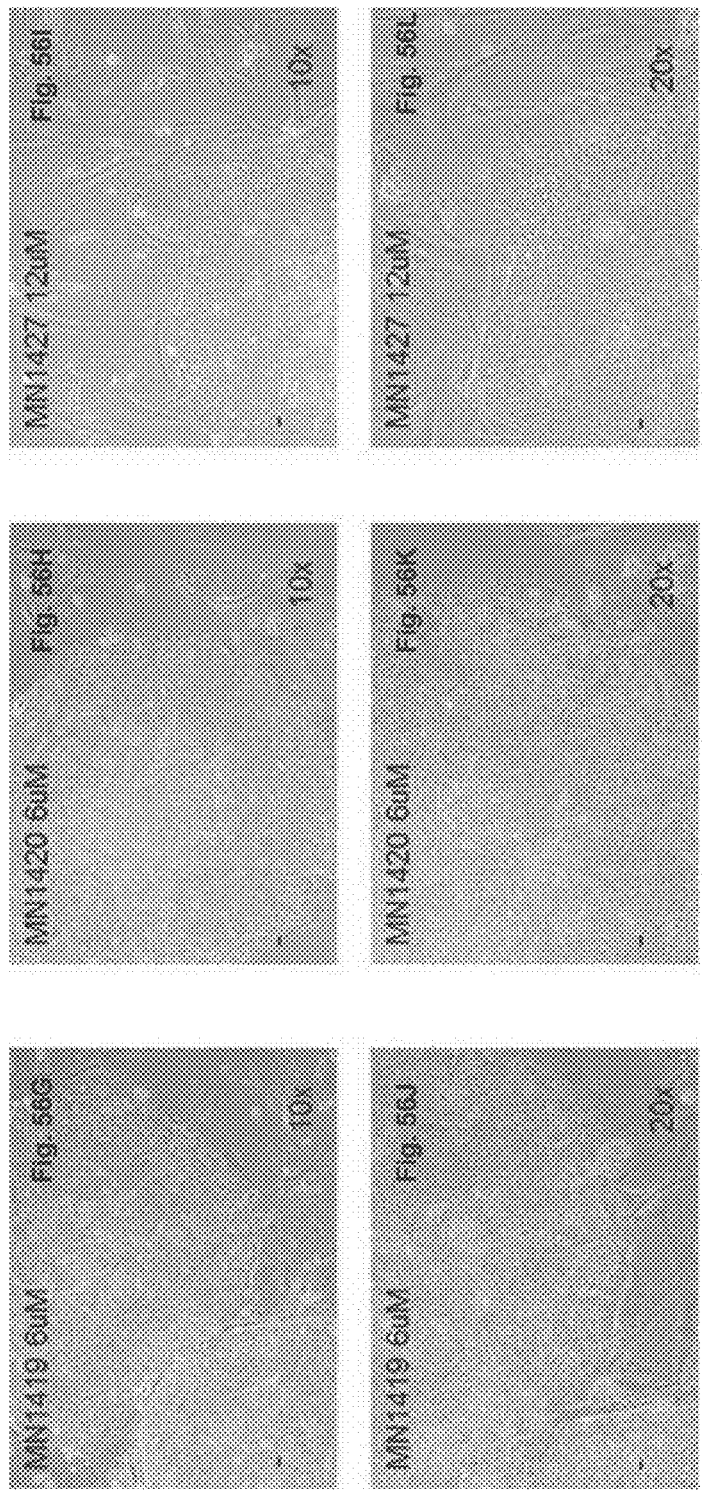
FIGS. 56G-56L, 57G-57L, 58G-58L, 59G-59L, 60G-60L, 61G-61L, 62G-62L, 63G-63L, and 64G-64J show photographs of human primed state stem cells, previously grown in FGF over a layer of MEFs, but cultured in the absence of FGF during the experiment, and treated for a brief 24 hours with a small molecule drug candidate at a final concentration of 6 uM. In each panel, a score of −, or +, ++, +++, or ++++ is given, wherein "−" indicates that at the indicated concentartion the drug candidate did not have an obvious effect on the pluripotency or proliferation of the stem cells. A "+" indicates a mild effect and "++++" indicates a profound effect on pluripotency or proliferation. Primed state stem cells grow in defined colonies rather than a uniform layer like naïve stem cells. Inhibition of proliferation can be seen as a reduction in the colony size. Inhibition of pluripotency, which is also induction of differentiation, is seen as increase in cell size with a decrease in the size of the nucleus, elongation and flattening of cells or rounding up of cells and floating off the plate.
Figure 56:
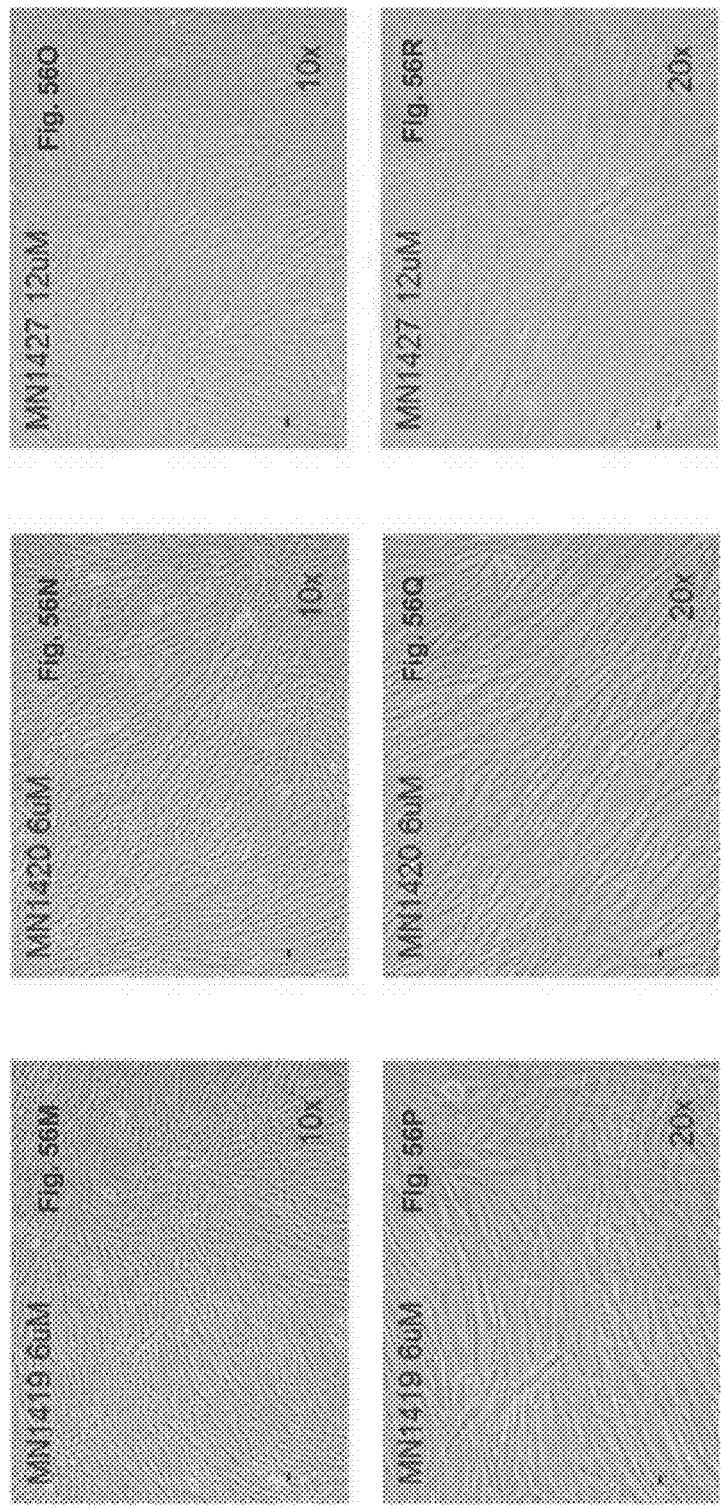
FIGS. 56M-56R, 57M-57R, 58M-58R, 59M-59R, 60M-60R, 61M-61R, 62M-62R, 63M-63R, and 64M-64P show photographs of human fibroblast cells treated for 3 days with a small molecule drug candidate at a final concentration of 6 uM. In each panel, a score of −, or +, ++, +++, or ++++ is given, wherein "−" indicates that at the indicated concentration the drug candidate did not have an obvious effect on the morphology or proliferation of the cells. A "+" indicates a mild effect and "++++" indicates a profound effect on morphology or proliferation of the cells.
Figures 57A, 57B, 57C, 57D, 57E, 57F:
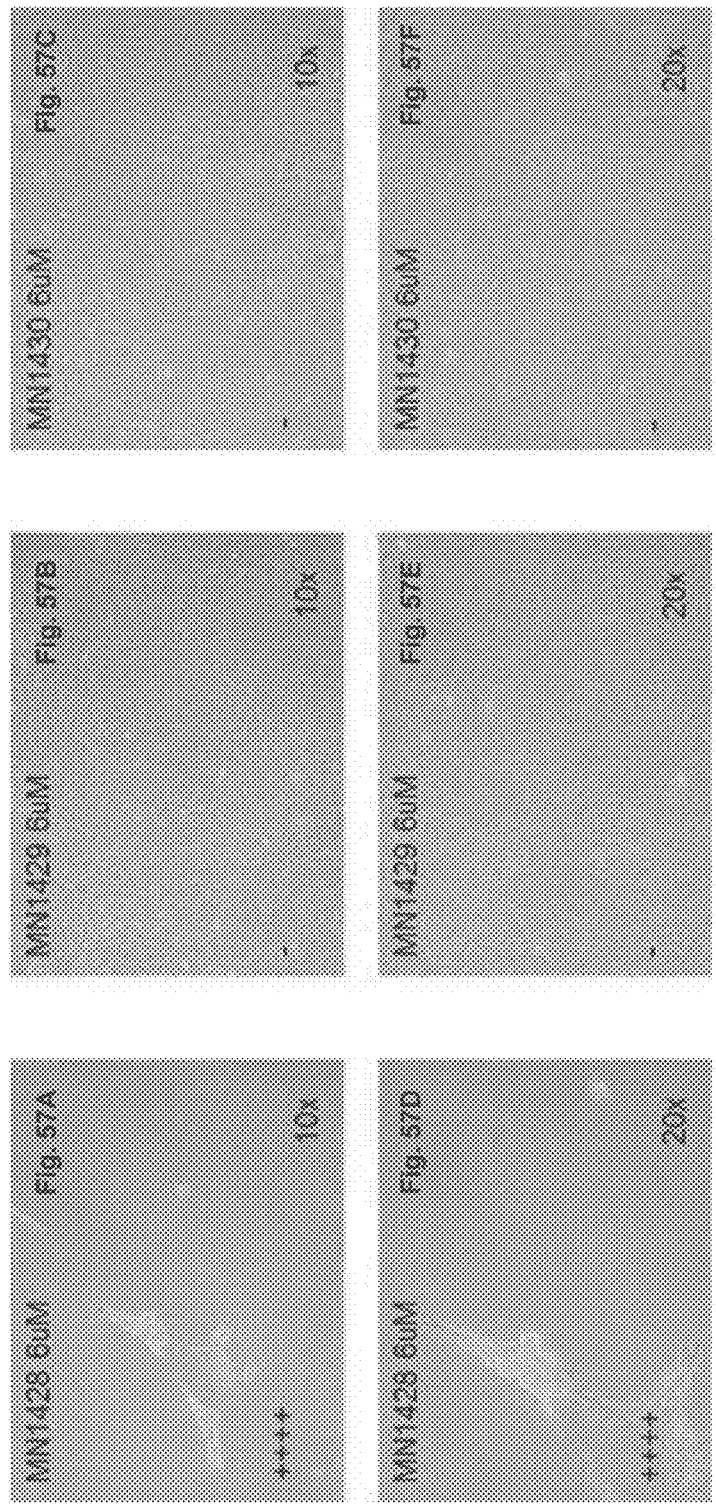
Figures 57G, 57H, 57I, 57J, 57K, 57L:
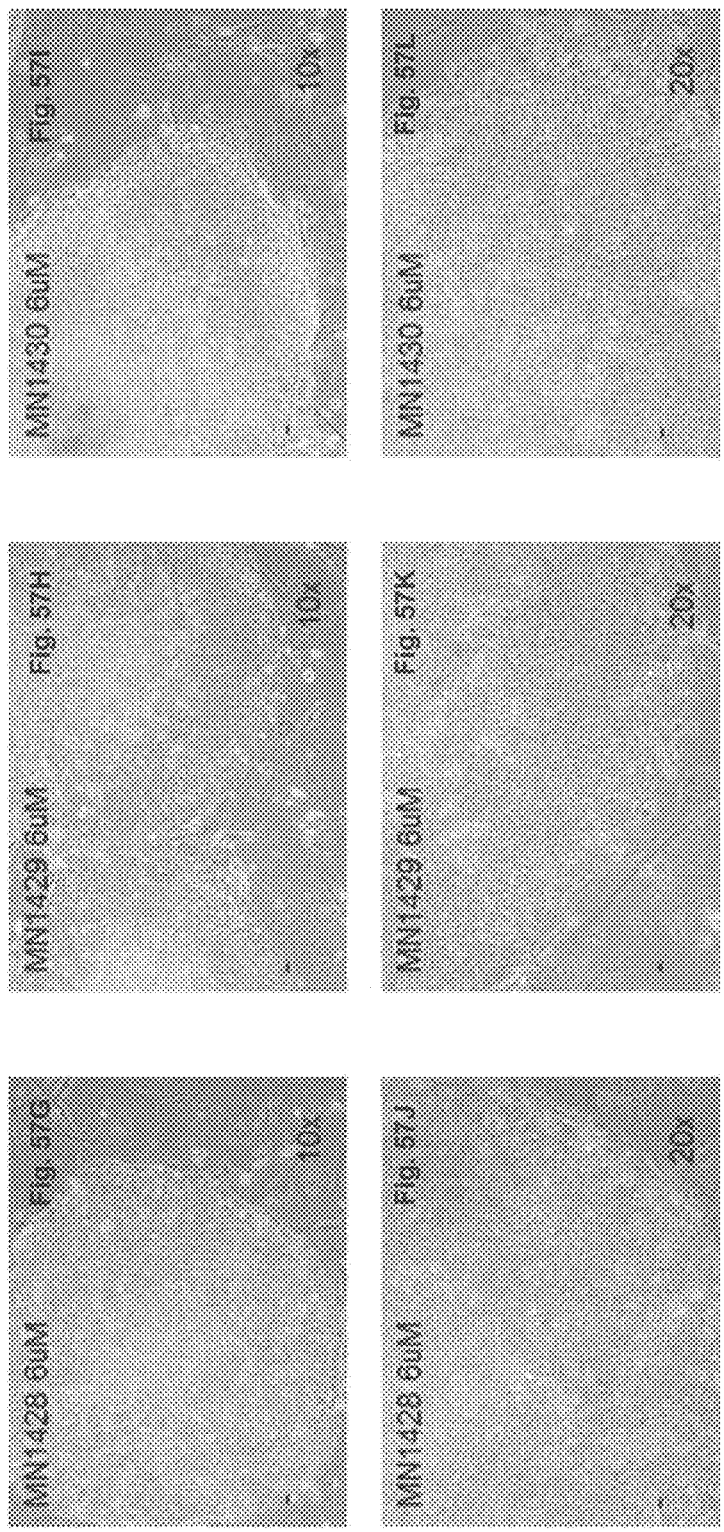
Figure 57:
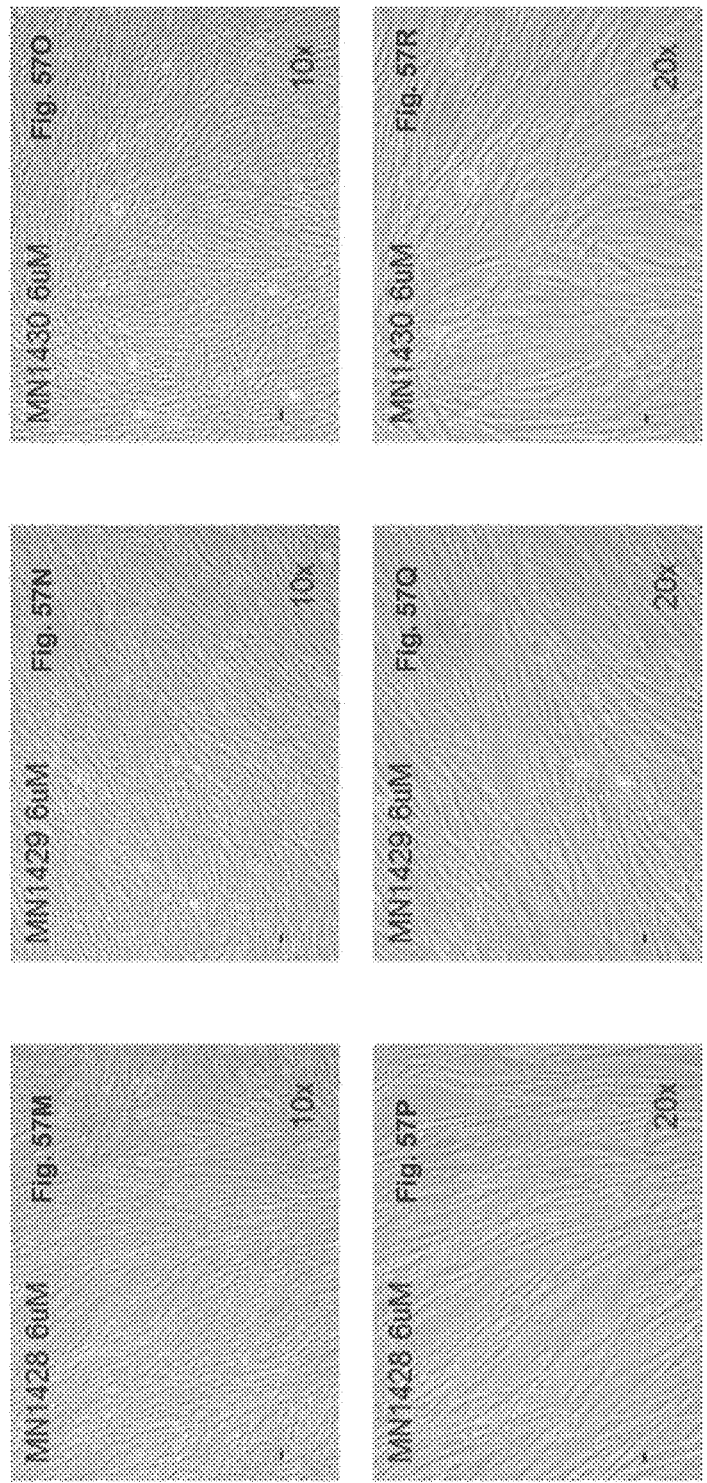
Figures 58A, 58B, 58C, 58D, 58E, 58F:
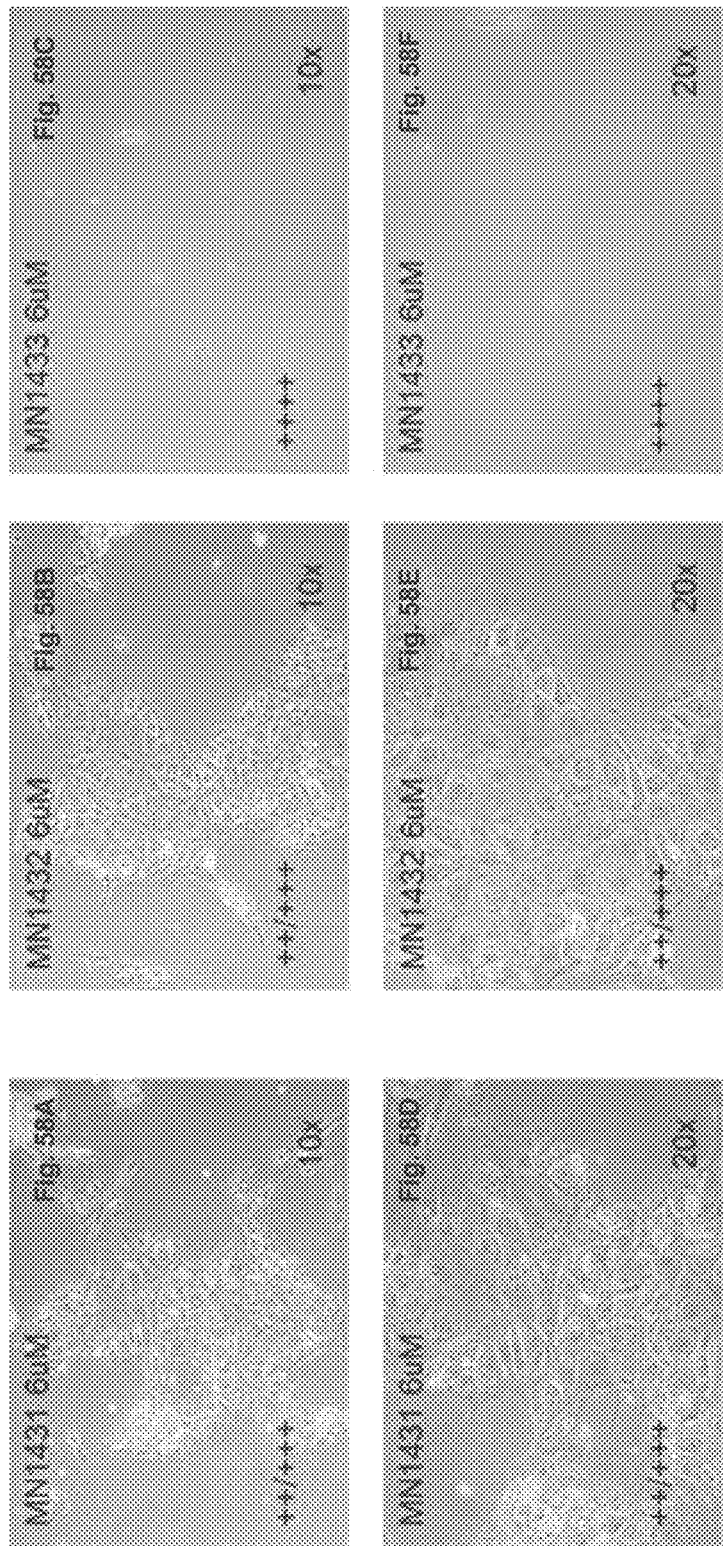
Figures 58G, 58H, 58I, 58J, 58K, 58L:
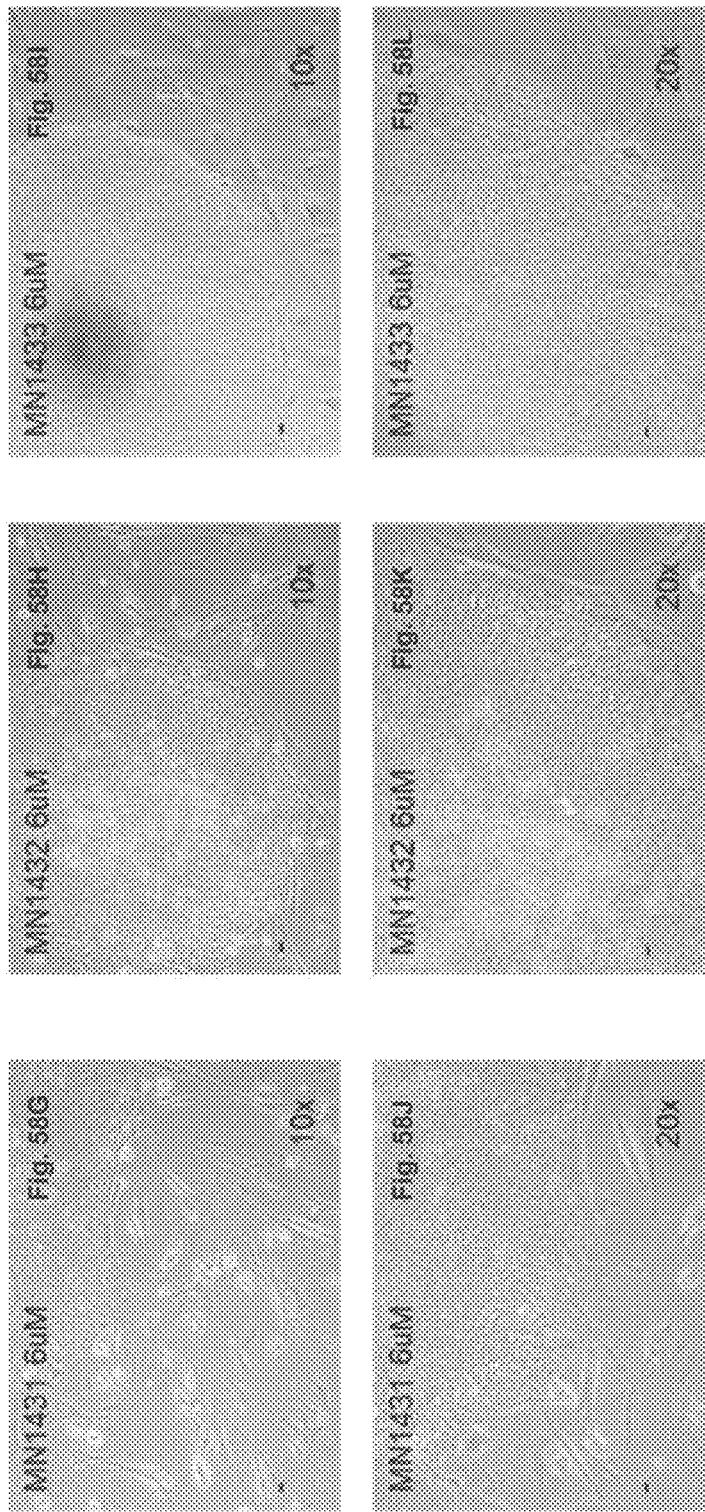
Figures 58M, 58N, 58O, 58P, 58Q, 58R:
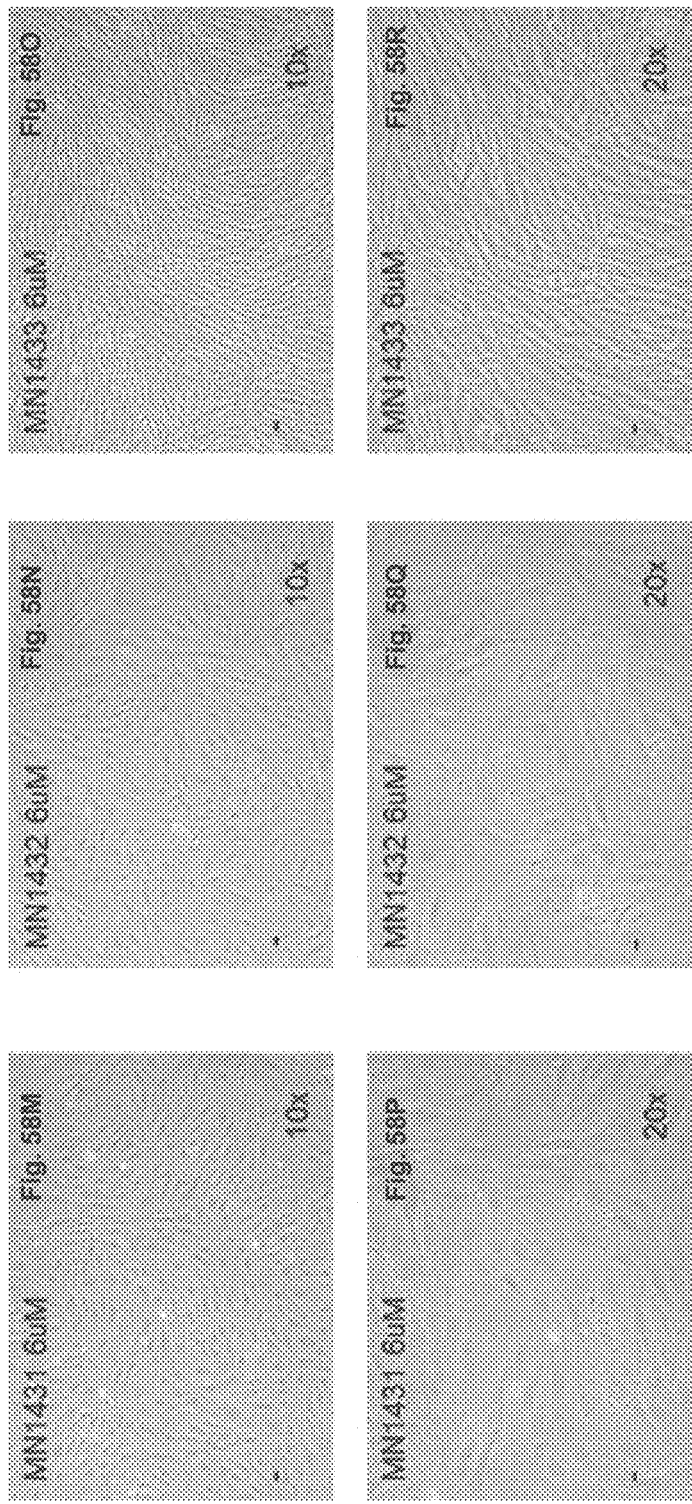
Figures 59A, 59B, 59C, 59D, 59E, 59F:
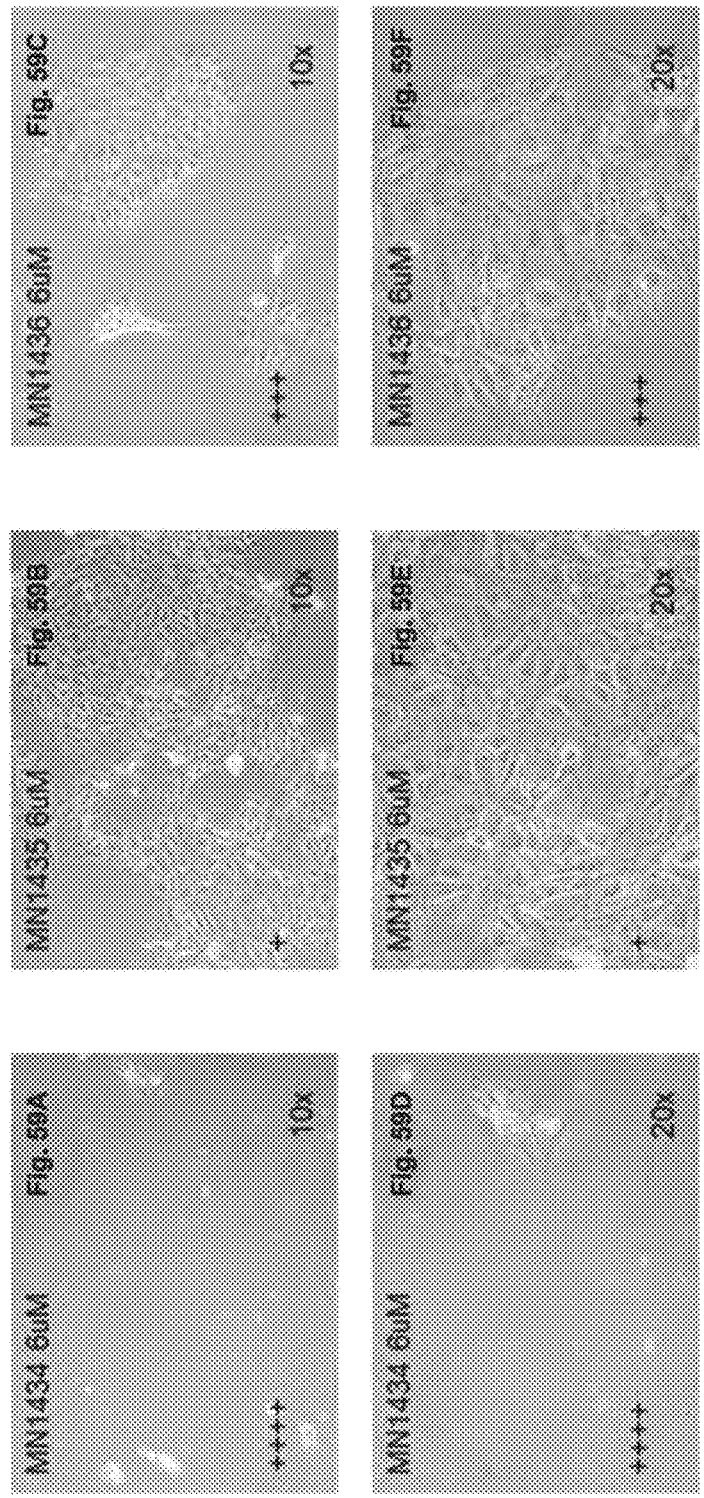
Figure 59:
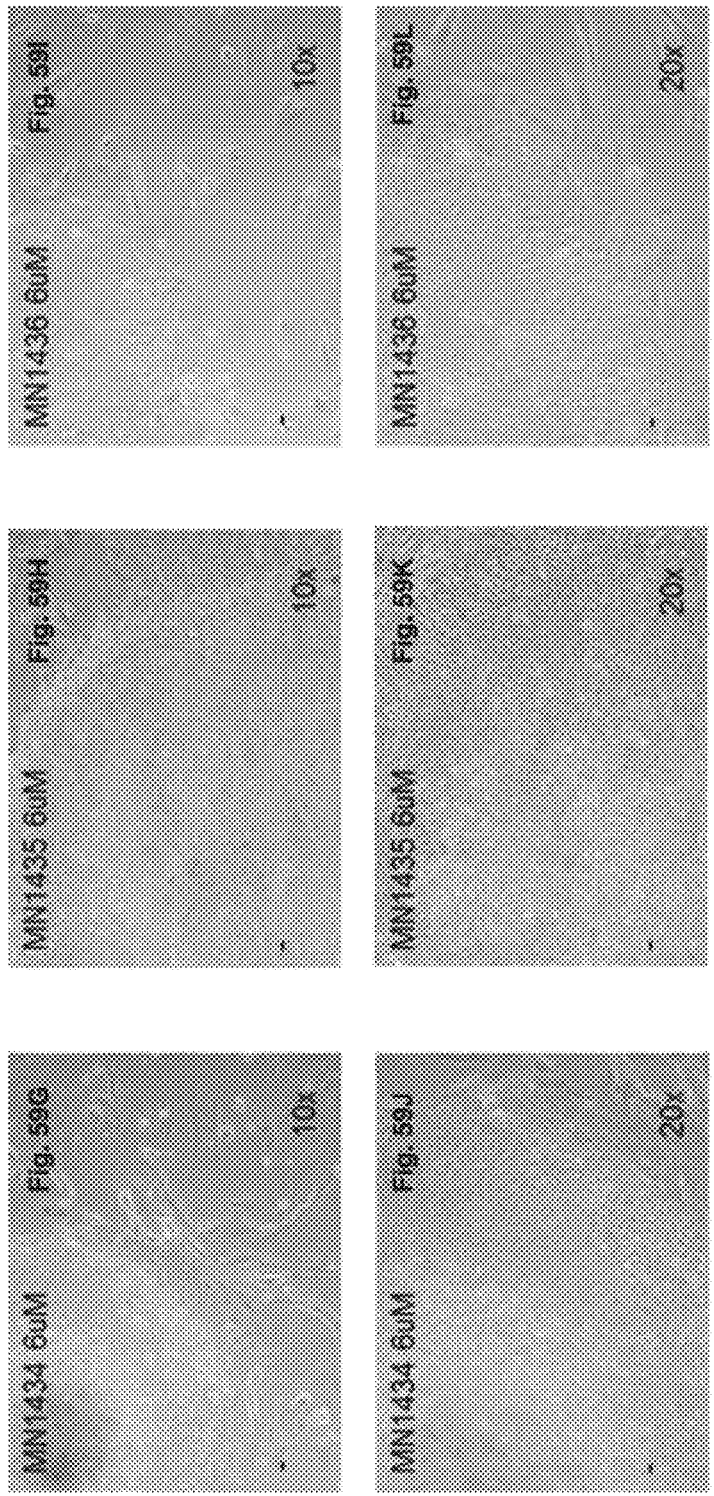
Figures 59M, 59N, 59O, 59P, 59Q, 59R:
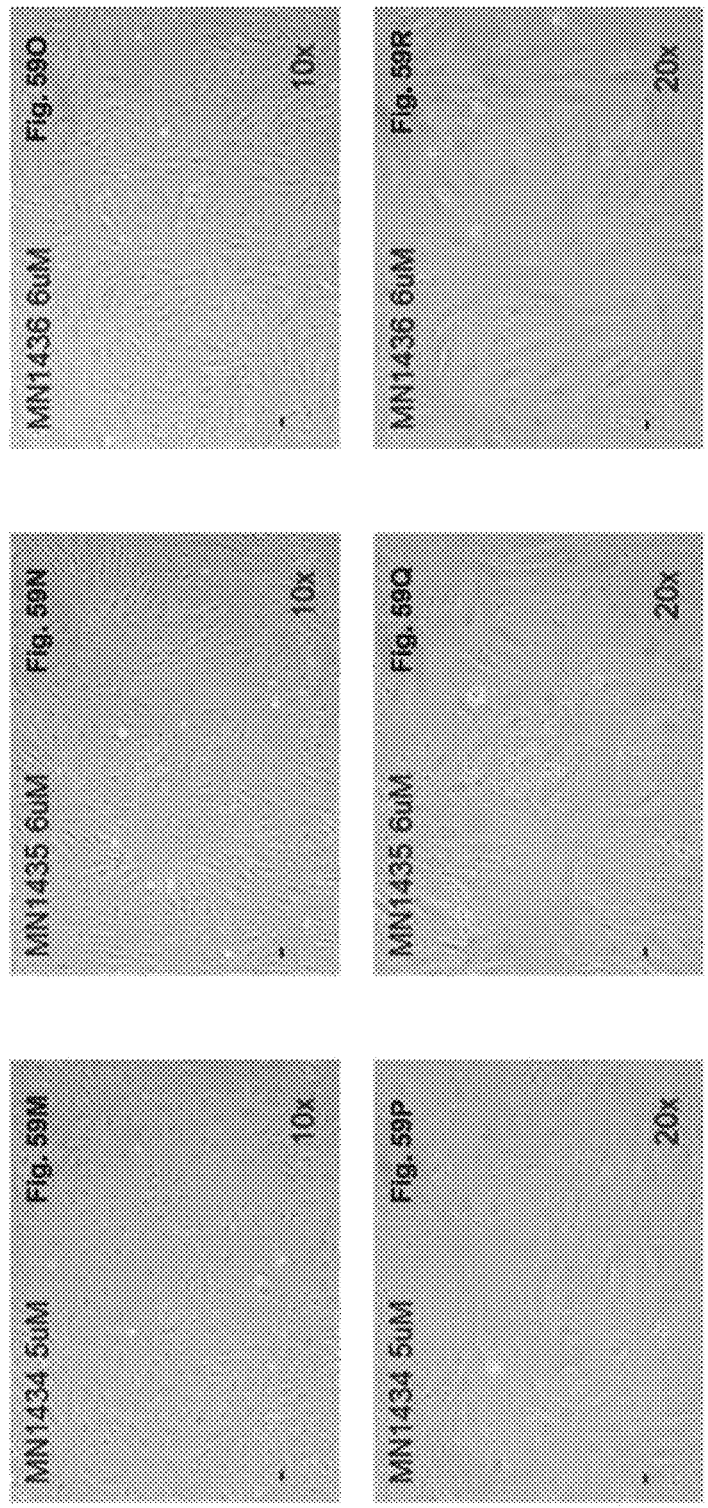
Figures 60A, 60B, 60C, 60D, 60E, 60F:
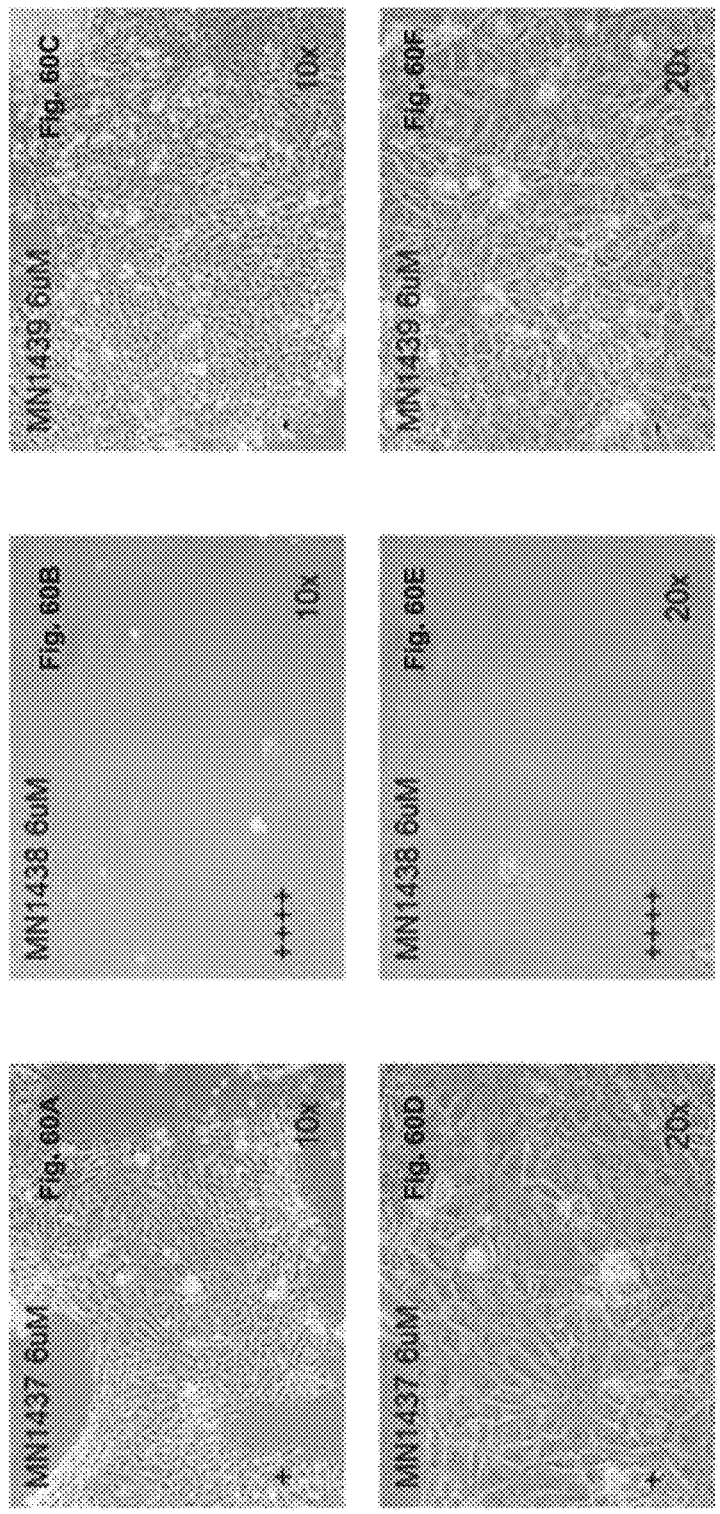
Figures 60G, 60H, 60I, 60J, 60K, 60L:
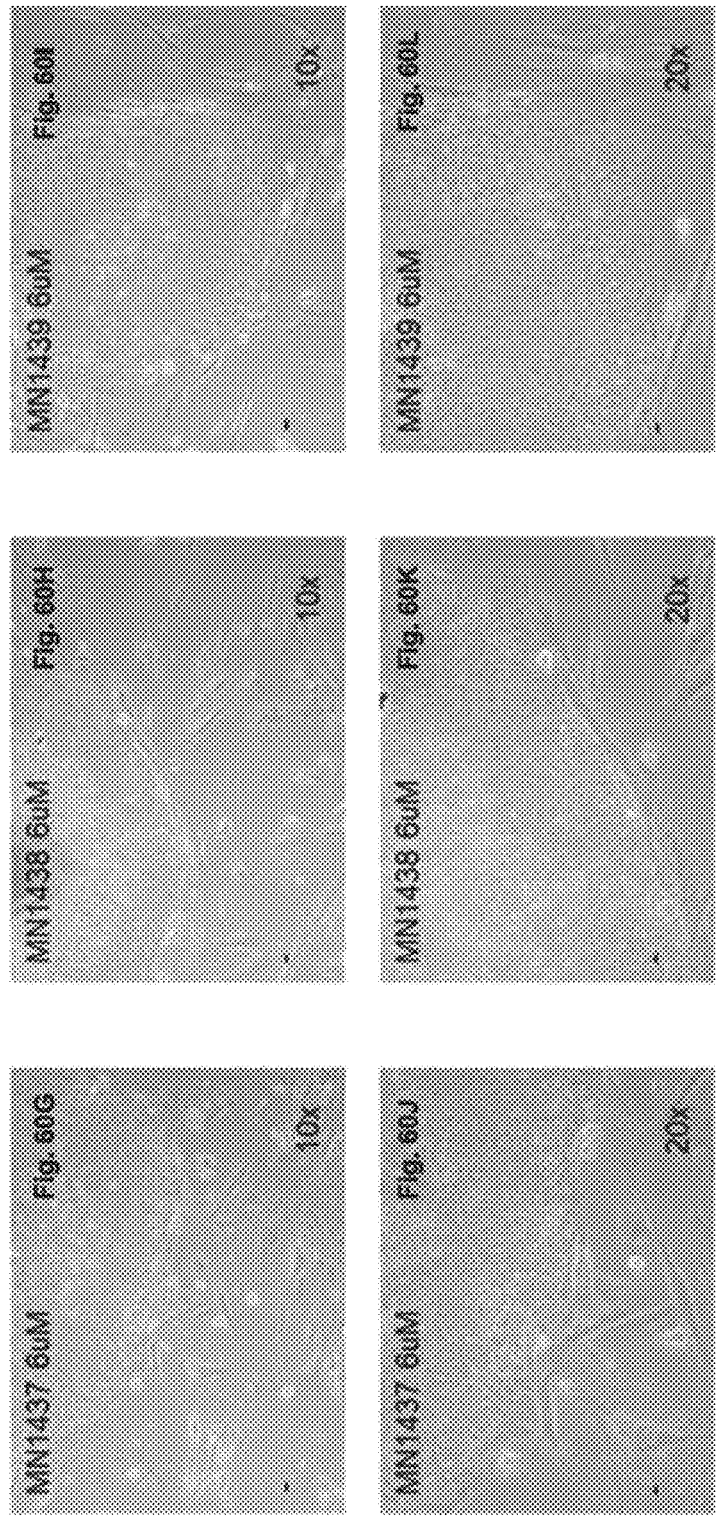
Figures 60M, 60N, 60O, 60P, 60Q, 60R:
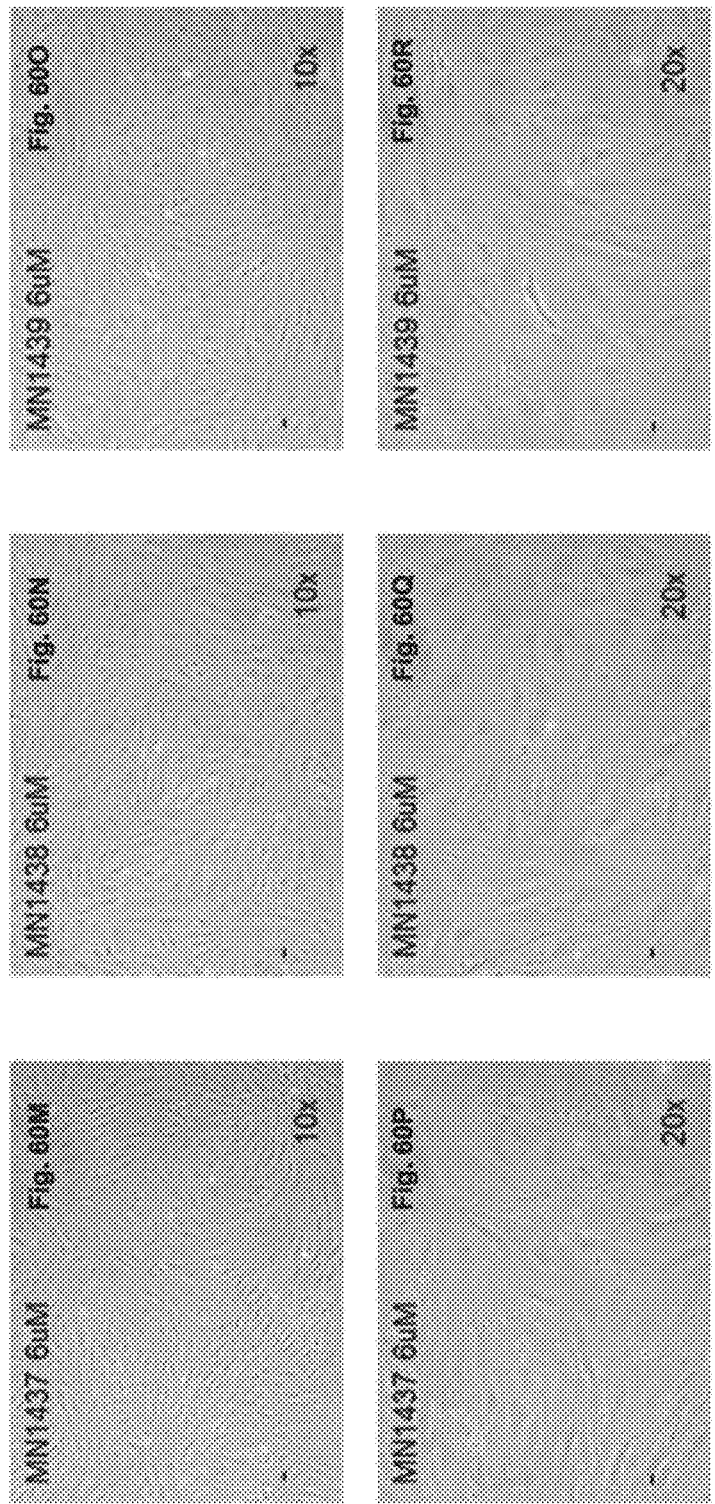
Figures 61A, 61B, 61C, 61D, 61E, 61F:
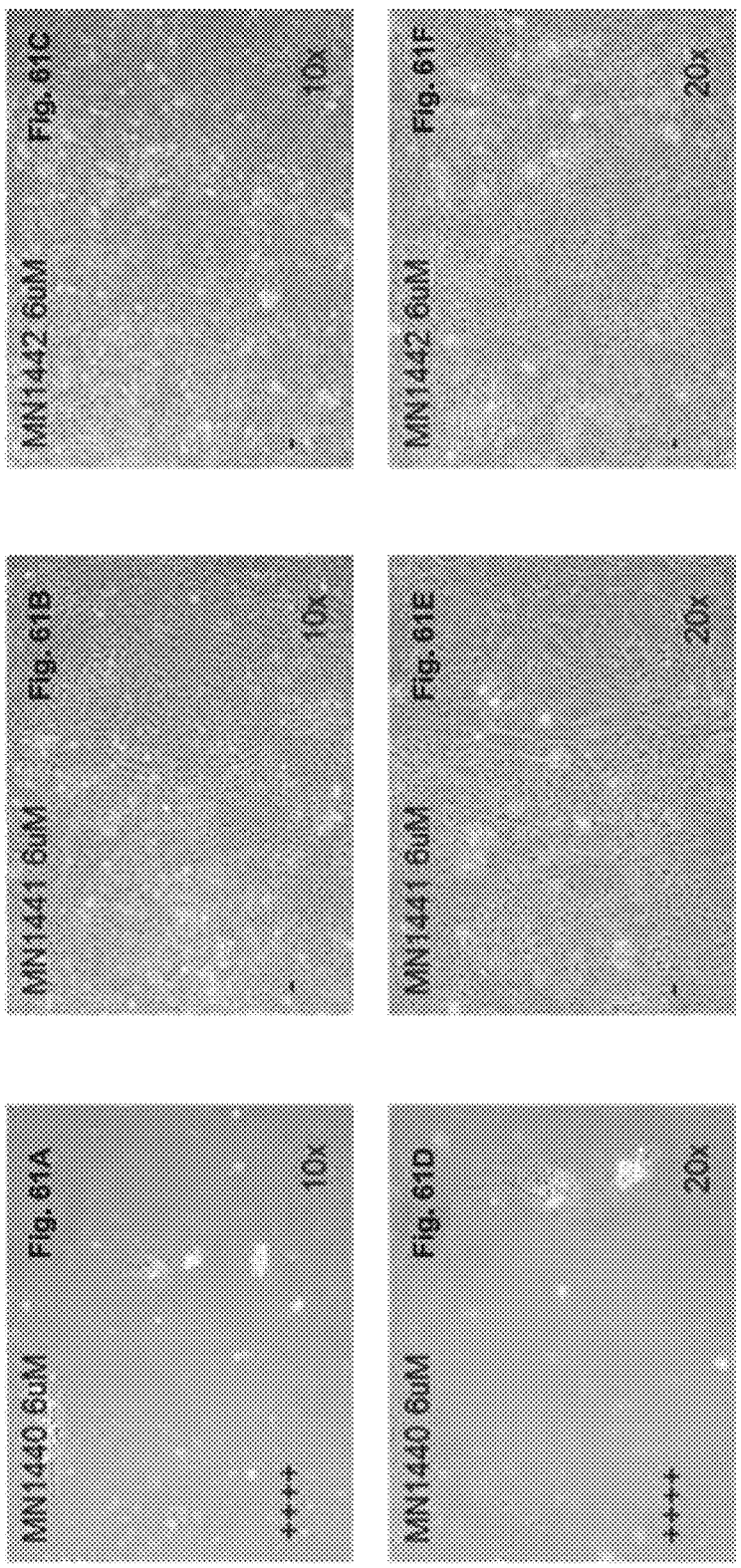
Figures 61G, 61H, 61I, 61J, 61K, 61L:
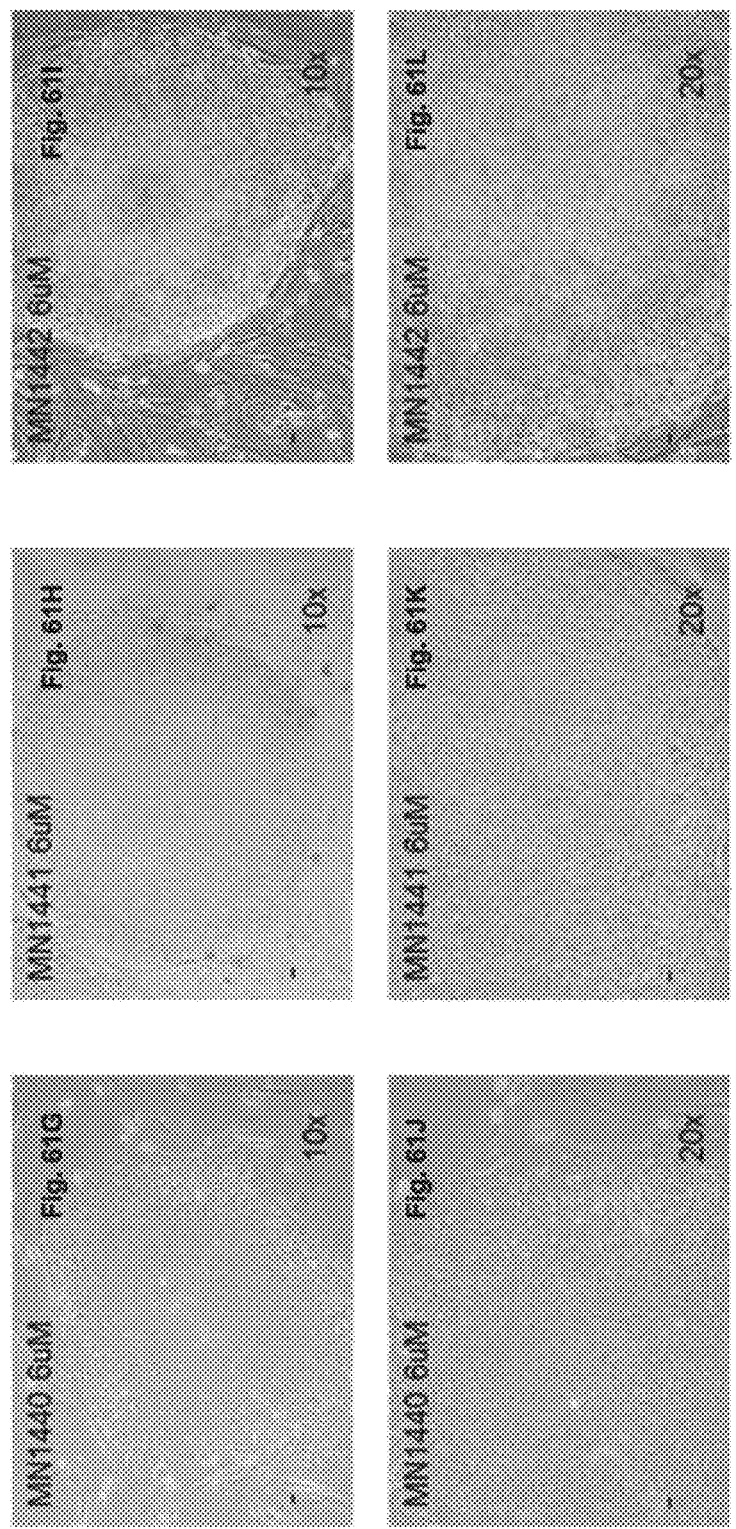
Figures 61M, 61N, 61O, 61P, 61Q, 61R:
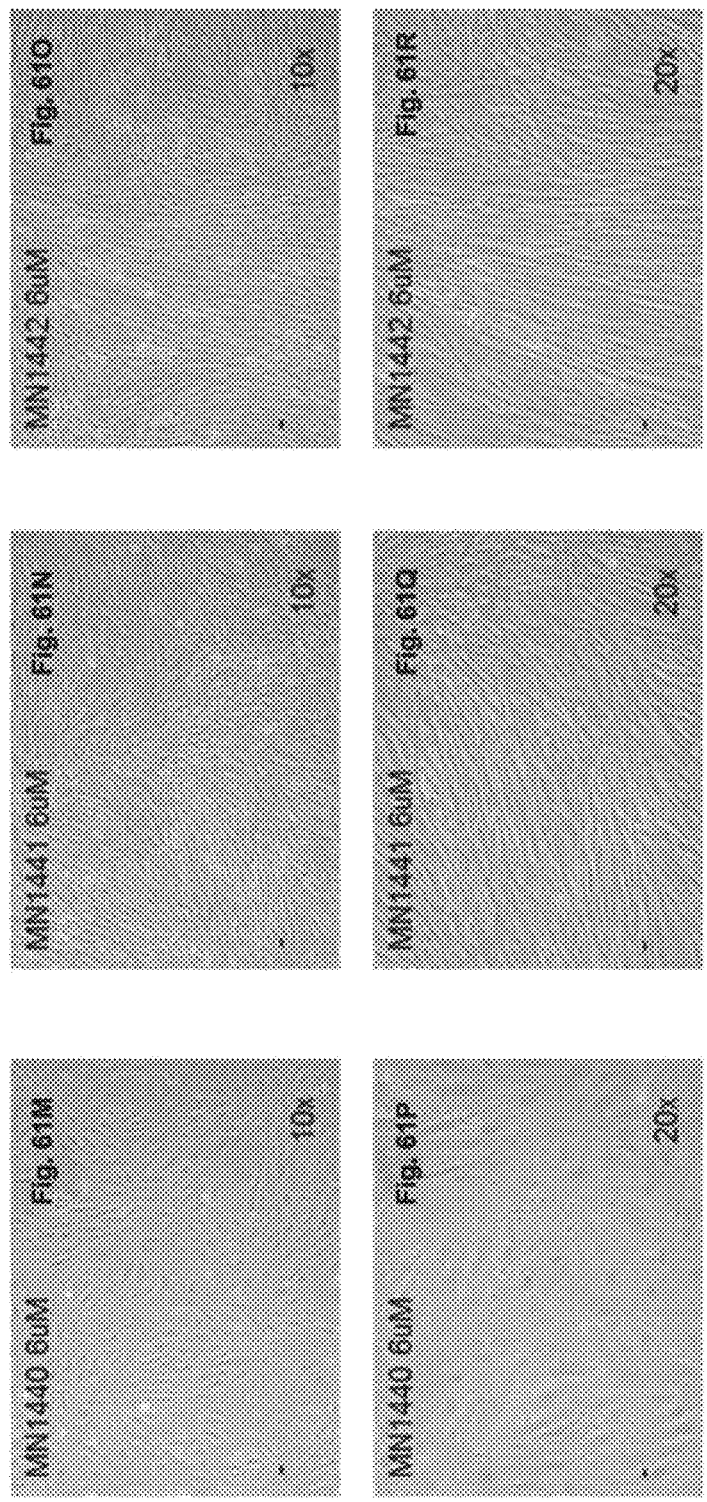
Figures 62A, 62B, 62C, 62D, 62E, 62F:
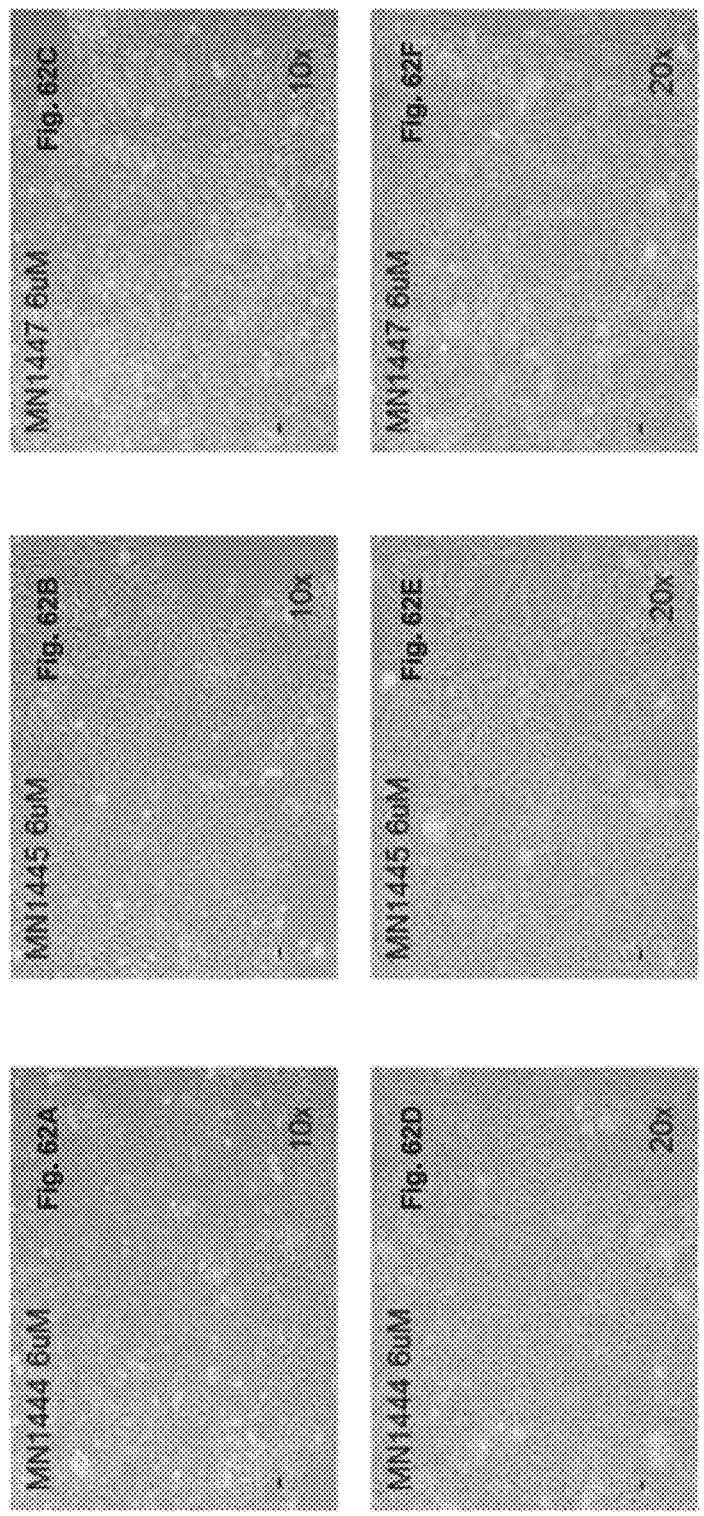
Figures 62G, 62H, 62I, 62J, 62K, 62L:
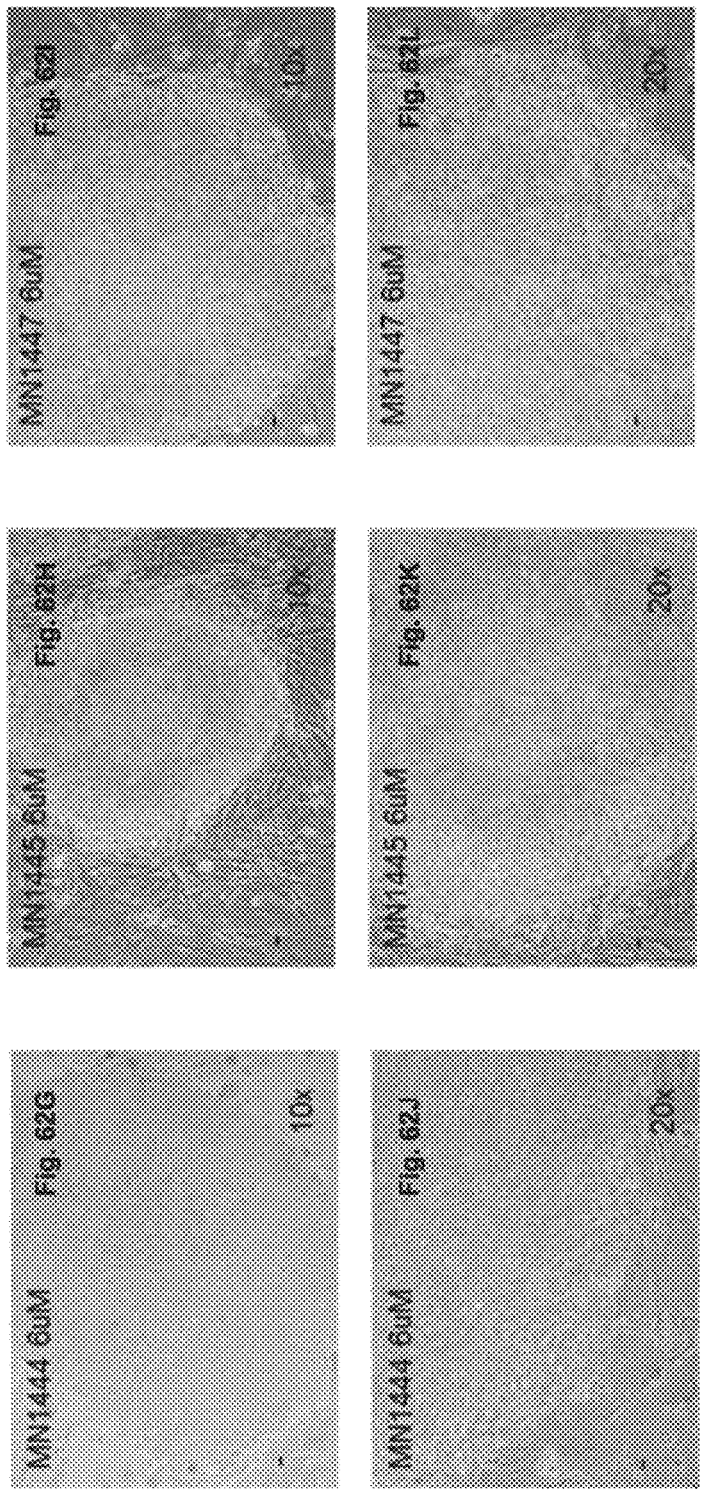
Figure 62:
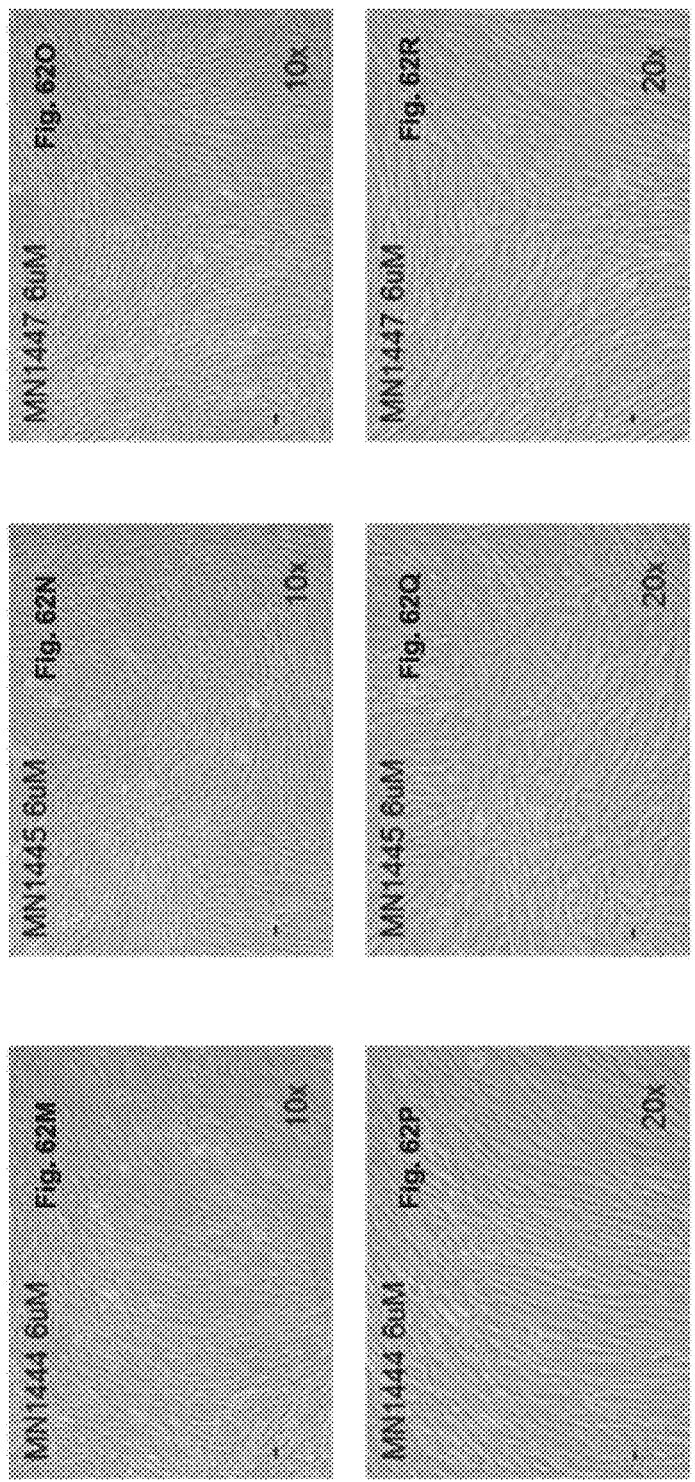
Figures 63A, 63B, 63C, 63D, 63E, 63F:
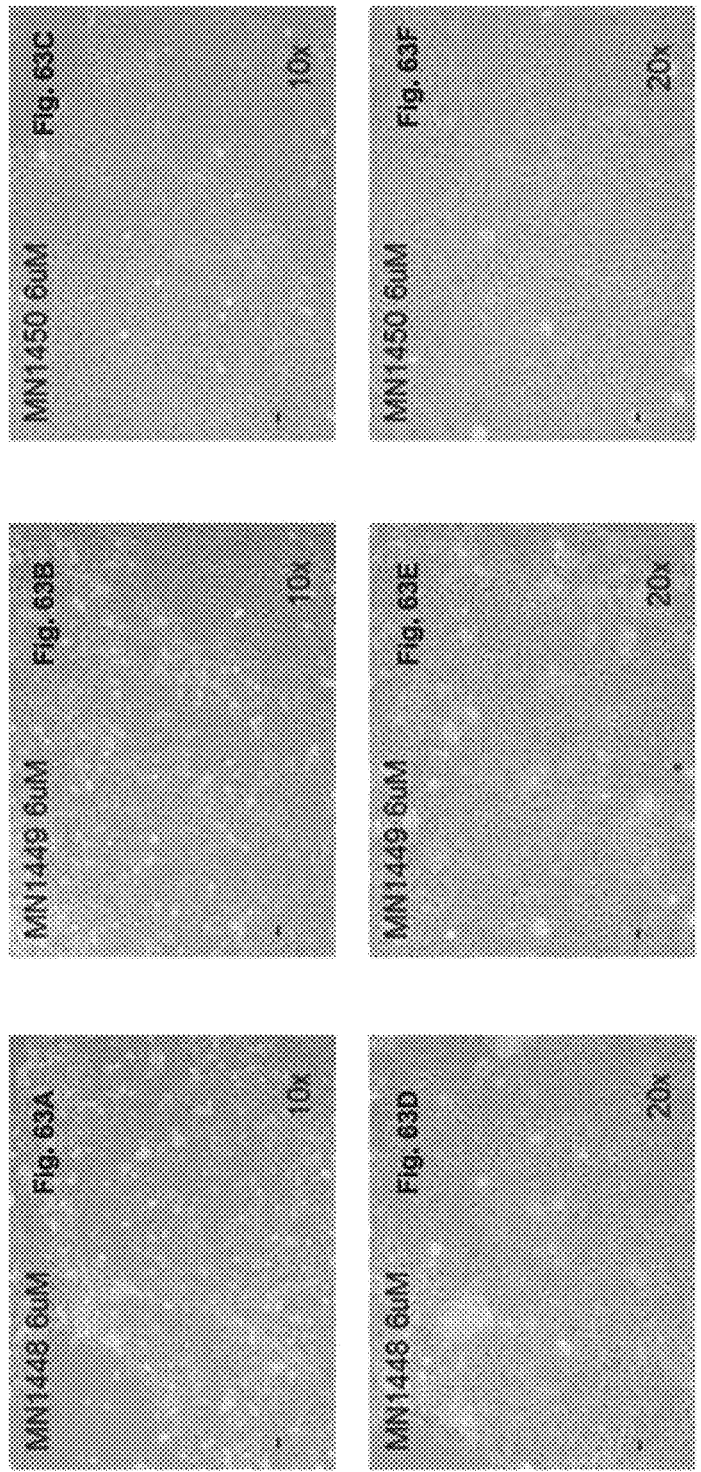
Figures 63G, 63H, 63I, 63J, 63K, 63L:
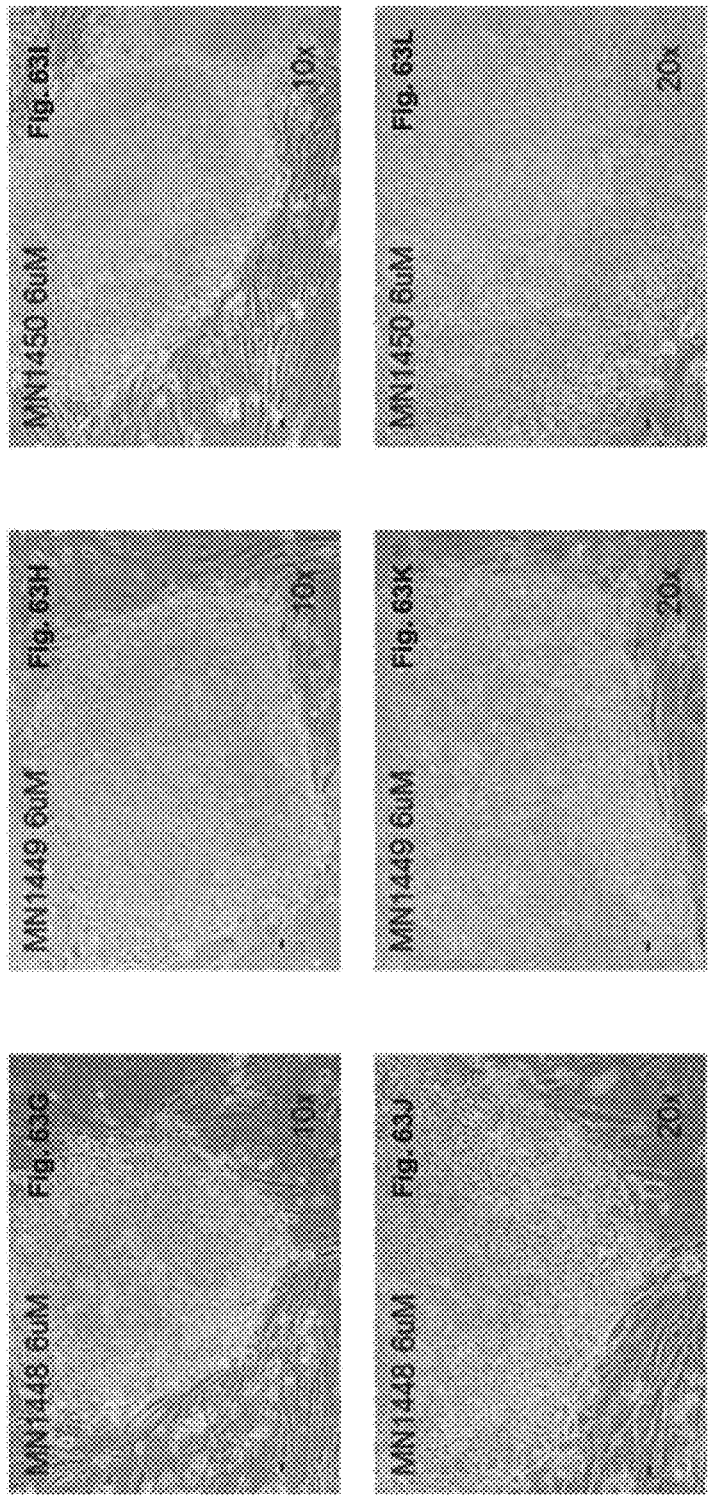
Figures 63M, 63N, 63O, 63P, 63Q, 63R:
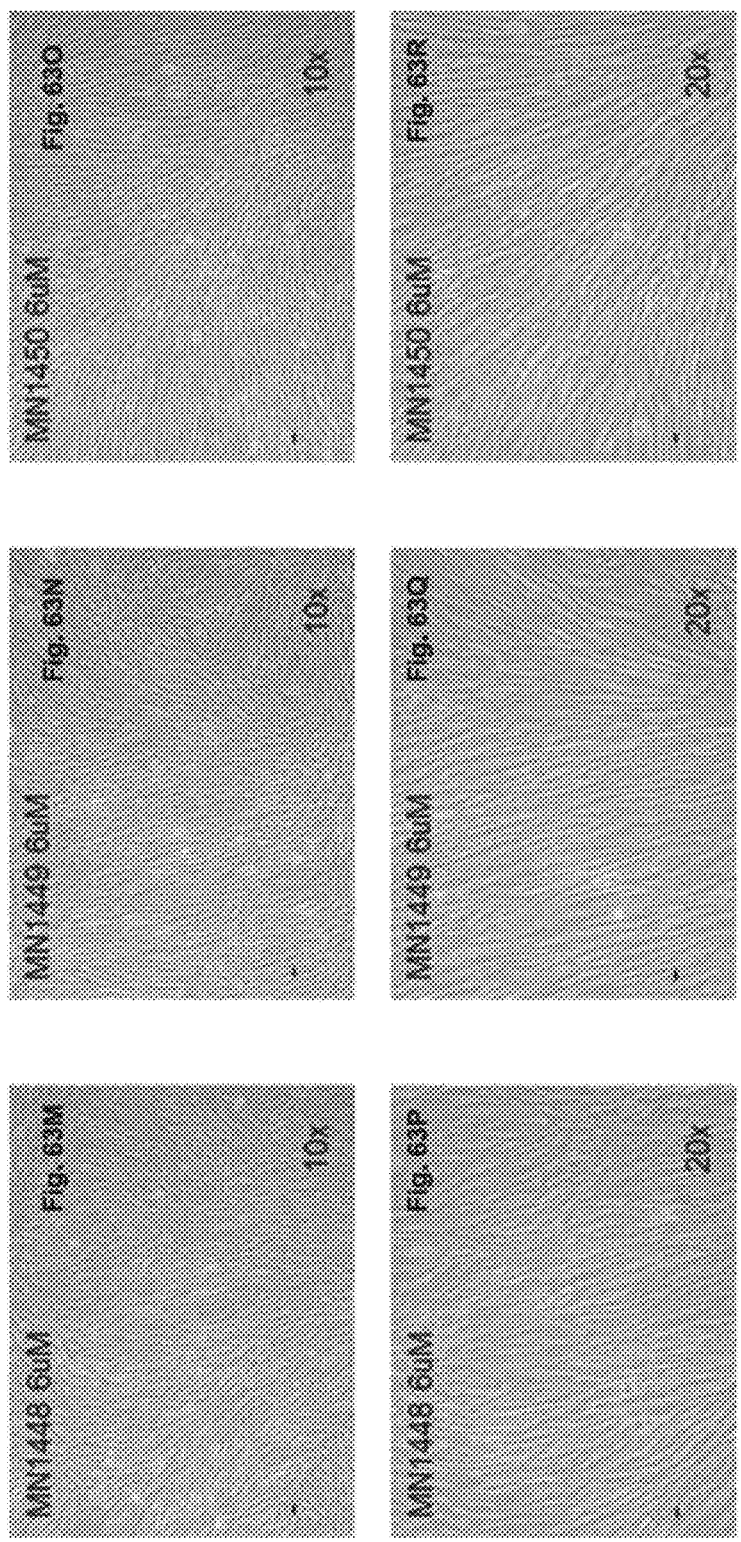
Figures 64A, 64B, 64C, 64D:
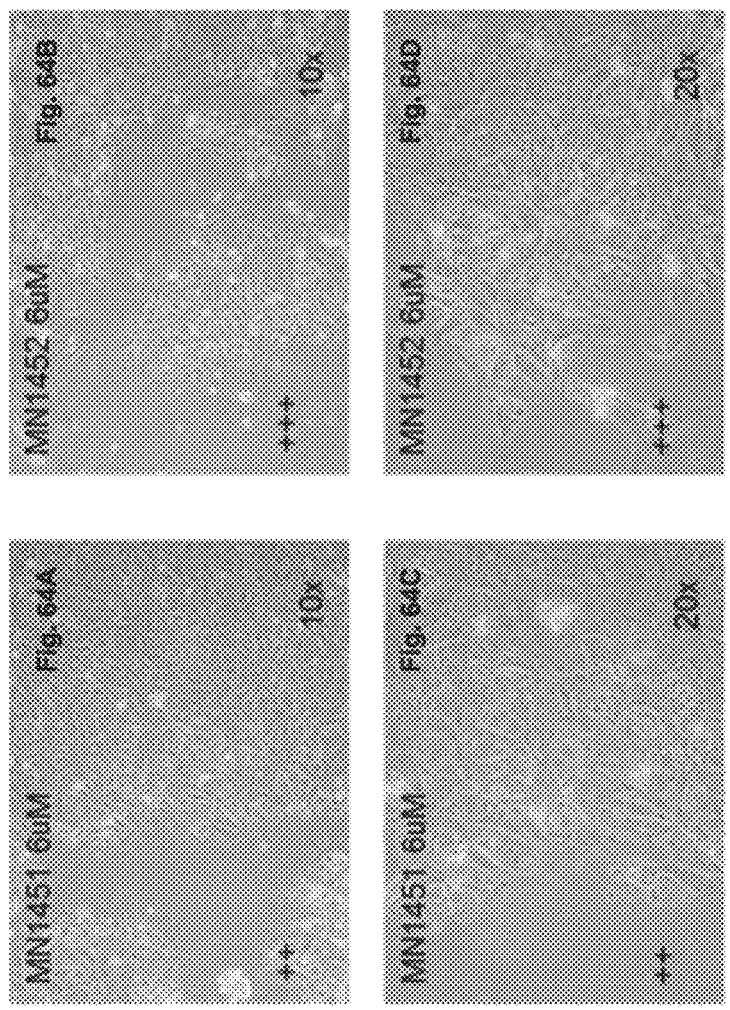
Figures 64G, 64H, 64I, 64J:
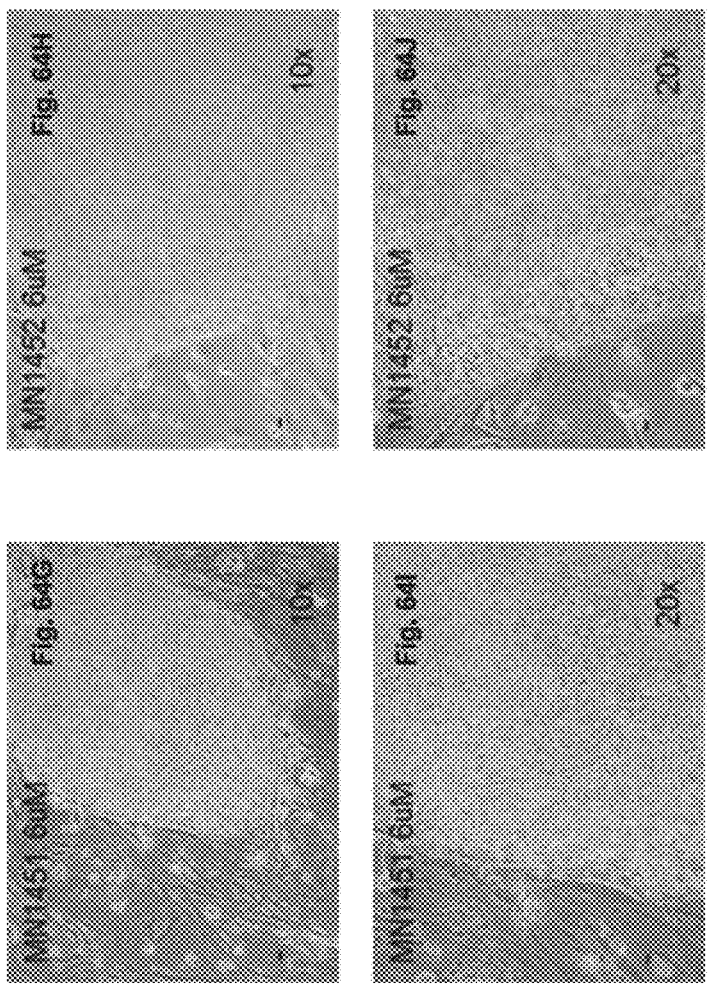
Figures 64M, 64N, 64O, 64P:
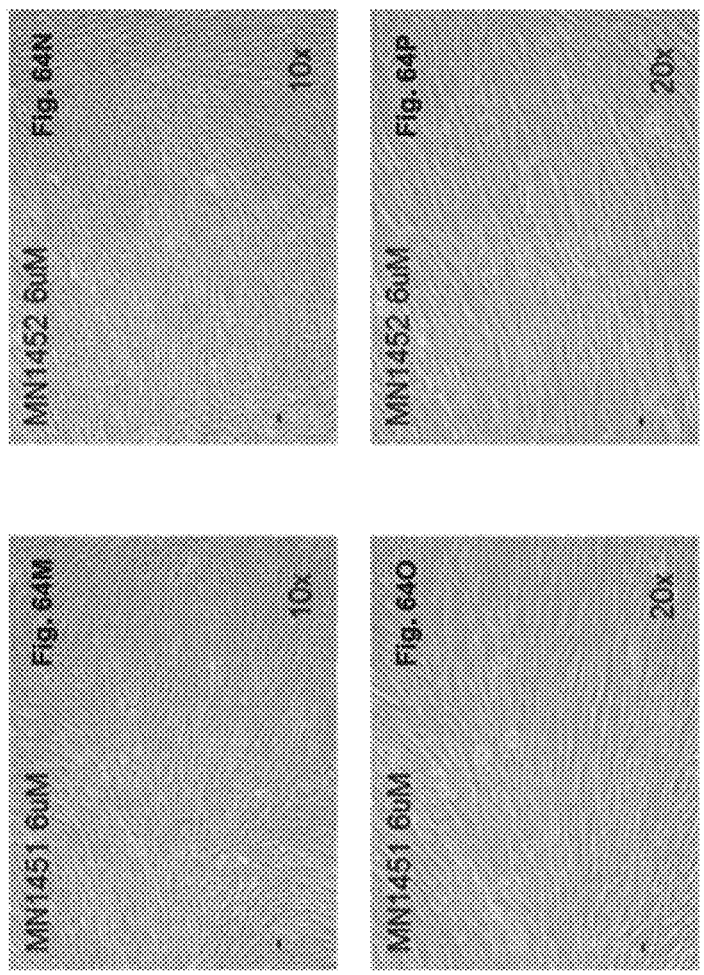
Figures 65A, 65B, 65C, 65D, 65E, 65F, 65G, 65H, 65I, 65J, 65K, 65L:
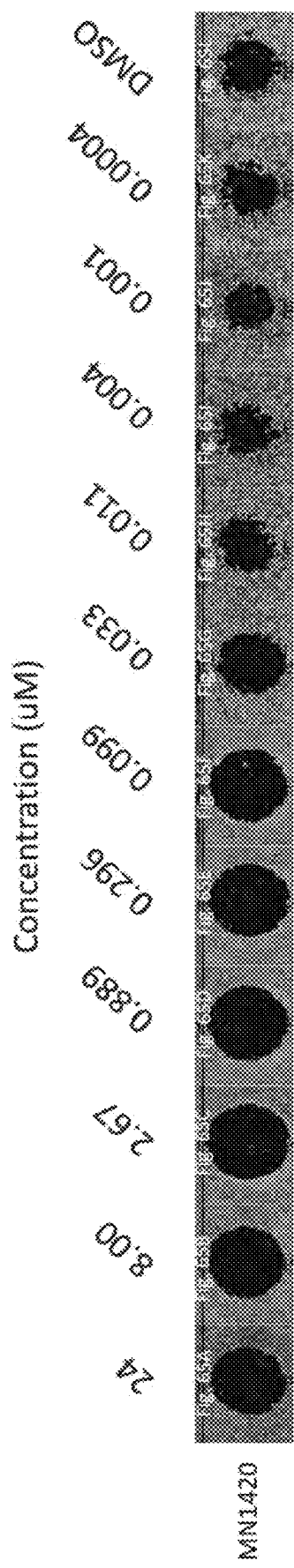
FIG. 65 shows photographs of a cancer cell migration assay in which the effect of novel compound 1420 is tested for its ability to inhibit the migration of T47D breast cancer cells, 120 hours after single addition of the compound at the indicated concentrations.
Figure 71:
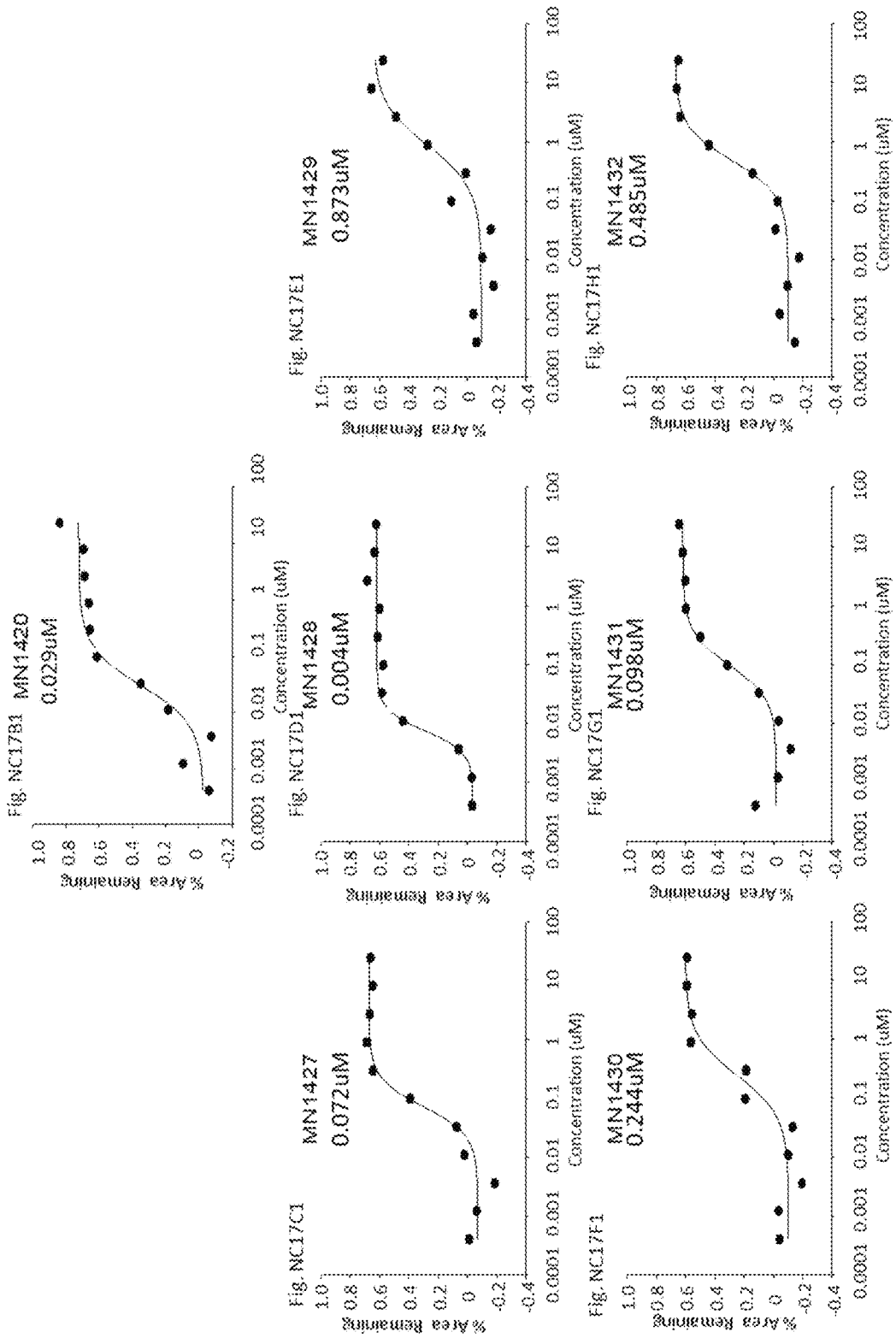
FIGS. 71-75 show measured IC50 curves for compounds of the invention for the ability to inhibit cancer cell migration or invasion of T47D breast cancer cells in the presence of compounds of the invention, over a range of concentrations, or the control, DMSO alone, at 120 hours.
Figure 72:
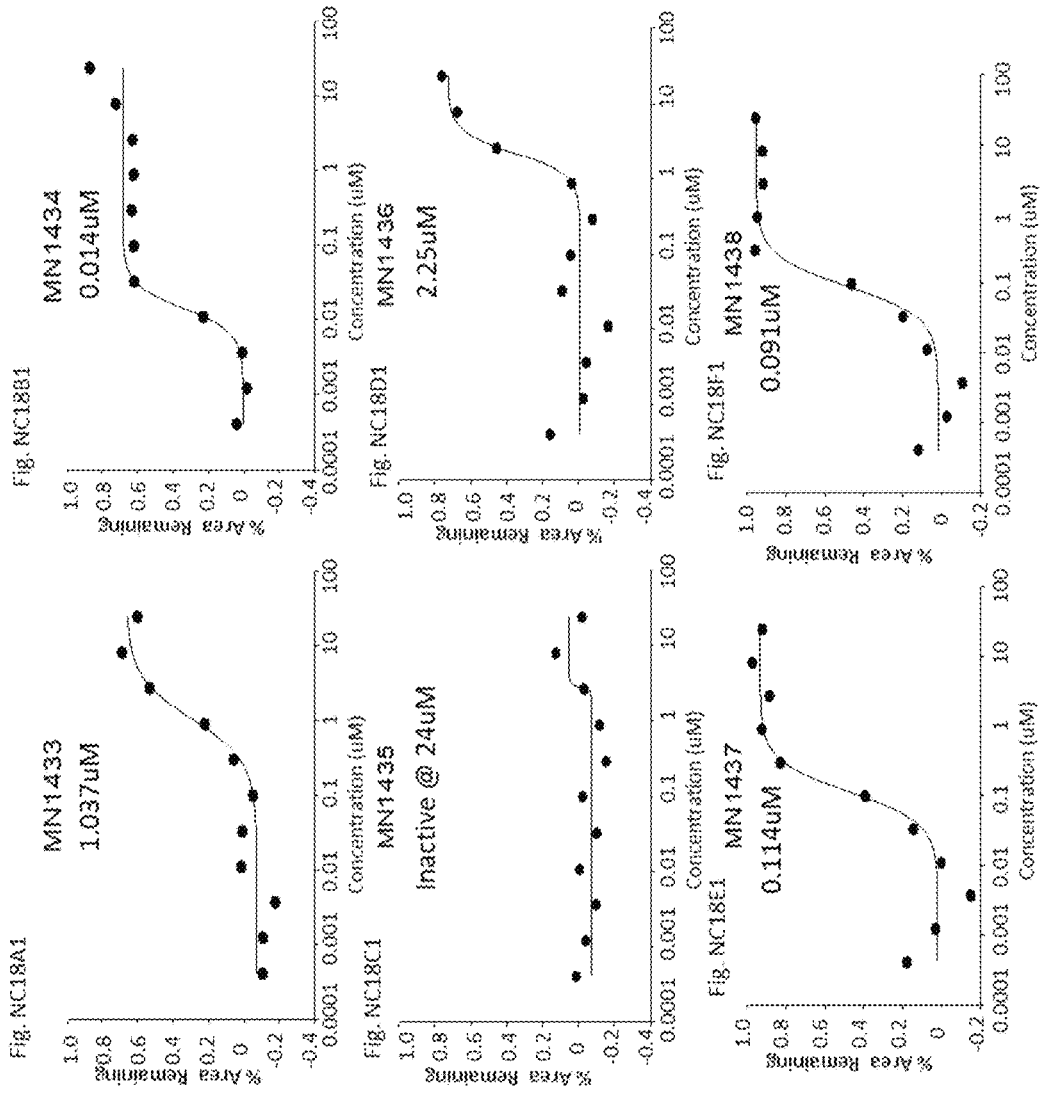
Figure 73:
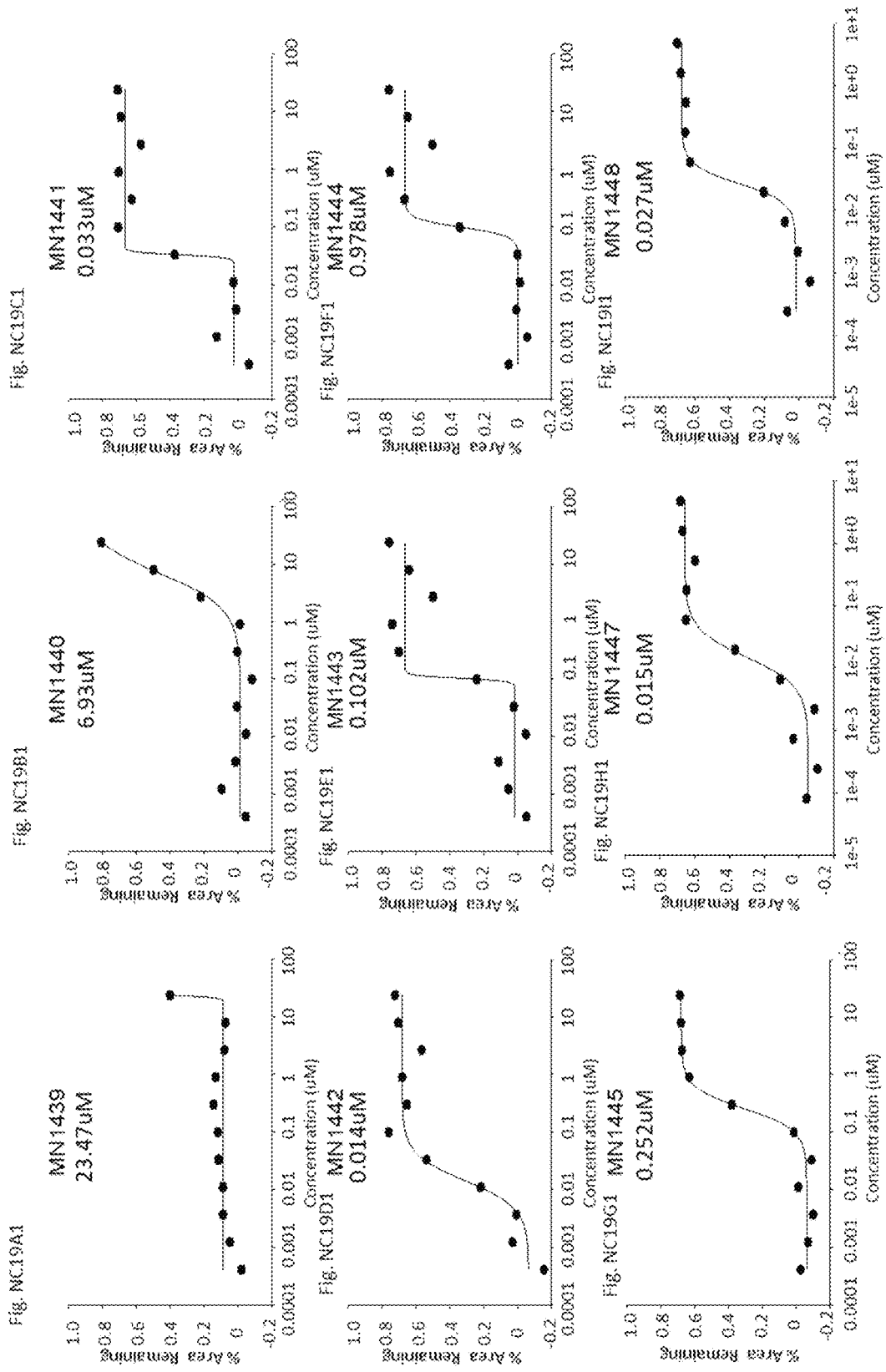
Figure 74:
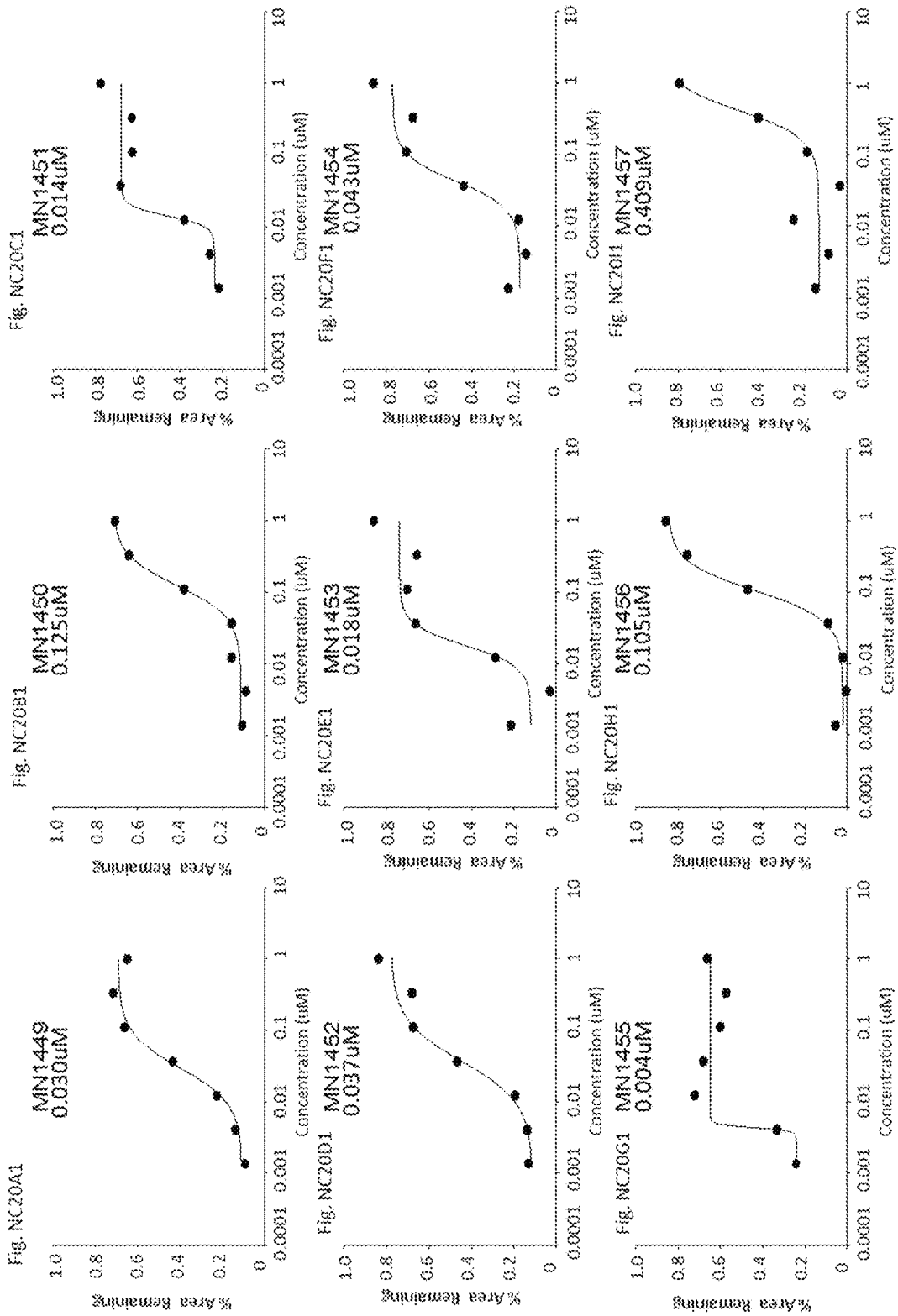
Figure 75:
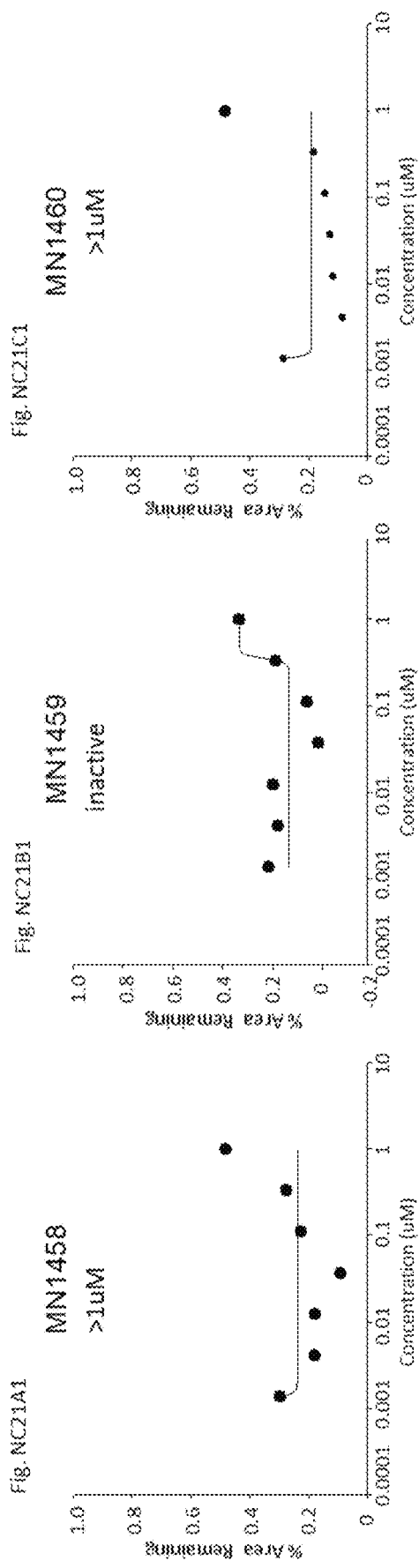
Figure 76:
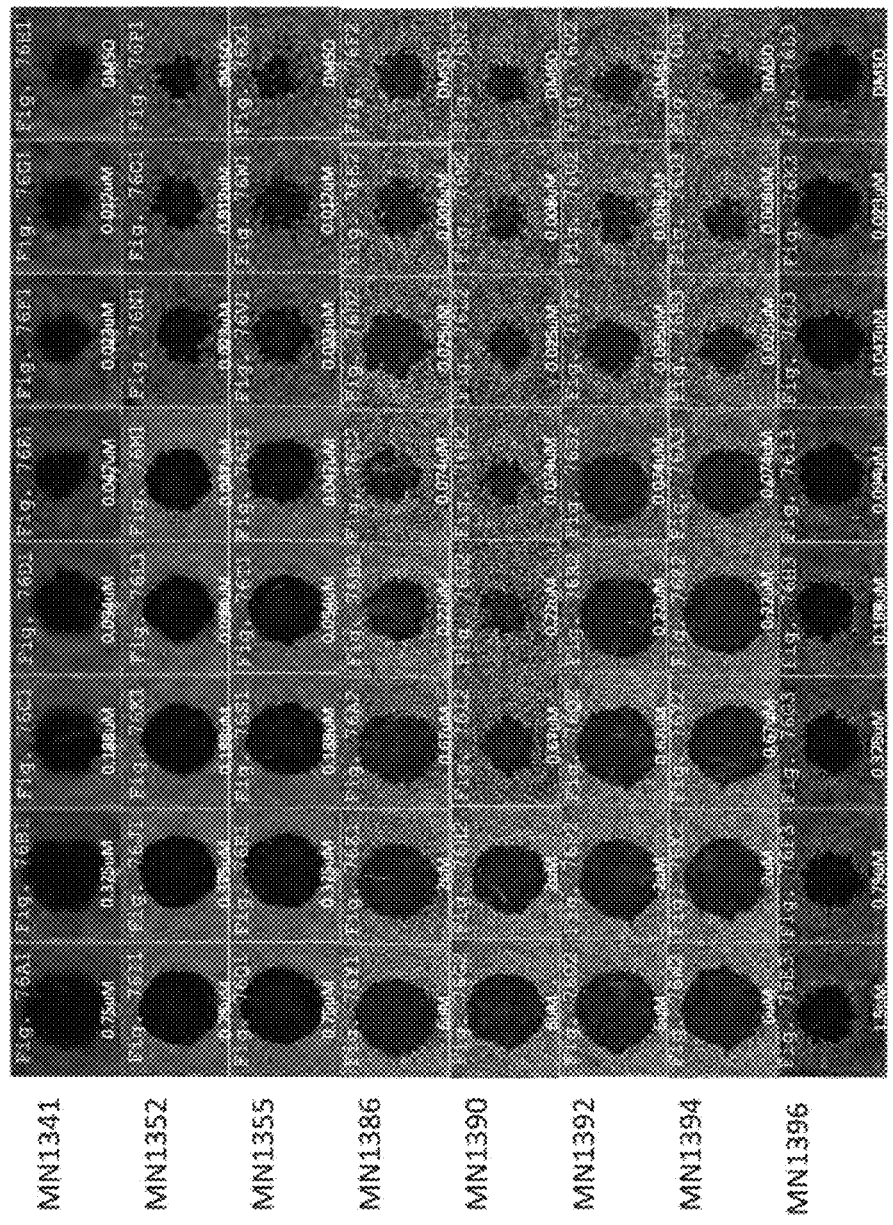
FIG. 76 shows photographs of a cancer cell migration assay in which the effect of compounds of the invention are tested for their ability to inhibit the migration of T47D breast cancer cells, 120 hours after single addition of the compound at the indicated concentrations.
Figure 77:
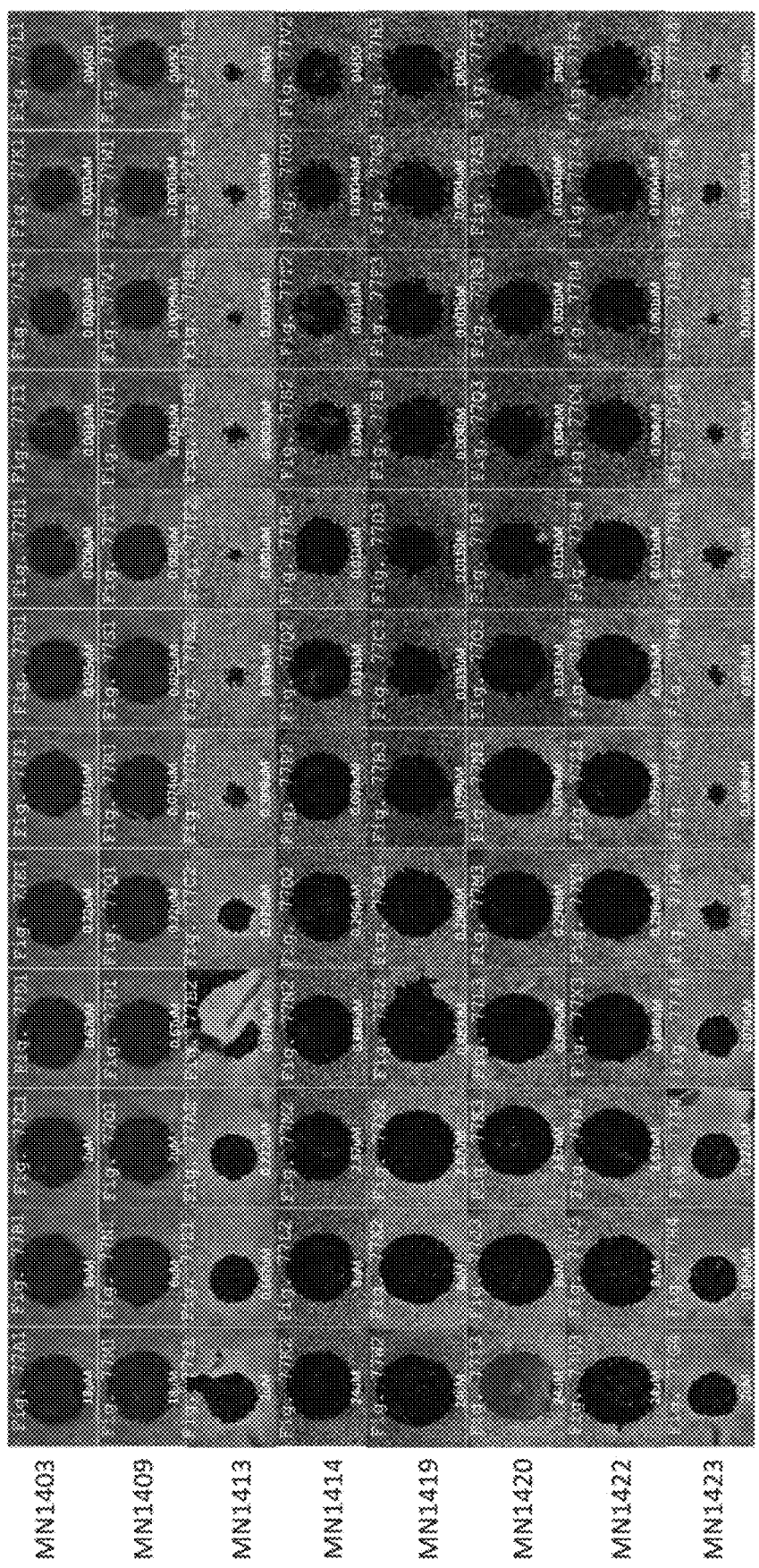
FIG. 77 shows photographs of a cancer cell migration assay in which the effect of compounds of the invention are tested for their ability to inhibit the migration of T47D breast cancer cells, 120 hours after single addition of the compound at the indicated concentrations.
Figure 78:
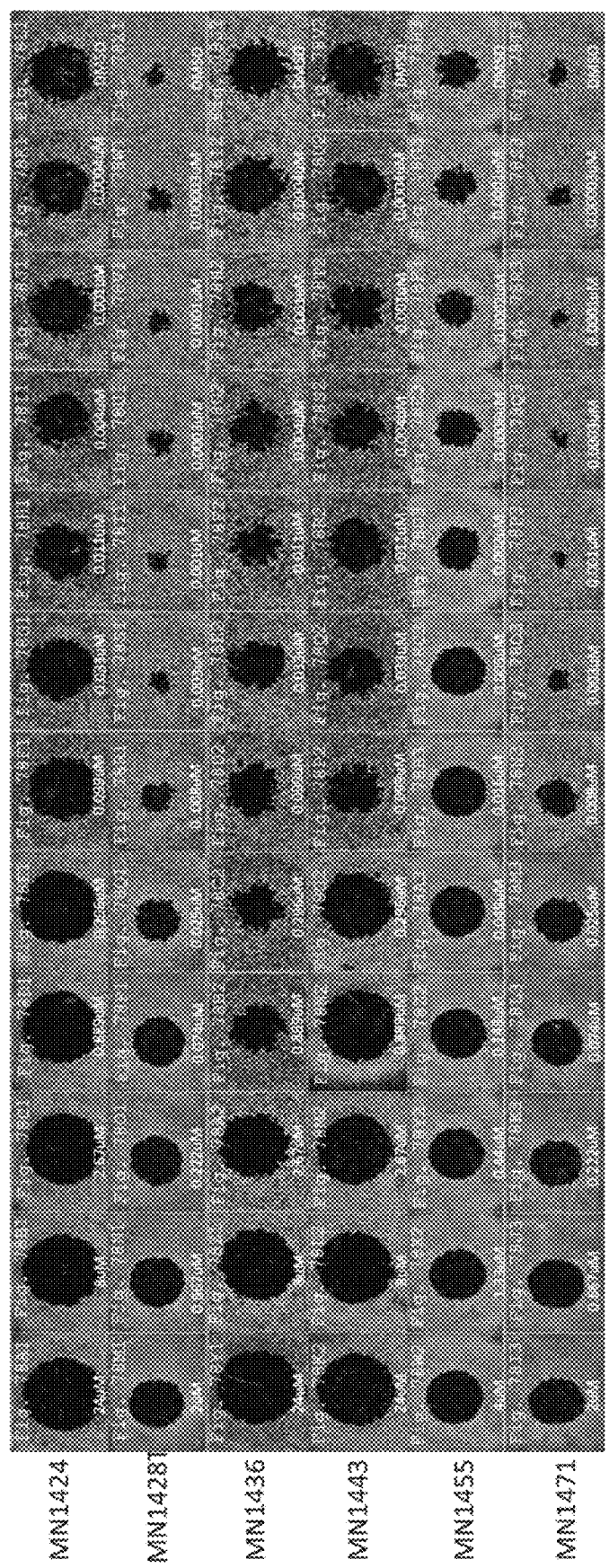
FIG. 78 shows photographs of a cancer cell migration assay in which the effect of compounds of the invention are tested for their ability to inhibit the migration of T47D breast cancer cells, 120 hours after single addition of the compound at the indicated concentrations.
Figure 79:
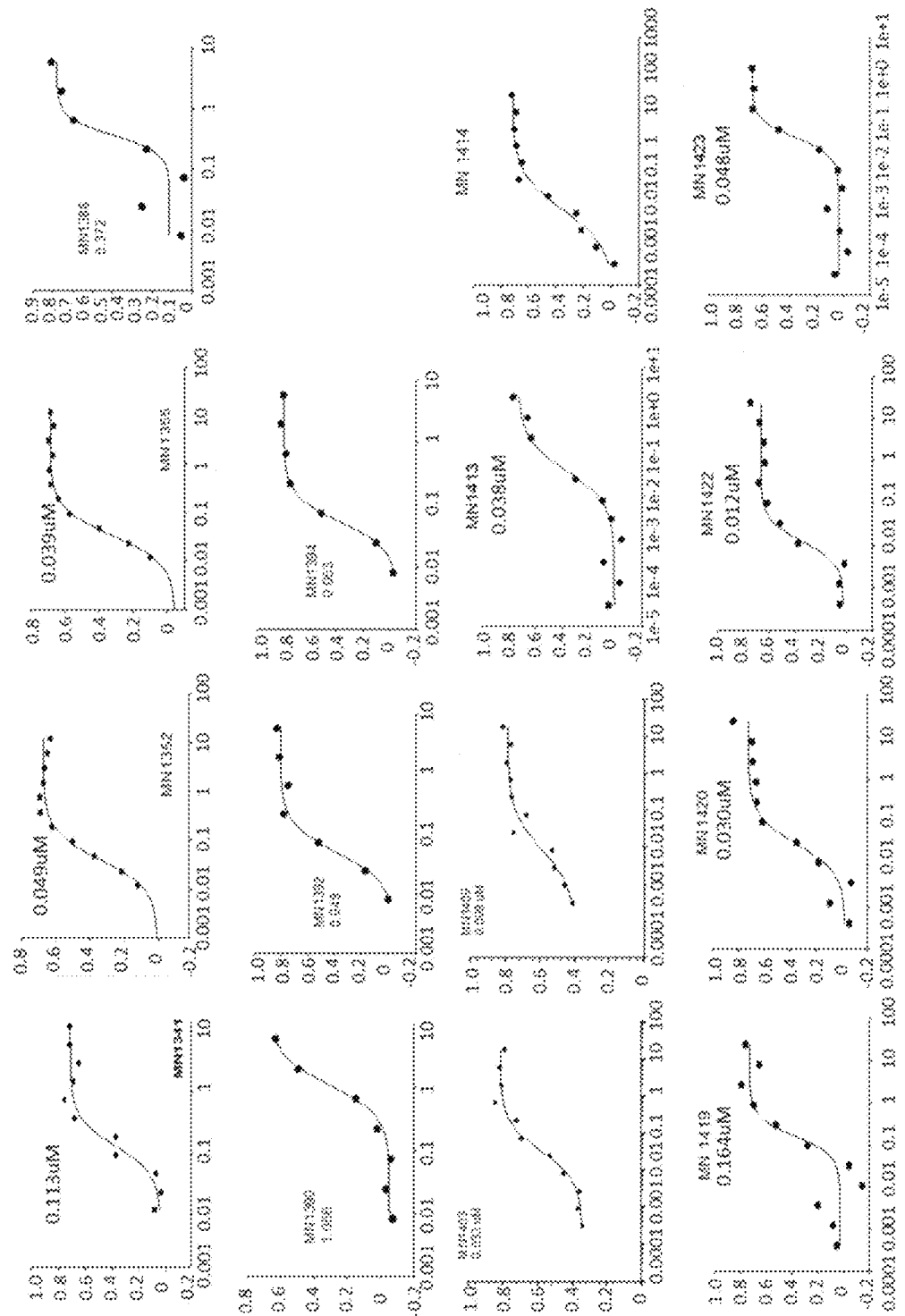
FIGS. 79-80 show measured IC50 curves for compounds of the invention for the ability to inhibit cancer cell migration or invasion of T47D breast cancer cells in the presence of compounds of the invention, over a range of concentrations, or the control, DMSO alone, at 120 hours.
Figure 80:
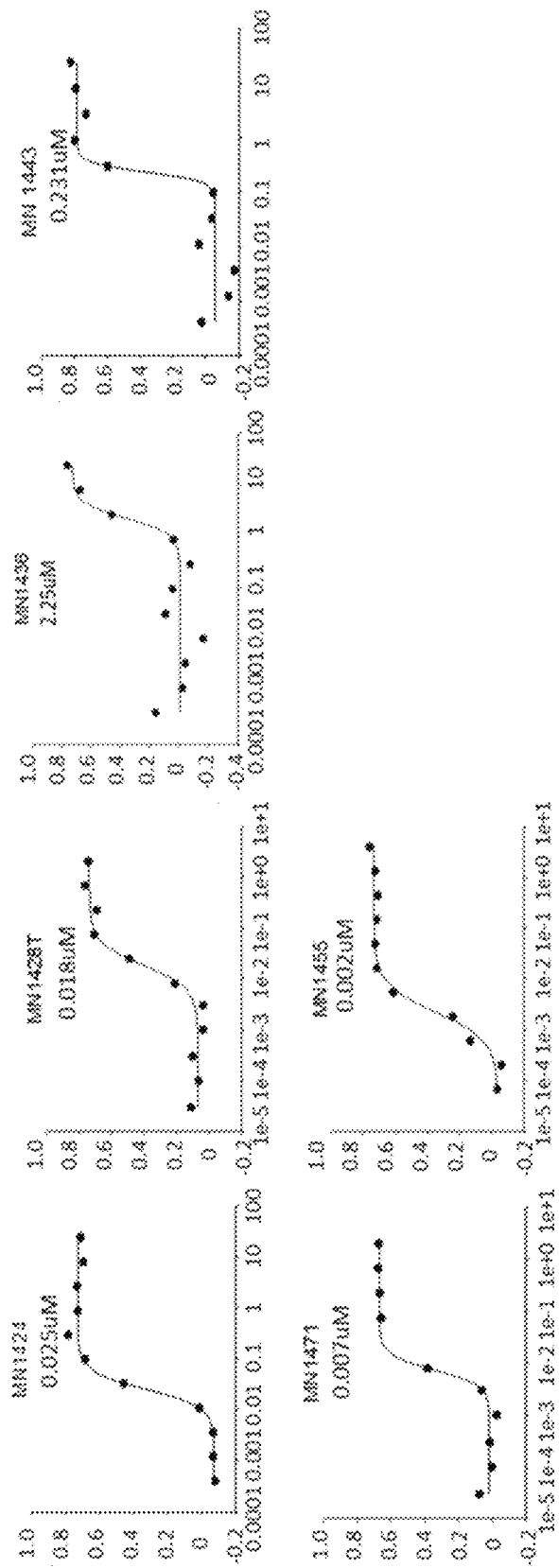
Figure 81:
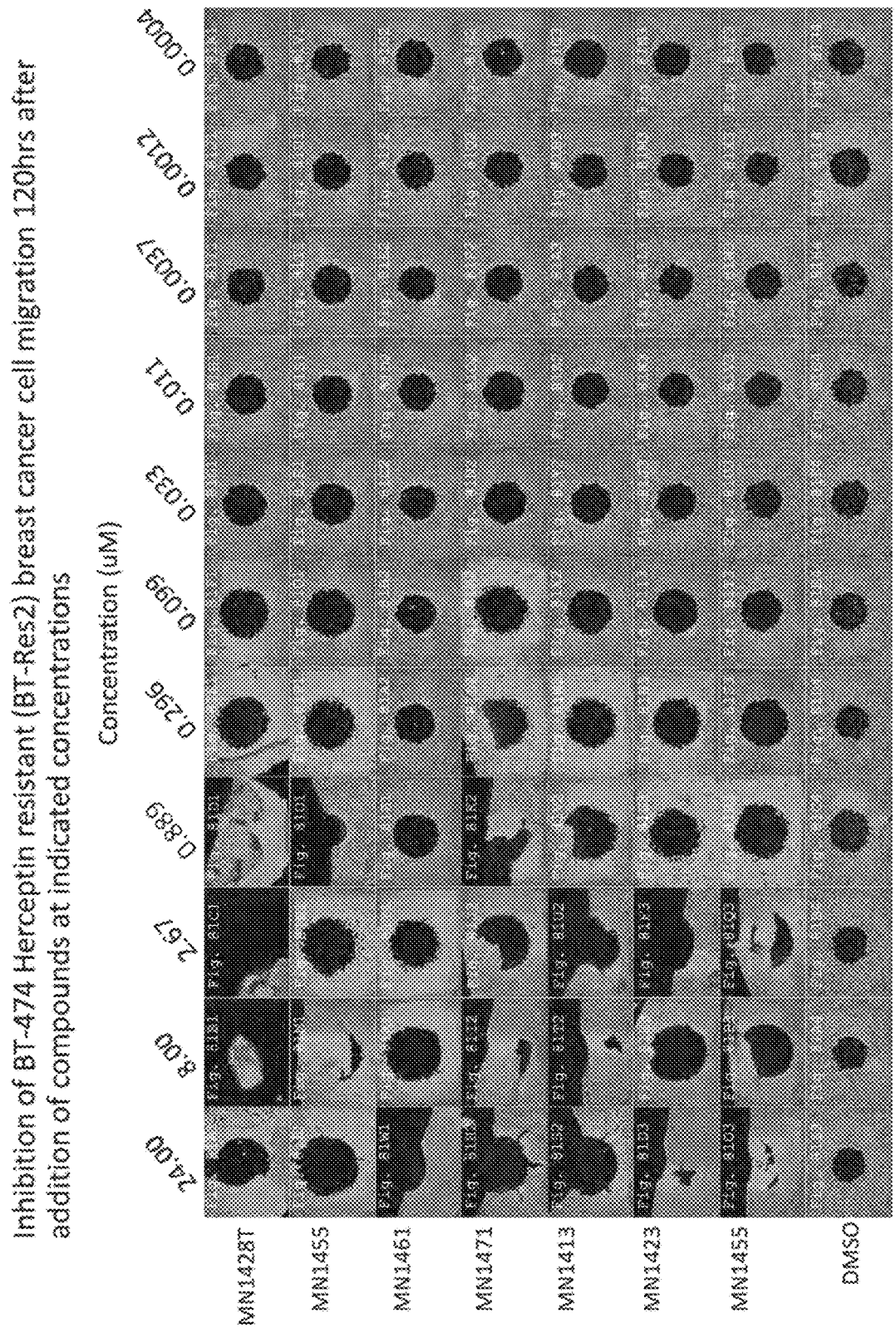
FIG. 81 shows photographs of a cancer cell migration assay in which the effect of compounds of the invention are tested for their ability to inhibit the migration of a Herceptin resistant breast cancer cell line, BT474-resistant, aka BT-Res2, 120 hours after single addition of the compound at the indicated concentrations.
Figure 82:
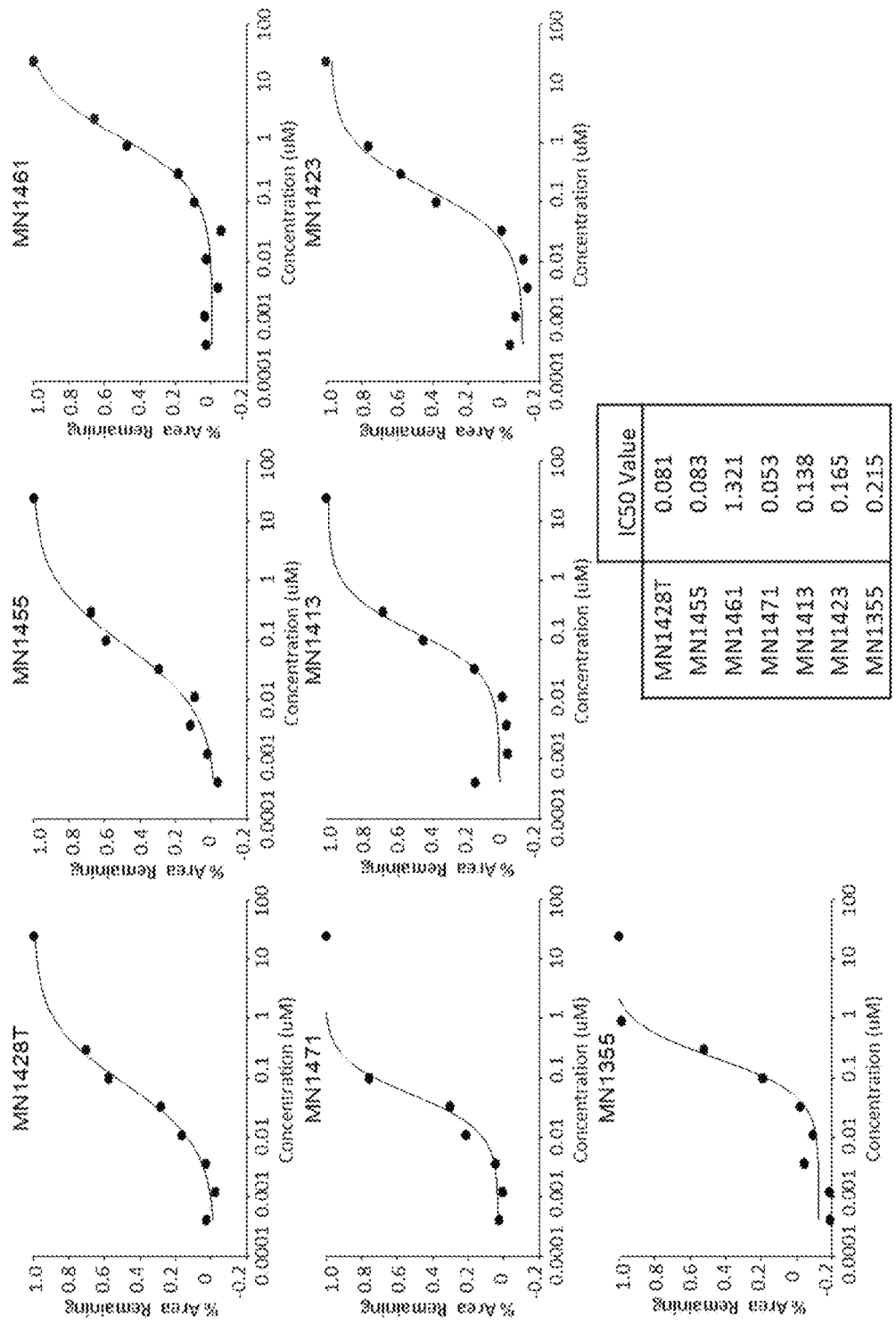
FIG. 82 shows measured IC50 curves for compounds of the invention for the ability to inhibit cancer cell migration or invasion of a Herceptin resistant breast cancer cell line, BT474-resistant, aka BT-Res2, over a range of concentrations, or the control, DMSO alone, at 120 hours.
Figure 83:
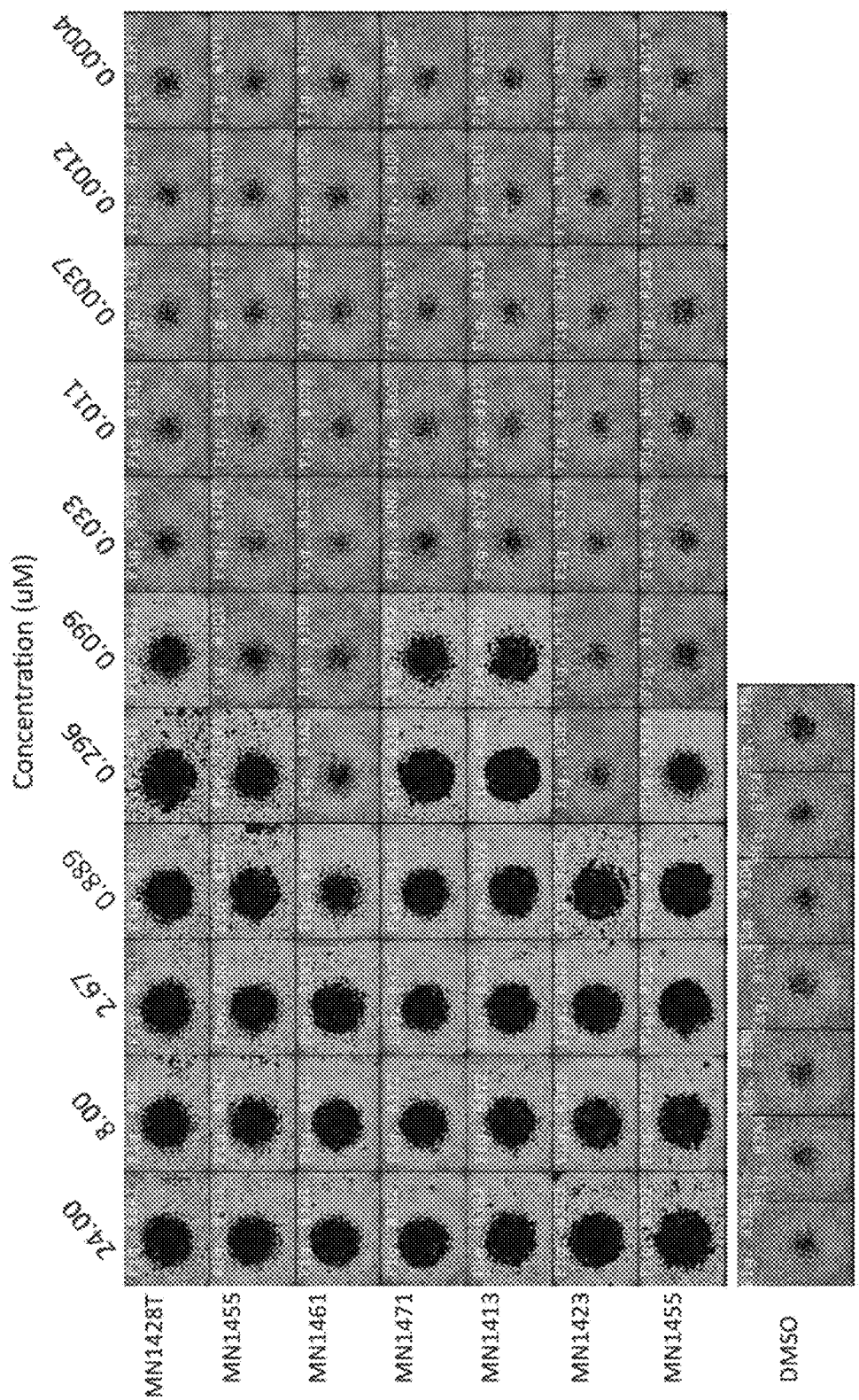
FIG. 83 shows photographs of a cancer cell migration assay in which the effect of compounds of the invention are tested for their ability to inhibit the migration of HCT-MUC1*, which is an engineered cell line, where MUC1-negative HCT-116 colon cancer cells were stably transfected with the growth factor receptor MUC1*. Compounds of the invention were added once over a range of concentrations and images were taken at 72 hours post addition of compound.
Figure 84:
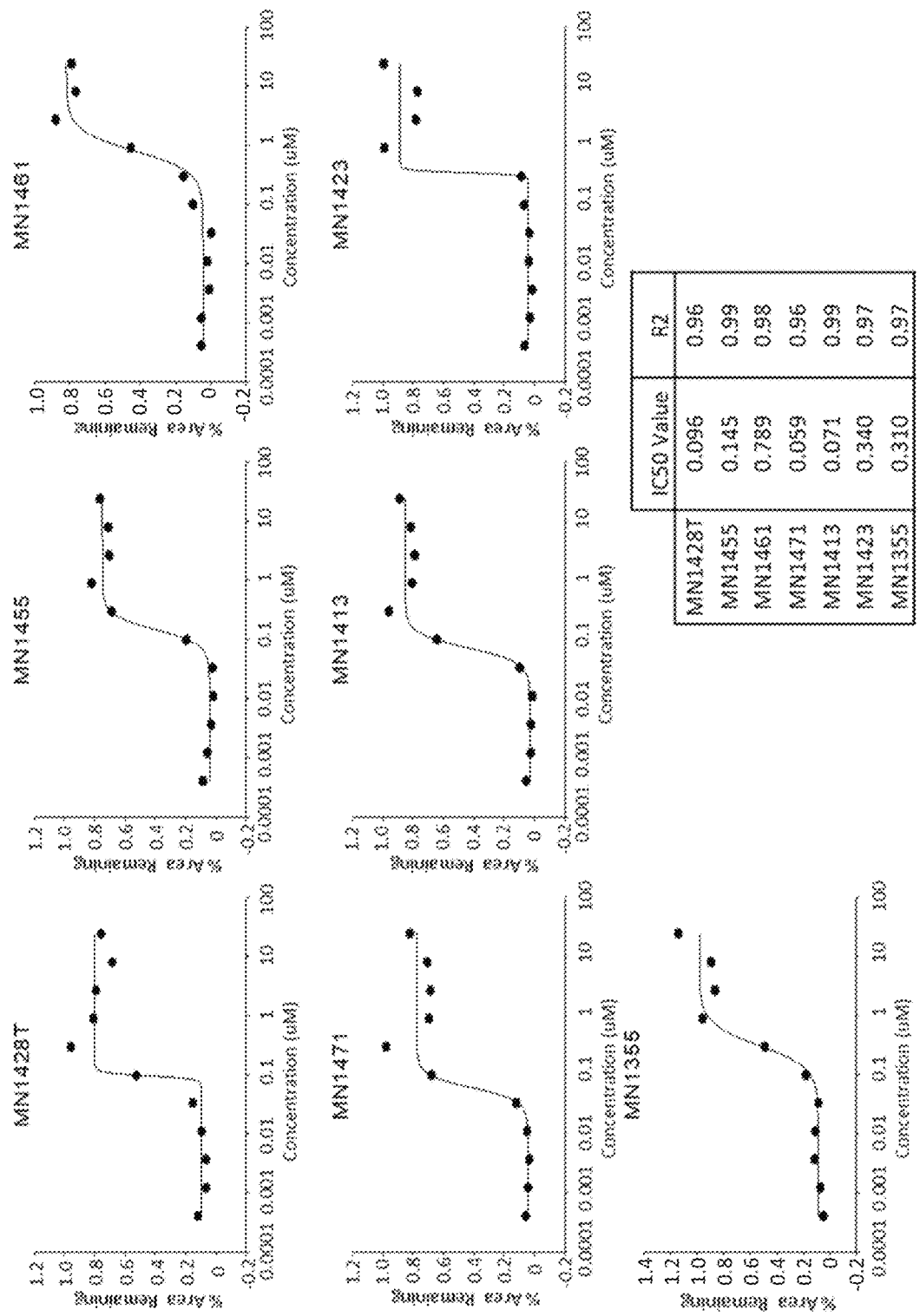
FIG. 84 shows measured IC50 curves for compounds of the invention for the ability to inhibit cancer cell migration or invasion of HCT-MUC1* cancer cells in the presence of compounds of the invention, over a range of concentrations, or the control, DMSO alone, at 72 hours.
Figure 85:
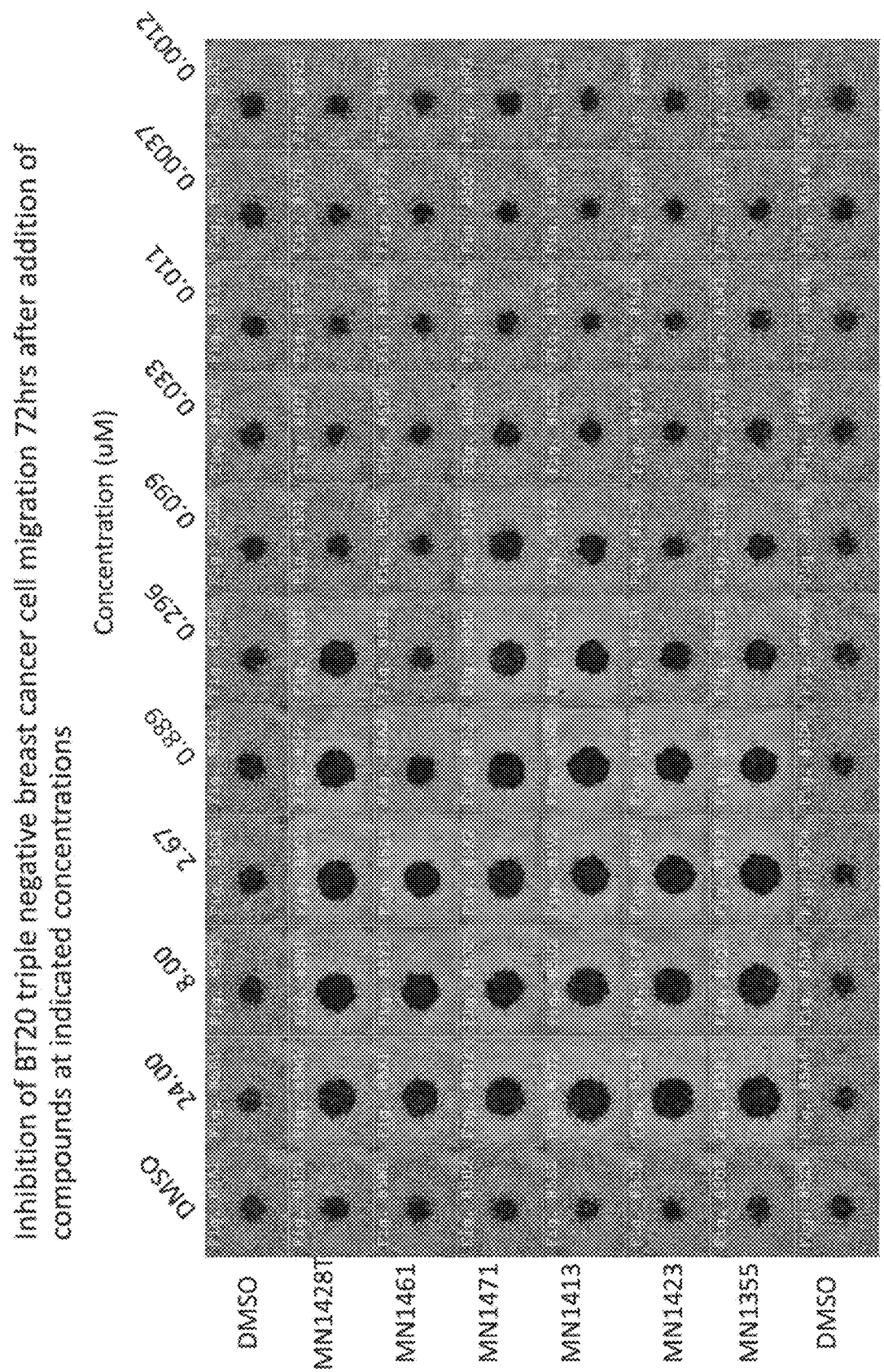
FIG. 85 shows photographs of a cancer cell migration assay in which the effect of compounds of the invention are tested for their ability to inhibit the migration of BT20s, a triple negative breast cancer cell line. Compounds of the invention were added once over a range of concentrations and images were taken at 72 hours post addition of compound.
Figure 86:
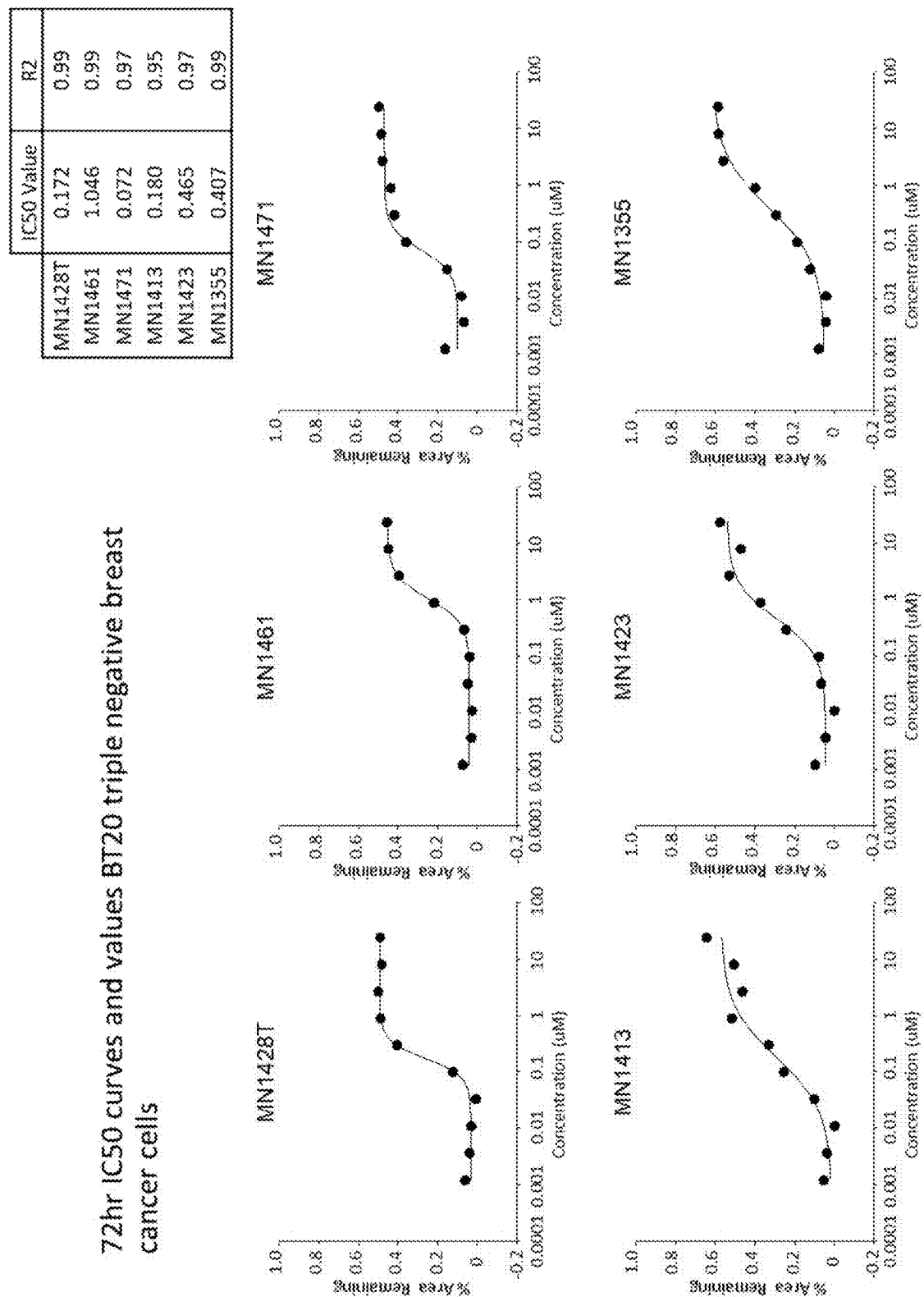
FIG. 86 shows measured IC50 curves for compounds of the invention for the ability to inhibit cancer cell migration or invasion of BT20s, triple negative breast cancer cells in the presence of compounds of the invention, over a range of concentrations, or the control, DMSO alone, at 72 hours.
Figure 87:
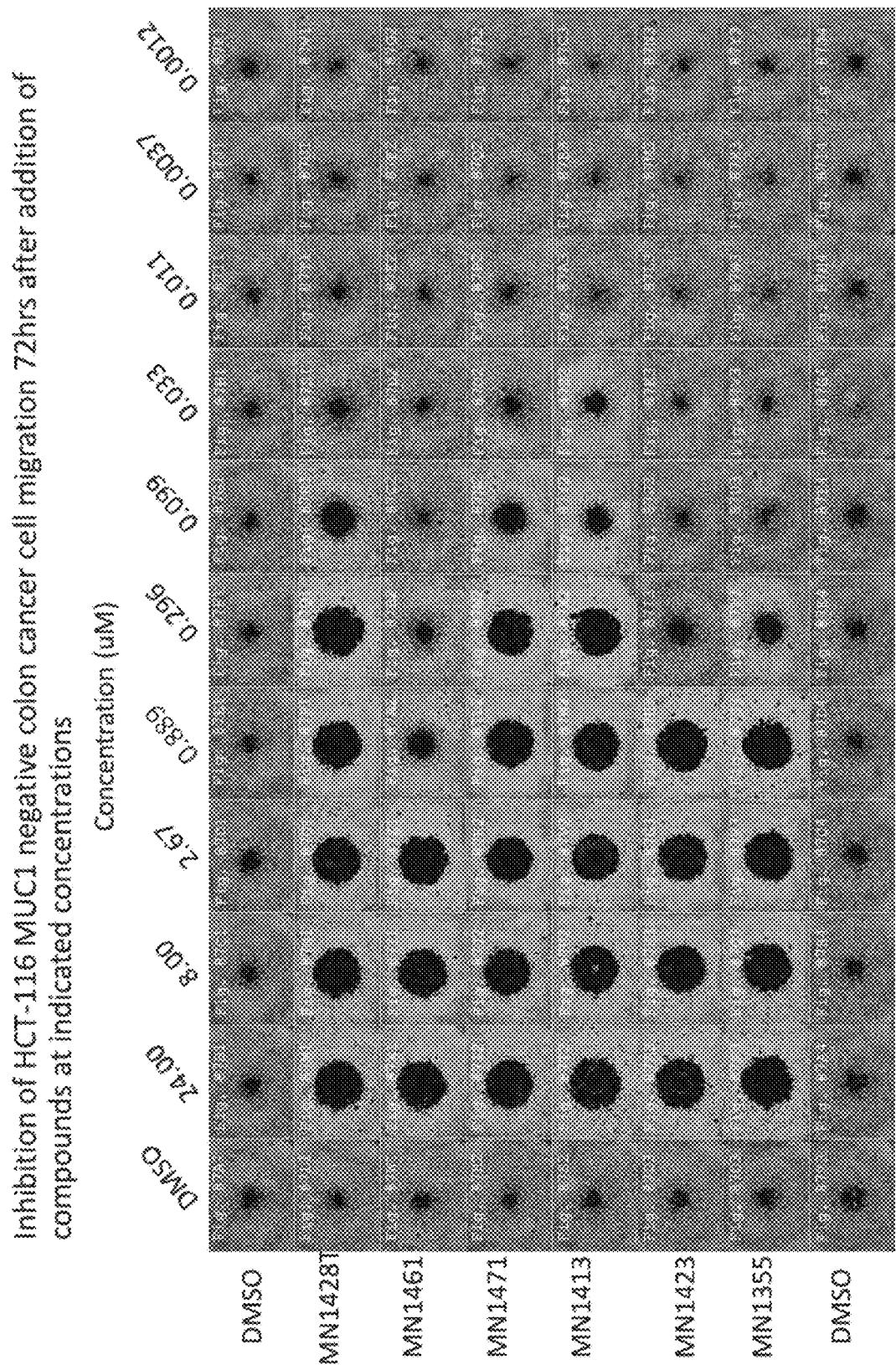
FIG. 87 shows photographs of a cancer cell migration assay in which the effect of compounds of the invention are tested for their ability to inhibit the migration of MUC1-negative HCT-116 colon cancer cells. Compounds of the invention were added once over a range of concentrations and images were taken at 72 hours post addition of compound.
Figure 88:
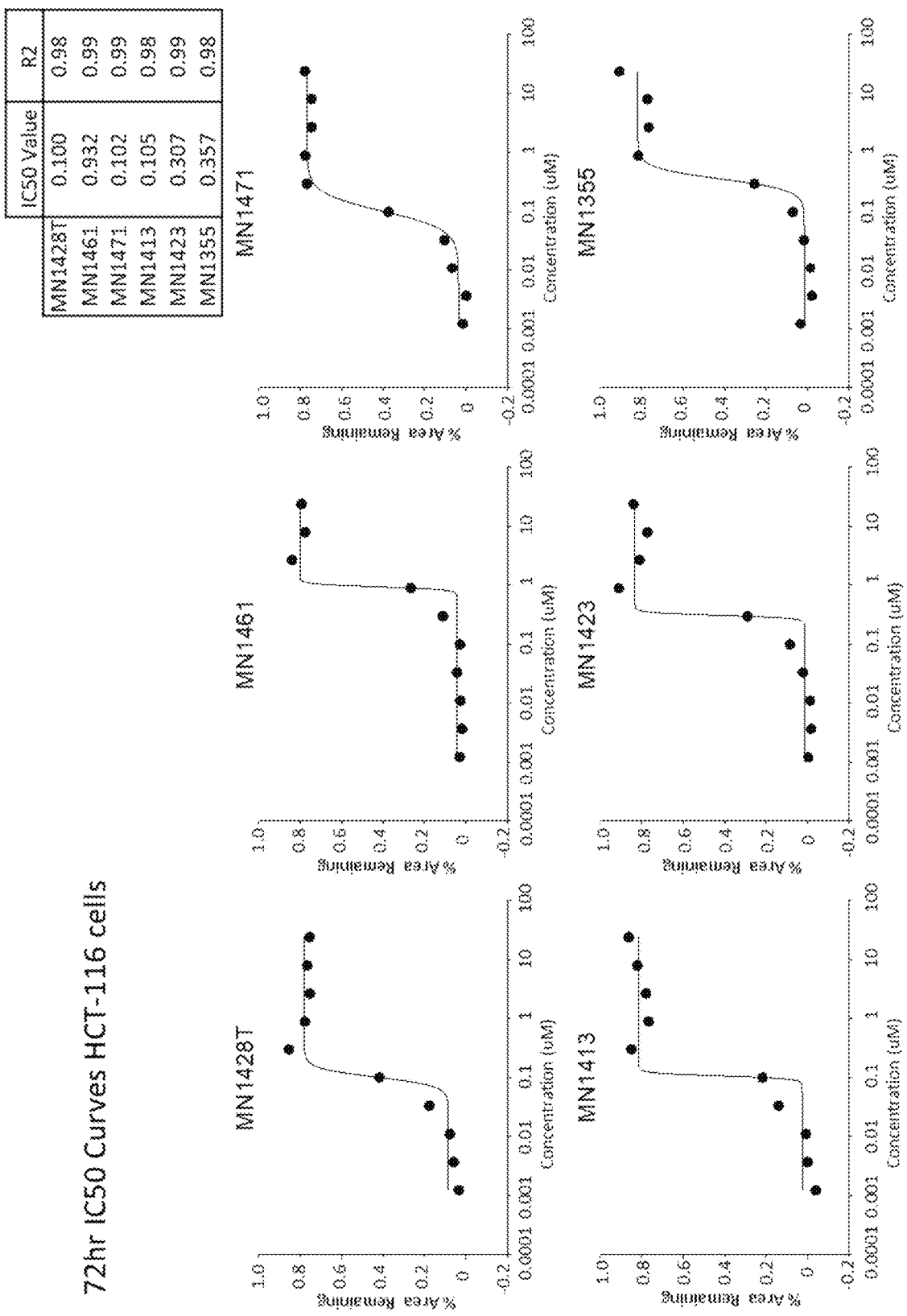
FIG. 88 shows measured IC50 curves for compounds of the invention for the ability to inhibit cancer cell migration or invasion of HCT-116 colon cancer cells in the presence of compounds of the invention, over a range of concentrations, or the control, DMSO alone, at 72 hours.

As cancer treatments become more targeted, the goal is to develop therapeutics that preferentially inhibit the proliferation, migration or invasiveness of cancer cells while having the smallest effect possible on normal, healthy cells. There are no "normal" cell lines because normal terminally differentiated cells do not keep dividing the way stem cell or cancer cells do. However, fibroblasts are more differentiated than stem cells but are able to self-replicate for defined periods of time. We tested selected compounds of the invention to determine if these compounds were just cytotoxic or if they selectively affected stem cells and, importantly, cancer cells, but not normal, healthy cells. Here, we used fibroblasts as a surrogate for normal cells. Since fibroblasts do not change morphology, the readout of this assay was only what effect the compounds had on proliferation. Photographs were taken 48 or 72 hours after the test compounds at 6 uM were separately added to growing human fibroblasts. Each compound was scored for its effect on fibroblast proliferation where "+" indicates 25% inhibition of fibroblast growth, "++" 50% inhibition and "+++" 75% inhibition of growth. FIG. 23A-23D shows photographs of human fibroblasts in culture, treated only with 0.2% DMSO as a control. FIG. 24A-24F shows photographs of the effect of JQ1+(FIG. 24A-24C) versus the effect of the inactive enantiomer JQ1−, both at 500 nM final concentration, (FIG. 24D-24F) on human naïve state stem cells (FIG. 24A, 24D), human primed state stem cells (FIG. 24B, 24E), or human fibroblasts (FIG. 24C, 24F). As can be seen, JQ1+ has the same effect on fibroblasts as it does on primed state stem cells, which indicates it would have more side effects than a compound that did not affect the later fibroblast progenitor cells. FIG. 25A-25F shows photographs of the effect of previously known cancer cell migration inhibitors JQ1 and SU11274 versus the original hits that led to the derivatives that are now compounds of this invention, on the growth of human fibroblast progenitor cells. As can be seen in the figures, most of the novel compounds of the invention have little or no effect on the growth of fibroblast cells. They also have little or no effect on primed state stem cells but have the most inhibitory effect on the naïve state stem cells that we believe are surrogates for cancer cells. The fact that the compounds of the invention robustly inhibit naïve stem cell pluripotency and proliferation, and cancer cell migration and proliferation, but have little or usually no effect on fibroblast progenitor cells shows that the compounds are not cytotoxic agents. In contrast, other previously reported cancer cell migration inhibitors had the same effect on fibroblast progenitor cells as they had on stem and cancer cells, which indicates that they would likely have toxic side effects for the patient.

Experiments indicate that the novel compounds of the invention inhibit pluripotency, proliferation and/or migration of both stem cells and cancer cells by inducing maturation, also known as differentiation. RT-PCR measurements of naïve stem cells that have been treated with compounds of the invention showed that the compounds of the invention induced upregulation of markers of differentiation. The genes whose expression increased as a result of treatment with the compounds of the invention, in a concentration dependent manner, are fibronectin and vimentin, which both increase as stem cells initiate differentiation and NF1, which is one of the first genes to increase when stem cells begin to differentiate down the neural lineage. The fact that fibronectin, vimentin or NF1 expression increases in response to treatment with compounds of the invention shows that the compounds induce differentiation and terminally differentiated cells do not self-replicate. Thus, compounds of the invention that induce markers of differentiation are useful for the treatment of cancers, because cancer cells, by definition, have de-differentiated, which allows them to continually self-replicate. E-cadherin, which is upregulated in cancers, was down regulated when the cancer cells were treated with compounds of the invention. Note that the previously known inhibitors of cancer cell migration and proliferation, JQ1+ and SU11274 did not cause up-regulation of markers of differentiation, i.e. induce differentiation of the stem cells. Similarly, novel compounds of the invention induced differentiation of cancer cells. Expression of metastatic marker E-cadherin was reduced and expression of differentiation markers fibronectin, vimentin and NF1 were increased.

Novel compounds of the invention are highly specific. They specifically inhibit pluripotency and/or proliferation of stem cells and cancer cells. Novel compounds of the invention are most effective against cancers that are MUC1* positive and/or $NME7_{AB}$ or NME7-X1 positive. Although we discovered that NME1 dimers, $NME7_{AB}$ and NME7-X1 are all activating ligands of the MUC1* growth factor receptor and they bind to its extracellular domain, we have developed ample evidence that both $NME7_{AB}$ and NME7-X1 have other binding partners and can exert oncogenic effects, independent of MUC1*.

$NME7_{AB}$ is the natural growth factor that makes the earliest naïve stem cells grow. $NME7_{AB}$ alone is sufficient for the growth and pluripotency of naïve human stem cells. In human Day 3 blastocysts, all cells are positive for $NME7_{AB}$. By Day 5, the $NME7_{AB}$ cells are restricted to the inner cell mass, which by definition contains naïve state stem cells. Although $NME7_{AB}$ is expressed in all naïve stem cells, it reportedly is not expressed in adult tissues except in testis. However, we have found it in every metastatic cancer we have examined. We have shown that both naïve stem cells and cancer cells secrete $NME7_{AB}$ and NME7-X1. We show that in both stem cells and cancer cells, both $NME7_{AB}$ and NME7-X1 bind to the extracellular domain of MUC1* and activate pluripotency and growth via ligand-induced dimerization of the MUC1* extracellular domain. Numerous immunohistochemistry studies we have performed show that both $NME7_{AB}$ and NME7-X1 are overexpressed in cancer cells and the increase in expression correlates to tumor stage. PCR experiments show that the compounds of the invention cause a decrease in the expression of $NME7_{AB}$ and NME7-X1 in cancer cells.

Structure Activity Relationship (SAR) of lead compounds were analyzed and new derivative compounds were designed and synthesized with the goal of increasing efficacy, decreasing the IC50 (concentration of half maximal effect) and improving solubility. The structures of these compounds are shown as compound numbers MN1292-MN1471. The Table of FIG. 18A-18E shows the results of the biological assays performed with each of these compounds. FIGS. 26-35 show photographs of the effects of the compounds on either naïve state stem cells, primed state stem cell or fibroblasts. Compounds that inhibit stem cell pluripotency, especially naïve state pluripotency but do not affect more mature cells like fibroblasts are predicted to be effective anti-cancer therapeutics. As can be seen in the tabulated data of FIG. 18, many of the new compounds MN1292-MN1471 potently inhibit cancer cell migration and proliferation, with IC50's in the low nanomolar range. In the stem cell screen, these compounds inhibited naïve stem cell pluripotency but had little or no effect on the more mature primed state stem cells or the still more mature fibroblasts. FIGS. 36-45 show photographs, graphs and IC50 curves that quantify the effect of these new compounds on cancer cell migration.

Further medicinal chemistry techniques and analysis of structure activity relationships led to the development of even more potent and selective inhibitors of cancer cell migration, invasion and proliferation. The data shows that the medicinal chemistry techniques and knowledge gained from structure-activity relationships, led to a great reduction in the IC50 concentrations of this group of compounds. For example, MN1413 inhibited naïve stem cell pluripotency and proliferation by 100% or a score of '4', while having no effect on the more mature primed state stem cells and also having no effect on fibroblast cells, which are a surrogate for normal cells. MN1413 inhibited cancer cell migration by 83% with an IC50 of 10 nM, and inhibited cancer cell proliferation by about 50%. MN1423 inhibited naïve stem cell pluripotency and proliferation by 100%, or score of '4', but had no effect on primed state stem cells or fibroblasts. MN1423 inhibited cancer cell migration by 84% with an IC50 of 12 nM and inhibited cancer cell proliferation by 50%. MN1428 also inhibited naïve stem cell pluripotency and proliferation by 100%, or score of '4', but had no effect on primed state stem cells or fibroblasts. MN1428 inhibited cancer cell migration by 79% with an IC50 of 7 nM. The results of the stem cell drug screening of these compounds are shown in FIGS. 46-64. These figures document the ability of these compounds to inhibit pluripotency and proliferation of naïve stem cells, while having virtually no effect on primed state stem cells or fibroblast cells, wherein fibroblasts are simulants of normal healthy cells. FIGS. 65-88 show photographs and graphs showing the effects of these compounds on cancer cell migration or invasion and graphs indicating the IC50 of each compound.

It is notable that the compounds of the invention inhibited tumor cell migration and invasion and such activity was independent of whether the cancer cells were positive or negative for the common cancer growth factor receptor, MUC1*. Recall that 100% of naïve stem cells are MUC1* positive. Most cancers are MUC1* positive as well. We have shown that the compounds of the invention inhibited cancer cell migration for MUC1* cancer cell lines including T47D breast cancer cells, BT20 triple negative breast cancer cells, BT474-Res2 chemo resistant HER2 positive breast cancer cells, SKOV3 ovarian cancer cells, DU145 prostate cancer cells and Capan2 pancreatic cancer cells, as well as many others. However, compounds of the invention have also been shown to inhibit migration of some MUC1* negative prostate cancer cells. For example, compounds of the invention inhibited migration and proliferation of PC3 prostate cancer cells and HCT-116 MUC1* negative colon cancer cells.

These data are consistent with a mechanism whereby compounds of the invention block cancer cell aggressiveness, evidenced by migration and invasion, by inducing expression of key genes that induce differentiation. RT-PCR measurements of naïve stem cells that were treated with compounds of the invention showed an upregulation of markers of differentiation. The genes whose expression increased as a result of treatment with the compounds of the invention, in a concentration dependent manner, were fibronectin, vimentin and NF1, which are all markers of differentiation.

In addition to typical genes that are related to differentiation, we looked at the expression of specific super-enhancer genes in both stem cells and cancer cells following treatment with compounds of the invention. In embryonic stem cells, roughly 40% of all Mediator components pile up at only a few hundred enhancer sites and so are called super-enhancers. Super-enhancers increase expression of the target genes by many times more than typical enhancers so in this way can rapidly execute key cell fate decisions, such as whether to grow pluripotently or differentiate, as is the case with stem cells. Bleed through in key cell fate decisions, such as whether stem cells should grow pluripotently or differentiate, would have devastating consequences for development of an embryo. Researchers recently found that this super-enhancer phenomenon only occurs in stem cells and cancer cells. These super-enhanced genes constitute Master ON/OFF switches that can toggle back and forth between a stem-like, or cancerous, de-differentiated state and a differentiated state. We hypothesized that the genes that are upregulated by super-enhancers in the more mature primed state stem cells, but not in the naïve stem cells would be critical mediators of differentiation of both stem cells and cancer cells. Cancer cells are de-differentiated, so induction of differentiation would inhibit cancer growth and metastasis. The genes that are super-upregulated in primed state stem cells, but not in naïve stem cells include LIN7A, VLDLR, GNAS, ZIC5, HES3, BDNF, FBXL17, RHOC, KLHL4, GREB1L, EXT1, FEZF1, SULF1, BRD2, CDH9, and LRRTM2. Of particular interest are BRD2, which itself regulates expression of 1,450 other genes through its interaction with chromatin, HES3, which regulates basic helix-loop-helix transcription factors, and GNAS, which mediates the activity of a host of factors that are critical for differentiation. Compounds that increase the expression of these genes, or any of the other super-enhancer genes listed above, would inhibit cancers by inducing their differentiation. In addition, we recently discovered that β-catenin is a key regulator of stem cell differentiation. A decrease in expression of activated, nuclear β-catenin induces differentiation of stem cells. Because it is technically difficult to quantify nuclear and activated β-catenin, it is common to measure AXIN2 as a surrogate for β-catenin, since its expression is directly driven by nuclear, activated β-catenin. We and others have shown that increased expression of microRNA-145 (miR-145) is a harbinger of the onset of stem cell differentiation (Xu, N, et al. MicroRNA-145 Regulates OCT4, SOX2, and KLF4 and Represses Pluripotency in Human Embryonic Stem Cells. *Cell.* 137(4), p 64'7-658, 15 May 2009. DOI:10.1016/j.cell.2009.02.038; and Smagghe et al PLoS ONE 2013). Sachdeva and Mo (Cancer Res: 70(1); 378-87, 2010) reported that increased expression of miR-145 inhibits tumor cell migration and invasion. They reported that miR-145 directly suppresses the tumor metastasis gene MUC1, and by extension MUC1*, which then suppresses expression of activated β-catenin.

Figures 89A, 89B, 89C, 89D:
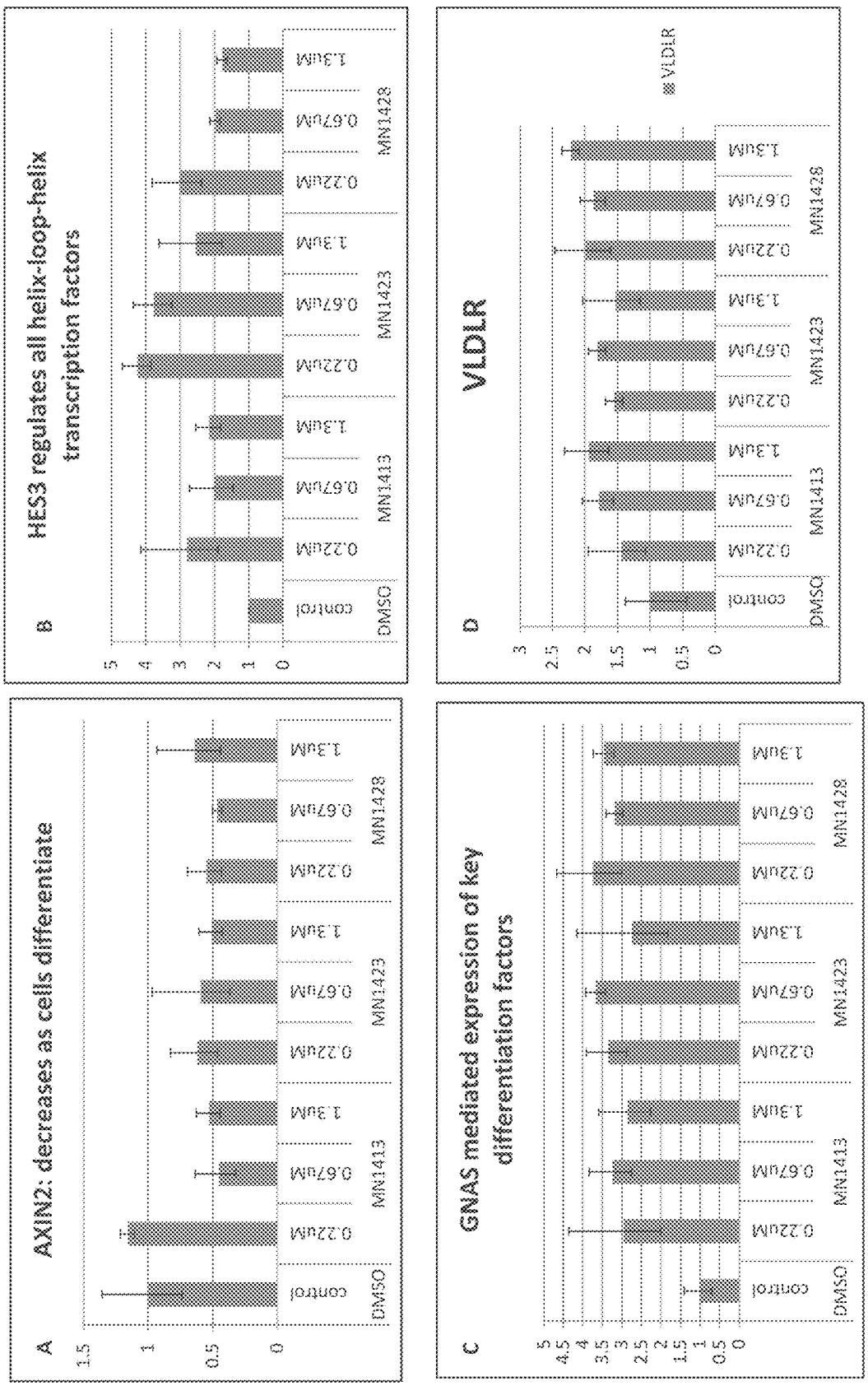
FIGS. 89A-89H show graphs of RT-PCR measurement of naïve state stem cells treated for 72 hours with compounds of the invention at the indicated concentrations, wherein the genes that are measured are AXIN2, a surrogate for beta-catenin, plus HES3, GNAS, VLDLR, EXT1, FBXL17, RHOC, and GREB1L, which are all super-enhancer target genes that are critical for induction of differentiation.
Figures 89E, 89F, 89G, 89H:
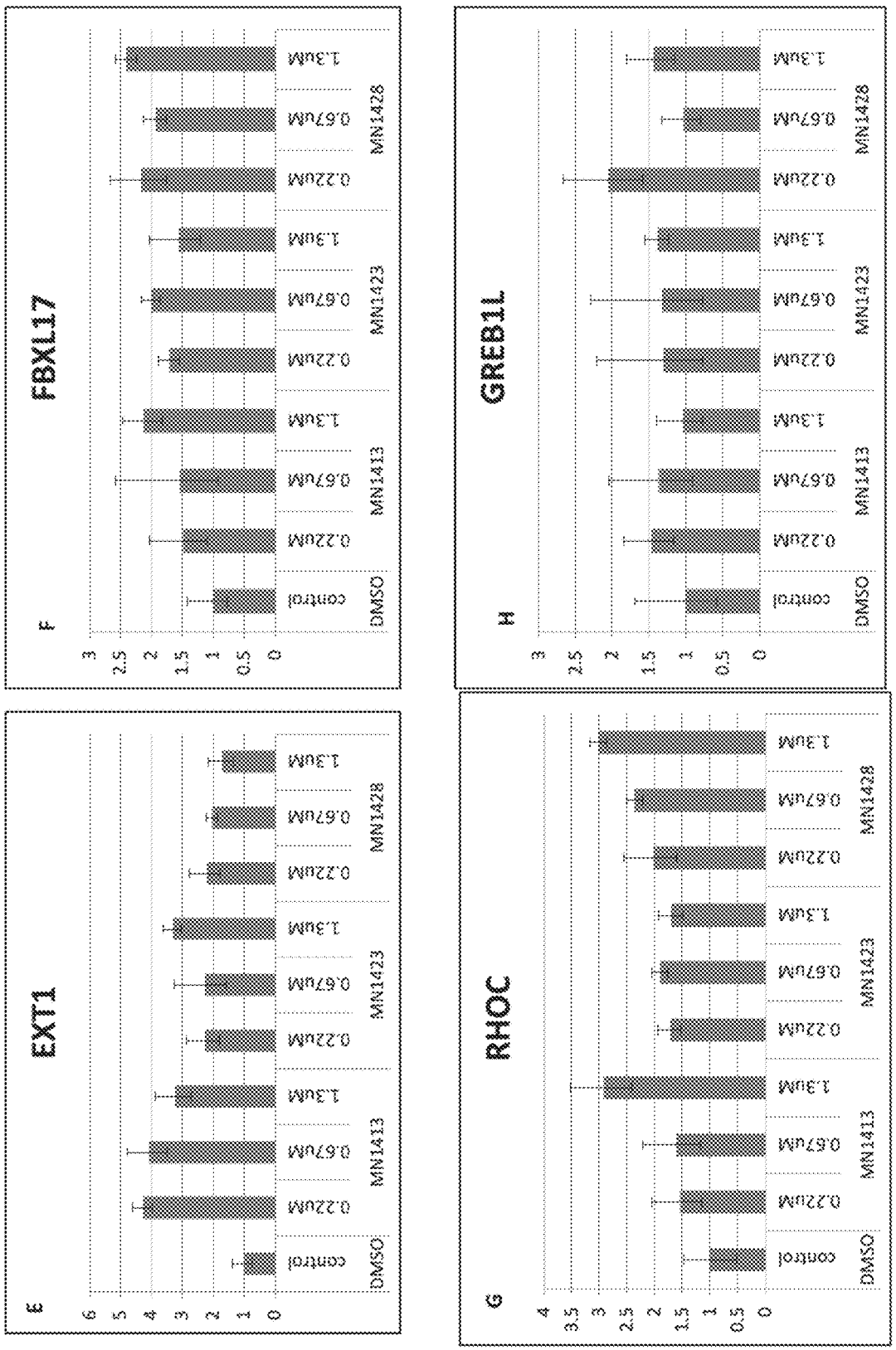
Figures 90A, 90B, 90C:
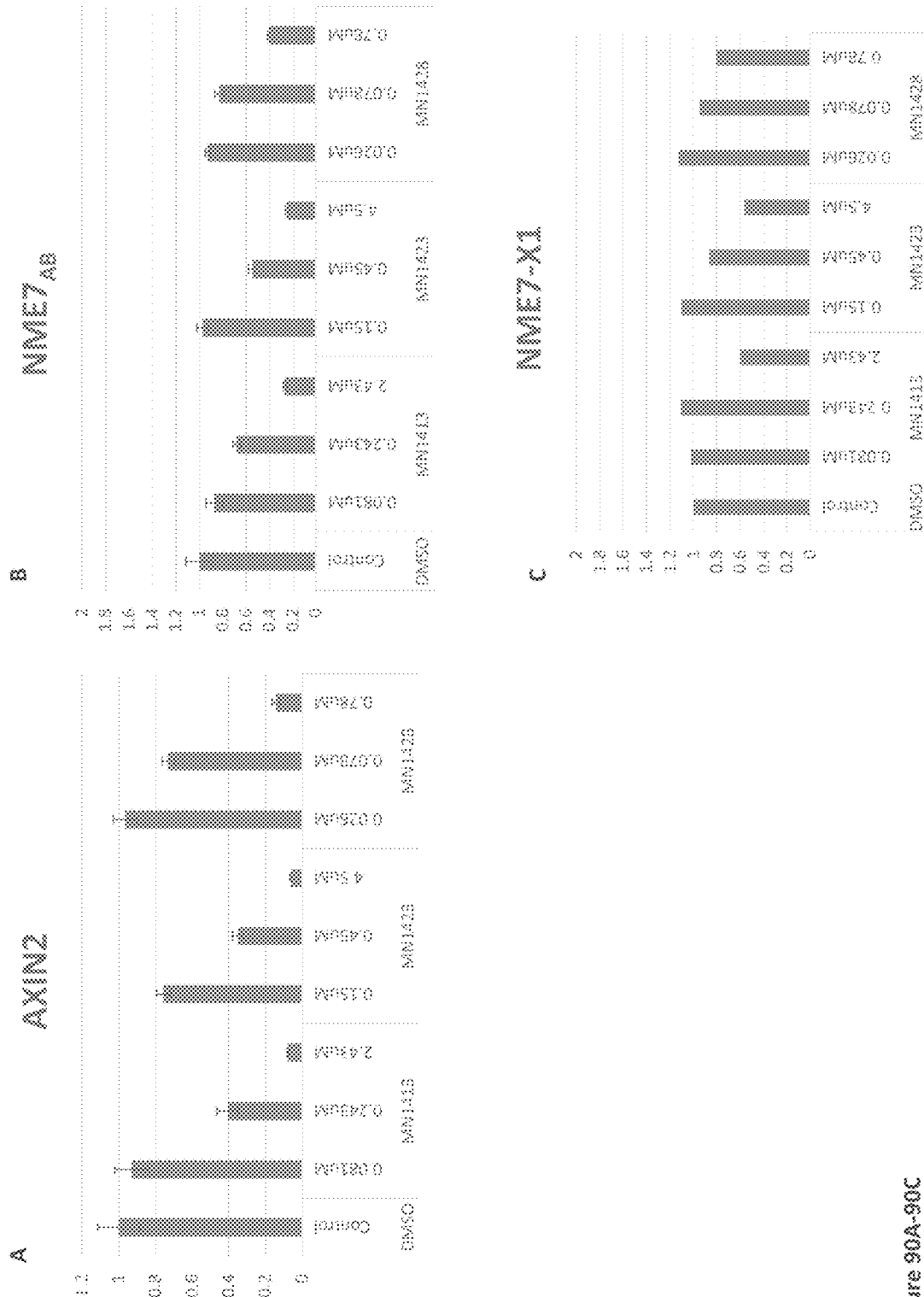
FIGS. 90A-90C show graphs of RT-PCR measurement of cancer cells treated for 72 hours with compounds of the invention at the indicated concentrations, wherein the genes that are measured are AXIN2, a surrogate for beta-catenin, which is suppressed as differentiation is induced, plus $NME7_{AB}$ and NME7-X1, which are metastatic growth factors.
Figures 91A, 91B, 91C:
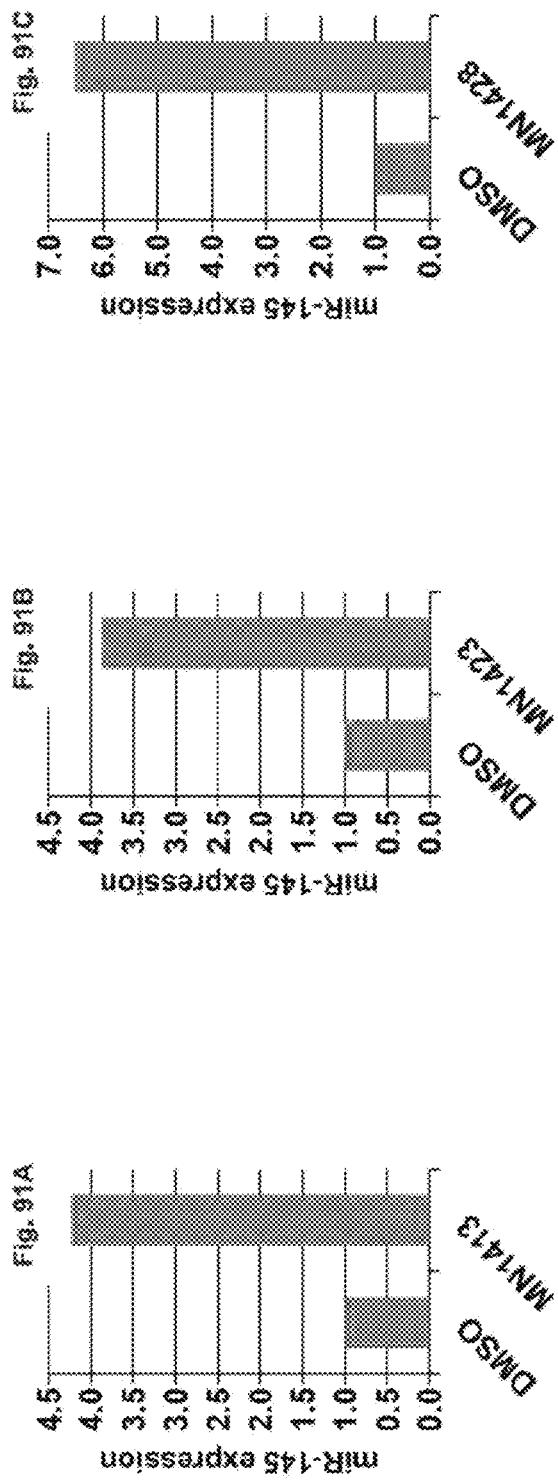
FIGS. 91A-91C show graphs of RT-PCR measurement of naïve state stem cells treated for 72 hours with compounds of the invention at the indicated concentrations, wherein the gene that is measured is micro-RNA-145, which is a harbinger of stem cell differentiation.
Figures 92A, 92B, 92C:
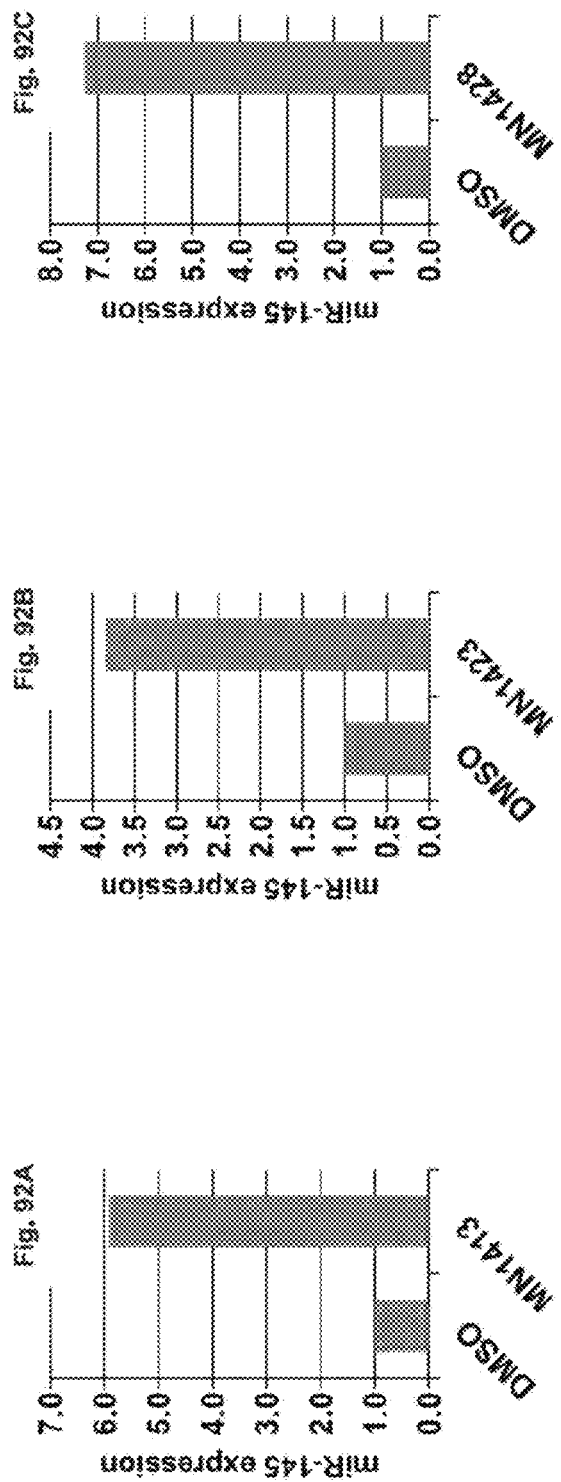
FIGS. 92A-92C show graphs of RT-PCR measurement of T47D cancer cells treated for 72 hours with compounds of the invention at the indicated concentrations, wherein the gene that is measured is micro-RNA-145, which is a harbinger of stem cell differentiation

We used RT-PCR to measure changes in the expression of some of these super-enhancer genes, AXIN2, which is a surrogate for activated β-catenin, miR-145, MUC1 and MUC1* ligands $NME7_{AB}$ and NME7-X1. These experiments showed that the compounds of the invention induce expression of several target genes of superenhancers that are critical mediators of differentiation. In addition, compounds of the invention suppressed expression of AXIN2, and by extension, β-catenin, which induces differentiation (FIG. 89A-89B). In addition, compounds of the invention suppressed expression of MUC1* ligands $NME7_{AB}$ and NME7-X1, which we have shown induce cancer metastasis in vitro and in animals (FIG. 90). Compounds of the invention also increased expression of miR-145 which has been shown to induce differentiation and suppress tumor cell invasiveness and migration. FIG. 91A-91C shows a graph of RT-PCR measurement of naïve state stem cells treated with compounds MN1413, MN1423 and 1428. As can be seen, these compounds increased expression of miR-145. FIG. 92A-92C shows a graph of RT-PCR measurement of T47D cancer cells treated with compounds MN1413, MN1423 and 1428. As can be seen, these compounds increased expression of miR-145 in cancer cells also. Thus, compounds of the invention, at least in part, inhibit tumor cell migration and invasiveness by inducing expression of genes that are critical for differentiation, some of which are super-enhancer target genes, and miR-145, while decreasing expression of β-catenin, MUC1 and its growth factor $NME7_{AB}$. Novel compounds of the invention are powerful agents for the treatment or prevention of cancers and metastatic cancers. The novel compounds of the invention will be most effective for the treatment of cancers that are MUC1* positive and/or $NME7_{AB}$ or NME7-X1 positive. In one aspect of the invention, a biological sample from a patient is tested for the presence of MUC1*, $NME7_{AB}$ or NME7-X1, and upon finding that the patient's cancer is positive for MUC1*, $NME7_{AB}$ or NME7-X1, a compound of the invention is administered to the patient in an amount suitable to prevent or treat the cancer. In one instance, the patient sample is subjected to a test, such as PCR, to determine the amount of nucleic acid that encodes MUC1, NME7 or NME7-X1. In one aspect of the invention, the patient's cancer is considered to be MUC1* positive, $NME7_{AB}$ positive or NME7-X1 positive if expression of those genes is comparable to, or higher than, their expression in human pluripotent stem cells. In another aspect of the invention, the patient's cancer is considered to be MUC1* positive, $NME7_{AB}$ positive or NME7-X1 positive if expression of those genes is equal to or greater than 0.5% of EEF1A1 expression in those cells. In yet another aspect of the invention, the patient's cancer is considered to be MUC1* positive if the patient's tissue specimen is contacted with an antibody that binds to the PSMGFR peptide or the N-10 peptide and stains the tissue with a pathologist's standard score 1-4 ("+-++++"). In another aspect of the invention, the patient's cancer is considered to be $NME7_{AB}$ positive or NME7-X1 positive if the patient's tissue specimen is contacted with an antibody that binds to the B3 peptide of NME7 and stains the tissue with a pathologist's standard score 1-4 ("+-++++").

Compounds

Set forth below are exemplified compounds for use in the treatment or prevention of cancer. A Table summarizing the below exemplified compounds is set forth in FIG. 18A-18E.

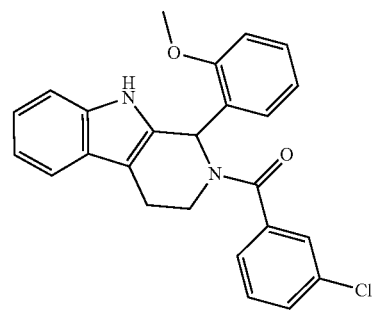

MN0477

MN0580
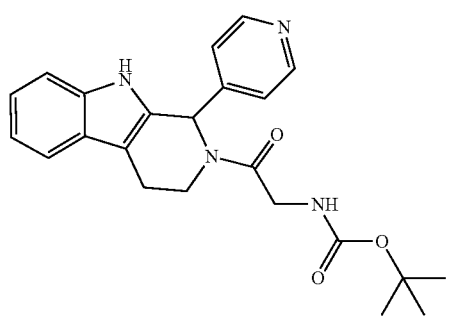
MN0618
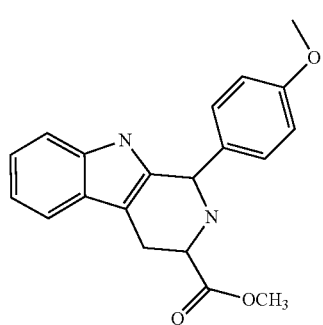
MN0642
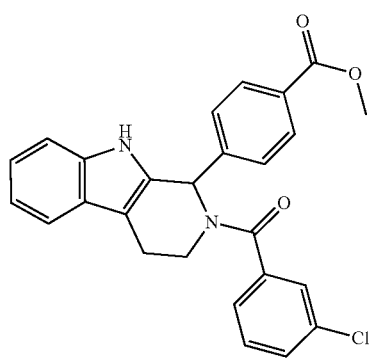
MN0716
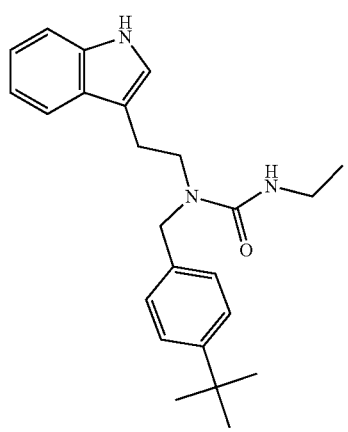
MN0733
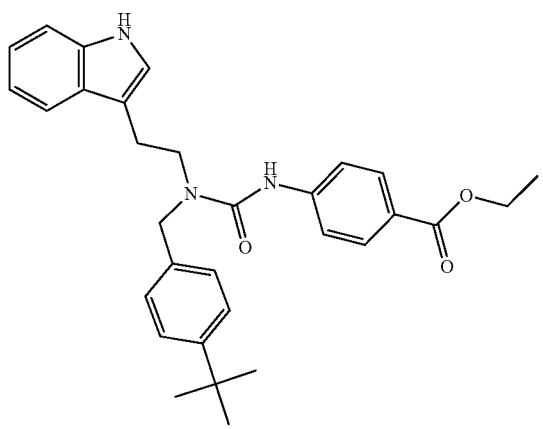
MN0908
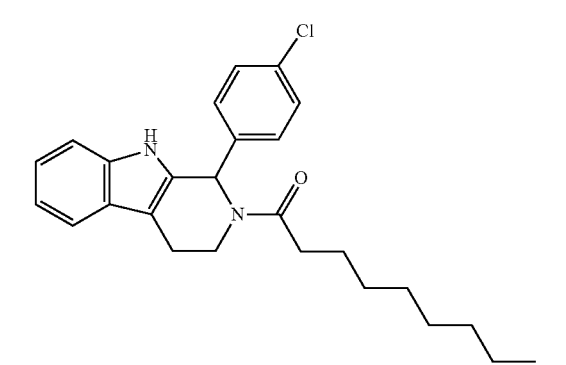
MN1058
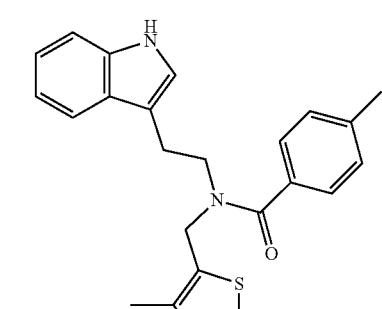
MN1130
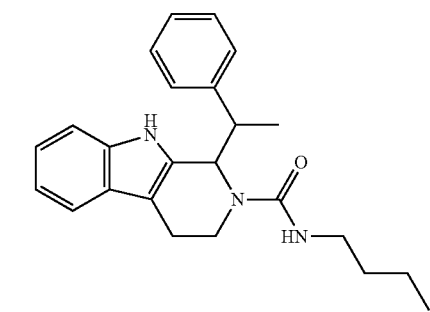

MN1131
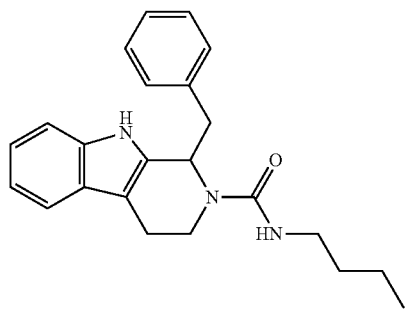
MN1132
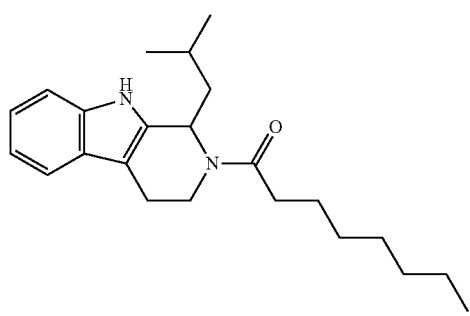
MN1133
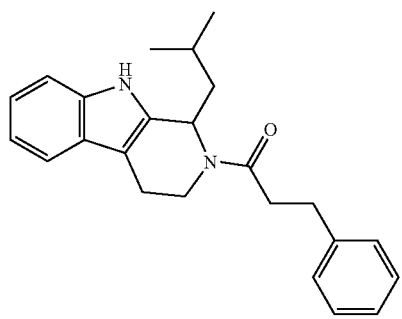
MN1292
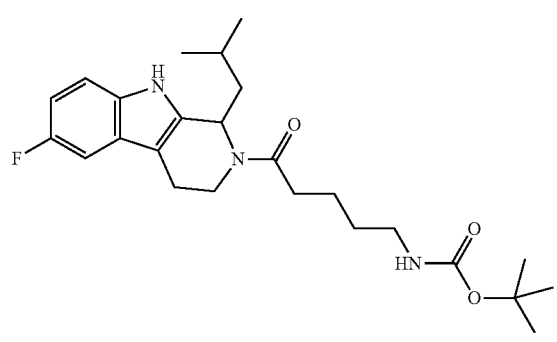
MN1293
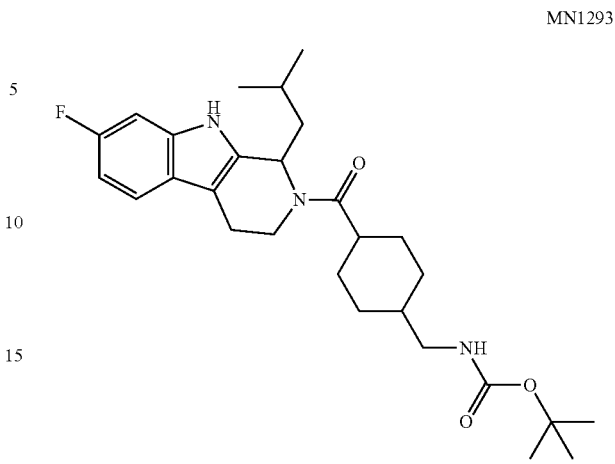
MN1294
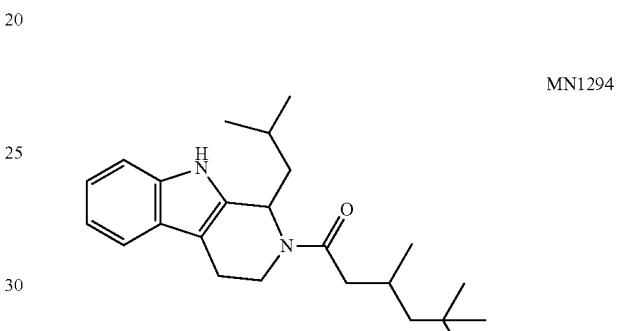
MN1305
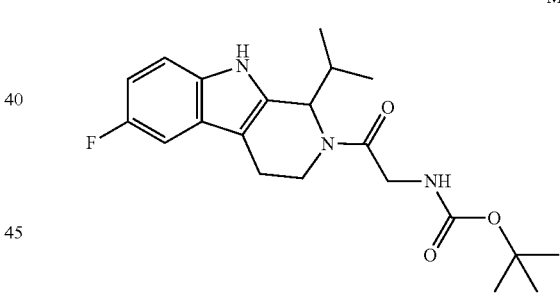
MN1306
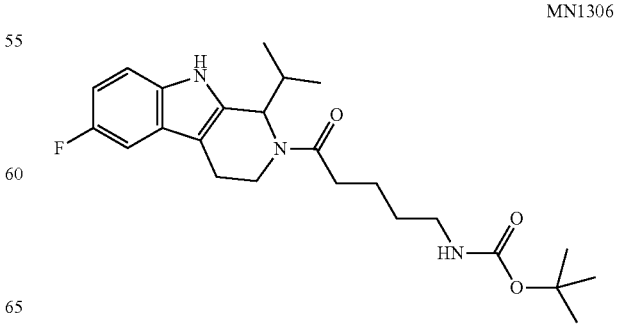

MN1307
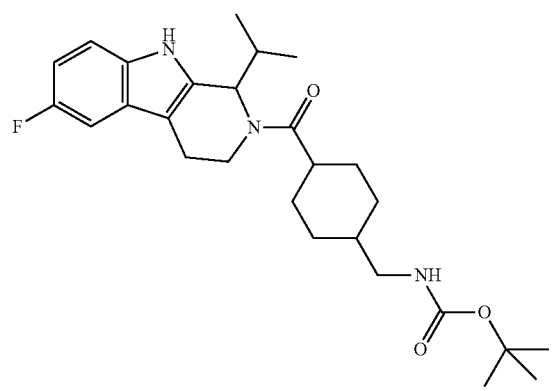
MN1308
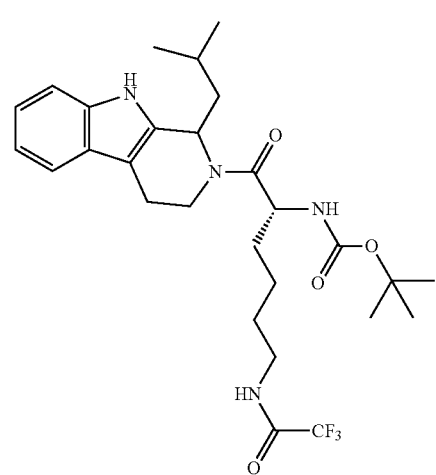
MN1309
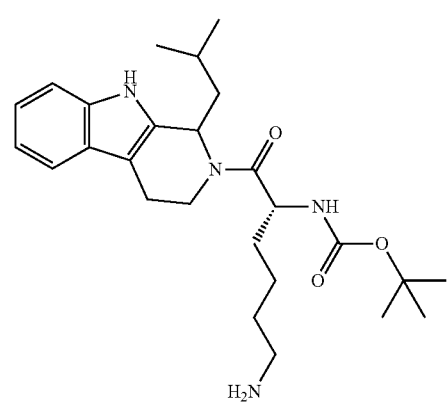
MN1310
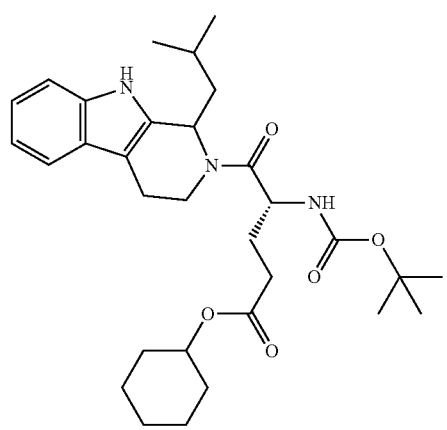
MN1311
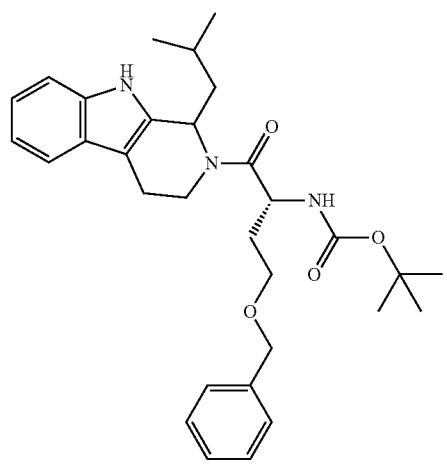
MN1312
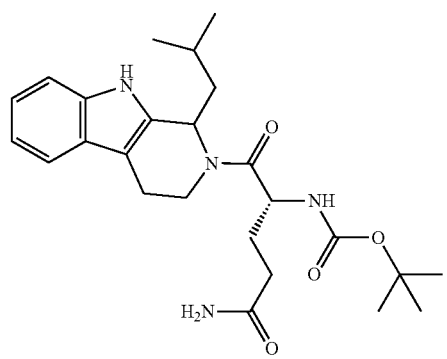
MN1317
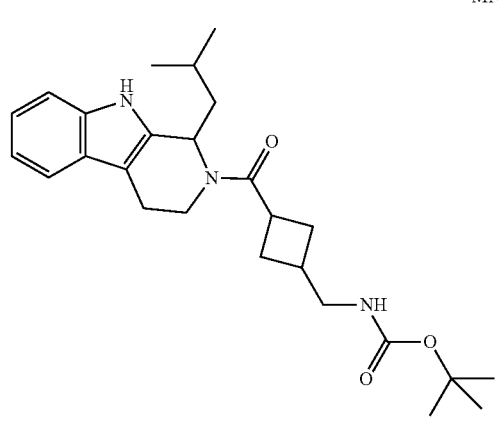

-continued
MN1318
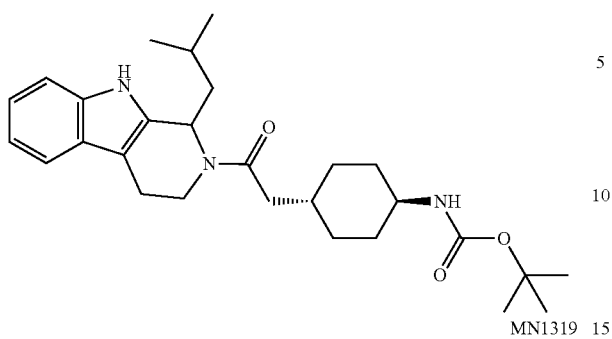
MN1319
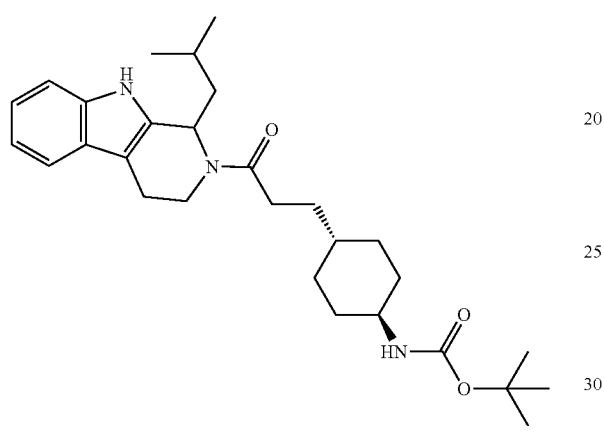
MN1320
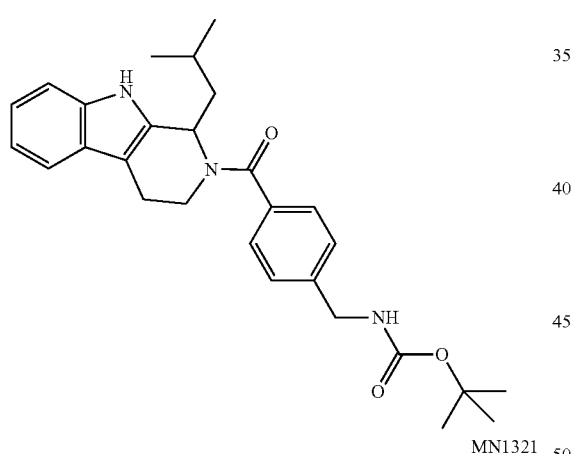
MN1321
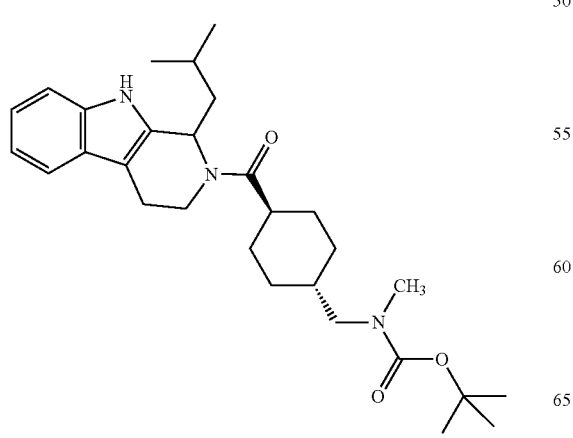
-continued
MN1322
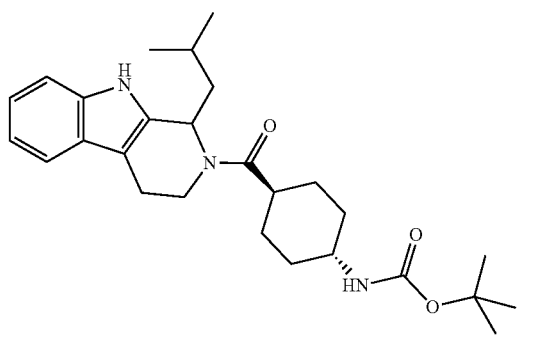
MN1329
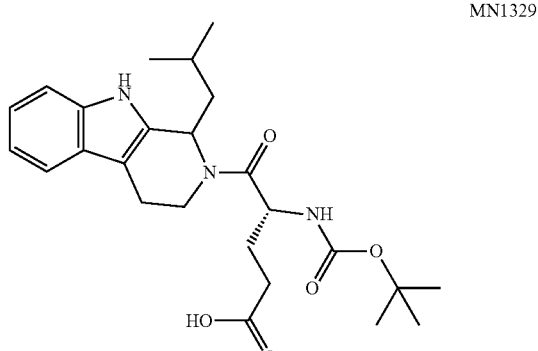
MN1330
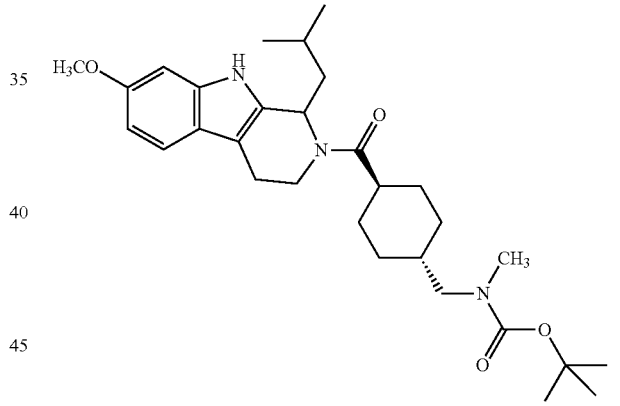
MN1331
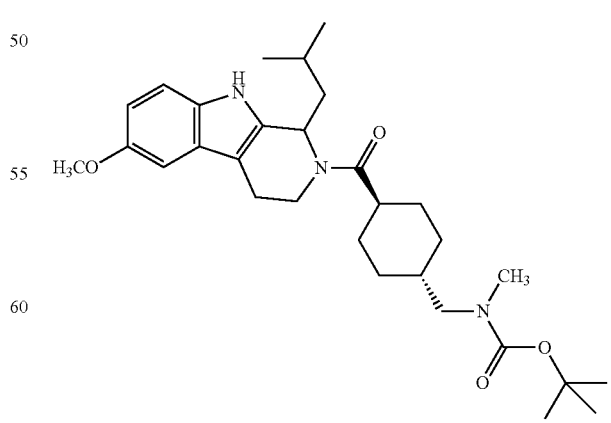

MN1332
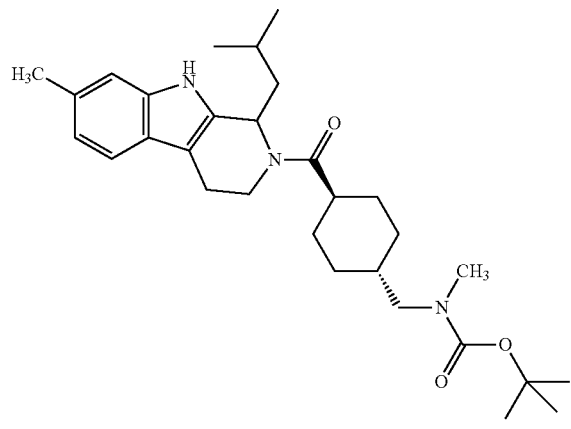
MN1335
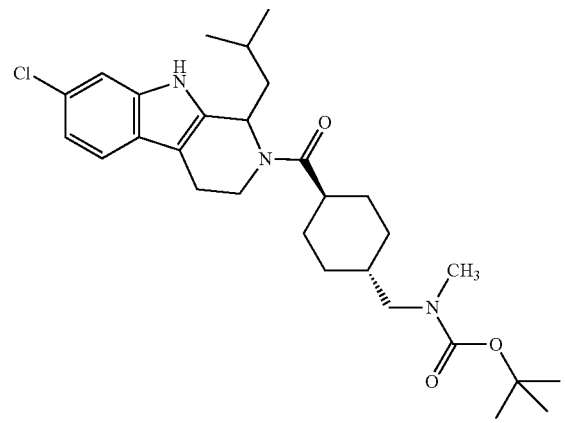
MN1333
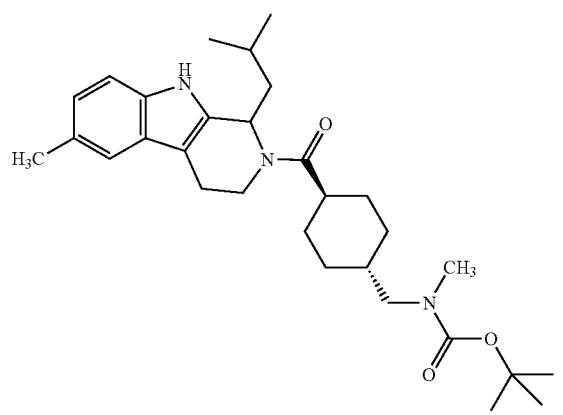
MN1336
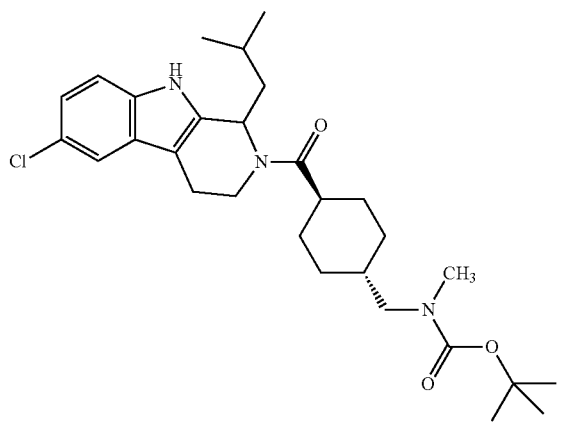
MN1334
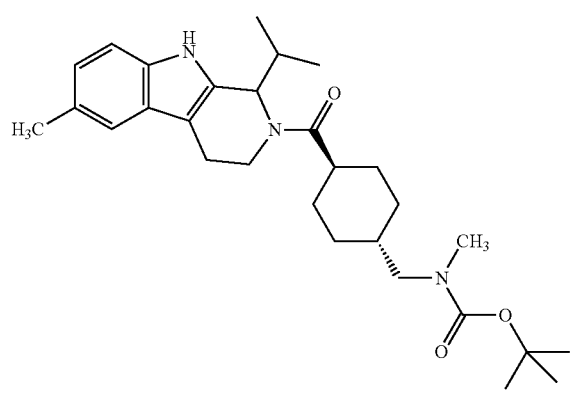
MN1337
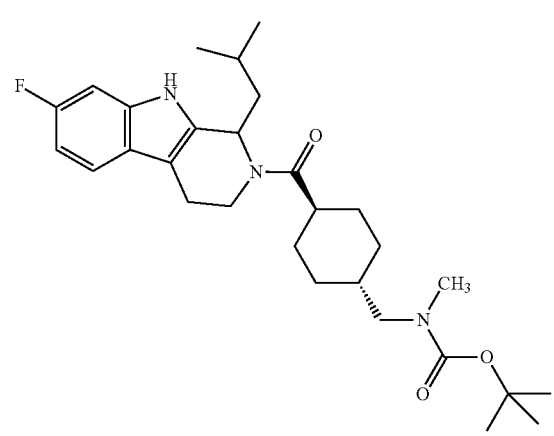

MN1338
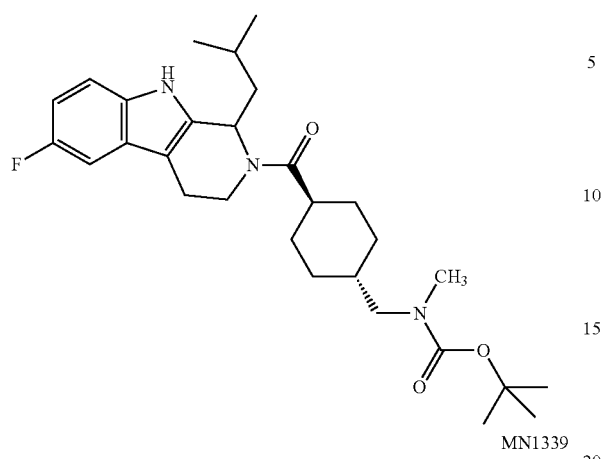
MN1339
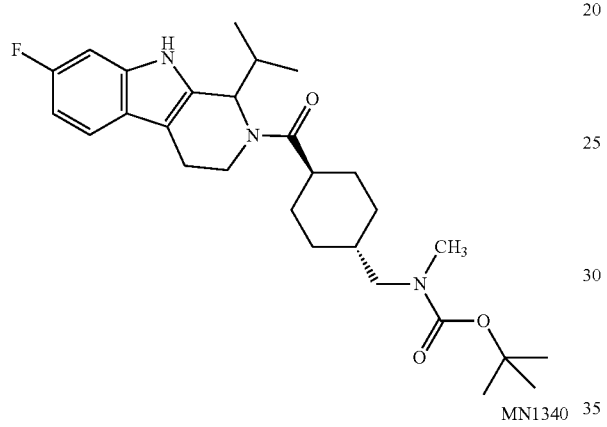
MN1340
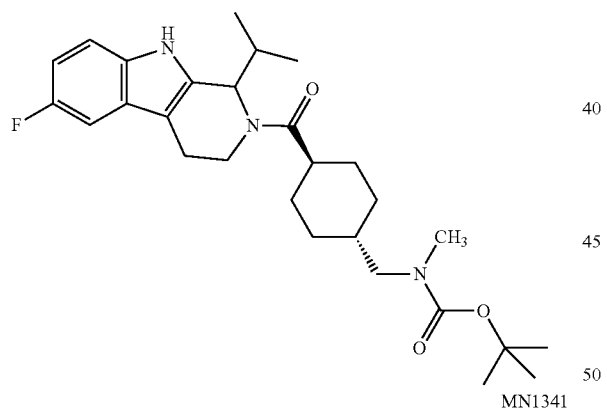
MN1341
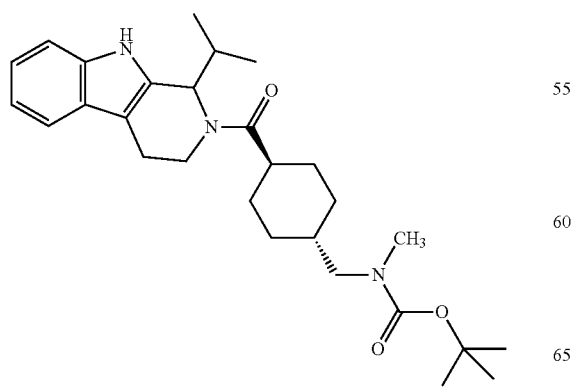
MN1351
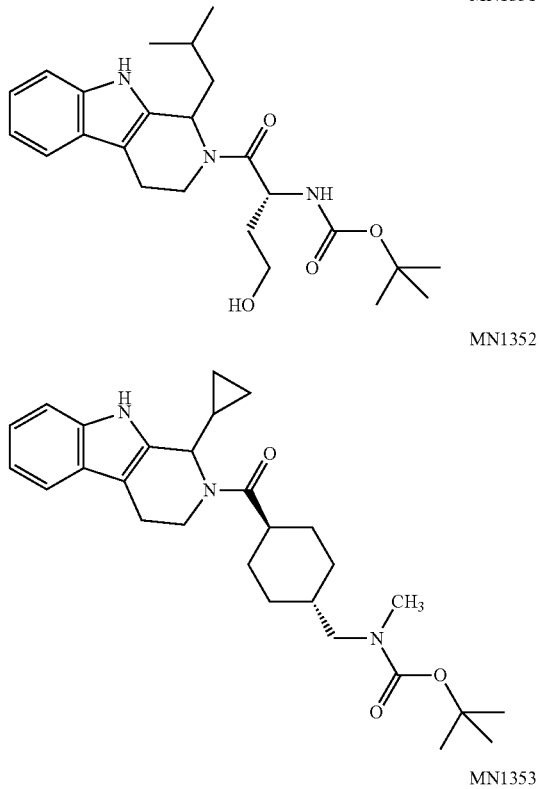
MN1352
MN1353
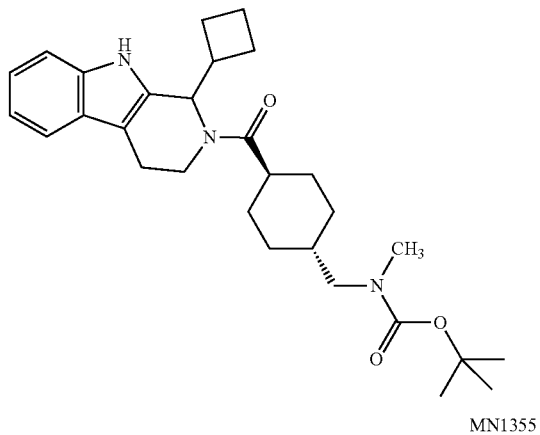
MN1355
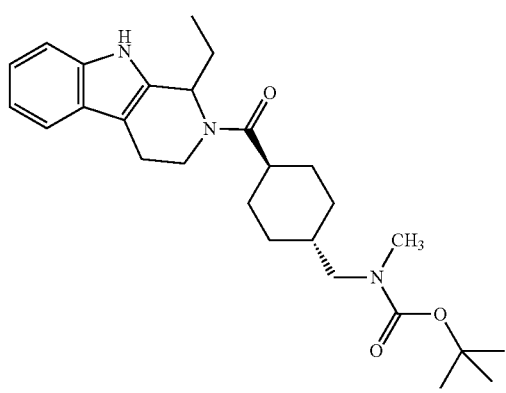

MN1356
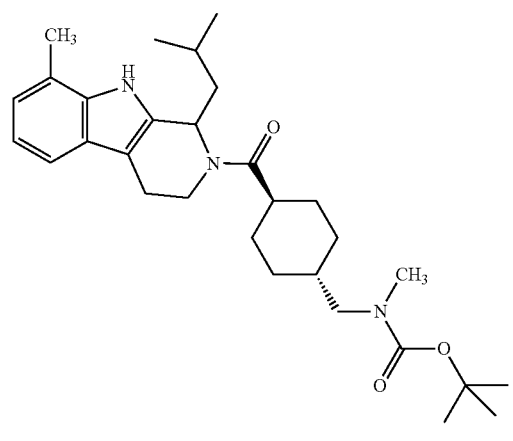
MN1359
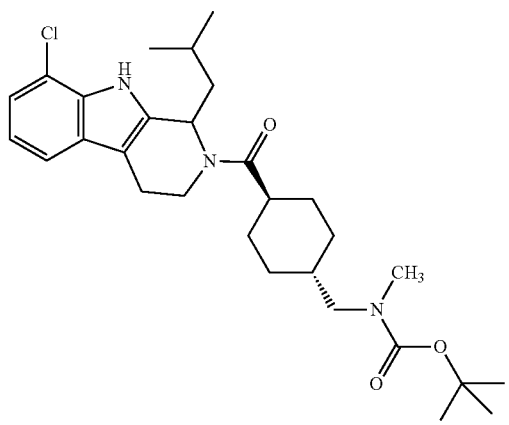
MN1357
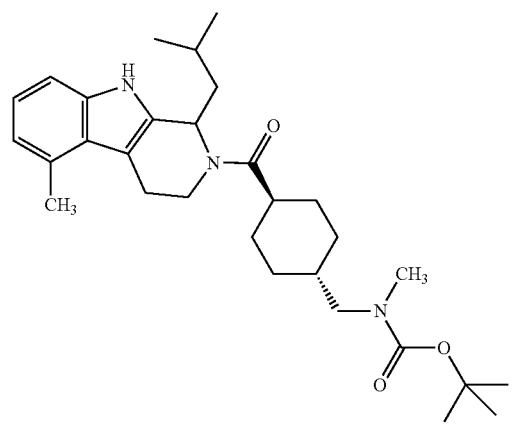
MN1360
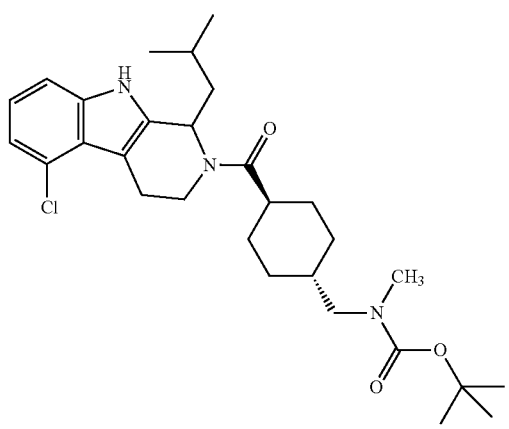
MN1358
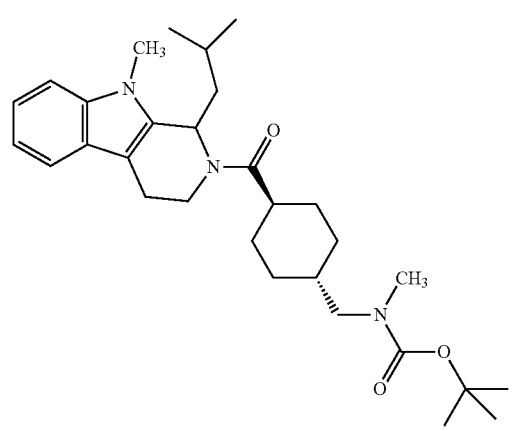
MN1362
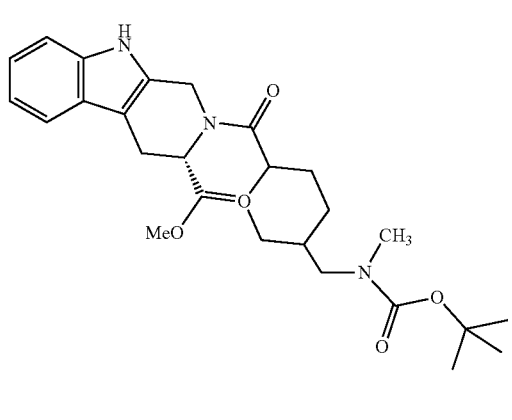

MN1363
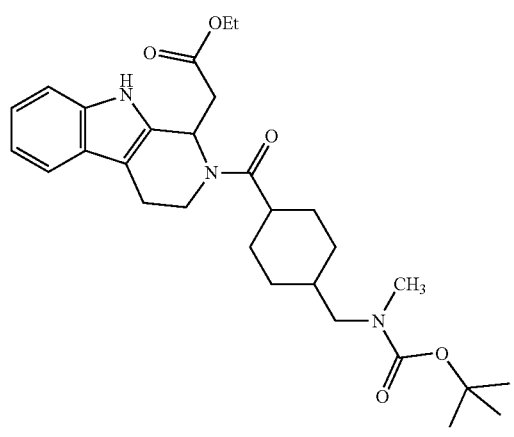
MN1371
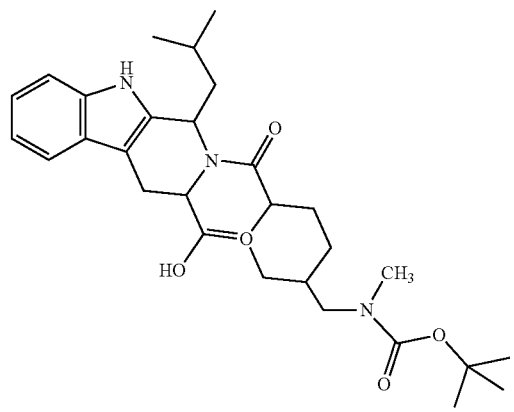
MN1369
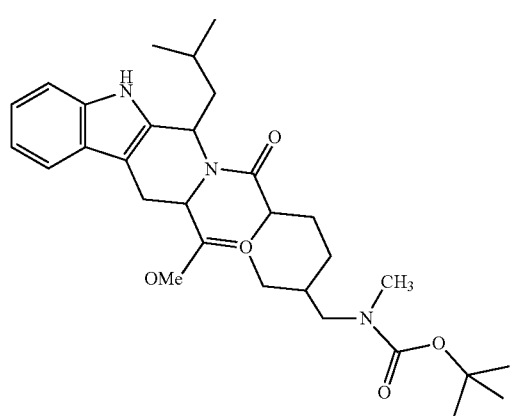
MN1372
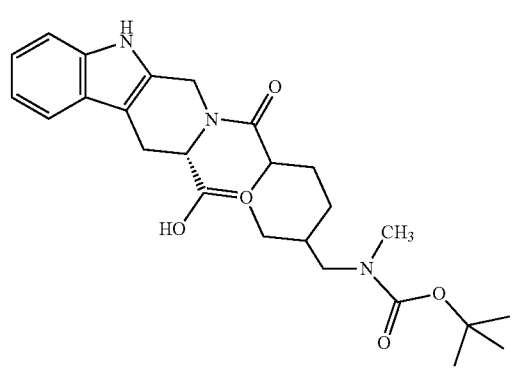
MN1370
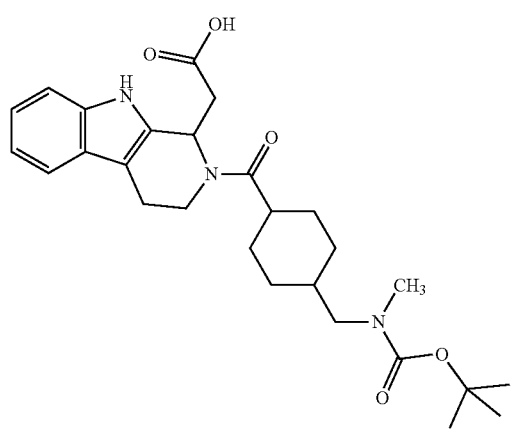
MN1377
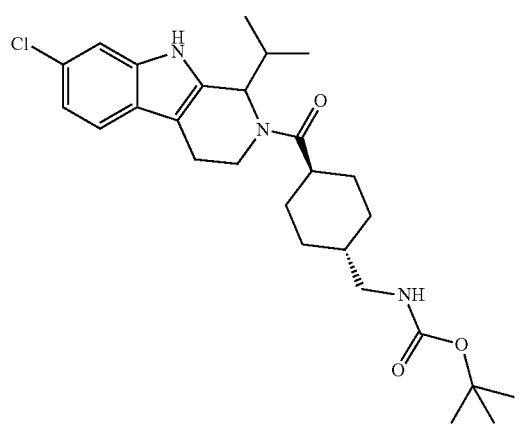

MN1378
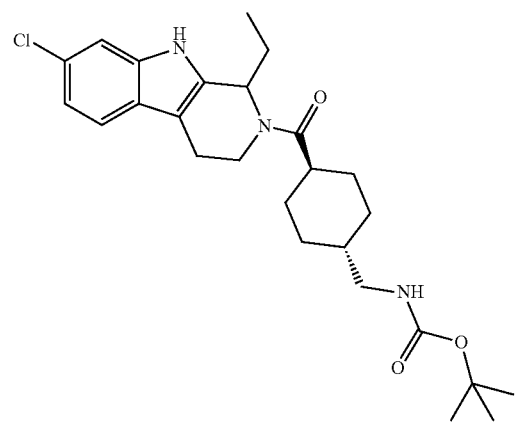
MN1381
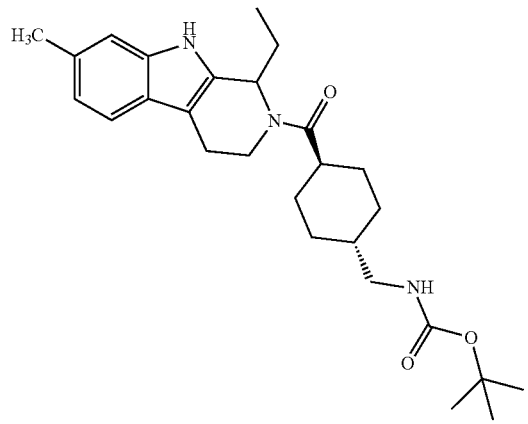
MN1379
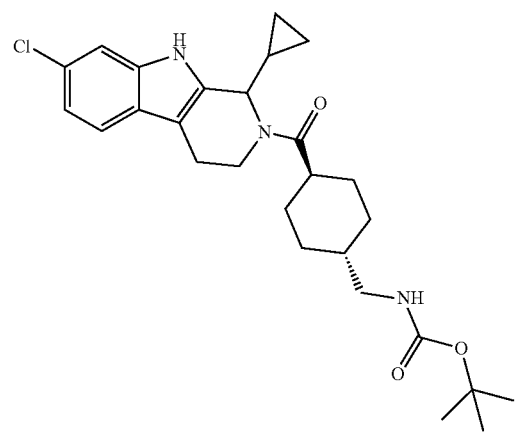
MN1382
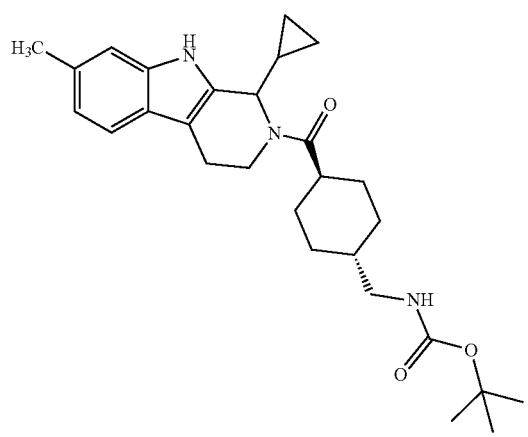
MN1380
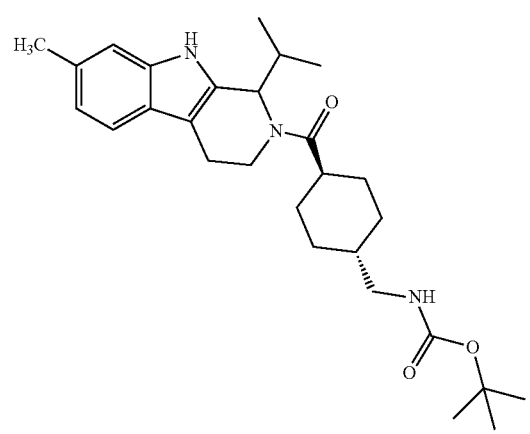
MN1383
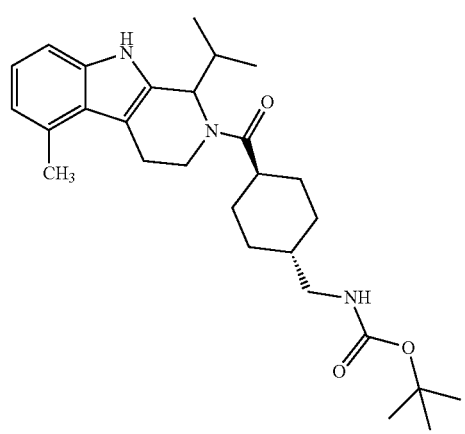

MN1384
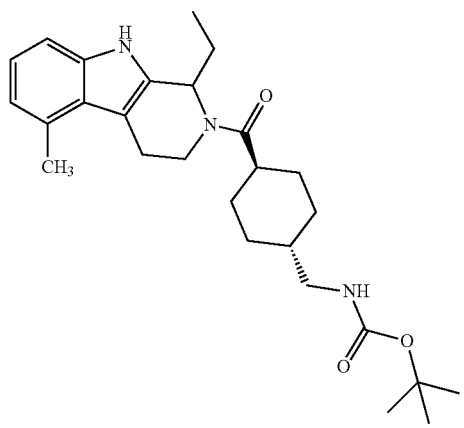
MN1385
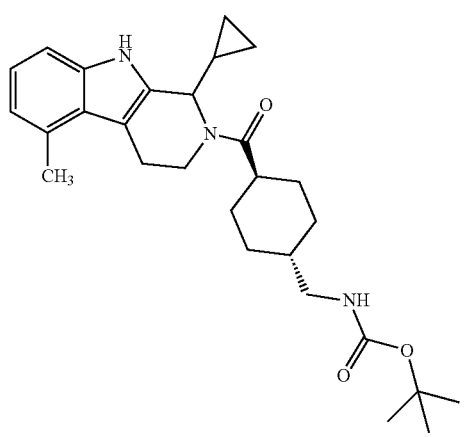
MN1420
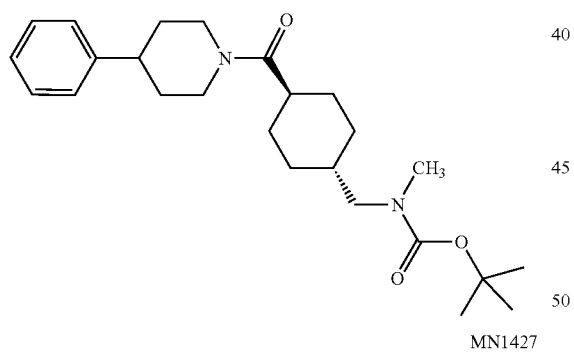
MN1427
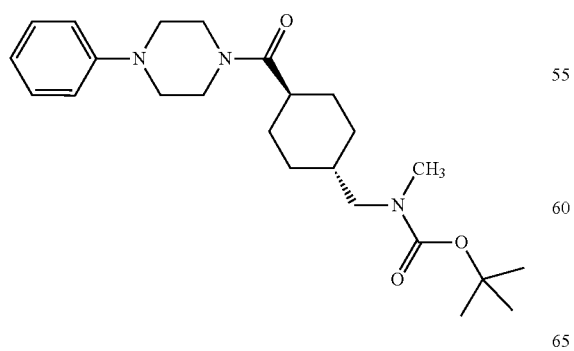
MN1428
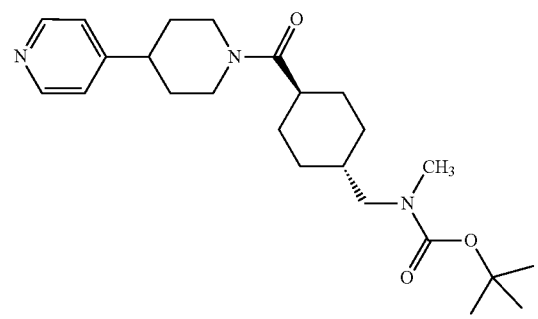
MN1429
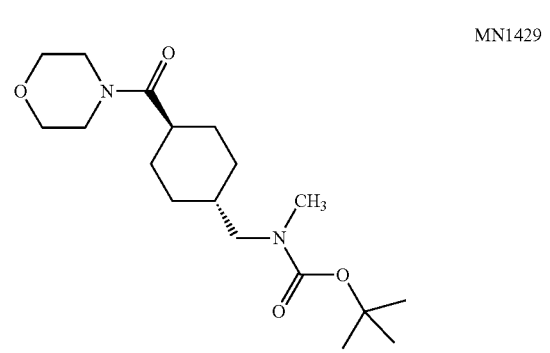
MN1430
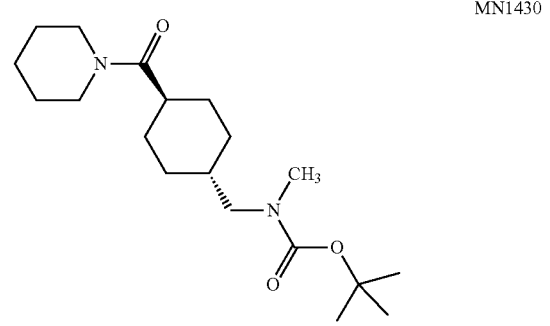
MN1431
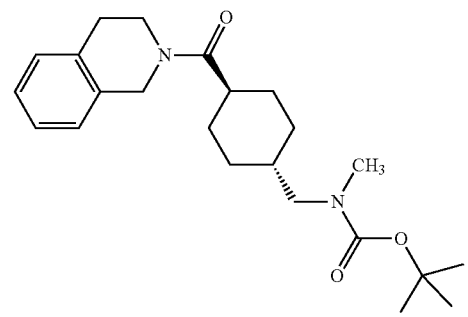

MN1432
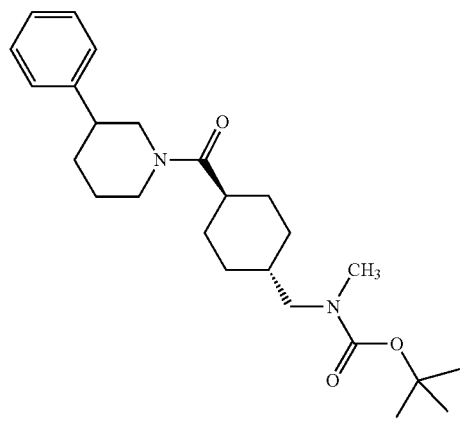
MN1433
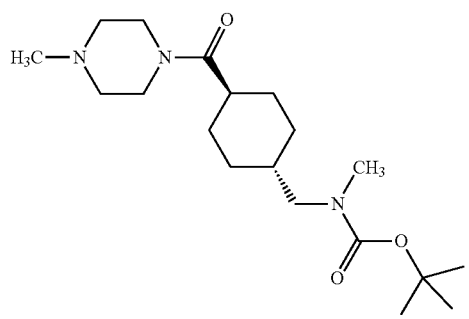
MN1434
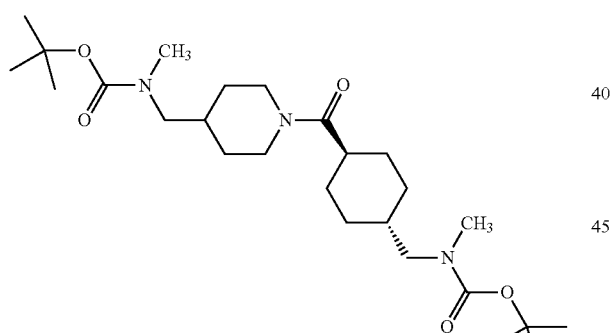
MN1435
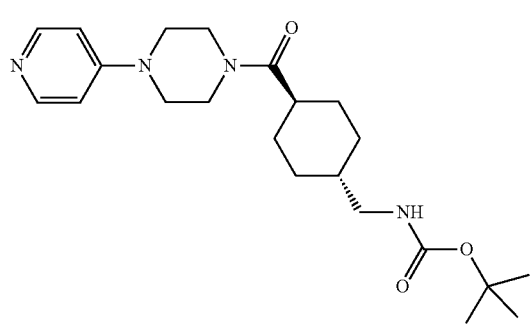
MN1436
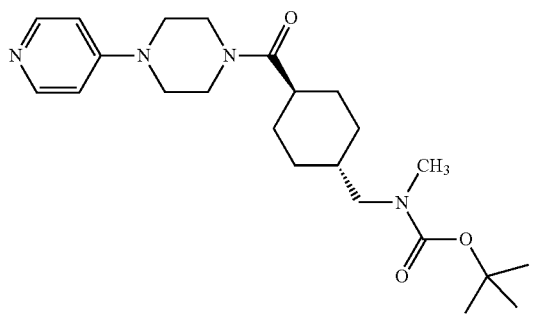
MN1437
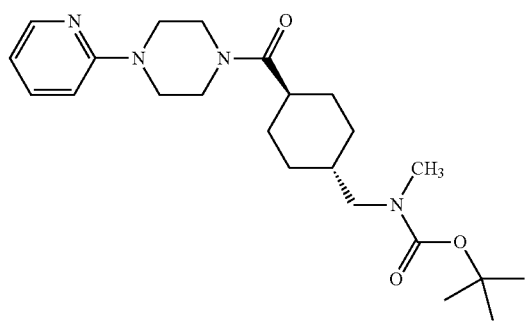
MN1438
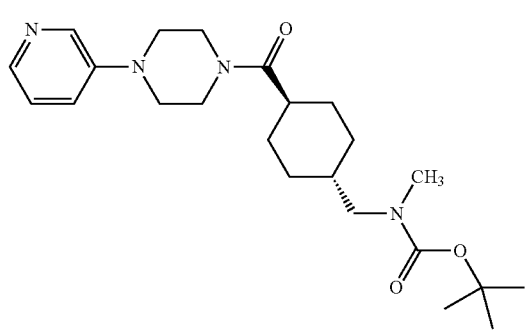
MN1439
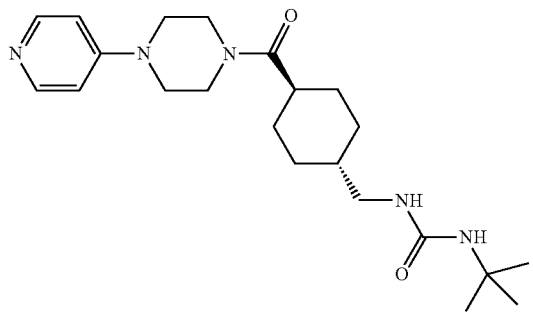

-continued
MN1440
MN1441
MN1442
MN1444
MN1445
MN1447
MN1448
MN1449
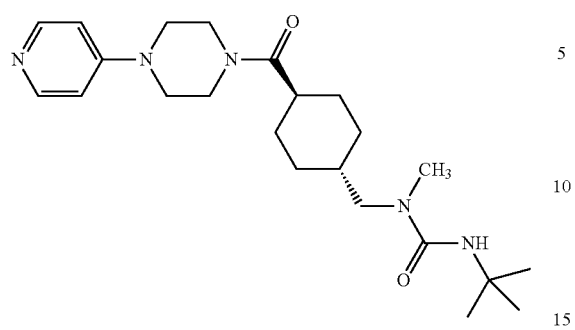
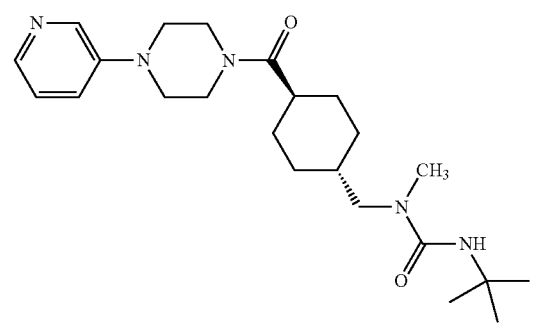

-continued
MN1450
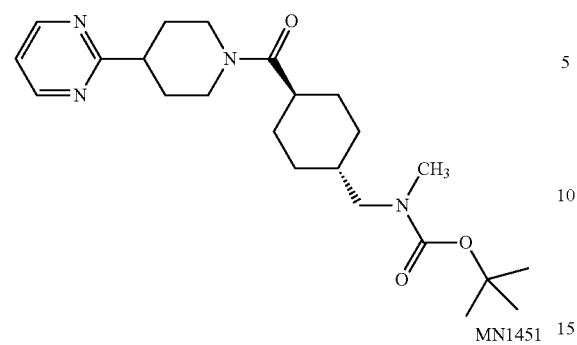
MN1451
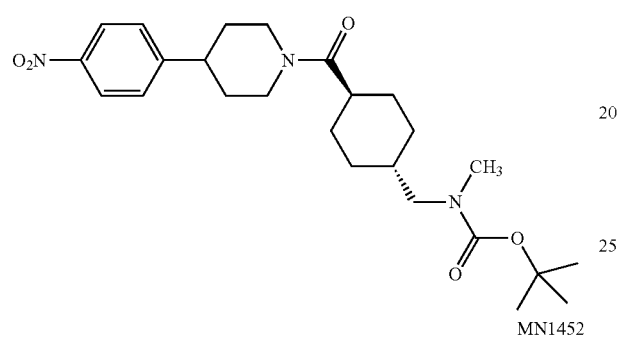
MN1452
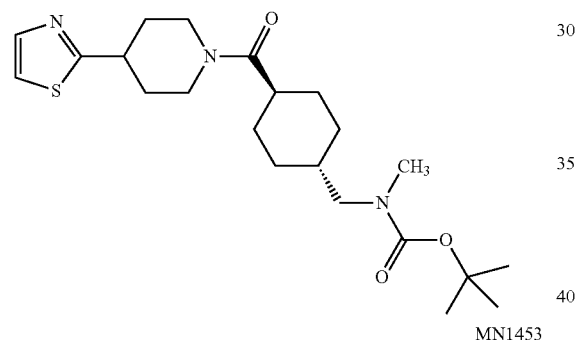
MN1453
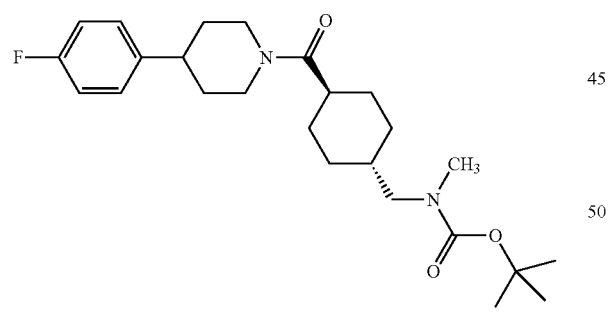
MN1454
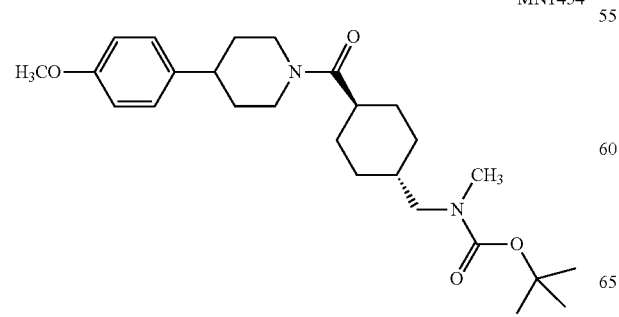
-continued
MN1455
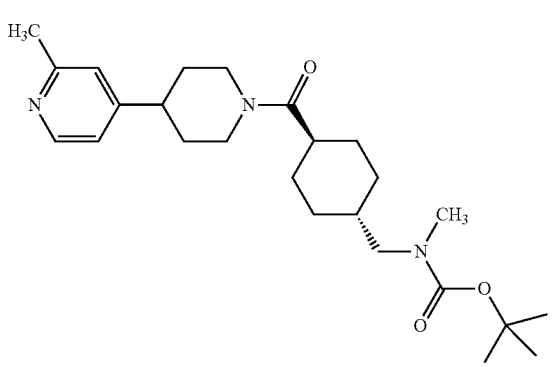
MN1456
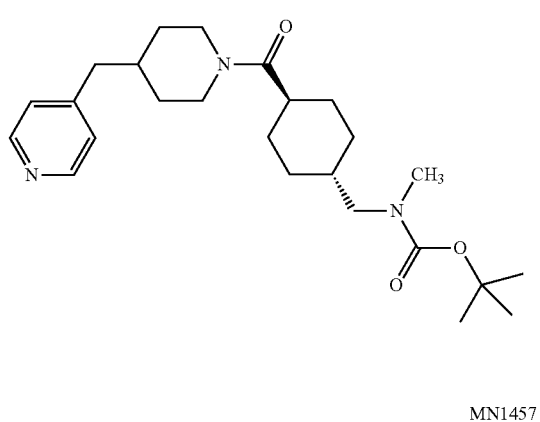
MN1457
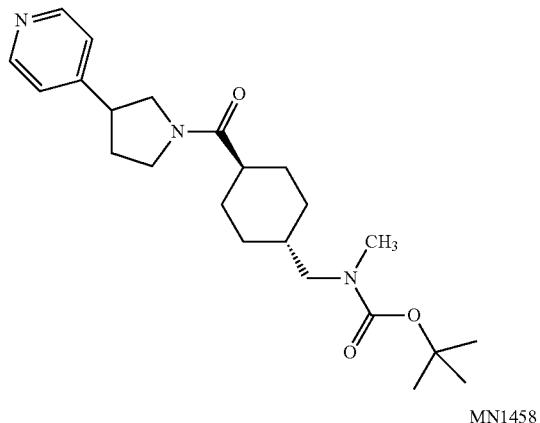
MN1458
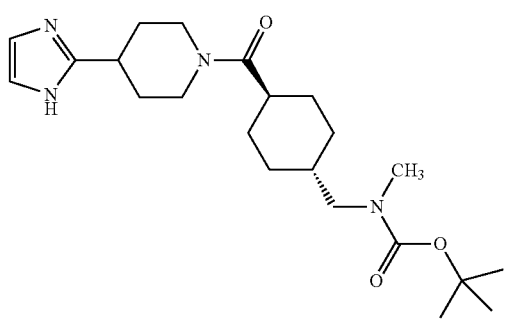

MN1459
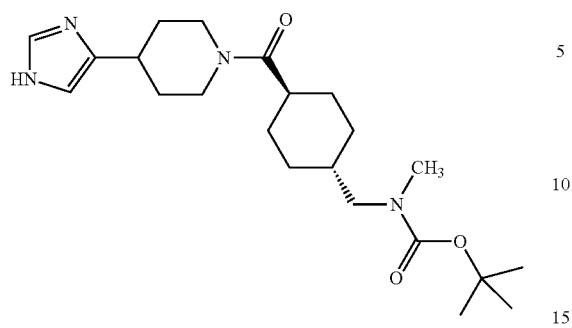
MN1460
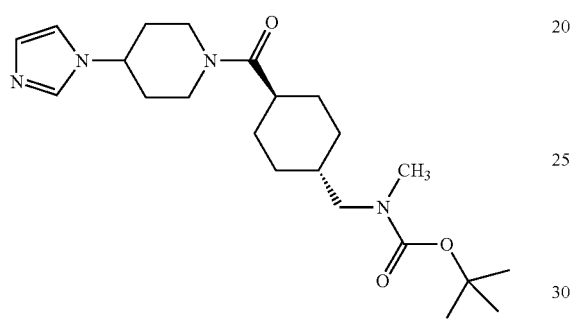
MN1461
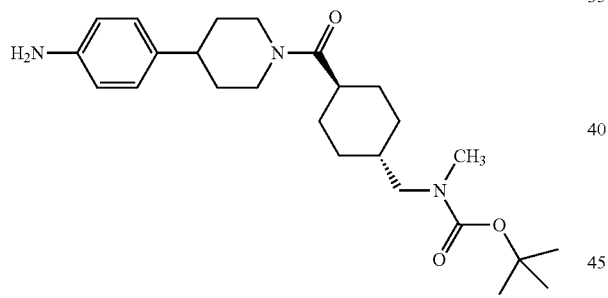
MN1462
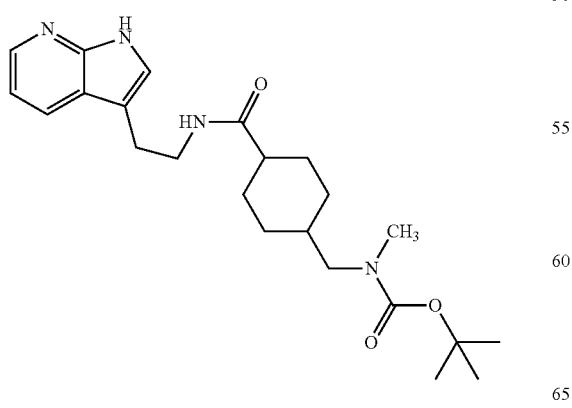
MN1463
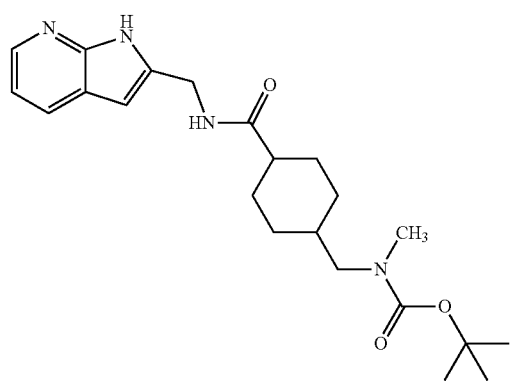
MN1464
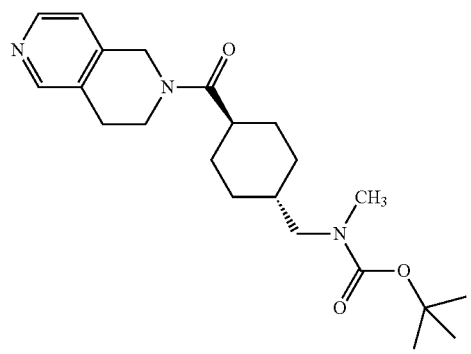
MN1465
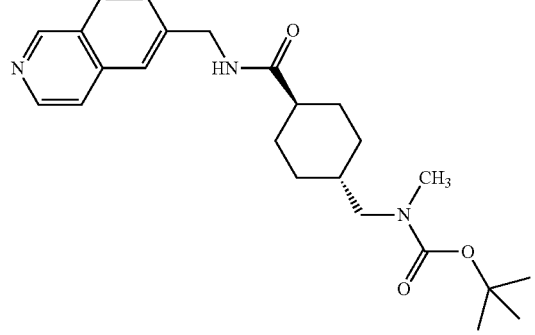
MN1466
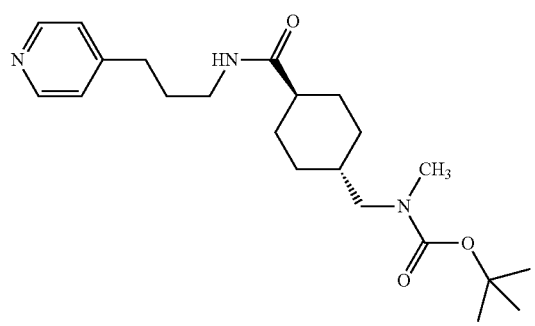

MN1467
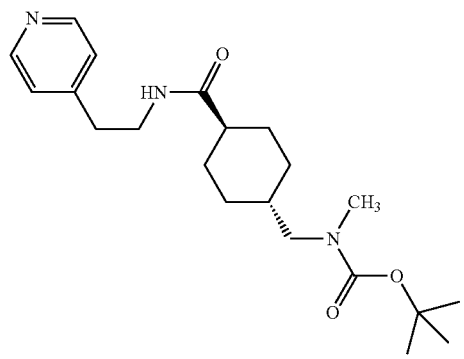
MN1468
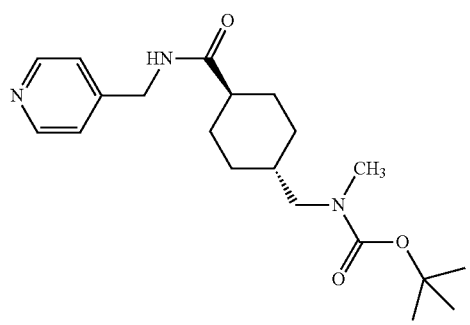
MN1469
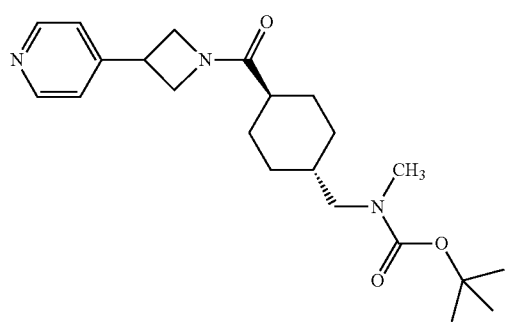
MN1470
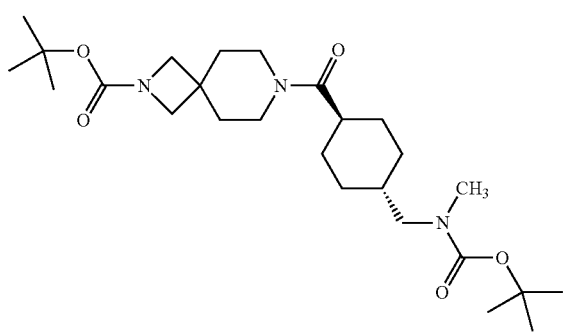
MN1354
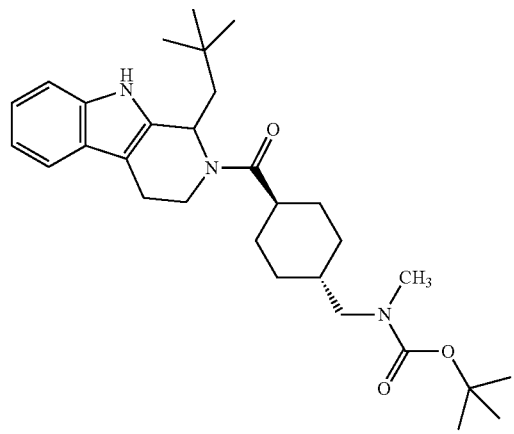
MN1386
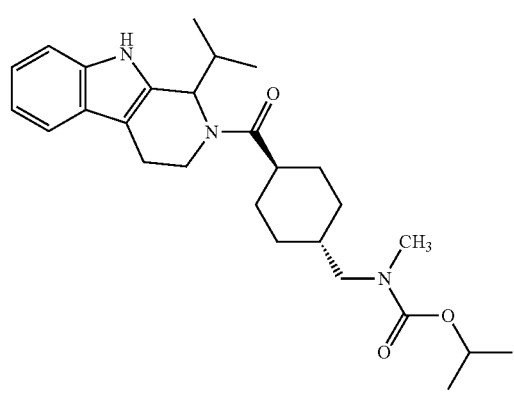
MN1387
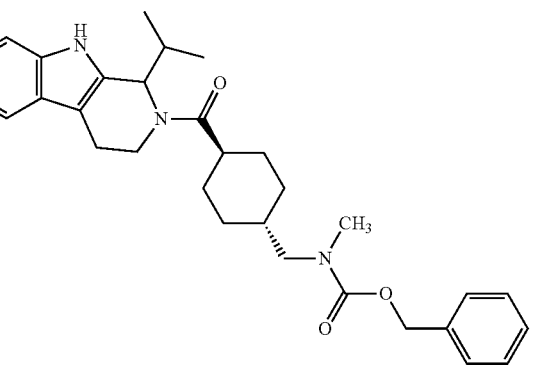
MN1388
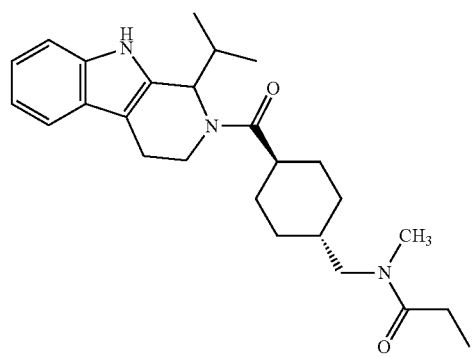

-continued
MN1389
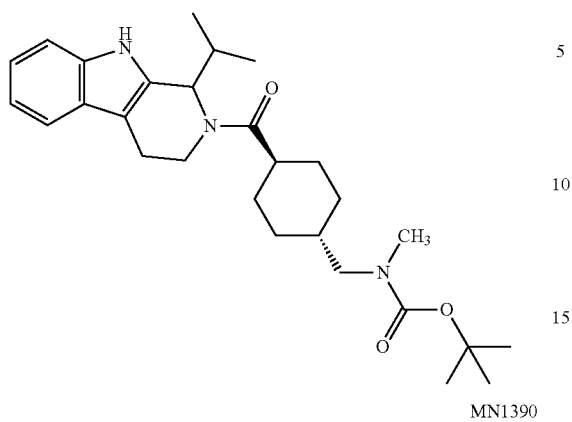
MN1390
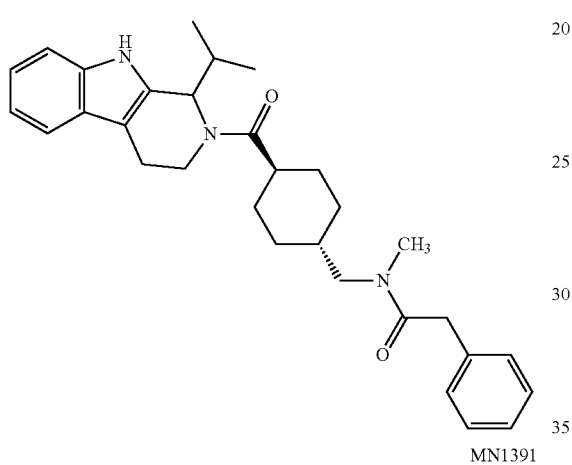
MN1391
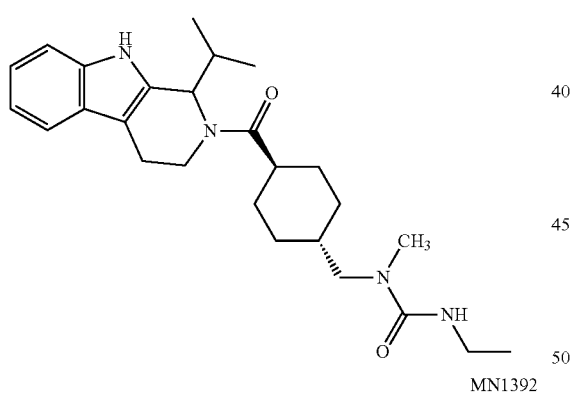
MN1392
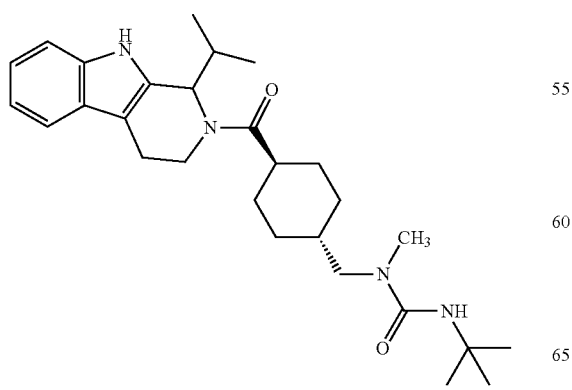
-continued
MN1393
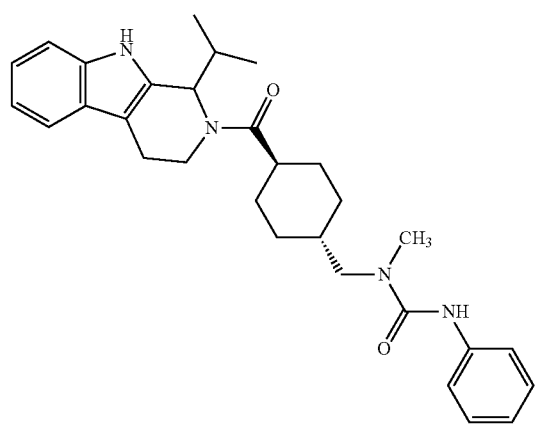
MN1394
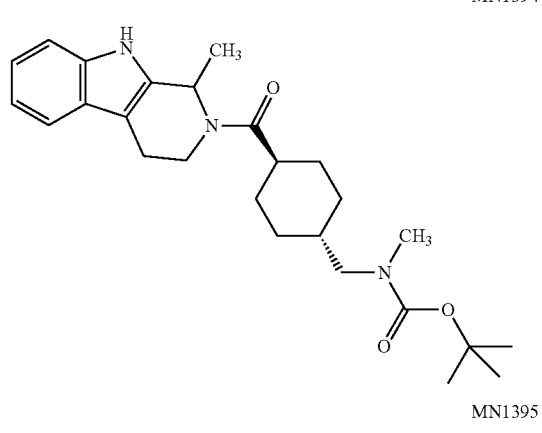
MN1395
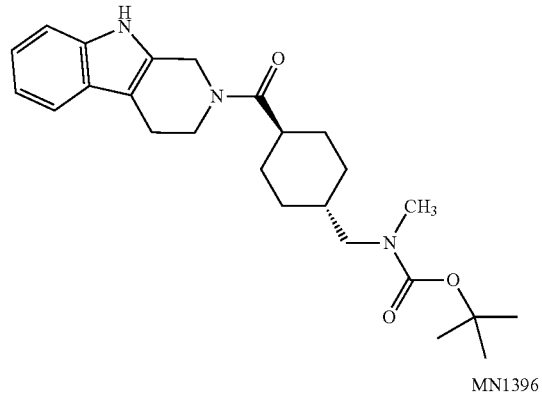
MN1396
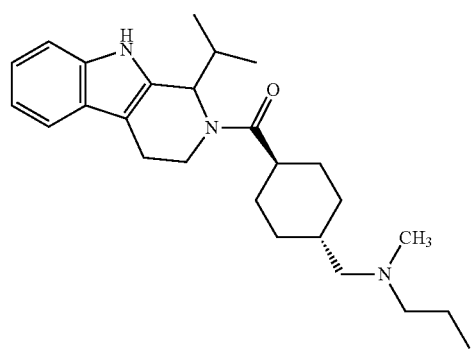

-continued
MN1397
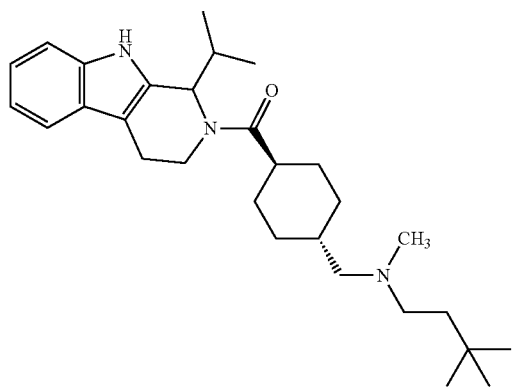
MN1398
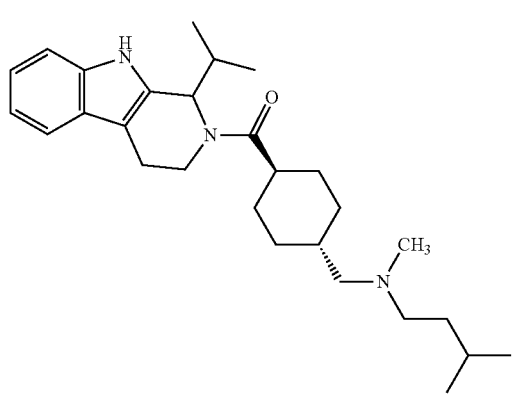
MN1399
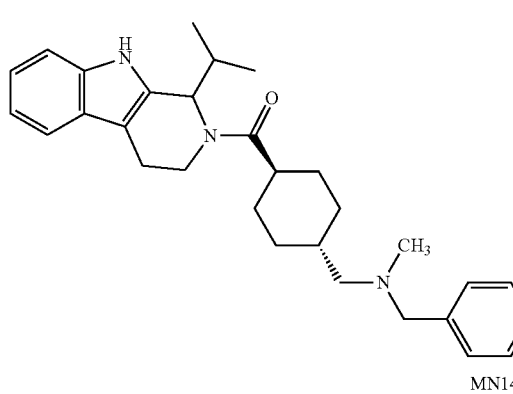
MN1400
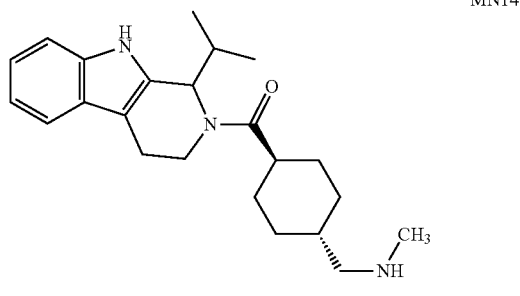
-continued
MN1401
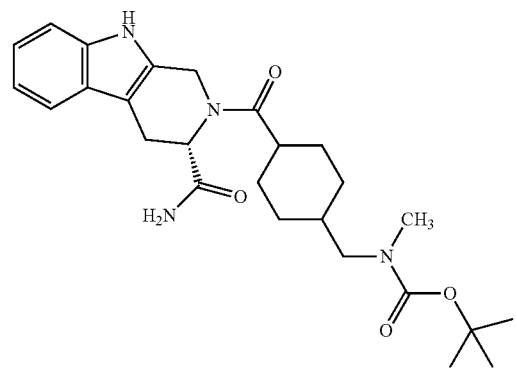
MN1402
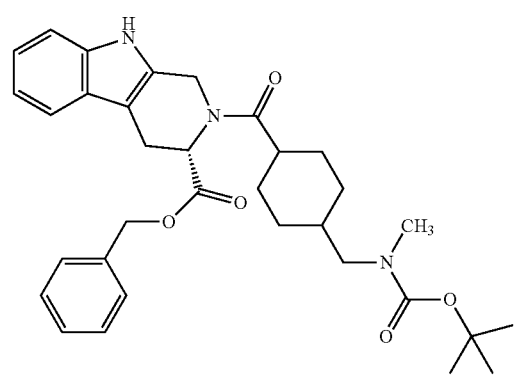
MN1403
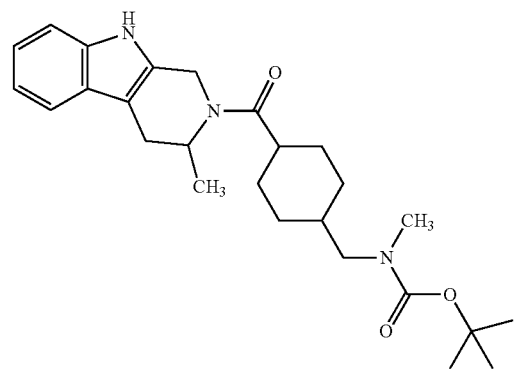
MN1409
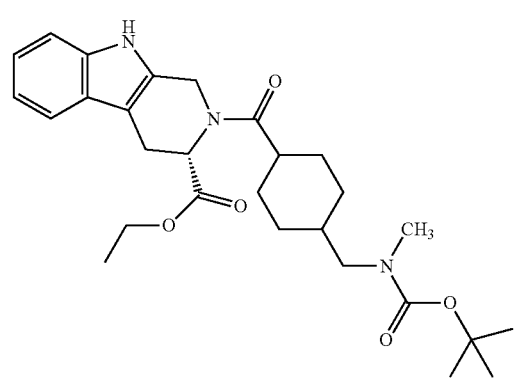

-continued
MN1410
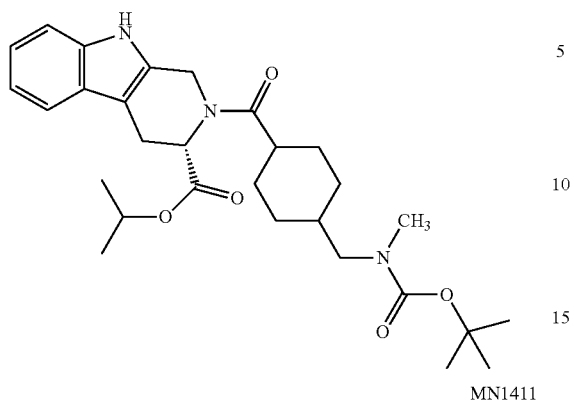
MN1411
MN1412
MN1413
MN1414
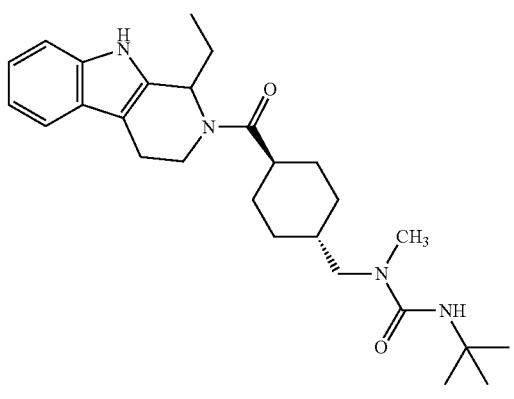
MN1415
MN1419
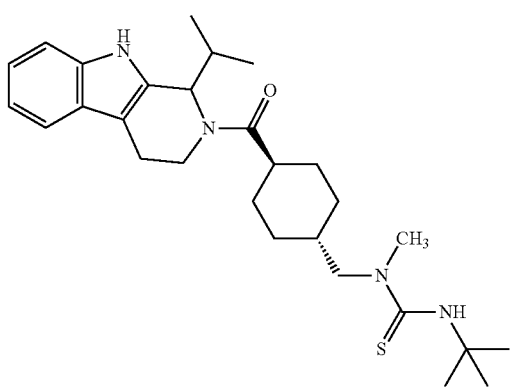
MN1422
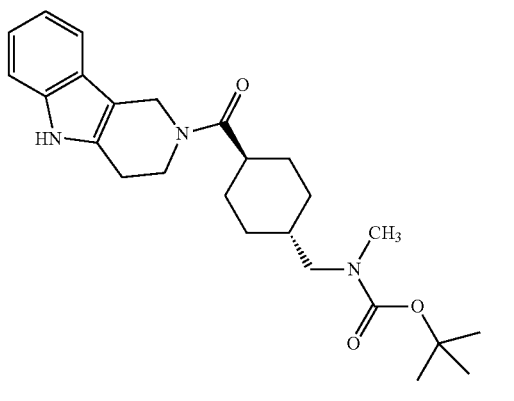
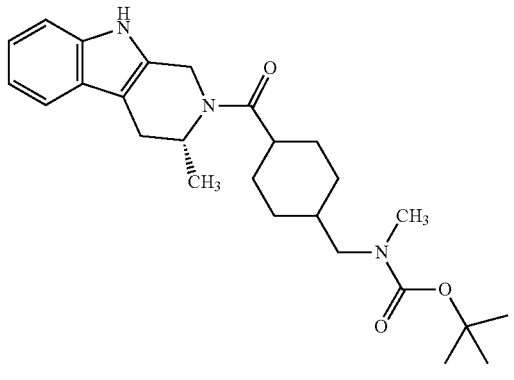

-continued

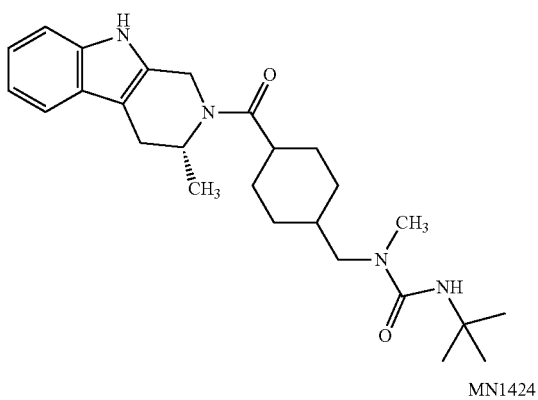
MN1423

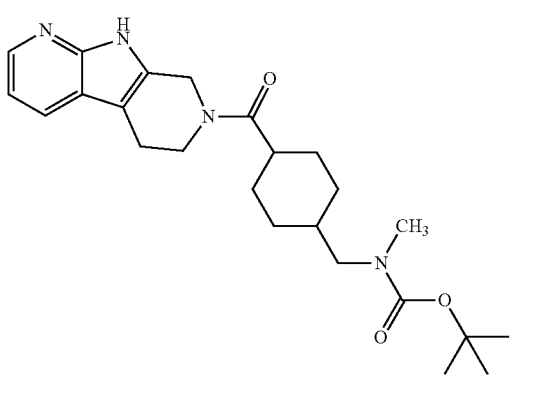
MN1424

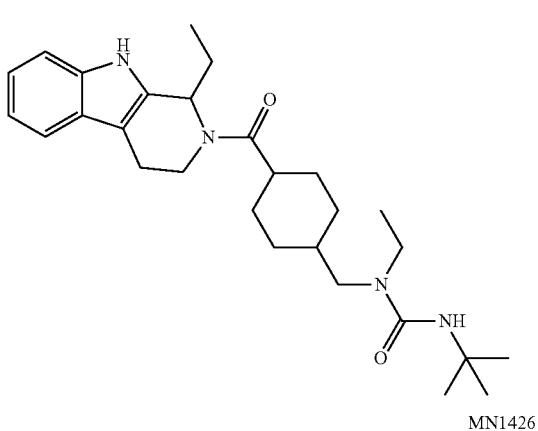
MN1425

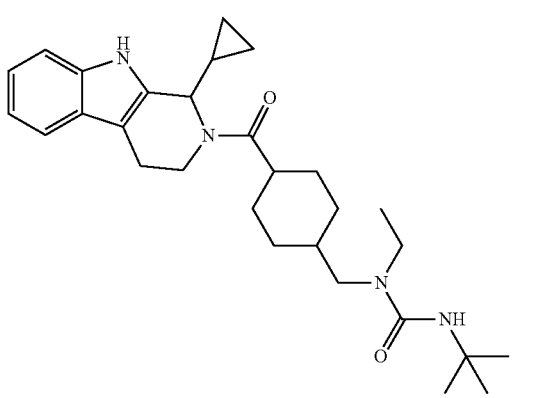
MN1426

-continued

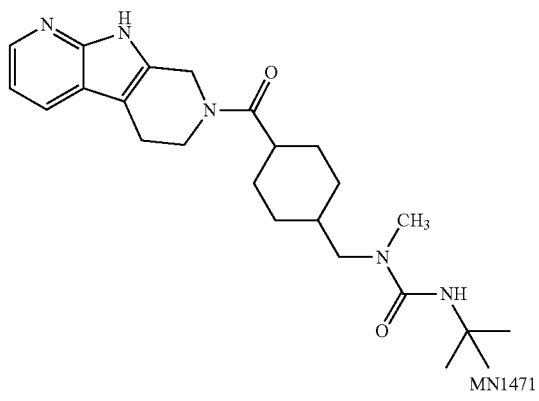
MN1443

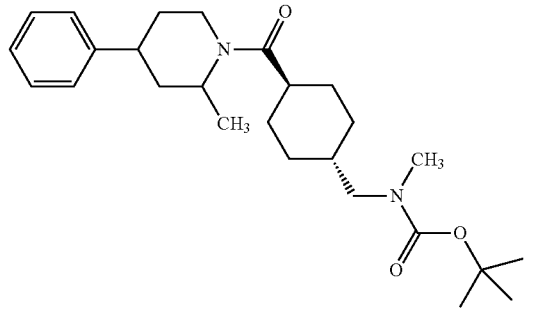
MN1471

Described herein are compounds for use in the treatment or prevention of cancer or cancer metastasis. In the context of the compounds described herein, the following definitions apply:

In the context of the present specification, unless otherwise stated, an "alkyl" substituent group or an alkyl moiety in a substituent group may be linear or branched, or be or include one or more cycloalkyl groups. Suitable alkyl groups include but are not limited to C1-C9 alkyl groups, C1-C6 alkyl groups, C1-C4 alkyl groups, and C1-C3 alkyl groups. Examples of alkyl groups/moieties include methyl, ethyl, n-propyl, i-propyl, n-butyl, i-butyl, t-butyl, n-pentyl, 2,4,4-trimethylpentyl, 2-methylcyclopentyl, cyclopentylmethyl and cycloalkyl groups/moieties as exemplified below. All alkyl groups, unless otherwise stated, may be substituted or unsubstituted.

"Alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —H(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$), —CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$—CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others.

"Halogen" or "halo" refers to chloro, bromo, fluoro, and iodo groups. The term "haloalkyl" refers to an alkyl radical substituted with one or more halogen atoms. The term "haloalkoxy" refers to an alkoxy radical substituted with one or more halogen atoms.

A "haloalkyl" substituent group or a haloalkyl moiety in a substituent group refers to an alkyl group or moiety in which one or more, e.g. one, two, three, four or five, hydrogen atoms are replaced independently by halogen atoms, i.e. by fluorine, chlorine, bromine or iodine atoms. Suitable haloalkyl groups include but are not limited to halo (C1-C3)alkyl, and halo(C1-C)alkyl. Examples of haloalkyl groups/moieties include fluoromethyl, difluoromethyl, trifluoromethyl and 2,2,2-trifluoroethyl.

A "cycloalkyl" substituent group or a cycloalkyl moiety in a substituent group refers to a saturated hydrocarbyl ring containing, for example, from 3 to 8 carbon atoms, examples of which include cyclopropyl, cyclobutyl, cyclopentyl and cyclohexyl. Unless stated otherwise, a cycloalkyl substituent group or moiety may include monocyclic, bicyclic (e.g. fused or spiro) and polycyclic hydrocarbyl rings. A "cycloalkyl" substituent group or a cycloalkyl moiety in a substituent group includes cyclopropyl, cyclobutyl, cyclopentyl and cyclohexyl.

A "heteroalkyl" substituent group or a heteroalkyl moiety in a substituent group refers to an alkyl group or moiety in which from 1 to 4 secondary or tertiary carbon atoms, including any secondary or tertiary carbon atoms through which the group or moiety is attached to the rest of the molecule, are replaced independently by heteroatoms selected from nitrogen, oxygen and sulphur in the case of secondary carbon atoms, or by nitrogen in the case of tertiary carbon atoms. Examples of heteroalkyl groups/moieties include methoxy, methylamino, methylsulphanyl, ethoxy, ethylamino, dimethylamino, ethylsulphanyl, propyloxy, methoxyethyl, propylamino, methylethylamino, propylsulphanyl, methyl sulphanylethyl, tetrahydropyranyloxy, N-methylpyrrolidinyl, and heterocycloalkyl groups/moieties as exemplified below.

A "heterocycloalkyl" substituent group or a heterocycloalkyl moiety in a substituent group refers to a cycloalkyl group or moiety in which from 1 to 4 secondary or tertiary carbon atoms, including any secondary or tertiary carbon atoms through which the group or moiety is attached to the rest of the molecule, are replaced independently by heteroatoms selected from nitrogen, oxygen and sulphur in the case of secondary carbon atoms, or by nitrogen in the case of tertiary carbon atoms. Examples of heterocycloalkyl groups/moieties include tetrahydrofuranyl, pyrrolidinyl, tetrahydrothiophenyl, tetrahydropyranyl, piperidinyl, piperazinyl, morpholinyl and thiomorpholinyl.

An "alkenyl" substituent group or an alkenyl moiety in a substituent group refers to an unsaturated alkyl group or moiety having one or more carbon-carbon double bonds. Suitable "alkenyl" group include but are not limited to C1-C9 alkenyl, C1-C6 alkenyl, C1-C4 alkenyl, and C1-C3 alkenyl. Examples of alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl, 1,4-hexadienyl and cycloalkenyl groups/moieties as exemplified below.

A "cycloalkenyl" substituent group or a cycloalkenyl moiety in a substituent group refers to an unsaturated hydrocarbyl ring having one or more carbon-carbon double bonds and containing, for example, from 3 to 8 carbon atoms, examples of which include cyclopent-1-en-1-yl, cyclohex-1-en-1-yl and cyclohex-1,3-dien-1-yl. Unless stated otherwise, a cycloalkenyl substituent group or moiety may include monocyclic, bicyclic (e.g. fused or spiro) and polycyclic hydrocarbyl rings.

A "heteroalkenyl" substituent group or a heteroalkenyl moiety in a substituent group refers to an alkenyl group or moiety in which from 1 to 4 secondary or tertiary carbon atoms, including any secondary or tertiary carbon atoms through which the group or moiety is attached to the rest of the molecule, are replaced independently by heteroatoms selected from nitrogen, oxygen and sulphur in the case of secondary carbon atoms, or by nitrogen in the case of tertiary carbon atoms. Examples of heteroalkenyl groups/moieties include ethenyloxy, ethenylamino, ethenylsulphanyl, ethenyloxyethyl and heterocycloalkenyl groups/moieties as exemplified below.

A "heterocycloalkenyl" substituent group or a heterocycloalkenyl moiety in a substituent group refers to a cycloalkenyl group or moiety in which from 1 to 4 secondary or tertiary carbon atoms, including any secondary or tertiary carbon atoms through which the group or moiety is attached to the rest of the molecule, are replaced independently by heteroatoms selected from nitrogen, oxygen and sulphur in the case of secondary carbon atoms, or by nitrogen in the case of tertiary carbon atoms. Examples of heterocycloalkenyl groups/moieties include dihydropyranyl and dihydrofuranyl.

An "alkynyl" substituent group or an alkynyl moiety in a substituent group refers to an unsaturated alkyl group or moiety having one or more carbon-carbon triple bonds. Examples of alkynyl groups/moieties include ethynyl, propargyl, but-1-ynyl and but-2-ynyl.

A "heteroalkynyl" substituent group or a heteroalkynyl moiety in a substituent group refers to an alkynyl group or moiety in which from 1 to 4 secondary or tertiary carbon atoms, including any secondary or tertiary carbon atoms through which the group or moiety is attached to the rest of the molecule, are replaced independently by heteroatoms selected from nitrogen, oxygen and sulphur in the case of secondary carbon atoms, or by nitrogen in the case of tertiary carbon atoms. Examples of heteroalkynyl groups/moieties include ethynyloxy and propargylamino.

An "aryl" substituent group or an aryl moiety in a substituent group includes monocyclic aromatic hydrocarbons and polycyclic fused ring aromatic hydrocarbons. Examples of aryl groups/moieties include phenyl, naphthyl, anthracenyl and phenanthrenyl.

A "heteroaryl" substituent group or a heteroaryl moiety in a substituent group includes monocyclic aromatic and polycyclic fused ring aromatic groups in which from 1 to 4 ring atoms are independently selected from nitrogen, oxygen and sulphur, with the remainder of the ring atoms being carbon. Examples of heteroaryl groups/moieties include the following:

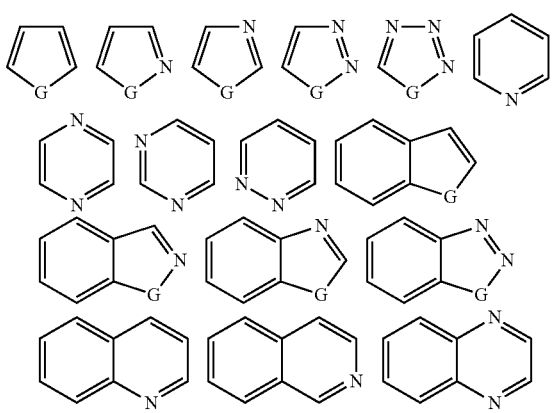

For the purposes of the present invention, where a combination of moieties is referred to as one group, for example, arylalkyl, arylalkenyl, arylalkynyl, alkylaryl, alkenylaryl or alkynylaryl, the last mentioned moiety contains the atom by which the group is attached to the rest of the molecule. An example of an arylalkyl group is benzyl. An example of cycloalkylalkyl is cyclopropylmethyl.

Where the prefix "hetero" is used in relation to a combination of moieties referred to as one group, for example "hetero(arylalkyl)", any or all of the moieties within the combination may be a hetero moiety. Thus, the term "hetero (arylalkyl)" encompasses heteroaryl-alkyl, aryl-heteroalkyl and heteroaryl-heteroalkyl. Examples of hetero(arylalkyl) groups/moieties include pyridinylmethyl, phenoxy, N-anilinyl and pyridinyloxyethyl.

Where it is stated that a group may be substituted, the group may be substituted by, for example, one or more independently selected from halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H In one aspect, the invention discloses compounds of Formula 1:

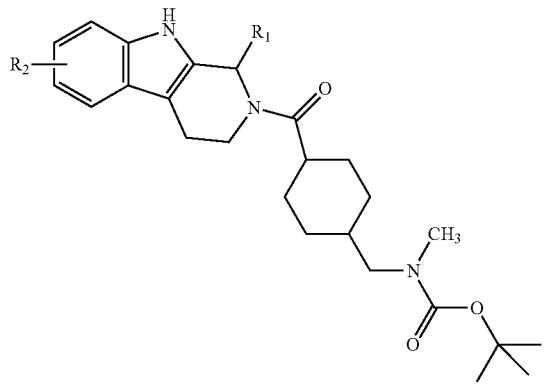

R1 is H, optionally substituted C1-C6 alkyl; optionally substituted C3-C4 cycloalkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

R2 is hydrogen, C1-C6 alkoxy such as but not limited to methoxy or ethoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —OCH$_3$, —OC$_2$H$_5$, —O—C1-C4 alkyl, —SH, —NH$_2$, —N$_3$, —CN, —NO$_2$, —CHO, —COOH, —CONH$_2$, —C(=NH) NH$_2$, or —SO$_3$H.

In one embodiment, R1 can be C2-C4 alkyl, or C3-C4 cycloalkyl.

In one embodiment, R1 can be methyl.

In one embodiment, R1 can be ethyl, isopropyl, cyclopropyl, or isobutyl.

In one embodiment, R1 can be ethyl, isopropyl, or cyclopropyl.

In one embodiment, R2 can be H, halogen or methyl.

In one embodiment, R2 can be H, F, Cl, or Me.

In one embodiment, R2 is H.

In one embodiment, R1 is ethyl, isopropyl, cyclopropyl, or isobutyl, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is ethyl, isopropyl, cyclopropyl, or isobutyl, R2 is hydrogen, halogen, trifluoromethyl, methylcarboxy, ethylcarboxy, C1-C6 alkoxy such as but not limited to methoxy and ethoxy, C1-C6 alkyl, —OH, —NH$_2$, —CN, —CHO, —COOH, or —CONH$_2$.

In another embodiment, R1 is ethyl, or isopropyl, or cyclopropyl and R2 is hydrogen, halogen, trifluoromethyl, methylcarboxy, ethylcarboxy, C1-C6 alkoxy such as but not limited to methoxy and ethoxy, or C1-C6 alkyl.

In one aspect, the invention discloses compounds of Formula 2:

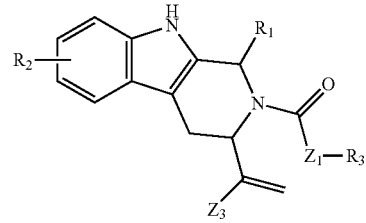

R1 is H, optionally substituted C1-C6 alkyl; optionally substituted C2-C$_6$ alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

R2 is H, C1-C6 alkoxy such as but not limited to methoxy or ethoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

Z1 is a bond, —NH—, —O—, —S—, —CH(CH$_3$)—, —(CH$_2$)$_n$—, —C3-C7 cycloalkyl-CH$_2$—, —CH=CH—, —CO—, —SO—, —SO$_2$— or —C(=NH)—, —CH$_2$NH(CO)—, —CH$_2$NH(CO) O—, —CH$_2$NH(CO)NH—; —(CH$_2$)$_n$NH(CO)—, —(CH$_2$)$_n$NH(CO)O—, —(CH$_2$)$_m$NH(CO)NH—; —C3-C7 cycloalkyl- CH$_2$NH(CO)—, —C3-C7 cycloalkyl-CH$_2$NCH3(CO)—, —C3-C7 cycloalkyl-CH$_2$NH(CO)O—, —C3-C7 cycloalkyl-CH$_2$NCH3 (CO)O—, —C3-C7 cycloalkyl-CH$_2$NH(CO)NH—, —C3-C7 cycloalkyl-CH₂NCH3(CO)NH—, —(CH₂)ₙN(CH₂CH₂C₆H₅)—, or optionally substituted C6-C12 aryl;

Z3 is —OH, —OCH₃, —O—C1-C6 alkyl, —O—CH₂C6H5, —NH₂, —NH(C1-C6 alkyl), —N(C1-C6 alkyl)₂, —C1-C6 alkyl;

R3 is H, optionally substituted C1-C9 alkyl, C2-C₆ alkenyl; optionally substituted C6-C12 aryl, optionally substituted C1-C9 heteroaryl with 1 to 4 ring atoms independently selected from N, S, and O; optionally substituted C7-C15 arylalkyl such as but not limited to benzyl or alpha-methylbenzyl; or an optionally substituted C3-C7 cycloalkyl; —(CH₂)ₙ—NH(CO)O—(C1-C6 alkyl); —CH₂O(CH₂)ₚ—NH(CO)O—(C1-C₆) alkyl; —(CH₂)ₚ—NHCO—(CH₂)ₘ—NH(CO)O—C1-C6 alkyl); —NH(CO)O-tert-butyl; —O-tert-butyl; or -tert-butyl; CONH-aryl;

m=1-5; n=1-8; p=1-9;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —OCH3, —OC2H5, —O—C1-C4 alkyl, —SH, —NH₂, —N₃, —CN, —NO₂, —CHO, —COOH, —CONH₂, —C(=NH)NH₂, or —SO₃H.

In one embodiment, R1 can be H, C1-C4 alkyl (e.g. methyl, ethyl, isopropyl, isobutyl), phenyl, phenyl substituted with halogen, methylcarboxy, methoxy, ethoxy, methyl; heteroaryl, pyridyl, benzyl or alpha-methylbenzyl.

In one embodiment, R1 can be H or C2-C4 alkyl.

In one embodiment, R1 is H.

In one embodiment, R2 can be H, halogen, methyl or methoxy.

In one embodiment, Z1 can be a bond, —NH—, —CH2-, —(CH2)2-, —(CH2)3-, —CH=CH—, substituted phenyl, —CH2NH(CO)O—, —(CH2)2NH(CO)O—, —(CH2)3NH(CO)O—, —(CH2)4NH(CO)O—, —(CH2)5NH(CO)O—, —CH2NH(CO)—, —CH(CH3)NH(CO)O—, —CH2NH(CO)NH—, —CH2NH(CO)CH2NH(CO)O—, —CH2O(CH2)2NH(CO)O— or -cyclohexyl-CH2NH(CO)O—.

In one embodiment, Z3 can be —OH, —OCH3, —O—C1-C6 alkyl, —NH2, —N(C1-C6 alkyl)2, or —C1-C6 alkyl.

In one embodiment, R3 can be ethyl, butyl, isobutyl, pentyl, 2,4,4-trimethylpentyl, heptyl, octyl, phenyl, phenyl substituted with methyl, ethyl, halogen, ethoxy or methoxy.

In one embodiment, R1 is isobutyl, and R3 is —NH(CO)O-tert-butyl, R2 can be hydrogen, halogen, trifluoromethyl, methylcarboxy, ethylcarboxy, methoxy, ethoxy, C1-C6 alkoxy, C1-C6 alkyl, —OH, —SH, —NH₂, —N₃, —CN, —NO₂, —CHO, —COOH, —CONH₂, —C(=NH)NH₂, or —SO₃H.

In another embodiment, R1 is isobutyl, Z1 is cyclohexylmethyl, R3 is —NH(CO)O-tert-butyl, R2 can be hydrogen, halogen, trifluoromethyl, methylcarboxy, ethylcarboxy, C1-C6 alkoxy such as but not limited to methoxy and ethoxy, C1-C6 alkyl, —OH, —SH, —NH₂, —N₃, —CN, —NO₂, —CHO, —COOH, —CONH₂, —C(=NH)NH₂, or —SO₃H.

In one embodiment, R1 is isobutyl, Z1 is C1-C5 alkyl, R3 is —NH(CO)O-tert-butyl or —NH(CO)CH₂-isopropyl, R2 can be hydrogen, halogen, trifluoromethyl, methylcarboxy, ethylcarboxy, C1-C6 alkoxy such as but not limited to methoxy and ethoxy, C1-C6 alkyl, —OH, —SH, —NH₂, —N₃, —CN, —NO₂, —CHO, —COOH, —CONH₂, —C(=NH)NH₂, or —SO₃H.

In one embodiment, R1 is isobutyl, R3 is —NH(CO)O-tert-butyl, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH₂, —N₃, —CN, —NO₂, —CHO, —COOH, —CONH₂, —C(=NH)NH₂, or —SO₃H.

In one embodiment, R1 is ethyl, isobutyl, isopropyl, benzyl, Z1 is (CH2)₄₋₉—, R3 is —NH(CO)O-tert-butyl, R2 is hydrogen, halogen, trifluoromethyl, methylcarboxy, ethylcarboxy, methoxy, ethoxy, C1-C6 alkoxy, C1-C6 alkyl, —OH, —SH, —NH₂, —N₃, —CN, —NO₂, —CHO, —COOH, —CONH₂, —C(=NH)NH₂, or —SO₃H.

In one embodiment, Z1 is (CH2)₄₋₉—, R3 is —NH(CO)O-tert-butyl, R2 can be hydrogen, R1 is a phenyl ring substituted with hydrogen, halogen, trifluoromethyl, methylcarboxy, ethylcarboxy, C1-C6 alkoxy such as but not limited to methoxy and ethoxy, C1-C6 alkyl, —OH, —SH, —NH₂, —N₃, —CN, —NO₂, —CHO, —COOH, —CONH₂, —C(=NH)NH₂, or —SO₃H.

In one embodiment, Z1 cyclohexylmethyl or a C3-C7 cycloalkyl-CH2- group, R3 is —NH(CO)O-tert-butyl, R1 is isobutyl, R2 is halogen, methyl, or methoxy.

In one aspect, the invention discloses compounds of Formula 3:

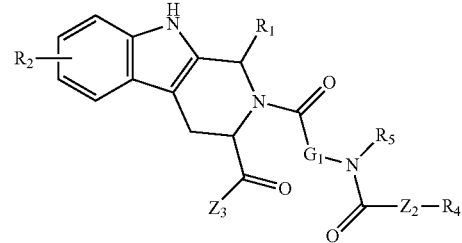

R1 is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; an optionally substituted unsubstituted C3-C8 cycloalkyl; or optionally substituted C4-C8 cycloalkylalkyl;

R2 is hydrogen, C1-C6 alkoxy such as but not limited to methoxy or ethoxy, trifluoromethyl, halogen, methylcarboxy, ethylcarboxy, optionally substituted C1-C6 alkyl, —OH, —SH, —NH₂, —N₃, —CN, —NO₂, —CHO, —COOH, —CONH₂, —C(=NH)NH₂, or —SO₃H;

G1 is a bond, —NH—, —O—, —S—, —CH(CH₃)—, —(CH₂)ₙ—, —C3-C7 cycloalkyl-, —C3-C7 cycloalkyl-CH2-, —CH=CH—, —CO—, —SO—, —SO₂— or —C(=NH)—, —CH₂NH(CO)—, —CH₂NH(CO)O—, —CH₂NH(CO)NH—; —(CH₂)ₙNH(CO)—, —(CH₂)ₙNH(CO) O—(CH₂)ₘNH(CO)NH—; —C3-C7 cycloalkyl-NH(CO)—, —C3-C7 cycloalkyl-CH₂NH(CO)O—, —C3-C7 cycloalkyl-NH(CO) NH—, —N(CH₂CH₂C₆H₅)—, —C3-C7 cycloalkyl-CH₂— such as but not limited to -cyclohexyl-CH₂—;

Z2 is a bond, —NH—, —O—, —S—, —CH(CH₃)—, —(CH₂)ₙ—, —CH=CH—, —CO—, —SO—,

—SO$_2$— or —C(=NH)—, —CH$_2$NH(CO)—, —CH$_2$NH(CO)O—, —CH$_2$NH(CO)NH—; —(CH$_2$)$_p$NH(CO)—, —(CH$_2$)$_p$NH(CO)O—, —(CH$_2$)$_p$NH(CO)NH—; —C3-C7 cycloalkyl-NH(CO)—, —C3-C7 cycloalkyl-NCH3(CO)—, —C3-C7 cycloalkyl-CH$_2$NH(CO)O—, —C3-C7 cycloalkyl-CH$_2$NCH3(CO)O—, —C3-C7 cycloalkyl-NH(CO)NH—, —C3-C7 cycloalkyl-NCH3(CO)NH—, —N(CH$_2$CH$_2$C$_6$H$_5$)—; or optionally substituted C6-C12 aryl;

Z3 is —OH, —OCH3, —O—C1-C6 alkyl, —O—CH2C6H5, —NH$_2$, —NH(C1-C6 alkyl), —N(C1-C6 alkyl)$_2$, —C1-C6 alkyl;

R5 is H, methyl, or optionally substituted C1-C6 alkyl;

R4 is H, optionally substituted C1-C9 alkyl such as but not limited to tert-butyl; optionally substituted C2-C6 alkenyl; optionally substituted C6-C12 aryl such as but not limited to optionally substituted naphthyl; optionally substituted C1-C9 heteroaryl with 1 to 4 ring atoms independently selected from N, S, and O; optionally substituted C7-C15 arylalkyl such as but not limited to benzyl or alpha-methylbenzyl; an optionally substituted C3-C7 cycloalkyl; —(CH$_2$)$_p$—NH(CO)O—(C1-C6 alkyl); —CH$_2$O(CH$_2$)$_p$—NH(CO)O—(C1-C6) alkyl; —(CH$_2$)$_p$—NHCO—(CH$_2$)$_n$—NH(CO)O—C1-C6 alkyl); —NH(CO)O-tert-butyl; or —O-tert-butyl; m=1-5; n=1-8; p=1-9;

where "substituted" means substituted with one or more independently selected from halogen, trifluoromethyl, methylcarboxy, ethylcarboxy, C1-C6 alkoxy such as but not limited to methoxy and ethoxy, C1-C6 alkyl, —OH, —OCH3, —OC2H5, —O—C1-C4 alkyl, —SH, —NH$_2$, —N$_3$, —CN, —NO$_2$, —CHO, —COOH, —CONH$_2$, —C(=NH)NH$_2$, or —SO$_3$H.

In one embodiment, R1 can be hydrogen, C1-C4 alkyl (e.g. methyl, ethyl, isopropyl, isobutyl), benzyl, heteroaryl such as pyridyl, phenyl, and phenyl substituted with halogen, trifluoromethyl, methoxy, cyano or dialkylamino.

In one embodiment, R1 can be H or C1-C4 alkyl.

In one embodiment, R1 is H.

In one embodiment, R2 can be hydrogen, halogen, methyl or methoxy.

In one embodiment, R2 is H.

In one embodiment, Z2 can be O, NH, —CH2-, —(CH2)2-, —(CH2)3-, —(CH2)4-, —(CH2)5-, —CH(CH3)-, —CH2NH(CO)CH2-, —CH2O(CH2)2-, -cyclohexyl-CH2- or a bond.

In one embodiment, Z2 is O.

In one embodiment, Z3 can be —OH, —OCH3, —O—C1-C6 alkyl, —NH2, —N(C1-C6 alkyl)2, or —C1-C6 alkyl.

In one embodiment, G1 is —(CH2)-, —(CH2)2-, —(CH2)3-, —(CH2)4-, —(CH2)5-, —CH2OCH2CH2-, —CH(CH3)-, —CH2NHCOCH2- or -cyclohexyl-CH2-.

In one embodiment, G1 is -cyclohexyl-CH2-.

In one embodiment, R5 can be hydrogen, methyl or 2-phenylethyl.

In one embodiment, R5 is methyl.

In one embodiment, R4 can be optionally substituted phenyl, naphthyl, benzyl, substituted isopropyl or t-butyl.

In one embodiment, R4 can be C4 alkyl, e.g. t-butyl.

In one embodiment, Z2 and R4 taken together are —O—C1-C4 alkyl, such as —O—C4 alkyl, e.g. —O-t-butyl.

In one embodiment, R1 is isobutyl, R5 is hydrogen, Z2 is oxygen and R4 is tert-butyl, G1 has no oxygens, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl, R5 is hydrogen, Z2 is oxygen, R4 is tert-butyl, G1 is cyclohexylmethyl, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl, R5 is hydrogen, Z2 is oxygen or CH2, R4 is tert-butyl or isopropyl, G1 is C1-C5 alkylene, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment R1, is isobutyl, R5 is hydrogen, Z2 is oxygen, R4 is tert-butyl, and R2 can be hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, R1 is ethyl, isobutyl, isopropyl, or benzyl, R5 is hydrogen, Z2 is oxygen, R4 is tert-butyl, G1 is (CH2)$_{4-9}$—, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, R5 is hydrogen, Z2 is oxygen, R4 is tert-butyl, G1 is (CH2)$_{4-9}$—, R2 is hydrogen, R1 is a phenyl ring substituted with hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R5 is hydrogen, Z2 is oxygen, R4 is tert-butyl, R1 is isobutyl, R2 is halogen, methyl, or methoxy, G1 is cyclohexylmethyl or C3-C7 cycloalkyl-CH2- group.

In one aspect, the invention discloses compounds of Formula 4:

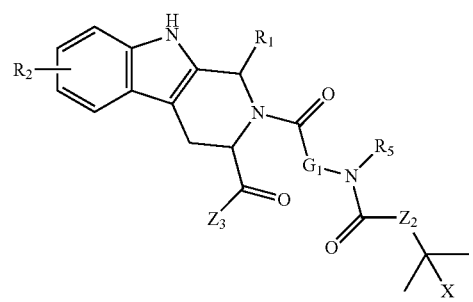

R1 is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

R2 is hydrogen, C1-C6 alkoxy such as but not limited to methoxy or ethoxy, trifluoromethyl, halogen, methylcarboxy, ethylcarboxy, optionally substituted C1-C6 alkyl, —OH, —SH, —$NH_2$, —$N_3$, —CN, —$NO_2$, —CHO, —COOH, —$CONH_2$, —C(=NH)$NH_2$, or —$SO_3H$;

G1 is a bond, —NH—, —O—, —S—, —CH($CH_3$)—, —$(CH_2)_n$—, —C3-C7 cycloalkyl-, —C3-C7 cycloalkyl-CH2-, —CH=CH—, —CO—, —SO—, —$SO_2$— or —C(=NH)—, —$CH_2$NH(CO)—, —$CH_2$NH(CO)O—, —$CH_2$NH(CO)NH—; —$(CH_2)_n$NH(CO)—, —$(CH_2)_n$NH(CO)O—, —$(CH_2)_m$NH(CO)NH—; —C3-C7 cycloalkyl-NH(CO)—, —C3-C7 cycloalkyl-CH2NH(CO)O—, —C3-C7 cycloalkyl-NH(CO)NH—, —N($CH_2CH_2C_6H_5$)—, —C3-C7 cycloalkyl-$CH_2$— such as but not limited to -cyclohexyl-CH2-;

Z2 is a bond, —NH—, —O—, —S—, —CH($CH_3$)—, —$(CH_2)_n$—; —CH=CH—, —CO—, —SO—, —$SO_2$— or —C(=NH)—, —$CH_2$NH(CO)—, —$CH_2$NH(CO)O—, —$CH_2$NH(CO)NH—; —$(CH_2)_p$NH(CO)—, —$(CH_2)_p$NH(CO)O—, —$(CH_2)_p$NH(CO)NH—; —C3-C7 cycloalkyl-NH(CO)—, —C3-C7 cycloalkyl-$CH_2$NH(CO)O—, —C3-C7 cycloalkyl-NH(CO)NH—, or —N($CH_2CH_2C_6H_5$)—;

Z3 is —OH, —OCH3, —O—C1-C6 alkyl, —$OCH_2C_6H_5$, —$NH_2$, —NH(C1-C6 alkyl), —N(C1-C6 alkyl)2, —C1-C6 alkyl;

R5 is H, methyl, or optionally substituted C1-C6 alkyl;

X is H, C1-C3 alkyl, or C1-C3 arylalkyl;

m=1-5; n=1-8; p=1-9;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —OCH3, —$OC_2H_5$, —O—C1-C4 alkyl, —SH, —$NH_2$, —$N_3$, —CN, —$NO_2$, —CHO, —COOH, —$CONH_2$, —C(=NH)$NH_2$, or —$SO_3H$.

In one embodiment, R1 can be hydrogen, methyl, ethyl, isopropyl, isobutyl, benzyl, heteroaryl such as pyridyl, phenyl and phenyl substituted with halogen, methyl, trifluoromethyl, methoxy, cyano, or dialkylamino.

In one embodiment, R1 can be H or C1-C4 alkyl.

In one embodiment, R1 is H

In one embodiment, R2 can be hydrogen, halogen, methyl or methoxy.

In one embodiment, R is H.

In one embodiment, G1 can be —(CH2)-, —(CH2)2-, —(CH2)3-, —(CH2)4-, —(CH2)5-, —CH2OCH2CH2-, —CH(CH3)-, —CH2NHCOCH2-, —CH2O(CH2)2-, -cyclohexyl-CH2- or a bond.

In one embodiment, G1 is -cyclohexyl-CH2-.

In one embodiment, Z2 can be O, NH, —CH2- or a bond.

In one embodiment, Z2 is O.

In one embodiment, Z3 can be —OH, —OCH3, —O—C1-C6 alkyl, —NH2, —N(C1-C6 alkyl)2, or —C1-C6 alkyl.

In one embodiment, Z3 can be C1-C4 alkyl.

In one embodiment, Z3 is methyl.

In one embodiment, R5 can be hydrogen or methyl.

In one embodiment, R5 is methyl.

In one embodiment, X can be hydrogen or methyl.

In one embodiment, X is methyl.

In one embodiment, R1 is isobutyl, R5 is hydrogen, X is methyl, Z2 is oxygen, G1 is a chain spanning 4-9 bond lengths and has no oxygen atoms, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —$NH_2$, —$N_3$, —CN, —$NO_2$, —CHO, —COOH, —$CONH_2$, —C(=NH)$NH_2$, or —$SO_3H$.

In another embodiment, R1 is isobutyl, R5 is hydrogen, X is methyl, Z2 is oxygen, G1 is cyclohexylmethyl, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —$NH_2$, —$N_3$, —CN, —$NO_2$, —CHO, —COOH, —$CONH_2$, —C(=NH)$NH_2$, or —$SO_3H$.

In another embodiment, R1 is isobutyl, R5 is hydrogen, X is methyl or hydrogen, Z2 is oxygen or CH2, G1 is C1-5 methylene group, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —$NH_2$, —$N_3$, —CN, —$NO_2$, —CHO, —COOH, —$CONH_2$, —C(=NH)$NH_2$, or —$SO_3H$.

In another embodiment, R1 is isobutyl, R5 is hydrogen, X is methyl, Z2 is oxygen, G1 is a linker of 4-9 bond lengths, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —$NH_2$, —$N_3$, —CN, —$NO_2$, —CHO, —COOH, —$CONH_2$, —C(=NH)$NH_2$, or —$SO_3H$.

In another embodiment, R1 is ethyl, isobutyl, isopropyl, benzyl, R5 is hydrogen, X is methyl, Z2 is oxygen, G1 is $(CH2)_{4-9}$—, R2 is hydrogen, halogen, trifluoromethyl, methylcarboxy, ethylcarboxy, C1-C6 alkoxy such as but not limited to methoxy and ethoxy, C1-C6 alkyl, —OH, —SH, —$NH_2$, —$N_3$, —CN, —$NO_2$, —CHO, —COOH, —$CONH_2$, —C(=NH)$NH_2$, or —$SO_3H$.

In another embodiment, R5 is hydrogen, X is methyl, Z2 is oxygen, G1 is $(CH2)_{4-9}$—, R2 is hydrogen, R1 is a phenyl ring substituted with hydrogen, halogen, trifluoromethyl, methylcarboxy, ethylcarboxy, methoxy, ethoxy, C1-C6 alkoxy, C1-C6 alkyl, —OH, —SH, —$NH_2$, —$N_3$, —CN, —$NO_2$, —CHO, —COOH, —$CONH_2$, —C(=NH)$NH_2$, or —$SO_3H$.

In another embodiment, R5 is hydrogen, X is methyl, Z2 is oxygen, R1 is isobutyl, R2 is halogen, methyl, or methoxy, G1 is cyclohexylmethyl or C3-C7 cycloalkyl-CH2- group.

In one aspect, the invention discloses compounds of Formula 5:

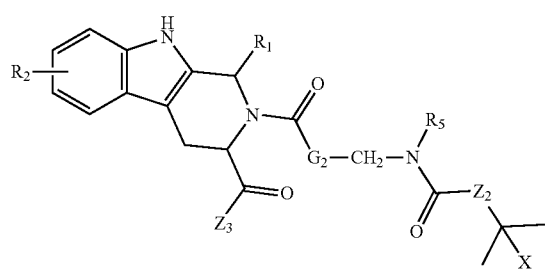

R1 is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted arylalkenyl; an optionally substituted C3-C8 cycloalkyl; or optionally substituted C4-C8 cycloalkylalkyl;

R2 is hydrogen, C1-C6 alkoxy such as but not limited to methoxy or ethoxy, trifluoromethyl, halogen, methylcarboxy, ethylcarboxy, optionally substititued C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

G2 is a bond, —NH—, —O—, —S—, —CH(CH$_3$)—, —(CH$_2$)$_n$—, —CH=CH—, —CO—, —SO—, —SO$_2$— or —C(=NH)—, —CH$_2$NH(CO)—, —CH$_2$NH(CO)O—, —CH$_2$NH(CO)NH—; —(CH$_2$)$_n$NH(CO)—, —(CH$_2$)$_n$NH(CO)O—, —(CH$_2$)$_m$NH(CO)NH—; —C3-C7 cycloalkyl- such as but not limited to -cyclohexyl-, or —N(CH$_2$CH$_2$C$_6$H$_5$)—;

Z2 is a bond, —NH—, —O—, —S—, —CH(CH$_3$)—, —(CH$_2$)$_n$—, —CH=CH—, —CO—, —SO—, —SO$_2$— or —C(=NH)—, —CH$_2$NH(CO)—, —CH$_2$NH(CO)O—, —CH$_2$NH(CO)NH—; —(CH$_2$)$_p$NH(CO)—, —(CH$_2$)$_p$NH(CO)O—, —(CH$_2$)$_p$NH(CO)NH—; —C3-C7 cycloalkyl-NH(CO)—, —C3-C7 cycloalkyl-CH$_2$NH(CO)O—, —C3-C7 cycloalkyl-NH(CO)NH—, or —N(CH$_2$CH$_2$C$_6$H$_5$)—;

Z3 is —OH, —OCH3, —O—C1-C6 alkyl, —OCH2C6H5, —NH$_2$, —NH(C1-C6 alkyl), —N(C1-C6 alkyl)2, —C1-C6 alkyl;

R5 is H, methyl, or optionally substituted C1-C6 alkyl;

X is H, C1-C3 alkyl, or C1-C3 arylalkyl;

m=1-5; n=1-8; p=1-9;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —OCH3, —OC2H5, —O—C1-C4 alkyl, —SH, —NH$_2$, —N$_3$, —CN, —NO$_2$, —CHO, —COOH, —CONH$_2$, —C(=NH)NH$_2$, or —SO$_3$H.

In one embodiment, R1 can be hydrogen, C1-C4 alkyl (e.g. methyl, ethyl, isopropyl, isobutyl), benzyl, heteroaryl such as pyridyl, phenyl, phenyl substituted with halogen, trifluoromethyl, methyl, methoxy, cyano, or dialkylamino.

In one embodiment, R1 can be H or C1-C4 alkyl.

In one embodiment, R1 is H.

In one embodiment, R2 can be hydrogen, halogen, methyl or methoxy.

In one embodiment, R2 is H.

In one embodiment, G2 can be a bond, —CH2-, —(CH2)2-, —(CH2)3-, —(CH2)4-, —CH2OCH2-, —CH(CH3)-, —CH2NHCO— or -cyclohexyl-.

In one embodiment, G2 is cyclohexyl.

In one embodiment, Z2 is O, CH2 or NH.

In one embodiment, Z2 is O.

In one embodiment, Z3 can be —OH, —OCH3, —O—C1-C6 alkyl, —NH$_2$, —N(C1-C6 alkyl)2, or —C1-C6 alkyl.

In one embodiment, Z3 is C1-C4 alkyl.

In one embodiment, Z3 is methyl.

In one embodiment, R5 can be hydrogen or methyl.

In one embodiment, R5 is methyl.

In one embodiment, X can be methyl.

In one embodiment, X is methyl.

In one embodiment, R1 is isobutyl, R5 is hydrogen, Z2 is oxygen, R5 is hydrogen, X is methyl, G2 has no oxygens, R2 is hydrogen, halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl, R5 is hydrogen, X is methyl, Z2 is oxygen, G2 is cyclohexyl, R2 is hydrogen, halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl, Z2 is oxygen or CH2, R5 is hydrogen or methyl, X is methyl, G2 is a bond or —(CH2)$_{1-4}$—, R2 is hydrogen, halogen, trifluoromethyl, methylcarboxy, ethylcarboxy, C1-C6 alkoxy such as methoxy or ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, R1 is isobutyl, Z2 is oxygen, R5 is hydrogen, X is methyl, and R2 is hydrogen, halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is ethyl, isobutyl, isopropyl, benzyl, Z2 is oxygen, R5 is hydrogen, X is methyl, G2 is —(CH2)$_{2-5}$, R2 can be hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R5 is hydrogen, X is methyl, Z2 is oxygen, G2 is —(CH2)$_{2-5}$, R2 is hydrogen, R1 is a phenyl ring substituted with hydrogen, halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R5 is hydrogen, X is methyl, Z2 is oxygen, R1 is isobutyl, R2 is halogen, methyl, or methoxy, G2 is cyclohexyl or C3-C7 cycloalkyl-CH2- group.

In one aspect, the invention discloses compounds of Formula 6:

R1 is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

R2 is hydrogen, C1-C6 alkoxy such as but not limited to methoxy or ethoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

R5 is H, methyl, or optionally substituted C1-C6 alkyl;

X is H, C1-C3 alkyl, or C1-C3 arylalkyl;

Z2 is a bond, —NH—, —O—, —S—, —CH(CH$_3$)—, —(CH$_2$)$_n$—; —CH=CH—, —CO—, —SO—, —SO$_2$—, —C(=NH)—, —CH$_2$NH(CO)—, —CH$_2$NH(CO)O—, —CH$_2$NH(CO)NH—; —(CH$_2$)$_n$NH(CO)—, —(CH$_2$)$_n$NH(CO)O—, —(CH$_2$)$_m$NH(CO)NH—; —C3-C7 cycloalkyl-NH(CO)—, —C3-C7 cycloalkyl-CH$_2$NH(CO)O—, —C3-C7 cycloalkyl-NH(CO)NH—, or —N(CH$_2$CH$_2$C$_6$H$_5$)—;

Z3 is —OH, —OCH3, —O—C1-C6 alkyl, —OCH2C6H5, —NH2, —NH(C1-C6 alkyl), —N(C1-C6 alkyl)2, —C1-C6 alkyl;

m=1-5; n=1-8;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —OCH3, —OC2H5, —O—C1-C4 alkyl, —SH, —NH$_2$, —N$_3$, —CN, —NO$_2$, —CHO, —COOH, —CONH$_2$, —C(=NH)NH$_2$, or —SO$_3$H.

In one embodiment, R1 can be isopropyl or isobutyl.

In one embodiment, R1 is H.

In one embodiment, R2 can be H, halogen or methyl.

In one embodiment, R2 is H.

In one embodiment, R5 can be H.

In one embodiment, X can be methyl.

In one embodiment, Z2 can be O.

In one embodiment, Z3 can be —OH, —OCH3, —O—C1-C6 alkyl, —NH2, —N(C1-C6 alkyl)2, or —C1-C6 alkyl.

In one embodiment, Z3 can be C1-C4 alkyl.

In one embodiment, Z3 is methyl.

In one embodiment, R1 is isobutyl, R5 is hydrogen, Z2 is oxygen, X is hydrogen, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment R1 is isopropyl, R5 is hydrogen, Z2 is oxygen, X is hydrogen, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl or isopropyl, R5 is hydrogen or methyl, Z2 is oxygen, X is hydrogen, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl or isopropyl, R5 is hydrogen, Z2 is —CH2- or oxygen, X is hydrogen or CH3, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one aspect, the invention discloses compounds of Formula 7:

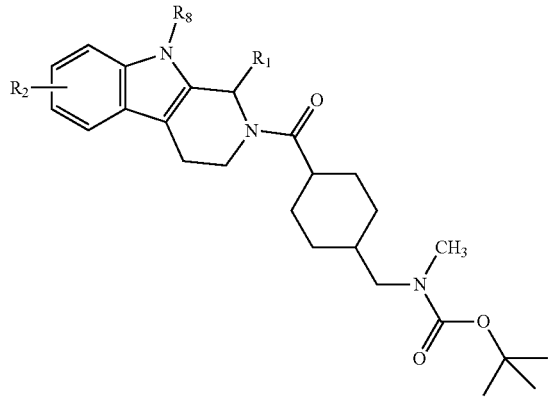

R1 is H, optionally substituted C1-C6 alkyl; C3-C4 cycloalkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

R2 is hydrogen, C1-C6 alkoxy such as but not limited to methoxy or ethoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

R8 is H, optionally substituted C1-C6 alkyl; C3-C4 cycloalkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —OCH3, —OC2H5, —O—C1-C4 alkyl, —SH, —NH$_2$, —N$_3$, —CN, —NO$_2$, —CHO, —COOH, —CONH$_2$, —C(=NH)NH$_2$, or —SO$_3$H.

In one embodiment, R1 can be C2-C4 alkyl, or C3-C4 cycloalkyl.

In one embodiment, R1 can be ethyl, isopropyl or isobutyl.

In one embodiment, R1 can be ethyl or isopropyl.

In one embodiment, R2 can be H, halogen or methyl.

In one embodiment, R2 can be H, F, Cl, or Me.

In one embodiment, R2 is H.

In one embodiment, R8 is H.

In one embodiment, R8 is Me.

In one embodiment, R1 is ethyl, isopropyl, or isobutyl, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is ethyl, isopropyl, or isobutyl, R2 is hydrogen, halogen, trifluoromethyl, methylcarboxy, ethylcarboxy, C1-C6 alkoxy such as but not limited to methoxy and ethoxy, C1-C6 alkyl, —OH, —NH$_2$, —CN, —CHO, —COOH, or —CONH$_2$.

In another embodiment, R1 is ethyl, or isopropyl, and R2 is hydrogen, halogen, trifluoromethyl, methylcarboxy, ethylcarboxy, C1-C6 alkoxy such as but not limited to methoxy and ethoxy, or C1-C6 alkyl.

In one aspect, the invention discloses compounds of Formula 8:

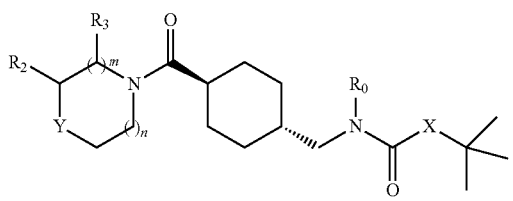

Wherein, X is O, NH, S, or CH2;
Y is O, N—R1, N—CH2-R1, CH—R1, or CH—CH2-R1;
R0 is H, or C1-C5 alkyl
R1 is H, C1-5 alkyl, optionally substituted aryl, or optionally substituted heteroaryl;
R2 is H, or optionally substituted aryl;
R3 is H or C1-3 alkyl;
m is 0 or 1; and
n is 0 or 1;
where "substituted" means substituted with one or more independently selected from halogen, trifluoromethyl, methylcarboxy, ethylcarboxy, methoxy, ethoxy, C1-C6 alkoxy, C1-C6 alkyl, —OH, —OCH3, —OC2H5, —O—C1-C4 alkyl, —SH, —NH$_2$, —N$_3$, —CN, —NO$_2$, —CHO, —COOH, —CONH$_2$, —C(=NH)NH$_2$, or —SO$_3$H.

In some embodiments, X may be O. Alternatively, X may be CH2.

In some embodiments, Y may be O, N—R1, or CH—R1. In some embodiments, Y may be N—R1. Alternatively, Y may be CH—R1.

In some embodiments, R0 is H or methyl.

In some embodiments, R1 is H, optionally substituted aryl, or optionally substituted heteroaryl; and R2 is H. Alternatively, R1 may be H, and R2 is optionally substituted aryl.

In the context of R1 and R2, the term "optionally substituted aryl" may refer to phenyl or substituted phenyl. Substituted aryl or phenyl may refer to aryl or phenyl substituted with one or more (e.g. 1-3 or 1-2) selected from halogen, methoxyl, methyl, amino, and nitro.

In the context of R1, the term "optionally substituted heteroaryl" may refer to optionally substituted pyridyl, thiazoyl, imidazolyl, or pyrimidinyl. The heteroaryls may be substituted with one or more (e.g. 1-3 or 1-2) selected from halogen, methoxy, methyl, amino and nitro.

In some embodiments, R1 is methyl, phenyl, 4-pyridyl, 3-pyridyl, 2-pyridyl, 4-aminophenyl, 4-fluorophenyl, 4-methoxyphenyl, 4-pyridyl, 3-pyridyl, 2-pyridyl, 4-pyrimidinyl, 4-nitrophenyl, 2-thiazolyl, 4-(2-methyl)pyridyl, 2-imidazolyl, 4-imidazolyl, or 1-imidazolyl In some embodiments, R3 is H or methyl.

In one embodiment, Y is N—R1; R0 is CH3; X is O or NH; R1 is phenyl, methyl, or pyridyl (such as 4-pyridyl, 3-pyridyl, or 2-pyridyl); R2 is H; R3 is H; m is 1; and n is 1.

In one embodiment, Y is CH—R1; R0 is CH3; X is O or NH; R1 is phenyl, phenyl substituted with halogen, amino, methoxy, or nitro (such as 4-aminophenyl, 4-fluorophenyl, 4-methoxyphenyl, and 4-nitrophenyl), pyridyl (such as 4-pyridyl, 3-pyridyl, 2-pyridyl), pyrimidinyl (such as 4-pyrimidinyl), 2-thiazolyl, 4-(2-methyl)pyridyl, 4-pyridylmethyl, 2-imidazolyl, 4-imidazolyl, or 1-imidazolyl; R2 is H; R3 is H; m is 1; and n is 0 or 1.

In one embodiment, Y is O; R0 is CH3; X is O; R2 is H; R3 is H; m is 1; and n is 1.

In one embodiment, Y is CH—R1; R0 is CH3; X is O; R1 is H; R2 is H; R3 is H; m is 1; and n is 1.

As exemplified herein, the compounds of Formula 8 may be selected from MN1420, MN1427, MN1428, MN1429, MN1430, MN1432, MN1433, MN1434, MN1435, MN1436, MN1437, MN1438, MN1439, MN1440, MN1441, MN1442, MN1444, MN1445, MN1447, MN1448, MN1449, MN1450, MN1451, MN1452, MN1453, MN1454, MN1455, MN1456, MN1457, MN1458, MN1459, MN1460, or MN1461.

In one embodiment, Y is N—R1; X is O; R0 is H or CH3; R1 is phenyl, methyl, 4-pyridyl, 3-pyridyl, or 2-pyridyl; R2 is H; R3 is H; m is 1; and n is 1.

In one embodiment, Y is N—R1; X is NH; R0 is H or CH3; R1 is phenyl, 2-pyridyl, or 3-pyridyl; R2 is H; R3 is H; m is 1; and n is 1.

In one embodiment, Y is CH—R1; X is NH; R0 is CH3; R1 is 4-pyridyl or 2-pyridyl; R2 is H; R3 is H; n is 1; and m is 1.

In one embodiment, Y is CH—R1; X is O; R0 is CH3; R1 is phenyl, 4-pyridyl, H, t-Bu-CON(CH3)-CH2-, 3-pyridyl, 4-pyrimidinyl, 2-pyrimidinyl, 4-nitrophenyl, 2-thiozolyl, 3-fluorophenyl, 4-methoxyphenyl, 4-(2-methyl)pyridyl, 4-pyridylmethyl, 4-pyridyl, 2-imidazolyl, 4-imidazolyl, 1-imidazolyl, or 4-aminophenyl.

In one aspect, the invention discloses compounds of Formula 9:

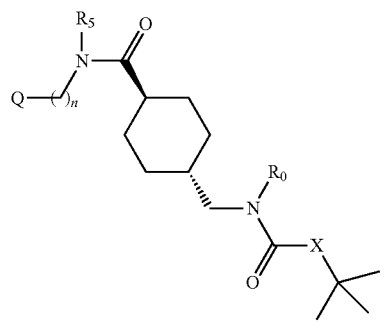

Wherein, Q is heteraryl;
R0 is H or C1-4 alkyl;
X is O, NH, CH2;
R5 is H or CH3; and
n is 1, 2, or 3.

In some embodiments, Q may be a monocyclic or bicyclic heteroaryl. For example, Q may be a monocyclic or bicyclic heteroaryl containing 1-2 nitrogen atoms. Q may be pyridine, isoquinoline, indole, or azaindole.

In some embodiments, R0 may be H or CH3. For example, R0 may be CH3.

In some embodiments, X is O.

In some embodiments, R5 is H.

As exemplified herein, the compounds of Formula 9 may be selected from MN1462, MN1463, MN1465, MN1468, MN1467, and MN1466.

In one aspect, the invention discloses compounds of Formula 10:

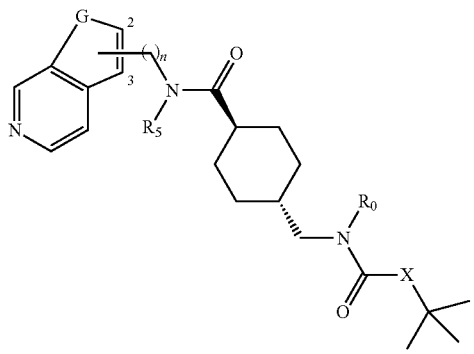

Wherein, R0 is H or C1-4 alkyl;
X is O, NH, or CH2;
R5 is H or C1-4 alkyl;
G is NH, —CH=CH—, O or S; and
n is 1 or 2.

For illustrative purposes, the heterocyclic moiety is connected at either position 2 or 3.

In some embodiments, R0 is H or CH3. For example, R0 may be CH3.

In some embodiments, X is O.

In some embodiments, R5 is H or CH3. For example, R5 may be H.

In some embodiments, G is NH or —CH=CH—.

As exemplified herein, the compounds of Formula 10 may be selected from MN1462, MN1463, and MN1465.

In one aspect, the invention discloses compounds of Formula 11:

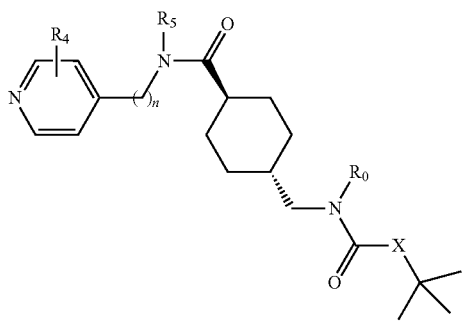

Wherein, R0 is H or C1-4 alkyl;
X is O, CH2, or NH;
R4 is H, CH3, OH, NH$_2$;
R5 is H or C1-4 alkyl; and
n is 1-3.

In some embodiments, R0 is H or CH3. For example, R0 is CH3.

In some embodiments, X is O.

In some embodiments, R5 is H or CH3. For example, R5 may be H.

In some embodiments, R4 is H.

As exemplified herein, the compounds of Formula 11 may be selected from MN1468, MN1467, and MN1466.

In one aspect, the invention discloses compounds of Formula 12:

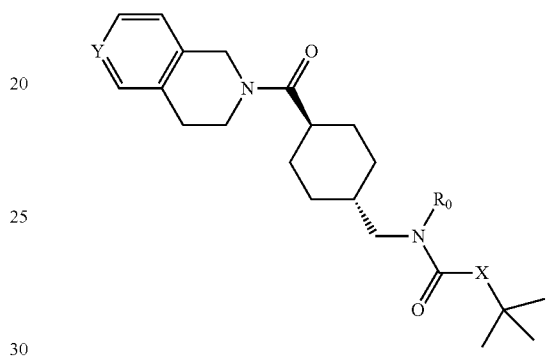

Wherein, R0 is H or C1-4 alkyl;
X is O, NH or CH2; and
Y is N or CH.

In some embodiments, R0 is H or CH3. For example, R0 is CH3.

In some embodiments, X is O.

In some embodiments, Y is CH or N.

As exemplified herein, the compounds of Formula 12 may be selected from MN1431, and MN1464.

In one aspect, the invention discloses compounds of Formula 13:

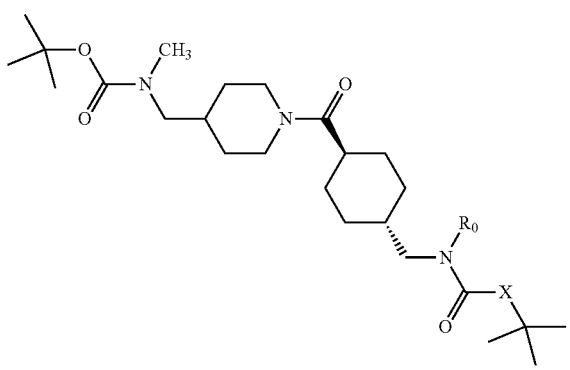

Wherein, R0 is H or C1-4 alkyl; and
X is O, NH or CH2.

In some embodiments, R0 is H or CH3. For example, R0 is CH3.

In some embodiments, X is O.

In one embodiment, R0 is CH3 and X is O.

As exemplified herein, the compound of Formula 13 is compound MN1434.

In one aspect, the invention discloses compounds of Formula 14:

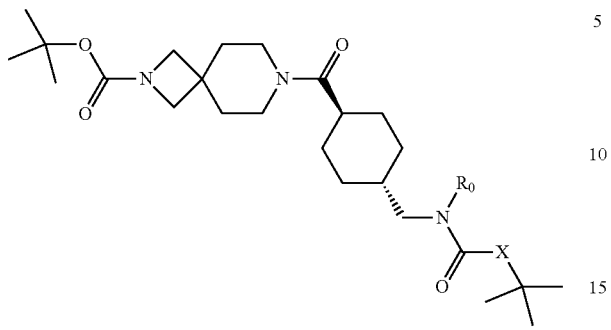

Wherein, R0 is H or C1-4 alkyl; and
X is O, NH or CH2.

In some embodiments, R0 is H or CH3. For example, R0 is CH3.

In some embodiments, X is O.

In one embodiment, R0 is CH3; and X is O.

As exemplified herein, the compound of Formula 14 is compound MN1460.

In one aspect, the invention discloses compounds of Formula 15:

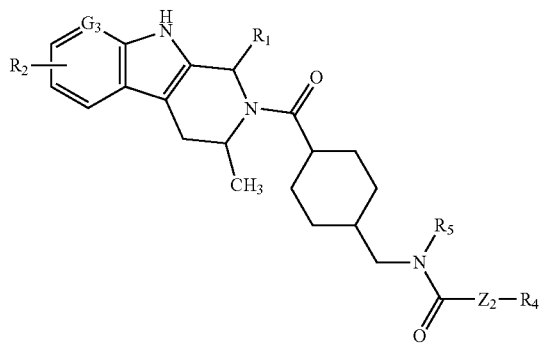

R1 is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

R2 is hydrogen, C1-C6 alkoxy such as but not limited to methoxy or ethoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

R5 is H, methyl, ethyl, C1-C6 alkyl, C1-C3 arylalkyl, or 2-phenylethyl;

Z2 is a bond, —NH—, —O—, —S—, —CH(CH$_3$)—, —CH2-, —(CH2)$_n$—, —CH=CH—, —CO—, —SO—, —SO$_2$—, —C(=NH)—, —CH$_2$NH(CO)—, —CH$_2$NH(CO)O—, —CH2NH(CO)NH—; —(CH$_2$)$_n$NH(CO)—, —(CH$_2$)$_n$NH(CO)O—, —(CH$_2$)$_m$NH(CO)NH—;

R4 is H, optionally substituted C1-C9 alkyl such as but not limited to tert-butyl; optionally substituted C2-C6 alkenyl; optionally substituted C6-C12 aryl such as but not limited to optionally substituted phenyl; optionally substituted C1-C9 heteroaryl with 1 to 4 ring atoms independently selected from N, S, and O; optionally substituted C7-C15 arylalkyl such as but not limited to benzyl or alpha-methylbenzyl; —O-tert-butyl;

m=1-5; n=1-8;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, R1 can be isopropyl or isobutyl.

In one embodiment, R1 can be H.

In one embodiment, R2 can be H, halogen or methyl.

In one embodiment, R5 can be H or CH3. For example, R5 is CH3.

In one embodiment, R4 is t-butyl.

In one embodiment, Z2 can be O.

In one embodiment, Z2 can be —NH—.

In one embodiment, R1 is isobutyl, R5 is hydrogen, Z2 is oxygen, R4 is t-butyl.

and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment R1 is isopropyl, R5 is hydrogen, Z2 is oxygen, R4 is t-butyl.

In another embodiment, R1 is H, and R5 is CH3. For example, R1 may be H; R5 may be CH3; R2 may be H, halogen or methyl; Z2 may be —O— or —NH—; and R4 may be C4 alkyl (such as t-butyl).

and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl or isopropyl, R5 is hydrogen or methyl, Z2 is oxygen, R4 is t-butyl, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl or isopropyl, R5 is hydrogen, Z2 is —CH2- or oxygen, R4 is t-butyl or CH3, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one aspect, the invention discloses compounds of Formula 16:

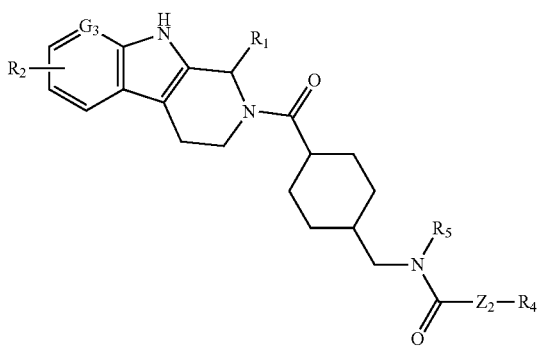

G3 is CH or N;

R1 is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

R2 is hydrogen, C1-C6 alkoxy such as but not limited to methoxy or ethoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

R5 is methyl, ethyl, C1-C6 alkyl, C1-C3 arylalkyl, or 2-phenylethyl;

Z2 is a bond, —NH—, —O—, —S—, —CH(CH$_3$)—, —CH2-, —(CH$_2$)$_n$—, —CH=CH—, —CO—, —SO—, —SO$_2$—, —C(=NH)—, —CH$_2$NH(CO)—, —CH$_2$NH(CO)O—, —CH$_2$NH(CO)NH—; —(CH$_2$)$_n$NH(CO)—, —(CH$_2$)$_n$NH(CO)O—, —(CH$_2$)$_m$NH(CO)NH—;

R4 is H, optionally substituted C1-C9 alkyl such as but not limited to tert-butyl; optionally substituted C2-C6 alkenyl; optionally substituted C6-C12 aryl such as but not limited to optionally substituted phenyl; optionally substituted C1-C9 heteroaryl with 1 to 4 ring atoms independently selected from N, S, and O; optionally substituted C7-C15 arylalkyl such as but not limited to benzyl or alpha-methylbenzyl; —O-tert-butyl;

m=1-5; n=1-8;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, G3 can be H or N.

In one embodiment, R1 can be a C1-4 alkyl, such as but not limited to methyl, ethyl, propyl, butyl, and cyclopropyl.

In one embodiment, R1 can be isopropyl or isobutyl.

In one embodiment, R1 can be methyl.

In one embodiment, R1 can be ethyl.

In one embodiment, R1 can be cyclopropyl.

In one embodiment, R1 can be H.

In one embodiment, R2 can be H, halogen or methyl.

In one embodiment, R5 can be H or CH3. For example, R5 can be CH3.

In one embodiment, R5 can be ethyl.

In one embodiment, R4 is t-butyl.

In one embodiment, Z2 can be —O— or —NH—. For example, Z2 can be O. Alternatively, Z2 can be —NH—.

In one embodiment, R5 is methyl; Z2 is —O—; and R4 is t-butyl.

In one embodiment, R5 is methyl; Z2 is —NH—; and R4 is t-butyl.

In one embodiment, R5 is H; Z2 is —O—; and R4 is t-butyl. For example, R1 is also C1-3 alkyl; and/or R2 is H or methyl.

In one embodiment, R1 is C1-4 alkyl; R2 is H, halogen or methyl; R5 is methyl; Z2 is —O—; R4 is t-butyl. In this context, G3 may be CH.

In one embodiment, G3 is N, R1 is isobutyl, R5 is hydrogen, Z2 is oxygen, R4 is t-butyl, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, G3 is N, R1 is isobutyl or isopropyl, R5 is hydrogen or methyl, Z2 is oxygen, R4 is t-butyl, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, G3 is N, R1 is isobutyl or isopropyl, R5 is hydrogen, Z2 is —CH2- or oxygen, R4 is t-butyl. or CH3, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one aspect, the invention discloses compounds of Formula 17:

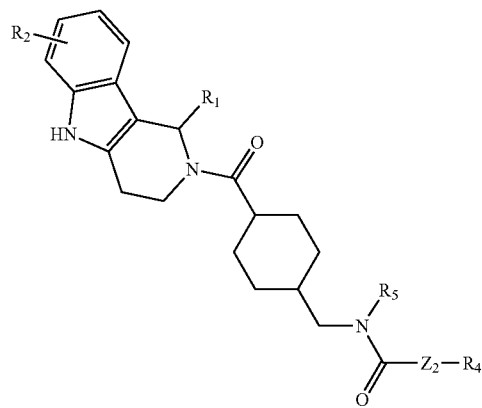

R1 is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl such as but not limited to benzyl or alpha-methylbenzyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

R2 is hydrogen, C1-C6 alkoxy such as but not limited to methoxy or ethoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

R5 is H, methyl, ethyl, C1-C6 alkyl, C1-C3 arylalkyl, or 2-phenylethyl;

Z2 is a bond, —NH—, —O—, —S—, —CH(CH3)-, —CH2-, —(CH2)$_n$—, —CH=CH—, —CO—, —SO—, —SO$_2$—, —C(=NH)—, —CH$_2$NH(CO)—, —CH$_2$NH(CO)O—, —CH2NH(CO)NH—; —(CH$_2$)$_n$NH(CO)—, —(CH$_2$)$_n$NH(CO)O—, —(CH$_2$)$_m$NH(CO)NH—;

R4 is H, optionally substituted C1-C9 alkyl such as but not limited to tert-butyl; optionally substituted C2-C6 alkenyl; optionally substituted C6-C12 aryl such as but not limited to optionally substituted phenyl; optionally substituted C1-C9 heteroaryl with 1 to 4 ring atoms independently selected from N, S, and O; optionally substituted C7-C15 arylalkyl such as but not limited to benzyl or alpha-methylbenzyl; —O-tert-butyl;

m=1-5; n=1-8;

where "substituted" means substituted with one or more independently selected from halogen, trifluoromethyl, methylcarboxy, ethylcarboxy, methoxy, ethoxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In one embodiment, R1 can be isopropyl or isobutyl.

In one embodiment, R1 can be H.

In one embodiment, R2 can be H, halogen or methyl. For example, R2 can be H.

In one embodiment, R5 can be H or CH3. For example, R5 can be CH3.

In one embodiment, R4 is t-butyl.

In one embodiment, Z2 can be —O— or —NH—. For example, Z2 can be O. Alternatively, Z2 can be —NH—.

In one embodiment, R5 is methyl; Z2 is —O—; and R4 is t-butyl.

In one embodiment, R5 is methyl; Z2 is —NH—; and R4 is t-butyl.

In one embodiment, R1 is isobutyl, R5 is hydrogen, Z2 is oxygen, R4 is t-butyl, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment R1 is isopropyl, R5 is hydrogen, Z2 is oxygen, R4 is t-butyl, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is isobutyl or isopropyl, R5 is hydrogen or methyl, Z2 is oxygen, R4 is t-butyl, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH) NH$_2$, or —SO$_3$H.

In another embodiment, R1 is isobutyl or isopropyl, R5 is hydrogen, Z2 is —CH2- or oxygen, R4 is t-butyl.or CH3, and R2 is hydrogen, halogen, trifluoromethyl, methylcarboxy, ethylcarboxy, C1-C6 alkoxy such as but not limited to methoxy and ethoxy, C1-C6 alkyl, —OH, —SH, —NH$_2$, —N$_3$, —CN, —NO$_2$, —CHO, —COOH, —CONH$_2$, —C(=NH)NH$_2$, or —SO$_3$H.

In another embodiment, R1 is H; R2 is H; R5 is CH3; Z2 is —O— or —NH—; and R4 is C4-alkyl (such as t-butyl).

Synthetic Routes to Chemical Analogs

The compounds described in this application were synthesized using well known organic chemistry techniques previously described in the literature (see Reaction Scheme).

Cyclization Methods A-E: Unsubstituted tryptamine and substituted tryptamines were reacted with aliphatic and aromatic aldehydes in a Pictet-Spangler-type heterocyclization reaction to provide tetrahydro-beta-carbolines with substitutions at R1 and R2, using either 1,1,1,3,3,3-hexafluoroisopropanol (Lewis acid) or trifluoroacetic acid (Bronsted acid) in various solvents and temperatures.

Coupling Methods F-H: The basic secondary nitrogen of the tetrahydro-beta-carboline was then acylated with a carboxylic acid (in the presence of coupling agents), an acid chloride in the presence of a base, or with an isocyanate to generate ureas.

See Physical Data and Synthetic Methods Table for the specific synthetic methods used for each analog described herein.

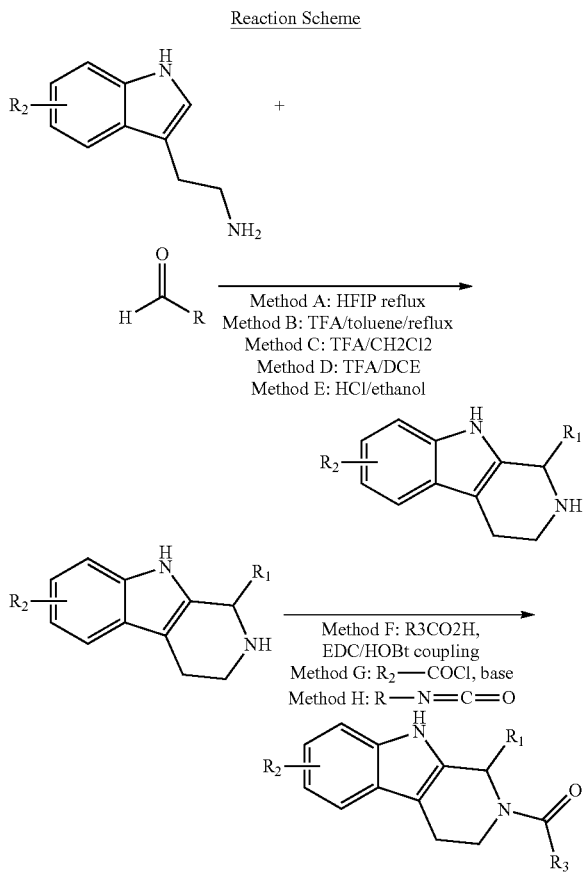

Reaction Scheme

Experimental Methods

All solvents and reagents were purchased from Sigma-Aldrich, Fisher Scientific, or other commercial vendors and were used without further purification. All deuterated solvents for use in NMR experiments were purchased from Sigma-Aldrich and used without further purification. All $^1$H NMR experiments were performed using a Varian 400 MHz Unity Inova NMR spectrometer. $^1$H NMR spectra were acquired with 16 scans, using a delay time (d1)=1 sec. Spectral width was =20 ppm (from −3 ppm to 20 ppm). NMR experiments were performed by Custom NMR Services (Ayer, MA). Mass spectroscopy experiments were performed using LC/MS. Samples were typically prepared in methylene chloride, at a concentration of 1 mg/mL, injecting 1 uL for each acquisition. Mass spectroscopy experiments were performed by Dr. Tun-Li Shen of Brown University (Providence, RI). pH measurements were determined either by using either Hydracid Papers 1-6 (Micro Essential Laboratory-Brookly, NY) or with a Fisher Scientific pH meter, model number AB15. Controlled additions of reagents were performed using a Hamilton 10 mL gas tight syringe attached to a KD Scientific, model 100 syringe pump. All inert atmospheres were achieved using compressed argon (ultra high purity-Igo's Welding Supply-Watertown, MA) either as a balloon, using a perfectum needle tubing connector attached to a needle or in a Sigma-Aldrich Atmos glove bag. Laboratory glassware was manufactured either by Sigma-Aldrich, Ace glass, Chemglass or VWR scientific. Silica gel purifications were performed using Sigma-Aldrich Silica Gel (230-400 mesh, grade 60, cat. #717185). TLC's were performed using EMD TLC Silica Gel 60 F254 plates (2.5×7.5 cm, cat. #1153410001). TLC's were visualized by either I2-silica gel or UV-light. High performance liquid chromatograph (HPLC) analyses were obtained on an Agilent HP1090 HPLC using a Luna 5u C18 (2) 100A column (50×2.00 mm, Phenomenex) with UV detection at 254 nm and 220 nm using a standard solvent gradient program; Solvent A is 0.4% TFA in water; Solvent B is 0.4% TFA in Acetonitrile; HPLC gradient: 5% B (0-0.5 min), 100% B (ramp 0.5-5 min), 100% B (5-7 min), 5% B (7-7.01 min), 5% B (7.01-9 min).

Synthesis Example 1 (Cyclization by Method D)

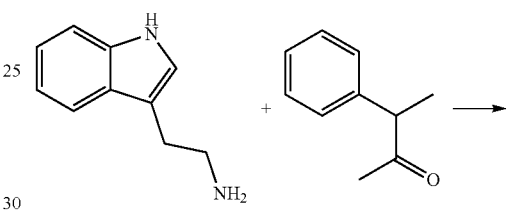

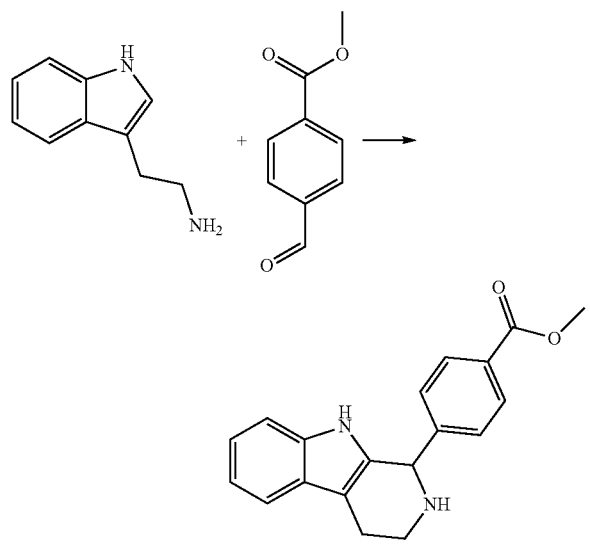

Tryptamine (1.00 g, 6.26 mmol), methyl 4-formylbenzoate (1.03 g, 6.24 mmol), and 4A molecular sieves (0.76 g) were suspended in 1,2-dichloroethene (DCE) (30 mL). Trifluoroacetic acid (TFA) (285 mg, 2.50 mmol) was added to the mixture and the reaction was brought to reflux, yielding a bright brown precipitate. The mixture was cooled to 30° C. and the 4A molecular sieves were removed by glass wool plug. The solution was quenched with sat. NaHCO$_3$ (15 mL) and diluted with EtOAc (50 mL). The organic layer was was with sat. NaCl and dried (anhyd. MgSO$_4$). The solvent was removed by vacuum, yielding a light brown solid. This material was further purified by flash column chromatography: eluting with of MeOH, EtOAc, and Hexane (1:3:6) were used. Fractions containing product were combined yielding a light brown solid (0.80 g, 42% yield; TLC R$_f$=0.129 (10% MeOH/30% EtOAc/Hexane); HPLC R$_t$=3.254 min). This intermediate was used in the synthesis of the following compounds: MN0642 and MN1210.

Synthesis Example 3: MN1179 (Cyclization by Method B)

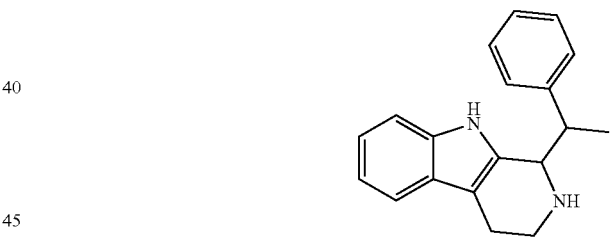

Tryptamine (5.00 g, 31.2 mmol) was added to toluene (100 mL). 2-phenylpropionaldehyde (4.2 mL, 31.2 mmol) and TFA (0.60 mL, 7.8 mmol) were added to the mixture. The reaction was stirred and refluxed overnight using a Dean-Stark trap to remove water. The reaction was cooled to room temperature, EtOAc (100 mL) was added, and the organic layer washed with sat. NaHCO3(3×25 mL) and then sat. NaCl (25 mL). The solvent was evaporated, yielding a brown solid. The solid was dissolved in EtOAc (50 mL), heptane (50 mL) was added, and the reaction was put on ice. The solution was filtered, and remaining mass was dried. The solid was dissolved in CH$_2$Cl$_2$ and further purified with vacuum flash chromatography: 5 fractions consisting of 0%, 1%, 3%, 5%, and 5% MeOH in CH$_2$Cl$_2$. Fractions containing product were combined, the solvent was removed under vacuum yielding a solid (5.10 g, 59.1% yield; TLC R$_f$=0.34 (3% MeOH/CH$_2$Cl$_2$); HPLC R$_t$=3.187 min). This intermediate was used in the synthesis of the following compounds: MN1130, MN1135, MN1151, MN1152, and MN1171.

Synthesis Example 4: MN1180 (Cyclization by Method A)

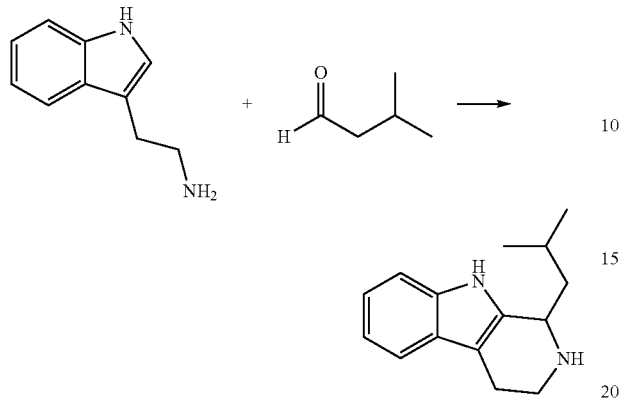

Tryptamine (1.6 g, 10 mmol) was dissolved in 1,1,1,3,3,3-hexafluoro-2-isopropanol (16 mL) and added to isovaleraldehyde (1.3 mL; 12 mmol) by syringe. The reaction was heated to reflux for 18.5 hrs and stirred under an inert atmosphere of nitrogen. The solvent was evaporated and azeotroped with $CHCl_3$ (3×50 mL) under vacuum. Hexane (16 mL) was added and the mixture was sonicated in a bath for 10 min and then stirred overnight. The mixture was filtered, yielding a solid (1.9 g). The material was further purified by trituration by stirring with 5N $NH_4OH$ (10 mL) for 20 min. The result was filtered then washed with H2O (2×20 mL). The resulting solid was filtered and dried in a vacuum dissicator, yielding a solid (1.60 g, 71.0% yield; TLC $R_f$=0.30 (10% MeOH/1% $NH_4OH/CH_2Cl_2$); HPLC $R_t$=3.081 min). This intermediate was used in the synthesis of the following compounds:

Synthesis Example 5: MN1180 (Cyclization by Method C)

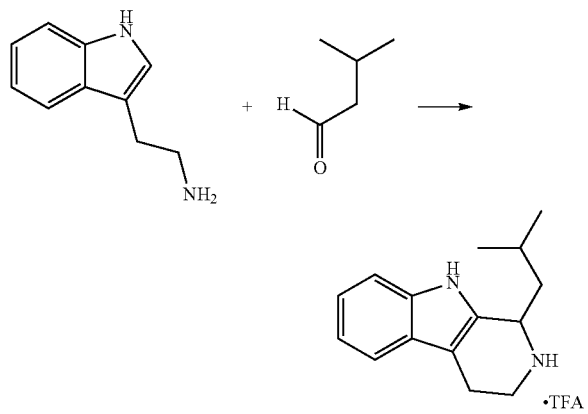

Tryptamine (8.0 g, 50 mmol) was dissolved in $CH_2Cl_2$ (400 mL) and placed under an inert atmosphere of argon for 20 min. Isovaleraldehyde (5.36 mL, 50.0 mmol) was added to the solution and the reaction was placed in a −80° C. ice bath for 20 minutes. TFA (38.3 mL) was added drop-wise over 15 minutes. The reaction was removed from the water bath, allowed to warm to room temperature, and stirred for 20 hrs. The solvent was evaporated, yielding a black oil. The oil was dissolved in $CH_2Cl_2$ (250 mL) and 1N NaOH was added and shaken. The precipitate was collected and dried under vacuum dissicator to provide 17.9 g of an olive-colored powder (TFA salt). The TFA salt was recrystallized from refluxing acetonitrile The collected solid was washed with cold ACN (~20 mL) and dried yielding a crystalline solid (9.3 g, 54% yield; TLC $R_f$=0.30 (10% MeOH/1% $NH_4OH/CH_2Cl_2$); HPLC $R_t$=3.099 min). This intermediate was used in the synthesis of the following compounds: MN1132, MN1133, MN1137, MN1138, MN1157, MN1186, MN1189, MN1190, MN1194, MN1195, MN1197, MN1203, MN1206, MN1207, MN1208, MN1209, MN1212, MN1213, MN1214, MN1220, MN1221, MN1222, MN1223, MN1224, MN1225, MN1226, MN1231, MN1232, MN1246.

Synthesis Example 7: MN1130 (Coupling by Method H)

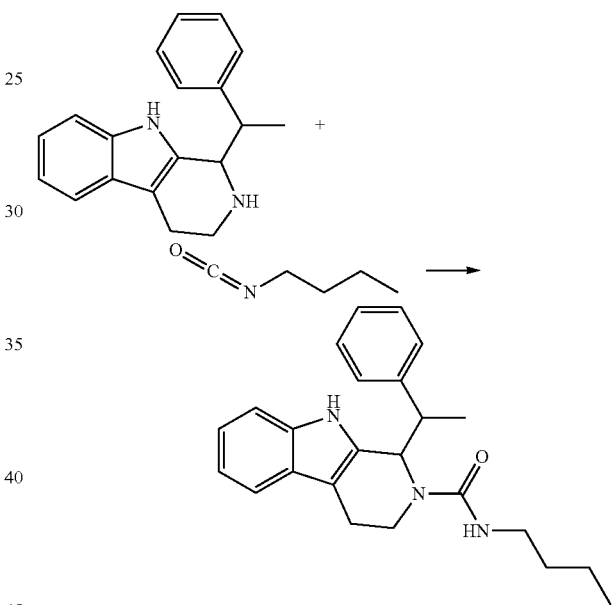

1-(1-Phenylethyl)-2,3,4,9-tetrahydro-1H-pyrido[3,4-b]indole (276 mg, 1.00 mmol) was dissolved in $CHCl_3$ (50 mL) and cooled in an ice bath under an inert atmosphere of nitrogen for 10 min. Butyl isocyanate (170 µL, 1.50 mmol) was added by syringe. The reaction was removed from the ice bath and allowed to warm to room temperature for 10 min. HPLC indicated the reaction was complete at 1 hr. The reaction was evaporated and dried under vacuum. The residue was dissolved in EtOAc (100 mL), washed with 1M citric acid (3×25 mL), sat. $NaHCO_3$ (3×25 mL), and sat. NaCl (25 mL). The organic layer was dried (anhyd. $Na_2SO_4$), filtered, and evaporated under vacuum to give of an off-white solid (339 mg). The material was further purified by trituration by stirring with 40% EtOAc/60% Hexane (3 mL) for 1 hr, followed by collecting the product by trituration. The trituration was repeated by stirring with 40% EtOAc/60% Hexane (3 mL) for 1 hr. The resulting solid was filtered and dried in a vacuum dissicator, yielding a white solid (138 mg, 36.7% yield; TLC $R_f$=0.46 (40% EtOAc in Hexane); HPLC $R_t$=4.598 min); MS m/z 375.2412 (100% rel. int.). This method was used in the synthesis of the following compounds: MN733, MN1130, MN1131, MN1158, MN1160, MN1169, MN1171, MN1172, MN1184.

Synthesis Example 8: MN1132 (Coupling by Method G)

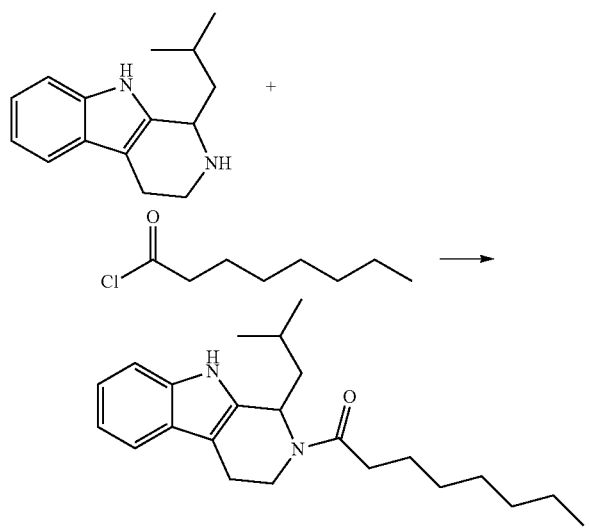

1-Isobutyl-2,3,4,9-tetrahydro-1H-pyrido[3,4-b]indole (228 mg, 1.00 mmol) was dissolved in $CH_2Cl_2$ (10 mL) and cooled in an ice bath under an inert atmosphere of nitrogen for 6 min. Octanoyl chloride (170 µL, 1.00 mmol) was added by syringe followed directly by triethylamine (TEA) (140 µL, 1.00 mmol). The reaction was removed from the ice bath and allowed to warm to room temperature for 10 min. HPLC indicated the reaction was complete at 10 min. The solution was diluted with EtOAc (100 mL), washed with 1N HCl (3×25 mL), sat. $NaHCO_3$ (3×50 mL), and sat. NaCl (25 mL). The organic layer was dried (anhyd. $Na_2SO_4$), filtered, and evaporated under vacuum. The resulting oil was dissolved in $CH_2Cl_2$ (5 mL), and the solvent was removed under vacuum. The oily residue was washed with hexanes (3 mL) top remove any hexane-soluable impurities. This material was further purified by silica gel chromatography: 5 fractions (200 mL each) consisting of 0%, 5%, 10%, 15%, and 20% EtOAc in hexane. Fractions containing product were combined, the solvent was removed under vacuum resulting in an oil. The oil was dissolved in $CH_2Cl_2$ (~1 mL) and was slowly evaporated in an ice bath, yielding a white solid. The solid was dried under high vacuum yielding a yellow oil (236 mg, 67.0% yield; TLC $R_f$=0.28 (10% EtOAc in Hexane); HPLC $R_t$=5.299 min); $^1$H NMR ($CDCl_3$, 0.003% v/v TMS, 400 MHz): δ 0.85-1.10 (9H, m), 1.20-1.40 (8H, m), 1.55-1.80 (5H, m), 2.30-2.55 (2H, dq), 2.65-2.90 (2H, m), 3.45-3.55 (1H, m), 4.00-4.10 (1H, dd), 5.87 (1H, t), 7.10 (1H, t), 7.15 (1H, t), 7.30 (1H, d), 7.47 (1H, d), 7.80 (1H, br s). This method was used in the synthesis of the following compounds: MN0477, MN0642, MN0908, MN1132, MN1133, MN1135, MN1137, MN1138, MN1152, MN1156, MN1157, MN1188, MN1193, MN1197, MN1203, MN1206, MN1207, MN1208, MN1209, MN1210, MN1211, MN1212, MN1213, MN1214, MN1216, MN1217, MN1218, MN1219.

Synthesis Example 11: MN1186 (Coupling by Method F)

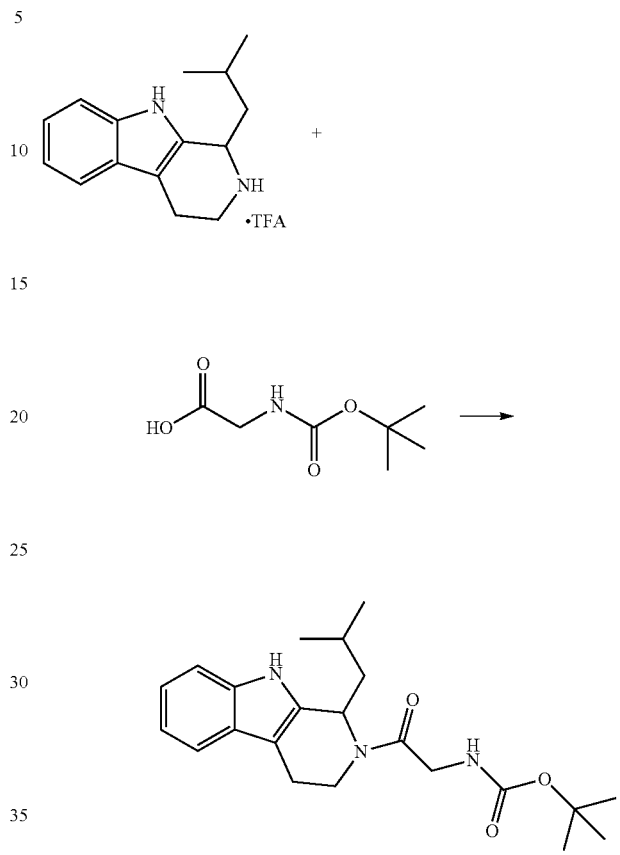

1-Isobutyl-2,3,4,9-tetrahydro-1H-pyrido[3,4-b]indole TFA salt (410 mg, 1.20 mmol), 1-ethyl-3-(3-dimethylaminopropyl)carbodiimide-HCl (EDC-HCl) (230 mg, 1.20 mmol), 4-dimethylaiminopyridine (DMAP) (13 mg, 0.12 mmol), hydroxybenzotriazole (HOBT) (61 mg, 0.40 mmol), and Boc-glycine (210 mg, 1.20 mmol) were all dissolved in acetonitrile (ACN) (1.5 mL), dimethylformamide (DMF) (6 mL), and diisopropylethylamine (DIEA) (240 µL, 1.44 mmol). The solution was stirred for 17 hours. The solution was diluted with EtOAc (100 mL), washed with 1N HCl (3×25 mL), sat. $NaHCO_3$ (3×25 mL), and sat. NaCl (25 mL). The organic layer was dried (anhyd. $Na_2SO_4$), filtered, and evaporated under vacuum, yielding an oil. This material was further purified by silica gel chromatography using: 9 fractions (200 mL) consisting of 0%, 1%, 2%, 4%, 4%, 5%, 5%, 5% and 5% EtOAc in $CH_2Cl_2$. Fractions containing product were combined, and the solvent was evaporated under vacuum, yielding a white solid (331 mg, 71.6% yield; TLC $R_f$=0.59 (10% EtOAc in $CH_2Cl_2$); HPLC $R_t$=4.577 min); $^1$H NMR ($CDCl_3$, 0.003% v/v TMS, 400 MHz): $δ_H$ 0.95 (3H, d) 1.10 (3H, d), 1.45 (9H, s), 1.55-1.85 (3H, m), 2.70-2.93 (2H, m), 3.40-3.55 (1H, m), 3.87-4.20 (3H, m), 5.60 (1H, br s), 5.80 (1H, dt), 7.05-7.20 (2H, m), 7.30 (1H, d), 7.45 (1H, d), 7.80 (1H, br s).

The following compounds were synthesized in a similar manner to MN1186: MN1462, MN1463, MN1464, MN1465, MN1466, MN1467, MN1468, MN1469, MN1470, and MN1471.

Synthesis Example 25: MN1254 (Cyclization by Method E)

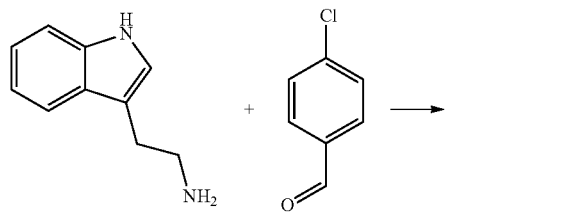

Tryptamine (1.60 g, 10 mmol) was dissolved in EtOAc (5 mL) by swirling and heating with a heat gun until dissolved. Then 4-chlorobenzaldehyde (1.48 g, 10.5 mmol) was added. The reaction vessel was swirled and heated with a heat gun to dissolve. The Schiff base intermediate precipitated within 2 min. The reaction mixture was cooled to room temperature and the intermediate Schiff base was collected on fritted glass and then dried under vacuum to yield 2.36 g of intermdieate as a tan powder. The Schiff base was dissolved in acetonitrile/absolute ethanol (12.5 mL/12.5 mL). 4N HCl in dioxane (4 mL, 16 mmol) was added. The solution was heated to reflux at which point the HCl salt of the cyclized product began to precipitate. The reaction mixture was then cooled to −20 C and the solid was collected on fritted glass. The product, 1-(4-chlorophenyl)-2,3,4,9-tetrahydro-1H-pyrido[3,4-b]indole hydrochloride, was dried under vacuum to yield 2.16 g, 85% yield (68% overall) of an off-white powder: Mp: 163-165 C (free base).

Synthesis Example 27: MN0716 (Indole Analog Synthesis)

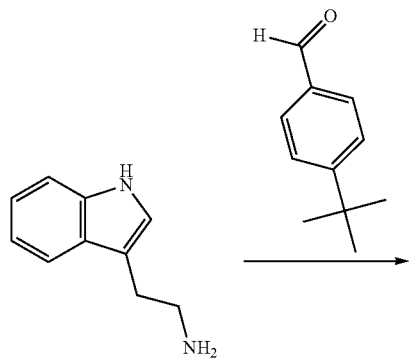

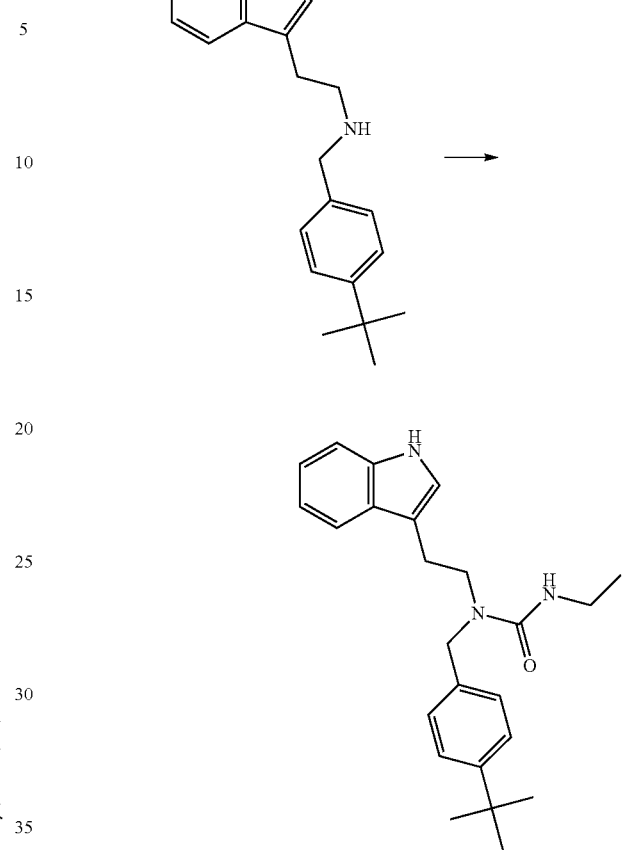

N-(4-tert-butylbenzyl)-2-(1H-indol-3-yl)ethanamine: To a solution of tryptamine (1.5 g, 9.4 mmol) was in abs. EtOH (15 mL) was added 4-t-butylbenzaldehyde (2.0 mL, 12 mmol). The reaction was stirred for 1 h before cooling to 0C and then adding NaBH4 (750 mg, 19 mmol). The solution was stirred for 1 h at 0 C. The solution was concentrated in vacuo and then dried under high vacuum. The reaction was then quenched with 1N HCl (~20 mL), then EtOAc (100 mL) was added to form a precipitate. The mixture was made basic (pH 10) with solid K2CO3. The layers were separated, dried over Na2O4 and evaporated to yield 300 mg of oil. This material was purified by first adding 1N HCl (10 mL), then EtOAc (50 mL) was added to precipitate N-(4-tert-butylbenzyl)-2-(1H-indol-3-yl)ethanamineas a solid: 260 mg (9% yield); HPLC $R_t$ (2.757 min).

To an ice-cold solution of N-(4-tert-butylbenzyl)-2-(1H-indol-3-yl)ethanamine (100 mg, 0.327 mmol) in CH2Cl2 was added ethyl isocyanate (26 uL, 0.327 mmol) (chilled to 0C in 1.5 mL of CH2Cl2). The reaction was stirred at 0C for 5 min. After 1 h, 0.2 equiv of ethyl isocyanate was then added and stirred for another 30 min. The solution was diluted with CH2Cl2 and washed with sat. NaHCO3. The solution was chromatographed on silica gel eluting with hexane/ethyl acetate [2:1 to 1:1] to provide 129 mg, 100% yield of product; HPLC $R_t$ 4.664 min; TLC $R_f$ 0.16, 10% EtOAc in CH2Cl2. This method was used in the synthesis of the following compounds: MN0716, MN0733, and MN1058.

Synthesis Example 28: MN1292

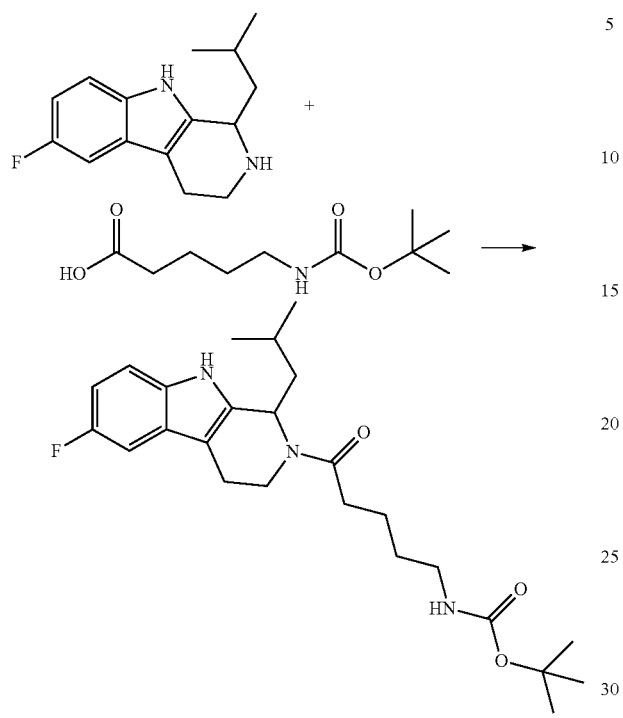

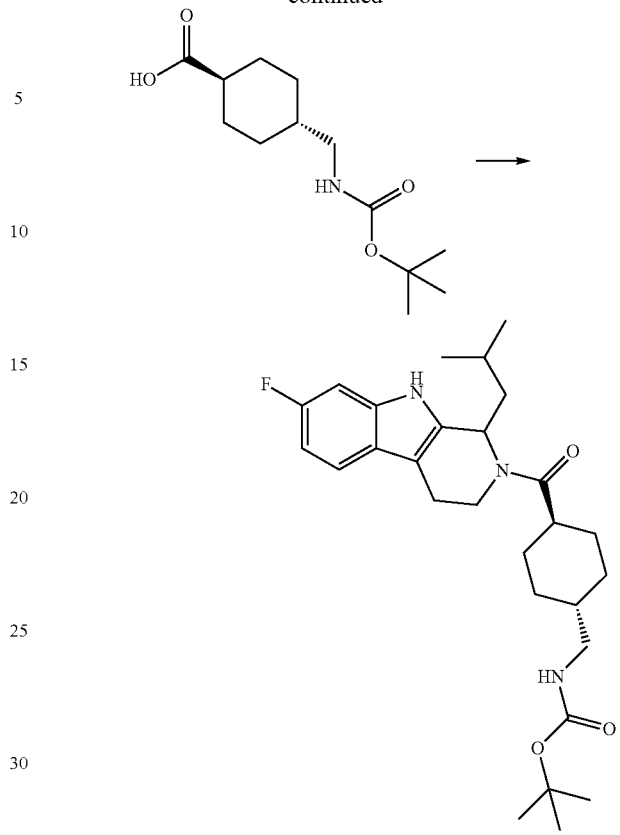

6-Fluoro-1-isobutyl-2,3,4,9-tetrahydro-1H-pyrido[3,4-b]indole (246 mg, 1.00 mmol), 1-ethyl-3-(3-dimethylaminopropyl)carbodiimide-HCl (EDC-HCl) (192 mg, 1.00 mmol), 4-dimethylaminopyridine (DMAP) (12 mg, 0.10 mmol), hydroxybenzotriazole (HOBT) (51 mg, 0.33 mmol), and 5-(tert-butoxycarbonylamino)pentanoic acid (217 mg, 1.00 mmol) were all dissolved in acetonitrile (1.25 mL), dimethylformamide (DMF) (5 mL), and diisopropylethylamine (DIEA) (200 µL, 1.20 mmol). The reaction was stirred for 18 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 3 fractions (200 mL) consisting of hexane, 27.5% EtOAc in hexane, and 35% EtOAc in hexane. Fractions containing product were combined, and the solvent was evaporated under vacuum, yielding a solid (269 mg, 60.4% yield; TLC $R_f$=0.14 (30% EtOAc in Hexane); HPLC $R_t$=4.683 min).

7-Fluoro-1-isobutyl-2,3,4,9-tetrahydro-1H-pyrido[3,4-b]indole (246 mg, 1.00 mmol), 1-ethyl-3-(3-dimethylaminopropyl)carbodiimide-HCl (EDC-HCl) (192 mg, 1.00 mmol), 4-dimethylaminopyridine (DMAP) (12 mg, 0.10 mmol), hydroxybenzotriazole (HOBT) (51 mg, 0.33 mmol), and trans-4-((tert-butoxycarbonylamino)methyl)cyclohexanecarboxylic acid (257 mg, 1.00 mmol) were all dissolved in acetonitrile (1.25 mL), dimethylformamide (DMF) (5 mL), and diisopropylethylamine (DIEA) (200 µL, 1.20 mmol). The reaction was stirred for 18 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 3 fractions (200 mL) consisting of hexane, 25% EtOAc in hexane, and 30% EtOAc in hexane. Fractions containing product were combined, and the solvent was evaporated under vacuum, yielding a solid (280 mg, 57.7% yield; TLC $R_f$=0.21 (30% EtOAc in Hexane); HPLC $R_t$=4.885 min).

Synthesis Example 29: MN1293

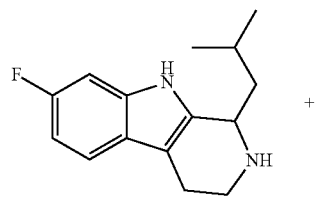

Synthesis Example 30: MN1294

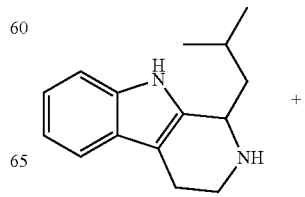

-continued

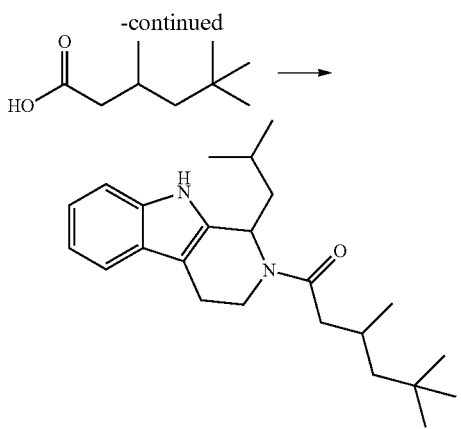

1-Isobutyl-2,3,4,9-tetrahydro-1H-pyrido[3,4-b]indole (228 mg, 1.00 mmol), 1-ethyl-3-(3-dimethylaminopropyl)carbodiimide-HCl (EDC-HCl) (192 mg, 1.00 mmol), 4-dimethylaminopyridine (DMAP) (12 mg, 0.10 mmol), hydroxybenzotriazole (HOBT) (51 mg, 0.33 mmol), and 3,5,5-trimethylhexanoic acid (158 mg, 1.00 mmol) were all dissolved in acetonitrile (1.25 mL), dimethylformamide (DMF) (5 mL), and diisopropylethylamine (DIEA) (200 µL, 1.20 mmol). The reaction was stirred for 18 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 3 fractions (200 mL) consisting of hexane, 10% EtOAc in hexane, and 17% EtOAc in hexane. Fractions containing product were combined, and the solvent was evaporated under vacuum, yielding a solid (315 mg, 85.5% yield; TLC R$_f$=0.12 (10% EtOAc in Hexane); HPLC R$_t$=5.271 min).

Synthesis Example 31: MN1305

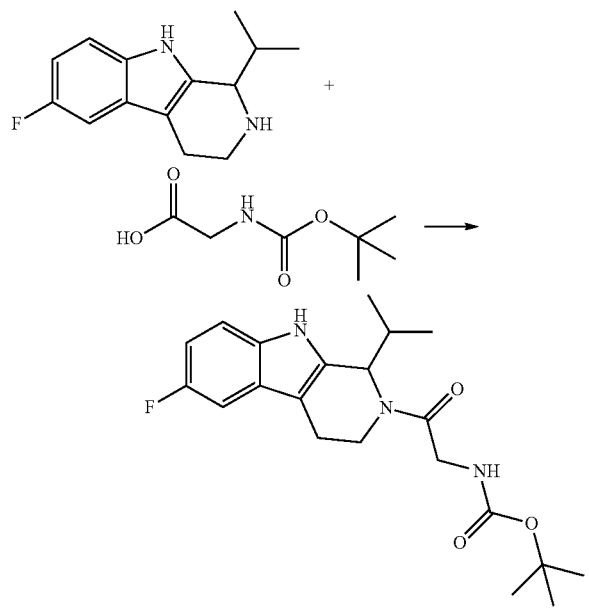

6-Fluoro-1-isopropyl-2,3,4,9-tetrahydro-1H-pyrido[3,4-b]indole (232 mg, 1.00 mmol), 1-ethyl-3-(3-dimethylaminopropyl)carbodiimide-HCl (EDC-HCl) (192 mg, 1.00 mmol), 4-dimethylaminopyridine (DMAP) (12 mg, 0.10 mmol), hydroxybenzotriazole (HOBT) (51 mg, 0.33 mmol), and boc-glycine (175 mg, 1.00 mmol) were all dissolved in acetonitrile (1.25 mL), dimethylformamide (DMF) (5 mL), and diisopropylethylamine (DIEA) (200 µL, 1.20 mmol). The reaction was stirred for 48 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 2 fractions (200 mL) consisting of hexane and 50% EtOAc in hexane. Fractions containing product were combined, and the solvent was evaporated under vacuum, yielding a solid (360 mg, 92.4% yield; TLC R$_f$=0.59 (50% EtOAc in Hexane); HPLC R$_t$=4.386 min).

MN1306—6-Fluoro-isopropyl Carboline with Valeric

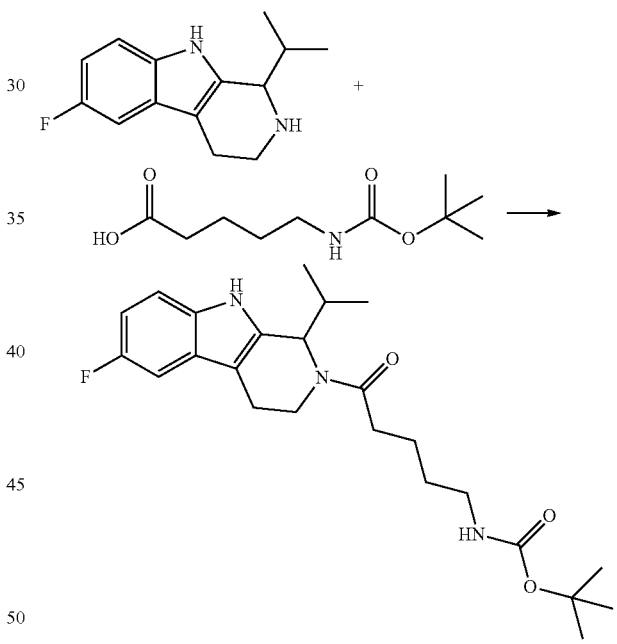

6-Fluoro-1-isopropyl-2,3,4,9-tetrahydro-1H-pyrido[3,4-b]indole (232 mg, 1.00 mmol), 1-ethyl-3-(3-dimethylaminopropyl)carbodiimide-HCl (EDC-HCl) (192 mg, 1.00 mmol), 4-dimethylaminopyridine (DMAP) (12 mg, 0.10 mmol), hydroxybenzotriazole (HOBT) (51 mg, 0.33 mmol), and boc-valeric acid (217 mg, 1.00 mmol) were all dissolved in acetonitrile (1.25 mL), dimethylformamide (DMF) (5 mL), and diisopropylethylamine (DIEA) (200 µL, 1.20 mmol). The reaction was stirred for 48 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 2 fractions (200 mL)

Synthesis Example 32: MN1307

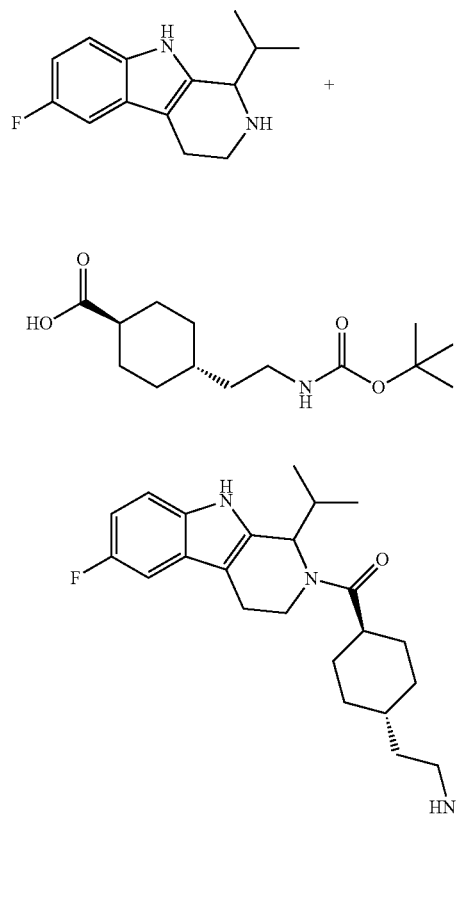

6-Fluoro-1-isopropyl-2,3,4,9-tetrahydro-1H-pyrido[3,4-b]indole (232 mg, 1.00 mmol), 1-ethyl-3-(3-dimethylaminopropyl)carbodiimide-HCl (EDC-HCl) (192 mg, 1.00 mmol), 4-dimethylaminopyridine (DMAP) (12 mg, 0.10 mmol), hydroxybenzotriazole (HOBT) (51 mg, 0.33 mmol), and boc-tranexamic acid (257 mg, 1.00 mmol) were all dissolved in acetonitrile (1.25 mL), dimethylformamide (DMF) (5 mL), and diisopropylethylamine (DIEA) (200 µL, 1.20 mmol). The reaction was stirred for 48 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 2 fractions (200 mL) consisting of hexane and 50% EtOAc in hexane. Fractions containing product were combined, and the solvent was evaporated under vacuum, yielding a solid (391 mg, 82.9% yield; TLC R$_f$=0.36 (50% EtOAc in Hexane); HPLC R$_t$=4.712 min).

consisting of hexane and 50% EtOAc in hexane. Fractions containing product were combined, and the solvent was evaporated under vacuum, yielding a solid (355 mg, 82.3% yield; TLC R$_f$=0.24 (50% EtOAc in Hexane); HPLC R$_t$=4.504 min).

Synthesis Example 33: MN1308

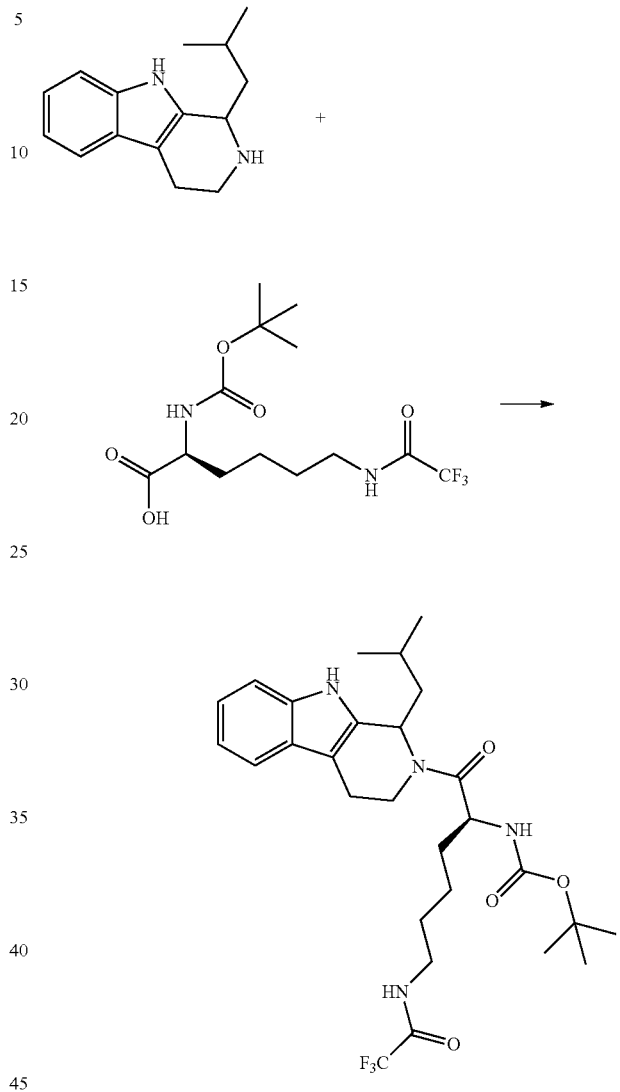

1-Isobutyl-2,3,4,9-tetrahydro-1H-pyrido[3,4-b]indole (456 mg, 2.00 mmol), 1-ethyl-3-(3-dimethylaminopropyl)carbodiimide-HCl (EDC-HCl) (383 mg, 2.00 mmol), 4-dimethylaminopyridine (DMAP) (24 mg, 0.20 mmol), hydroxybenzotriazole (HOBT) (102 mg, 0.66 mmol), and (S)-2-(tert-butoxycarbonylamino)-6-(2,2,2-trifluoroacetamido)hexanoic acid (684 mg, 2.00 mmol) were all dissolved in acetonitrile (2.5 mL), dimethylformamide (DMF) (10 mL), and diisopropylethylamine (DIEA) (400 µL, 2.40 mmol). The reaction was stirred for 18 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: a hexane (200 mL) wash, 3 fractions (200 mL) consisting of 20%, 25%, and 30% EtOAc in hexane. Fractions containing product were combined, and the solvent was evaporated under vacuum, yielding a solid (820 mg, 74% yield; TLC R$_f$=0.10 (25% EtOAc in Hexane); HPLC R$_t$=4.743 min).

Synthesis Example 34: MN1309

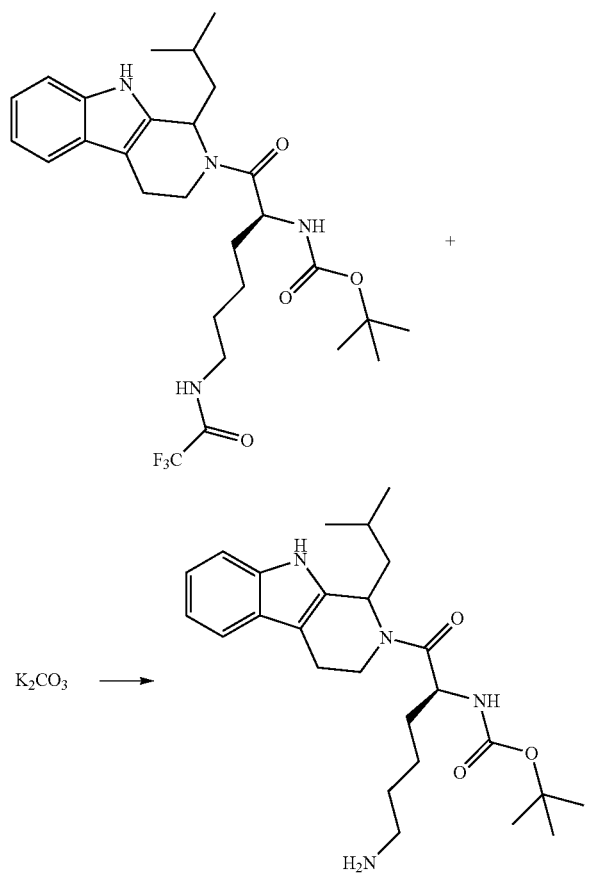

Tert-butyl (2S)-1-(1-isobutyl-3,4-dihydro-1H-pyrido[3,4-b]indol-2(9H)-yl)-1-oxo-6-(2,2,2-trifluoroacetamido)hexan-2-ylcarbamate (553 mg, 1.00 mmol) was dissolved in MeOH (100 mL). $K_2CO_3$ (690 mg, 5.00 mmol) was added to the solution. The solution was refluxed for 18 hrs. The solvent was removed under vacuum and the resulting oil was dissolved in EtOAc (100 mL). The solution was washed with 1M NaOH (25 mL) and sat. NaCl (25 mL). The organic layer was dried (anhyd. $Na_2SO_4$), filtered, and evaporated under vacuum yielding a solid (371 mg, 81.2% yield; TLC $R_f$=0.05 (5% MeOH in CH2Cl2+1% $NH_{40}H$); HPLC $R_t$=3.909 and 3.955 min (diastereomers)).

Synthesis Example 35: MN1310

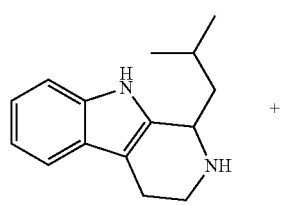

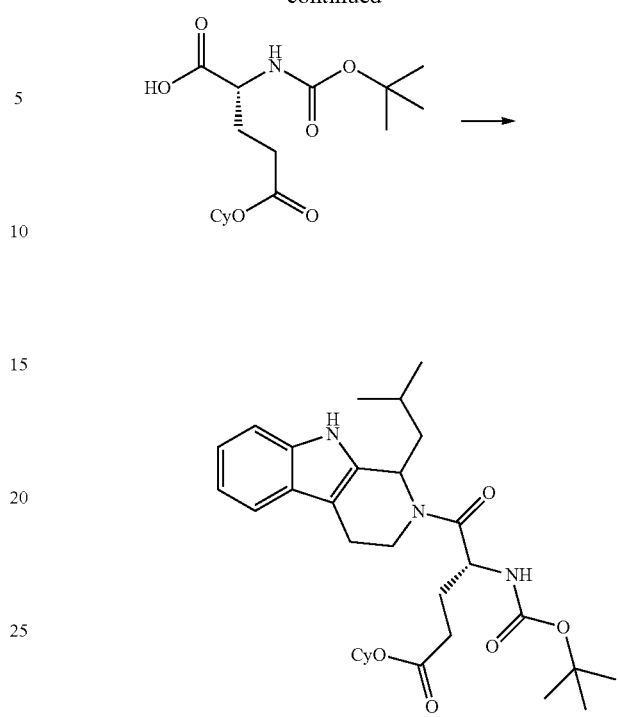

1-Isobutyl-2,3,4,9-tetrahydro-1H-pyrido[3,4-b]indole (456 mg, 2.00 mmol), 1-ethyl-3-(3-dimethylaminopropyl)carbodiimide-HCl (EDC-HCl) (383 mg, 2.00 mmol), 4-dimethylaminopyridine (DMAP) (24 mg, 0.20 mmol), hydroxybenzotriazole (HOBT) (102 mg, 0.66 mmol), and (R)-2-(tert-butoxycarbonylamino)-5-(cyclohexyloxy)-5-oxopentanoic acid (659 mg, 2.00 mmol) were all dissolved in acetonitrile (2.5 mL), dimethylformamide (DMF) (10 mL), and diisopropylethylamine (DIEA) (400 µL, 2.40 mmol). The reaction was stirred for 18 hours at RT. The reaction mixture was diluted with EtOAc (100 mL), washed with sat. NaCl (2×50 mL), 1M citric acid (3×25 mL), sat. $NaHCO_3$ (3×25 mL), and sat. NaCl (50 mL). The organic layer was dried (anhyd. $Na_2SO_4$), filtered, and evaporated under vacuum. This material was further purified by silica gel (25-30 g) chromatography using: 4 fractions (200 mL) consisting of hexane, 15% EtOAc in hexane, 17.5% EtOAc in hexane, and 22.5% EtOAc in hexane. Fractions containing product were combined, and the solvent was evaporated under vacuum, yielding a solid (808 mg, 74.9% yield; TLC $R_f$=0.20 (20% EtOAc in Hexane); HPLC $R_t$=5.269 min).

Synthesis Example 36: MN1311

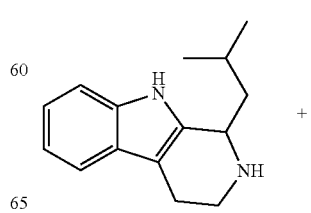

-continued

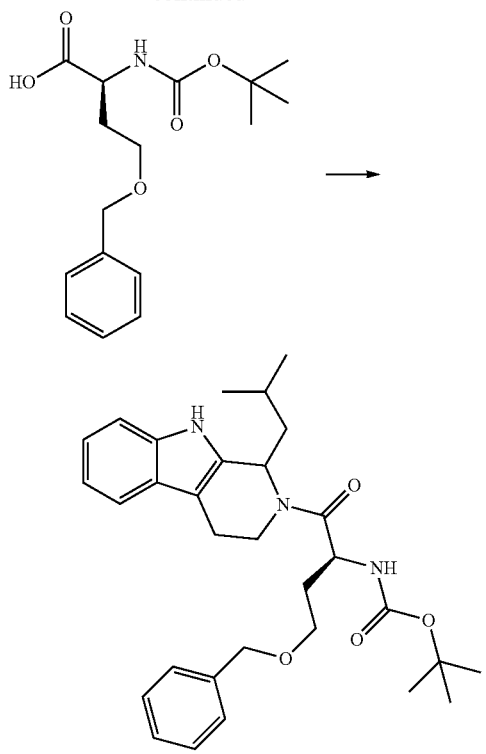

1-Isobutyl-2,3,4,9-tetrahydro-1H-pyrido[3,4-b]indole (457 mg, 2.00 mmol), 1-ethyl-3-(3-dimethylaminopropyl) carbodiimide-HCl (EDC-HCl) (383 mg, 2.00 mmol), 4-dimethylaminopyridine (DMAP) (24 mg, 0.20 mmol), hydroxybenzotriazole (HOBT) (102 mg, 0.66 mmol), (S)-4-(benzyloxy)-2-(tert-butoxycarbonylamino)butanoic acid (619 mg, 2.00 mmol) were all dissolved in acetonitrile (2.5 mL), dimethylformamide (DMF) (10 mL), and diisopropylethylamine (DIEA) (400 µL, 2.40 mmol). The reaction was stirred for 18 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 15% EtOAc in hexane, 20% EtOAc in hexane, and 25% EtOAc in hexane. Fractions containing product were combined, and the solvent was evaporated under vacuum, yielding a solid (688 mg, 66.2% yield; TLC R$_f$=0.34 (30% EtOAc in Hexane); HPLC R$_t$=5.107 min).

Synthesis Example 37: MN1312

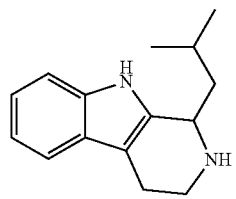

-continued

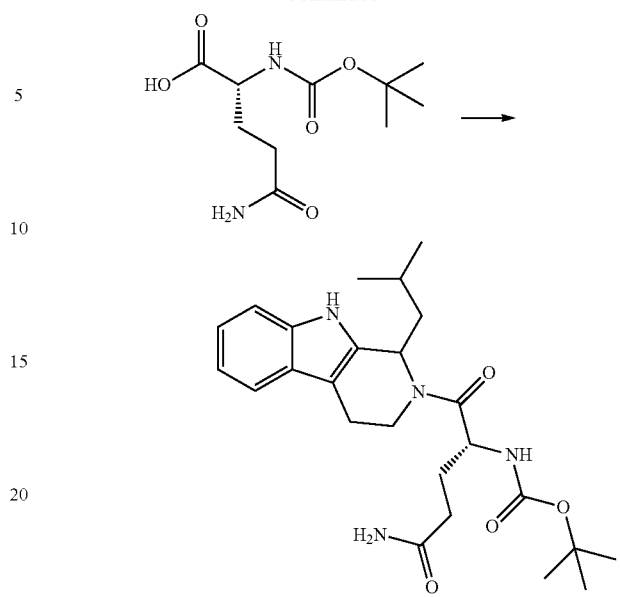

1-Isobutyl-2,3,4,9-tetrahydro-1H-pyrido[3,4-b]indole (228 mg, 1.00 mmol), 1-ethyl-3-(3-dimethylaminopropyl) carbodiimide-HCl (EDC-HCl) (192 mg, 1.00 mmol), 4-dimethylaminopyridine (DMAP) (12 mg, 0.10 mmol), hydroxybenzotriazole (HOBT) (51 mg, 0.33 mmol), and (R)-5-amino-2-(tert-butoxycarbonylamino)-5-oxopentanoic acid (246 mg, 1.00 mmol) were all dissolved in acetonitrile (1.25 mL), dimethylformamide (DMF) (5 mL), and diisopropylethylamine (DIEA) (200 µL, 1.20 mmol). The reaction was stirred for 18 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of CH$_2$Cl$_2$, 4%, 4.5%, and 5% MeOH in CH$_2$Cl$_2$. Fractions containing product were combined, and the solvent was evaporated under vacuum, yielding a solid (264 mg, 57.8% yield; TLC R$_f$=0.05 (4% MeOH in CH$_2$Cl$_2$); HPLC R$_t$=4.149 min).

Synthesis Example 38: MN1317

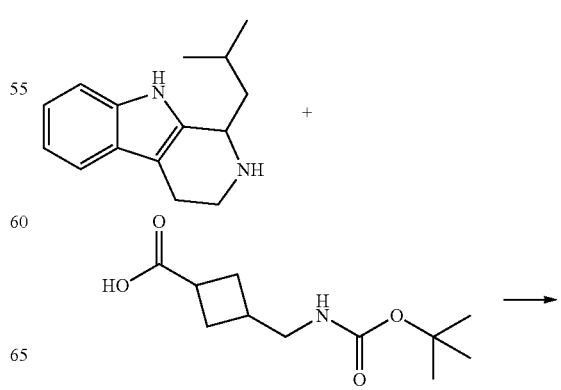

-continued

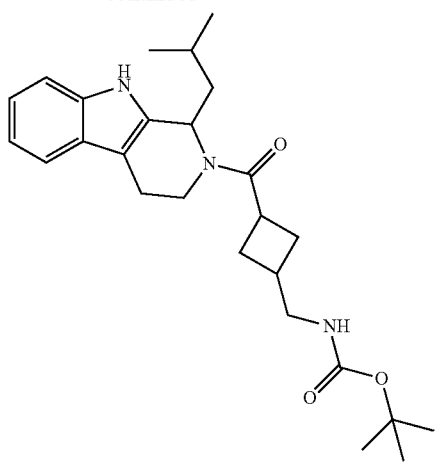

1-Isobutyl-2,3,4,9-tetrahydro-1H-pyrido[3,4-b]indole (158.5 mg, 0.694 mmol), 1-ethyl-3-(3-dimethylaminopropyl)carbodiimide-HCl (EDC-HCl) (133 mg, 0.694 mmol), 4-dimethylaminopyridine (DMAP) (8.5 mg, 0.0694 mmol), hydroxybenzotriazole (HOBT) (35 mg, 0.229 mmol), and 3-((tert-butoxycarbonylamino)methyl)cyclobutanecarboxylic acid (159 mg, 0.694 mmol) were all dissolved in acetonitrile (867.5 μL), dimethylformamide (DMF) (3.47 mL), and diisopropylethylamine (DIEA) (134 μL, 0.833 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 20% EtOAc in hexane, 25% EtOAc in hexane, and 32% EtOAc in hexane. Fractions containing product were combined, and the solvent was evaporated under vacuum, yielding a solid (149 mg, 48.8% yield; TLC R$_f$=0.12 (25% EtOAc in Hexane); HPLC R$_t$=4.713 min).

Synthesis Example 39: MN1318

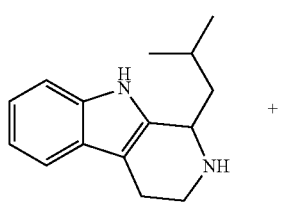

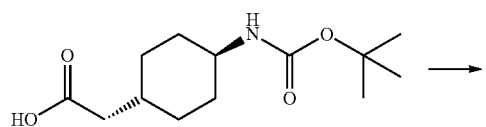

-continued

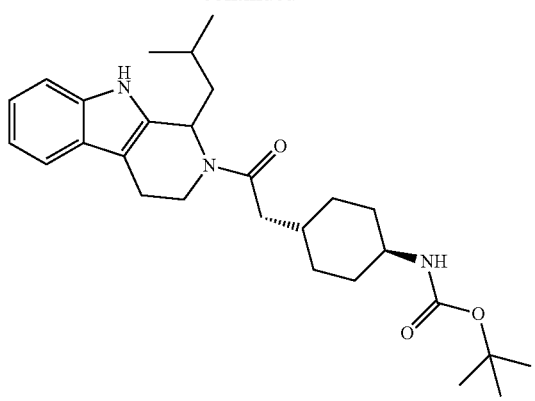

1-Isobutyl-2,3,4,9-tetrahydro-1H-pyrido[3,4-b]indole (158.5 mg, 0.694 mmol), 1-ethyl-3-(3-dimethylaminopropyl)carbodiimide-HCl (EDC-HCl) (133 mg, 0.694 mmol), 4-dimethylaminopyridine (DMAP) (8.5 mg, 0.0694 mmol), hydroxybenzotriazole (HOBT) (35 mg, 0.229 mmol), and 2-(trans-4-(tert-butoxycarbonylamino)cyclohexyl)acetic acid (178 mg, 0.694 mmol) were all dissolved in acetonitrile (867.5 μL), dimethylformamide (DMF) (3.47 mL), and diisopropylethylamine (DIEA) (134 μL, 0.833 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 20% EtOAc in hexane, 25% EtOAc in hexane, and 32% EtOAc in hexane. Fractions containing product were combined, and the solvent was evaporated under vacuum, yielding a solid (163 mg, 50.2% yield; TLC R$_f$=0.17 (25% EtOAc in Hexane); HPLC R$_t$=4.870 min).

Synthesis Example 40: MN1319

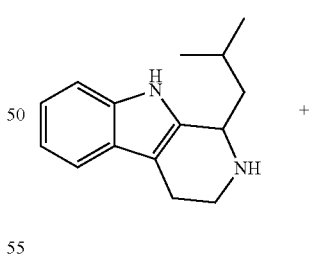

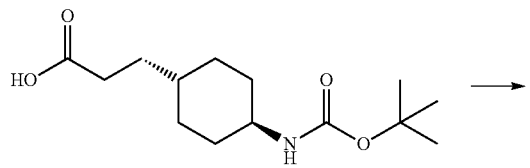

121

-continued

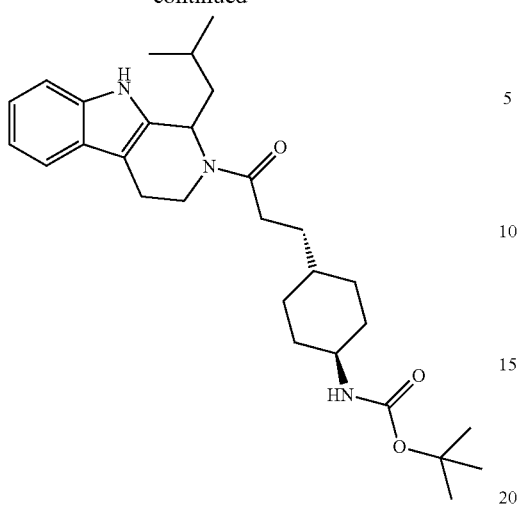

1-Isobutyl-2,3,4,9-tetrahydro-1H-pyrido[3,4-b]indole (158.5 mg, 0.694 mmol), 1-ethyl-3-(3-dimethylaminopropyl)carbodiimide-HCl (EDC-HCl) (133 mg, 0.694 mmol), 4-dimethylaminopyridine (DMAP) (8.5 mg, 0.0694 mmol), hydroxybenzotriazole (HOBT) (35 mg, 0.229 mmol), and 3-(trans-4-(tert-butoxycarbonylamino)cyclohexyl)propanoic acid (188 mg, 0.694 mmol) were all dissolved in acetonitrile (867.5 µL), dimethylformamide (DMF) (3.47 mL), and diisopropylethylamine (DIEA) (134 µL, 0.833 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 20% EtOAc in hexane, 25% EtOAc in hexane, and 32% EtOAc in hexane. Fractions containing product were combined, and the solvent was evaporated under vacuum, yielding a solid (176 mg, 52.7% yield; TLC R$_f$=0.13 (25% EtOAc in Hexane); HPLC R$_t$=4.984 min).

Synthesis Example 41: MN1320

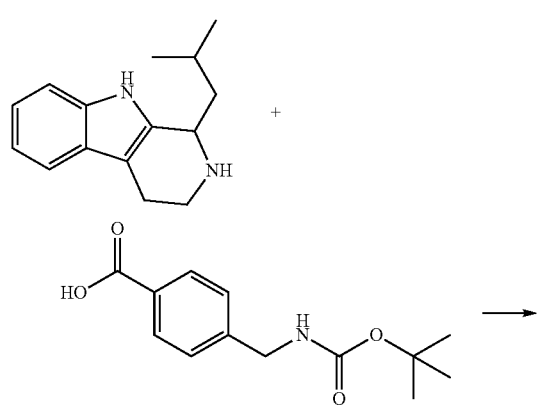

122

-continued

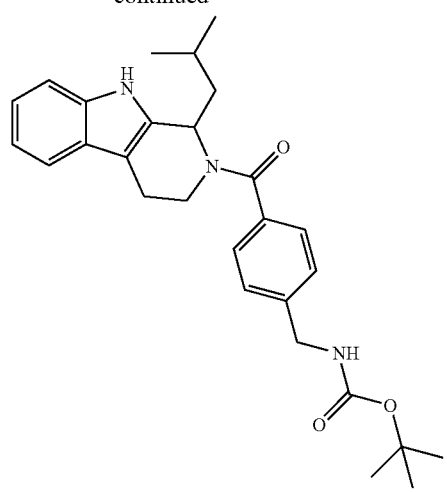

1-Isobutyl-2,3,4,9-tetrahydro-1H-pyrido[3,4-b]indole (158.5 mg, 0.694 mmol), 1-ethyl-3-(3-dimethylaminopropyl)carbodiimide-HCl (EDC-HCl) (133 mg, 0.694 mmol), 4-dimethylaminopyridine (DMAP) (8.5 mg, 0.0694 mmol), hydroxybenzotriazole (HOBT) (35 mg, 0.229 mmol), and 4-((tert-butoxycarbonylamino)methyl)benzoic acid (174 mg, 0.694 mmol) were all dissolved in acetonitrile (867.5 µL), dimethylformamide (DMF) (3.47 mL), and diisopropylethylamine (DIEA) (134 µL, 0.833 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 20% EtOAc in hexane, 25% EtOAc in hexane, and 32% EtOAc in hexane. Fractions containing product were combined, and the solvent was evaporated under vacuum, yielding a solid (162 mg, 50.6% yield; TLC R$_f$=0.10 (25% EtOAc in Hexane); HPLC R$_t$=4.771 min).

Synthesis Example 42: MN1321

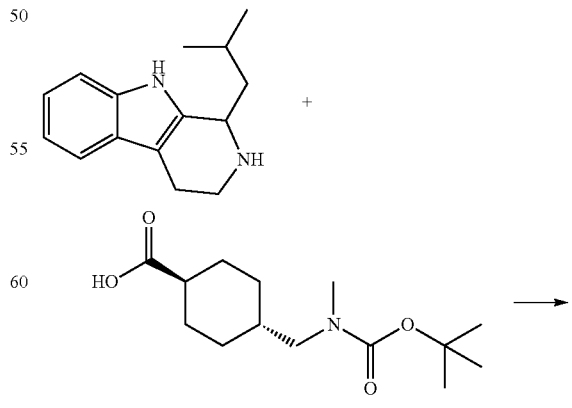

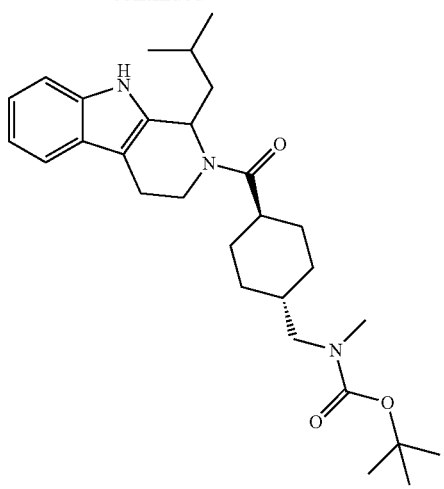

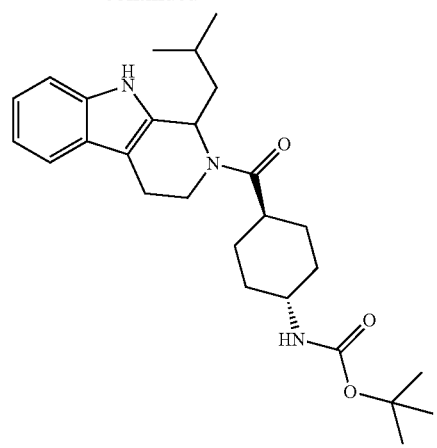

1-Isobutyl-2,3,4,9-tetrahydro-1H-pyrido[3,4-b]indole (158.5 mg, 0.694 mmol), 1-ethyl-3-(3-dimethylaminopropyl)carbodiimide-HCl (EDC-HCl) (133 mg, 0.694 mmol), 4-dimethylaminopyridine (DMAP) (8.5 mg, 0.0694 mmol), hydroxybenzotriazole (HOBT) (35 mg, 0.229 mmol), and trans-4-((tert-butoxycarbonyl(methyl)amino)methyl)cyclohexanecarboxylic acid (188 mg, 0.694 mmol) were all dissolved in acetonitrile (867.5 μL), dimethylformamide (DMF) (3.47 mL), and diisopropylethylamine (DIEA) (134 μL, 0.833 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 20% EtOAc in hexane, 25% EtOAc in hexane, and 30% EtOAc in hexane. Fractions containing product were combined, and the solvent was evaporated under vacuum, yielding a solid (165 mg, 49.4% yield; TLC R$_f$=0.15 (25% EtOAc in Hexane); HPLC R$_t$=5.096 min).

1-Isobutyl-2,3,4,9-tetrahydro-1H-pyrido[3,4-b]indole (228 mg, 1.00 mmol), 1-ethyl-3-(3-dimethylaminopropyl)carbodiimide-HCl (EDC-HCl) (192 mg, 1.00 mmol), 4-dimethylaminopyridine (DMAP) (12 mg, 0.10 mmol), hydroxybenzotriazole (HOBT) (51 mg, 0.33 mmol), and boc-tranexamic acid (250 mg, 1.00 mmol) were all dissolved in acetonitrile (1.25 mL), dimethylformamide (DMF) (5 mL), and diisopropylethylamine (DIEA) (200 μL, 1.20 mmol). The reaction was stirred for 18 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 3 fractions (200 mL) consisting of 25%, 35%, and 40% EtOAc in hexane. Fractions containing product were combined, and the solvent was evaporated under vacuum, yielding a solid (250 mg, 55.1% yield; TLC R$_f$=0.19 (30% EtOAc in Hexane); HPLC R$_t$=4.739 min).

Synthesis Example 43: MN1322

Synthesis Example 44: MN1329

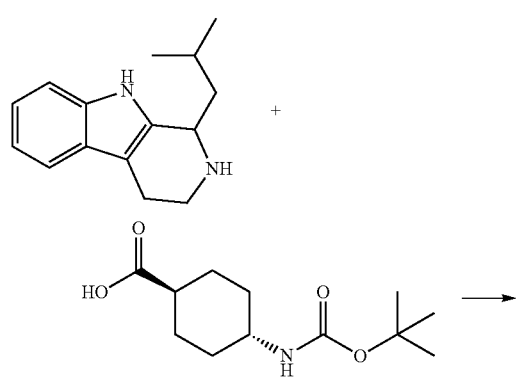

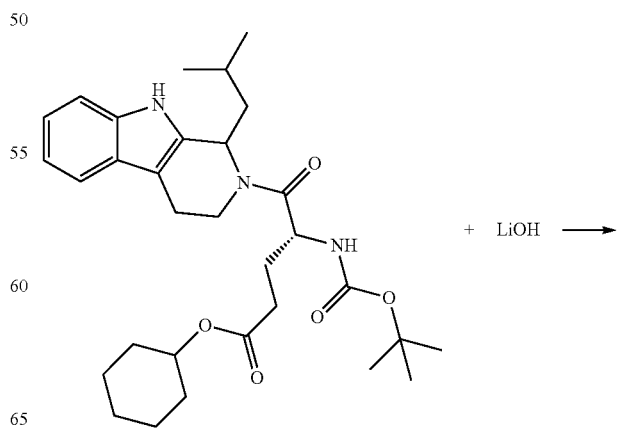

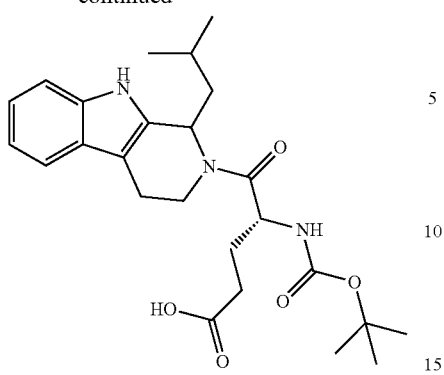

(4R)-Cyclohexyl-4-(tert-butoxycarbonylamino)-5-(1-isobutyl-3,4-dihydro-1H-pyrido[3,4-b]indol-2(9H)-yl)-5-oxopentanoate (540 mg, 1.00 mmol) was dissolved in MeOH (18.4 mL). $H_2O$ (5.3 mL) and LiOH (210 mg, 5 mmol) were added to the mixture and stirred. After four hours, 75% of the solvent was removed under the vacuum. The mixture was transferred to a separatory funnel and diluted with $H_2O$ (25 mL). The solution was washed with diethylether (4×25 mL). The aqueous layer was acidified with 1N HCl (5 mL) to pH 2 determined by pH paper, extracted with $CH_2Cl_2$ (4×50 mL). The solvent was removed under vacuum, yielding a white solid (369 mg, 80.7% yield; TLC $R_f$=0.59 (5% MeOH in $CH_2Cl_2$+1% HOAc); HPLC $R_t$=4.304 min).

Synthesis Example 45: MN1330

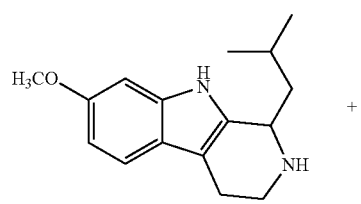

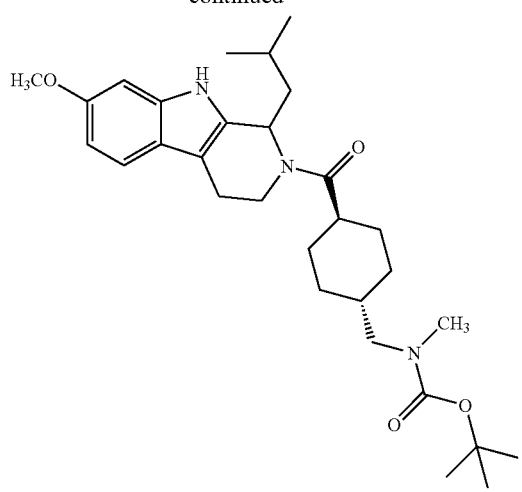

1-Isobutyl-7-methoxy-2,3,4,9-tetrahydro-1H-pyrido[3,4-b]indole (159 mg, 0.614 mmol), 1-ethyl-3-(3-dimethylaminopropyl)carbodiimide-HCl (EDC-HCl) (118 mg, 0.614 mmol), 4-dimethylaminopyridine (DMAP) (7.5 mg, 0.0614 mmol), hydroxybenzotriazole (HOBT) (31 mg, 0.203 mmol), and trans-4-(Boc-methylaminomethyl)cyclohexane carboxylic acid (167 mg, 0.614 mmol) were all dissolved in acetonitrile (768 μL), dimethylformamide (DMF) (3.07 mL), and diisopropylethylamine (DIEA) (122 μL, 0.737 mmol). The reaction was stirred for 17 hours at RT. The reaction mixture was diluted with EtOAc (100 mL), washed with sat. NaCl (2×50 mL), 1M citric acid (3×25 mL), sat. $NaHCO_3$ (3×25 mL), and sat. NaCl (50 mL). The organic layer was dried (anhyd. $Na_2SO_4$), filtered, and evaporated under vacuum. This material was further purified by silica gel (25-30 g) chromatography using: 4 fractions (200 mL) consisting of hexane, 30% EtOAc in hexane, 40% EtOAc in hexane, and 50% EtOAc in hexane. Fractions containing product were combined, and the solvent was evaporated under vacuum, yielding a solid (218 mg, 69.4% yield; TLC $R_f$=0.33 (40% EtOAc in Hexane); HPLC $R_t$=5.031 min).

Synthesis Example 46: MN1331

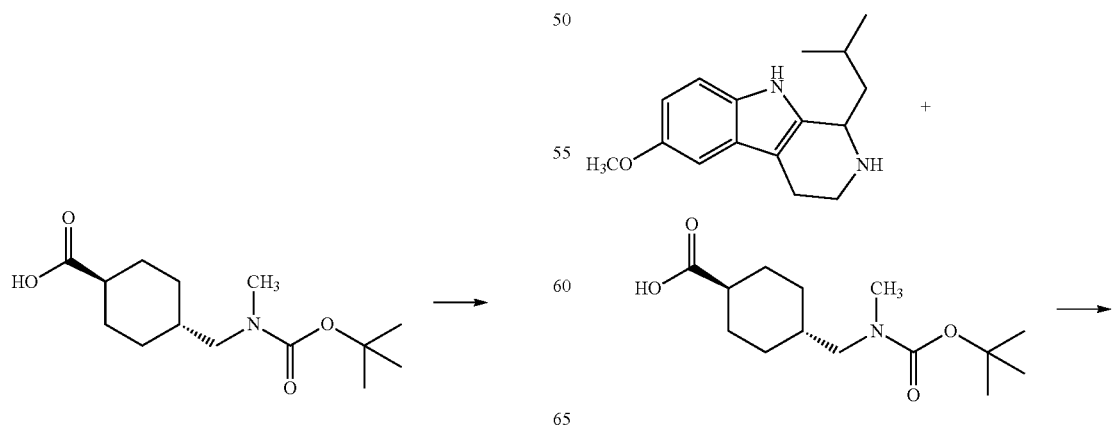

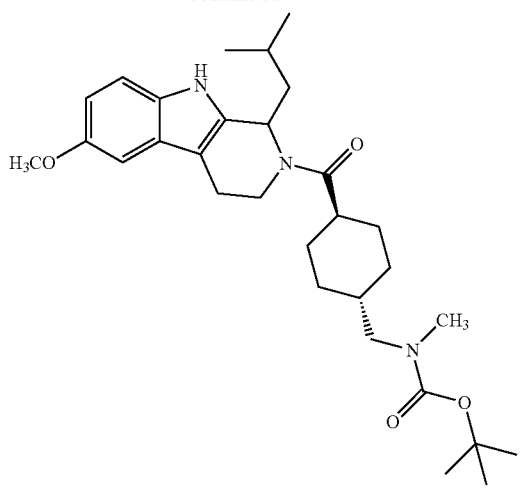
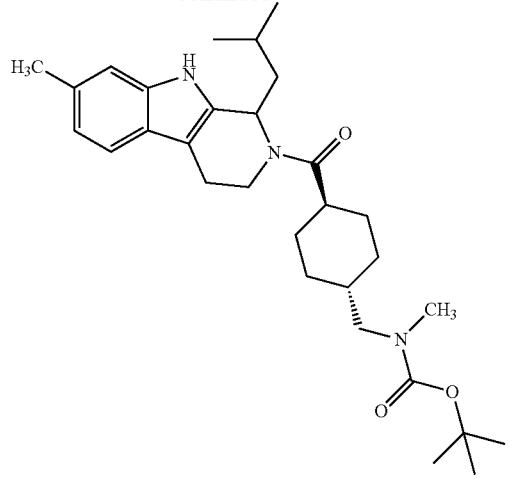

1-Isobutyl-6-methoxy-2,3,4,9-tetrahydro-1H-pyrido[3,4-b]indole (159 mg, 0.614 mmol), 1-ethyl-3-(3-dimethylaminopropyl)carbodiimide-HCl (EDC-HCl) (118 mg, 0.614 mmol), 4-dimethylaminopyridine (DMAP) (7.5 mg, 0.0614 mmol), hydroxybenzotriazole (HOBT) (31 mg, 0.203 mmol), and trans-4-(Boc-methylaminomethyl)cyclohexane carboxylic acid (167 mg, 0.614 mmol) were all dissolved in acetonitrile (768 μL), dimethylformamide (DMF) (3.07 mL), and diisopropylethylamine (DIEA) (122 μL, 0.737 mmol). The reaction was stirred for 17 hours at RT. The reaction mixture was diluted with EtOAc (100 mL), washed with sat. NaCl (2×50 mL), 1M citric acid (3×25 mL), sat. NaHCO₃ (3×25 mL), and sat. NaCl (50 mL). The organic layer was dried (anhyd. Na₂SO₄), filtered, and evaporated under vacuum. This material was further purified by silica gel (25-30 g) chromatography using: 4 fractions (200 mL) consisting of hexane, 15% EtOAc in hexane, 25% EtOAc in hexane, and 35% EtOAc in hexane. Fractions containing product were combined, and the solvent was evaporated under vacuum, yielding a solid (159 mg, 50.6% yield; TLC $R_f$=0.15 (30% EtOAc in Hexane); HPLC $R_t$=4.986 min).

Synthesis Example 47: MN1332

1-Isobutyl-7-methyl-2,3,4,9-tetrahydro-1H-pyrido[3,4-b]indole HCl (171 mg, 0.614 mmol), 1-ethyl-3-(3-dimethylaminopropyl)carbodiimide-HCl (EDC-HCl) (118 mg, 0.614 mmol), 4-dimethylaminopyridine (DMAP) (7.5 mg, 0.0614 mmol), hydroxybenzotriazole (HOBT) (31 mg, 0.203 mmol), and trans-4-(Boc-methylaminomethyl)cyclohexane carboxylic acid (167 mg, 0.614 mmol) were all dissolved in acetonitrile (768 μL), dimethylformamide (DMF) (3.07 mL), and diisopropylethylamine (DIEA) (122 μL, 0.737 mmol). The reaction was stirred for 17 hours at RT. The reaction mixture was diluted with EtOAc (100 mL), washed with sat. NaCl (2×50 mL), 1M citric acid (3×25 mL), sat. NaHCO₃ (3×25 mL), and sat. NaCl (50 mL). The organic layer was dried (anhyd. Na₂SO₄), filtered, and evaporated under vacuum. This material was further purified by silica gel (25-30 g) chromatography using: 3 fractions (200 mL) consisting of 20%, 25%, and 35% EtOAc in hexane. Fractions containing product were combined, and the solvent was evaporated under vacuum, yielding a solid (238 mg, 78.2% yield; TLC $R_f$=0.22 (30% EtOAc in Hexane); HPLC $R_t$=5.231 min); LCMS +ESI (14.555-14.672 min), 496.3594 (M+1), 518.3415 (M+23); ¹H NMR (CDCl₃, 0.003% v/v TMS, 400 MHz): $\delta_H$ 0.90-1.15 (9H, m), 1.46 (9H, s), 1.52-1.94 (10H, m), 2.56 (1H, t), 2.72-2.90 (5H, m), 2.97-3.21 (2H, m), 3.42-3.54 (1H, m), 4.10 (1H, d), 5.88 (1H, q), 7.05 (1H, dd), 7.28-7.39 (2H, m), 7.97 (1H, br s).

Synthesis Example 48: MN1333

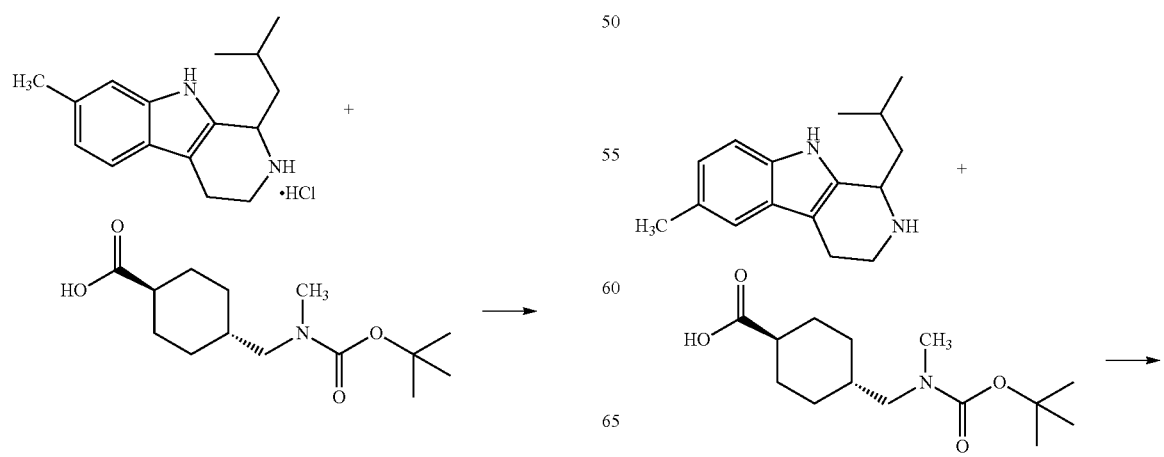

-continued

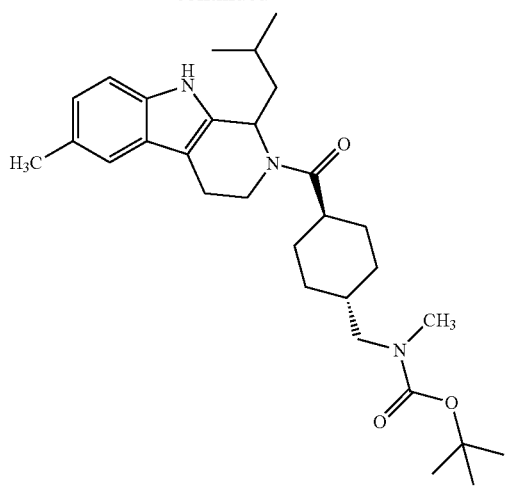

1-Isobutyl-6-methyl-2,3,4,9-tetrahydro-1H-pyrido[3,4-b]indole (150 mg, 0.614 mmol), 1-ethyl-3-(3-dimethylaminopropyl)carbodiimide-HCl (EDC-HCl) (118 mg, 0.614 mmol), 4-dimethylaminopyridine (DMAP) (7.5 mg, 0.0614 mmol), hydroxybenzotriazole (HOBT) (31 mg, 0.203 mmol), and trans-4-(Boc-methylaminomethyl)cyclohexane carboxylic acid (167 mg, 0.614 mmol) were all dissolved in acetonitrile (768 µL), dimethylformamide (DMF) (3.07 mL), and diisopropylethylamine (DIEA) (122 µL, 0.737 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 15% EtOAc in hexane, 25% EtOAc in hexane, and 35% EtOAc in hexane. Fractions containing product were combined, and the solvent was evaporated under vacuum, yielding a solid (233 mg, 76.6% yield; TLC R$_f$=0.32 (30% EtOAc in Hexane); HPLC R$_t$=5.238 min).

Synthesis Example 49: MN1334

-continued

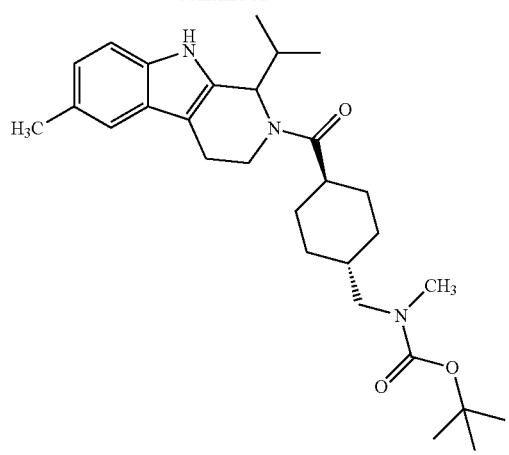

1-Isopropyl-6-methyl-2,3,4,9-tetrahydro-1H-pyrido[3,4-b]indole (140 mg, 0.614 mmol), 1-ethyl-3-(3-dimethylaminopropyl)carbodiimide-HCl (EDC-HCl) (118 mg, 0.614 mmol), 4-dimethylaminopyridine (DMAP) (7.5 mg, 0.0614 mmol), hydroxybenzotriazole (HOBT) (31 mg, 0.203 mmol), and trans-4-(Boc-methylaminomethyl)cyclohexane carboxylic acid (167 mg, 0.614 mmol) were all dissolved in acetonitrile (768 µL), dimethylformamide (DMF) (3.07 mL), and diisopropylethylamine (DIEA) (122 µL, 0.737 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 30% EtOAc in hexane, 40% EtOAc in hexane, and 50% EtOAc in hexane. Fractions containing product were combined, and the solvent was evaporated under vacuum, yielding a solid (191 mg, 64.6% yield; TLC R$_f$=0.35 (40% EtOAc in Hexane); HPLC R$_t$=5.081 min).

Synthesis Example 50: MN1335

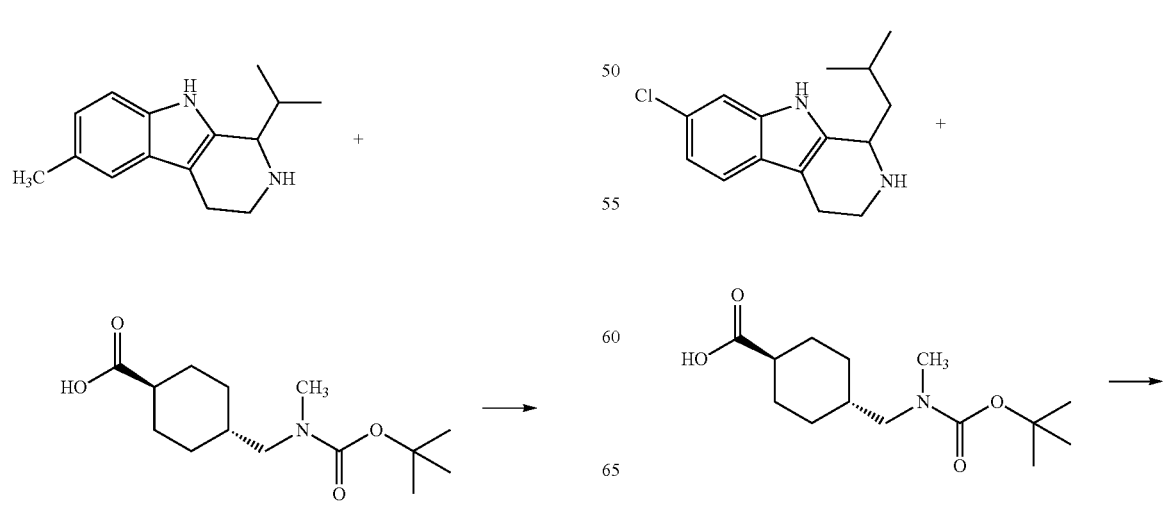

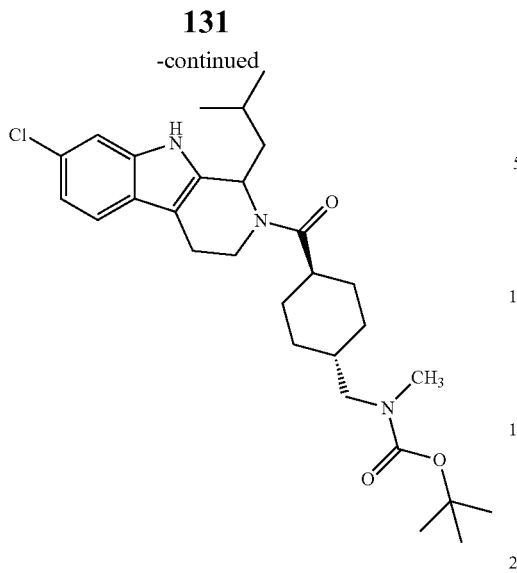

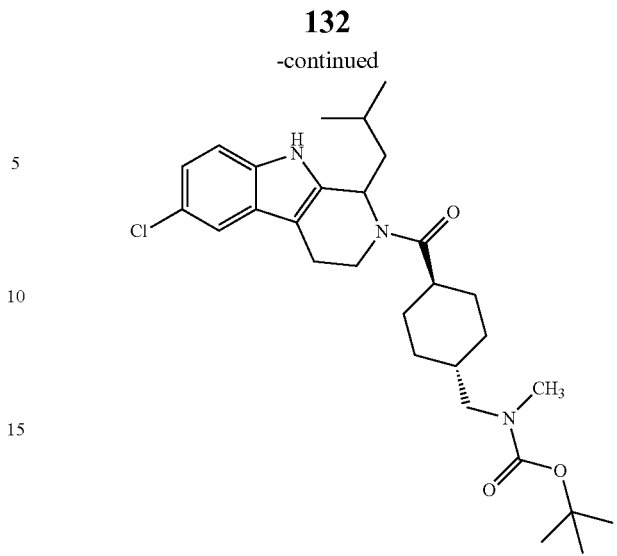

7-Chloro-1-isobutyl-2,3,4,9-tetrahydro-1H-pyrido[3,4-b]indole (161 mg, 0.614 mmol), 1-ethyl-3-(3-dimethylaminopropyl)carbodiimide-HCl (EDC-HCl) (118 mg, 0.614 mmol), 4-dimethylaminopyridine (DMAP) (7.5 mg, 0.0614 mmol), hydroxybenzotriazole (HOBT) (31 mg, 0.203 mmol), and trans-4-(Boc-methylaminomethyl)cyclohexane carboxylic acid (167 mg, 0.614 mmol) were all dissolved in acetonitrile (768 µL), dimethylformamide (DMF) (3.07 mL), and diisopropylethylamine (DIEA) (122 µL, 0.737 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 15% EtOAc in hexane, 25% EtOAc in hexane, and 35% EtOAc in hexane. Fractions containing product were combined, and the solvent was evaporated under vacuum, yielding a solid (250 mg, 78.9% yield; TLC R$_f$=0.30 (30% EtOAc in Hexane); HPLC R$_t$=5.282 min); LCMS +ESI (14.672-14.905 min), 516.3049 (M+1), 538.2867 (M+23); $^1$H NMR (CDCl$_3$, 0.003% v/v TMS, 400 MHz): δ$_H$ 0.94-1.15 (8H, m), 1.41 (9H, s), 1.60-1.94 (10H, m), 2.55 (1H, t), 2.71-2.91 (5H, m), 3.00-3.18 (2H, m), 3.48 (1H, t), 4.07 (1H, d), 5.79-5.91 (1H, m), 6.92 (1H, m), 7.10 (1H, s), 7.32 (1H, d), 7.66 (1H, br s).

Synthesis Example 51: MN1336

6-Chloro-1-isobutyl-2,3,4,9-tetrahydro-1H-pyrido[3,4-b]indole·TFA salt (221 mg, 0.614 mmol), 1-ethyl-3-(3-dimethylaminopropyl)carbodiimide-HCl (EDC-HCl) (118 mg, 0.614 mmol), 4-dimethylaminopyridine (DMAP) (7.5 mg, 0.0614 mmol), hydroxybenzotriazole (HOBT) (31 mg, 0.203 mmol), and trans-4-(Boc-methylaminomethyl)cyclohexane carboxylic acid (167 mg, 0.614 mmol) were all dissolved in acetonitrile (768 µL), dimethylformamide (DMF) (3.07 mL), and diisopropylethylamine (DIEA) (244 µL, 1.47 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: a hexane (200 mL) wash, 3 fractions (200 mL) consisting of 25%, 30%, and 35% EtOAc in hexane. Fractions containing product were combined, and the solvent was evaporated under vacuum, yielding a solid (92 mg, 29.0% yield; TLC R$_f$=0.20 (30% EtOAc in Hexane); HPLC R$_t$=5.278 min).

Synthesis Example 52: MN1337

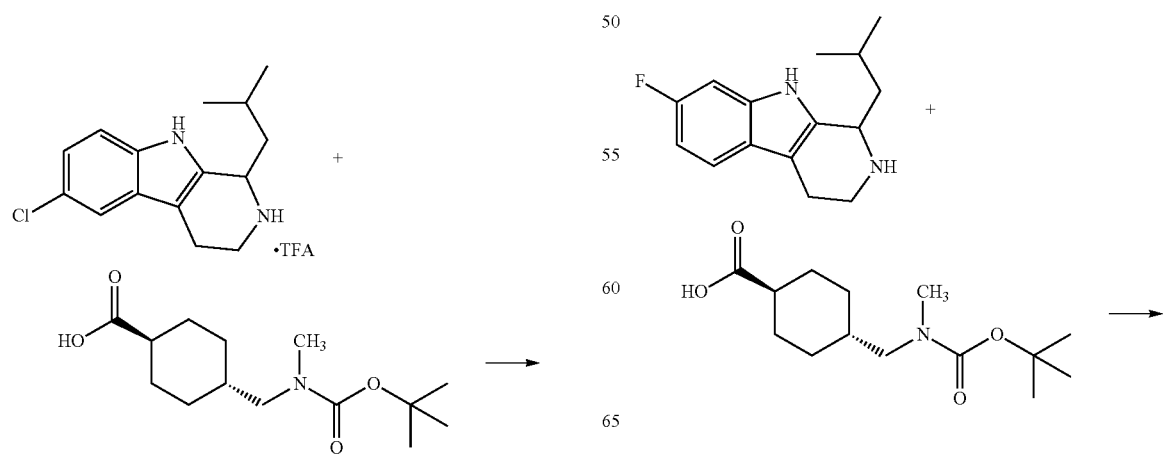

133

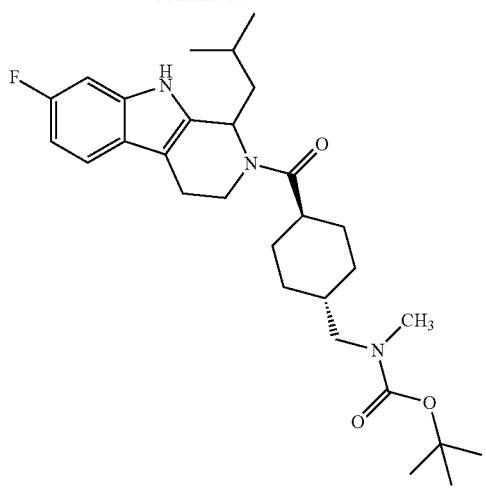

7-Fluoro-1-isobutyl-2,3,4,9-tetrahydro-1H-pyrido[3,4-b]indole (151 mg, 0.614 mmol), 1-ethyl-3-(3-dimethylaminopropyl)carbodiimide-HCl (EDC-HCl) (118 mg, 0.614 mmol), 4-dimethylaminopyridine (DMAP) (7.5 mg, 0.0614 mmol), hydroxybenzotriazole (HOBT) (31 mg, 0.203 mmol), and trans-4-(Boc-methylaminomethyl)cyclohexane carboxylic acid (167 mg, 0.614 mmol) were all dissolved in acetonitrile (768 µL), dimethylformamide (DMF) (3.07 mL), and diisopropylethylamine (DIEA) (122 µL, 0.737 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 15% EtOAc in hexane, 25% EtOAc in hexane, and 35% EtOAc in hexane. Fractions containing product were combined, and the solvent was evaporated under vacuum, yielding a solid (159 mg, 51.8% yield; TLC R$_f$=0.28 (30% EtOAc in Hexane); HPLC R$_t$=5.124 min).

Synthesis Example 53: MN1338

134

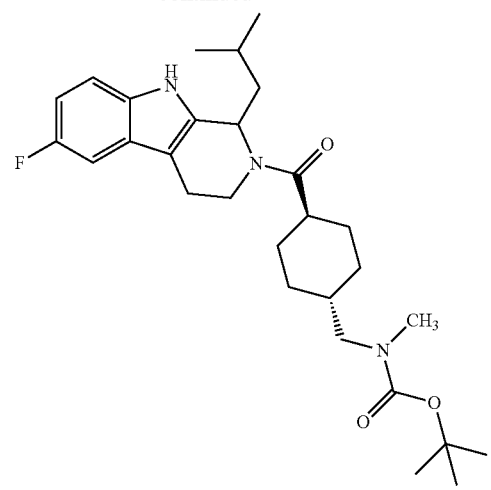

6-Fluoro-1-isobutyl-2,3,4,9-tetrahydro-1H-pyrido[3,4-b]indole (151 mg, 0.614 mmol), 1-ethyl-3-(3-dimethylaminopropyl)carbodiimide-HCl (EDC-HCl) (118 mg, 0.614 mmol), 4-dimethylaminopyridine (DMAP) (7.5 mg, 0.0614 mmol), hydroxybenzotriazole (HOBT) (31 mg, 0.203 mmol), and trans-4-(Boc-methylaminomethyl)cyclohexane carboxylic acid (167 mg, 0.614 mmol) were all dissolved in acetonitrile (768 µL), dimethylformamide (DMF) (3.07 mL), and diisopropylethylamine (DIEA) (122 µL, 0.737 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 30% EtOAc in hexane, 40% EtOAc in hexane, and 50% EtOAc in hexane. Fractions containing product were combined, and the solvent was evaporated under vacuum, yielding a solid (100 mg, 32.6% yield; TLC R$_f$=0.42 (40% EtOAc in Hexane); HPLC R$_t$=5.106 min).

Synthesis Example 54: MN1339

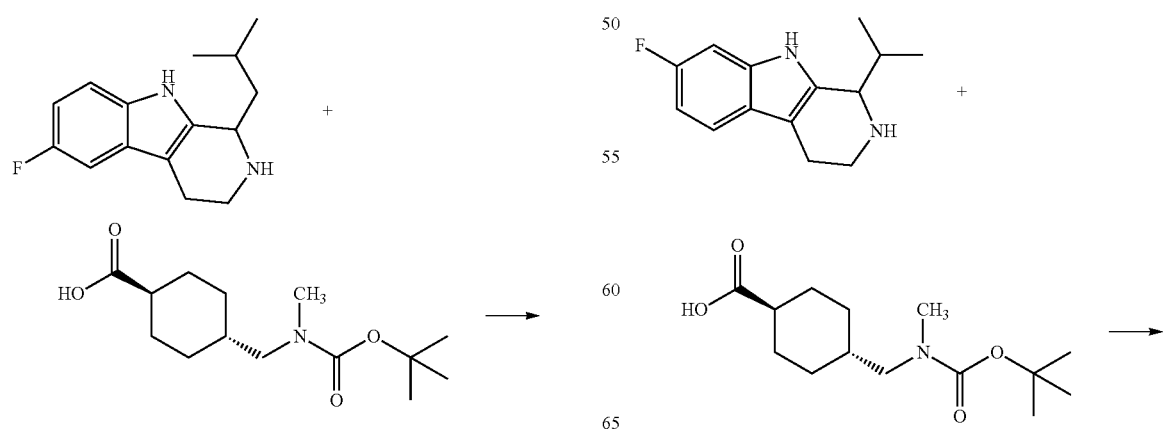

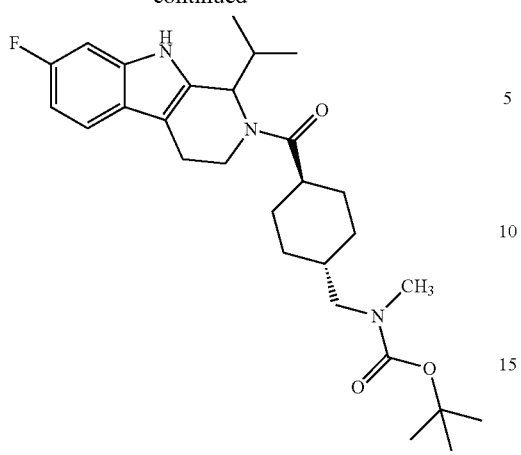
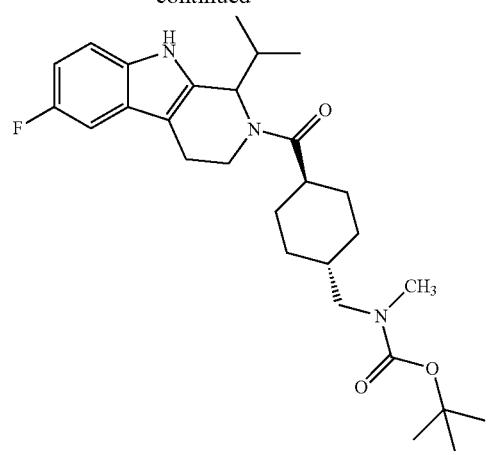

7-Fluoro-1-isopropyl-2,3,4,9-tetrahydro-1H-pyrido[3,4-b]indole (143 mg, 0.614 mmol), 1-ethyl-3-(3-dimethylaminopropyl)carbodiimide-HCl (EDC-HCl) (118 mg, 0.614 mmol), 4-dimethylaminopyridine (DMAP) (7.5 mg, 0.0614 mmol), hydroxybenzotriazole (HOBT) (31 mg, 0.203 mmol), and trans-4-(Boc-methylaminomethyl)cyclohexane carboxylic acid (167 mg, 0.614 mmol) were all dissolved in acetonitrile (768 µL), dimethylformamide (DMF) (3.07 mL), and diisopropylethylamine (DIEA) (122 µL, 0.737 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 30% EtOAc in hexane, 40% EtOAc in hexane, and 50% EtOAc in hexane. Fractions containing product were combined, and the solvent was evaporated under vacuum, yielding a solid (148 mg, 49.6% yield; TLC R$_f$=0.32 (40% EtOAc in Hexane); HPLC R$_t$=4.966 min).

6-Fluoro-1-isopropyl-2,3,4,9-tetrahydro-1H-pyrido[3,4-b]indole (65 mg, 0.280 mmol), 1-ethyl-3-(3-dimethylaminopropyl)carbodiimide-HCl (EDC-HCl) (54 mg, 0.280 mmol), 4-dimethylaminopyridine (DMAP) (3.4 mg, 0.028 mmol), hydroxybenzotriazole (HOBT) (14 mg, 0.092 mmol), and trans-4-(Boc-methylaminomethyl)cyclohexane carboxylic acid (76 mg, 0.280 mmol) were all dissolved in acetonitrile (350 µL), dimethylformamide (DMF) (1.40 mL), and diisopropylethylamine (DIEA) (56 µL, 0.336 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 30% EtOAc in hexane, 40% EtOAc in hexane, and 50% EtOAc in hexane. Fractions containing product were combined, and the solvent was evaporated under vacuum, yielding a solid (94 mg, 69.1% yield; TLC R$_f$=0.28 (40% EtOAc in Hexane); HPLC R$_t$=4.947 min).

Synthesis Example 55: MN1340

Synthesis Example 56: MN1341

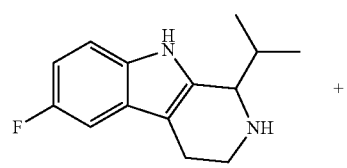
+
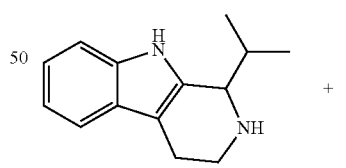
+

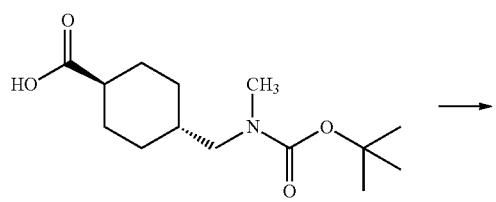
→

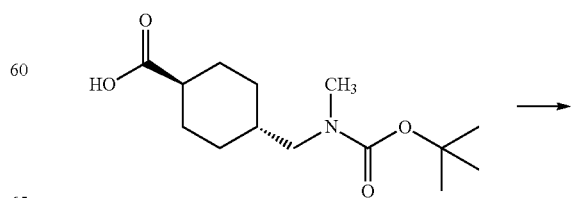
→

137
-continued

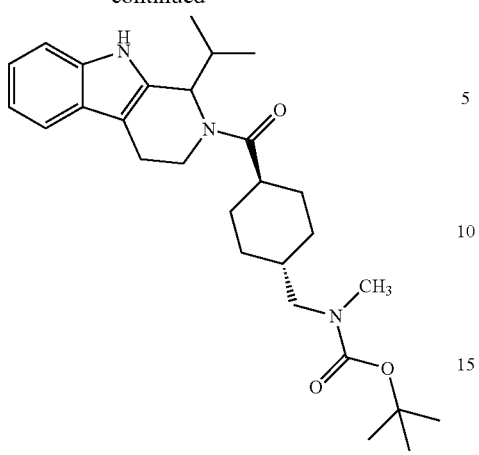

138
-continued

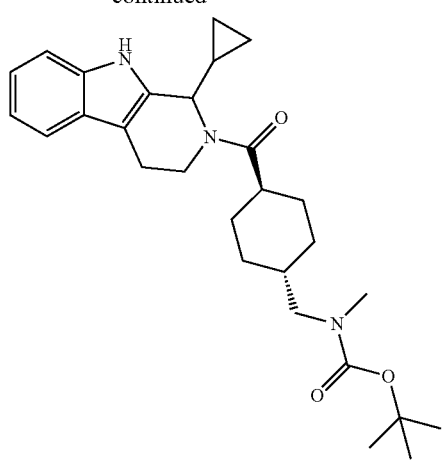

1-Isopropyl-2,3,4,9-tetrahydro-1H-pyrido[3,4-b]indole (132 mg, 0.614 mmol), 1-ethyl-3-(3-dimethylaminopropyl)carbodiimide-HCl (EDC-HCl) (118 mg, 0.614 mmol), 4-dimethylaminopyridine (DMAP) (7.5 mg, 0.0614 mmol), hydroxybenzotriazole (HOBT) (31 mg, 0.203 mmol), and trans-4-(Boc-methylaminomethyl)cyclohexane carboxylic acid (167 mg, 0.614 mmol) were all dissolved in acetonitrile (768 μL), dimethylformamide (DMF) (3.07 mL), and diisopropylethylamine (DIEA) (122 μL, 0.737 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 30% EtOAc in hexane, 40% EtOAc in hexane, and 50% EtOAc in hexane. Fractions containing product were combined, and the solvent was evaporated under vacuum, yielding a solid (215 mg, 74.9% yield; TLC R$_f$=0.12 (30% EtOAc in Hexane); HPLC R$_t$=4.928 min).

Synthesis Example 57: MN1352

1-Cyclopropyl-2,3,4,9-tetrahydro-1H-pyrido[3,4-b]indole (178 mg, 0.84 mmol), 1-ethyl-3-(3-dimethylaminopropyl)carbodiimide-HCl (EDC-HCl) (161 mg, 0.84 mmol), 4-dimethylaminopyridine (DMAP) (10.3 mg, 0.084 mmol), hydroxybenzotriazole (HOBT) (42 mg, 0.277 mmol), and trans-4-(Boc-methylaminomethyl)cyclohexane carboxylic acid (228 mg, 0.84 mmol) were all dissolved in acetonitrile (1.05 mL), dimethylformamide (DMF) (4.2 mL), and diisopropylethylamine (DIEA) (167 μL, 1.01 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 25% EtOAc in hexane, 35% EtOAc in hexane, and 45% EtOAc in hexane. Fractions containing product were combined, and the solvent was evaporated under vacuum, yielding a solid (316 mg, 80.8% yield; TLC R$_f$=0.27 (40% EtOAc in Hexane); HPLC R$_t$=4.851 min).

Synthesis Example 58: MN1353

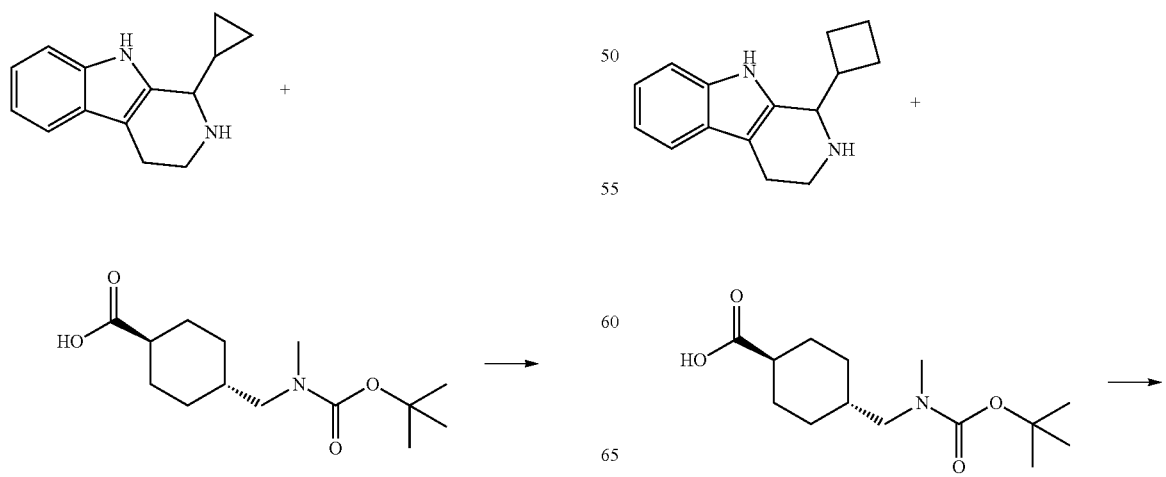

-continued

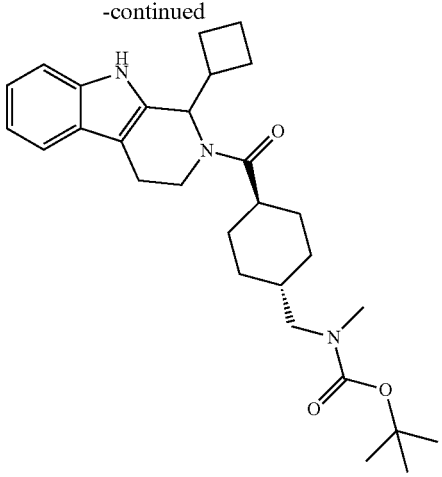

1-Cyclobutyl-2,3,4,9-tetrahydro-1H-pyrido[3,4-b]indole (190 mg, 0.84 mmol), 1-ethyl-3-(3-dimethylaminopropyl)carbodiimide-HCl (EDC-HCl) (161 mg, 0.84 mmol), 4-dimethylaminopyridine (DMAP) (10.3 mg, 0.084 mmol), hydroxybenzotriazole (HOBT) (42 mg, 0.277 mmol), and trans-4-(Boc-methylaminomethyl)cyclohexane carboxylic acid (228 mg, 0.84 mmol) were all dissolved in acetonitrile (1.05 mL), dimethylformamide (DMF) (4.2 mL), and diisopropylethylamine (DIEA) (167 µL, 1.01 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 25% EtOAc in hexane, 30% EtOAc in hexane, and 40% EtOAc in hexane. Fractions containing product were combined, and the solvent was evaporated under vacuum, yielding a solid (370 mg, 75.7% yield; TLC R$_f$=0.32 (40% EtOAc in Hexane); HPLC R$_t$=5.002 min).

Synthesis Example 59: MN1355 Intermediate

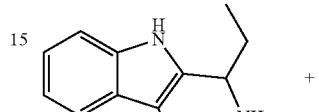

Tryptamine (4.00 g, 25.0 mmol) was dissolved in a solution of 10% water in MeOH (25 mL total). Propionaldehyde (2.7 mL, 37.4 mmol) was added via syringe followed by conc. H2SO4 (1.4 mL) slowly via syringe (caution exothermic). The reaction was refluxed overnight. The reaction was cooled to room temperature, made basic with ammonium hydroxide to give a solid. This solid was collected on a funnel and rinsed with hexanes (2×15 mL) followed by diethyl ether (2×20 mL). The filtrate was evaporated to give the crude product which was dissolved in EtOAc (20 mL) and filtered. The filtrate was evaporated and the residue dissolved in Et2O (20 mL), filtered through 0.45 um PTFE, and evaporated to give 2.0 g solid.

Synthesis Example 59: MN1355

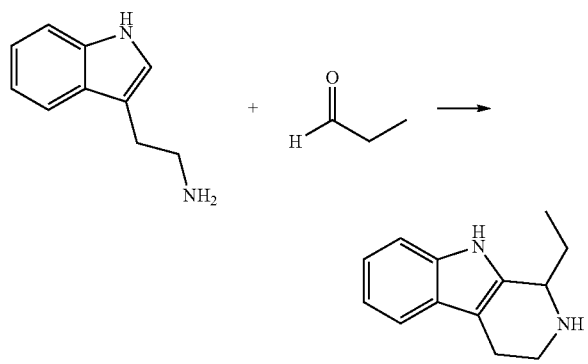

1-Ethyl-2,3,4,9-tetrahydro-1H-pyrido[3,4-b]indole (168 mg, 0.84 mmol), 1-ethyl-3-(3-dimethylaminopropyl)carbodiimide-HCl (EDC-HCl) (161 mg, 0.84 mmol), 4-dimethylaminopyridine (DMAP) (10.3 mg, 0.084 mmol), hydroxybenzotriazole (HOBT) (42 mg, 0.277 mmol), and trans-4-(Boc-methylaminomethyl)cyclohexane carboxylic acid (228 mg, 0.84 mmol) were all dissolved in acetonitrile (1.05 mL), dimethylformamide (DMF) (4.2 mL), and diisopropylethylamine (DIEA) (167 µL, 1.01 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 30% EtOAc in hexane, 40% EtOAc in hexane, and 50% EtOAc in hexane. Fractions containing product were combined, and the solvent was evaporated under vacuum, yielding a solid (229 mg, 60.1% yield; TLC R$_f$=0.21 (40% EtOAc in Hexane); HPLC R$_t$=4.812 min).

Synthesis Example 60: MN1356

Synthesis Example 61: MN1357

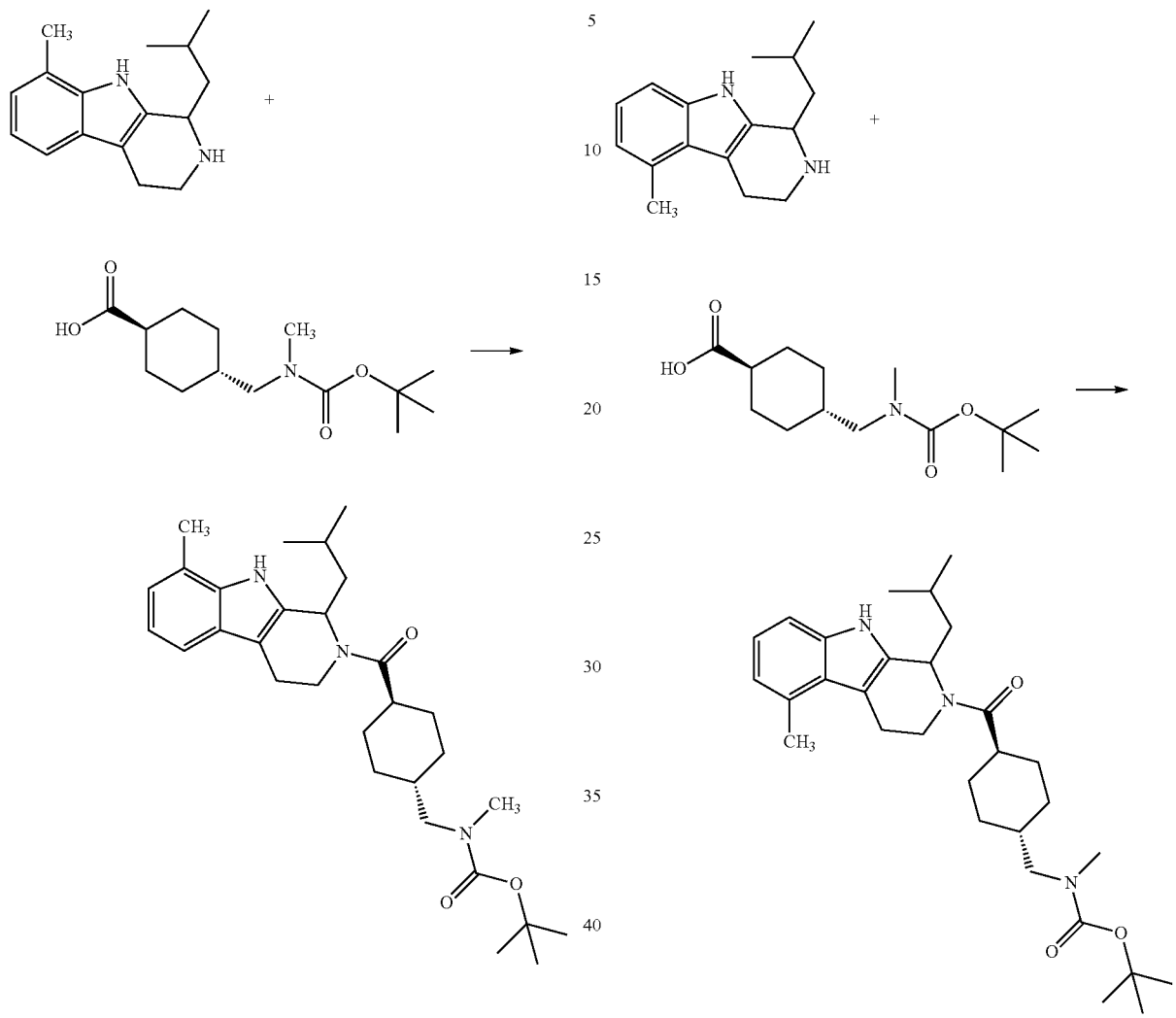

1-Isobutyl-8-methyl-2,3,4,9-tetrahydro-1H-pyrido[3,4-b] indole (204 mg, 0.84 mmol), 1-ethyl-3-(3-dimethylaminopropyl)carbodiimide-HCl (EDC-HCl) (161 mg, 0.84 mmol), 4-dimethylaminopyridine (DMAP) (10.3 mg, 0.084 mmol), hydroxybenzotriazole (HOBT) (42 mg, 0.277 mmol), and trans-4-(Boc-methylaminomethyl)cyclohexane carboxylic acid (228 mg, 0.84 mmol) were all dissolved in acetonitrile (1.05 mL), dimethylformamide (DMF) (4.2 mL), and diisopropylethylamine (DIEA) (167 µL, 1.01 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 20% EtOAc in hexane, 25% EtOAc in hexane, and 35% EtOAc in hexane. Fractions containing product were combined, and the solvent was evaporated under vacuum, yielding a solid (266 mg, 63.9% yield; TLC R$_f$=0.22 (30% EtOAc in Hexane); HPLC R$_t$=5.247 min).

1-Isobutyl-5-methyl-2,3,4,9-tetrahydro-1H-pyrido[3,4-b] indole (204 mg, 0.84 mmol), 1-ethyl-3-(3-dimethylaminopropyl)carbodiimide-HCl (EDC-HCl) (161 mg, 0.84 mmol), 4-dimethylaminopyridine (DMAP) (10.3 mg, 0.084 mmol), hydroxybenzotriazole (HOBT) (42 mg, 0.277 mmol), and trans-4-(Boc-methylaminomethyl)cyclohexane carboxylic acid (228 mg, 0.84 mmol) were all dissolved in acetonitrile (1.05 mL), dimethylformamide (DMF) (4.2 mL), and diisopropylethylamine (DIEA) (167 µL, 1.01 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 20% EtOAc in hexane, 25% EtOAc in hexane, and 35% EtOAc in hexane. Fractions containing product were combined, and the solvent was evaporated under vacuum, yielding a solid (370 mg, 88.9% yield; TLC R$_f$=0.22 (30% EtOAc in Hexane); HPLC R$_t$=5.197 min).

Synthesis Example 62: MN1358

Synthesis Example 63: MN1359

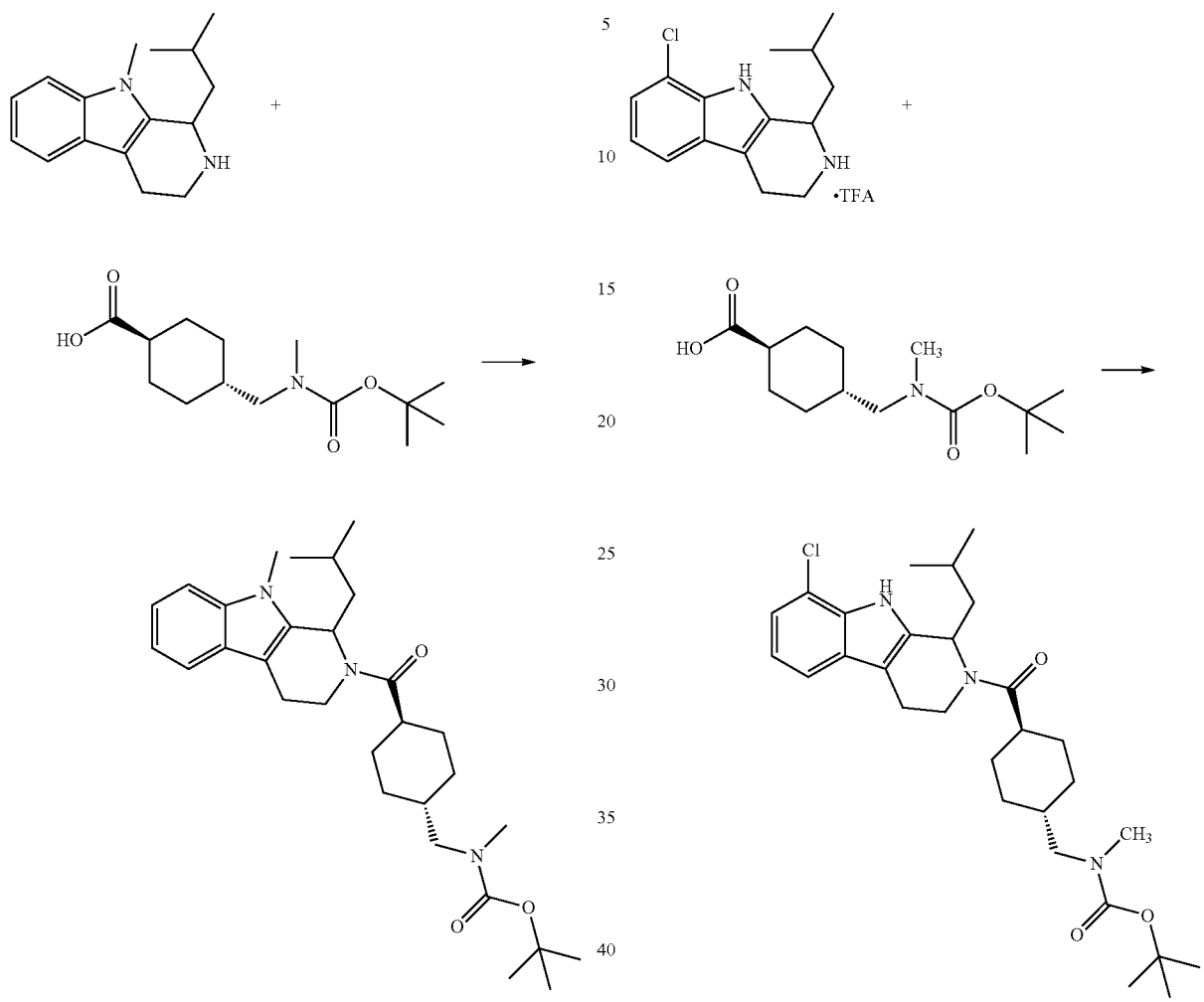

1-Isobutyl-9-methyl-2,3,4,9-tetrahydro-1H-pyrido[3,4-b]indole (204 mg, 0.84 mmol), 1-ethyl-3-(3-dimethylaminopropyl)carbodiimide-HCl (EDC-HCl) (161 mg, 0.84 mmol), 4-dimethylaminopyridine (DMAP) (10.3 mg, 0.084 mmol), hydroxybenzotriazole (HOBT) (42 mg, 0.277 mmol), and trans-4-(Boc-methylaminomethyl)cyclohexane carboxylic acid (228 mg, 0.84 mmol) were all dissolved in acetonitrile (1.05 mL), dimethylformamide (DMF) (4.2 mL), and diisopropylethylamine (DIEA) (167 µL, 1.01 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 20% EtOAc in hexane, 25% EtOAc in hexane, and 35% EtOAc in hexane. Fractions containing product were combined, and the solvent was evaporated under vacuum, yielding a solid (327 mg, 78.5% yield; TLC R$_f$=0.31 (30% EtOAc in Hexane); HPLC R$_t$=5.312 min).

8-Chloro-1-isobutyl-2,3,4,9-tetrahydro-1H-pyrido[3,4-b]indole TFA salt (158 mg, 0.42 mmol), 1-ethyl-3-(3-dimethylaminopropyl)carbodiimide-HCl (EDC-HCl) (81 mg, 0.42 mmol), 4-dimethylaminopyridine (DMAP) (5.1 mg, 0.042 mmol), hydroxybenzotriazole (HOBT) (21 mg, 0.139 mmol), and trans-4-(Boc-methylaminomethyl)cyclohexane carboxylic acid (114 mg, 0.42 mmol) were all dissolved in acetonitrile (525 µL), dimethylformamide (DMF) (2.1 mL), and diisopropylethylamine (DIEA) (83 µL, 0.50 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 20% EtOAc in hexane, 25% EtOAc in hexane, and 35% EtOAc in hexane. Fractions containing product were combined, and the solvent was evaporated under vacuum, yielding a solid (183 mg, 84.4% yield; TLC R$_f$=0.32 (30% EtOAc in Hexane); HPLC R$_t$=5.321 min).

Synthesis Example 64: MN1360

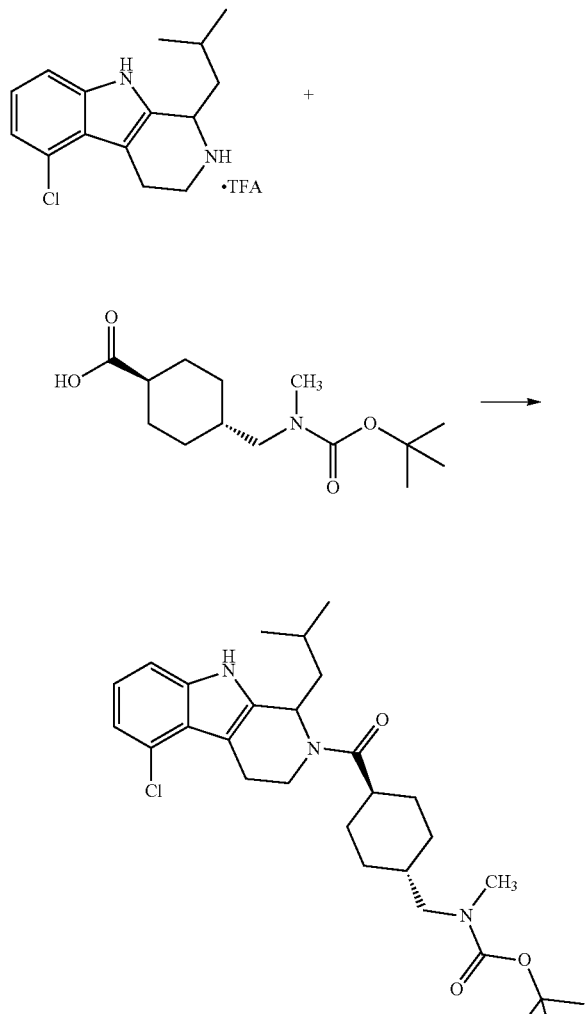

5-Chloro-1-isobutyl-2,3,4,9-tetrahydro-1H-pyrido[3,4-b]indole TFA salt (158 mg, 0.42 mmol), 1-ethyl-3-(3-dimethylaminopropyl)carbodiimide-HCl (EDC-HCl) (81 mg, 0.42 mmol), 4-dimethylaminopyridine (DMAP) (5.1 mg, 0.042 mmol), hydroxybenzotriazole (HOBT) (21 mg, 0.139 mmol), and trans-4-(Boc-methylaminomethyl)cyclohexane carboxylic acid (114 mg, 0.42 mmol) were all dissolved in acetonitrile (525 µL), dimethylformamide (DMF) (2.1 mL), and diisopropylethylamine (DIEA) (83 µL, 0.50 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 20% EtOAc in hexane, 25% EtOAc in hexane, and 35% EtOAc in hexane. Fractions containing product were combined, and the solvent was evaporated under vacuum, yielding a solid (135 mg, 62.3% yield; TLC R$_f$=0.19 (30% EtOAc in Hexane); HPLC R$_t$=5.327 min).

Synthesis Example 65: MN1369

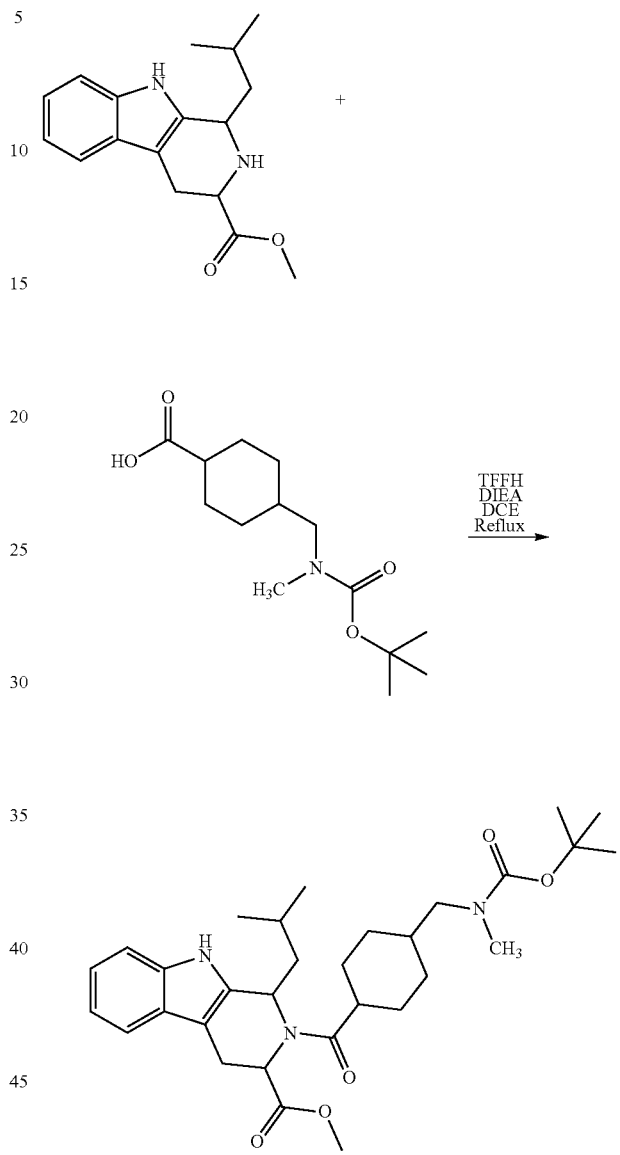

Boc-N-methy-tranexamic acid (176 mg, 0.65 mmol) and fluoro-N,N,N',N'-tetramethylformamidinium hexafluorophosphate (TFFH) (198 mg, 0.75 mmol) were dissolved in 1,2-dichloroethane (DCE) (2.25 mL) and diisopropylethylamine (DIEA) (372 uL, 2.25 mmol). This was stirred at room temperature for 30 minutes before the addition of methyl 1-isobutyl-2,3,4,9-tetrahydro-1H-pyrido[3,4-b]indole-3-carboxylate (143 mg, 0.5 mmol). The reaction was refluxed at 80° C. for 1 hour before adding a solution of Boc-N-methy-tranexamic acid (176 mg, 0.65 mmol), fluoro-N,N,N',N'-tetramethylformamidinium hexafluorophosphate (198 mg, 0.75 mmol), diisopropylethylamine (372 uL, 2.25 mmol), and 1,2-dichloroethane (2.25 mL). This was refluxed at 80° C. for 1.5 hours before being azeotroped with toluene (3×50 mL). The crude product was purified by silica gel chromatography. Product was recovered as a solid (141 mg, 52%).

Synthesis Example 65: MN1342

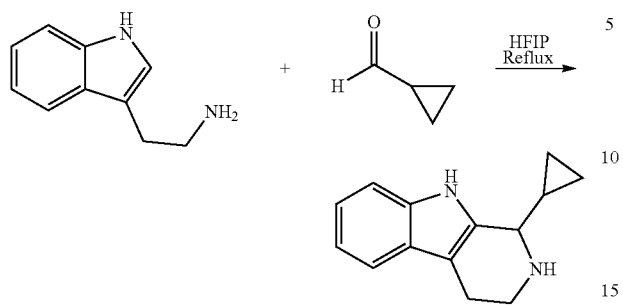

Tryptamine (801 mg, 5 mmol) was dissolved in 1,1,1,3,3,3-hexafluoroisopropanol (HFIP) (8 mL) prior to the addition of cyclopropane carboxaldehyde (415 uL, 5.5 mmol) via syringe. The reaction was refluxed overnight. The result was concentrated under vacuum and azeotroped with CHCl3 (3×50 mL). The resulting crude product was triturated with hexanes (2×10 mL) and the solid was collected on a filter (899 mg, 85%).

Synthesis Example 66: MN1362 (EDC Coupling)

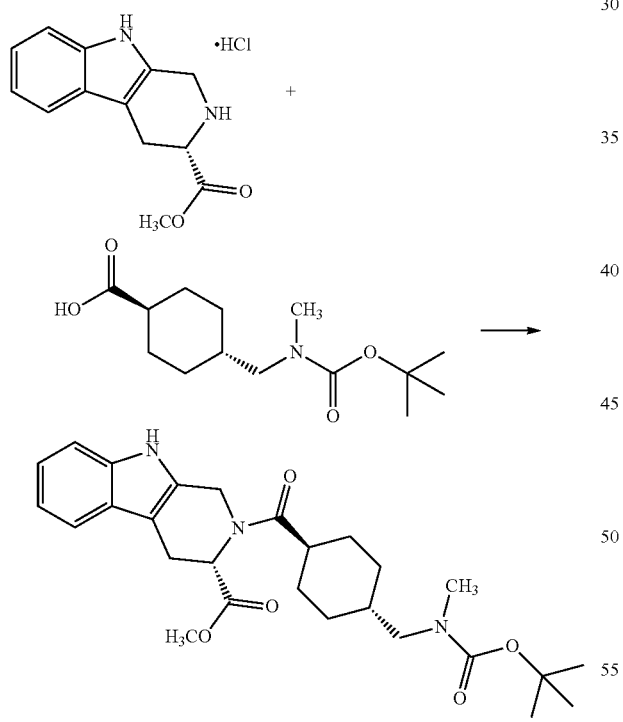

L-1,2,3,4-Tetrahydronorharman-3-carboxylic acid methyl ester HCl (267 mg, 1.00 mmol), 4-dimethylaminopyridine (DMAP) (12 mg, 0.1 mmol), hydroxybenzotriazole (HOBT) (51 mg, 0.33 mmol), and trans-4-(Boc-methylaminomethyl)cyclohexane carboxylic acid (271 mg, 1.00 mmol) were all dissolved in acetonitrile (1.25 mL), dimethylformamide (DMF) (5 mL), and diisopropylethylamine (DIEA) (396 uL, 2.4 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using fractions (200 mL) consisting of hexane and EtOAc in hexane. Fractions containing product were combined, and the solvent was evaporated under vacuum, yielding a solid (280 mg, 57.9% yield; TLC R$_f$=0.14 (40% EtOAc in Hexane); HPLC R$_t$=4.507 min).

Synthesis Example 67: MN1363 (EDC Coupling)

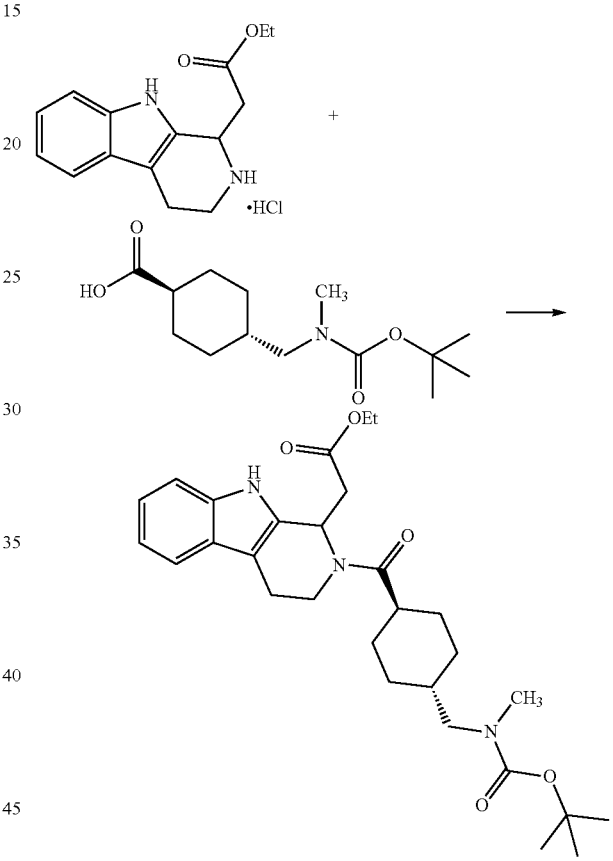

Ethyl 2-(2,3,4,9-tetrahydro-1H-indeno[2,1-c]pyridin-1-yl)acetate HCl (160 mg, 0.42 mmol), 1-ethyl-3-(3-dimethylaminopropyl)carbodiimide-HCl (EDC-HCl) (81 mg, 0.42 mmol), 4-dimethylaminopyridine (DMAP) (5.1 mg, 0.042 mmol), hydroxybenzotriazole (HOBT) (21 mg, 0.139 mmol), and trans-4-(Boc-methylaminomethyl)cyclohexanecarboxylic acid (114 mg, 0.42 mmol) were all dissolved in acetonitrile (525 µL), dimethylformamide (DMF) (2.1 mL), and diisopropylethylamine (DIEA) (83 µL, 0.50 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 35% EtOAc in hexane, 45% EtOAc in hexane, and 65% EtOAc in hexane. Fractions containing product were combined, and the solvent was evaporated under vacuum, yielding a solid (116 mg, 54.1% yield; TLC $R_f$=0.20 (40% EtOAc in Hexane); HPLC $R_t$=4.846 min).

Synthesis Example 68: Intermediate (HFIP Cyclization)

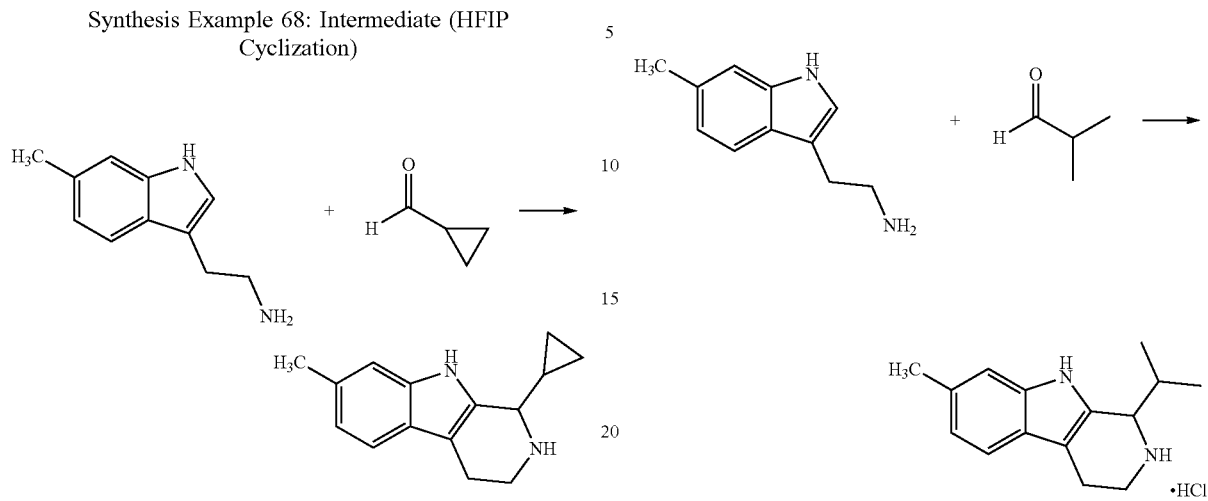

6-Methyltryptamine (380 mg, 2.18 mmol) was dissolved in 1,1,1,3,3,3-hexafluoroisopropanol (3.5 mL). Cyclopropanecarbaldehyde (96 uL, 2.62 mmol) was added by syringe. The reaction was placed an aluminum heating block at 60° C. for 16 hrs. The solvent was removed under vacuum, azeotroped with CHCl₃ (3×50 mL). The product was filtered, dried under vacuum, yielding a solid (413 mg, 83.7% yield; TLC $R_f$=0.23 (5% MeOH in CH2Cl2+1% NH₃); HPLC $R_t$=2.942 min).

Synthesis Example 69: Intermediate (HFIP Cyclization)

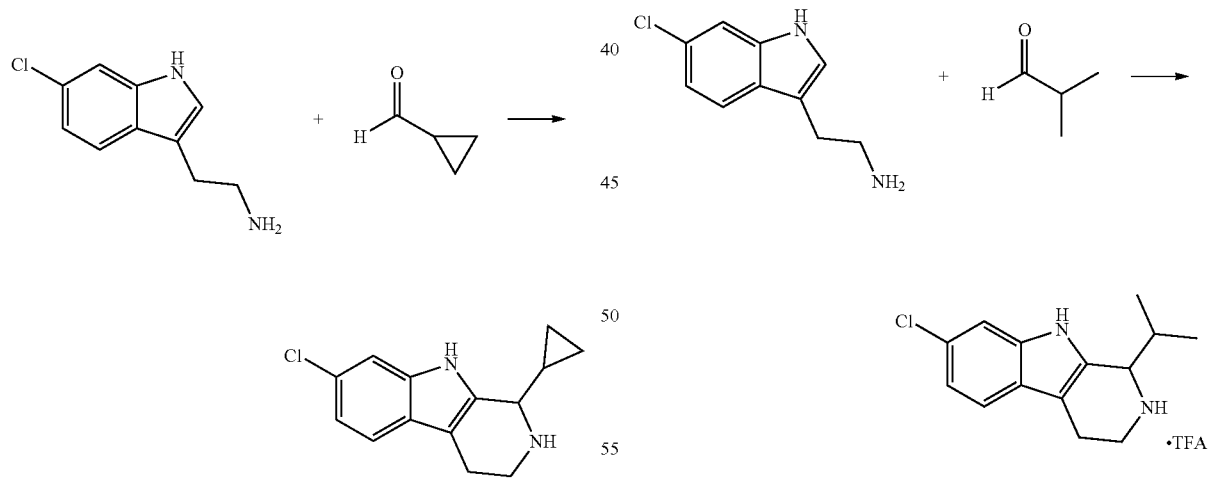

6-Chlorotryptamine (424 mg, 2.18 mmol) was dissolved in 1,1,1,3,3,3-hexafluoroisopropanol (3.5 mL). Cyclopropanecarbaldehyde (196 uL, 2.62 mmol) was added by syringe. The reaction was placed an aluminum heating block at 60° C. for 16 hrs. The solvent was removed under vacuum, azeotroped with CHCl₃ (3×50 mL). The product was filtered, dried under vacuum, yielding a solid (414 mg, 77.0% yield; TLC $R_f$=0.20 (5% MeOH in CH₂Cl₂+1% NH₃); HPLC $R_t$=3.102 min).

Synthesis Example 70: Intermediate (HFIP Cyclization)

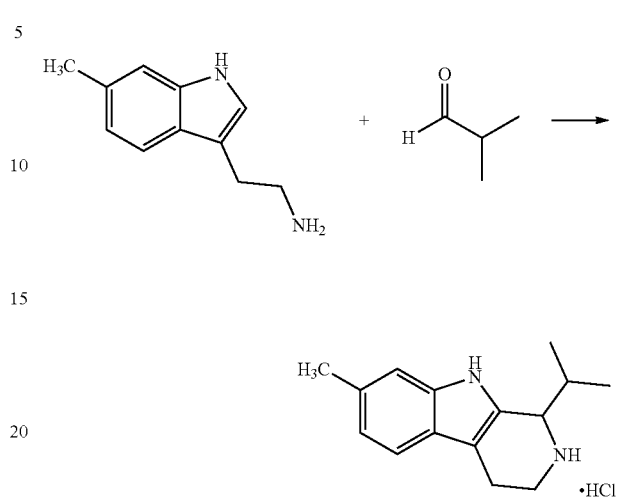

6-Methyltryptamine (370 mg, 2.12 mmol) was dissolved in HFIP (3.4 mL). Isobutyraldehyde was added and the reaction was refluxed at 60° C. for 16 hrs. The reaction was concentrated under vacuum and azeotroped with CHCl₃ (3×50 mL). The result was filtered and dried under vacuum, yielding a solid (164 mg, 29.2% yield; TLC $R_f$=0.20 (5% MeOH in CH₂Cl₂+1% NH₃); HPLC $R_t$=3.095 min).

Synthesis Example 71: Intermediate (TFA Cyclization)

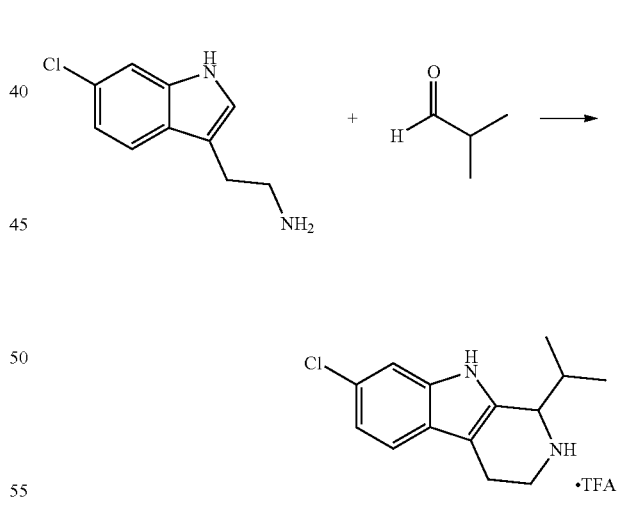

6-Chlorotryptamine (500 mg, 2.57 mmol) was dissolved in CH₂Cl₂ (21 mL). Isobutyraldehyde (234 uL, 2.57 mmol) was added via syringe to the solution and the mixture was placed in a dry ice propanol bath for 5 min. TFA (1.97 mL, 25.7 mmol) was added to the reaction mixture dropwise over 6 min and then was removed from the ice bath and allowed to warm to RT. The reaction was azeotroped with toluene (3×50 mL) and triturated with diethylether (5×10 mL), yielding a white solid (793 mg, 85.1% yield; TLC $R_f$=0.25 (5% MeOH in CH₂Cl₂+1% NH₃); HPLC $R_t$=3.156 min).

Synthesis Example 72: Intermediate (HFIP Cyclization)

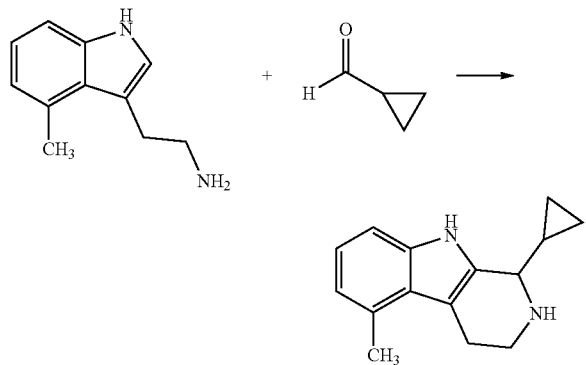

5-Methyltryptamine (172 mg, 1.00 mmol) was dissolved in 1,1,1,3,3,3-hexafluoroisopropanol (1.6 mL). Cyclopropanecarbaldehyde (90 uL, 1.0 mmol) was added by syringe. After 16 hr, the solvent was removed under vacuum and the resulting solid was azeotroped with CHCl$_3$ (3×50 mL). The solid was dissolved in EtOH (5 mL) and Et$_2$O (60 mL) and 1N HCl in Et$_2$O (1.2 mL) were added to the solution. The product was filtered, dried under vacuum, yielding a solid (138 mg, 61.0% yield; TLC R$_f$=0.21 (5% MeOH in CH$_2$Cl$_2$+ 1% NH$_3$); HPLC R$_t$=2.910 min).

Synthesis Example 73: MN1369 (Alternative Coupling Method Using TFFH)

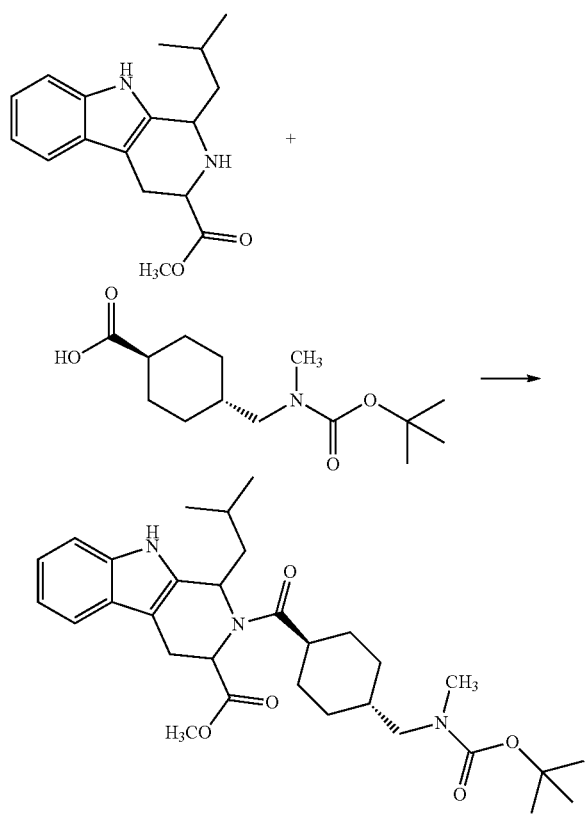

Methyl 1-isobutyl-2,3,4,9-tetrahydro-1H-indeno[2,1-c] pyridine-3-carboxylate (143 mg, 0.50 mmol), trans-4-(Boc-methylaminomethyl)cyclohexanecarboxylic acid (352 mg, 1.30 mmol), and Tetramethylfluoroformamidinium hexafluorophosphate (TFFH) (396 mg, 1.50 mmol) were dissolved in 1,2-dichloroethane (DCE) (4.50 mL) and diisopropylethylamine (DIEA) (744 uL, 4.50 mmol) and stirred for 90 minutes. The reaction mixture was azeotroped with toluene (3×50 mL). This material was further purified by silica gel (25-30 g) chromatography using: 5 fractions (200 mL) consisting of CH$_2$Cl$_2$, 6% EtOAc in CH$_2$Cl$_2$, 10% EtOAc in CH$_2$Cl$_2$, 15% EtOAc in CH$_2$Cl$_2$, and 20% EtOAc in CH$_2$Cl$_2$. Fractions containing product were combined, and the solvent was evaporated under vacuum, yielding a solid (190 mg). This material was further purified by silica gel (25-30 g) chromatography using: 6 fractions (200 mL) consisting of hexane, 25% EtOAc in hexane, 30% EtOAc in hexane, 35% EtOAc in hexane, 40% EtOAc in hexane, and 65% EtOAc in hexane. Fractions containing product were combined, and the solvent was evaporated under vacuum, yielding a solid (141 mg, 52.3% yield; TLC R$_f$=0.29 (40% EtOAc in hexane); HPLC R$_t$=4.910 min).

Synthesis Example 74: MN1370 (Ester Hydrolysis)

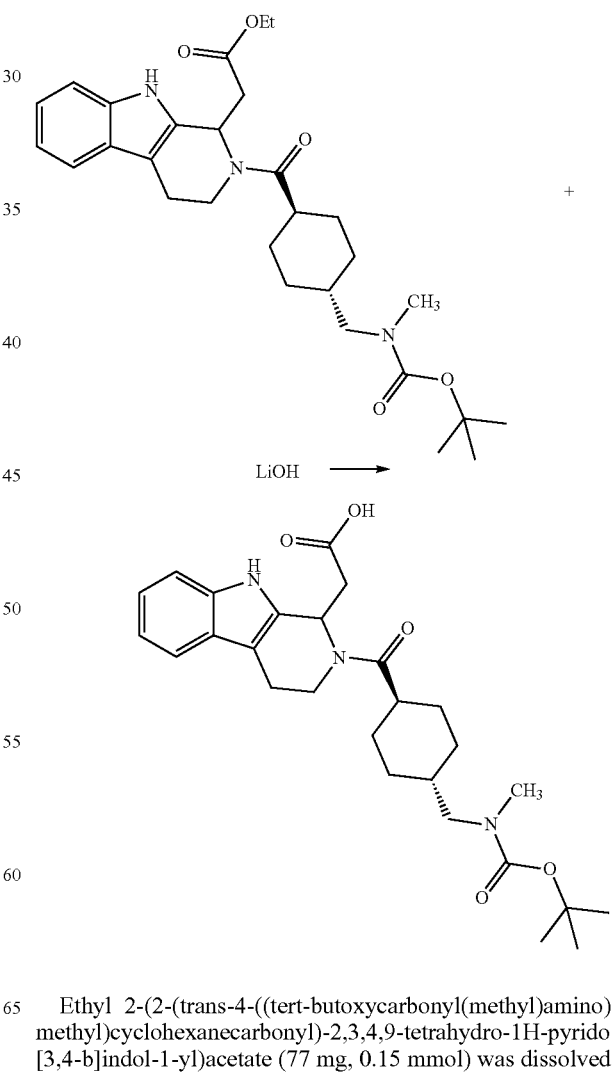

Ethyl 2-(2-(trans-4-((tert-butoxycarbonyl(methyl)amino) methyl)cyclohexanecarbonyl)-2,3,4,9-tetrahydro-1H-pyrido [3,4-b]indol-1-yl)acetate (77 mg, 0.15 mmol) was dissolved in MeOH (2.76 mL) and H₂O (800 uL) was added via syringe to the mixture. LiOH (32 mg, 0.75 mmol) was added to the mixture. Reaction was deemed complete after 1 hr by HPLC and solvent was evaporated under vacuum. The solid was dissolved in H₂O (25 mL), washed with diethylether (4×50 mL). The aqueous layer was acidified with 1N HCl (5 mL). Product was extracted with CH₂Cl₂ (4×50 mL), dried (anhyd. MgSO₄), filtered, and evaporated under vacuum yielding a solid (66 mg, 91% yield; TLC $R_f$=0.17 (2% MeOH in CH₂Cl₂+1% HOAc); HPLC $R_t$=4.373 min).

Synthesis Example 75: MN1371 (Ester Hydrolysis)

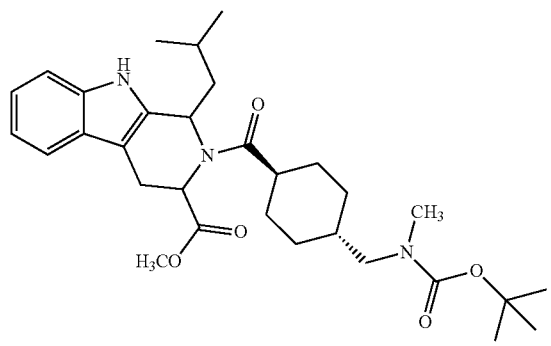

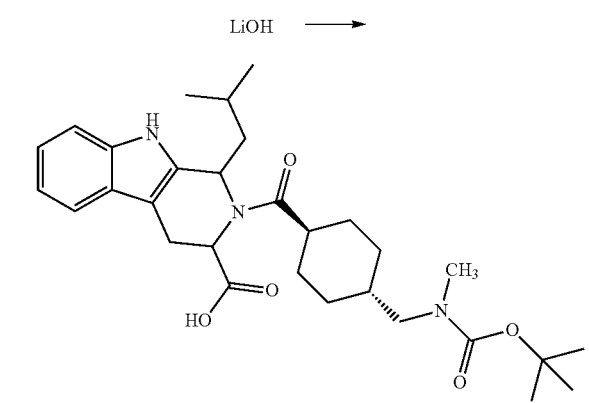

Methyl 2-(trans-4-((tert-butoxycarbonyl(methyl)amino)methyl)cyclohexanecarbonyl)-1-isobutyl-2,3,4,9-tetrahydro-1H-pyrido[3,4-b]indole-3-carboxylate (81 mg, 0.15 mmol) was dissolved in MeOH (4.76 mL) and H₂O (800 uL) was added via syringe to the mixture. LiOH (32 mg, 0.75 mmol) and dimethylformamide (DMF) (2 mL) was added to the mixture. Reaction was deemed complete after 23 hr by HPLC and solvent was evaporated under the hood. The solid was dissolved in H₂O (35 mL), washed with diethylether (4×50 mL). The aqueous layer was acidified with 1N HCl (7 mL). Product was extracted with CH₂Cl₂ (4×50 mL), dried (anhyd. MgSO₄), filtered, and evaporated under vacuum yielding a solid (60 mg, 74% yield; TLC $R_f$=0.36 (2% MeOH in CH₂Cl₂+1% HOAc); HPLC $R_t$=4.506 min).

Synthesis Example 76: MN1372 (Ester Hydrolysis)

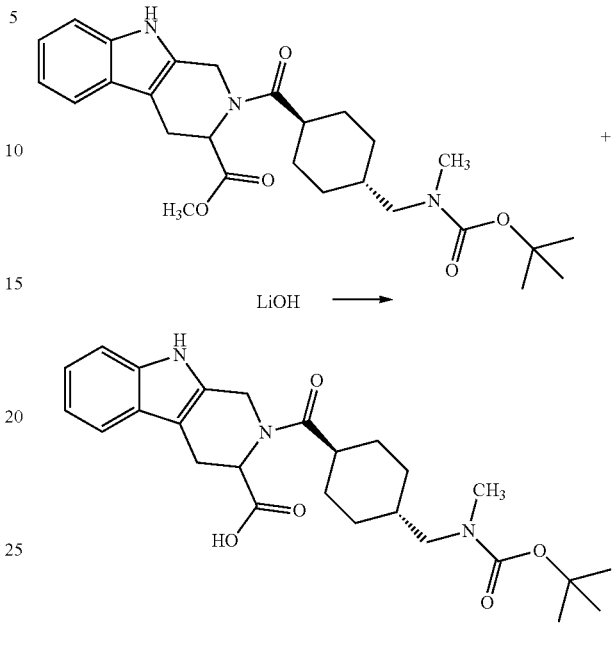

Methyl 2-(trans-4-((tert-butoxycarbonyl(methyl)amino)methyl)cyclohexanecarbonyl)-2,3,4,9-tetrahydro-1H-pyrido[3,4-b]indole-3-carboxylate (73 mg, 0.15 mmol) was dissolved in MeOH (2.76 mL) and H₂O (800 uL) was added via syringe to the mixture. LiOH (32 mg, 0.75 mmol) was added to the mixture. Reaction was deemed complete after 1 hr by HPLC and solvent was evaporated under vacuum. The solid was dissolved in H₂O (25 mL), washed with diethylether (4×50 mL). The aqueous layer was acidified with 1N HCl (5 mL). Product was extracted with CH₂Cl₂ (4×50 mL), dried (anhyd. MgSO₄), filtered, and evaporated under vacuum yielding a solid (63 mg, 89% yield; TLC $R_f$=0.15 (2% MeOH in CH₂Cl₂+1% HOAc); HPLC $R_t$=4.216 min).

Synthesis Example 77: Intermediate (H2SO₄ Cyclization)

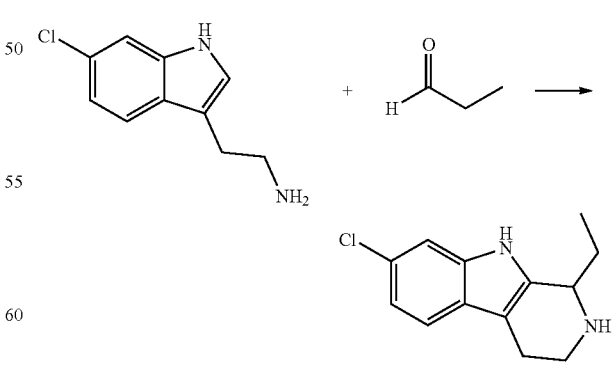

6-Chlorotryptamine (389 mg, 2.00 mmol) was dissolved in a solution of 10% water in MeOH (2 mL). Propionaldehyde (216 uL mL, 3.00 mmol) was added via syringe followed by conc. H2SO₄ (1.4 mL) slowly via syringe. The reaction was refluxed for 17 hrs. The reaction was cooled to room temperature and then made basic with ammonium hydroxide to give a solid. The solution was triturated with hexane (2×15 mL) and Et$_2$O (2×20 mL). The result was filtered, and the filtrate was evaporated. The resulting solid was dissolved in EtOAc (20 mL) and filtered. The filtrate was dissolved in Et$_2$O (15 mL), filtered with a 0.45 um PTFE, and dried under hood. The result was dissolved in ammonia (3 mL) and extracted with EtOAc (2×10 mL). Product was extracted with EtOAc (8 mL) and washed with H2O (3 mL), 1N NaOH (1 mL), and sat. NaCl (3 mL). The result was dried, filtered, and solvent was removed under vacuum. The solid was dissolved in diethyl ether (10 mL) and filtered. The filtrate was evaporated yielding a solid (161 mg, 34.3% yield; TLC R$_f$=0.19 (5% MeOH in CH$_2$Cl$_2$+1% NH$_3$); HPLC R$_t$=3.071 min).

Synthesis Example 78: Intermediate (TFA Cyclization)

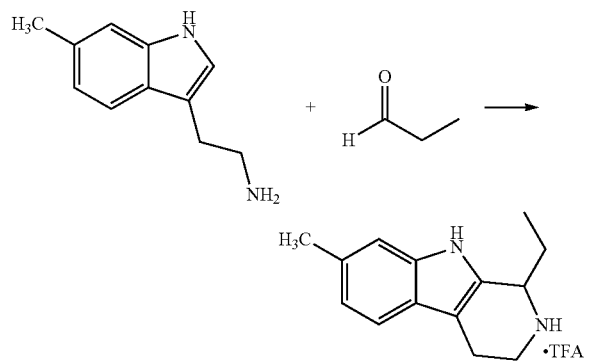

6-Methyltryptamine (360.7 mg, 2.07 mmol) was dissolved in CH$_2$Cl$_2$ (16 mL). The mixture was stirred while propionaldehyde (180 uL, 2.48 mmol) was added via syringe, causing the solution to become clear. The reaction mixture was cooled in a dry ice/2-propanol bath for 5 min and then 10% TFA solution in CH$_2$Cl$_2$ (4.76 mL) was added dropwise via syringe over 8 min. The reaction was stirred for 17 hrs and was allowed to warm slowly to RT. The mixture was concentrated and dried under vacuum, resulting in a brown solid. The result was triturated with ACN (2×2 mL) and EtOAc (2 mL). The solid was collected on a filter and dried under high vacuum, yielding an off-white solid (395 mg, 61.3% yield; TLC R$_f$=0.14 (5% MeOH in CH$_2$Cl$_2$+1% NH$_3$); HPLC R$_t$=2.933 min).

Synthesis Example 79: Intermediate (TFA Cyclization)

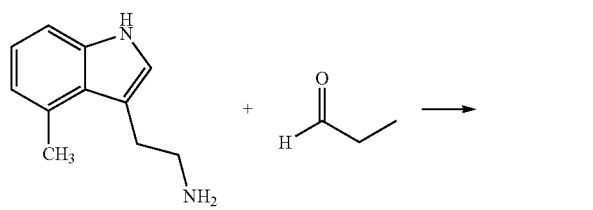

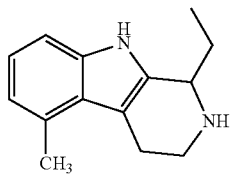

4-Methyltryptamine (348 mg, 2.00 mmol) was dissolved in CH$_2$Cl$_2$ (16 mL). The mixture was stirred while propionaldehyde (174 uL, 2.40 mmol) was added via syringe, causing the solution to become clear, and was stirred for 5 min. The reaction mixture was cooled in a dry ice propanol bath for 5 min and then 10% TFA solution in CH$_2$Cl$_2$ (4.6 mL) was added dropwise via syringe over 8 min. The reaction was stirred for 17 hrs and was allowed to slowly warm to RT. The mixture was concentrated and dried under vacuum, resulting in a brown solid. The result was triturated with diethylether (25 mL) and ACN (10 mL). The solid was collected on a filter and dried under high vacuum, yielding an off-white solid (443 mg, 103% yield; TLC R$_f$=0.14 (5% MeOH in CH$_2$Cl$_2$+1% NH$_3$); HPLC R$_t$=2.916 min).

Synthesis Example 80: Intermediate (TFA Cyclization)

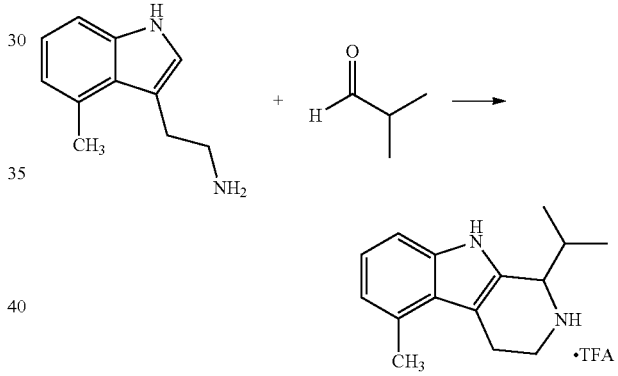

4-Methyltrpytamine (174 mg, 1.00 mmol) was dissolved in CH$_2$Cl$_2$ (8 mL). Isobutyraldehyde (90 uL, 1.0 mmol) was added to the solution and the mixture was placed in a dry ice/2-propanol bath for 5 min. TFA (765 uL, 10 mmol) was added dropwise via syringe to the reaction mixture over 2 min. The reaction was removed from the dry ice bath and allowed to warm to RT for 1 hr. The solvent was removed under vacuum and the resulting red oily substance was dried under vacuum. The result was azeotroped with toluene (3×50 mL) and triturated with Et2O (2×6 mL) and ACN, yielding a solid (183 mg, 56.2% yield; TLC R$_f$=0.26 (5% MeOH in CH$_2$Cl$_2$+1% NH$_3$); HPLC R$_t$=3.009 min).

Synthesis Example 81: MN1377 (EDC Coupling)

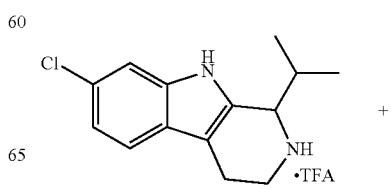

157
-continued

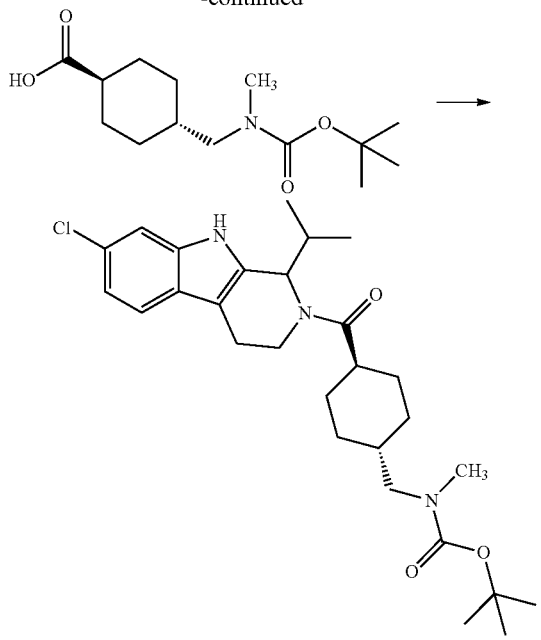

7-Chloro-1-isopropyl-2,3,4,9-tetrahydro-1H-pyrido[3,4-b]indole TFA salt (181 mg, 0.50 mmol), 1-ethyl-3-(3-dimethylaminopropyl)carbodiimide-HCl (EDC-HCl) (96 mg, 0.50 mmol), 4-dimethylaminopyridine (DMAP) (6 mg, 0.05 mmol), hydroxybenzotriazole (HOBT) (51 mg, 0.165 mmol), and trans-4-(Boc-methylaminomethyl)cyclohexane carboxylic acid (136 mg, 0.50 mmol) were all dissolved in acetonitrile (625 uL), dimethylformamide (DMF) (2.5 mL), and diisopropylethylamine (DIEA) (100 uL, 0.60 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 30% EtOAc in hexane, 40% EtOAc in hexane, and 45% EtOAc in hexane. Fractions containing product were combined, and the solvent was evaporated under vacuum, yielding a solid (200 mg, 79.7% yield; TLC R$_f$=0.29 (40% EtOAc in Hexane); HPLC R$_t$=5.103 min).

Synthesis Example 82: MN1378 (EDC Coupling)

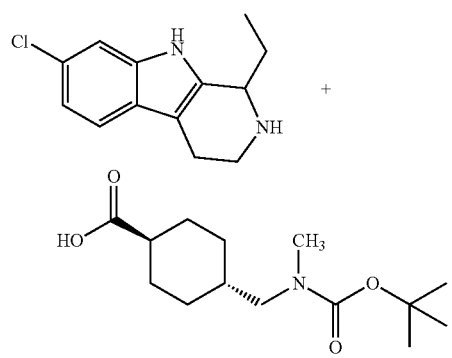

158
-continued

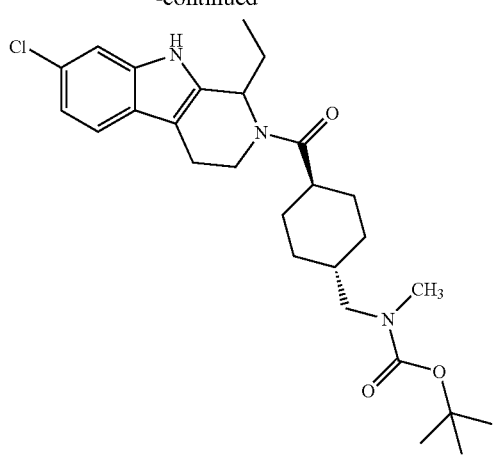

7-Chloro-1-ethyl-2,3,4,9-tetrahydro-1H-pyrido[3,4-b]indole (117 mg, 0.50 mmol), 1-ethyl-3-(3-dimethylaminopropyl)carbodiimide-HCl (EDC-HCl) (96 mg, 0.50 mmol), 4-dimethylaminopyridine (DMAP) (6 mg, 0.05 mmol), hydroxybenzotriazole (HOBT) (51 mg, 0.165 mmol), and trans-4-(Boc-methylaminomethyl)cyclohexane carboxylic acid (136 mg, 0.50 mmol) were all dissolved in acetonitrile (625 uL), dimethylformamide (DMF) (2.5 mL), and diisopropylethylamine (DIEA) (100 uL, 0.60 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 30% EtOAc in hexane, 40% EtOAc in hexane, and 45% EtOAc in hexane. Fractions containing product were combined, and the solvent was evaporated under vacuum, yielding a solid (187 mg, 76.6% yield; TLC R$_f$=0.18 (40% EtOAc in Hexane); HPLC R$_t$=4.978 min).

Synthesis Example 83: MN1379 (EDC Coupling)

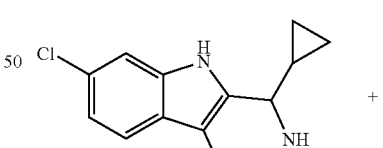

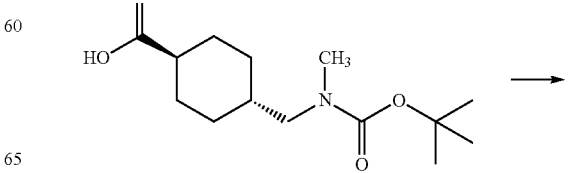

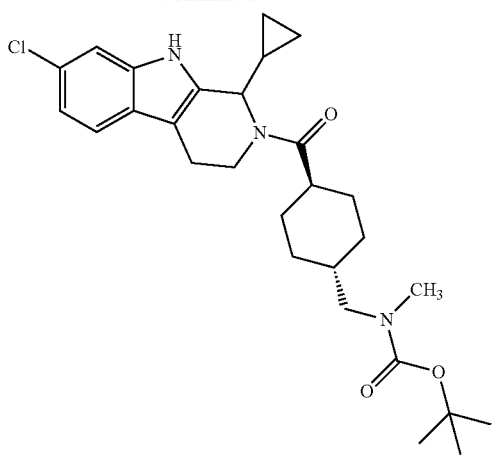

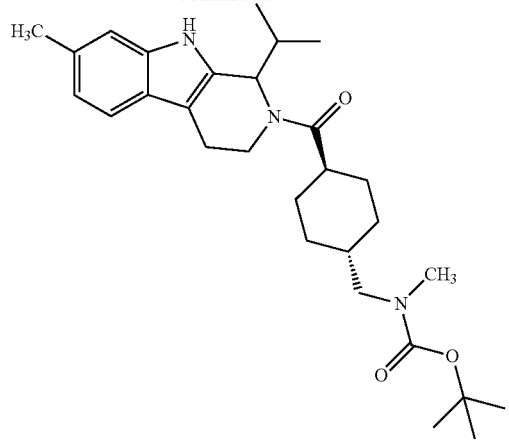

7-Chloro-1-cyclopropyl-2,3,4,9-tetrahydro-1H-pyrido[3,4-b]indole (123 mg, 0.50 mmol), 1-ethyl-3-(3-dimethylaminopropyl)carbodiimide-HCl (EDC-HCl) (96 mg, 0.50 mmol), 4-dimethylaminopyridine (DMAP) (6 mg, 0.05 mmol), hydroxybenzotriazole (HOBT) (51 mg, 0.165 mmol), and trans-4-(Boc-methylaminomethyl)cyclohexane carboxylic acid (136 mg, 0.50 mmol) were all dissolved in acetonitrile (625 uL), dimethylformamide (DMF) (2.5 mL), and diisopropylethylamine (DIEA) (100 uL, 0.60 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 30% EtOAc in hexane, 40% EtOAc in hexane, and 45% EtOAc in hexane. Fractions containing product were combined, and the solvent was evaporated under vacuum, yielding a solid (128 mg, 51.2% yield; TLC R$_f$=0.23 (40% EtOAc in Hexane); HPLC R$_t$=5.008 min).

Synthesis Example 84: MN1380 (EDC Coupling)

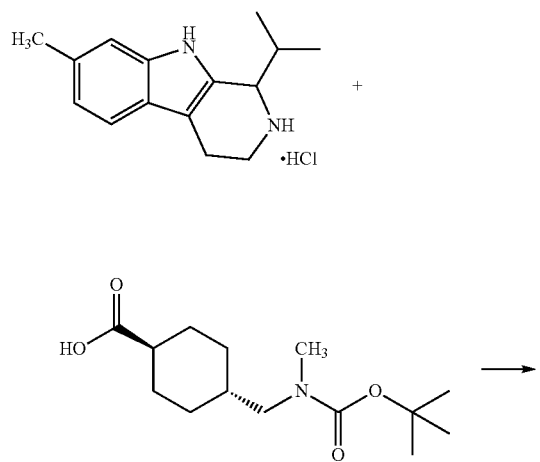

1-Isopropyl-7-methyl-2,3,4,9-tetrahydro-1H-pyrido[3,4-b]indole HCl (132 mg, 0.50 mmol), 1-ethyl-3-(3-dimethylaminopropyl)carbodiimide-HCl (EDC-HCl) (96 mg, 0.50 mmol), 4-dimethylaminopyridine (DMAP) (6 mg, 0.05 mmol), hydroxybenzotriazole (HOBT) (51 mg, 0.165 mmol), and trans-4-(Boc-methylaminomethyl)cyclohexane carboxylic acid (136 mg, 0.50 mmol) were all dissolved in acetonitrile (625 uL), dimethylformamide (DMF) (2.5 mL), and diisopropylethylamine (DIEA) (200 uL, 1.20 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 32% EtOAc in hexane, 42% EtOAc in hexane, and 65% EtOAc in hexane. Fractions containing product were combined, and the solvent was evaporated under vacuum, yielding a solid (200 mg, 83.0% yield; TLC R$_f$=0.25 (40% EtOAc in Hexane); HPLC R$_t$=5.034 min).

Synthesis Example 85: MN1381 (EDC Coupling)

1-Ethyl-7-methyl-2,3,4,9-tetrahydro-1H-pyrido[3,4-b]indole·TFA salt (164 mg, 0.50 mmol), 1-ethyl-3-(3-dimethylaminopropyl)carbodiimide-HCl (EDC-HCl) (96 mg, 0.50 mmol), 4-dimethylaminopyridine (DMAP) (6 mg, 0.05 mmol), hydroxybenzotriazole (HOBT) (51 mg, 0.165 mmol), and trans-4-(Boc-methylaminomethyl)cyclohexane carboxylic acid (136 mg, 0.50 mmol) were all dissolved in acetonitrile (625 uL), dimethylformamide (DMF) (2.5 mL), and diisopropylethylamine (DIEA) (100 uL, 0.60 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 32% EtOAc in hexane, 42% EtOAc in hexane, and 50% EtOAc in hexane. Fractions containing product were combined, and the solvent was evaporated under vacuum, yielding a solid (202 mg, 86.4% yield; TLC R$_f$=0.21 (40% EtOAc in Hexane); HPLC R$_t$=4.913 min).

Synthesis Example 86: MN1382 (EDC Coupling)

1-Cyclopropyl-7-methyl-2,3,4,9-tetrahydro-1H-pyrido[3,4-b]indole (113 mg, 0.50 mmol), 1-ethyl-3-(3-dimethylaminopropyl)carbodiimide-HCl (EDC-HCl) (96 mg, 0.50 mmol), 4-dimethylaminopyridine (DMAP) (6 mg, 0.05 mmol), hydroxybenzotriazole (HOBT) (51 mg, 0.165 mmol), and trans-4-(Boc-methylaminomethyl)cyclohexane carboxylic acid (136 mg, 0.50 mmol) were all dissolved in acetonitrile (625 uL), dimethylformamide (DMF) (2.5 mL), and diisopropylethylamine (DIEA) (100 uL, 0.60 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 32% EtOAc in hexane, 42% EtOAc in hexane, and 50% EtOAc in hexane. Fractions containing product were combined, and the solvent was evaporated under vacuum, yielding a solid (217 mg, 90.5% yield; TLC $R_f$=0.26 (40% EtOAc in Hexane); HPLC $R_t$=4.939 min).

Synthesis Example: MN1376 Intermediate (TFA Cyclization)

4-Methyltryptamine (174 mg, 1.00 mmol) was dissolved in CH$_2$Cl$_2$ (8 mL). The mixture was stirred while isobutyraldehyde (91 uL, 1.00 mmol) was added via syringe, causing the solution to become clear, and was stirred for 5 min. The reaction mixture was cooled in a dry ice propanol bath for 5 min and then trifluoroacetic acid (765 uL, 10.00 mmol) was added drop-wise via syringe over 2 min. The reaction was stirred for 1 hr and was allowed to slowly warm to RT. The mixture was concentrated and dried under vacuum, resulting in a red solid. The result was azeotroped with toluene (3×50 mL) and triturated with diethylether (2×6 mL) and ACN (10 mL). The solid was collected on a filter and dried under high vacuum, yielding 1-isopropyl-5-methyl-2,3,4,9-tetrahydro-1H-pyrido[3,4-b]indole (183 mg, 56.2% yield; TLC $R_f$=0.71 (20% MeOH in CH$_2$Cl$_2$+1% NH$_3$); HPLC $R_t$=3.064 min).

Synthesis Example: MN1383 (EDC Coupling)

1-Isopropyl-5-methyl-2,3,4,9-tetrahydro-1H-pyrido[3,4-b]indole (171 mg, 0.50 mmol), 1-ethyl-3-(3-dimethylaminopropyl)carbodiimide-HCl (EDC-HCl) (96 mg, 0.50 mmol), 4-dimethylaminopyridine (DMAP) (6 mg, 0.05 mmol), hydroxybenzotriazole (HOBT) (25 mg, 0.165 mmol), and trans-4-(Boc-methylaminomethyl)cyclohexane carboxylic acid (136 mg, 0.50 mmol) were all dissolved in acetonitrile (625 uL), dimethylformamide (DMF) (2.5 mL), and diisopropylethylamine (DIEA) (100 uL, 0.60 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 3 fractions (200 mL) consisting of hexane, 32% EtOAc in hexane, 42% EtOAc in hexane, and 50% EtOAc in hexane. Fractions containing product were combined, and the solvent was evaporated under vacuum, yielding a solid (155 mg, 64.4% yield; TLC $R_f$=0.28 (40% EtOAc in Hexane); HPLC $R_t$=4.993 min).

Synthesis Example 88: MN1384 (EDC Coupling)

1-Ethyl-5-methyl-2,3,4,9-tetrahydro-1H-pyrido[3,4-b]indole·TFA salt (164 mg, 0.50 mmol), 1-ethyl-3-(3-dimethylaminopropyl)carbodiimide-HCl (EDC-HCl) (96 mg, 0.50 mmol), 4-dimethylaminopyridine (DMAP) (6 mg, 0.05 mmol), hydroxybenzotriazole (HOBT) (51 mg, 0.165 mmol), and trans-4-(Boc-methylaminomethyl)cyclohexane carboxylic acid (136 mg, 0.50 mmol) were all dissolved in acetonitrile (625 uL), dimethylformamide (DMF) (2.5 mL), and diisopropylethylamine (DIEA) (100 uL, 0.60 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 32% EtOAc in hexane, 42% EtOAc in hexane, and 50% EtOAc in hexane. Fractions containing product were combined, and the solvent was evaporated under vacuum, yielding a solid (203 mg, 86.9% yield; TLC $R_f$=4.877 (40% EtOAc in Hexane); HPLC $R_t$=0.19 min).

Synthesis Example 89: MN1385 (EDC Coupling)

1-Cyclopropyl-5-methyl-2,3,4,9-tetrahydro-1H-pyrido[3,4-b]indole (131 mg, 0.50 mmol), 1-ethyl-3-(3-dimethylaminopropyl)carbodiimide-HCl (EDC-HCl) (96 mg, 0.50 mmol), 4-dimethylaminopyridine (DMAP) (6 mg, 0.05 mmol), hydroxybenzotriazole (HOBT) (51 mg, 0.165 mmol), and trans-4-(Boc-methylaminomethyl)cyclohexane carboxylic acid (136 mg, 0.50 mmol) were all dissolved in acetonitrile (625 uL), dimethylformamide (DMF) (2.5 mL), and diisopropylethylamine (DIEA) (200 uL, 1.20 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 32% EtOAc in hexane, 42% EtOAc in hexane, and 50% EtOAc in hexane. Fractions containing product were combined, and the solvent was evaporated under vacuum, yielding a solid (212 mg, 88.4% yield; TLC $R_f$=0.26 (40% EtOAc in Hexane); HPLC $R_t$=4.909 min).

Synthesis Example 90: MN1386 (Carbamate Formation)

(1-Isopropyl-3,4-dihydro-1H-pyrido[3,4-b]indol-2(9H)-yl)(trans-4-((methylamino)methyl)cyclohexyl)methanone (110 mg, 0.30 mmol) was dissolved in CH$_2$Cl$_2$ (4.5 mL) and cooled in an ice bath for 5 min. Isopropyl chloroformate (150 uL, 0.30 mmol) followed by triethylamine (TEA) (167 uL, 1.20 mmol) were added dropwise to the solution. The reaction mixture was warmed to RT and the solvent was evaporated. The resulting solid was dissolved in EtOAc (200 mL) and washed with 1N NaOH (3×50 mL), 1N HCl (3×50 mL), and sat. NaCl (50 mL). The organic layer was dried (anhyd. Na$_2$SO$_4$), filtered, and evaporated under vacuum. This material was further purified by silica gel (25-30 g) chromatography using fractions (200 mL) consisting of hexane and EtOAc in hexane. Fractions containing product were combined, and the solvent was evaporated under vacuum, yielding a solid (131 mg, 96.3% yield; TLC $R_f$=0.43 (50% EtOAc in Hexane); HPLC $R_t$=4.769 min).

Synthesis Example 91: MN1387 (Carbamate Formation)

(1-Isopropyl-3,4-dihydro-1H-pyrido[3,4-b]indol-2(9H)-yl)(trans-4-((methylamino)methyl)cyclohexyl)methanone (110 mg, 0.30 mmol) was dissolved in CH$_2$Cl$_2$ (4.5 mL) and cooled in an ice bath for 5 min. Benzyl chloroformate (176 uL, 0.30 mmol) followed by triethylamine (TEA) (167 uL, 1.20 mmol) were added dropwise to the solution. The reaction mixture was warmed to RT and the solvent was evaporated. The resulting solid was dissolved in EtOAc (200 mL) and washed with 1N NaOH (3×50 mL), 1N HCl (3×50 mL), and sat. NaCl (50 mL). The organic layer was dried (anhyd. Na$_2$SO$_4$), filtered, and evaporated under vacuum. This material was further purified by silica gel (25-30 g) chromatography using fractions (200 mL) consisting of hexane and EtOAc in hexane. Fractions containing product were combined, and the solvent was evaporated under vacuum, yielding a solid (138 mg, 91.7% yield; TLC R$_f$=0.46 (50% EtOAc in Hexane); HPLC R$_t$=4.891 min).

Synthesis Example 92: MN1388 (Amide Formation)

(1-Isopropyl-3,4-dihydro-1H-pyrido[3,4-b]indol-2(9H)-yl)(trans-4-((methylamino)methyl)cyclohexyl)methanone (220 mg, 0.60 mmol) was dissolved in CH$_2$Cl$_2$ (9 mL) and cooled in an ice bath for 5 min. Propionyl chloride (53 uL, 0.60 mmol) and triethylamine (TEA) (335 uL, 2.4 mmol) were added drop wise to the solution. The reaction mixture was warmed to RT and solvent was evaporated. The resulting solid was dissolved in EtOAc (200 mL) and washed with 1N NaOH (1×25 mL), 1N HCl (1×25 mL), and sat. NaCl (1×50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 75% EtOAc in hexane, 90% EtOAc in hexane, and EtOAc. Fractions containing product were combined, and the solvent was evaporated under vacuum, yielding a solid (201 mg, 76.6% yield; TLC R$_f$=0.14 (70% EtOAc in Hexane); HPLC R$_t$=4.292 min).

Synthesis Example 93: MN1389 (Amide Formation)

(1-Isopropyl-3,4-dihydro-1H-pyrido[3,4-b]indol-2(9H)-yl)(trans-4-((methylamino)methyl)cyclohexyl)methanone (220 mg, 0.60 mmol) was dissolved in CH$_2$Cl$_2$ (9 mL) and cooled in an ice bath for 5 min. 3,3-Dimethylbutanoyl chloride (84 uL, 0.60 mmol) and triethylamine (TEA) (335 uL, 2.4 mmol) were added drop wise to the solution. The reaction mixture was warmed to RT and solvent was evaporated. The resulting solid was dissolved in EtOAc (200 mL) and washed with 1N NaOH (1×25 mL), 1N HCl (1×25 mL), and sat. NaCl (1×50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 50% EtOAc in hexane, 60% EtOAc in hexane, and 70% EtOAc in hexane. Fractions containing product were combined, and the solvent was evaporated under vacuum, yielding a solid (230 mg, 82.3% yield; TLC R$_f$=0.17 (50% EtOAc in Hexane); HPLC R$_t$=4.723 min).

Synthesis Example 94: MN1390 (Amide Formation)

(1-Isopropyl-3,4-dihydro-1H-pyrido[3,4-b]indol-2(9H)-yl)(trans-4-((methylamino)methyl)cyclohexyl)methanone (220 mg, 0.60 mmol) was dissolved in CH$_2$Cl$_2$ (9 mL) and cooled in an ice bath for 5 min. Phenylacetyl chloride (80 uL, 0.60 mmol) and triethylamine (TEA) (335 uL, 2.4 mmol) were added drop wise to the solution. The reaction mixture was warmed to RT and solvent was evaporated. The resulting solid was dissolved in EtOAc (200 mL) and washed with 1N NaOH (1×25 mL), 1N HCl (1×25 mL), and sat. NaCl (1×50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 60% EtOAc in hexane, 70% EtOAc in hexane, and 80% EtOAc in hexane. Fractions containing product were combined, and the solvent was evaporated under vacuum, yielding a solid (221 mg, 75.8% yield; TLC R$_f$=0.15 (60% EtOAc in Hexane); HPLC R$_t$=4.569 min).

Synthesis Example 95: MN1391 (Urea Formation)

(1-Isopropyl-3,4-dihydro-1H-pyrido[3,4-b]indol-2(9H)-yl)(trans-4-((methylamino)methyl)cyclohexyl)methanone (129 mg, 0.35 mmol) was dissolved in CHCl$_3$ (8.75 mL) and cooled in an ice bath under an inert atmosphere of nitrogen for 5 min. Ethyl isocyanate (56 uL, 0.7 mmol) was added to the solution and the reaction mixture was warmed to RT. The mixture was concentrated and dried under vacuum. This material was further purified by silica gel (25-30 g) chromatography using: 4 fractions (200 mL) consisting of CH$_2$Cl$_2$, 3% MeOH in CH$_2$Cl$_2$, 4% MeOH in CH$_2$Cl$_2$, and 5% MeOH in CH$_2$Cl$_2$. Fractions containing product were combined, and the solvent was evaporated under vacuum, yielding a solid (138 mg, 89.9% yield; TLC R$_f$=0.23 (4% MeOH in CH$_2$Cl$_2$); HPLC R$_t$=4.178 min).

Synthesis Example 96: MN1392 (Boc Group Substitution)

(1-Isopropyl-3,4-dihydro-1H-pyrido[3,4-b]indol-2(9H)-yl)(trans-4-((methylamino)methyl)cyclohexyl)methanone (129 mg, 0.35 mmol) was dissolved in CHCl$_3$ (8.75 mL) and cooled in an ice bath under an inert atmosphere of nitrogen for 5 min. t-Butyl isocyanate (82 uL, 0.7 mmol) was added to the solution and the reaction mixture was warmed to RT. The mixture was concentrated and dried under vacuum. This material was further purified by silica gel (25-30 g) chromatography using: 4 fractions (200 mL) consisting of hexane, 50% EtOAc in hexane, 60% EtOAc in hexane, and 70% EtOAc in hexane. Fractions containing product were combined, and the solvent was evaporated under vacuum, yielding a solid (152 mg, 93.1% yield; TLC R$_f$=0.14 (50% EtOAc in Hexane); HPLC R$_t$=4.524 min).

Synthesis Example 97: MN1393 (Boc Group Substitution)

(1-Isopropyl-3,4-dihydro-1H-pyrido[3,4-b]indol-2(9H)-yl)(trans-4-((methylamino)methyl)cyclohexyl)methanone (129 mg, 0.35 mmol) was dissolved in CHCl$_3$ (8.75 mL) and cooled in an ice bath under an inert atmosphere of nitrogen for 5 min. Phenyl isocyanate (76 uL, 0.7 mmol) was added to the solution and the reaction mixture was warmed to RT. The mixture was concentrated and dried under vacuum. This material was further purified by silica gel (25-30 g) chromatography using: 4 fractions (200 mL) consisting of hexane, 50% EtOAc in hexane, 60% EtOAc in hexane, and 70% EtOAc in hexane. Fractions containing product were combined, and the solvent was evaporated under vacuum, yielding a solid (144 mg, 84.5% yield; TLC $R_f$=0.13 (50% EtOAc in Hexane); HPLC $R_t$=4.484 min).

Synthesis Example 98: MN1394 (EDC Coupling)

1-Methyl-2,3,4,9-tetrahydro-1H-pyrido[3,4-b]indole (186 mg, 1.00 mmol), 1-ethyl-3-(3-dimethylaminopropyl) carbodiimide-HCl (EDC-HCl) (192 mg, 1.00 mmol), 4-dimethylaminopyridine (DMAP) (12 mg, 0.1 mmol), hydroxybenzotriazole (HOBT) (51 mg, 0.33 mmol), and trans-4-(Boc-methylaminomethyl)cyclohexane carboxylic acid (271 mg, 1.00 mmol) were all dissolved in acetonitrile (1.25 mL), dimethylformamide (DMF) (5 mL), and diisopropylethylamine (DIEA) (200 uL, 1.20 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 40% EtOAc in hexane, 52% EtOAc in hexane, and 60% EtOAc in hexane. Fractions containing product were combined, and the solvent was evaporated under vacuum, yielding a solid (342 mg, 77.9% yield; TLC $R_f$=0.31 (50% EtOAc in Hexane); HPLC $R_t$=4.672 min).

Synthesis Example 99: MN1395 (EDC Coupling)

2,3,4,9-Tetrahydro-1H-pyrido[3,4-b]indole (172 mg, 1.00 mmol), 1-ethyl-3-(3-dimethylaminopropyl)carbodiimide-HCl (EDC-HCl) (192 mg, 1.00 mmol), 4-dimethylaminopyridine (DMAP) (12 mg, 0.1 mmol), hydroxybenzotriazole (HOBT) (51 mg, 0.33 mmol), and trans-4-(Boc-methylaminomethyl)cyclohexane carboxylic acid (271 mg, 1.00 mmol) were all dissolved in acetonitrile (1.25 mL), dimethylformamide (DMF) (5 mL), and diisopropylethylamine (DIEA) (200 uL, 1.20 mmol). The reaction was stirred for 17 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 40% EtOAc in hexane, 60% EtOAc in hexane, and 70% EtOAc in hexane. Fractions containing product were combined, and the solvent was evaporated under vacuum, yielding a solid (339 mg, 79.7% yield; TLC $R_f$=0.23 (50% EtOAc in Hexane); HPLC $R_t$=4.555 min).

Synthesis Example 100: MN1396 (Reductive Amination)

(1-Isopropyl-3,4-dihydro-1H-pyrido[3,4-b]indol-2(9H)-yl)(trans-4-((methylamino)methyl)cyclohexyl)methanone (110 mg, 0.30 mmol) and NaBH(OAc)$_3$ (95 mg, 0.45 mmol) were dissolved in 1,2-dichloroethane (1,2-DCE) (3 mL). Propionaldehyde (22 uL, 0.30 mmol) was added and the mixture was heated to 80° C. and stirred for 4.5 hrs. The reaction mixture was diluted with EtOAc (50 mL) and 1M K$_2$CO$_3$. The aqueous layer was extracted with EtOAc (2×50 mL) and the aqueous layers were combined. The EtOAc layer was washed with sat. NaCl (20 mL), dried (anhyd. Na$_2$SO$_4$), filtered, and evaporated under vacuum. This material was further purified by silica gel (25-30 g) chromatography using: 5 fractions (200 mL) consisting of CH$_2$Cl$_2$, 4% MeOH in CH$_2$Cl$_2$+1% NH$_3$, 5% MeOH in CH$_2$Cl$_2$+1% NH$_3$, 7% MeOH in CH$_2$Cl$_2$+1% NH$_3$, and 9% MeOH in CH$_2$Cl$_2$+1% NH$_3$. Fractions containing product were combined, and the solvent was evaporated under vacuum, yielding a solid (50 mg, 40.7% yield; TLC $R_f$=0.26 (5% MeOH in CH$_2$Cl$_2$+1% NH$_3$); HPLC $R_t$=3.735 min).

Synthesis Example 101: MN1397 (Reductive Amination)

(1-Isopropyl-3,4-dihydro-1H-pyrido[3,4-b]indol-2(9H)-yl)(trans-4-((methylamino)methyl)cyclohexyl)methanone (110 mg, 0.30 mmol) was dissolved in 1,2-dichloroethane (3 mL). 3,3-Dimethylbutanal (38 uL, 0.30 mmol) and NaBH(OAc)$_3$ (64 mg, 0.45 mmol) were added to the solution, stirred, and heated to 80° C. for 30 min. The solution was diluted with EtOAc (50 mL) and washed with 1M K$_2$CO$_3$ (25 mL). Product was extracted with EtOAc (2×50 mL), washed with sat. NaCl (1×20 mL), dried (anhy. Na$_2$SO$_4$), and filtered. The solvent was evaporated under vacuum yielding a solid (154 mg, 114% yield; TLC $R_f$=0.15 (5% MeOH in CH$_2$Cl$_2$); HPLC $R_t$=4.044 min).

Synthesis Example 102: MN1398 (Reductive Amination)

(1-Isopropyl-3,4-dihydro-1H-pyrido[3,4-b]indol-2(9H)-yl)(trans-4-((methylamino)methyl)cyclohexyl)methanone (110 mg, 0.30 mmol) was dissolved in 1,2-dichloroethane (3 mL). Isovaleraldehyde (33 uL, 0.30 mmol) and NaBH(OAc)$_3$ (64 mg, 0.45 mmol) were added to the solution, stirred, and heated to 80° C. for 30 min. The solution was diluted with EtOAc (50 mL) and washed with 1M K$_2$CO$_3$ (25 mL). Product was extracted with EtOAc (2×50 mL), washed with sat. NaCl (1×20 mL), dried (anhyd. Na$_2$SO$_4$), and filtered. The solvent was evaporated under vacuum yielding a solid (132 mg, 101% yield; TLC $R_f$=0.46 (10% MeOH in CH$_2$Cl$_2$); HPLC $R_t$=3.972 min).

Synthesis Example 102: MN1399 (Amide Formation)

(1-Isopropyl-3,4-dihydro-1H-pyrido[3,4-b]indol-2(9H)-yl)(trans-4-((methylamino)methyl)cyclohexyl)methanone (110 mg, 0.30 mmol) and NaHB(OAc)$_3$ (95 mg, 0.45 mmol) were dissolved in 1,2-dichloroethane (1,2-DCE) (3 mL). Benzaldehyde (31 uL, 0.30 mmol) was added and the mixture was heated to 80° C. and stirred for 4.5 hrs. The reaction mixture was diluted with EtOAc (50 mL) and 1M H$_2$CO$_3$. The aqueous layer was extracted with EtOAc (2×50 mL) and the aqueous layers were combined. The EtOAc layer was washed with sat. NaCl (20 mL), dried (anhyd. Na$_2$SO$_4$), filtered, and evaporated under vacuum. This material was further purified by silica gel (25-30 g) chromatography using: 6 fractions (200 mL) consisting of CH$_2$Cl$_2$, 1% MeOH in CH$_2$Cl$_2$+1% NH$_3$, 2% MeOH in CH$_2$Cl$_2$+1% NH$_3$, 3% MeOH in CH$_2$Cl$_2$+1% NH$_3$, 4% MeOH in CH$_2$Cl$_2$+1% NH$_3$, and 5% MeOH in CH$_2$Cl$_2$+1% NH$_3$. Fractions containing product were combined, and the solvent was evaporated under vacuum, yielding a solid (83 mg, 60.4% yield; TLC $R_f$=0.26 (5% MeOH in CH$_2$Cl$_2$+1% NH$_3$); HPLC $R_t$=3.929 min).

Synthesis Example 104: MN1400 (Boc Cleavage)

tert-Butyl (trans-4-(1-isopropyl-2,3,4,9-tetrahydro-1H-pyrido[3,4-b]indole-2-carbonyl)cyclohexyl)methyl(methyl)

carbamate (2.2814 g, 4.88 mmol) was dissolved in $CH_2Cl_2$ (30 mL). Trifluoroacetic acid (TFA) (30 mL) was added to the solution and at 30 min. was concentrated under vacuum. The result was dissolved in $H_2O$ (80 mL) and $CH_2Cl_2$ (100 mL) and basified with 10M NaOH (1 mL). Product was extracted with $CH_2Cl_2$ (2×100 mL), dried (anhyd. $MgSO_4$), filtered and the solvent was removed under vacuum yielding an off-while/yellow solid (1.667 g). The solid was dissolved in cold acetonitrile (ACN) (2×5 mL), stirred for 30 sec, and filtered. The solvent was evaporated yielding a solid (1.38 g). The solid was dissolved in RT ACN (5 mL), stirred for 30 sec, and filtered. The solvent was evaporated yielding a solid. The solid was stirred in RT ACN (5 mL) at RT for 4 min. The solvent was evaporated yielding a solid (707 mg, 39.4% yield; TLC $R_f$=0.16 (10% MeOH in $CH_2Cl_2$+1% $NH_3$); HPLC $R_t$=3.559 min).

Synthesis Example 105: MN1401 (EDC Coupling)

2,3,4,9-Tetrahydro-1H-pyrido[3,4-b]indole-3-carboxamide (215 mg, 1.00 mmol), 1-ethyl-3-(3-dimethylaminopropyl)carbodiimide-HCl (EDC-HCl) (192 mg, 1.00 mmol), 4-dimethylaminopyridine (DMAP) (12 mg, 0.1 mmol), hydroxybenzotriazole (HOBT) (51 mg, 0.33 mmol), and trans-4-(Boc-methylaminomethyl)cyclohexane carboxylic acid (271 mg, 1.00 mmol) were all dissolved in acetonitrile (1.25 mL), dimethylformamide (DMF) (5 mL), and diisopropylethylamine (DIEA) (200 uL, 1.20 mmol). The reaction was stirred for 17 hours at RT. The reaction mixture was diluted with EtOAc (100 mL), washed with sat. NaCl (2×50 mL), 1M citric acid (3×25 mL), sat. $NaHCO_3$ (3×25 mL), and sat. NaCl (50 mL). The organic layer was dried (anhyd. $Na_2SO_4$), filtered, and evaporated under vacuum. This material was further purified by silica gel (25-30 g) chromatography using: 7 fractions (200 mL) consisting of $CH_2Cl_2$, 3% MeOH in $CH_2Cl_2$, 4% MeOH in $CH_2Cl_2$, 4.5% MeOH in $CH_2Cl_2$, 5% MeOH in $CH_2Cl_2$, and 6% MeOH in $CH_2Cl_2$. Fractions containing product were combined, and the solvent was evaporated under vacuum, yielding a solid (210 mg, 44.8% yield; TLC $R_f$=0.15 (4% MeOH in $CH_2Cl_2$); HPLC $R_t$=4.089 min).

Synthesis Example 106: MN1402 (EDC Coupling)

Benzyl 2,3,4,9-tetrahydro-1H-pyrido[3,4-b]indole-3-carboxylate (306 mg, 1.00 mmol), 1-ethyl-3-(3-dimethylaminopropyl)carbodiimide-HCl (EDC-HCl) (192 mg, 1.00 mmol), 4-dimethylaminopyridine (DMAP) (12 mg, 0.1 mmol), hydroxybenzotriazole (HOBT) (51 mg, 0.33 mmol), and trans-4-(Boc-methylaminomethyl)cyclohexane carboxylic acid (271 mg, 1.00 mmol) were all dissolved in acetonitrile (1.25 mL), dimethylformamide (DMF) (5 mL), and diisopropylethylamine (DIEA) (200 uL, 1.20 mmol). The reaction was stirred for 17 hours at RT. The reaction mixture was diluted with EtOAc (100 mL), washed with sat. NaCl (2×50 mL), 1M citric acid (3×25 mL), sat. $NaHCO_3$ (3×25 mL), and sat. NaCl (50 mL). The organic layer was dried (anhyd. $Na_2SO_4$), filtered, and evaporated under vacuum. This material was further purified by silica gel (25-30 g) chromatography using: 4 fractions (200 mL) consisting of hexane, 30% EtOAc in hexane, 40% EtOAc in hexane, and 55% EtOAc in hexane. Fractions containing product were combined, and the solvent was evaporated under vacuum, yielding a solid (246 mg, 43.9% yield; TLC $R_f$=0.24 (40% EtOAc in Hexane); HPLC $R_t$=4.919 min).

Synthesis Example 107: MN1403 (EDC Coupling)

3-Methyl-2,3,4,9-tetrahydro-1H-pyrido[3,4-b]indole (186 mg, 1.00 mmol), 1-ethyl-3-(3-dimethylaminopropyl)carbodiimide-HCl (EDC-HCl) (192 mg, 1.00 mmol), 4-dimethylaminopyridine (DMAP) (12 mg, 0.1 mmol), hydroxybenzotriazole (HOBT) (51 mg, 0.33 mmol), and trans-4-(Boc-methylaminomethyl)cyclohexane carboxylic acid (271 mg, 1.00 mmol) were all dissolved in acetonitrile (1.25 mL), dimethylformamide (DMF) (5 mL), and diisopropylethylamine (DIEA) (200 uL, 1.20 mmol). The reaction was stirred for 17 hours at RT. The reaction mixture was diluted with EtOAc (100 mL), washed with sat. NaCl (2×50 mL), 1M citric acid (3×25 mL), sat. $NaHCO_3$ (3×25 mL), and sat. NaCl (50 mL). The organic layer was dried (anhyd. $Na_2SO_4$), filtered, and evaporated under vacuum. This material was further purified by silica gel (25-30 g) chromatography using: 4 fractions (200 mL) consisting of hexane, 30% EtOAc in hexane, 50% EtOAc in hexane, and 60% EtOAc in hexane. Fractions containing product were combined, and the solvent was evaporated under vacuum, yielding a solid (352 mg, 80.1% yield; TLC $R_f$=0.30 (50% EtOAc in Hexane); HPLC $R_t$=4.674 min).

Synthesis Example 108: MN1404 (HFIP Cyclization)

α-Methyltryptamine (174 mg, 1.00 mmol) was dissolved in hexafluoro-2-propanol (HFIP) (1.6 mL). Paraformaldehyde (30 mg, 1.0 mmol) was dissolved in HFIP (1.0 mL) and added to the former solution dropwise in 250 uL portions. Over 90 minutes, the reaction mixture was azeotroped with $CHCl_3$ (3×50 mL) yielding a solid (188 mg, 101% yield; TLC $R_f$=0.31 (10% MeOH in $CH_2Cl_2$+1% $NH_3$); HPLC $R_t$=2.717 min).

Synthesis Example 109: MN1405 (HFIP Cyclization)

D-Tryptophan benzyl ester (400 mg, 1.36 mmol) was dissolved in hexafluoro-2-propanol (HFIP) (2.2 mL). Paraformaldehyde (45 mg, 1.49 mmol) was dissolved in HFIP (1.61 mL) and added to the former solution dropwise in 340 uL portions over 1 hr and stirred. After 20 hrs, the solvent was removed under vacuum. The reaction mixture was azeotroped with $CHCl_3$ (3×50 mL), dried under vacuum yielding a solid (3.0 mg, 0.72% yield; TLC $R_f$=0.26 (5% MeOH in $CH_2Cl_2$+1% $NH_3$); HPLC $R_t$=3.505 min).

Synthesis Example 110: MN1406 (Ester to Amide)

Lanthanum (III) trifluoromethanesulfonate (La(OTf)$_3$) (80 mg, 0.136 mmol) was heated using a heat gun to 200+° C. under vacuum. Argon was back-filled into the tube and L-1,2,3,4-tetrahydronorharman-3-carboxylic acid methyl ester·HCl (520 mg, 1.95 mmol) was added. The solids were dissolved in 2N $NH_3$ in EtOH (12 mL). The reaction mixture was capped and heated to 60° C. for 48 hr. The mixture was cooled to RT, filtered with a 0.45 um syringe, and dried under vacuum. La(TFI)$_3$ (80 mg, 0.136 mmol) was added and heated at 90° C. for 20 min. The filtrate was dissolved in 2N $NH_3$ in EtOH and heated at 60° C. for 3 days. The solvent was evaporated and the resulting solid was dissolved in $H_2O$ (50 mL) and EtOAc (20 mL), washed with EtOAc (25 mL), and extracted with $H_2O$ (2×10 mL). The aqueous layer was evaporated. This material was further purified by silica gel (25-30 g) chromatography using fractions (400 mL) consisting of $CH_2Cl_2$ and MeOH and 1% $NH_3$ in $CH_2Cl_2$. Fractions containing product were combined, and the solvent was evaporated under vacuum, yielding a solid (48 mg, 11.4% yield; TLC $R_f$=0.26 (10% MeOH in $CH_2Cl_2$+ 1% $NH_3$); HPLC $R_t$=1.460 min).

Synthesis Example 111: MN1407 (Ester to Carboxylic Acid)

L-1,2,3,4-Tetrahydronorharman-3-carboxylic acid methyl ester·HCl (532 mg, 2.00 mmol) was dissolved in 1N NaOH (20 mL) and heated to reflux for 30 min. The result was transferred to an Erlenmeyer flask and placed in an ice bath. Upon cooling, the salt solidified, 1N HCl (23 mL) was added until pH was 5 and precipitate remained. A white solid was collected on fritted glass. The solid was dried in desiccator overnight and dried further under high vacuum for 2 days yielding a solid (396 mg, 91.6% yield; TLC $R_f$=0.60 (butanol:water:acetic acid [3:1:1]); HPLC $R_t$=2.418 min).

Synthesis Example 112: MN1408 (Ester to Amide)

Lanthanum (III) trifluoromethanesulfonate ($La(OTf)_3$) (20 mg, 0.0341 mmol) was heated to 113-114° C. in an oven for 30 min. The material was placed under high vacuum, heated for 2-3 minutes with heat gun, and cooled to RT under vacuum. L-1,2,3,4-Tetrahydronorharman-3-carboxylic acid methyl ester·HCl (130 mg, 0.30 mmol) was added to the mixture, dried under vacuum for 30 min, and heated briefly to about 150° C. with a heat gun. The reaction mixture was heated at 60° C. for 2 hr, resulting in a thick white solution. The solution was placed in an ice bath and white crystals were collected on fritted glass. The solid was washed with cold $H_2O$ (3 mL) and dried under vacuum over 2 days, yielding a solid (101 mg, 88.1% yield; TLC $R_f$=0.42 (10% MeOH in $CH_2Cl_2$+1% $NH_3$); HPLC $R_t$=2.404 min).

Synthesis Example 113: MN1409 (EDC Coupling)

Ethyl 2,3,4,9-tetrahydro-1H-pyrido[3,4-b]indole-3-carboxylate (181 mg, 0.74 mmol), 1-ethyl-3-(3-dimethylaminopropyl)carbodiimide-HCl (EDC-HCl) (150 mg, 0.78 mmol), 4-dimethylaminopyridine (DMAP) (10 mg, 0.078 mmol), hydroxybenzotriazole (HOBT) (40 mg, 0.26 mmol), and trans-4-(Boc-methylaminomethyl)cyclohexane carboxylic acid (212 mg, 0.78 mmol) were all dissolved in acetonitrile (975 uL), dimethylformamide (DMF) (3.9 mL), and diisopropylethylamine (DIEA) (156 uL, 0.94 mmol). The reaction was stirred for 5 days at RT. The reaction mixture was diluted with EtOAc (100 mL), washed with sat. NaCl (2×50 mL), 1M citric acid (3×25 mL), sat. $NaHCO_3$ (3×25 mL), and sat. NaCl (50 mL). The organic layer was dried (anhyd. $Na_2SO_4$), filtered, and evaporated under vacuum. This material was further purified by silica gel (25-30 g) chromatography using: 5 fractions (200 mL) consisting of hexane, 30% EtOAc in hexane, 37% EtOAc in hexane, 40% EtOAc in hexane, and 50% EtOAc in hexane. Fractions containing product were combined, and the solvent was evaporated under vacuum, yielding a solid (100 mg, 27.2% yield; TLC $R_f$=0.18 (40% EtOAc in Hexane); HPLC $R_t$=4.680 min).

Synthesis Example 114: MN1410 (EDC Coupling)

Isopropyl 2,3,4,9-tetrahydro-1H-pyrido[3,4-b]indole-3-carboxylate (201 mg, 0.78 mmol), 1-ethyl-3-(3-dimethylaminopropyl)carbodiimide-HCl (EDC-HCl) (150 mg, 0.78 mmol), 4-dimethylaminopyridine (DMAP) (10 mg, 0.078 mmol), hydroxybenzotriazole (HOBT) (40 mg, 0.26 mmol), and trans-4-(Boc-methylaminomethyl)cyclohexane carboxylic acid (212 mg, 0.78 mmol) were all dissolved in acetonitrile (975 uL), dimethylformamide (DMF) (3.9 mL), and diisopropylethylamine (DIEA) (156 uL, 0.94 mmol). The reaction was stirred for 5 days at RT. The reaction mixture was diluted with EtOAc (100 mL), washed with sat. NaCl (2×50 mL), 1M citric acid (3×25 mL), sat. $NaHCO_3$ (3×25 mL), and sat. NaCl (50 mL). The organic layer was dried (anhyd. $Na_2SO_4$), filtered, and evaporated under vacuum. This material was further purified by silica gel (25-30 g) chromatography using: 5 fractions (200 mL) consisting of hexane, 30% EtOAc in hexane, 37% EtOAc in hexane, 40% EtOAc in hexane, and 50% EtOAc in hexane. Fractions containing product were combined, and the solvent was evaporated under vacuum, yielding a solid (125 mg, 31.3% yield; TLC $R_f$=0.21 (40% EtOAc in Hexane); HPLC $R_t$=4.790 min).

Synthesis Example 115: MN1411 (EDC Coupling)

(S)—N-methyl-2,3,4,9-tetrahydro-1H-pyrido[3,4-b]indole-3-carboxamide (200 mg, 0.872 mmol), 4-dimethylaminopyridine (DMAP) (10.6 mg, 0.087 mmol), hydroxybenzotriazole (HOBT) (88 mg, 0.576 mmol), and trans-4-(Boc-methylaminomethyl)cyclohexane carboxylic acid (237 mg, 0.872 mmol) were all dissolved in acetonitrile (1.1 mL), dimethylformamide (DMF) (8 mL), and diisopropylethylamine (DIEA) (396 uL, 2.4 mmol). The reaction was stirred for 2 days at RT and then 6 hr at 60° C. The reaction mixture was diluted with EtOAc (100 mL), washed with sat. NaCl (2×50 mL), 1M citric acid (3×25 mL), sat. $NaHCO_3$ (3×25 mL), and sat. NaCl (50 mL). The organic layer was dried (anhyd. $Na_2SO_4$), filtered, and evaporated under vacuum. The result was triturated with hexane (20 mL) and eluted with 20% EtOAc in hexane (20 mL). The solvent was evaporated under vacuum, yielding a solid (200 mg, 47.5% yield; TLC $R_f$=0.32 (5% MeOH in $CH_2Cl_2$); HPLC $R_t$=4.187 min).

Synthesis Example 116: MN1412 (Urea Formation)

(1-Isobutyl-3,4-dihydro-1H-pyrido[3,4-b]indol-2(9H)-yl)(trans-4-((methylamino)methyl)cyclohexyl)methanone (114 mg, 0.30 mmol) was dissolved in $CHCl_3$ (7.5 mL) and cooled in an ice bath 5 min. t-Butyl isocyanate (68 uL, 0.60 mmol) was added to the solution and the reaction mixture was stirred for 10 min. The reaction was removed from the ice bath and warmed to RT. The mixture was concentrated and dried under vacuum. This material was further purified by silica gel (25-30 g) chromatography using: 4 fractions (200 mL) consisting of hexane, 40% EtOAc in hexane, 70% EtOAc in hexane, and 80% EtOAc in hexane. Fractions containing product were combined, and the solvent was evaporated under vacuum, yielding a solid (50 mg, 34.7% yield; TLC $R_f$=0.37 (60% EtOAc in Hexane); HPLC $R_t$=4.703 min).

Synthesis Example 117: MN1413 (Urea Formation)

(1-Cyclopropyl-3,4-dihydro-1H-pyrido[3,4-b]indol-2 (9H)-yl)(trans-4-((methylamino)methyl)cyclohexyl)methanone (1.803 g, 5.1 mmol) was dissolved in $CHCl_3$ (50 mL) and cooled in an ice bath 5 min. t-Butyl isocyanate (1.16 mL, 10.2 mmol) was added to the solution and the reaction mixture was stirred for 20 min. The mixture was concentrated and dried under vacuum, yielding a solid (2.6969 g). This material was further purified by silica gel (160 g) chromatography using: 6 fractions (1 L) consisting of hexane, 30% EtOAc in hexane, 40% EtOAc in hexane, 50% EtOAc in hexane, 60% EtOAc in hexane, and 70% EtOAc in hexane. Fractions containing product were combined, and the solvent was evaporated under vacuum, yielding an off-white solid (2.0442 mg, 86.3% yield; TLC $R_f$=0.22 (60% EtOAc in Hexane); HPLC $R_t$=4.410 min); LCMS (ESI) m/z: [M+H]+ Calcd for C28H40N4O2 464.6428; Found 465.3244; $^1$H NMR (CDCl$_3$, 0.003% v/v TMS, 400 MHz): $\delta_H$ 0.40-0.50 (m, 1H), 0.57-0.80 (m, 3H), 1.00-1.15 (m, 2H), 1.20-1.27 (m, 1H), 1.35 (s, 9H), 1.50-1.70 (m, 3H), 1.75-1.85 (m, 3H), 1.95 (d, 1H), 2.56 (t, 1H), 2.85 (s, 4H), 3.13 (d, 2H), 3.56-3.70 (m, 1H), 4.10-4.23 (m, 2H), 5.20 (d, 1H), 7.01 (dd, 1H), 7.16 (dd, 1H), 7.33 (d, 1H), 7.46 (d, 1H), 8.02 (s, 1H).

Synthesis Example 118: MN1414 (Urea Formation)

(1-Ethyl-3,4-dihydro-1H-pyrido[3,4-b]indol-2(9H)-yl)(trans-4-((methylamino)methyl)cyclohexyl)methanone (73 mg, 0.20 mmol) was dissolved in CHCl$_3$ (5 mL) and cooled in an ice bath 5 min. t-Butyl isocyanate (46 uL, 0.40 mmol) was added to the solution and the reaction mixture was stirred for 10 min. The reaction was removed from the ice bath and warmed to RT. The mixture was concentrated and dried under vacuum. This material was further purified by silica gel (25-30 g) chromatography using: 4 fractions (200 mL) consisting of hexane, 40% EtOAc in hexane, 70% EtOAc in hexane, and 80% EtOAc in hexane. Fractions containing product were combined, and the solvent was evaporated under vacuum, yielding a solid (63 mg, 69.6% yield; TLC $R_f$=0.17 (60% EtOAc in Hexane); HPLC $R_t$=4.414 min).

Synthesis Example 119: MN1415 (Thiourea Formation)

(1-Isopropyl-3,4-dihydro-1H-pyrido[3,4-b]indol-2(9H)-yl)(trans-4-((methylamino)methyl)cyclohexyl)methanone (92 mg, 0.25 mmol) was dissolved in CHCl$_3$ (6.25 mL). tert-Butyl isothiocyanate (38.5 uL, 0.303 mmol) and was stirred overnight. At 21 hrs, Tris(2-aminoethyl)amine, polymer bound (188 mg, 0.75 mmol) was added to the reaction to react with excess isothiocyante. At 22 hrs, the reaction was filtered through a 0.45 um PTFE filter. The solvent was evaporated under vacuum and dried under high vacuum. This material was further purified by silica gel (25-30 g) chromatography using: 4 fractions (200 mL) consisting of hexane, 40% EtOAc in hexane, 45% EtOAc in hexane, and 50% EtOAc in hexane. Fractions containing product were combined, and the solvent was evaporated under vacuum, yielding a solid (101 mg, 83.7% yield; TLC $R_f$=0.17 (50% EtOAc in Hexane); HPLC $R_t$=4.760 min).

Synthesis Example 120: MN1416 (Boc Cleavage)

tert-Butyl (trans-4-(1-isobutyl-2,3,4,9-tetrahydro-1H-pyrido[3,4-b]indole-2-carbonyl)cyclohexyl)methyl(methyl)carbamate (330 mg, 0.685 mmol) was dissolved in CH$_2$Cl$_2$ (10 mL) and TFA (10 mL). The reaction was stirred for 10 minutes, the solvent was removed, and the result placed under high vacuum. The resulting solid was suspended in H$_2$O (50 mL) and CH$_2$Cl$_2$ (50 mL) while stirred. 10N NaOH was added until the solution was basic, and product was extracted with CH$_2$Cl$_2$ (3×50 mL), dried (anhyd. MgSO$_4$), and filtered. The solvent was removed under vacuum yielding a solid (250 mg, 48.2% yield; TLC $R_f$=0.24 (10% MeOH in CH$_2$Cl$_2$+1% NH$_3$); HPLC $R_t$=3.689 min).

Synthesis Example 121: MN1417 (Boc Cleavage)

tert-Butyl (trans-4-(1-ethyl-2,3,4,9-tetrahydro-1H-pyrido[3,4-b]indole-2-carbonyl)cyclohexyl)methyl(methyl)carbamate (212 mg, 0.467 mmol) was dissolved in CH$_2$Cl$_2$ (10 mL) and TFA (10 mL). The reaction was stirred for 10 minutes, the solvent was removed, and the result placed under high vacuum. The resulting solid was suspended in H$_2$O (50 mL) and CH$_2$Cl$_2$ (50 mL) while stirred. 10N NaOH was added until the solution was basic, and product was extracted with CH$_2$Cl$_2$ (3×50 mL), dried (anhyd. MgSO$_4$), and filtered. The solvent was removed under vacuum yielding a solid (146 mg, 88.4% yield; TLC $R_f$=0.19 (10% MeOH in CH$_2$Cl$_2$+1% NH$_3$); HPLC $R_t$=3.407 min).

Synthesis Example 122: MN1418 (Thermolytic Boc Cleavage)

tert-Butyl (trans-4-(1-cyclopropyl-2,3,4,9-tetrahydro-1H-pyrido[3,4-b]indole-2-carbonyl)cyclohexyl)methyl(methyl)carbamate (308, 0.66 mmol) was heated neat in an aluminum block to 225° C. for 38 min. After cooling to RT, the resulting oil was placed under high vacuum, yielding a powdery light brown solid (225 mg, 93.3% yield; TLC $R_f$=0.21 (10% OMeOH in CH$_2$Cl$_2$+1% NH$_3$); HPLC $R_t$=3.461 min).

Synthesis Example 123: MN1421 (α-methyl Tryptamine Cyclization)

(R)-α-Methyltryptamine (990 mg, 5.68 mmol) was dissolved in 1,1,1,3,3,3-hexafluoroisopropanol (9.1 mL). A 2.0M solution of paraformaldehyde (2.85 mL) in HFIP was added drop wise to the solution over 28 min. The reaction mixture was concentrated under vacuum and azeotroped with CHCl3 (3×100 mL), yielding a solid (1.053 g). The solid was titrated with ACN (6 mL), filtered, and dried under high vacuum yielding a solid (919 mg, 86.7% yield; TLC $R_f$=0.27 (10% MeOH in CH$_2$Cl$_2$+1% NH$_3$); HPLC $R_t$=2.660 min).

Synthesis Example 124: MN1422 (EDC Coupling)

(R)-3-Methyl-2,3,4,9-tetrahydro-1H-pyrido[3,4-b]indole (867.5 mg, 4.66 mmol), 1-ethyl-3-(3-dimethylaminopropyl)carbodiimide-HCl (EDC-HCl) (983 mg, 5.13 mmol), 4-dimethylaminopyridine (DMAP) (57 mg, 0.466 mmol), hydroxybenzotriazole (HOBT) (236 mg, 1.54 mmol), and trans-4-(Boc-methylaminomethyl)cyclohexane carboxylic acid (1.264, 4.66 mmol) were all dissolved in acetonitrile (5.8 mL), dimethylformamide (DMF) (23 mL), and diisopropylethylamine (DIEA) (925 uL, 5.59 mmol). The reaction was stirred for 17 hours at RT. The reaction mixture was diluted with EtOAc (250 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum, yielding a solid (1.9213 g, 93.8% yield; TLC $R_f$=0.26 (50% EtOAc in Hexane); HPLC $R_t$=4.633 min).

Synthesis Example 125: MN1423 (Urea Formation)

((R)-3-methyl-3,4-dihydro-1H-pyrido[3,4-b]indol-2(9H)-yl)(trans-4-((methylamino)methyl)cyclohexyl)methanone (1.14 g, 3.36 mmol) was dissolved in CHCl3 (50 mL) and placed in an ice bath. tert-Butyl isocyanate (767 uL, 6.72 mmol) was added via syringe to the solution. The reaction was deemed complete at 20 min. The reaction mixture was concentrate under vacuum and dried under high vacuum, yielding a solid (1.64 g). This material was further purified by silica gel (160 g) chromatography using: 6 fractions (200 mL) consisting of hexane, 50% EtOAc in hexane, 60% EtOAc in hexane, 70% EtOAc in hexane, 80% EtOAc in hexane, and 90% EtOAc in hexane. Fractions containing product were combined, and the solvent was evaporated under vacuum, yielding a solid (1.28 g, 87.0% yield; TLC $R_f$=0.20 (70% EtOAc in Hexane); HPLC $R_t$=4.259 min); LCMS (ESI) m/z: [M+H]+ Calcd for C26H38N4O2 438.6055; Found 439.3105; $^1$H NMR (CDCl$_3$, 0.003% v/v TMS, 400 MHz): $\delta_H$ 1.00-1.30 (m, 5H), 1.35 (s, 9H), 1.45-1.55 (m, 3H), 1.55-1.70 (m, 3H), 1.75-1.90 (m, 4H), 2.50-2.63 (m, 1H), 2.65-2.77 (m, 1H), 2.82 (s, 3H), 3.00-3.10 (m, 1H), 3.12 (d, 2H), 4.00-4.20 (m, 2H), 4.55-4.65 (m, 1H), 5.40-5.50 (m, 2H), 7.07 (dd, 1H), 7.15 (dd, 1H), 7.31 (d, 1H), 7.44 (d, 1H), 7.93 (s, 1H).

Synthesis Example 126: Intermediate (Ester Formation)

4-[(Ethylamino)methyl]cyclohexane-1-carboxylic acid hydrochloride salt (500 mg, 2.26 mmol) was dissolved in 1.25M HCl in EtOH (10 mL, 12.5 mmol), heated and stirred at 78° C. using a condenser under an inert atmosphere of argon. The solution was then refluxed for 48 hrs, resulting in a solid. The solid was dissolved in EtOH (10 mL) and rotovaped, yielding a white solid. The solid was dissolved in EtOAc (100 mL) and washed with 1M K$_2$CO$_3$ (2×10 mL), sat. NaCl (10 mL), and evaporated under vacuum, yielding an oil (564 mg, 99% yield; HPLC (200 nm) $R_t$=2.540 min).

Synthesis Example 127: Intermediate (Urea Formation)

Ethyl 4-((ethylamino)methyl)cyclohexanecarboxylate (564 mg, 2.26 mmol) was dissolved in CHCl3 (20 mL) and cooled in an ice bath. t-Butyl isocyante (387 uL, 3.39 mmol) was added to the solution and triethylamine (TEA) was added dropwise to the solution over 2 min. The reaction mixture was removed from the ice bath stirred at RT for 45 min. The reaction mixture was rotovaped and dried under high vacuum. The result was dissolved in EtOAc (100 mL) and washed with 1M citric acid (3×25 mL), 1M NaHCO$_3$ (3×25 mL), and sat. NaCl (50 mL). The result was dried with Na$_2$SO$_4$, filtered, and rotovaped yielding an oil. The oil was dried under high vacuum, crystalizing and yielding a solid (677 mg, 96.0% yield; HPLC-ELSD $R_t$=4.306 min).

Synthesis Example 128: Intermediate (Ester Hydrolysis)

Ethyl 4-((3-tert-butyl-1-ethylureido)methyl)cyclohexanecarboxylate (677 mg, 2.17 mmol) was dissolved in 1N NaOH (10 mL, 10 mmol) and heated to 90° C. while stirring under an inert atmosphere of argon. After 2 hrs, 10M NaOH (3 mL, 30 mmol) and EtOH (3 mL) were added to the reaction mixture. The mixture was heated at 80° C. for 1 hr and then was allowed to cool to RT. The solution was rotovaped and the result was dissolved in H$_2$O (6 mL) and acidified with cold conc. H$_2$SO$_4$ until the pH was 2. The product was extracted with EtOAc (3×200 mL) and 1N HCl (20 mL). The organic layer was washed with 35 mL sat. NaCl+1N HCl and dried over Na$_2$SO$_4$. The solvent was evaporated under high vacuum, yielding a solid (370 mg, 60% yield; HPLC (200 nm) [cis/trans (1:2)] $R_t$=3.563, 3.475 min).

Synthesis Example 129: MN1424 (EDC Coupling)

6,7,8,9-Tetrahydro-5H-pyrrolo[2,3-b:5,4-c']dipyridine (250 mg, 1.44 mmol), 1-ethyl-3-(3-dimethylaminopropyl) carbodiimide-HCl (EDC-HCl) (331 mg, 1.73 mmol), 4-dimethylaminopyridine (DMAP) (18 mg, 0.144 mmol), hydroxybenzotriazole (HOBT) (74 mg, 0.48 mmol), and trans-4-(Boc-methylaminomethyl)cyclohexane carboxylic acid (392 mg, 1.44 mmol) were all dissolved in acetonitrile (1.8 mL), dimethylformamide (DMF) (7.2 mL), and diisopropylethylamine (DIEA) (357 uL, 2.16 mmol). The reaction was stirred for 20 hours at RT. The reaction mixture was diluted with EtOAc (100 mL), washed with sat. NaCl (2×50 mL), 0.2M 2-(N-morpholino)ethanesulfonic acid (MES), pH 7 buffer, (2×25 mL), sat. NaHCO$_3$ (3×25 mL), and sat. NaCl (50 mL). The organic layer was dried (anhyd. Na$_2$SO$_4$), filtered, and evaporated under vacuum, yielding a solid (408 mg). The product was dissolved in EtOAc (20 mL), extracted with 1M citric acid (3×50 mL), and washed with EtOAc (10 mL). 10M NaOH was added to the solution until the pH was 7.8. The product was extracted with EtOAc (3×100 mL), dried (anhyd. Na$_2$SO$_4$), filtered, and evaporated under hood. This material was further purified by silica gel (25-30 g) chromatography using: 6 fractions (200 mL) consisting of CH$_2$Cl$_2$, 2% MeOH in CH$_2$Cl$_2$, 4% MeOH in CH$_2$Cl$_2$, 6% MeOH in CH$_2$Cl$_2$, 8% MeOH in CH$_2$Cl$_2$, and 10% MeOH in CH$_2$Cl$_2$. Fractions containing product were combined, and the solvent was evaporated under vacuum, yielding a solid (217 mg, 35.3% yield; TLC $R_f$=0.19 (4% MeOH in CH$_2$Cl$_2$); HPLC $R_t$=3.579 min).

Synthesis Example 130: MN1425 (EDC Coupling)

1-Ethyl-2,3,4,9-tetrahydro-1H-pyrido[3,4-b]indole (100 mg, 0.50 mmol), 1-ethyl-3-(3-dimethylaminopropyl)carbodiimide-HCl (EDC-HCl) (105 mg, 0.55 mmol), 4-dimethylaminopyridine (DMAP) (6 mg, 0.05 mmol), hydroxybenzotriazole (HOBT) (25 mg, 0.165 mmol), and trans-4-((3-tert-butyl-1-ethylureido)methyl)cyclohexanecarboxylic acid (136 mg, 0.50 mmol) were all dissolved in acetonitrile (625 uL), dimethylformamide (DMF) (2.5 mL), and diisopropylethylamine (DIEA) (100 uL, 0.60 mmol). The reaction was stirred for 48 hours at RT. The reaction mixture was diluted with EtOAc (100 mL), washed with sat. NaCl (2×50 mL), 1M citric acid (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of hexane, 40% EtOAc in hexane, 50% EtOAc in hexane, and 60% EtOAc in hexane. Fractions containing product were combined, and the solvent was evaporated under vacuum, yielding a solid (73 mg). This material was further purified by silica gel (25-30 g) chromatography using: 5 fractions (200 mL) consisting of CH$_2$Cl$_2$, 12% EtOAc in CH$_2$Cl$_2$, 22% EtOAc in CH$_2$Cl$_2$, 25% EtOAc in CH$_2$Cl$_2$, and 35% EtOAc in CH$_2$Cl$_2$. Fractions containing product were combined, and the solvent was evaporated under vacuum, yielding a solid (81 mg, 34.7% yield; TLC $R_f$=0.30 (60% EtOAc in Hexane); HPLC [cis/trans (1:4)] $R_t$=4.648, 4.514 min).

Synthesis Example 131: MN1426 (EDC Coupling)

1-Cyclopropyl-2,3,4,9-tetrahydro-1H-pyrido[3,4-b]indole (106 mg, 0.50 mmol), 1-ethyl-3-(3-dimethylaminopropyl)carbodiimide-HCl (EDC-HCl) (105 mg, 0.55 mmol), 4-dimethylaminopyridine (DMAP) (6 mg, 0.05 mmol), hydroxybenzotriazole (HOBT) (25 mg, 0.165 mmol), and trans-4-((3-tert-butyl-1-ethylureido)methyl)cyclohexanecarboxylic acid (136 mg, 0.50 mmol) were all dissolved in acetonitrile (625 uL), dimethylformamide (DMF) (2.5 mL), and diisopropylethylamine (DIEA) (100 uL, 0.60 mmol). The reaction was stirred for 48 hours at RT. The reaction mixture was diluted with EtOAc (100 mL), washed with sat. NaCl (2×50 mL), 1M citric acid (3×25 mL), sat. NaHCO₃ (3×25 mL), and sat. NaCl (50 mL). The organic layer was dried (anhyd. Na₂SO₄), filtered, and evaporated under vacuum. This material was further purified by silica gel (25-30 g) chromatography using: 4 fractions (200 mL) consisting of hexane, 40% EtOAc in hexane, 50% EtOAc in hexane, and 60% EtOAc in hexane. Fractions containing product were combined, and the solvent was evaporated under vacuum, yielding a solid (142 mg). This material was further purified by silica gel (25-30 g) chromatography using: 5 fractions (200 mL) consisting of CH₂Cl₂, 10% EtOAc in CH₂Cl₂, 20% EtOAc in CH₂Cl₂, 25% EtOAc in CH₂Cl₂, and 35% EtOAc in CH₂Cl₂. Fractions containing product we nre combined, and the solvent was evaporated under vacuum, yielding a solid (85 mg, 35.5% yield; TLC R$_f$=0.37 (60% EtOAc in Hexane); HPLC [cis/trans (1:4)] R$_t$=4.687, 4.554 min).

Synthesis Example 132: MN1443 (Urea Formation)

Azacarboline intermediate (114 mg, 0.26 mmol), was dissolved in CHCl₃ (20 mL) and diisopropylethylamine (DIEA) (100 uL, 0.60 mmol). t-Butyl isocyante (32 uL, 0.286 mmol) was added to the solution via syringe. The reaction was stirred at RT for 45 min. The reaction mixture was rotovaped and dried under high vacuum. The result was purified by silica gel (25-30 g) chromatography using: 4 fractions (200 mL) consisting of CH₂Cl₂, 2% MeOH in CH₂Cl₂, 5% MeOH in CH₂Cl₂, and 8% MeOH in CH₂Cl₂. Fractions containing product were combined, and the solvent was evaporated under vacuum. The product was then dissolved in EtOAc (100 mL) and washed with 1M NaOH (3×20 mL), pH 7.0 0.2M MES buffer (3×20 mL), 1M NaOH (1×20 mL), and brine (1×25 mL). The organic layer was dried (anhyd. Na₂SO₄), filtered, and evaporated under vacuum yielding a solid (70 mg, 63.3% yield; TLC R$_f$=0.15 (5% MeOH in CH₂Cl₂); HPLC R$_t$=3.212 min).

Example: EDC Coupling with Citric Acid, NaHCO₃ workup—MN1420—EDC Coupling

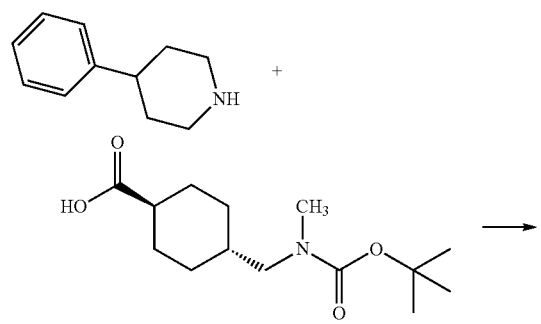

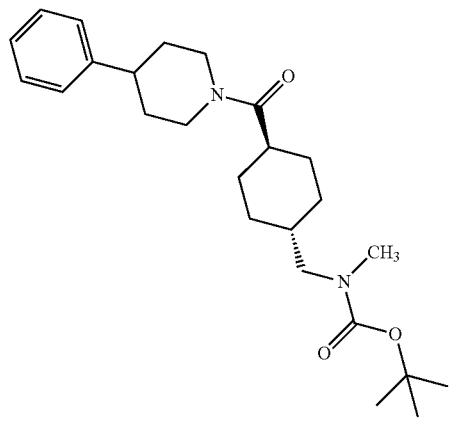

4-Phenylpiperidine (161 mg, 1.00 mmol), 1-ethyl-3-(3-dimethylaminopropyl)carbodiimide-HCl (EDC-HCl) (192 mg, 1.00 mmol), 4-dimethylaminopyridine (DMAP) (12 mg, 0.1 mmol), hydroxybenzotriazole (HOBT) (51 mg, 0.33 mmol), and trans-4-(Boc-methylaminomethyl)cyclohexane carboxylic acid (271 mg, 1.00 mmol) were all dissolved in acetonitrile (1.25 mL), dimethylformamide (DMF) (5 mL), and diisopropylethylamine (DIEA) (200 uL, 1.20 mmol). The reaction was stirred for 17 hours at RT. The reaction mixture was diluted with EtOAc (100 mL), washed with sat. NaCl (2×50 mL), 1M citric acid (3×25 mL), sat. NaHCO₃ (3×25 mL), and sat. NaCl (50 mL). The organic layer was dried (anhyd. Na₂SO₄), filtered, and evaporated under vacuum. This material was further purified by silica gel (25-30 g) chromatography using: 4 fractions (200 mL) consisting of hexane, 25% EtOAc in hexane, 30% EtOAc in hexane, and 35% EtOAc in hexane. Fractions containing product were combined, and the solvent was evaporated under vacuum, yielding a solid (330 mg, 79.6% yield; TLC R$_f$=0.39 (50% EtOAc in Hexane); HPLC R$_t$=4.702 min).

MN1429, MN1430, MN1431, MN1432, MN1434, MN1449, MN1450, MN1451, MN1452, MN1453 and MN1454 were prepared in a similar matter to MN1420.

Example: EDC Coupling with MES Buffer, NaHCO₃ Workup: MN1428-EDC Coupling

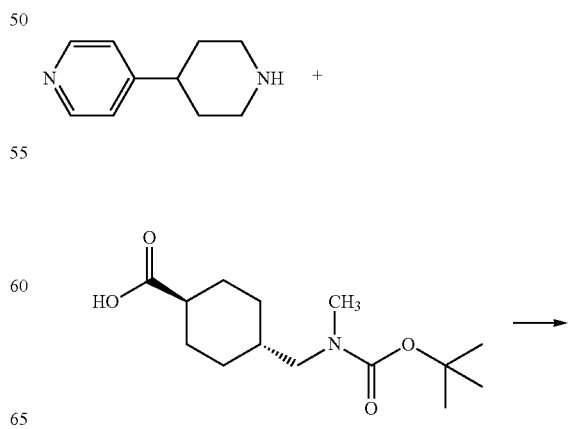

-continued

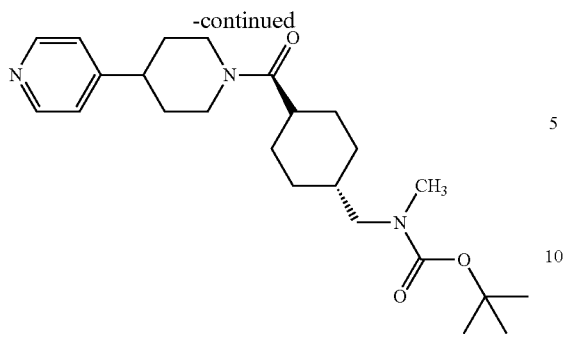

4-(4-Pyridinyl)piperidine (65 mg, 0.40 mmol), 1-ethyl-3-(3-dimethylaminopropyl)carbodiimide-HCl (EDC-HCl) (84 mg, 0.44 mmol), 4-dimethylaminopyridine (DMAP) (5 mg, 0.04 mmol), hydroxybenzotriazole (HOBT) (20 mg, 0.132 mmol), and trans-4-(Boc-methylaminomethyl)cyclohexane carboxylic acid (82 mg, 0.30 mmol) were all dissolved in acetonitrile (500 uL), dimethylformamide (DMF) (2 mL), and diisopropylethylamine (DIEA) (79 uL, 0.48 mmol). The reaction was stirred for 17 hrs at RT. The reaction mixture was diluted with EtOAc (100 mL), washed with sat. NaCl (2×50 mL), 0.2M MES, pH 7 buffer, (3×25 mL), sat. NaHCO$_3$ (3×25 mL), and sat. NaCl (50 mL). The organic layer was dried (anhyd. Na$_2$SO$_4$), filtered, and evaporated under vacuum. This material was further purified by silica gel (25-30 g) chromatography using: 4 fractions (200 mL) consisting of CH$_2$Cl$_2$, 2% MeOH in CH$_2$Cl$_2$, 4% MeOH in CH$_2$Cl$_2$, and 5% MeOH in CH$_2$Cl$_2$. Fractions containing product were combined, and the solvent was evaporated under vacuum, yielding a solid (124 mg, 99.5% yield; TLC R$_f$=0.22 (4% MeOH in CH$_2$Cl$_2$); HPLC R$_t$=3.409 min).

MN1427, MN1447 and MN1448 were prepared in a similar manner as MN1428.

Synthesis Example: MN1428T (tosyl)

Tert-butyl methyl((4-(4-(pyridin-4-yl)piperidine-1-carbonyl)cyclohexyl)methyl)carbamate (3.3066 g, 7.9568 mmol) was dissolved in diethylether (250 mL) and then filtered through a 0.45 um PTFE syringe filter. This solution was combined with p-toluene sulfonic acid (1.5144 g, 7.956 mmol) dissolved in diethylether (150 mL) resulting in a precipitate. The mixture was concentrated and dried under vacuum. The result was recrystallized from boiling acetonitrile (10 mL), cooled quickly, and the resulting solid was collected on a funnel. This was then recrystallized again from boiling acetonitrile (20 mL), cooled slowly to RT over 3 days, and the mother liquor was decanted off. The solid was rinsed with acetonitrile (5 mL) at RT, collected on a funnel, and dried in a vacuum desiccator for 16 hrs, yielding a white solid (2.08 g, 44.5% yield; HPLC R$_t$=3.329 min).

Example of DCC Coupling with K2CO3 Workup: MN1433—DCC Coupling

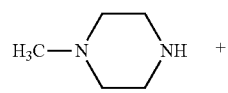

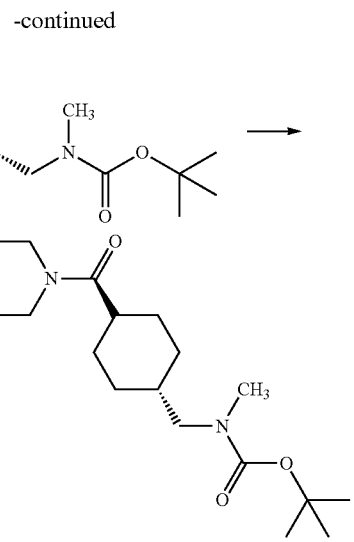

Synthesis Example MN1433 (DCC Coupling)

1-Methylpiperazine (100 mg, 1.00 mmol), N,N'-Dicyclohexylcarbodiimide (227 mg, 1.10 mmol), 1-hydroxybenzotriazole (51 mg, 0.33 mmol) and trans-4-(Boc-methylaminomethyl)cyclohexane carboxylic acid (271 mg, 1.00 mmol) were all dissolved in acetonitrile (10.0 mL). The reaction was stirred for 16 hours at RT. The resulting precipitate was removed and collected on a funnel and the filtrate was evaporated under vacuum. The resulting oil from the filtrate was dissolved in EtOAc (5 mL) and filtered through a 0.22 um PTFE syringe filter and then diluted with EtOAc (95 mL). This solution was washed with 1M K2CO3 (3×33 mL) and brine (1×50 mL). The organic layer was dried (anhyd. Na$_2$SO$_4$), filtered, and evaporated under vacuum. This material was further purified by silica gel (25-30 g) chromatography using: 5 fractions (200 mL) consisting of CH2Cl2+1% NH$_3$, 1% MeOH in CH2Cl2+1% NH$_3$, 2% MeOH in CH2Cl2+1% NH3, 5% MeOH in CH2Cl2+1% NH$_3$, and 10% MeOH in CH2Cl2+1% NH$_3$. Fractions containing product were combined, and the solvent was evaporated under vacuum, yielding an oil (319 mg, 90.2% yield; TLC R$_f$=0.16 (4% MeOH in CH2Cl2+1% NH$_3$); HPLC R$_t$=3.133 min). The following compounds were synthesized in a similar manner: MN1433, MN1437, MN1438, MN1455, MN1456, MN1457, MN1458, MN1459, MN1460.

Example of DCC Coupling with NaOH/MOPS/HCl Workup: MN1456—DCC Coupling

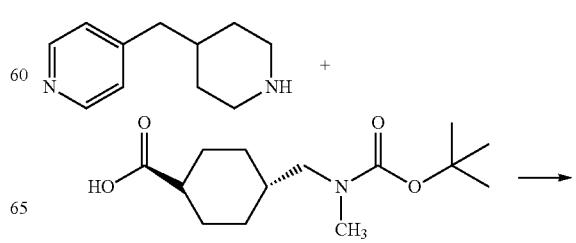

-continued

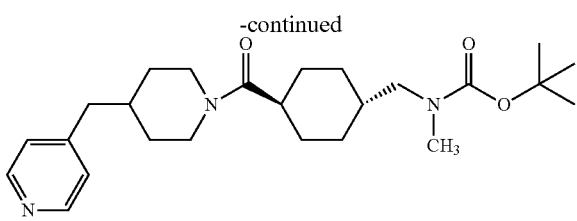

4-(Piperidin-4-ylmethyl)pyridine (88 mg, 0.5 mmol) and trans-4-(Boc-methylaminomethyl)cyclohexane carboxylic acid (136 mg, 0.5 mmol) were both dissolved in acetonitrile (5 mL) prior to the addition of N,N'-dicyclohexylcarbodiimide (DCC) (113 mg, 0.55 mmol). At 24 hours the reaction was filtered through fritted glass and the solvent solvent was removed under vacuum yielding a solid. The resulting solid was dissolved in EtOAc (100 mL) and was washed with 1N NaOH (3×25 mL) and pH 8 0.2M MOPS buffer (3×20 mL). The product was extracted with 0.1N HCl (3×50 mL), made basic with 10N NaOH (5 mL), extracted with CH2Cl2 (3×50 mL), and washed with brine (30 mL). The organic layer was dried (anhy. MgSO4), filtered, the solvent was removed under vacuum, and the resulting solid was dried under vacuum. This was further purified by silica gel (25-30 g) chromatography using: 4 fractions (200 mL) consisting of hexane, 35% acetone in hexane, 50% acetone in hexane, and 65% acetone in hexane. Fractions containing product were combined, and the solvent was evaporated under vacuum, yielding a solid (46 mg, 21% yield; TLC $R_f$=0.29 (5% MeOH in $CH_2Cl_2$); HPLC-200 nm $R_t$=3.401 min).

MN1456, MN1457, MN1458, MN1459, and MN1460 were synthesized in a matter similar to MN1455.

Example of EDC Coupling with NaOH/Brine Workup: MN1435—DCC Coupling

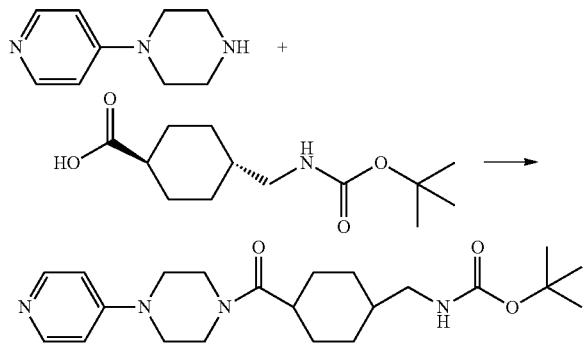

1-(4-pyridyl)piperazine (326 mg, 2.00 mmol), hydroxybenzotriazole (HOBT) (101 mg, 0.66 mmol), N,N'-Dicyclohexylcarbodiimide (DCC) (454 mg, 2.2 mmol) and Boc-trans-4-(aminomethyl)cyclohexane-1-carboxylic acid (515 mg, 2.00 mmol) were all dissolved in acetonitrile (100 mL). The reaction was stirred for 72 hrs at RT. The reaction mixture was filtered and the filtrate was evaporated under vacuum. The result was dissolved in EtOAc (8 mL) and filtered through a 0.22 um PTFE filter using a syringe. The filtrate was diluted with EtOAc (100 mL) and washed with 1M NaOH (3×25 mL) and sat. NaCl (50 mL). The organic layer was dried (anhyd. $Na_2SO_4$), filtered, and evaporated under vacuum. This material was further purified by silica gel (25-30 g) chromatography using: 3 fractions (200 mL) consisting of $CH_2Cl_2$+1% $NH_3$, 5% MeOH in $CH_2Cl_2$+1% $NH_3$, 12% MeOH in $CH_2Cl_2$+1% $NH_3$, and 20% MeOH in $CH_2Cl_2$+1% $NH_3$. Fractions containing product were combined, and the solvent was evaporated under vacuum, yielding a solid (755.5 mg mg, 93.8% yield; TLC $R_f$=0.33 (10% MeOH in $CH_2Cl_2$+1% $NH_3$); HPLC-200 nm $R_t$=3.137 min).

MN1436, MN1437, and MN1438 were synthesized in a similar manner to MN1435.

Example of the Synthesis of t-Butyl Urea Analogs: MN1439—Coupling, Boc-Cleavage, Urea Formation Scheme

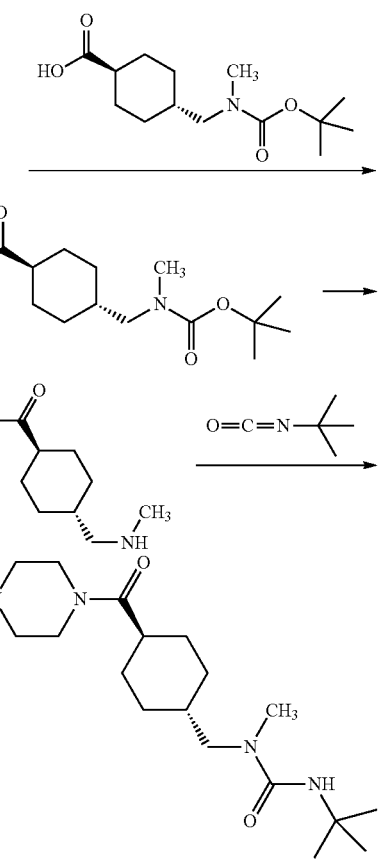

MN1435 Boc Cleavage tert-Butyl methyl(((1s,4s)-4-(4-(pyridin-4-yl)piperazine-1-carbonyl)cyclohexyl)methyl)carbamate (652.8 mg, 1.62 mmol) was dissolved in CH2Cl2 (7 mL) before adding trifluoroacetic acid (7 mL). The reaction was stirred for 20 min then diluted with toluene (100 mL) and evaporated. The resulting residue was dissolved in 1,4-dioxane (25 mL) and evaporated under vacuum. This was dried under vacuum, yielding a solid (1.401 g, 201% yield [residual TFA]; TLC $R_f$=0.24 (10% MeOH in $CH_2Cl_2$+1% $NH_3$); HPLC-200 nm $R_t$=0.846 min).

MN1439—Urea Formation

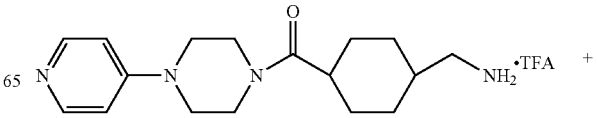

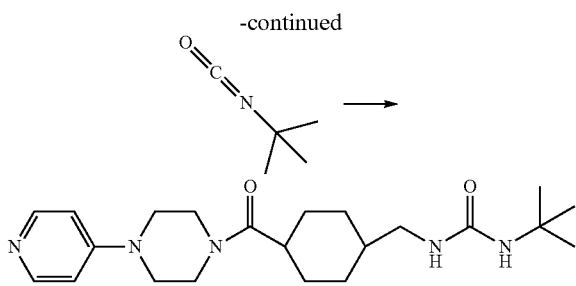

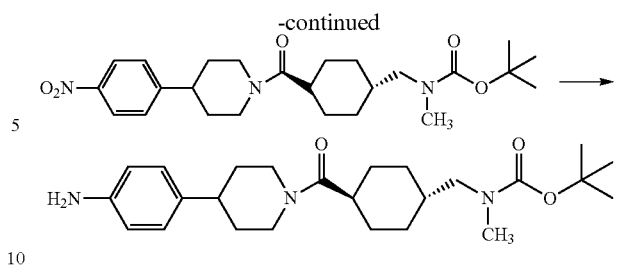

(4-(Aminomethyl)cyclohexyl)(4-(pyridin-4-yl)piperazin-1-yl)methanone X-TFA complex (1.62 mmol) was suspended in CHCl3 (50 mL) before adding tert-butyl isocyanate (457 uL, 4 mmol) and N,N-diisopropylethylamine (2.4 mL, 13.78 mmol) via syringe. The reaction was stirred for 16 hrs at RT. The reaction mixture was evaporated under vacuum. This material was purified by silica gel (25-30 g) chromatography using: 3 fractions (200 mL) consisting of $CH_2Cl_2$+1% $NH_3$, 5% MeOH in $CH_2Cl_2$ with 1% $NH_3$, 10% MeOH in $CH_2Cl_2$ with 1% $NH_3$, and 15% MeOH in $CH_2Cl_2$ with 1% $NH_3$. Fractions containing product were combined, and the solvent was evaporated under vacuum, yielding a solid (469 mg). This material was contaminated with TFA-DIEA and was further purified by dissolving in EtOAc, then washing with 1N NaOH (3×25 mL) and brine (25 mL), dried $Na_2SO_4$, and evaporated to give 292 mg (45% yield); TLC $R_f$=0.24 (10% MeOH in $CH_2Cl_2$+1% $NH_3$); HPLC-200 nm $R_t$=2.887 min).

MN1440, MN1441, MN1442, MN1444, and MN1445 were synthesized in a similar manner to MN1439.

MN1461—EDC Coupling—Nitro Reduction

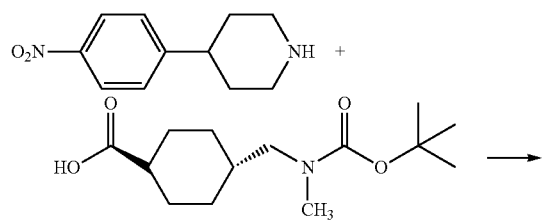

4-(4-Nitrophenyl)piperidine (206 mg, 1 mmol), 1-ethyl-3-(3-dimethylaminopropyl)carbodiimide-HCl (EDC-HCl) (211 mg, 1.10 mmol), 4-dimethylaminopyridine (DMAP) (12 mg, 0.10 mmol), hydroxybenzotriazole (HOBT) (51 mg, 0.33 mmol), and trans-4-(Boc-methylaminomethyl)cyclohexane carboxylic acid (271 mg, 1.00 mmol) were dissolved in acetonitrile (1.25 mL), dimethylformamide (DMF) (5 mL), and diisopropylethylamine (DIEA) (200 uL, 1.2 mmol). The reaction was stirred for 17 hrs at RT. The reaction mixture was then diluted with EtOAc (100 mL), washed with sat. NaCl (2×50 mL), 1M citric acid (3×25 mL), sat. $NaHCO_3$ (3×25 mL), and sat. NaCl (50 mL). The organic layer was dried (anhyd. $Na_2SO_4$), filtered, and evaporated under vacuum. This material was further purified by silica gel (25-30 g) chromatography using: 4 fractions (200 mL) consisting of hexane, 20% acetone in hexane, 30% acetone in hexane, and 40% acetone in hexane. Fractions containing product were combined, and the solvent was evaporated under vacuum, yielding a solid (274.6 mg, 60% yield; TLC $R_f$=0.31 (5% MeOH in $CH_2Cl_2$); HPLC (200 nm) $R_t$=3.263 min).

tert-Butyl methyl(((1s,4s)-4-(4-(4-nitrophenyl)cyclohexanecarbonyl)cyclohexyl)methyl) carbamate (147 mg, 0.32 mmol) was dissolved in methanol (5 mL) before the addition of palladium on carbon (37 mg). The reaction was hydrogenated using a balloon for 2 hours before evacuating the hydrogen gas under an inert atmosphere of Ar. The reaction mixture was filtered through celite then the filtrate was evaporated under vacuum yielding a solid (120 mg, 87% yield; TLC $R_f$=0.31 (5% MeOH in CH2Cl2); HPLC (200 nm) $R_t$=3.263 min).

TABLE 1

Physical Data and Synthetic Methods Table

| Compound | HPLC Rt (min) | TLC Rf | TLC eluent | Cyclization Method | Amide Formation Method |
|---|---|---|---|---|---|
| MN1292 | 4.683 | 0.14 | 30% EtOAc in Hexane | A | F |
| MN1293 | 4.885 | 0.21 | 30% EtOAc in Hexane | A | F |
| MN1294 | 5.271 | 0.12 | 10% EtOAc in Hexane | A | F |
| MN1305 | 4.386 | 0.59 | 50% EtOAc in Hexane | A | F |
| MN1306 | 4.504 | 0.24 | 50% EtOAc in Hexane | A | F |
| MN1307 | 4.712 | 0.36 | 50% EtOAc in Hexane | A | F |
| MN1308 | 4.743 | 0.10 | 25% EtOAc in Hexane | A | F |
| MN1309 | 3.909 & 3.955 | 0.05 | 5% MeOH in $CH_2Cl_2$ + 1% $NH_4OH$ | A | F |
| MN1310 | 5.269 | 0.20 | 20% EtOAc in Hexane | A | F |
| MN1311 | 5.107 | 0.34 | 30% EtOAc in Hexane | A | F |
| MN1312 | 4.149 | 0.05 | 4% MeOH in $CH_2Cl_2$ | A | F |
| MN1317 | 4.713 | 0.12 | 25% EtOAc in Hexane | A | F |
| MN1318 | 4.870 | 0.17 | 25% EtOAc in Hexane | A | F |
| MN1319 | 4.984 | 0.13 | 25% EtOAc in Hexane | A | F |
| MN1320 | 4.771 | 0.10 | 25% EtOAc in Hexane | A | F |
| MN1321 | 5.096 | 0.15 | 25% EtOAc in Hexane | A | F |
| MN1322 | 4.739 | 0.19 | 30% EtOAc in Hexane | A | F |
| MN1329 | 4.304 | 0.59 | 5% MeOH in $CH_2Cl_2$ + | | |

TABLE 1-continued

Physical Data and Synthetic Methods Table

| Compound | HPLC Rt (min) | TLC Rf | TLC eluent | Cyclization Method | Amide Formation Method |
|---|---|---|---|---|---|
| | | | 1% HOAc | | |
| MN1330 | 5.031 | 0.33 | 40% EtOAc in Hexane | A | F |
| MN1331 | 4.986 | 0.15 | 30% EtOAc in Hexane | A | F |
| MN1332 | 5.231 | 0.22 | 30% EtOAc in Hexane | A | F |
| MN1333 | 5.238 | 0.32 | 30% EtOAc in Hexane | A | F |
| MN1334 | 5.081 | 0.35 | 40% EtOAc in Hexane | A | F |
| MN1335 | 5.282 | 0.30 | 30% EtOAc in Hexane | A | F |
| MN1336 | 5.278 | 0.20 | 30% EtOAc in Hexane | A | F |
| MN1337 | 5.124 | 0.28 | 30% EtOAc in Hexane | A | F |
| MN1338 | 5.106 | 0.42 | 40% EtOAc in Hexane | A | F |
| MN1339 | 4.966 | 0.32 | 40% EtOAc in Hexane | A | F |
| MN1340 | 4.947 | 0.28 | 40% EtOAc in Hexane | A | F |
| MN1341 | 4.928 | 0.12 | 30% EtOAc in Hexane | Commercial | F |
| MN1351 | 4.294 | 0.39 & 0.43 | 50% EtOAc in Hexane | A | F |
| MN1352 | 4.851 | 0.27 | 40% EtOAc in Hexane | A | F |
| MN1353 | 5.002 | 0.32 | 40% EtOAc in Hexane | A | F |
| MN1355 | 4.812 | 0.21 | 40% EtOAc in Hexane | H2SO4 | F |
| MN1356 | 5.247 | 0.22 | 30% EtOAc in Hexane | A | F |
| MN1357 | 5.197 | 0.22 | 30% EtOAc in Hexane | A | F |
| MN1358 | 5.312 | 0.31 | 30% EtOAc in Hexane | A | F |
| MN1359 | 5.321 | 0.32 | 30% EtOAc in Hexane | C | F |
| MN1360 | 5.327 | 0.19 | 30% EtOAc in Hexane | C | F |
| MN1362 | 4.507 | 0.14 | 40% EtOAc in Hexane | Commercial | F |
| MN1363 | 4.846 | 0.20 | 40% EtOAc in Hexane | Commercial | F |
| MN1369 | 4.910 | 0.29 | 40% EtOAc in Hexane | ester of commercial | TFFH |
| MN1370 | 4.373 | 0.17 | 2% MeOH in $CH_2Cl_2$ + 1% HOAc | multistep with ester hydrolysis | |
| MN1371 | 4.506 | 0.36 | 2% MeOH in $CH_2Cl_2$ + 1% HOAc | multistep with ester hydrolysis | |
| MN1372 | 4.216 | 0.15 | 2% MeOH in $CH_2Cl_2$ + 1% HOAc | multistep with ester hydrolysis | |
| MN1377 | 5.103 | 0.29 | 40% EtOAc in Hexane | TFA | F |
| MN1378 | 4.978 | 0.18 | 40% EtOAc in Hexane | H2SO4 | F |
| MN1379 | 5.008 | 0.23 | 40% EtOAc in Hexane | A | F |
| MN1380 | 5.034 | 0.25 | 40% EtOAc in Hexane | A | F |
| MN1381 | 4.913 | 0.21 | 40% EtOAc in Hexane | TFA | F |
| MN1382 | 4.939 | 0.26 | 40% EtOAc in Hexane | A | F |
| MN1383 | 4.993 | 0.28 | 40% EtOAc in Hexane | TFA | F |
| MN1384 | 4.877 | 0.19 | 40% EtOAc in Hexane | TFA | F |
| MN1385 | 4.909 | 0.26 | 40% EtOAc in Hexane | A | F |
| MN1386 | 4.769 | 0.43 | 50% EtOAc in Hexane | multistep reaction with chloroformate | |
| MN1387 | 4.891 | 0.46 | 50% EtOAc in Hexane | multistep reaction with chloroformate | |
| MN1388 | 4.292 | 0.14 | 70% EtOAc in Hexane | multistep reaction with acylchloride | |
| MN1389 | 4.723 | 0.17 | 50% EtOAc in Hexane | multistep reaction with acylchloride | |
| MN1390 | 4.569 | 0.15 | 60% EtOAc in Hexane | multistep reaction with acylchloride | |
| MN1391 | 4.178 | 0.226 | 4% MeOH in $CH_2Cl_2$ | multistep with isocyanate | |
| MN1392 | 4.524 | 0.14 | 50% EtOAc in Hexane | multistep with isocyanate | |
| MN1393 | 4.484 | 0.13 | 50% EtOAc in Hexane | multistep with isocyanate | |
| MN1394 | 4.672 | 0.31 | 50% EtOAc in Hexane | Commercial | F |
| MN1395 | 4.555 | 0.23 | 50% EtOAc in Hexane | Commercial | F |
| MN1396 | 3.735 | 0.26 | 5% MeOH in $CH_2Cl_2$ + 1% NH3 | multistep with reductive amination | |
| MN1397 | 4.044 | 0.15 | 5% MeOH in $CH_2Cl_2$ | multistep with reductive amination | |
| MN1398 | 3.972 | 0.46 | 10% MeOH in $CH_2Cl_2$ | multistep with reductive amination | |
| MN1399 | 3.929 | 0.26 | 5% MeOH in $CH_2Cl_2$ + 1% NH3 | multistep with reductive amination | |
| MN1401 | 4.089 | 0.15 | 4% MeOH in $CH_2Cl_2$ | La(Tfl)3 amine of ester | F |
| MN1402 | 4.919 | 0.24 | 40% EtOAc in Hexane | A | F |
| MN1403 | 4.674 | 0.3 | 50% EtOAc in Hexane | A | F |
| MN1409 | 4.68 | 0.18 | 40% EtOAc in Hexane | multistep ester formation | F |
| MN1410 | 4.79 | 0.21 | 40% EtOAc in Hexane | multistep ester formation | F |
| MN1411 | 4.187 | 0.32 | 5% MeOH in $CH_2Cl_2$ | amidation of ester | F |

TABLE 1-continued

Physical Data and Synthetic Methods Table

| Compound | HPLC Rt (min) | TLC Rf | TLC eluent | Cyclization Method | Amide Formation Method |
|---|---|---|---|---|---|
| MN1412 | 4.703 | 0.37 | 60% EtOAc in Hexane | multistep with isocyanate | |
| MN1413 | 4.410 | 0.22 | 60% EtOAc in Hexane | multistep with isocyanate | |
| MN1414 | 4.414 | 0.17 | 60% EtOAc in Hexane | multistep with isocyanate | |
| MN1415 | 4.76 | 0.28 | 50% EtOAc in Hexane | multistep with isothiocyanate | |
| MN1419 | 4.416 | 0.28 | 60% EtOAc in Hexane | Commercial | F |
| MN1420 | 4.702 | 0.39 | 50% EtOAc in Hexane | Commercial | F |
| MN1422 | 4.633 | 0.26 | 50% EtOAc in Hexane | A | F |
| MN1423 | 4.259 | 0.2 | 70% EtOAc in Hexane | multistep with isocyanate | |
| MN1424 | 3.579 | 0.19 | 4% MeOH in $CH_2Cl_2$ | Commercial | F |
| MN1425 | 4.514 | 0.3 | 60% EtOAc in Hexane | H2SO4 | F |
| MN1426 | 4.554 | 0.37 | 60% EtOAc in Hexane | A | F |
| MN1427 | 4.086 | 0.17 | 40% EtOAc in Hexane | Commercial | F |
| MN1428 | 3.409 | 0.22 | 4% MeOH in $CH_2Cl_2$ | Commercial | F |
| MN1429 | 3.746 | 0.23 | 60% EtOAc in Hexane | Commercial | F |
| MN1430 | 4.231 | 0.23 | 40% EtOAc in Hexane | Commercial | F |
| MN1431 | 4.496 | 0.28 | 40% EtOAc in Hexane | Commercial | F |
| MN1432 | 4.774 | 0.4 | 40% EtOAc in Hexane | Commercial | F |
| MN1433 | 3.133 | 0.16 | 4% MeOH in $CH_2Cl_2$ + 1% NH3 | Commercial | DCC |
| MN1434 | 4.602 | 0.26 | 60% EtOAc in Hexane | Commercial | F |
| MN1435 | 3.137 | 0.33 | 10% MeOH in $CH_2Cl_2$ + 1% NH3 | Commercial | F |
| MN1436 | 3.378 | 0.36 | 10% MeOH in $CH_2Cl_2$ + 1% NH3 | Commercial | F |
| MN1437 | 3.36 | 0.2 | 2% MeOH in $CH_2Cl_2$ + 1% NH3 | Commercial | DCC |
| MN1438 | 3.373 | 0.14 | 4% MeOH in $CH_2Cl_2$ + 1% NH3 | Commercial | DCC |
| MN1439 | 2.887 | 0.24 | 10% MeOH in $CH_2Cl_2$ + 1% NH3 | multistep with isocyanate | |
| MN1440 | 3.067 | 0.34 | 10% MeOH in $CH_2Cl_2$ + 1% NH3 | multistep with isocyanate | |
| MN1441 | 3.639 | 0.2 | 2% MeOH in $CH_2Cl_2$ + 1% NH3 | multistep with isocyanate | |
| MN1442 | 3.068 | 0.26 | 5% MeOH in $CH_2Cl_2$ + 1% NH3 | multistep with isocyanate | |
| MN1443 | 3.212 | 0.15 | 5% MeOH in $CH_2Cl_2$ | multistep with isocyanate | |
| MN1444 | 3.044 | 0.17 | 3% MeOH in $CH_2Cl_2$ + 1% NH3 | multistep with isocyanate | |
| MN1445 | 3.066 | 0.11 | 3% MeOH in $CH_2Cl_2$ + 1% NH3 | multistep with isocyanate | |
| MN1447 | 3.333 | 0.18 | 3% MeOH in $CH_2Cl_2$ | Commercial | F |
| MN1448 | 3.354 | 0.29 | 5% MeOH in $CH_2Cl_2$ | Commercial | F |
| MN1449 | 3.843 | 0.28 | 5% MeOH in $CH_2Cl_2$ | Commercial | F |
| MN1450 | 3.917 | 0.26 | 5% MeOH in $CH_2Cl_2$ | Commercial | F |
| MN1451 | 4.824 | 0.41 | 5% MeOH in $CH_2Cl_2$ | Commercial | F |
| MN1452 | 4.030 | 0.34 | 5% MeOH in $CH_2Cl_2$ | Commercial | F |
| MN1453 | 4.957 | 0.33 | 50% EtOAc in Hexane | Commercial | F |
| MN1454 | 4.876 | 0.35 | 50% EtOAc in Hexane | Commercial | F |
| MN1455 | 3.382 | 0.42 | 10% MeOH in $CH_2Cl_2$ | Commercial | DCC |
| MN1456 | 3.401 | 0.29 | 5% MeOH in $CH_2Cl_2$ | Commercial | DCC |
| MN1457 | 3.242 | 0.28 | 5% MeOH in $CH_2Cl_2$ | Commercial | DCC |
| MN1458 | 3.258 | 0.74 | 20% MeOH in $CH_2Cl_2$ | Commercial | DCC |
| MN1459 | 3.306 | 0.67 | 20% MeOH in $CH_2Cl_2$ | Commercial | DCC |
| MN1460 | 3.263 | 0.31 | 5% MeOH in $CH_2Cl_2$ | Commercial | DCC |
| MN1461 | 3.499 | 0.32 | 5% MeOH in $CH_2Cl_2$ | multistep with nitro reduction | |
| MN1462 | 3.392 | 0.31 | 60% Acetone in Hexane | Commercial | F |
| MN1463 | 3.416 | 0.49 | 60% Acetone in Hexane | Commercial | F |
| MN1464 | 3.289 | 0.29 | 60% Acetone in Hexane | Commercial | F |
| MN1465 | 3.36 | 0.4 | 60% Acetone in Hexane | Commercial | F |
| MN1466 | 3.268 | 0.29 | 60% Acetone in Hexane | Commercial | F |
| MN1467 | 3.204 | 0.3 | 60% Acetone in Hexane | Commercial | F |
| MN1468 | 3.207 | 0.29 | 60% Acetone in Hexane | Commercial | F |
| MN1469 | 3.208 | 0.26 | 5% MeOH in $CH_2Cl_2$ | Commercial | F |
| MN1470 | 4.668 | 0.84 | 60% Acetone in Hexane | Commercial | F |
| MN1471 | 5.044 | 0.29 | 40% EtOAc in Hexane | Commercial | F |

Summary of Biological Activity of the Compounds

FIG. 18A-18E shows a structure activity relationship chart. Percent inhibition of cancer cell migration was performed in a wound healing assay. The percent area that the invading cancer cells occupied, in the presence of a drug candidate compared to the controls, was quantified by Image J cell software which enables cell counting from photographs. IC50's were calculated by performing migration experiments at several compound concentrations and then applying Hill's equation. Inhibition of cancer cell proliferation was quantified by automated cell counting in the presence or absence of a drug candidate. The quantified data are presented in FIG. 18A-18E. Here, the inhibition of cancer cell proliferation was scored 1 if proliferation was inhibited by 2500, 2 if inhibited by 5000, 3 for 750% and 4 for the highest degree of inhibition of proliferation, and 0 for the lowest. The effect of the drug candidates on stem cell pluripotency or proliferation was scored by eye, based on cell morphology and cell density, with 0 being no change in morphology or cell number and 4 being the most profound effect, with the stem cells taking on the morphology of a differentiating cell, along with much fewer cells indicative of inhibition of proliferation. As an example, FIGS. 30A-30F show photographs of naïve stem cell, primed stem cell and fibroblast controls. FIGS. 31A-31F show the effect of compounds of the invention on naïve state stem cells, where the number of '+' signs indicates the score from 0-4 of ability of compound to inhibit pluripotency, proliferation of naïve stem cells or ability to induce their differentiation. FIGS. 31G-31L shows the relative lack of effect on the more mature primed stae stem cells and FIGS. 31M-31R shows that these compounds have no effect on the fibroblast cells which are a surrogate for normal, healthy cells. FIGS. 36-44 and 65-87 show photographs and IC50 graphs of the compounds of the invention, inhibiting cancer cell migration and invasion. Cancer cell migration is a hallmark of metastatic cancer.

Here we have described a method of identifying agents that are inhibitors of tumor invasion, migration and metastasis comprising the steps of:
1) culturing naïve stem cells and fibroblasts in the presence of a compound;
2) observing that the compound inhibited growth and/or pluripotency of the naïve stem cells;
3) observing that said compound had little or no effect on fibroblast cells; and
4) concluding that said compound would inhibit the growth or invasiveness of cancer cells.

In summary, the compounds that had the greatest effect on naïve stem cells, in that they inhibited naïve stem cell pluripotency and/or growth, but had little or no effect on primed state stem cells or fibroblasts, were potent inhibitors of cancer cell migration and invasion. In some cases, the compounds also inhibited cancer cell growth. Because the compounds of the invention are potent inhibitors of cancer cell migration, also known as invasion, these compounds are useful for the treatment or prevention of cancer metastasis.

The inventors hypothesized that genes occupied by super-enhancers in primed state stem cells but not in naïve state stem cells, are master regulators of differentiation. Indeed, HES3, which regulates basic helix-loop-helix transcription factors, and GNAS, which mediates the activity of a host of factors that are critical for differentiation, plus other super-enhancer gene targets upregulated in primed state stem cells, but not in naïve state stem cells, are upregulated by compounds of the invention (FIG. 89A-89H). Elevated β-catenin and MUC1 have been linked to cancer migration, invasion and metastasis (Sachdeva and Mo, Cancer Res: 70(1); 378-87, 2010). Compounds of the invention cause a decrease in the amount of active, β-catenin (FIG. 89A; FIG. 90A) and a decrease in the expression of MUC1* ligands $NME7_{AB}$ and NME7-X1 (FIG. 90B, 90C). Since it is technically difficult to measure activated, nuclear β-catenin, it is common to measure instead AXIN2, whose expression is directly driven by activated, nuclear β-catenin. MicroRNA-145 has been identified as a harbinger of stem cell differentiation (Xu, N, et al. MicroRNA-145 Regulates OCT4, SOX2, and KLF4 and Represses Pluripotency in Human Embryonic Stem Cells. *Cell.* 137(4), p 647-658, 15 May 2009. DOI:10.1016/j.cell.2009.02.038; Smagghe et al, "MUC1* Ligand, NM23-H1, is a Novel Growth Factor that Maintains Human Stem Cells in a More Naïve State," PLoS ONE http://dx.plos.org/10.1371/journal.pone.0058601 2013). Sachdeva and Mo reported that miR-145 inhibits tumor migration and invasion. Here we report that the compounds of the invention increase expression of miR-145 (FIGS. 91A-91C and FIGS. 92A-92C).

In one aspect of the invention, an effective amount of one or more of the compounds MN1292-MN1471 is administered to a patient diagnosed with or at risk of developing cancer. In another aspect of the invention, an effective amount of one or more of the compounds described by Formulae 1-17 is administered to a patient diagnosed with or at risk of developing cancer. In one aspect, compounds of the invention are administered to a patient for the treatment or prevention of metastasis. In another aspect compounds of the invention are administered to a patient for the treatment of a cancer characterized by invasiveness. In yet another aspect, compounds of the invention are administered to a patient diagnosed with a cancer that is Grade or Stage 2. In yet another aspect, compounds of the invention are administered to a patient diagnosed with a cancer that is scored with a non-zero T, N, or M. In yet another aspect, compounds of the invention are administered to a patient diagnosed with a MUC1 positive or a MUC1* positive cancer. In another aspect, compounds of the invention are administered to a patient diagnosed with an NME7, $NME7_{AB}$ or NME7-X1 positive cancer.

Pharmaceutical Composition

Certain of the compounds of the invention comprise asymmetrically substituted carbon atoms. Such asymmetrically substituted carbon atoms can result in the compounds of the invention comprising mixtures of stereoisomers at a particular asymmnetrically substituted carbon atom or a single stereoisomer. As a result, racemic mixtures, mixtures of diastereomers, as well as single diastereomers of the compounds of the invention are included in the present invention. The terms "S" and "R" configuration, as used herein, are as defined by the IUPAC 1974 "RECOMMENDATIONS FOR SECTION E, FUNDAMENTAL STEREOCHEMISTRY," Pure Appl. Chem. 45:13-30, 1976. The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the "Chemical Abstracts Index Guide," Appendix IV, paragraph 203, 1987.

As used herein, the term "pharmaceutically acceptable salts" refers to the nontoxic acid or alkaline earth metal salts of the compounds of the invention. These salts can be prepared in situ during the final isolation and purification of the compounds, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2-hydroxyethanesulfonate, lactate, maleate, methanesulfonate, nicotinate, 2-napth-alenesulfonate, oxalate, pamoate, pectinate, persulfate, 3-phenylproionate, picrate, pivalate, propionate, succinate, sulfate, tartrate, thiocyanate, p-toluenesulfonate, and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the inventive compounds, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine, and the like.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in Higuchi, T., and V. Stella, "Pro-drugs as Novel Delivery Systems," A.C.S. Symposium Series 14, and in "Bioreversible Carriers in Drug Design," in Edward B. Roche (ed.), American Pharmaceutical Association, Pergamon Press, 1987, both of which are incorporated herein by reference.

The compounds of the invention are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinyl-pyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey, 1991, incorporated herein by reference.

Effective amounts of the compounds of the invention generally include any amount sufficient to detectably inhibit MUC1* positive activity by any of the assays described herein, by other MUC1* positive activity assays known to those having ordinary skill in the art, or by detecting an inhibition or alleviation of symptoms of cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose.

The compounds of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

While the compounds of the invention can be administered as the sole active pharmaceutical agent, they can also be used in combination with one or more other agents used in the treatment of cancer. Representative agents useful in combination with the compounds of the invention for the treatment of cancer include, for example, irinotecan, topotecan, gemcitabine, gleevec, herceptin, 5-fluorouracil, leucovorin, carboplatin, cisplatin, taxanes, tezacitabine, cyclophosphamide, vinca alkaloids, imatinib, anthracyclines, rituximab, trastuzumab, topoisomerase I inhibitors, as well as other cancer chemotherapeutic agents.

The above compounds to be employed in combination with the compounds of the invention will be used in therapeutic amounts as indicated in the Physicians' Desk Reference (PDR) 47th Edition (1993), which is incorporated herein by reference, or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

In hematological cancers, such as chronic myelogenous leukemia (CML), chromosomal translocation is responsible for the constitutively activated BCR-ABL tyrosine kinase. The afflicted patients are responsive to GLEEVEC©, a small molecule tyrosine kinase inhibitor, as a result of inhibition of Abl kinase activity. However, many patients with advanced stage disease respond to GLEEVEC© initially, but then relapse later due to resistance-conferring mutations in the Abl kinase domain. In vitro studies have demonstrated that BCR-Av1 employs the Raf kinase pathway to elicit its effects. In addition, inhibiting more than one kinase in the same pathway provides additional protection against resistance-conferring mutations. Accordingly, in another aspect of the invention, the inventive compounds are used in combination with at least one additional agent, such as GLEEVEC©, in the treatment of hematological cancers, such as chronic myelogenous leukemia (CML), to reverse or prevent resistance to the at least one additional agent.

In another aspect of the invention, kits that include one or more compounds of the invention are provided. Representative kits include a compound of the invention and a package insert or other labeling including directions for treating a cellular proliferative disease by administering MUC1* inhibitory amount of the compound.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1. Growth of Naïve State Stem Cells

Stem cells whether embryonic or induced pluripotent stem (iPS) cells were cultured in a minimal, serum-free media that contained human recombinant $NME7_{AB}$ at a concentration of 2-32 nM wherein 4-8 nM is preferred and 4 nM is more preferred. To facilitate surface attachment, cell culture plates were coated with an anti-MUC1* monoclonal antibody called MN-C3 or C3 or MN-C8 at a concentration of 2-100 ug/mL coating solution, wherein 3-50 ug/mL is preferred and 6-12.5 ug/mL is more preferred. In these experiments, 12.5 ug/mL of MN-C3 was used. Antibody coated plates were incubated at 4 degrees C. overnight prior to plating stem cells. A Rho kinase I inhibitor was added to enhance surface attachment. In some cases, $NME7_{AB}$ was substituted with human recombinant NME1 dimers which also induce stem cells to revert to a naïve-like state.

Example 2. Growth of Primed State Stem Cells

Stem cells whether embryonic or induced pluripotent stem (iPS) cells were cultured in a minimal, serum-free media that contained human recombinant bFGF at a concentration of 8 ng/mL. The stem cells were plated over a layer of inactivated mouse embryonic fibroblasts, aka MEFs, which secrete additional uncharacterized growth factors and cytokines.

Example 3. Drug Screen for Inhibitors of Metastatic Cancer

Human naïve state and primed stem cells were cultured in parallel for at least 5 passages to guarantee normal differentiation-free growth. The stem cells were plated in 12-well cell culture plates with 50,000 cells per well. Cells were cultured in their respective media, either bFGF media or $NME7_{AB}$ media for 24 hours. Media was then removed and replaced with media devoid of bFGF or $NME7_{AB}$, when indicated. Agents being tested for their ability to induce differentiation of naïve stem cells were added to the media at the concentrations indicated. After 72 hours, photographs were taken see FIGS. 1-10.

Example 4. Drug Screen for Inhibitors of Cancer or Metastatic Cancer

Human naïve state and primed stem cells were cultured in parallel for at least 5 passages to guarantee normal differentiation-free growth. The stem cells were plated in 12-well cell culture plates with 50,000 cells per well. Cells were cultured in their respective media, either bFGF media or NME7$_{AB}$ media for 24 hours. Media was then removed and replaced with media devoid of bFGF or NME7$_{AB}$. BRD4 inhibitor JQ1 or an inactive stereoisomer were added at 500 nM or 1 uM and tested for their ability to induce differentiation of naïve stem cells. Media was changed after 48 hours and replaced with fresh media containing the BRD4 inhibitors. After 4 days the experiment was stopped. Photographs were taken and cell pellets collected for further analysis, see FIGS. 11-16.

Example 5. Migration Assay

For the cancer cell migration experiment cancer cells were plated at varying densities into an Oris Cell Migration Assay Collagen-1 coated 96-well plate (Platypus Technologies LLC, Madison, WI). The Collagen-1 coated 96-well plate incorporates a specific vacuum plug which attaches to the bottom of each well, creating an area in which the cells cannot grow into. Once the cells have been plated at high densities into each well, they are allotted an 18-24 hour time period to attach to the bottom of the wells. Post-24 hour plugs are removed from the plate and then small molecule analogs are added to the wells. Images are taken of each well and represent time 0 (T=0) for each well. Images are taken of the wells at the 24, 48, 72, 96 and 120 hour time points. Data analysis is conducted using the images taken at these specific time point. Images are imported into ImageJ (Rasband, W. S., ImageJ, U. S. National Institutes of Health, Bethesda, Maryland, USA, http://imagej.nih.gov/ij/, 1997-2016.) and the area remaining free of cells is calculated. To determine the effectiveness of the small molecule analogs versus the DMSO control the areas collected at each time point are compared to the areas of the T=0 images resulting in a percent area remaining of each well. The data collected is then normalized to the DMSO controls in each experiment.

Example 6. Proliferation Assay

For the cancer cell proliferation experiment cancer cells were plated at constant densities (6000 cells/well) into a 96-well White-walled/Clear-bottom Tissue Culture Treated plate (Corning Incorporated, Big Flats, NY). Small molecule analogs are added at T=24 hours in media with 2% FBS. Following the addition of the small molecules, the cells remain untouched for 120 hours with visual confirmations/inspections at 24, 48, 72 and 96 hours post plating. At the 120 hour mark a calcein fluorescence assay (Thermo Fisher Scientific, Waltham, MA) is performed on the plate. Calcein fluorescence (final concentration 0.5 uM) is used to assess cell viability. Cancer cell fluorescence is measured in a TECAN SAFIRE$^2$ spectrophotometer plate reader. The plate is then imaged using an Olympus IX71 fluorescence imaging microscope and montage of the resulting images are assembled using ImageJ.

REFERENCES

Nichols J, Smith A. Naive and primed pluripotent states. Cell Stem Cell. 2009; 4:487-492.

Silva J, Barrandon O, Nichols J, Kawaguchi J, Theunissen T W, A Smith. Promotion of reprogramming to ground state pluripotency by signal inhibition. PLoS Biol. 2008; 6:e253.

Gafni O, Weinberger L, Mansour A A, Manor Y S, Chomsky E, Ben-Yosef D, Kalma Y, Viukov S, Maza I, Zviran A, Rais Y, Shipony Z, Mukamel Z, Krupalnik V, Zerbib M, Geula S, Caspi I, Schneir D, Shwartz T, Gilad S, Amann-Zalcenstein D, Benjamin S, Amit I, Tanay A, Massarwa R, Novershtern N, Hanna J H. Derivation of novel human ground state naïve pluripotent stem cells. Nature. 2013; 504:282-286.

Theunissen T W, Powell B E, Wang H, Mitalipova M, Faddah D A, Reddy J, Fan Z P, Maetzel D, Ganz K, Shi L, Lungjangwa T, Imsoonthornruksa S, Stelzer Y, Rangarajan S, D'Alessio A, Zhang J, Gao Q, Dawlaty M M, Young R A, Gray N S, Jaenisch R. Systematic identification of culture conditions for induction and maintenance of naïve human pluripotency. Cell Stem Cell. 2014; 15:471-487.

Smagghe B J, Stewart A K, Carter M G et al. MUC1* ligand, NM23-H1, is a novel growth factor that maintains human stem cells in a more naïve state. PLoS One. 2013; 8:e58601.

Hikita S T, Kosik K S, Clegg D O et al. MUC1* mediates the growth of human pluripotent stem cells. PLoS One. 2008; 3:e3312.

Hanna J, Cheng A W, Saha K, Kim J, Lengner C J, Soldner F, Cassady J P, Muffat J, Carey B W, Jaenisch R. Human embryonic stem cells with biological and epigenetic characteristics similar to those of mouse ESCs. Proc Natl Acad Sci USA. 2010; 107:9222-9227.

Ware C B, Nelson A M, Mecham B, Hesson J, Zhou W, Jonlin E C, Jimenez-Caliani A J, Deng X, Cavanaugh C, Cook S, Tesar P J, Okada J, Margaretha L, Sperber H, Choi M, Blau C A, Treuting P M, Hawkins R D, Cirulli V, Ruohola-Baker H. Derivation of naïve human embryonic stem cells. Proc Natl Acad Sci USA. 2014; 111:4484-4489.

Belkina A C, Nikolajczyk B S, Denis G V. BET protein function is required for inflammation: Brd2 genetic disruption and BET inhibitor JQ1 impair mouse macrophage inflammatory responses. J Immunol. 2013; 190(7):3670-8.

Tang X, Peng R, Phillips J E, Deguzman J, Ren Y, Apparsundaram S, Luo Q, Bauer C M, Fuentes M E, DeMartino J A, Tyagi G, Garrido R, Hogaboam C M, Denton C P, Holmes A M, Kitson C, Stevenson C S, Budd D C. Assessment of Brd4 inhibition in idiopathic pulmonary fibrosis lung fibroblasts and in vivo models of lung fibrosis. Am J Pathol. 2013 183(2):470-9

Filippakopoulos P, Qi J, Picaud S, Shen Y, Smith W B, Fedorov O, Morse E M, Keates T, Hickman T T, Felletar I, Philpott M, Munro S, McKeown M R, Wang Y, Christie A L, West N, Cameron M J, Schwartz B, Heightman T D, La Thangue N, French C A, Wiest O, Kung A L, Knapp S, Bradner J E. Selective inhibition of BET bromodomains. Nature. 2010; 468(7327):1067-73

Tang X, Peng R, Phillips J E, Deguzman J, Ren Y, Apparsundaram S, Luo Q, Bauer C M, Fuentes M E, DeMartino J A, Tyagi G, Garrido R, Hogaboam C M, Denton C P, Holmes A M, Kitson C, Stevenson C S, Budd D C. Assessment of Brd4 inhibition in idiopathic pulmonary fibrosis lung fibroblasts and in vivo models of lung fibrosis. Am J Pathol. 2013; 183(2):470-9

Horm T M, Bitler B G, Broka D M, Louderbough J M, Schroeder J A. MUC1 drives c-Met-dependent migration and scattering. Mol Cancer Res. 2012 10(12):1544-54

Meng X G, Yue S W. Dexamethasone disrupts cytoskeleton organization and migration of T47D Human breast cancer cells by modulating the AKT/mTOR/RhoA pathway. Asian Pac J Cancer Prev. 2014; 15(23):10245-50.

Zheng C[1], Fang Y, Tong W, Li G, Wu H, Zhou W, Lin Q, Yang F, Yang Z, Wang P, Peng Y, Pang X, Yi Z, Luo J, Liu M, Chen Y. Synthesis and biological evaluation of novel tetrahydro-β-carboline derivatives as antitumor growth and metastasis agents through inhibiting the transforming growth factor-O signaling pathway. J Med Chem. 2014; 57(3)

Carter M G, Smagghe B J, Stewart A K, Rapley J A, Lynch E, Bernier K J, Keating K W, Hatziioannou V M, Hartman E J, Bamdad C C. A Primitive Growth Factor, NME7$_{AB}$, Is Sufficient to Induce Stable Näive State Human Pluripotency; Reprogramming in This Novel Growth Factor Confers Superior Differentiation.Stem Cells. 2016; 34(4): 847-59.

Mani S A, Guo W, Liao M J, Eaton E N, Ayyanan A, Zhou A Y, Brooks M, Reinhard F, Zhang C C, Shipitsin M, Campbell L L, Polyak K, Brisken C, Yang J, Weinberg R A. The epithelial-mesenchymal transition generates cells with properties of stem cells. Cell. 2008; 133(4)

S. Meng, L. Zhang, Y. Tang, Q. Tu, L. Zheng, L. Yu, D. Murray, J. Cheng, S. H. Kim, X. Zhou and J. Chen, BET Inhibitor JQ1 Blocks Inflammation and Bone Destruction. J Dent Res. 2014; 93(7): 657-662.

All of the references cited herein are incorporated by reference in their entirety.

Those skilled in the art will recognize, or be able to ascertain using no more than routine experimentation, many equivalents to the specific embodiments of the invention specifically described herein.

What is claimed is:

1. A compound, or pharmaceutically acceptable salt thereof, according to:

(a) Formula 15:

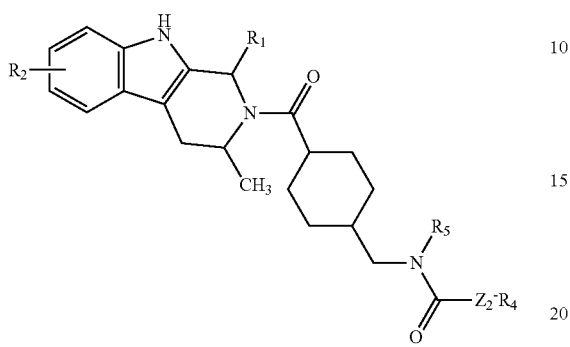

(b) Formula 16:

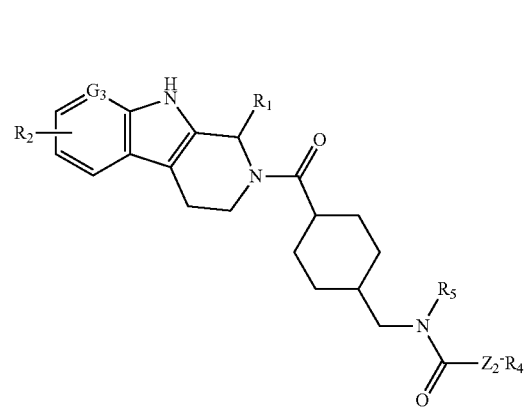

wherein,

G$_3$ is CH or N;

R$_1$ is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

R$_2$ is hydrogen, optionally substituted C1-C6 alkoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

R$_5$ is optionally substituted C1-C6 alkyl, optionally substituted C$_7$-C$_{15}$ arylalkyl, or 2-phenylethyl;

Z$_2$ is a bond, —NH—, —O—, —S—, —CH(CH$_3$)—, —(CH$_2$)$_n$—, —CH=CH—, —CO—, —SO—, —SO$_2$—, —C(=NH)—, —CH$_2$NH(CO)—, —CH$_2$NH(CO)O—, —CH$_2$NH(CO)NH—; —(CH$_2$)$_n$NH(CO)—, —(CH$_2$)$_n$NH(CO)O—, —(CH$_2$)$_m$NH(CO)NH—; and R$_4$ is H, optionally substituted C1-C9 alkyl; optionally substituted C2-C6 alkenyl; optionally substituted C6-C12 aryl; optionally substituted C1-C9 heteroaryl with 1 to 4 ring atoms independently selected from N, S, and O; optionally substituted C7-C15 arylalkyl; or —O-tert-butyl;

wherein m=1-5; n=1-8;

where "substituted" means substituted with one or more substituents independently selected from halogen, trifluoromethyl, methylcarboxy, ethylcarboxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, and —SO$_3$H; or

--- wherein,

R$_1$ is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

R$_2$ is hydrogen, optionally substituted C1-C6 alkoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

R$_5$ is H, optionally substituted C1-C6 alkyl, optionally substituted C$_7$-C$_{15}$ arylalkyl, or 2-phenylethyl;

Z$_2$ is a bond, —NH—, —O—, —S—, —CH(CH$_3$)—, —(CH$_2$)$_n$—, —CH=CH—, —CO—, —SO—, —SO$_2$—, —C(=NH)—, —CH$_2$NH(CO)—, —CH$_2$NH(CO)O—, —CH$_2$NH(CO)NH—; —(CH$_2$)$_n$NH(CO)—, —(CH$_2$)$_n$NH(CO)O—, —(CH$_2$)$_m$NH(CO)NH—; and R$_4$ is H, optionally substituted C1-C9 alkyl; optionally substituted C2-C6 alkenyl; optionally substituted C6-C12 aryl; optionally substituted C1-C9 heteroaryl with 1 to 4 ring atoms independently selected from N, S, and O; optionally substituted C7-C15 arylalkyl; —O-tert-butyl;

wherein m=1-5; n=1-8;

where "substituted" means substituted with one or more substituents independently selected from halogen, trifluoromethyl, methylcarboxy, ethylcarboxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, and —SO$_3$H; or (c) Formula 17:

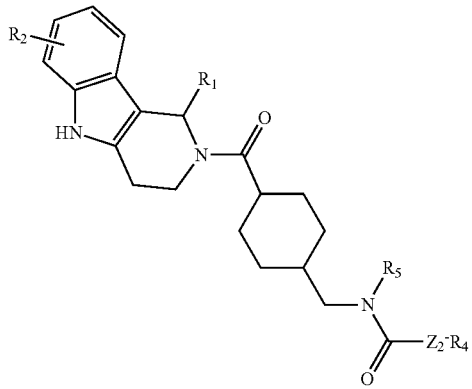

wherein, $R_1$ is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

$R_2$ is hydrogen, optionally substituted C1-C6 alkoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

$R_5$ is H, optionally substituted C1-C6 alkyl, optionally substituted $C_7$-$C_{15}$ arylalkyl, or 2-phenylethyl;

$Z_2$ is a bond, —NH—, —O—, —S—, —CH(CH$_3$)—, —(CH$_2$)$_n$—, —CH=CH—, —CO—, —SO—, —SO$_2$—, —C(=NH)—, —CH$_2$NH(CO)—, —CH$_2$NH(CO)O—, —CH$_2$NH(CO)NH—; —(CH$_2$)$_n$NH(CO)—, —(CH$_2$)$_n$NH(CO)O—, —(CH$_2$)$_m$NH(CO)NH—; and $R_4$ is H, optionally substituted C1-C9 alkyl; optionally substituted C2-C6 alkenyl; optionally substituted C6-C12 aryl; optionally substituted C1-C9 heteroaryl with 1 to 4 ring atoms independently selected from N, S, and O; optionally substituted C7-C15 arylalkyl; or —O-tert-butyl;

where m=1-5; n=1-8;

where "substituted" means substituted with one or more substituents independently selected from halogen, trifluoromethyl, methylcarboxy, ethylcarboxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, and —SO$_3$H;

or a pharmaceutically acceptable salt thereof.

2. The compound or pharmaceutically acceptable salt thereof, according to claim 1, wherein the compound is a compound of Formula 15:

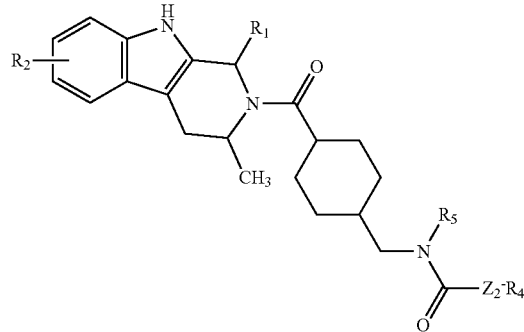

wherein, $R_1$ is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

$R_2$ is hydrogen, optionally substituted C1-C6 alkoxy, trifluoromethyl, halogen, methylcarboxy, ethylcarboxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H;

$R_5$ is H, optionally substituted C1-C6 alkyl, optionally substituted $C_7$-$C_{15}$ arylalkyl, or 2-phenylethyl;

$Z_2$ is a bond, —NH—, —O—, —S—, —CH(CH$_3$)—, —(CH$_2$)$_n$—, —CH=CH—, —CO—, —SO—, —SO$_2$—, —C(=NH)—, —CH$_2$NH(CO)—, —CH$_2$NH(CO)O—, —CH$_2$NH(CO)NH—; —(CH$_2$)$_n$NH(CO)—, —(CH$_2$)$_n$NH(CO)O—, —(CH$_2$)$_m$NH(CO)NH—; and $R_4$ is H, optionally substituted C1-C9 alkyl; optionally substituted C2-C6 alkenyl; optionally substituted C6-C12 aryl 1; optionally substituted C1-C9 heteroaryl with 1 to 4 ring atoms independently selected from N, S, and O; optionally substituted C7-C15 arylalkyl; —O-tert-butyl;

wherein m=1-5; n=1-8;

where "substituted" means substituted with one or more substituents independently selected from halogen, trifluoromethyl, methylcarboxy, ethylcarboxy, C1-C6 alkoxy, C1-C6 alkyl, —OH, —SH, —NH$_2$, —N$_3$, —CN, —NO$_2$, —CHO, —COOH, —CONH$_2$, —C(=NH)NH$_2$, and —SO$_3$H.

3. The compound or pharmaceutically acceptable salt thereof, according to claim 1, wherein the compound is a compound of Formula 16:

217

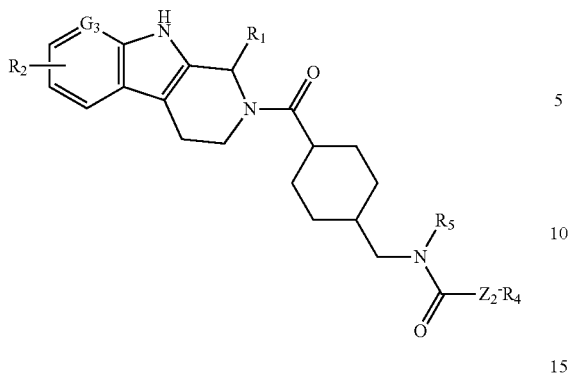

wherein,

G₃ is CH or N;

R₁ is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

R₂ is hydrogen, optionally substituted C1-C6 alkoxy, trifluoromethyl, halogen, methylcarboxy, ethylcarboxy, optionally substituted C1-C6 alkyl, —OH, —SH, —NH₂, —N₃, —CN, —NO₂, —CHO, —COOH, —CONH₂, —C(=NH)NH₂, or —SO₃H;

R₅ is optionally substituted C1-C6 alkyl, optionally substituted C₇-C₁₅ arylalkyl, or 2-phenylethyl;

Z₂ is a bond, —NH—, —O—, —S—, —CH(CH₃)—, —(CH₂)ₙ—, —CH=CH—, —CO—, —SO—, —SO₂—, —C(=NH)—, —CH₂NH(CO)—, —CH₂NH(CO)O—, —CH₂NH(CO)NH—, —(CH₂)ₙNH(CO)—, —(CH₂)ₙNH(CO)O—, —(CH₂)ₘNH(CO)NH—; and R₄ is H, optionally substituted C1-C9 alkyl; optionally substituted C2-C6 alkenyl; optionally substituted C6-C12 aryl; optionally substituted C1-C9 heteroaryl with 1 to 4 ring atoms independently selected from N, S, and O; optionally substituted C7-C15 arylalkyl; or —O-tert-butyl;

wherein m=1-5; n=1-8;

where "substituted" means substituted with one or more substitutents independently selected from halogen, trifluoromethyl, methylcarboxy, ethylcarboxy, C1-C6 alkoxy, C1-C6 alkyl, —OH, —SH, —NH₂, —N₃, —CN, —NO₂, —CHO, —COOH, —CONH₂, —C(=NH)NH₂, and —SO₃H.

4. The compound or pharmaceutically acceptable salt thereof, according to claim 1, wherein the compound is a compound of Formula 17:

218

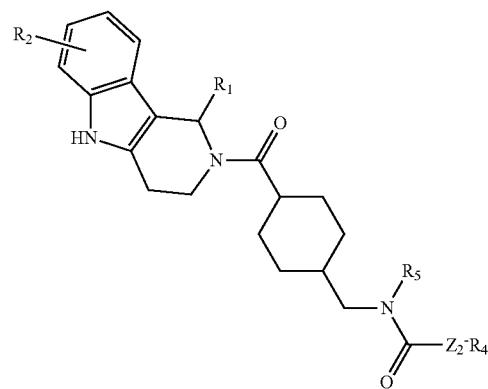

wherein,

R₁ is H, optionally substituted C1-C6 alkyl; optionally substituted C2-C6 alkenyl; optionally substituted C1-C6 alkoxy; optionally substituted C6-C12 aryl; optionally substituted C1-C9 heteroaryl with 1 to 4 ring atoms independently selected from N, S, and O; optionally substituted C7-C15 arylalkyl; optionally substituted C2-C15 heteroarylalkyl with 1 to 4 ring atoms independently selected from N, S, and O; optionally substituted C7-C15 arylalkenyl; optionally substituted C3-C8 cycloalkyl; or an optionally substituted C4-C8 cycloalkylalkyl;

R₂ is hydrogen, optionally substituted C1-C6 alkoxy, trifluoromethyl, halogen, methylcarboxy, ethylcarboxy, optionally substituted C1-C6 alkyl, —OH, —SH, —NH₂, —N₃, —CN, —NO₂, —CHO, —COOH, —CONH₂, —C(=NH)NH2, or —SO₃H;

R₅ is H, optionally substituted C1-C6 alkyl, optionally substituted C₇-C₁₅ arylalkyl, or 2-phenylethyl;

Z₂ is a bond, —NH—, —O—, —S—, —CH(CH₃)—, —(CH₂)ₙ—, —CH—CH—, —CO—, —SO—, —SO₂—, —C(=NH)—, —CH₂NH(CO)—, —CH₂NH(CO)O—, —CH₂NH(CO)NH—; —(CH₂)ₙNH(CO)—, —(CH₂)ₙNH(CO)O—, —(CH₂)ₘNH(CO)NH—; and R₄ is H, optionally substituted C1-C9 alkyl; optionally substituted C2-C6 alkenyl; optionally substituted C6-C12 aryl; optionally substituted C1-C9 heteroaryl with 1 to 4 ring atoms independently selected from N, S, and O; optionally substituted C7-C15 arylalkyl; or —O-tert-butyl;

wherein m=1-5, n=1-8;

where "substituted" means substituted with one or more substitutents independently selected from halogen, trifluoromethyl, methylcarboxy, ethylcarboxy, C1-C6 alkoxy, C1-C6 alkyl, —OH, —SH, —NH₂, —N₃, —CN, —NO₂, —CHO, —COOH, —CONH₂, —C(=NH)NH₂, and —SO₃H.

5. The compound or pharmaceutically acceptable salt thereof, according to claim 1, wherein the compound is a compound of Formula 15, Formula 16, or Formula 17, and wherein R₁ is H.

6. The compound or pharmaceutically acceptable salt thereof, according to claim 1, wherein the compound is a compound of Formula 15, Formula 16, or Formula 17, wherein Z₂ is —O—, —NH—, or —CH₂—.

7. The compound or pharmaceutically acceptable salt thereof, according to claim 1, wherein the compound is a compound of Formula 15, Formula 16, or Formula 17, wherein R₅ is methyl, Z₂ is —O—, —NH—, or —CH₂—, $R_4$ is t-butyl, and $R_2$ is hydrogen, halogen, trifluoromethyl, methylcarboxy, ethylcarboxy, optionally substituted C1-C6 alkoxy, optionally substituted C1-C6 alkyl, —OH, —SH, —NH$_2$, —N$_3$, —CN, —NO$_2$, —CHO, —COOH, —CONH$_2$, —C(=NH)NH$_2$, or —SO$_3$H.
8. A compound selected from the group consisting of:
MN1293
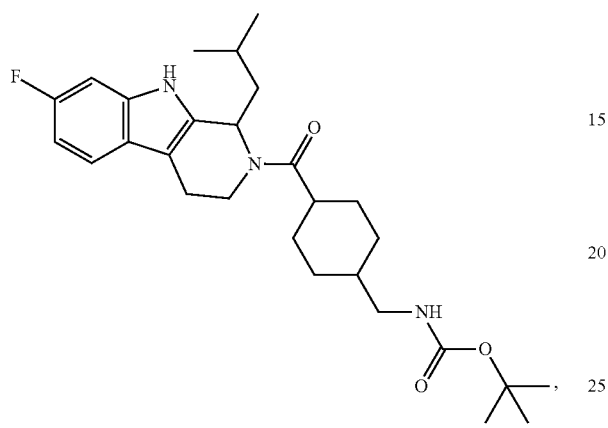
MN1307
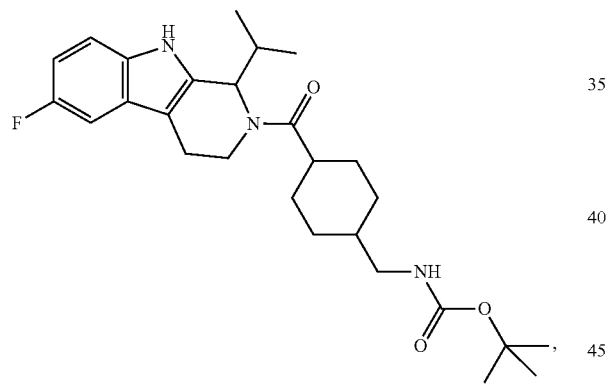
MN1318
MN1319
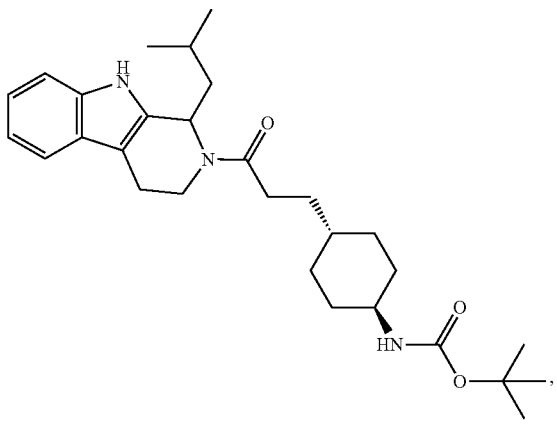
MN1321
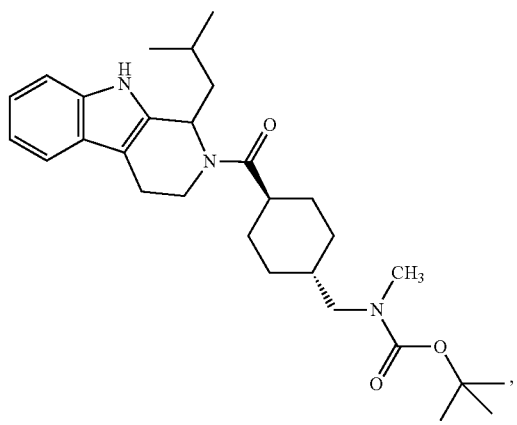
MN1322
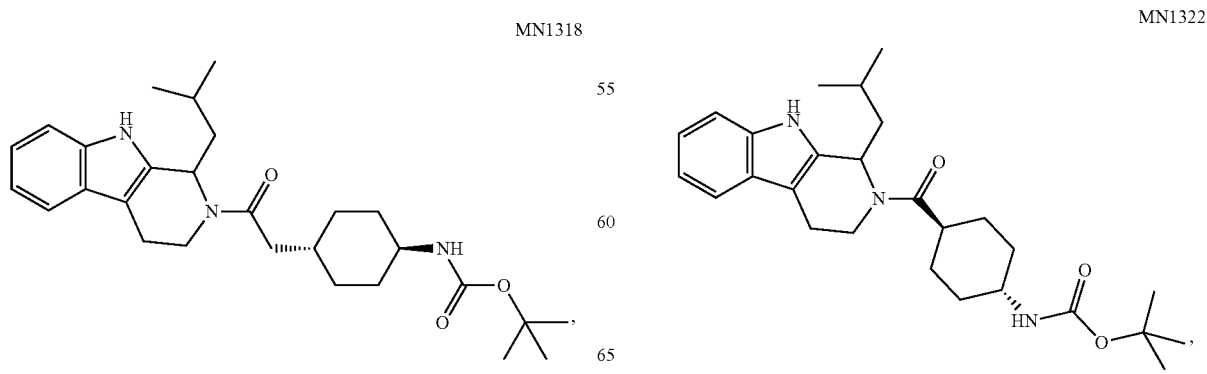

MN1330
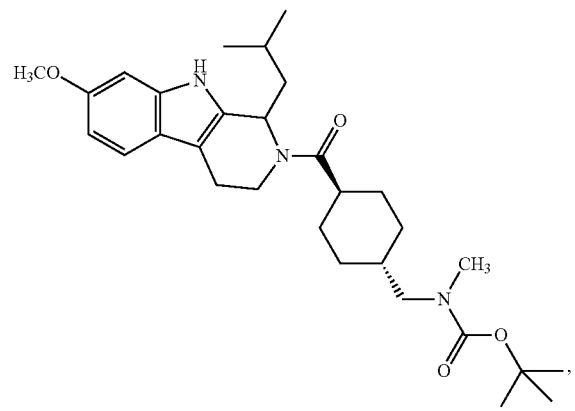
MN1333
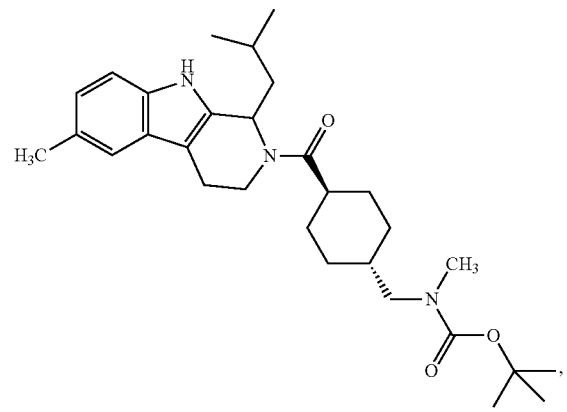
MN1331
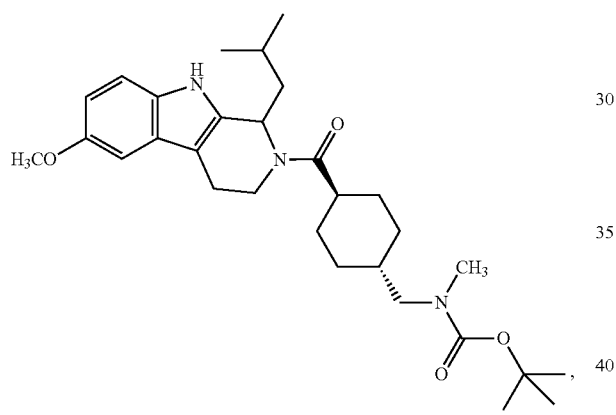
MN1334
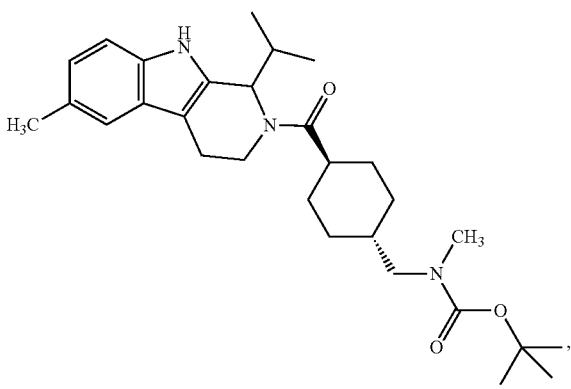
MN1332
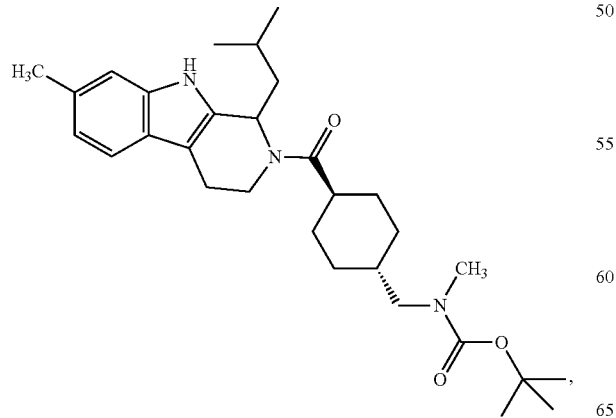
MN1335
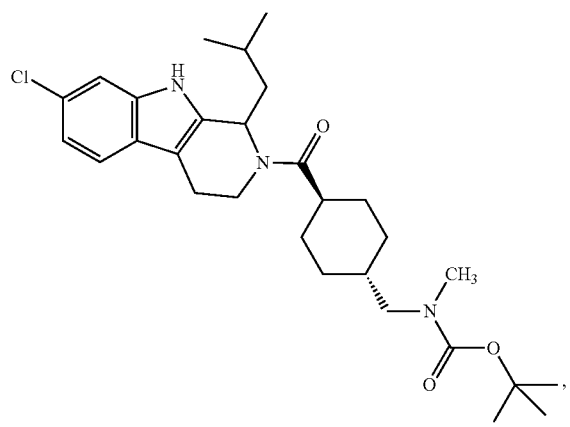

-continued
MN1336
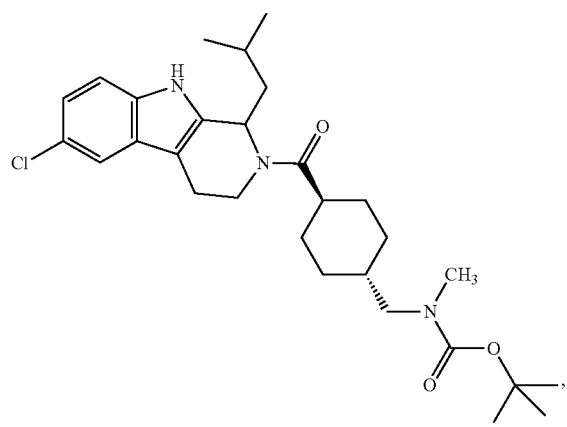
MN1337
MN1339
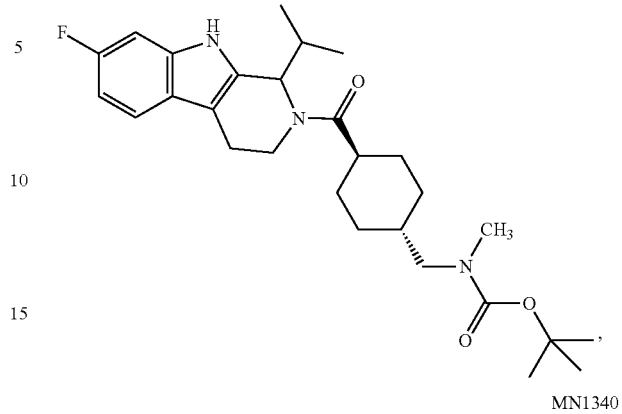
MN1340
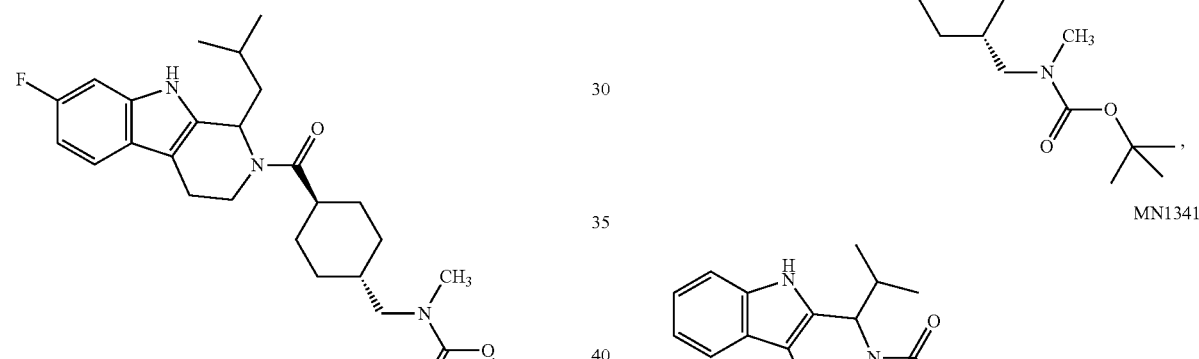
MN1341
MN1338
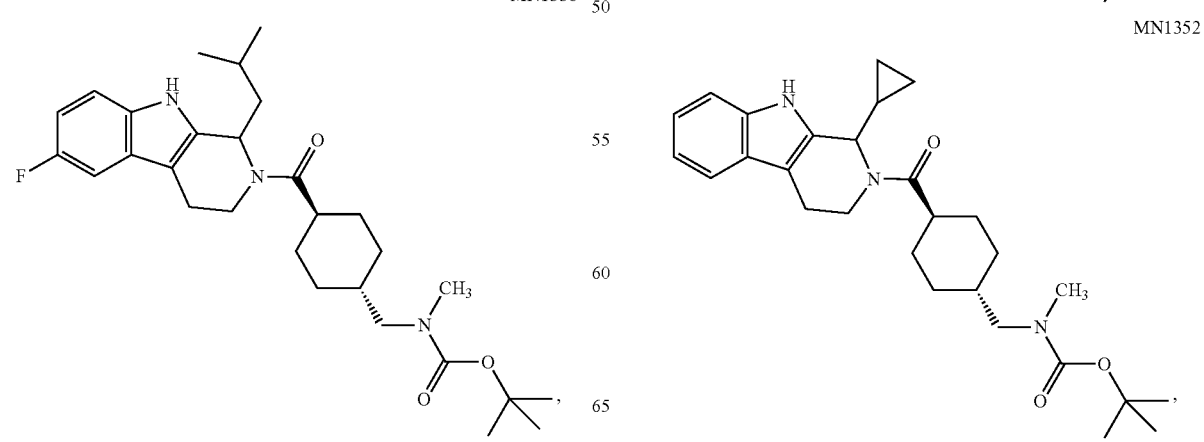
MN1352

MN1353
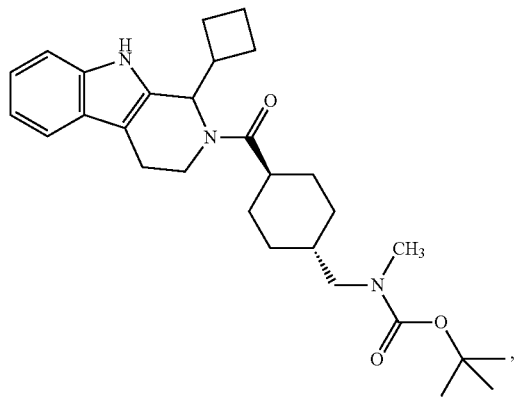
MN1355
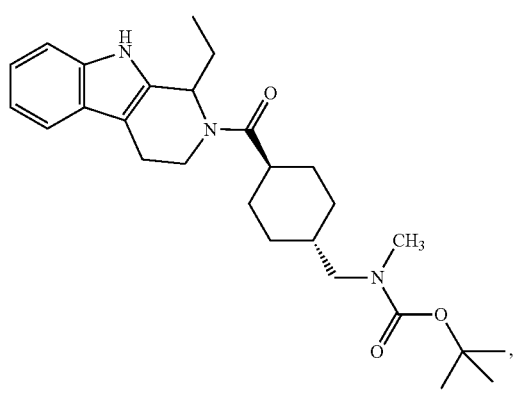
MN1356
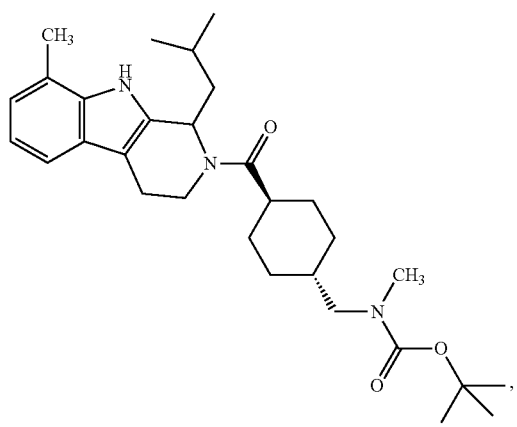
MN1357
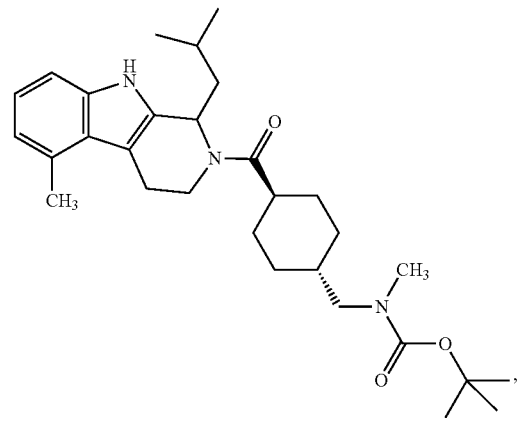
MN1358
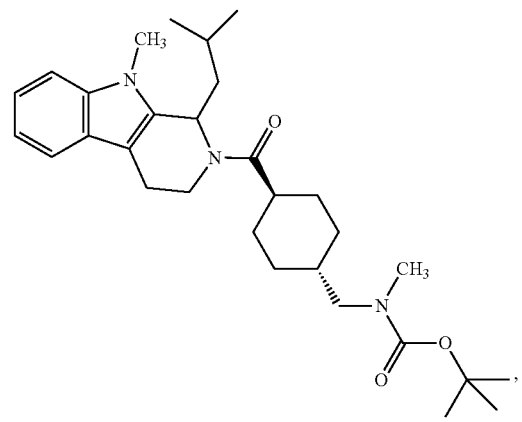
MN1359
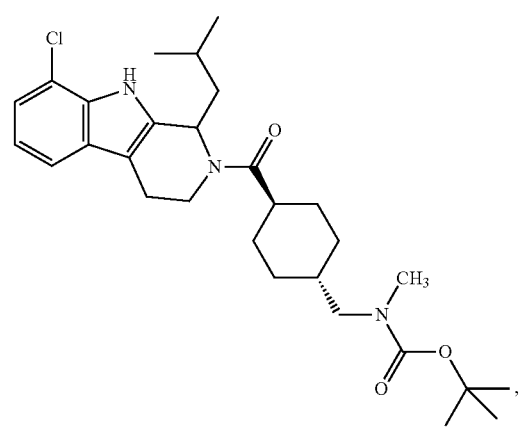

MN1360
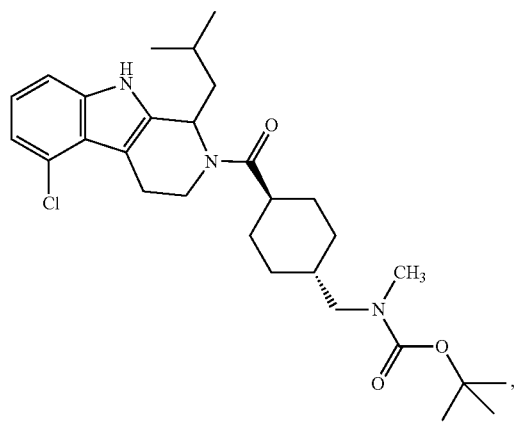
MN1369
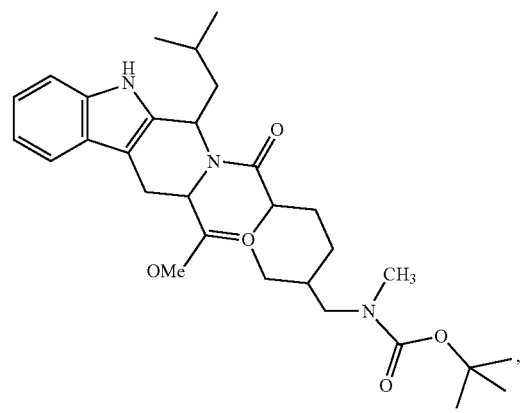
MN1362
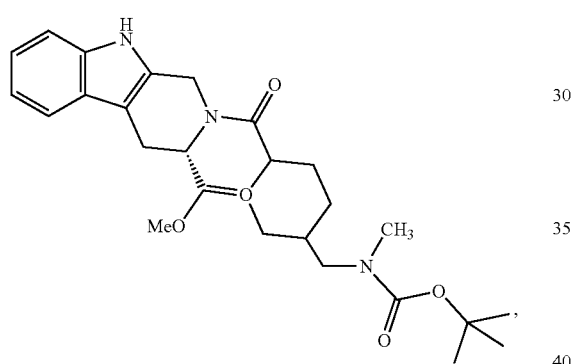
MN1370
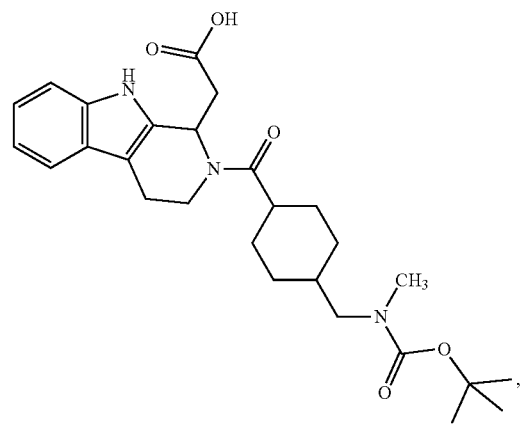
MN1363
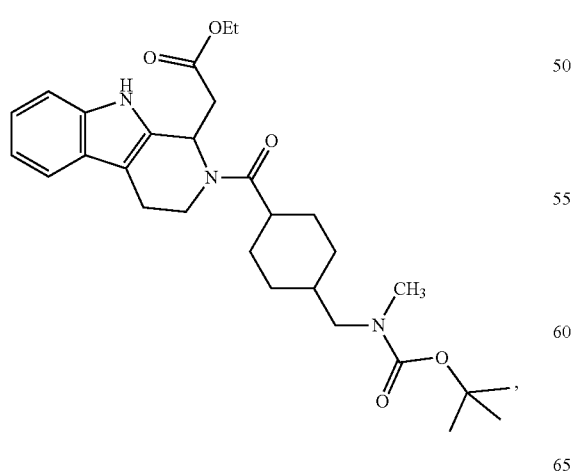
MN1371
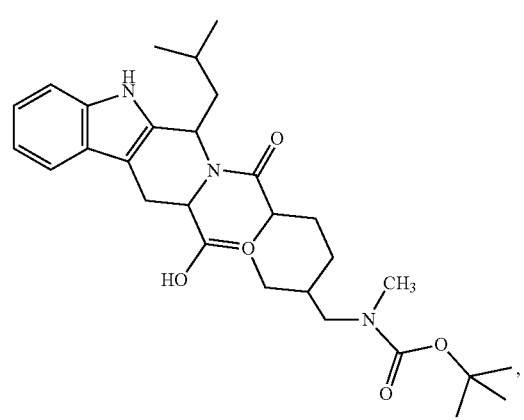

MN1372
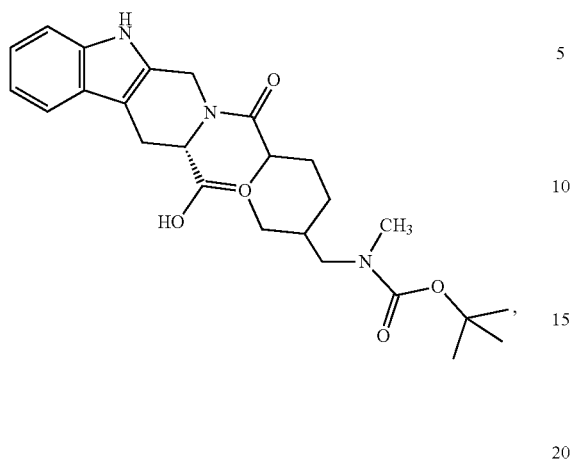
MN1377
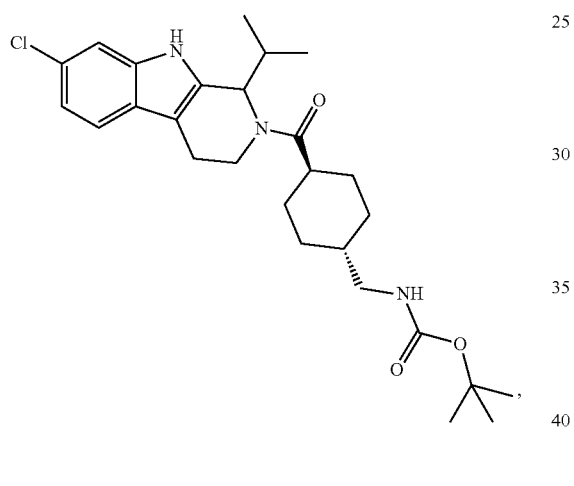
MN1378
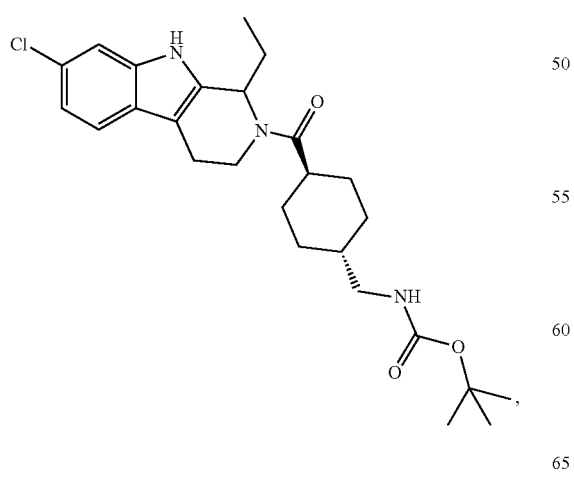
MN1379
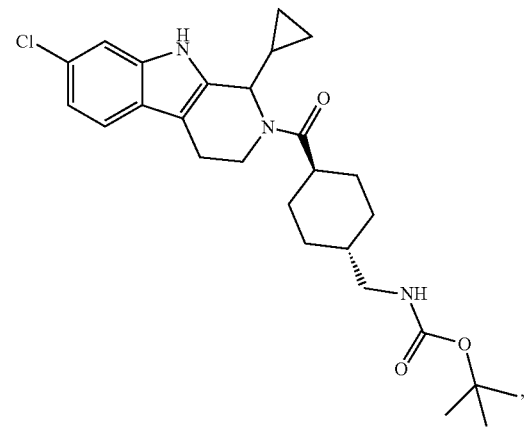
MN1380
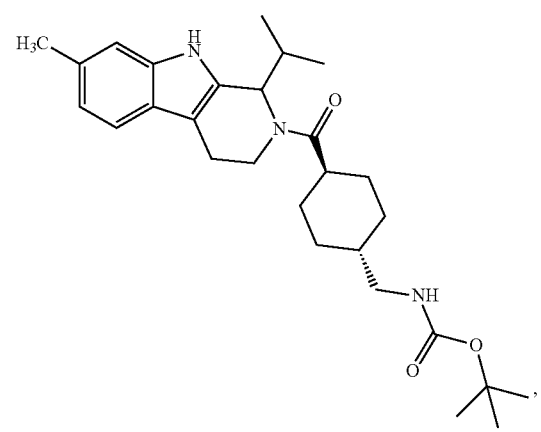
MN1381
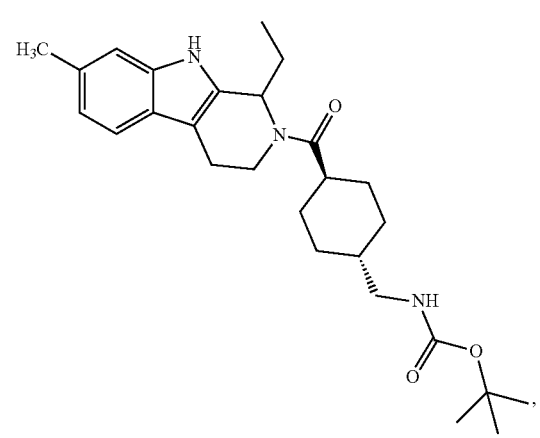

-continued
MN1382
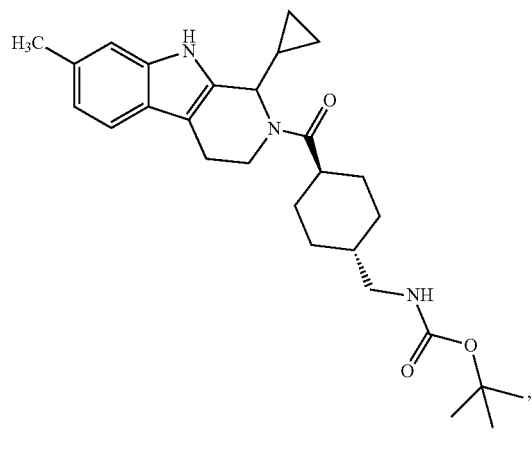
MN1385
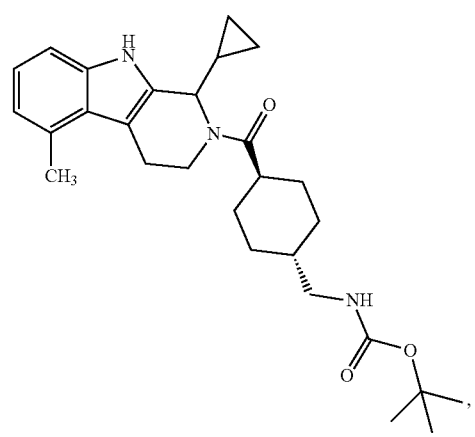
MN1383
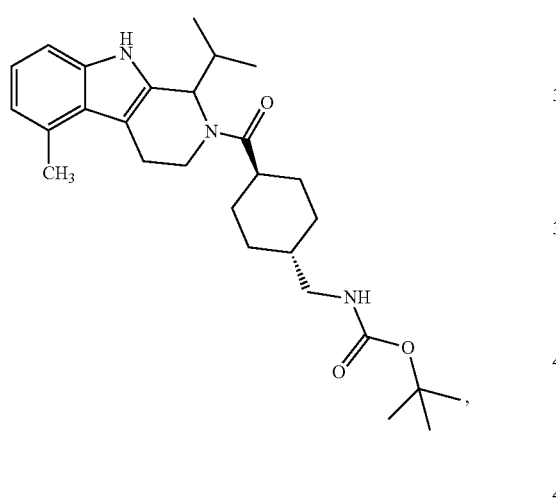
MN1354
MN1384
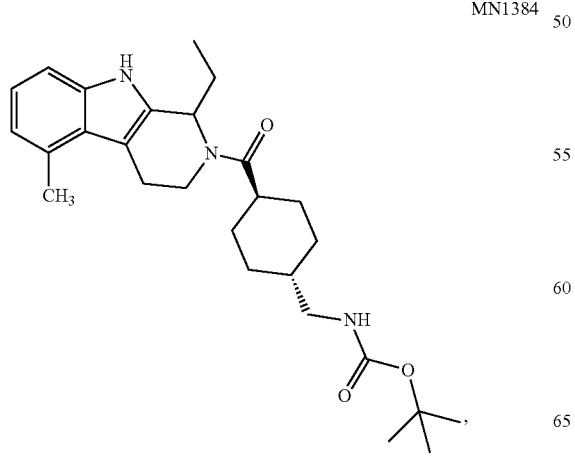
MN1386

-continued
MN1387
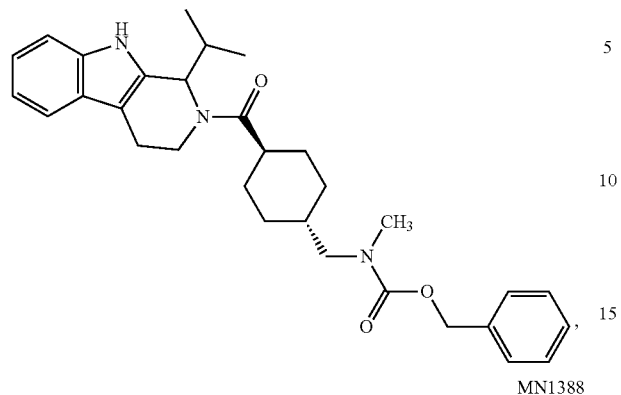
MN1388
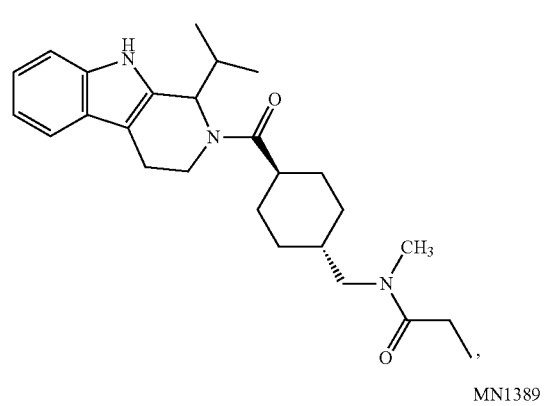
MN1389
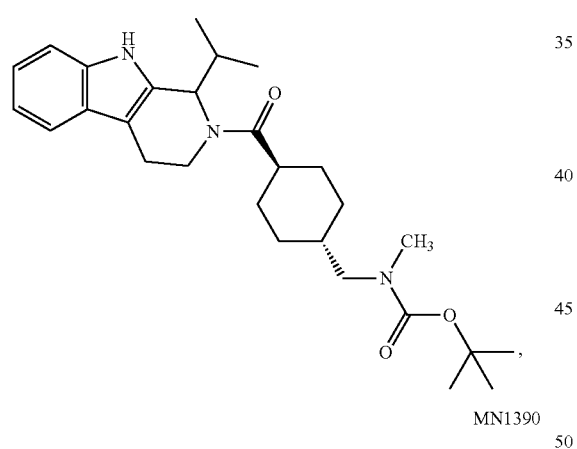
MN1390
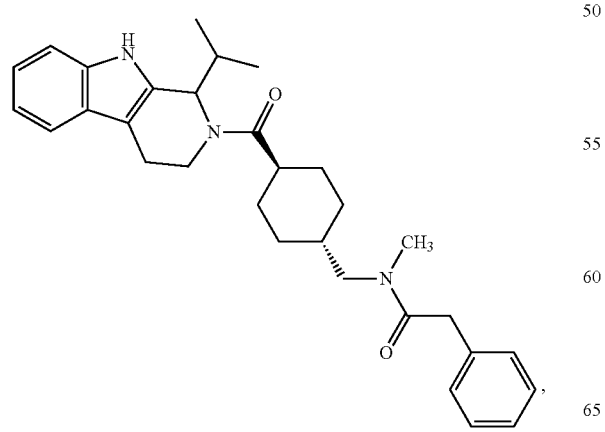
-continued
MN1391
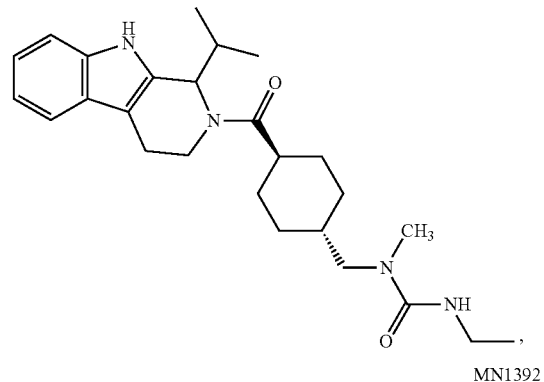
MN1392
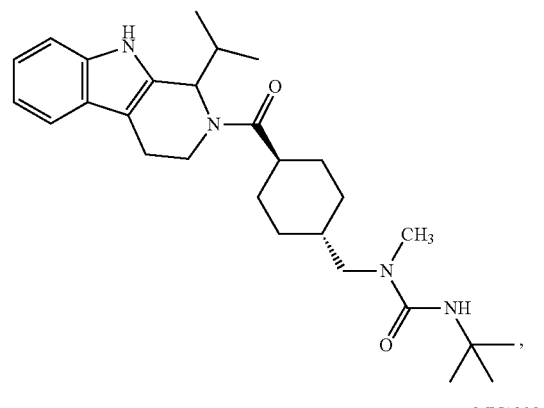
MN1393
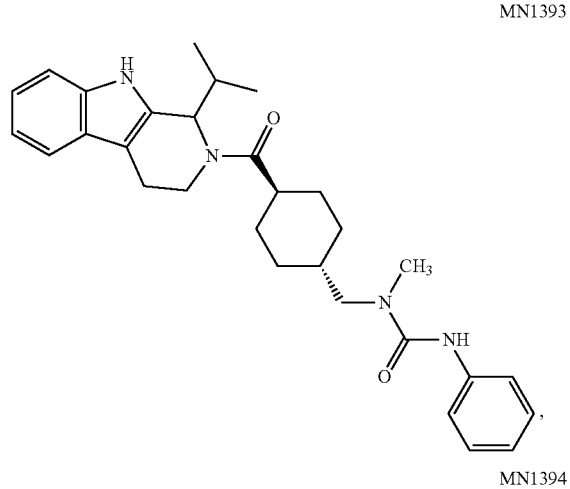
MN1394
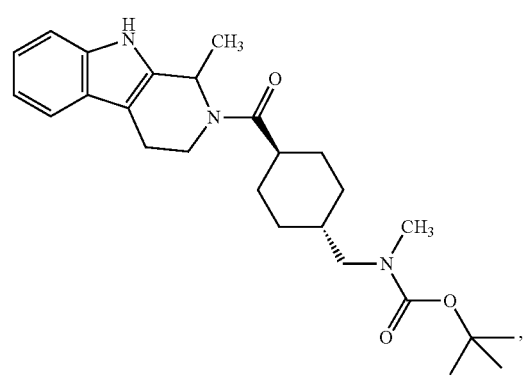

-continued
MN1395
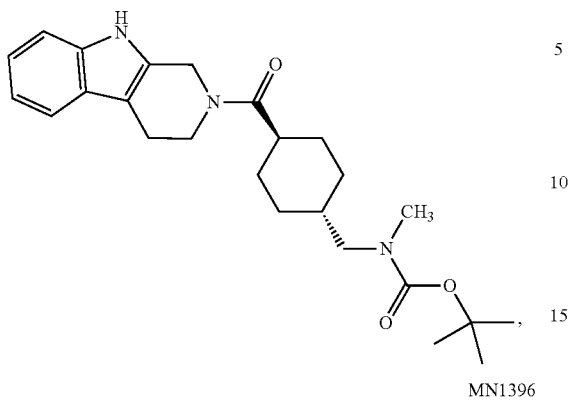
MN1396
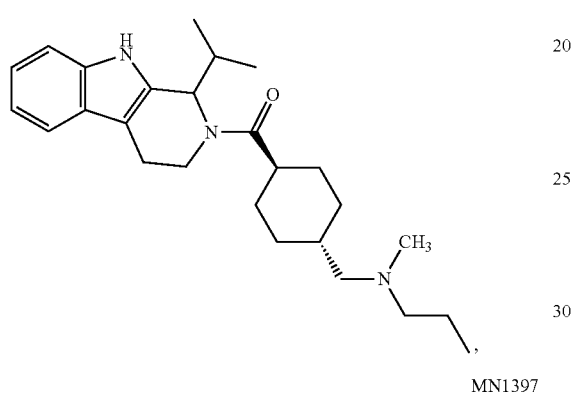
MN1397
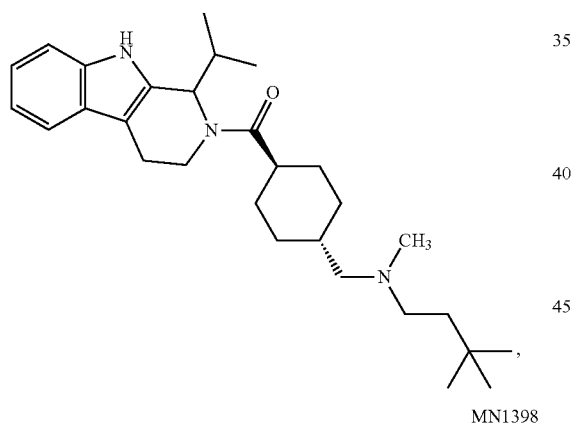
MN1398
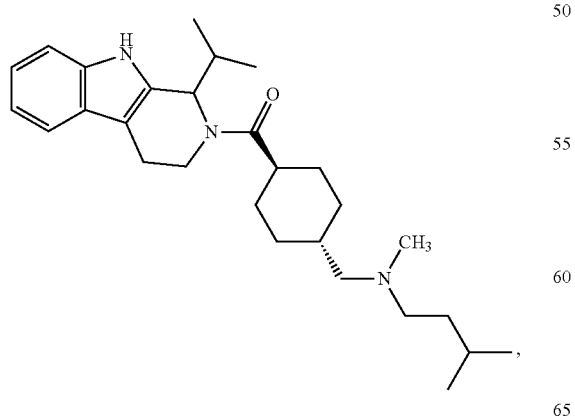
-continued
MN1399
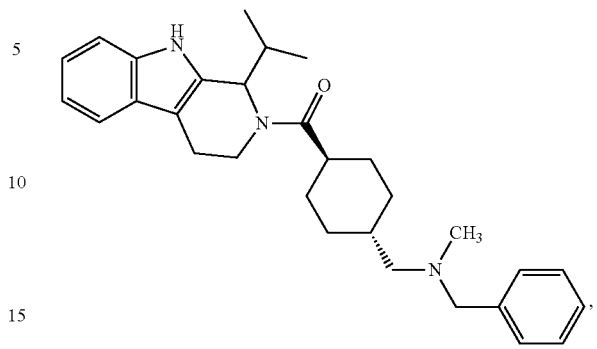
MN1400
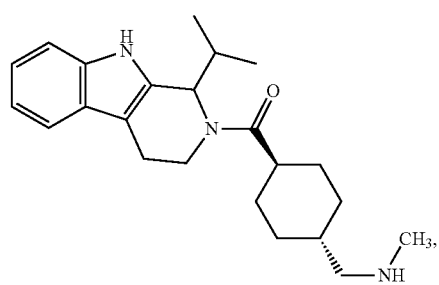
MN1401
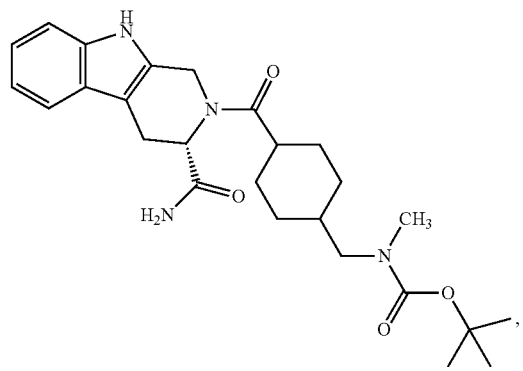
MN1402
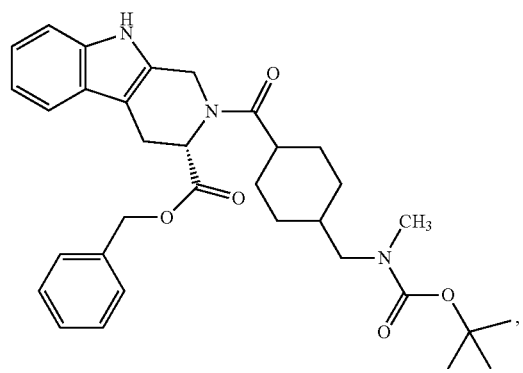

MN1403
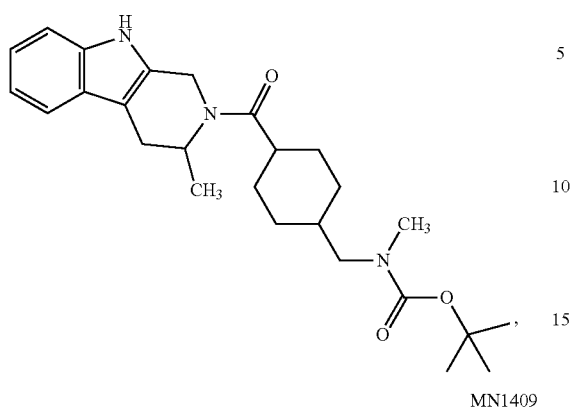
MN1409
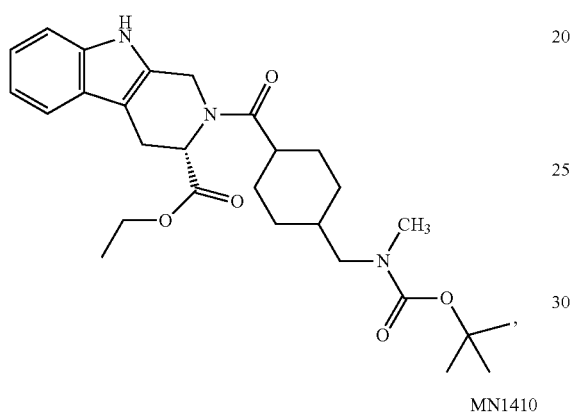
MN1410
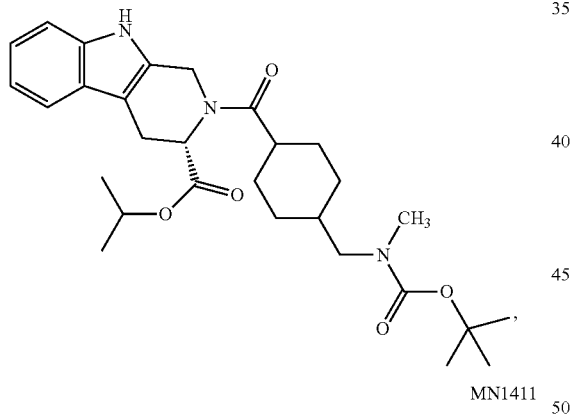
MN1411
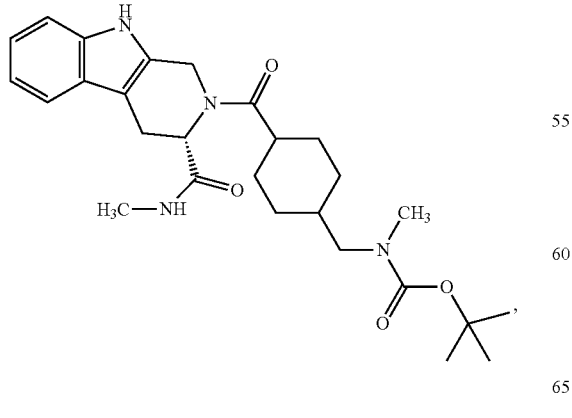
MN1412
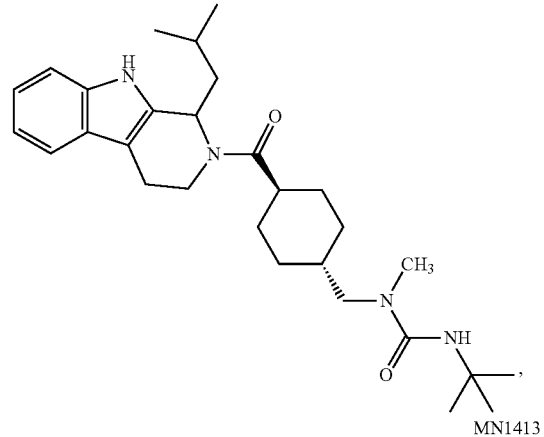
MN1413
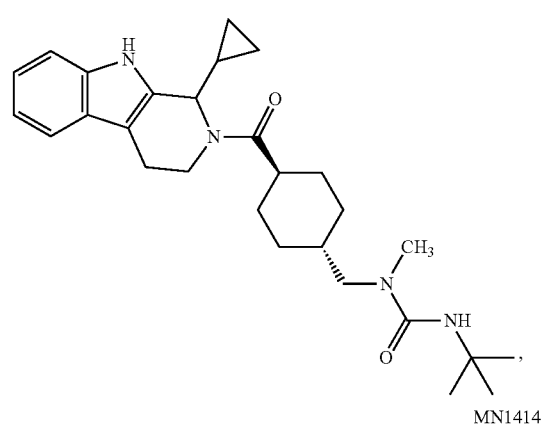
MN1414
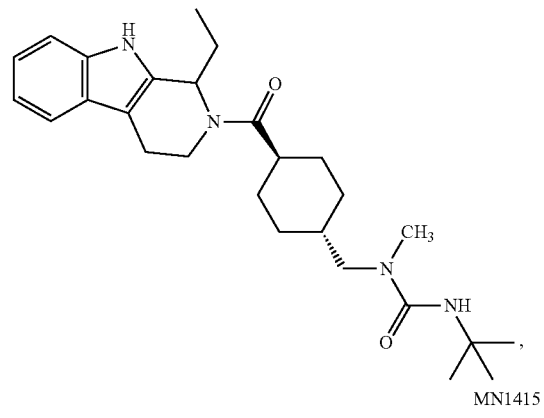
MN1415
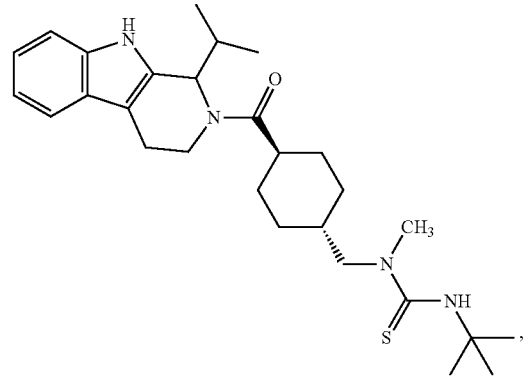

-continued

MN1419
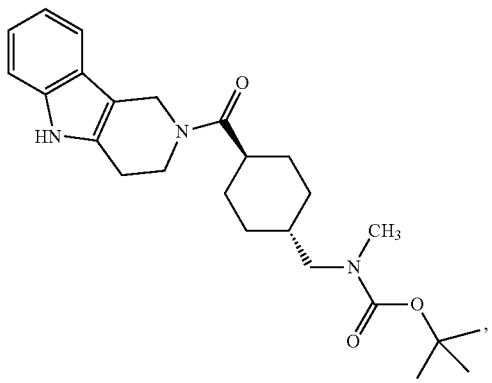

MN1422
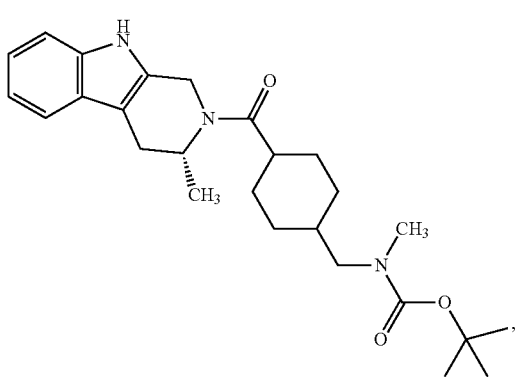

MN1423
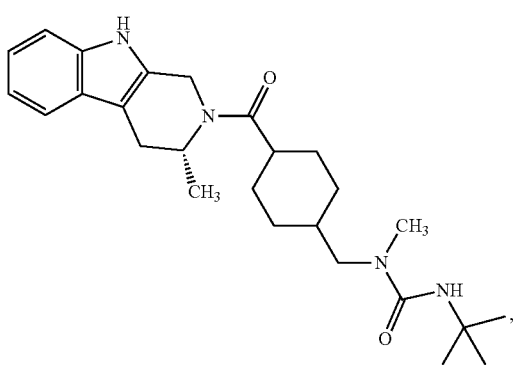

MN1424
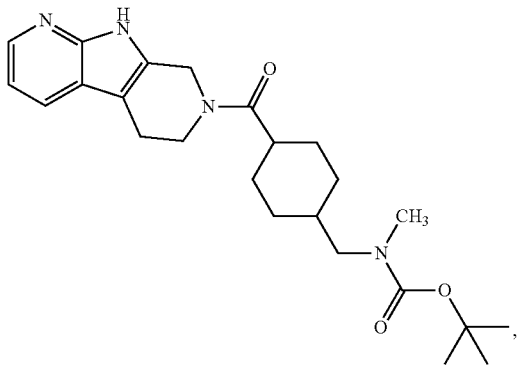

-continued

MN1425
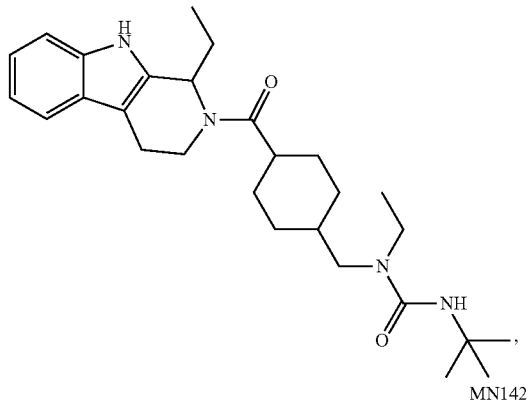

MN1426
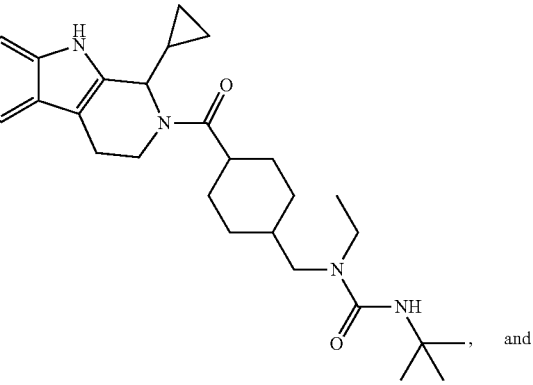, and

MN1443
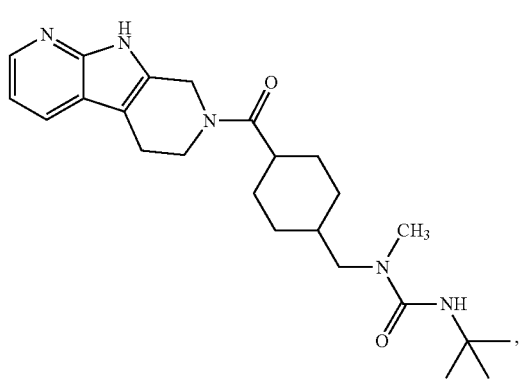

or a pharmaceutically acceptable salt thereof.

9. The compound, or pharmaceutically acceptable salt thereof, according to claim 2, wherein the compound is a compound of Formula 15, and wherein $R_1$ is H; $R_2$ is H, $R_4$ is tertbutyl; and $R_5$ is $CH_3$.

10. The compound, or pharmaceutically acceptable salt thereof, according to claim 2, wherein the compound is a compound of Formula 15, and wherein $Z_2$ is NH.

11. The compound, or pharmaceutically acceptable salt thereof, according to claim 9, wherein the compound is a compound of Formula 15, and wherein $Z_2$ is NH.

12. A pharmaceutical composition comprising the compound, or pharmaceutically acceptable salt thereof, according to claim 1, and a pharmaceutically acceptable carrier or excipient.

13. A method of treating a cancer in a subject in need thereof, comprising administering to the subject in need thereof a therapeutically effective amount of the compound, or pharmaceutically acceptable salt thereof, of claim 1.

14. The method according to claim 13, wherein the cancer is a MUC1 positive or MUC1* positive cancer.

15. The method according to claim 13, wherein the cancer is an $NME7_{AB}$ or NME7-X1 positive cancer.

16. The method according to claim 13, further comprising analyzing a cancerous sample from the subject and determining the cancer is a MUC1* positive, $NME74_{AB}$ positive or NME7-X1 cancer.

17. A method of treating an inflammatory disease or condition comprising administering to a subject in need thereof a therapeutically effective amount of the compound, or pharmaceutically acceptable salt thereof, of claim 1.

18. The method according to claim 17, wherein the inflammatory disease or condition is rheumatoid arthritis, inflammatory bowel syndrome, Crohn's disease, osteoarthritis, asthma, dermatitis, psoriasis, cystic fibrosis, post transplantation late and chronic solid organ rejection, multiple sclerosis, systemic lupus erythematosus, Sjogren syndrome, Hashimoto thyroiditis, polymyositis, scleroderma, Addison disease, vitiligo, pernicious anemia, glomerulonephritis, pulmonary fibrosis, autoimmune diabetes, diabetic retinopathy, rhinitis, ischemia-reperfusion injury, post-angioplasty restenosis, chronic obstructive pulmonary diseases (COPD), Graves' disease, gastrointestinal allergy, conjunctivitis, atherosclerosis, coronary artery disease, angina, cancer metastasis, small artery disease, or mitochondrial disease.

\* \* \* \* \*